US011572356B2

(12) United States Patent
Hopkins et al.

(10) Patent No.: US 11,572,356 B2
(45) Date of Patent: *Feb. 7, 2023

(54) BIARYL INHIBITORS OF BRUTON'S TYROSINE KINASE

(71) Applicant: BIOGEN MA INC., Cambridge, MA (US)

(72) Inventors: Brian T. Hopkins, Newton, MA (US); Bin Ma, Arlington, MA (US); Timothy Raymond Chan, Sammamish, WA (US); Lihong Sun, Lexington, MA (US); Lei Zhang, Westford, MA (US); Gnanasambandam Kumaravel, Westford, MA (US); Joseph P. Lyssikatos, Piedmont, CA (US); Kevin Koch, Cambridge, MA (US); Hua Miao, Newton, MA (US)

(73) Assignee: BIOGEN MA INC., Cambridge, MA (US)

( * ) Notice: Subject to any disclaimer, the term of this patent is extended or adjusted under 35 U.S.C. 154(b) by 118 days.

This patent is subject to a terminal disclaimer.

(21) Appl. No.: 17/004,411

(22) Filed: Aug. 27, 2020

(65) Prior Publication Data

US 2022/0332705 A1 Oct. 20, 2022

Related U.S. Application Data

(63) Continuation of application No. 16/108,755, filed on Aug. 22, 2018, now Pat. No. 10,759,783, which is a continuation of application No. 15/699,857, filed on Sep. 8, 2017, now Pat. No. 10,081,619, which is a continuation of application No. 15/103,749, filed as application No. PCT/US2014/069853 on Dec. 11, 2014, now Pat. No. 9,809,577.

(60) Provisional application No. 61/914,886, filed on Dec. 11, 2013.

(51) Int. Cl.
| | | |
|---|---|---|
| *C07D 403/12* | (2006.01) |
| *C07D 417/14* | (2006.01) |
| *C07D 495/04* | (2006.01) |
| *C07D 409/14* | (2006.01) |
| *C07D 401/14* | (2006.01) |
| *C07D 513/04* | (2006.01) |
| *C07D 413/14* | (2006.01) |
| *A61K 31/506* | (2006.01) |
| *C07D 239/30* | (2006.01) |
| *C07F 5/02* | (2006.01) |
| *C07D 417/12* | (2006.01) |
| *C07D 487/04* | (2006.01) |

(52) U.S. Cl.
CPC .......... *C07D 403/12* (2013.01); *A61K 31/506* (2013.01); *C07D 239/30* (2013.01); *C07D 401/14* (2013.01); *C07D 409/14* (2013.01); *C07D 413/14* (2013.01); *C07D 417/12* (2013.01); *C07D 417/14* (2013.01); *C07D 487/04* (2013.01); *C07D 495/04* (2013.01); *C07D 513/04* (2013.01); *C07F 5/027* (2013.01)

(58) Field of Classification Search
CPC .. C07D 403/12; C07D 239/30; C07D 401/14; C07D 487/04; C07D 409/14; C07D 417/12; C07D 417/14; C07D 495/04; C07D 513/04; C07D 413/14; A61K 31/506; C07F 5/027
See application file for complete search history.

(56) References Cited

U.S. PATENT DOCUMENTS

| | | |
|---|---|---|
| 7,528,143 B2 | 5/2009 | Noronha et al. |
| 8,334,292 B1 | 12/2012 | Chiang |
| 8,834,292 B2 | 9/2014 | Tsuji et al. |
| 9,809,577 B2 | 11/2017 | Hopkins et al. |
| 10,081,619 B2 | 9/2018 | Hopkins et al. |
| 10,189,829 B2 | 1/2019 | Hopkins et al. |
| 10,227,341 B2 | 3/2019 | Hopkins et al. |
| 10,759,783 B2 | 9/2020 | Hopkins et al. |
| 10,961,237 B2 | 3/2021 | Hopkins et al. |

FOREIGN PATENT DOCUMENTS

| | | |
|---|---|---|
| WO | 2004/089286 A2 | 10/2004 |
| WO | 2007/089768 A2 | 8/2007 |
| WO | 2008/116064 A2 | 9/2008 |
| WO | 2009/045175 A1 | 4/2009 |
| WO | 2012/062704 A1 | 5/2012 |
| WO | 2012/142329 A1 | 10/2012 |
| WO | 2015/089327 A1 | 6/2015 |
| WO | 2016/201280 A1 | 12/2016 |

OTHER PUBLICATIONS

Damasio, Alzheimer's Disease and Related Dementias. Cecil Textbook of Medicine, 20th Edition, vol. 2. J. Claude Bennett (Ed.), W.B. Saunders Company, Philadelphia. pp. 1992-1996, (1996).
Di Paolo et al., Specific Btk inhibition suppresses B cell- and myeloid cell-mediated arthritis. Nat Chem Biol. Jan. 2011;7(1):41-50.
Hayter et al., Updated assessment of the prevalence, spectrum and case definition of autoimmune disease. Autoimmun Rev. Aug. 2012;11(10):754-65.
Jaworska et al., Review of Methods for Assessing the Applicability Domains of SARS and QSARS. Paper 4: SAR Applicability Domain. 9 pages. Sep. 27, 2004.
Declaration under 37 C.F.R. 1.132 by Brian Hopkins, Ph.D., U.S. Appl. No. 15/103,749. 2 pages, dated Jul. 17, 2017.
U.S. Appl. No. 15/103,749, filed Jun. 10, 2016, U.S. Pat. No. 9,809,577, Issued.
U.S. Appl. No. 15/651,788, filed Jul. 17, 2017, Abandoned.

(Continued)

*Primary Examiner* — Shirley V Gembeh
(74) *Attorney, Agent, or Firm* — McCarter & English, LLP; Steven G. Davis; Xin Zhang

(57) ABSTRACT

The present invention provides compounds and compositions thereof which are useful as inhibitors of Bruton's tyrosine kinase and which exhibit desirable characteristics for the same.

17 Claims, No Drawings

(56) References Cited

OTHER PUBLICATIONS

U.S. Appl. No. 15/699,857, filed Sep. 8, 2017, U.S. Pat. No. 10,081,619, Issued.
U.S. Appl. No. 16/108,755, filed Aug. 22, 2018, U.S. Pat. No. 10,759,783, Issued.
U.S. Appl. No. 15/952,505, filed Apr. 13, 2018, U.S. Pat. No. 10,227,341, Issued.
U.S. Appl. No. 16/113,455, filed Aug. 27, 2018, U.S. Pat. No. 10,189,829, Issued.
U.S. Appl. No. 16/246,986, filed Jan. 14, 2019, Abandoned.
U.S. Appl. No. 16/534,540, filed Aug. 7, 2019, U.S. Pat. No. 10,961,237, Issued.
U.S. Appl. No. 17/183,702, filed Feb. 24, 2021, Pending.

BIARYL INHIBITORS OF BRUTON'S TYROSINE KINASE

CROSS REFERENCE TO RELATED APPLICATIONS

This application is a continuation of U.S. application Ser. No. 16/108,755, filed Aug. 22, 2018, which is a continuation of U.S. application Ser. No. 15/699,857, filed Sep. 8, 2017, now U.S. Pat. No. 10,081,619, which is a continuation application of U.S. application Ser. No. 15/103,749, filed Jun. 10, 2016, now issued as U.S. Pat. No. 9,809,577, which is a 35 U.S.C. § 371 national stage filing of International Application No. PCT/US2014/069853, filed Dec. 11, 2014, which claims priority to U.S. provisional patent application No. 61/914,886, filed Dec. 11, 2013. The entire contents of each of the foregoing applications are hereby incorporated by reference.

BACKGROUND OF THE INVENTION

Protein kinases are a large multigene family consisting of more than 500 proteins which play a critical role in the development and treatment of a number of human diseases in oncology, neurology and immunology. The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk) and Bmx (bone-marrow tyrosine kinase gene on chromosome X; also known as Etk)) and are primarily expressed in haematopoietic cells, although expression of Bmx and Tec has been detected in endothelial and liver cells. Tec kinases (Itk, Rlk and Tec) are expressed in T cell and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCγ), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors of Btk. The present invention fulfills these and other needs.

SUMMARY OF THE INVENTION

In certain embodiments, the present invention provides a compound of formula I:

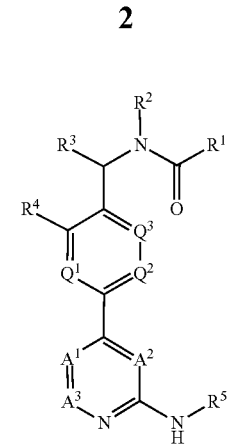

or a pharmaceutically acceptable salt thereof, wherein each of $R^1$, $R^2$, $R^3$, $R^4$, $R^5$, $Q^1$, $Q^2$, $Q^3$, $A^1$, $A^2$, and $A^3$ is as defined and described in classes and subclasses herein.

DETAILED DESCRIPTION OF CERTAIN EMBODIMENTS

In some embodiments, the present invention provides a compound of formula I:

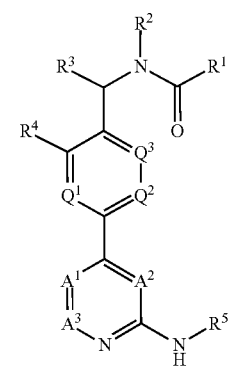

or a pharmaceutically acceptable salt thereof, wherein:
one of $A^1$ and $A^2$ is C—$R^6$, and the other of $A^1$ and $A^2$ is C—$R^6$ or N;
$A^3$ is selected from C—H or N, and is C—H when $A^1$ or $A^2$ is N;
$Q^1$ is selected from C—$R^7$ and N;
$Q^2$ is selected from C—$R^7$ and N;
$Q^3$ is selected from C—$R^7$ and N;
wherein at most one of $Q^1$, $Q^2$, and $Q^3$ is N;
$R^1$ is —N(R)$_2$ or an optionally substituted group selected from phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, and 8- to 10-membered bicyclic aryl;

$R^2$ is H or optionally substituted $C_{1-6}$ aliphatic,
  or $R^1$ and $R^2$, together with their intervening atoms, form an optionally substituted ring selected from 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, and 7- to 10-membered bicyclic heteroaryl having 1-4 heteroatoms selected from oxygen, nitrogen;
$R^3$ is selected from H, halogen, —C(O)N(R)$_2$, —C(O)OR, —C(O)R, and optionally substituted $C_{1-6}$ aliphatic;
$R^4$ is selected from halogen, —NO$_2$, —CN, —OR, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, and optionally substituted $C_{1-6}$ aliphatic;
  or $R^3$ and $R^4$, together with their intervening atoms, form an optionally substituted fused Ring A, wherein fused Ring A is selected from fused 5- to 7-membered monocyclic carbocycle and fused 5- to 7-membered heterocycle having 1-2 heteroatoms selected from oxygen, nitrogen, or sulfur;
$R^5$ is selected from H, —C(O)R, —C(O)OR, —S(O)R, —S(O)$_2$R, —C(O)N(R)$_2$, or an optionally substituted group selected from $C_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl;
each of $R^6$ and $R^7$ is independently selected from H, halogen, —NO$_2$, —CN, —OR, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, or optionally substituted $C_{1-6}$ aliphatic; and
each R is independently hydrogen or an optionally substituted group selected from $C_{1-6}$ aliphatic, phenyl, 3- to 8-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, or:
two R groups on the same nitrogen are taken together with their intervening atoms to form an optionally substituted ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocyclyl," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocyclyl" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "fused 5- to 7-membered monocyclic carbocycle" refers to a monocyclic hydrocarbon that shares three carbon atoms with the core structure. By way of illustration, the compound of Example I-90 possesses a 5-membered fused monocyclic carbocycle, as indicated by the dotted lines below:

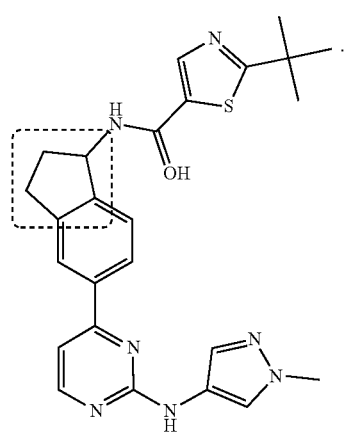

I-90

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR⁺ (as in N-substituted pyrrolidinyl)).

The term "unsaturated," as used herein, means that a moiety has one or more units of unsaturation.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In some embodiments, an 8-10 membered bicyclic aryl group is an optionally substituted naphthyl ring. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroarl", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in this context in reference to a ring atom, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or ⁺NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

The term "fused 5- to 7-membered monocyclic heterocycle" refers to a monocyclic heterocyclic moiety that shares three carbon atoms with the core structure. By way of illustration, the compound of Example I-98 possesses a 6-membered fused monocyclic heterocycle, as indicated by the dotted lines below:

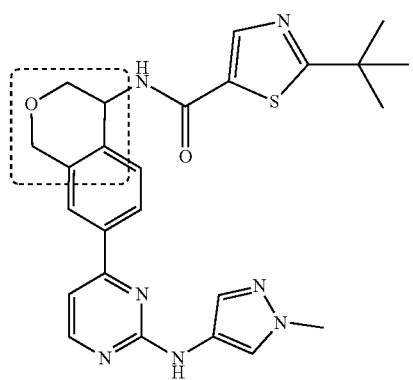

I-98

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}$ Ph, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°S(O)_2R°$; —$N(OR°)R°$; —$C(NH)NR°_2$; —$P(O)_2R°$; —$P(O)R°_2$; $OP(O)R°_2$; —$OP(O)(OR°)_2$; $SiR°_3$; —$(C_{1-4}$ straight or branched)alkylene)O—$N(R°)_2$; or —$(C_{1-4}$ straight or branched alkylene)C(O)O—$N(R°)_2$, wherein each $R°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —$O(haloR^{\bullet})$, —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —$(C_{1-4}$ straight or branched alkylene)C(O)OR$^{\bullet}$, or —$SSR^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^{\bullet}$, -(halo$R^{\bullet}$), —OH, —$OR^{\bullet}$, —$O(haloR^{\bullet})$, —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^{\dagger}$, —$NR^{\dagger}_2$, —$C(O)R^{\dagger}$, —$C(O)OR^{\dagger}$, —$C(O)C(O)R^{\dagger}$, —$C(O)CH_2C(O)R^{\dagger}$, —$S(O)_2R^{\dagger}$, —$S(O)_2NR^{\dagger}_2$, —$C(S)NR^{\dagger}_2$, —$C(NH)NR^{\dagger}_2$, or —$N(R^{\dagger})S(O)_2R^{\dagger}$; wherein each $R^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, —$R^{\bullet}$, -(halo$R^{\bullet}$), —OH, —$OR^{\bullet}$, —$O(haloR^{\bullet})$, —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "oxo," as used herein, means an oxygen that is double bonded to a carbon atom, thereby forming a carbonyl.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. Suitable protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. In certain embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. Amino-protecting groups include methyl carbamate, 9-fluorenylmethyl carbamate (Fmoc), 9-(2,7-dibromo)fluoroenylmethyl carbamate, 4-methoxyphenacyl carbamate (Phenoc), 2,2,2-trichloroethyl carbamate (Troc), 2-trimethylsilylethyl carbamate (Teoc), 1-methyl-1-(4-biphenylyl)ethyl carbamate (Bpoc), 2-(2'- and 4'-pyridyl)ethyl carbamate (Pyoc), 2-(N,N-dicyclohexylcarboxamido)ethyl carbamate, t-butyl carbamate (BOC), allyl carbamate (Alloc), 4-nitrocinnamyl carbamate (Noc), N-hydroxypiperidinyl carbamate, alkyldithio carbamate, benzyl carbamate (Cbz), p-nitobenzyl carbamate, p-chlorobenzyl carbamate, diphenylmethyl carbamate, 2-methylsulfonylethyl carbamate, 2-(p-toluenesulfonyl) ethyl carbamate, 2,4-dimethylthiophenyl carbamate (Bmpc), 2-triphenylphosphonioisopropyl carbamate (Ppoc), m-chloro-p-acyloxybenzyl carbamate, p-(dihydroxyboryl) benzyl carbamate, m-nitrophenyl carbamate, 3,5-dimethoxybenzyl carbamate, o-nitrobenzyl carbamate, phenyl(o-nitrophenyl)methyl carbamate, N'-p-toluenesulfonylaminocarbonyl derivative, N'-phenylaminothiocarbonyl derivative, t-amyl carbamate, p-cyanobenzyl carbamate, cyclohexyl carbamate, cyclopentyl carbamate, p-decyloxybenzyl carbamate, 2,2-dimethoxycarbonylvinyl carbamate, 2-furanylmethyl carbamate, isobornyl carbamate, isobutyl carbamate, 1-methyl-1-phenylethyl carbamate, 1-methyl-1-(4-pyridyl)ethyl carbamate, phenyl carbamate, formamide, acetamide, chloroacetamide, trichloroacetamide, trifluoroacetamide, phenylacetamide, 3-phenylpropanamide, picolinamide, N-benzoylphenylalanyl derivative, benzamide, p-phenylbenzamide, o-nitrophenoxyacetamide, acetoacetamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-2,5-dimethylpyrrole, N-methylamine, N-allylamine, N-[2-(trimethylsilyl)ethoxy]methylamine (SEM), N-3-acetoxypropylamine, N-benzylamine, N-triphenylmethylamine (Tr), N-2-picolylamino N'-oxide, N-1,1-dimethylthiomethyleneamine, N-benzylideneamine, N-p-methoxybenzylideneamine, N—(N',N'-dimethylaminomethylene)amine, N,N'-isopropylidenediamine, N-p-nitrobenzylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-nitroamine, N-nitrosoamine, amine N-oxide, diphenylphosphinamide (Dpp), dimethylthiophosphinamide (Mpt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), methanesulfonamide (Ms), β-trimethylsilylethanesulfonamide (SES), benzylsulfonamide, trifluoromethylsulfonamide, and phenacylsulfonamide Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

The symbol "~~~", except when used as a bond to depict unknown or mixed stereochemistry, denotes the point of attachment of a chemical moiety to the remainder of a molecule or chemical formula.

Compounds

As described above, in certain embodiments provided compounds are of formula I:

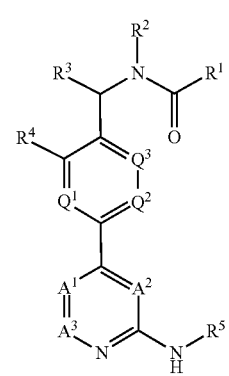

I or a pharmaceutically acceptable salt thereof, wherein each of $R^1$, $R^2$, $R^3$, $R^4$, $R^5$, $Q^1$, $Q^2$, $Q^3$, $A^1$, $A^2$, and $A^3$ is as defined above and described in classes and subclasses herein, both singly and in combination.

As used herein, unless otherwise stated, references to formula I also include all subgenera of formula I defined and described herein (e.g., formulae I', I-a, II-a, II-b, II-c, III, IV-a, IV-b, IV-c, V-a, V-b, VI-a, VI-b, VII-a, VII-b, VII-c and VII-d).

In some embodiments, $A^1$ and $A^2$ are C—$R^6$ and $A^3$ is C—H. In some embodiments, $A^1$ is C—$R^6$, $A^2$ is N, and $A^3$ is C—H. In some embodiments, $A^1$ is C—$R^6$, $A^2$ is C—$R^6$, and $A^3$ is N. In some embodiments, $A^1$ is N, $A^2$ is C—$R^6$, and $A^3$ is C—H.

In some embodiments, $Q^1$, $Q^2$, and $Q^3$ are C—$R^7$. In some embodiments, $Q^1$ is N, and $Q^2$ and $Q^3$ are C—$R^7$. In some embodiments, $Q^2$ is N, and $Q^1$ and $Q^3$ are C—$R^7$. In some embodiments, $Q^3$ is N, and $Q^1$ and $Q^2$ are C—$R^7$.

In certain embodiments, $R^1$ is an optionally substituted group selected from 5- to 6-membered heteroaryl having 1-4 heteroatoms selected from oxygen, nitrogen, or sulfur, phenyl, or 3- to 7-membered saturated or partially unsaturated monocyclic heterocyclyl having 1-2 heteroatoms selected from oxygen, nitrogen, or sulfur.

In some embodiments, $R^1$ is optionally substituted phenyl. In some embodiments, $R^1$ is phenyl substituted with halogen.

In some embodiments, $R^1$ is optionally substituted 5-membered heteroaryl having 1-4 heteroatoms selected from oxygen, nitrogen, or sulfur. In some embodiments, $R^1$ is an optionally substituted group selected from thiazolyl, pyrazolyl, isoxazolyl, or thiophenyl. In some embodiments, $R^1$ is thiazolyl, pyrazolyl, or isoxazolyl substituted with t-butyl or —$CF_3$.

In some embodiments, $R^1$ is optionally substituted 6-membered heteroaryl having 1-4 heteroatoms selected from oxygen, nitrogen, or sulfur. In some embodiments, $R^1$ is optionally substituted pyridyl. In some embodiments, $R^1$ is pyridyl substituted with t-butyl or —$CF_3$.

In other embodiments, $R^1$ is optionally substituted 3- to 7-membered saturated or partially unsaturated monocyclic heterocyclyl having 1-2 heteroatoms selected from oxygen, nitrogen, or sulfur. In some embodiments, $R^1$ is an optionally substituted group selected from piperidinyl or azetidinyl. In some embodiments, $R^1$ is piperidinyl substituted with t-butyl or —$CF_3$. In some embodiments, $R^1$ is azetidinyl substituted with —$OC_{1-6}$ alkyl.

In some embodiments, $R^1$ is optionally substituted 7- to 10-membered saturated or partially unsaturated bicyclic heterocyclyl having 1-4 heteroatoms selected from oxygen, nitrogen, or sulfur. In some embodiments, $R^1$ is optionally substituted 7- to 10-membered bicyclic heteroaryl having 1-4 heteroatoms selected from oxygen, nitrogen, or sulfur.

In some embodiments, $R^1$ is optionally substituted with one or more groups selected from halogen, $C_{1-6}$ aliphatic optionally substituted with halogen, or —OR.

In some embodiments, $R^1$ is selected from:

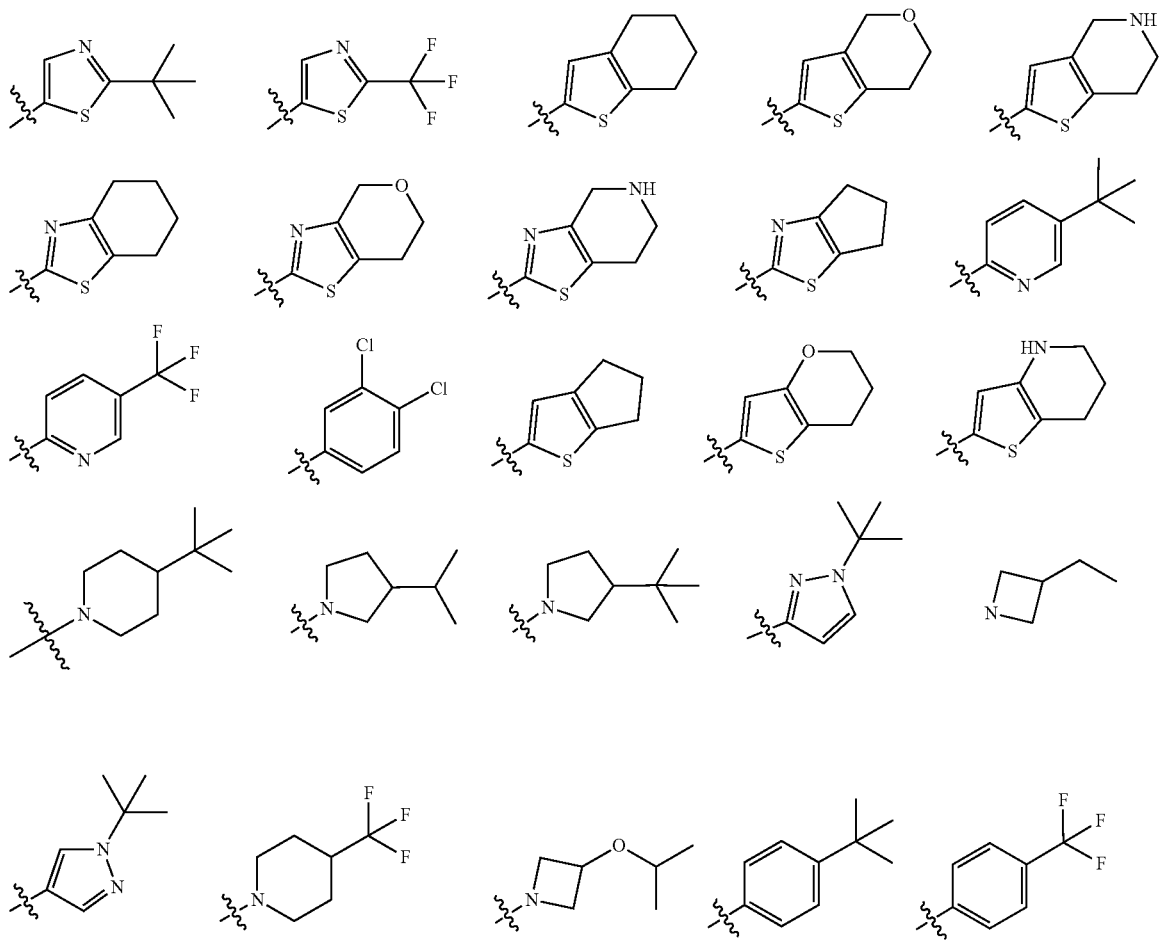

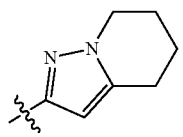 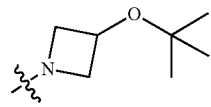 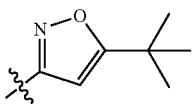 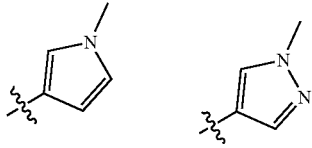

In certain embodiments, R¹ is

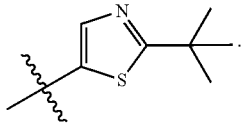 [SMILES: *c1cnc(C(C)(C)C)s1]

In certain embodiments, R¹ is

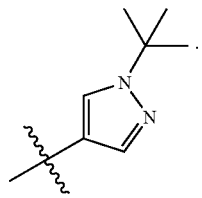 [SMILES: *c1cnn(C(C)(C)C)c1]

In certain embodiments, R¹ is

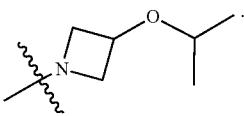 [SMILES: *N1CC(OC(C)C)C1]

In certain embodiments, R¹ is

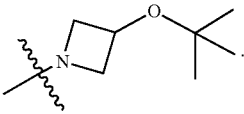 [SMILES: *N1CC(OC(C)(C)C)C1]

In some embodiments, R¹ is —N(R)₂. In some embodiments, R¹ is —N(R)₂ and R is an optionally substituted group selected from phenyl, 3- to 8-membered saturated or partially unsaturated carbocyclyl ring, 3- to 7-membered saturated or partially unsaturated monocyclic heterocyclyl having 1-2 heteroatoms selected from oxygen, nitrogen, or sulfur, and 5- to 6-membered heteroaryl having 1-4 heteroatoms selected from oxygen, nitrogen, or sulfur. In some embodiments, R¹ is —N(R)₂ and R is a 3- to 8-membered saturated or partially unsaturated carbocyclyl ring.

In some embodiments, R² is hydrogen. In some embodiments, R² is optionally substituted $C_{1-6}$ aliphatic. In some embodiments, R² is methyl.

In some embodiments, R¹ and R², together with their intervening atoms, form an optionally substituted ring selected from 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, or 7- to 10-membered bicyclic heteroaryl having 1-4 heteroatoms selected from oxygen, nitrogen.

In some embodiments, when R¹ and R² are taken together they form a 7- to 10-membered bicyclic heterocyclyl having 1-4 heteroatoms selected from oxygen, nitrogen, or sulfur, optionally substituted with $C_{1-6}$ aliphatic. In some embodiments, when R¹ and R² are taken together they form a 7- to 10-membered bicyclic heterocyclyl having 1-4 heteroatoms selected from oxygen, nitrogen, or sulfur, optionally substituted with t-butyl or cyclopropyl. In some embodiments, R¹ and R² are taken together to form a 7- to 10-membered bicyclic heterocyclyl selected from:

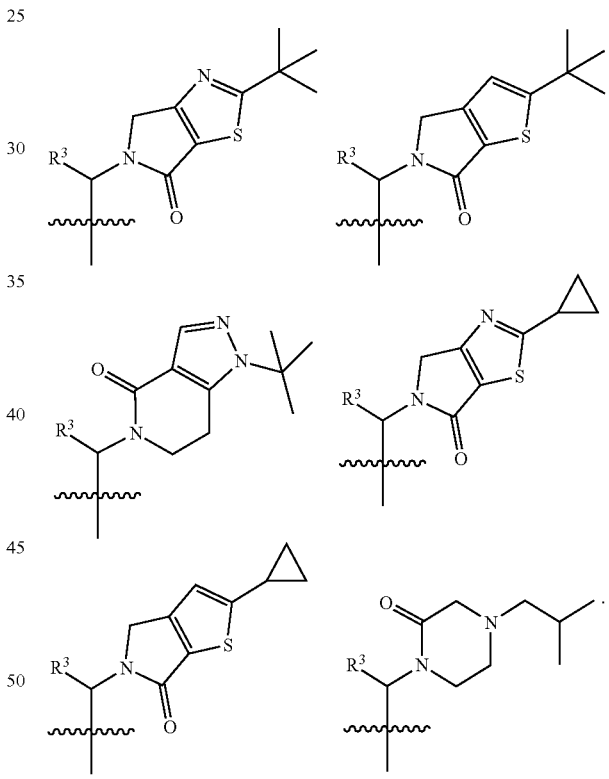

In some embodiments, R³ is hydrogen. In some embodiments, R³ is optionally substituted $C_{1-6}$ aliphatic. In some embodiments, R³ is $C_{1-6}$ alkyl. In some embodiments, R³ is methyl.

In certain embodiments, R⁴ is halogen, —OR, —SR, —N(R)₂, —C(O)R, —C(O)OR, —S(O)R, —S(O)₂R, —C(O)N(R)₂, —SO₂N(R)₂, —OC(O)R, —N(R)C(O)R, —N(R)C(O)OR, —N(R)SO₂R, —OC(O)N(R)₂, or optionally substituted $C_{1-6}$ aliphatic. In some embodiments, R⁴ is optionally substituted $C_{1-6}$ aliphatic. In some embodiments, R⁴ is $C_{1-6}$ alkyl. In some embodiments, R⁴ is methyl. In some embodiments, R⁴ is trifluoromethyl.

In some embodiments, R⁴ is halogen.

In certain embodiments, $R^3$ and $R^4$, together with their intervening atoms, form optionally substituted fused Ring A (indicated by the dotted lines in the structure below):

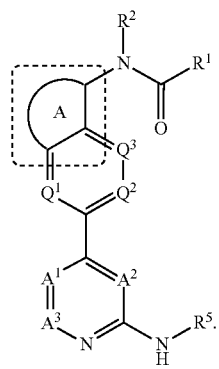

Fused Ring A is selected from fused 5- to 7-membered monocyclic carbocycle and 5- to 7-membered monocyclic heterocycle having 1-2 heteroatoms selected from oxygen, nitrogen, and sulfur.

In some embodiments, fused Ring A is fused 5- to 7-membered monocyclic carbocycle. In some embodiments, fused Ring A is fused 7-membered monocyclic carbocycle. It is to be understood that in the context of "fused Ring A," the carbon chain formed by $R^3$ and $R^4$ is a saturated carbon chain. For example, in the compound of Example 90, fused Ring A (indicated by dotted lines in the structure below) is a five-membered ring in which $R^3$ and $R^4$ form a —CH$_2$—CH$_2$— chain:

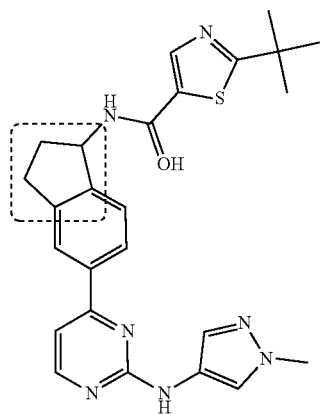

I-90

In some embodiments, fused Ring A is fused 5- to 7-membered monocyclic heterocycle having 1 heteroatom selected from oxygen or nitrogen. It is to be understood that in the context of "fused Ring A," the chain formed by $R^3$ and $R^4$ is a saturated chain. For example, in the compound of Example 98, fused Ring A (indicated by dotted lines in the structure below) is a six-membered ring in which $R^3$ and $R^4$ form a —CH$_2$—O—CH$_2$— chain:

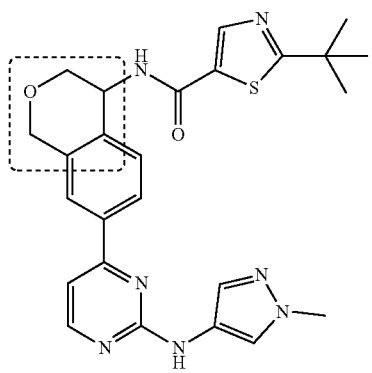

I-98

In some embodiments, fused Ring A is fused 5-membered monocyclic heterocycle having 1 oxygen. In some embodiments, fused Ring A is fused 6-membered monocyclic heterocycle having 1 oxygen. In some embodiments, fused Ring A is fused 7-membered monocyclic heterocycle having 1 oxygen. In some embodiments, fused Ring A is fused 5-membered monocyclic heterocycle having 1 nitrogen. In some embodiments, fused Ring A is fused 6-membered monocyclic heterocycle having 1 nitrogen. In some embodiments, fused Ring A is fused 7-membered monocyclic heterocycle having 1 nitrogen.

In some embodiments, $R^5$ is selected from hydrogen, —C(O)R, or optionally substituted 5- to 6-membered heteroaryl having 1-4 heteroatoms selected from oxygen, nitrogen, or sulfur. In some embodiments, $R^5$ is hydrogen. In some embodiments, $R^5$ is —C(O)R, wherein R is $C_{1-6}$ aliphatic. In some embodiments, $R^5$ is —C(O)Me.

In some embodiments, $R^5$ is optionally substituted 5- to 6-membered heteroaryl having 1-4 heteroatoms selected from oxygen, nitrogen, or sulfur. In some embodiments, $R^5$ is an optionally substituted group selected from pyrazolyl, imidazolyl, isoxazolyl, triazolyl, tetrazolyl, thiadiazolyl, or pyridyl.

In some embodiments, $R^5$ is pyrazolyl optionally substituted with methyl, ethyl, isopropyl, —(CH$_2$)$_2$OH, —(CH$_2$)$_2$OMe, —(CH$_2$)$_2$NH$_2$, —CH$_2$CHOHCH$_2$NH$_2$, —CH$_2$CHNH$_2$COOH, —CH$_2$CHNH$_2$CH$_2$OH, —CH$_2$-morpholinyl, tetrahydropyranyl, azetidinyl, pyrrolidinyl, cyclobutyl, piperidinyl, or cyclohexyl, any of which may be substituted with $C_{1-6}$ aliphatic, hydroxyl, or carboxyl.

In some embodiments, $R^5$ is pyridyl optionally substituted with piperazinyl.

In some embodiments, $R^5$ is imidazolyl optionally substituted with $C_{1-6}$ aliphatic.

In some embodiments, $R^5$ is triazolyl optionally substituted with $C_{1-6}$ aliphatic.

In some embodiments, $R^5$ is an optionally substituted group selected from:

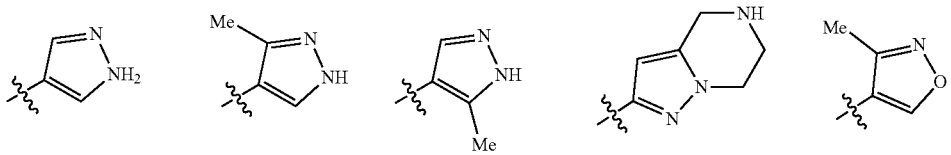

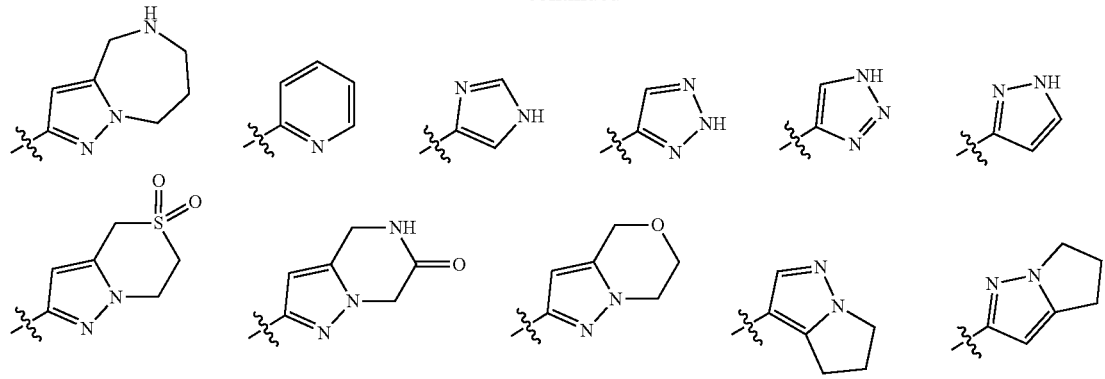

In some embodiments, said groups are substituted with one or more moieties selected from methyl, ethyl, isopropyl, —C(O)OC$_{1-6}$ alkyl; —(CH$_2$)$_2$OH, —(CH$_2$)$_2$OMe, —(CH$_2$)$_2$NH$_2$, —CH$_2$CHOHCH$_2$NH$_2$, —CH$_2$CHNH$_2$COOH, —C(CH$_3$)$_2$C(O)NH$_2$, —CH$_2$CHNH$_2$CH$_2$OH, —CH$_2$-morpholinyl, tetrahydropyranyl, azetidinyl, pyrrolidinyl, cyclobutyl, piperidinyl, piperizinyl, or cyclohexyl, any of which may be substituted with C$_{1-6}$ aliphatic, halogen, hydroxyl, or carboxyl.

In some embodiments, R$^5$ is

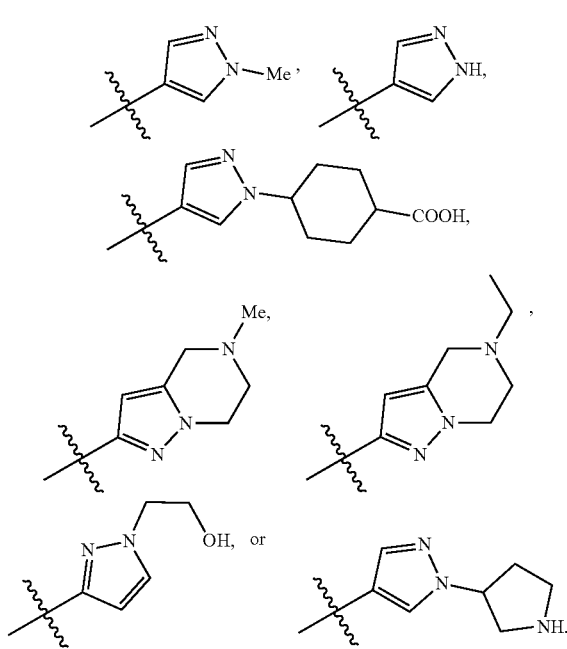

In some embodiments, each R$^6$ is independently selected from hydrogen, halogen, or C$_{1-6}$ aliphatic. In some embodiments, each R$^6$ is independently selected from hydrogen, fluoro, or methyl. In some embodiments, each R$^6$ is hydrogen.

In certain embodiments, each R$^7$ is independently selected from hydrogen or halogen. In some embodiments, each R$^7$ is hydrogen. In some embodiments, when R$^4$ is halogen, one R$^7$ is halogen and other R$^7$ groups are hydrogen.

In some embodiments, provided compounds are of formula I':

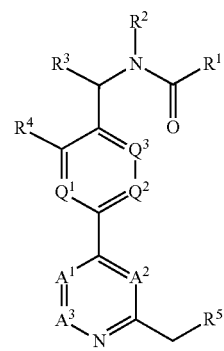

I' or a pharmaceutically acceptable salt thereof, wherein:
one of A$^1$ and A$^2$ is C—R$^6$, and the other of A$^1$ and A$^2$ is selected from C—R$^6$ or N;
A$^3$ is selected from C—H or N, and is C—H when A$^1$ or A$^2$ is N;
Q$^1$ is selected from C—R$^7$ and N;
Q$^2$ is selected from C—R$^7$ and N;
Q$^3$ is selected from C—R$^7$ and N;
wherein at most one of Q$^1$, Q$^2$, and Q$^3$ is N;
R$^1$ is selected from —N(R)$_2$, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, wherein said phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl are optionally substituted with one or more $R^{10}$;

$R^2$ is H or $C_{1-6}$ aliphatic;

or $R^1$ and $R^2$, together with their intervening atoms, form a ring selected from 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, or 7- to 10-membered bicyclic heteroaryl having 1-4 heteroatoms selected from oxygen, nitrogen, wherein said ring is optionally substituted with one or more $R^{20}$;

$R^3$ is selected from H, halogen, —C(O)N(R)$_2$, —C(O)OR, —C(O)R, and $C_{1-6}$ aliphatic, wherein the $C_{1-6}$ aliphatic group is optionally substituted with hydroxyl;

each $R^4$ is independently selected from halogen, —NO$_2$, —CN, —OR, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, or $C_{1-6}$ aliphatic, wherein said $C_{1-6}$ aliphatic is optionally substituted with one or more $R^{40}$;

or $R^3$ and $R^4$ together with their intervening atoms form fused Ring A selected from fused 5- to 7-membered monocyclic carbocycle, fused 5- to 7-membered monocyclic heterocycle having 1-2 heteroatoms selected from oxygen, nitrogen, or sulfur, wherein said fused Ring A is optionally substituted with one or more $R^{40}$;

$R^5$ is selected from H, —C(O)R, —C(O)OR, —S(O)R, —S(O)$_2$R, —C(O)N(R)$_2$, or $C_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, wherein said $C_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, are optionally substituted with one or more $R^{50}$;

each of $R^6$ and $R^7$ is independently selected from H, halogen, —NO$_2$, —CN, —OR, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, or $C_{1-6}$ aliphatic;

each R is independently hydrogen or $C_{1-6}$ aliphatic, phenyl, 3- to 8-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said $C_{1-6}$ aliphatic, phenyl, 3- to 7-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, are optionally substituted with one or more $R^{50}$; or two R groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said ring is optionally substituted with one or more $R^{50}$;

each $R^{10}$ is independently selected from halogen, —OR$^{10a}$, $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, wherein said $C_{1-6}$ aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, are optionally substituted with one or more $R^{15}$;

each $R^{15}$ is independently selected from halogen and —OR$^{15a}$;

$R^{10a}$ is $C_{1-6}$alkyl optionally substituted with halogen;

$R^{15a}$ is $C_{1-6}$alkyl;

each $R^{20}$ is independently selected from halogen, $C_{1-6}$ aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, wherein said $C_{1-6}$ aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, are optionally substituted with one or more $R^{15}$;

each $R^{40}$ is independently selected from halogen, $C_{1-6}$ alkyl, 4- to 6-membered monocyclic heterocyclyl having 1-2 heteroatoms selected from carbon, nitrogen, or sulfur, —C(O)H, —N(R$^{40a}$)$_2$, —N(R$^{40a}$)C(O)(R$^{40b}$), —N(R$^{40a}$)C(O)$_2$(R$^{40a}$), —OR$^{40a}$, —SR$^{40a}$, and —C(O)$_2$R$^{40a}$, wherein said $C_{1-6}$ alkyl group is optionally substituted with halogen or —OR$^{40a}$;

each $R^{40a}$ is independently selected from H and $C_{1-6}$alkyl; or two $R^{40a}$ groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur;

each $R^{40b}$ is independently selected from $C_{2-6}$ alkenyl and 5- or 6-membered heterocyclyl having 1-2 heteroatoms selected from oxygen, nitrogen, or sulfur, wherein said 5- or 6-membered heterocyclyl having 1-2 heteroatoms selected from oxygen, nitrogen, or sulfur, is optionally substituted with one or more $R^{45}$;

$R^{45}$ is $C_{1-6}$ alkyl;

each $R^{50}$ is independently selected from $C_{1-6}$ aliphatic, —OR$^{50a}$, —N(R$^{50a}$)$_2$, —C(O)N(R$^{50a}$)$_2$, —C(O)$_2$R$^{50a}$, oxo, 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclylalkyl having 1-4 heteroatoms selected from oxygen, nitrogen, or sulfur, wherein said $C_{1-6}$ alkyl, 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclyalkyl having 1-4 heteroatoms selected from oxygen, nitrogen, or sulfur, are optionally substituted with one or more $R^{55}$;

$R^{50a}$ is selected from H and $C_{1-6}$ alkyl;

each $R^{55}$ is independently selected from 5- to 6-membered heterocyclyl having 1-2 heteroatoms selected from nitrogen, oxygen, or sulfur, $C_{1-6}$ alkyl, —$OR^{55a}$, —$C(O)N(R^{55a})_2$, halogen, —$N(R^{55a})_2$, —$C(O)_2R^{55a}$, —$S(O)_2R^{55b}$, and —$S(O)_2(NR^{55a})_2$;

$R^{55a}$ is selected from H and $C_{1-6}$alkyl, wherein said $C_{1-6}$ alkyl is optionally substituted with halogen; and $R^{55b}$ is $C_{1-6}$ alkyl.

In some embodiments, provided compounds are of formula I' or a pharmaceutically acceptable salt thereof, wherein:

one of $A^1$ and $A^2$ is C—$R^6$, and the other of $A^1$ and $A^2$ is selected from C—$R^6$ or N;

$A^3$ is selected from C—H or N, and is C—H when $A^1$ or $A^2$ is N;

$Q^1$ is selected from C—$R^7$ and N;
$Q^2$ is selected from C—$R^7$ and N;
$Q^3$ is selected from C—$R^7$ and N;
wherein at most one of $Q^1$, $Q^2$, and $Q^3$ is N;

$R^1$ is selected from —$N(R)_2$, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, wherein said phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl are optionally substituted with one or more $R^{10}$;

$R^2$ is H or $C_{1-6}$ aliphatic;

or $R^1$ and $R^2$, together with their intervening atoms, form a ring selected from 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, or 7- to 10-membered bicyclic heteroaryl having 1-4 heteroatoms selected from oxygen, nitrogen, wherein said ring is optionally substituted with one or more $R^{20}$;

$R^3$ is selected from H, halogen, —$C(O)N(R)_2$, —$C(O)OR$, —$C(O)R$, and $C_{1-6}$ aliphatic, wherein the $C_{1-6}$ aliphatic group is optionally substituted with hydroxyl;

each $R^4$ is independently selected from halogen, —$NO_2$, —$CN$, —$OR$, —$SR$, —$N(R)_2$, —$C(O)R$, —$C(O)OR$, —$S(O)R$, —$S(O)_2R$, —$C(O)N(R)_2$, —$SO_2N(R)_2$, —$OC(O)R$, —$N(R)C(O)R$, —$N(R)C(O)OR$, —$N(R)SO_2R$, —$OC(O)N(R)_2$, or $C_{1-6}$ aliphatic, wherein said $C_{1-6}$ aliphatic is optionally substituted with one or more $R^{40}$;

or $R^3$ and $R^4$ together with their intervening atoms form fused Ring A selected from fused 5- to 7-membered monocyclic carbocycle, fused 5- to 7-membered monocyclic heterocycle having 1-2 heteroatoms selected from oxygen, nitrogen, or sulfur, wherein said fused Ring A is optionally substituted with one or more $R^{40}$;

$R^5$ is selected from H, —$C(O)R$, —$C(O)OR$, —$S(O)R$, —$S(O)_2R$, —$C(O)N(R)_2$, or $C_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, wherein said $C_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, are optionally substituted with one or more $R^{50}$;

each of $R^6$ and $R^7$ is independently selected from H, halogen, —$NO_2$, —$CN$, —$OR$, —$SR$, —$N(R)_2$, —$C(O)R$, —$C(O)OR$, —$S(O)R$, —$S(O)_2R$, —$C(O)N(R)_2$, —$SO_2N(R)_2$, —$OC(O)R$, —$N(R)C(O)R$, —$N(R)C(O)OR$, —$N(R)SO_2R$, —$OC(O)N(R)_2$, or $C_{1-6}$ aliphatic;

each R is independently hydrogen or $C_{1-6}$ aliphatic, phenyl, 3- to 8-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said $C_{1-6}$ aliphatic, phenyl, 3- to 7-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, are optionally substituted with one or more $R^{50}$; or two R groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said ring is optionally substituted with one or more $R^{50}$;

each $R^{10}$ is independently selected from halogen, —$OR^{10a}$, $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, wherein said $C_{1-6}$ aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, are optionally substituted with one or more $R^{15}$;

each $R^{15}$ is independently selected from halogen and —$OR^{15a}$;

$R^{10a}$ is $C_{1-6}$alkyl;

$R^{15a}$ is $C_{1-6}$alkyl;

each $R^{20}$ is independently selected from halogen, $C_{1-6}$ aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, wherein said $C_{1-6}$ aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, are optionally substituted with one or more $R^{15}$;

each $R^{40}$ is independently selected from halogen, 4- to 6-membered monocyclic heterocyclyl, —$N(R^{40a})_2$, —$N(R^{40a})C(O)(R^{40b})$, —$N(R^{40a})C(O)_2(R^{40a})$, —$OR^{40a}$, $SR^{40a}$a, and $C(O)_2R^{40a}$;

each $R^{40a}$ is independently selected from H and $C_{1-6}$alkyl; or two $R^{40a}$ groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur;

each $R^{40b}$ is independently selected from $C_{2-6}$ alkenyl and 5- or 6-membered heterocyclyl having 1-2 heteroatoms selected from oxygen, nitrogen, or sulfur, wherein said 5- or 6-membered heterocyclyl having 1-2 heteroatoms selected from oxygen, nitrogen, or sulfur, is optionally substituted with one or more $R^{45}$;

$R^{45}$ is $C_{1-6}$ alkyl;

each $R^{50}$ is independently selected from $C_{1-6}$ alkyl, —$OR^{50a}$, —$N(R^{50a})_2$, —$C(O)N(R^{50a})_2$; —$C(O)_2R^{50a}$; 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclyalkyl having 1-4 heteroatoms selected from oxygen, nitrogen, or sulfur, wherein said $C_{1-6}$ alkyl, 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclyalkyl having 1-4 heteroatoms selected from oxygen, nitrogen, or sulfur, are optionally substituted with one or more $R^{55}$;

$R^{50a}$ is selected from H and $C_{1-6}$alkyl;

each $R^{55}$ is independently selected from 5- to 6-membered heterocyclyl having 1-2 heteroatoms selected from nitrogen, oxygen, or sulfur, $C_{1-6}$ alkyl, —$OR^{55a}$, —$N(R^{55a})_2$, —$C(O)_2R^{55a}$, —$S(O)_2R^{55b}$, and —$S(O)_2(NR^{55a})_2$;

$R^{55a}$ is selected from H and $C_{1-6}$alkyl; and $R^{55b}$ is $C_{1-6}$ alkyl.

In some embodiments, provided compounds are of formula II-a, II-b, or II-c:

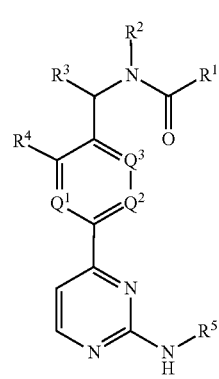

II-a

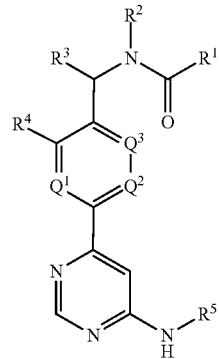

II-b

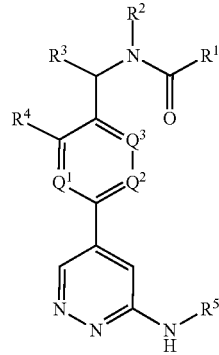

II-c or a pharmaceutically acceptable salt thereof, wherein each of $R^1$, $R^2$, $R^3$, $R^4$, $R^5$, $Q^1$, $Q^2$, and $Q^3$ is as defined above and described in classes and subclasses herein, both singly and in combination.

In some embodiments, $Q^1$, $Q^2$, and $Q^3$ are each C—$R^7$ and $R^7$ is hydrogen. In some embodiments, provided compounds are of formula III:

III

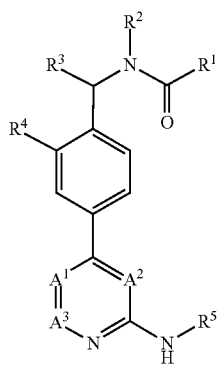

or a pharmaceutically acceptable salt thereof, wherein each of $R^1$, $R^2$, $R^3$, $R^4$, $R^5$, $A^1$, $A^2$, and $A^3$ is as defined above and described in classes and subclasses herein, both singly and in combination.

In certain embodiments, one of $Q^1$, $Q^2$, and $Q^3$ is N, the other two are C—$R^7$, and $R^7$ is hydrogen. In some embodiments, provided compounds are of formula IV-a, IV-b, or IV-c:

IV-a

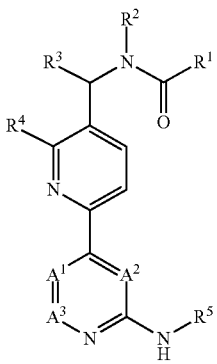

IV-b

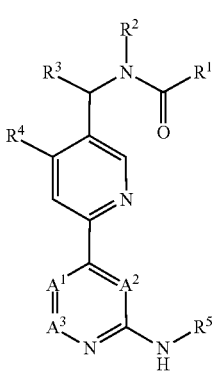

IV-c

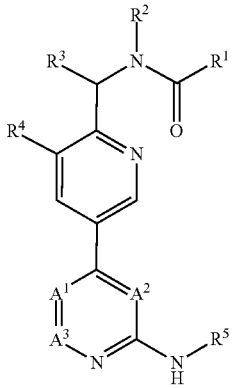

or a pharmaceutically acceptable salt thereof, wherein each of $R^1$, $R^2$, $R^3$, $R^4$, $R^5$, $A^1$, $A^2$, and $A^3$ is as defined above and described in classes and subclasses herein, both singly and in combination.

In some embodiments, provided compounds are of formula V-a or V-b:

V-a

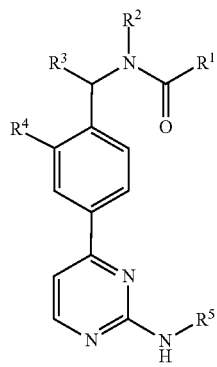

V-b or a pharmaceutically acceptable salt thereof, wherein each of $R^1$, $R^2$, $R^3$, $R^4$, and $R^5$ is as defined above and described in classes and subclasses herein, both singly and in combination.

In certain embodiments, provided compounds are of formula VI-a, VI-b, VI-c, or VI-d:

VI-a
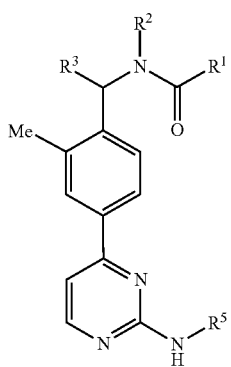
VI-b
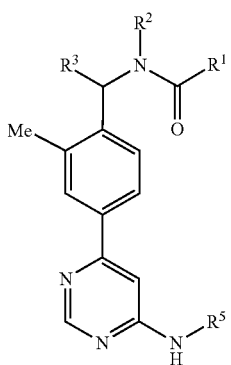
VI-c
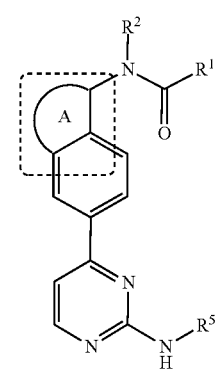
VI-d
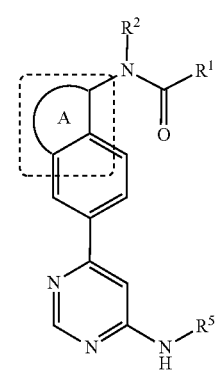
or a pharmaceutically acceptable salt thereof, wherein each of fused Ring A, $R^1$, $R^2$, $R^3$, and $R^5$ is as defined above and described in classes and subclasses herein, both singly and in combination.
In certain embodiments, provided compounds are of formula VII-a, VII-b, VII-c, or VII-d:
VII-a
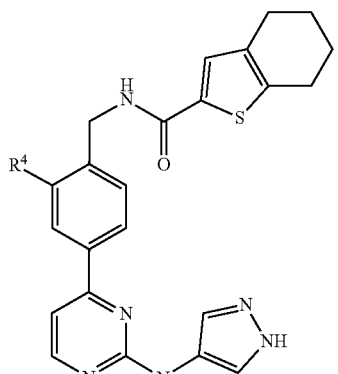
VII-b
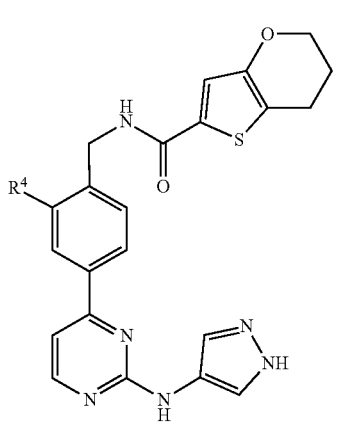
VII-c
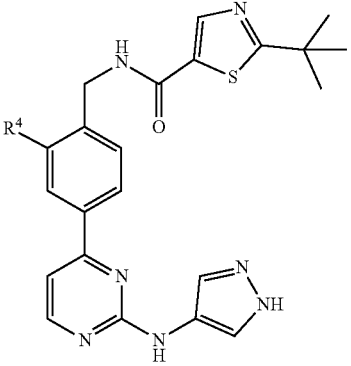
VII-d
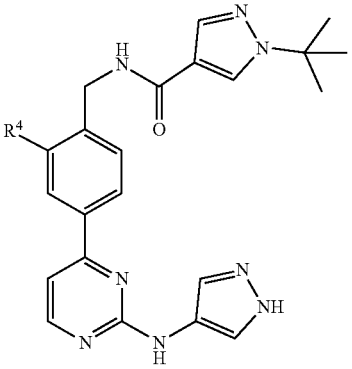

or a pharmaceutically acceptable salt thereof, wherein:
R⁴ is methyl or CF₃; and the

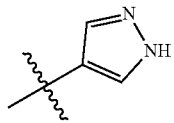

moiety is optionally substituted with one or more groups selected from $C_{1-6}$ aliphatic, pyrrolidinyl, piperidinyl, or cyclohexyl, any of which may be optionally substituted with hydroxyl, $C_{1-6}$ aliphatic, or carboxyl.

In certain embodiments, provided compounds are of formula VIII-a, VIII-b, or VIII-c:

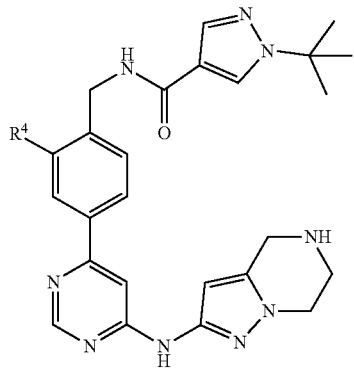

VIII-a

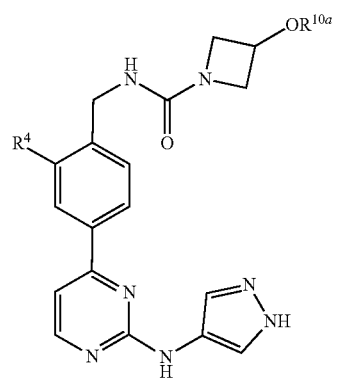

VIII-b

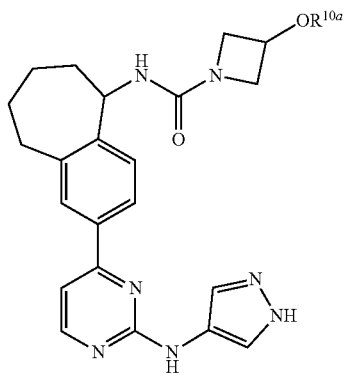

VIII-c or a pharmaceutically acceptable salt thereof, wherein: $R^{10a}$ is $C_{1-6}$ alkyl, R⁴ is methyl or CF₃, and the

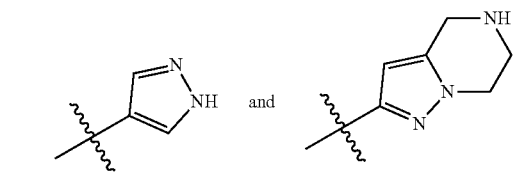 [SMILES: *c1cn[nH]c1 ; "and" ; *c1cc2n(n1)CCNC2]

moieties are optionally substituted with one or more $C_{1-6}$ aliphatic groups.

In certain embodiments, provided compounds are of formula IX:

IX or a pharmaceutically acceptable salt thereof, wherein:
$R^{10a}$ is $C_{1-6}$ alkyl and the

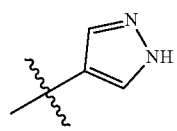 [SMILES: *c1cn[nH]c1]

moiety is optionally substituted with one or more $C_{1-6}$ aliphatic groups.

In some embodiments, a provided compound is a compound selected from the following, or a pharmaceutically acceptable salt thereof: 2-(tert-butyl)-N-(2-methyl-4-(2-((1-methyl-1H-pyrazol-4-yl)amino)pyrimidin-4-yl)benzyl)thiazole-5-carboxamide (I-1), N-(2-methyl-4-(2-((1-methyl-1H-pyrazol-4-yl)amino)pyrimidin-4-yl)benzyl)-4,5,6,7-tetrahydrothieno[3,2-c]pyridine-2-carboxamide (I-2), N-(2-methyl-4-(2-((1-methyl-1H-pyrazol-4-yl)amino)pyrimidin-4-yl)benzyl)-6,7-dihydro-4H-thieno[3,2-c]pyran-2-carboxamide (I-3), N-(2-methyl-4-(2-((1-methyl-1H-pyrazol-4-yl)amino)pyrimidin-4-yl)benzyl)-2-(trifluoromethyl)thiazole-5-carboxamide (I-4), N-(2-methyl-4-(2-((1-methyl-1H-pyrazol-4-yl)amino)pyrimidin-4-yl)benzyl)-4,5,6,7-tetrahydrobenzo[b]thiophene-2-carboxamide (I-5), 5-(tert-butyl)-N-(2-methyl-4-(2-((1-methyl-1H-pyrazol-4-yl)amino)pyrimidin-4-yl)benzyl) picolinamide (I-6), 4-(tert-butyl)-N-(2-methyl-4-(2-((1-methyl-1H-pyrazol-4-yl)amino)pyrimidin-4-yl)benzyl) benzamide (I-7), 3,4-dichloro-N-(2-methyl-4-(2-((1-methyl-1H-pyrazol-4-yl)amino)pyrimidin-4-yl)benzyl)benzamide (I-8), N-(2-methyl-4-(2-((1-methyl-1H-pyrazol-4-yl)amino) pyrimidin-4-yl)benzyl)-4,5,6,7-tetrahydrobenzo[d]thiazole-2-carboxamide (I-9), N-(2-methyl-4-(2-((1-methyl-1H- pyrazol-4-yl)amino)pyrimidin-4-yl)benzyl)-5,6-dihydro-4H-cyclopenta[d]thiazole-2-carboxamide (I-10), trans-N-(2-methyl-4-(2-((1-methyl-1H-pyrazol-4-yl)amino)pyrimidin-4-yl)benzyl)-4-(trifluoromethyl)cyclohexanecarboxamide (I-11), 2-(tert-butyl)-5-(2-methyl-4-(2-((1-methyl-1H-pyrazol-4-yl)amino)pyrimidin-4-yl)benzyl)-4H-pyrrolo[3,4-d]thiazol-6(5H)-one (I-12), 2-cyclopropyl-5-(2-methyl-4-(2-((1-methyl-1H-pyrazol-4-yl)amino)pyrimidin-4-yl)benzyl)-4H-thieno[2,3-c]pyrrol-6(5H)-one (I-13), 4-methyl-N-(2-methyl-4-(2-((1-methyl-1H-pyrazol-4-yl)amino)pyrimidin-4-yl)benzyl)-4,5,6,7-tetrahydrothieno[3,2-c]pyridine-2-carboxamide (I-14), N-(2-methyl-4-(2-((1-methyl-1H-pyrazol-4-yl)amino)pyrimidin-4-yl)benzyl)-6,7-dihydro-5H-thieno[3,2-b]pyran-2-carboxamide (I-15), 1-methyl-N-(2-methyl-4-(2-((1-methyl-1H-pyrazol-4-yl)amino)pyrimidin-4-yl)benzyl)piperidine-4-carboxamide (I-16), cis-N-(2-methyl-4-(2-((1-methyl-1H-pyrazol-4-yl)amino)pyrimidin-4-yl)benzyl)-4-(trifluoromethyl)cyclohexanecarboxamide (I-17), 5-methyl-N-(2-methyl-4-(2-((1-methyl-1H-pyrazol-4-yl)amino)pyrimidin-4-yl)benzyl)isoxazole-4-carboxamide (I-18), N-(2-methyl-4-(2-((1-methyl-1H-pyrazol-4-yl)amino)pyrimidin-4-yl)benzyl)-4-(trifluoromethyl)piperidine-1-carboxamide (I-19), 4-(tert-butyl)-N-(2-methyl-4-(2-((1-methyl-1H-pyrazol-4-yl)amino)pyrimidin-4-yl)benzyl)piperidine-1-carboxamide (I-20), 3-isopropoxy-N-(2-methyl-4-(2-((1-methyl-1H-pyrazol-4-yl)amino)pyrimidin-4-yl)benzyl)azetidine-1-carboxamide (I-21), 1-(bicyclo[2.2.2]octan-1-yl)-3-(2-methyl-4-(2-((1-methyl-1H-pyrazol-4-yl)amino)pyrimidin-4-yl)benzyl)urea (I-22), 4-(tert-butyl)-N-(2-methyl-4-(2-((1-methyl-1H-pyrazol-4-yl)amino)pyrimidin-4-yl)benzyl)piperazine-1-carboxamide (I-23), 2-isopropyl-N-(2-methyl-4-(2-((1-methyl-1H-pyrazol-4-yl)amino)pyrimidin-4-yl)benzyl)morpholine-4-carboxamide (I-24), 2-(tert-butyl)-N-(2-methyl-4-(2-((1-methylpiperidin-4-yl)amino)pyrimidin-4-yl)benzyl)thiazole-5-carboxamide (I-25), 2-(tert-butyl)-N-(2-methyl-4-(2-((tetrahydro-2H-pyran-4-yl)amino)pyrimidin-4-yl)benzyl)thiazole-5-carboxamide (I-26), (R)-2-(tert-butyl)-N-(4-(2-((1-cyclohexylethyl)amino)pyrimidin-4-yl)-2-methylbenzyl)thiazole-5-carboxamide (I-27), (S)-2-(tert-butyl)-N-(4-(2-((1-cyclohexylethyl)amino)pyrimidin-4-yl)-2-methylbenzyl)thiazole-5-carboxamide (I-28), 2-(tert-butyl)-N-(2-methyl-4-(2-((1-(pyridin-4-yl)ethyl)amino)pyrimidin-4-yl)benzyl)thiazole-5-carboxamide (I-29), 2-(tert-butyl)-N-(4-(2-((1,1-dioxidotetrahydro-2H-thiopyran-4-yl)amino)pyrimidin-4-yl)-2-methylbenzyl)thiazole-5-carboxamide (I-30), 2-(tert-butyl)-N-(4-(2-(((1,1-dioxidotetrahydro-2H-thiopyran-4-yl)methyl)amino)pyrimidin-4-yl)-2-methylbenzyl)thiazole-5-carboxamide (I-31), 2-(tert-butyl)-N-(2-methyl-4-(2-((pyridin-4-ylmethyl)amino)pyrimidin-4-yl)benzyl)thiazole-5-carboxamide (I-32), 2-(tert-butyl)-N-(2-methyl-4-(2-(methylamino)pyrimidin-4-yl)benzyl)thiazole-5-carboxamide (I-33), 2-(tert-butyl)-N-(4-(2-(ethylamino)pyrimidin-4-yl)-2-methylbenzyl)thiazole-5-carboxamide (I-34), 2-(tert-butyl)-N-(4-(2-(isopropylamino)pyrimidin-4-yl)-2-methylbenzyl)thiazole-5-carboxamide (I-35), N-(4-(2-((1H-pyrazol-4-yl)amino)pyrimidin-4-yl)-2-methylbenzyl)-2-(tert-butyl)thiazole-5-carboxamide (I-36), 2-(tert-butyl)-N-(4-(2-((1-(2-hydroxyethyl)-1H-pyrazol-4-yl)amino)pyrimidin-4-yl)-2-methylbenzyl)thiazole-5-carboxamide (I-37), 2-(tert-butyl)-N-(2-methyl-4-(2-((1-(tetrahydro-2H-pyran-4-yl)-1H-pyrazol-4-yl)amino)pyrimidin-4-yl)benzyl)thiazole-5-carboxamide (I-38), 2-(tert-butyl)-N-(4-(2-((1-(2-methoxyethyl)-1H-pyrazol-4-yl)amino)pyrimidin-4-yl)-2-methylbenzyl)thiazole-5-carboxamide (I-39), 2-(tert-butyl)-N-(4-(2-((1-ethyl-1H-pyrazol-4-yl)amino)pyrimidin-4-yl)-2-methylbenzyl)thiazole-5-carboxamide (I-40), 2-(tert-butyl)-N-(4-(2-((1-isopropyl-1H-pyrazol-4-yl)amino)pyrimidin-4-yl)-2-methylbenzyl)thiazole-5-carboxamide (I-41), N-(4-(2-((1-(azetidin-3-yl)-1H-pyrazol-4-yl)amino)pyrimidin-4-yl)-2-methylbenzyl)-2-(tert-butyl)thiazole-5-carboxamide (I-42), 2-(tert-butyl)-N-(2-methyl-4-(2-((1-(1-methylazetidin-3-yl)-1H-pyrazol-4-yl)amino)pyrimidin-4-yl)benzyl)thiazole-5-carboxamide (I-43), 3-(4-((4-(2-(tert-butyl)thiazole-5-carboxamido)methyl)-3-methylphenyl)pyrimidin-2-yl)amino)-1H-pyrazol-1-yl)cyclobutanecarboxylic acid (I-44), 2-(tert-butyl)-N-(2-methyl-4-(2-((1-(piperidin-4-yl)-1H-pyrazol-4-yl)amino)pyrimidin-4-yl)benzyl)thiazole-5-carboxamide (I-45), 2-(tert-butyl)-N-(2-methyl-4-(2-((1-(1-methylpiperidin-4-yl)-1H-pyrazol-4-yl)amino)pyrimidin-4-yl)benzyl)thiazole-5-carboxamide (I-46), 2-(tert-butyl)-N-(2-methyl-4-(2-((1-(1-(methylsulfonyl)piperidin-4-yl)-1H-pyrazol-4-yl)amino)pyrimidin-4-yl)benzyl)thiazole-5-carboxamide (I-47), cis-4-(4-((4-(4-((2-(tert-butyl)thiazole-5-carboxamido)methyl)-3-methylphenyl)pyrimidin-2-yl)amino)-1H-pyrazol-1-yl)cyclohexanecarboxylic acid (I-48), trans-4-(4-((4-(4-((2-(tert-butyl)thiazole-5-carboxamido)methyl)-3-methylphenyl)pyrimidin-2-yl)amino)-1H-pyrazol-1-yl)cyclohexanecarboxylic acid (I-49), N-(4-(2-((1-(2-aminoethyl)-1H-pyrazol-4-yl)amino)pyrimidin-4-yl)-2-methylbenzyl)-2-(tert-butyl)thiazole-5-carboxamide (I-50), 2-(tert-butyl)-N-(4-(2-((1,3-dimethyl-1H-pyrazol-4-yl)amino)pyrimidin-4-yl)-2-methylbenzyl)thiazole-5-carboxamide (I-51), 2-(tert-butyl)-N-(4-(2-((1,5-dimethyl-1H-pyrazol-4-yl)amino)pyrimidin-4-yl)-2-methylbenzyl)thiazole-5-carboxamide (I-52), 2-(tert-butyl)-N-(2-methyl-4-(2-((1,3,5-trimethyl-1H-pyrazol-4-yl)amino)pyrimidin-4-yl)benzyl)thiazole-5-carboxamide (I-53), 2-(tert-butyl)-N-(2-methyl-4-(2-((4,5,6,7-tetrahydropyrazolo[1,5-a]pyrazin-2-yl)amino)pyrimidin-4-yl)benzyl)thiazole-5-carboxamide (I-54), 2-(tert-butyl)-N-(2-methyl-4-(2-((5-methyl-4,5,6,7-tetrahydropyrazolo[1,5-a]pyrazin-2-yl)amino)pyrimidin-4-yl)benzyl)thiazole-5-carboxamide (I-55), 2-(tert-butyl)-N-(4-(2-((5-ethyl-4,5,6,7-tetrahydropyrazolo[1,5-a]pyrazin-2-yl)amino)pyrimidin-4-yl)-2-methylbenzyl)thiazole-5-carboxamide (I-56), 2-(tert-butyl)-N-(2-methyl-4-(2-((3-methylisoxazol-4-yl)amino)pyrimidin-4-yl)benzyl)thiazole-5-carboxamide (I-57), 2-(tert-butyl)-N-(2-methyl-4-(2-((1-methyl-1H-1,2,3-triazol-4-yl)amino)pyrimidin-4-yl)benzyl)thiazole-5-carboxamide (I-58), 2-(tert-butyl)-N-(2-methyl-4-(2-((5-methyl-1,3,4-thiadiazol-2-yl)amino)pyrimidin-4-yl)benzyl)thiazole-5-carboxamide (I-59), 2-(tert-butyl)-N-(2-methyl-4-(2-(pyridin-2-ylamino)pyrimidin-4-yl)benzyl)thiazole-5-carboxamide (I-60), 2-(tert-butyl)-N-(4-(2-((5-(dimethylamino)pyridin-2-yl)amino)pyrimidin-4-yl)-2-methylbenzyl)thiazole-5-carboxamide (I-61), 2-(tert-butyl)-N-(2-methyl-4-(2-((5-(4-methylpiperazin-1-yl)pyridin-2-yl)amino)pyrimidin-4-yl)benzyl)thiazole-5-carboxamide (I-62), 2-(tert-butyl)-N-(2-methyl-4-(6-((5-methyl-4,5,6,7-tetrahydropyrazolo[1,5-a]pyrazin-2-yl)amino)pyrimidin-4-yl)benzyl)thiazole-5-carboxamide (I-63), 2-(tert-butyl)-N-(2-methyl-4-(6-((1-methyl-1H-pyrazol-4-yl)amino)pyrimidin-4-yl)benzyl)thiazole-5-carboxamide (I-64), 2-(tert-butyl)-N-(2-methyl-4-(6-((1-methyl-1H-imidazol-4-yl)amino)pyrimidin-4-yl)benzyl)thiazole-5-carboxamide (I-65), 2-(tert-butyl)-N-(2-methyl-4-(6-((1-methyl-1H-pyrazol-3-yl)amino)pyrimidin-4-yl)benzyl)thiazole-5-carboxamide (I-66), 2-(tert-butyl)-N-(2-methyl-4-(6-((2-methyl-2H-1,2,3-triazol-4-yl)amino)pyrimidin-4-yl)benzyl)thiazole-5-carboxamide (I-67), 2-(tert-butyl)-N-(2-methyl-4-(6-((2-methyl-2H-tetrazol-5-yl)amino)pyrimidin-4-yl)

benzyl)thiazole-5-carboxamide (I-68), 2-(tert-butyl)-N-(2-methyl-4-(6-((5-(4-methylpiperazin-1-yl)pyridin-2-yl)amino)pyrimidin-4-yl)benzyl)thiazole-5-carboxamide (I-69), 2-(tert-butyl)-N-(2-methyl-4-(2-((5-(4-methylpiperazin-1-yl)pyridin-2-yl)amino)pyridin-4-yl)benzyl)thiazole-5-carboxamide (I-70), 2-(tert-butyl)-N-(2-methyl-4-(2-(1-methylpiperidine-4-carboxamido)pyridin-4-yl)benzyl)thiazole-5-carboxamide (I-71), N-(4-(2-aminopyrimidin-4-yl)-2-methylbenzyl)-5,6,7,8-tetrahydro-4H-pyrazolo[1,5-a][1,4]diazepine-2-carboxamide (I-72), N-(4-(2-aminopyrimidin-4-yl)-2-methylbenzyl)-5,6,7,8-tetrahydro-4H-thiazolo[4,5-d]azepine-2-carboxamide (I-73), N-(4-(2-aminopyrimidin-4-yl)-2-methylbenzyl)-5,6,7,8-tetrahydroimidazo[1,2-a]pyrazine-2-carboxamide (I-74), N-(4-(2-aminopyrimidin-4-yl)-2-methylbenzyl)-4,5,6,7-tetrahydrothiazolo[5,4-c]pyridine-2-carboxamide (I-75), N-(4-(2-aminopyrimidin-4-yl)-2-methylbenzyl)-4,5,6,7-tetrahydro pyrazolo[1,5-a]pyrazine-2-carboxamide (I-76), N-(4-(2-aminopyrimidin-4-yl)-2-methylbenzyl)-1,2,3,4-tetrahydroisoquinoline-6-carboxamide (I-77), N-(4-(2-aminopyrimidin-4-yl)-2-methylbenzyl)-5,6,7,8-tetrahydro-1,6-naphthyridine-2-carboxamide (I-78), (7R,9aR)—N-(4-(2-aminopyrimidin-4-yl)-2-methylbenzyl)octahydro-1H-pyrido[1,2-a]pyrazine-7-carboxamide (I-79), N-(4-(2-aminopyrimidin-4-yl)-2-methylbenzyl)-1-methyl-1H-pyrazole-4-carboxamide (I-80), N-(4-(2-aminopyrimidin-4-yl)-2-methylbenzyl)octahydrocyclopenta[c]pyrrole-5-carboxamide (I-81), N-(4-(2-aminopyrimidin-4-yl)-2-methylbenzyl)-4,5,6,7-tetrahydrothieno[2,3-c]pyridine-2-carboxamide (I-82), N-(4-(2-aminopyrimidin-4-yl)-2-methylbenzyl)-2-(trifluoromethyl)thiazole-5-carboxamide (I-83), N-(4-(2-aminopyrimidin-4-yl)-2-methylbenzyl)thiazole-5-carboxamide (I-84), N-(4-(2-aminopyrimidin-4-yl)-2-methylbenzyl)-2-cyclopropylthiazole-5-carboxamide (I-85), N-(4-(2-aminopyrimidin-4-yl)-2-methylbenzyl)-2-isopropylthiazole-5-carboxamide (I-86), N-(4-(2-aminopyrimidin-4-yl)-2-methylbenzyl)-2-(1-methoxyethyl)thiazole-5-carboxamide (I-87), N-(4-(2-aminopyrimidin-4-yl)-2-methylbenzyl)-2-(tetrahydrofuran-2-yl)thiazole-5-carboxamide (I-88), 2-(tert-butyl)-N-(2-(2-((1-methyl-1H-pyrazol-4-yl)amino)pyrimidin-4-yl)-6,7,8,9-tetrahydro-5H-benzo[7]annulen-5-yl)thiazole-5-carboxamide (I-89), 2-(tert-butyl)-N-(5-(2-((1-methyl-1H-pyrazol-4-yl)amino)pyrimidin-4-yl)-2,3-dihydro-1H-inden-1-yl)thiazole-5-carboxamide (I-90), 2-(tert-butyl)-N-(6-(2-((1-methyl-1H-pyrazol-4-yl)amino)pyrimidin-4-yl)-1,2,3,4-tetrahydronaphthalen-1-yl)thiazole-5-carboxamide (I-91), 2-(tert-butyl)-N-(6-(6-((1-methyl-1H-pyrazol-4-yl)amino)pyrimidin-4-yl)-1,2,3,4-tetrahydronaphthalen-1-yl)thiazole-5-carboxamide (I-92), N-(6-(6-((1H-pyrazol-4-yl)amino)pyrimidin-4-yl)-1,2,3,4-tetrahydronaphthalen-1-yl)-2-(tert-butyl)thiazole-5-carboxamide (I-93), N-(6-(6-((1-methyl-1H-pyrazol-4-yl)amino)pyrimidin-4-yl)-1,2,3,4-tetrahydronaphthalen-1-yl)-6,7-dihydro-4H-thieno[3,2-c]pyran-2-carboxamide (I-94), N-(6-(2-((1-methyl-1H-pyrazol-4-yl)amino)pyrimidin-4-yl)-1,2,3,4-tetrahydronaphthalen-1-yl)-6,7-dihydro-4H-thieno[3,2-c]pyran-2-carboxamide (I-95), 2-(tert-butyl)-N-(6-(2-((5-(4-methylpiperazin-1-yl)pyridin-2-yl)amino)pyrimidin-4-yl)-1,2,3,4-tetrahydronaphthalen-1-yl)thiazole-5-carboxamide (I-96), 2-(tert-butyl)-N-(7-(2-((1-methyl-1H-pyrazol-4-yl)amino)pyrimidin-4-yl)chroman-4-yl)thiazole-5-carboxamide (I-97), 2-(tert-butyl)-N-(7-(2-((1-methyl-1H-pyrazol-4-yl)amino)pyrimidin-4-yl)isochroman-4-yl)thiazole-5-carboxamide (I-98), 2-(tert-butyl)-N-(7-(2-((1-methyl-1H-pyrazol-4-yl)amino)pyrimidin-4-yl)-1,2,3,4-tetrahydroquinolin-4-yl)thiazole-5-carboxamide (I-99), 2-(tert-butyl)-N-((3-methyl-5-(2-((1-methyl-1H-pyrazol-4-yl)amino)pyrimidin-4-yl)pyridin-2-yl)methyl)thiazole-5-carboxamide (I-100), N-((3-methyl-5-(2-((1-methyl-1H-pyrazol-4-yl)amino)pyrimidin-4-yl)pyridin-2-yl)methyl)-6,7-dihydro-4H-thieno[3,2-c]pyran-2-carboxamide (I-101), 2-(tert-butyl)-N-((6-methyl-2'-((1-methyl-1H-pyrazol-4-yl)amino)-[2,4'-bipyridin]-5-yl)methyl)thiazole-5-carboxamide (I-102), 2-(tert-butyl)-N-((2-methyl-6-(2-((1-methyl-1H-pyrazol-4-yl)amino)pyrimidin-4-yl)pyridin-3-yl)methyl)thiazole-5-carboxamide (I-103), N-((2-methyl-6-(2-((1-methyl-1H-pyrazol-4-yl)amino)pyrimidin-4-yl)pyridin-3-yl)methyl)-6,7-dihydro-4H-thieno[3,2-c]pyran-2-carboxamide (I-104), N-(1-(2-methyl-4-(2-((1-methyl-1H-pyrazol-4-yl)amino)pyrimidin-4-yl)phenyl)ethyl)-6,7-dihydro-4H-thieno[3,2-c]pyran-2-carboxamide (I-105), 2-(tert-butyl)-N-(1-(2-methyl-4-(2-((1-methyl-1H-pyrazol-4-yl)amino)pyrimidin-4-yl)phenyl)ethyl)thiazole-5-carboxamide (I-106), N-(1-(4-(2-aminopyrimidin-4-yl)-2-methylphenyl)ethyl)-2-(trifluoromethyl)thiazole-5-carboxamide (I-107), 2-(tert-butyl)-N-(2-hydroxy-1-(2-methyl-4-(2-((1-methyl-1H-pyrazol-4-yl)amino)pyrimidin-4-yl)phenyl)ethyl)thiazole-5-carboxamide (I-108), N-(2-hydroxy-1-(2-methyl-4-(2-((1-methyl-1H-pyrazol-4-yl)amino)pyrimidin-4-yl)phenyl)ethyl)-6,7-dihydro-4H-thieno[3,2-c]pyran-2-carboxamide (I-109), N-(4-(2-amino-5-fluoropyrimidin-4-yl)-2-methylbenzyl)-2-(tert-butyl)thiazole-5-carboxamide (I-110), 2-(tert-butyl)-N-(4-(5-fluoro-2-((1-methyl-1H-pyrazol-4-yl)amino)pyrimidin-4-yl)-2-methylbenzyl)thiazole-5-carboxamide (I-111), 2-(tert-butyl)-N-(2-methyl-4-(5-methyl-2-((1-methyl-1H-pyrazol-4-yl)amino)pyrimidin-4-yl)benzyl)thiazole-5-carboxamide (I-112), N-((5-(2-aminopyrimidin-4-yl)-3-fluoropyridin-2-yl)methyl)-4,5,6,7-tetrahydrobenzo[b]thiophene-2-carboxamide (I-113), 2-(tert-butyl)-N-(2-methyl-4-(6-((1-methyl-1H-pyrazol-4-yl)amino)pyridazin-4-yl)benzyl)thiazole-5-carboxamide (I-114), N-(4-(2-((1-methyl-1H-pyrazol-4-yl)amino)pyrimidin-4-yl)-2-(trifluoromethyl)benzyl)-6,7-dihydro-4H-thieno[3,2-c]pyran-2-carboxamide (I-115), 2-(tert-butyl)-N-(4-(2-((1-methyl-1H-pyrazol-4-yl)amino)pyrimidin-4-yl)-2-(trifluoromethyl)benzyl)thiazole-5-carboxamide. (I-116), N-(2-fluoro-4-(2-((1-methyl-1H-pyrazol-4-yl)amino)pyrimidin-4-yl)benzyl)-6,7-dihydro-4H-thieno[3,2-c]pyran-2-carboxamide (I-117), 2-(tert-butyl)-N-(2-chloro-5-fluoro-4-(2-((1-methyl-1H-pyrazol-4-yl)amino)pyrimidin-4-yl)benzyl)thiazole-5-carboxamide (I-118), N-(2-methyl-4-(2-((5-(4-methylpiperazin-1-yl)pyridin-2-yl)amino)pyrimidin-4-yl)benzyl)-4,5,6,7-tetrahydrothieno[3,2-c]pyridine-2-carboxamide (I-119), N-(4-(2-((1-(2-hydroxyethyl)-1H-pyrazol-4-yl)amino)pyrimidin-4-yl)-2-methylbenzyl)-6,7-dihydro-4H-thieno[3,2-c]pyran-2-carboxamide (I-120), 3-isopropoxy-N-(2-methyl-4-(6-((5-methyl-4,5,6,7-tetrahydropyrazolo[1,5-a]pyrazin-2-yl)amino)pyrimidin-4-yl)benzyl)azetidine-1-carboxamide (I-121), (R)-2-(tert-butyl)-N-(2-methyl-4-(2-((1-(pyrrolidin-3-yl)-1H-pyrazol-4-yl)amino)pyrimidin-4-yl)benzyl)thiazole-5-carboxamide (I-122), (R)-2-(tert-butyl)-N-(2-methyl-4-(2-((1-(1-methylpyrrolidin-3-yl)-1H-pyrazol-4-yl)amino)pyrimidin-4-yl)benzyl)thiazole-5-carboxamide (I-123), (S)-2-(tert-butyl)-N-(2-methyl-4-(2-((1-(pyrrolidin-3-yl)-1H-pyrazol-4-yl)amino)pyrimidin-4-yl)benzyl)thiazole-5-carboxamide (I-124), (S)-2-(tert-butyl)-N-(2-methyl-4-(2-((1-(1-methylpyrrolidin-3-yl)-1H-pyrazol-4-yl)amino)pyrimidin-4-yl)benzyl)thiazole-5-carboxamide (I-125), (S)-2-(tert-butyl)-N-(2-methyl-4-(2-((1-(morpholin-2-ylmethyl)-1H-pyrazol-4-yl)amino)pyrimidin-4-yl)benzyl)thiazole-5-carboxamide (I-126), (R)—N-(4-(2-((1-(3-amino-2-hydroxypropyl)-1H-pyrazol-4-yl)amino)pyrimidin-4-yl)-2-methylbenzyl)-2-

(tert-butyl)thiazole-5-carboxamide (I-127), (R)-2-(tert-butyl)-N-(2-methyl-4-(2-((1-(morpholin-2-ylmethyl)-1H-pyrazol-4-yl)amino)pyrimidin-4-yl)benzyl)thiazole-5-carboxamide (I-128), (S)—N-(4-(2-((1-(3-amino-2-hydroxypropyl)-1H-pyrazol-4-yl)amino)pyrimidin-4-yl)-2-methylbenzyl)-2-(tert-butyl)thiazole-5-carboxamide (I-129), (S)-2-amino-3-(4-((4-(4-((2-(tert-butyl)thiazole-5-carboxamido)methyl)-3-methylphenyl)pyrimidin-2-yl)amino)-1H-pyrazol-1-yl)propanoic acid (I-130), (S)—N-(4-(2-((1-(2-amino-3-hydroxypropyl)-1H-pyrazol-4-yl)amino)pyrimidin-4-yl)-2-methylbenzyl)-2-(tert-butyl)thiazole-5-carboxamide (I-131), (R)-2-amino-3-(4-((4-(4-((2-(tert-butyl)thiazole-5-carboxamido)methyl)-3-methylphenyl)pyrimidin-2-yl)amino)-1H-pyrazol-1-yl)propanoic acid (I-132), (R)—N-(4-(2-((1-(2-amino-3-hydroxypropyl)-1H-pyrazol-4-yl)amino)pyrimidin-4-yl)-2-methylbenzyl)-2-(tert-butyl)thiazole-5-carboxamide (I-133), 2-(tert-butyl)-N-(6-(6-((5-methyl-4,5,6,7-tetrahydropyrazolo[1,5-a]pyrazin-2-yl)amino)pyrimidin-4-yl)-1,2,3,4-tetrahydronaphthalen-1-yl)thiazole-5-carboxamide (I-134), N-(4-(2-aminopyrimidin-4-yl)-2-methylbenzyl)-2-(tert-butyl)thiazole-5-carboxamide (I-135), N-(6-(2-aminopyrimidin-4-yl)-1,2,3,4-tetrahydronaphthalen-1-yl)-2-(tert-butyl)thiazole-5-carboxamide (I-136), N-(6-(2-aminopyrimidin-4-yl)-1,2,3,4-tetrahydronaphthalen-1-yl)-4,5,6,7-tetrahydrobenzo[b]thiophene-2-carboxamide (I-137), N-(4-(2-aminopyrimidin-4-yl)-2-methylbenzyl)-6,7-dihydro-4H-thieno[3,2-c]thiopyran-2-carboxamide 5,5-dioxide (I-138), N-(4-(2-aminopyrimidin-4-yl)-2-methylbenzyl)-6,7-dihydro-4H-thieno[3,2-c]pyran-2-carboxamide (I-139), N-(4-(2-aminopyrimidin-4-yl)-2-methylbenzyl)-4,5,6,7-tetrahydrothieno[3,2-c]pyridine-2-carboxamide (I-140), N-(4-(2-aminopyrimidin-4-yl)-2-methylbenzyl)-5-methyl-4,5,6,7-tetrahydrothieno[3,2-c]pyridine-2-carboxamide (I-141), N-(4-(2-aminopyrimidin-4-yl)-2-methylbenzyl)-4,5,6,7-tetrahydrobenzo[b]thiophene-2-carboxamide (I-142), N-(4-(6-acetamidopyrimidin-4-yl)-2-methylbenzyl)-4,5,6,7-tetrahydrobenzo[b]thiophene-2-carboxamide (I-143), tert-butyl 5-(2-aminopyrimidin-4-yl)-2-((4,5,6,7-tetrahydrobenzo[b]thiophene-2-carboxamido)methyl)benzyl(methyl)carbamate (I-144), N-(4-(2-aminopyrimidin-4-yl)-2-((methylamino)methyl)benzyl)-4,5,6,7-tetrahydrobenzo[b]thiophene-2-carboxamide (I-145), N-(4-(2-aminopyrimidin-4-yl)-2-((N-methylacrylamido)methyl)benzyl)-4,5,6,7-tetrahydrobenzo[b]thiophene-2-carboxamide (I-146), 2-(tert-butyl)-N-(2-methyl-4-(6-((5-methyl-5,6,7,8-tetrahydro-4H-pyrazolo[1,5-a][1,4]diazepin-2-yl)amino)pyrimidin-4-yl)benzyl)thiazole-5-carboxamide (I-147), 2-(tert-butyl)-N-(2-methyl-4-(6-((5,6,7,8-tetrahydro-4H-pyrazolo[1,5-a][1,4]diazepin-2-yl)amino)pyrimidin-4-yl)benzyl)thiazole-5-carboxamide (I-148), tert-butyl 2-((6-(4-((2-(tert-butyl)thiazole-5-carboxamido)methyl)-3-methylphenyl)pyrimidin-4-yl)amino)-7,8-dihydro-4H-pyrazolo[1,5-a][1,4]diazepine-5(6H)-carboxylate (I-149), 1-(tert-butyl)-N-(2-methyl-4-(6-((5-methyl-4,5,6,7-tetrahydropyrazolo[1,5-a]pyrazin-2-yl)amino)pyrimidin-4-yl)benzyl)-1H-pyrazole-4-carboxamide (I-150), 2-(tert-butyl)-N-(4-(6-((1-(2-hydroxyethyl)-1H-pyrazol-3-yl)amino)pyrimidin-4-yl)-2-methylbenzyl)thiazole-5-carboxamide (I-151), 3-(tert-butoxy)-N-(2-methyl-4-(2-((1-methyl-1H-pyrazol-4-yl)amino)pyrimidin-4-yl)benzyl)azetidine-1-carboxamide (I-152), 5-(tert-butyl)-N-(2-methyl-4-(2-((1-methyl-1H-pyrazol-4-yl)amino)pyrimidin-4-yl)benzyl)isoxazole-3-carboxamide (I-153), 1-(tert-butyl)-N-(2-methyl-4-(2-((1-methyl-1H-pyrazol-4-yl)amino)pyrimidin-4-yl)benzyl)-1H-pyrazole-4-carboxamide (I-154), 1-Methyl-N-(2-methyl-4-(2-((1-methyl-1H-pyrazol-4-yl)amino)pyrimidin-4-yl)benzyl)-1H-pyrrole-3-carboxamide (I-155), N-(2-Methyl-4-(2-((1-methyl-1H-pyrazol-4-yl)amino)pyrimidin-4-yl)benzyl)-5,6,7,8-tetrahydroimidazo[1,2-a]pyridine-2-carboxamide (I-156), 1-Methyl-N-(2-methyl-4-(2-((1-methyl-1H-pyrazol-4-yl)amino)pyrimidin-4-yl)benzyl)-1H-pyrazole-4-carboxamide (I-157), 1-Methyl-N-(2-methyl-4-(2-((1-methyl-1H-pyrazol-4-yl)amino)pyrimidin-4-yl)benzyl)-1H-pyrrole-2-carboxamide (I-158), N-(2-Methyl-4-(2-((1-methyl-1H-pyrazol-4-yl)amino)pyrimidin-4-yl)benzyl)-4,5,6,7-tetrahydropyrazolo[1,5-a]pyridine-2-carboxamide (I-159), 3-isopropoxy-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide (I-160), (R)-3-isopropoxy-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide (I-161), (S)-3-isopropoxy-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide (I-162), 3-(tert-butoxy)-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide (I-163), (R)-3-(tert-butoxy)-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide (I-164), (S)-3-(tert-butoxy)-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide (I-165), N-(2-(2-((1-ethyl-1H-pyrazol-4-yl)amino)pyrimidin-4-yl)-6,7,8,9-tetrahydro-5H-benzo[7]annulen-5-yl)-3-isopropoxyazetidine-1-carboxamide (I-166), 3-isopropoxy-N-(2-(2-((1-isopropyl-1H-pyrazol-4-yl)amino)pyrimidin-4-yl)-6,7,8,9-tetrahydro-5H-benzo[7]annulen-5-yl)azetidine-1-carboxamide (I-167), N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropoxyazetidine-1-carboxamide (I-168), (R)—N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropoxyazetidine-1-carboxamide (I-169), (S)—N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropoxyazetidine-1-carboxamide (I-170), 3-isopropoxy-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide (I-171), 3-isopropoxy-N-(2-(2-((1-(tetrahydro-2H-pyran-4-yl)-1H-pyrazol-4-yl)amino)pyrimidin-4-yl)-6,7,8,9-tetrahydro-5H-benzo[7]annulen-5-yl)azetidine-1-carboxamide (I-172), 3-(tert-butoxy)-N-(2-(2-((1-ethyl-1H-pyrazol-4-yl)amino)pyrimidin-4-yl)-6,7,8,9-tetrahydro-5H-benzo[7]annulen-5-yl)azetidine-1-carboxamide (I-173), 3-(tert-butoxy)-N-(2-(2-((1-isopropyl-1H-pyrazol-4-yl)amino)pyrimidin-4-yl)-6,7,8,9-tetrahydro-5H-benzo[7]annulen-5-yl)azetidine-1-carboxamide (I-174), 3-(tert-butoxy)-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide (I-175), (R)-3-(tert-butoxy)-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide (I-176), (S)-3-(tert-butoxy)-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide (I-177), 3-(tert-butoxy)-N-(2-(2-((1-(2-hydroxyethyl)-1H-pyrazol-4-yl)amino)pyrimidin-4-yl)-6,7,8,9-tetrahydro-5H-benzo[7]annulen-5-yl)azetidine-1-carboxamide (I-178), 3-(tert-butoxy)-N-(2-(2-((1-(tetrahydro-2H-pyran-4-yl)-1H-pyrazol-4-yl)amino)pyrimidin-4-yl)-6,7,8,9-tetrahydro-5H-benzo[7]annulen-5-yl)azetidine-1-carboxamide (I-179), 3-(tert-butoxy)-N-(2-(2-((1-(1-methylpiperidin-4-yl)-1H-pyrazol-4-yl)amino)pyrimidin-4-yl)-6,7,8,9-tetrahydro-5H-benzo[7]annulen-5-yl)azetidine-1-carboxamide (I-180), N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropylpyrrolidine-1-carboxamide (I-181), 3-(tert-butoxy)-N-(2-(2-((5,6-dihydro-4H-pyrrolo[1,2-b]pyrazol-3-yl)amino)pyrimidin-4-yl)-6,7,8,9-tetrahydro-5H-benzo[7]annulen-5-yl)azetidine-1-carboxamide (I-182), 3-Isopropyl-N-(2-(2-((1-(2-methoxyethyl)-1H-pyrazol-4-yl)amino)pyrimidin-4-yl)-6,7,8,9-tetrahydro-5H-benzo[7]annulen-5-yl)pyrrolidine-1-carboxamide (I-183), 3-(tert-butyl)-N-(2-(2-((1-methyl-1H-pyrazol-4-yl)amino)pyrimidin-4-yl)-6,7,8,9-tetrahydro-5H-benzo[7]annulen-5-yl)pyrrolidine-1-carboxamide (I-184), 3-(tert-butyl)-N-(2-(2-((1-(2-hydroxyethyl)-1H-pyrazol-4-yl)amino)pyrimidin-4-yl)-6,7,8,9-tetrahydro-5H-benzo[7]annulen-5-yl)pyrrolidine-1-carboxamide (I-185), 3-(tert-butyl)-N-(2-(2-((1-(2-methoxyethyl)-1H-pyrazol-4-yl)amino)pyrimidin-4-yl)-6,7,8,9-tetrahydro-5H-benzo[7]annulen-5-yl)pyrrolidine-1-carboxamide (I-186), 3-isopropoxy-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)azetidine-1-carboxamide (I-187), 3-isopropoxy-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)azetidine-1-carboxamide (I-188), 3-(tert-butoxy)-N-(8-(2-((1-methyl-1H-pyrazol-4-yl)amino)pyrimidin-4-yl)-2,3,4,5-tetrahydrobenzo[b]oxepin-5-yl)azetidine-1-carboxamide (I-189), 3-(tert-butoxy)-N-(2-(2-hydroxyethyl)-4-(2-((1-methyl-1H-pyrazol-4-yl)amino)pyrimidin-4-yl)benzyl)azetidine-1-carboxamide (I-190), 1-(tert-butyl)-N-(2-(2-hydroxyethyl)-4-(2-((1-methyl-1H-pyrazol-4-yl)amino)pyrimidin-4-yl)benzyl)-1H-pyrazole-4-carboxamide (I-191), 1-(tert-butyl)-5-(2-methyl-4-(2-((1-methyl-1H-pyrazol-4-yl)amino)pyrimidin-4-yl)benzyl)-6,7-dihydro-1H-pyrazolo[4,3-c]pyridin-4(5H)-one (I-192), 1-(tert-butyl)-N-(4-(6-((5,6-dihydro-4H-pyrrolo[1,2-b]pyrazol-2-yl)amino)pyrimidin-4-yl)-2-methylbenzyl)-1H-pyrazole-4-carboxamide (I-193), 3-(tert-butyl)-N-(4-(2-((5,6-dihydro-4H-pyrrolo[1,2-b]pyrazol-3-yl)amino)pyrimidin-4-yl)-2-methylbenzyl)pyrrolidine-1-carboxamide (I-194), cis-4-(4-((4-(4-((1-(tert-butyl)-1H-pyrazole-4-carboxamido)methyl)-3-methylphenyl)pyrimidin-2-yl)amino)-1H-pyrazol-1-yl)cyclohexanecarboxylic acid (I-195), 5-(tert-butyl)-N-(2-methyl-4-(2-((1-(1-methylpiperidin-4-yl)-1H-pyrazol-4-yl)amino)pyrimidin-4-yl)benzyl)isoxazole-3-carboxamide (I-196), 1-(tert-butyl)-N-(2-methyl-4-(2-((1-(1-methylpiperidin-4-yl)-1H-pyrazol-4-yl)amino)pyrimidin-4-yl)benzyl)-1H-pyrazole-4-carboxamide (I-197), 3-(tert-butoxy)-N-(4-(2-((1-methyl-1H-pyrazol-4-yl)amino)pyrimidin-4-yl)-2-(trifluoromethyl)benzyl)azetidine-1-carboxamide (I-198), 3-(tert-butoxy)-N-(4-(2-((1-isopropyl-1H-pyrazol-4-yl)amino)pyrimidin-4-yl)-2-(trifluoromethyl)benzyl)azetidine-1-carboxamide (I-199), 3-(tert-butoxy)-N-(4-(2-((1-(1-methylpiperidin-4-yl)-1H-pyrazol-4-yl)amino)pyrimidin-4-yl)-2-(trifluoromethyl)benzyl)azetidine-1-carboxamide (I-200), 1-(tert-butyl)-N-(4-(2-((1-(1-methylazetidin-3-yl)-1H-pyrazol-4-yl)amino)pyrimidin-4-yl)-2-(trifluoromethyl)benzyl)-1H-pyrazole-4-carboxamide (I-201), 1-(tert-butyl)-N-(4-(2-((1-methyl-1H-pyrazol-4-yl)amino)pyrimidin-4-yl)-2-(trifluoromethyl)benzyl)-1H-pyrazole-4-carboxamide (I-202), 3-(tert-butoxy)-N-(4-(2-((1-ethyl-1H-pyrazol-4-yl)amino)pyrimidin-4-yl)-2-(trifluoromethyl)benzyl)azetidine-1-carboxamide (I-203), 3-(tert-butoxy)-N-(4-(2-((1-(2-methoxyethyl)-1H-pyrazol-4-yl)amino)pyrimidin-4-yl)-2-(trifluoromethyl)benzyl)azetidine-1-carboxamide (I-204), 3-(tert-butoxy)-N-(4-(2-((1-(2-hydroxyethyl)-1H-pyrazol-4-yl)amino)pyrimidin-4-yl)-2-(trifluoromethyl)benzyl)azetidine-1-carboxamide (I-205), 3-(tert-butoxy)-N-(4-(2-((1-(1-methylazetidin-3-yl)-1H-pyrazol-4-yl)amino)pyrimidin-4-yl)-2-(trifluoromethyl)benzyl)azetidine-1-carboxamide (I-206), 3-(tert-butyl)-N-(4-(2-((1-((S)-1-methylpyrrolidin-3-yl)-1H-pyrazol-4-yl)amino)pyrimidin-4-yl)-2-(trifluoromethyl)benzyl)pyrrolidine-1-carboxamide (I-207), 3-(tert-butyl)-N-(4-(2-((1-((R)-1-methylpyrrolidin-3-yl)-1H-pyrazol-4-yl)amino)pyrimidin-4-yl)-2-(trifluoromethyl)benzyl)pyrrolidine-1-carboxamide (I-208), 3-(tert-butyl)-N-(4-(2-((1-(2-hydroxyethyl)-1H-pyrazol-4-yl)amino)pyrimidin-4-yl)-2-(trifluoromethyl)benzyl)pyrrolidine-1-carboxamide (I-209), 3-(tert-butyl)-N-(2-cyano-4-(2-((1-methyl-1H-pyrazol-4-yl)amino)pyrimidin-4-yl)benzyl)pyrrolidine-1-carboxamide (I-210), 1-(tert-butyl)-N-(2-cyano-4-(2-((1-methyl-1H-pyrazol-4-yl)amino)pyrimidin-4-yl)benzyl)-1H-pyrazole-4-carboxamide (I-211), 3-isopropoxy-N-(2-methyl-4-(2-((1-(2-methyl-1-(methylamino)-1-oxopropan-2-yl)-1H-pyrazol-4-yl)amino)pyrimidin-4-yl)benzyl)azetidine-1-carboxamide (I-212), 3-isopropoxy-N-(4-(2-((1-(2-methoxyethyl)-1H-pyrazol-4-yl)amino)pyrimidin-4-yl)-2-methylbenzyl)azetidine-1-carboxamide (I-213), 3-(tert-butoxy)-N-(4-(2-((1-(2-hydroxyethyl)-1H-pyrazol-4-yl)amino)pyrimidin-4-yl)-2-methylbenzyl)azetidine-1-carboxamide (I-214), 3-(tert-butoxy)-N-(2-methyl-4-(2-((1-(1-methylazetidin-3-yl)-1H-pyrazol-4-yl)amino)pyrimidin-4-yl)benzyl)azetidine-1-carboxamide (I-215), 3-(tert-butoxy)-N-(4-(2-((1-ethyl-1H-pyrazol-4-yl)amino)pyrimidin-4-yl)-2-methylbenzyl)azetidine-1-carboxamide (I-216), N-(4-(2-((1-(2-hydroxyethyl)-1H-pyrazol-4-yl)amino)pyrimidin-4-yl)-2-methylbenzyl)-3-isopropoxyazetidine-1-carboxamide (I-217), 3-isopropoxy-N-(2-methyl-4-(2-((1-(1-methylazetidin-3-yl)-1H-pyrazol-4-yl)amino)pyrimidin-4-yl)benzyl)azetidine-1-carboxamide (I-218), 3-isopropoxy-N-(2-methyl-4-(2-((1-(1-methylpiperidin-4-yl)-1H-pyrazol-4-yl)amino)pyrimidin-4-yl)benzyl)azetidine-1-carboxamide (I-219), trans-N-(4-(2-((1-((3-fluoropiperidin-4-yl)-1H-pyrazol-4-yl)amino)pyrimidin-4-yl)-2-methylbenzyl)-3-isopropoxyazetidine-1-carboxamide (I-220), 3-isopropoxy-N-(2-methyl-4-(2-((1-(tetrahydro-2H-pyran-4-yl)-1H-pyrazol-4-yl)amino)pyrimidin-4-yl)benzyl)azetidine-1-carboxamide (I-221), N-(4-(2-((1H-pyrazol-4-yl)amino)pyrimidin-4-yl)-2-methylbenzyl)-3-isopropoxyazetidine-1-carboxamide (I-222), 3-(tert-butoxy)-N-(4-(2-((1,5-dimethyl-1H-pyrazol-4-yl)amino)pyrimidin-4-yl)-2-methylbenzyl)azetidine-1-carboxamide (I-223), 3-(tert-butyl)-N-(2-methyl-4-(2-((1-methyl-1H-pyrazol-4-yl)amino)pyrimidin-4-yl)benzyl)pyrrolidine-1-carboxamide (I-224), 1-(tert-butyl)-N-(2-methyl-4-(6-((5-(4-methylpiperazin-1-yl)pyridin-2-yl)amino)pyrimidin-4-yl)benzyl)-1H-pyrazole-4-carboxamide (I-225), 1-(tert-butyl)-N-(2-methyl-4-(6-((5-(4-methylpiperazin-1-yl)pyridin-2-yl)amino)pyrimidin-4-yl)benzyl)-1H-pyrazole-3-carboxamide (I-226), (R)-3-isopropoxy-N-(2-(2-((1-(2-methoxyethyl)-1H-pyrazol-4-yl)amino)-pyrimidin-4-yl)-6,7,8,9-tetrahydro-5H-benzo[7]annulen-5-yl)azetidine-1-carboxamide (I-227), (S)-3-isopropoxy-N-(2-(2-((1-(2-methoxyethyl)-1H-pyrazol-4-yl)amino)-pyrimidin-4-yl)-6,7,8,9-tetrahydro-5H-benzo[7]annulen-5-yl)azetidine-1-carboxamide (I-228), (R)-3-(tert-butoxy)-N-(2-(2-((1-(2-hydroxyethyl)-1H-pyrazol-4-yl)amino)-pyrimidin-4-yl)-6,7,8,9-tetrahydro-5H-benzo[7]annulen-5-yl)azetidine-1-carboxamide (I-229), (S)-3-(tert-butoxy)-N-(2-(2-((1-(2-hydroxyethyl)-1H-pyrazol-4-yl)amino)-pyrimidin-4-yl)-6,7,8,9-tetrahydro-5H-benzo[7]annulen-5-yl)azetidine-1- carboxamide (I-230), 1-(tert-butyl)-N-(2-methyl-4-(6-((4,5,6,7-tetrahydropyrazolo[1,5-a]pyrazin-2-yl)amino)pyrimidin-4-yl)benzyl)-1H-pyrazole-4-carboxamide (I-231), 1-(tert-butyl)-N-(4-(6-((5-ethyl-4,5,6,7-tetrahydropyrazolo[1,5-a]pyrazin-2-yl)amino)pyrimidin-4-yl)-2-methylbenzyl)-1H-pyrazole-4-carboxamide (I-232), 1-(tert-butyl)-N-(4-(6-((5-(2-hydroxyethyl)-4,5,6,7-tetrahydropyrazolo[1,5-a]pyrazin-2-yl)amino)pyrimidin-4-yl)-2-methylbenzyl)-1H-pyrazole-4-carboxamide (I-233), 1-(tert-butyl)-N-(2-methyl-4-(6-((5,6,7,8-tetrahydro-4H-pyrazolo[1,5-a][1,4]diazepin-2-yl)amino)pyrimidin-4-yl)benzyl)-1H-pyrazole-4-carboxamide (I-234), 1-(tert-butyl)-N-(4-(6-((5-(2-hydroxyethyl)-5,6,7,8-tetrahydro-4H-pyrazolo[1,5-a][1,4]diazepin-2-yl)amino)pyrimidin-4-yl)-2-methylbenzyl)-1H-pyrazole-4-carboxamide (I-235), 1-(tert-butyl)-N-(2-methyl-4-(6-((5-methyl-5,6,7,8-tetrahydro-4H-pyrazolo[1,5-a][1,4]diazepin-2-yl)amino)pyrimidin-4-yl)benzyl)-1H-pyrazole-4-carboxamide (I-236), 1-(tert-butyl)-N-(4-(6-((6,7-dihydro-4H-pyrazolo[5,1-c][1,4]oxazin-2-yl)amino)pyrimidin-4-yl)-2-methylbenzyl)-1H-pyrazole-4-carboxamide (I-237), 3-Ethyl-N-(2-methyl-4-(2-((1-methyl-1H-pyrazol-4-yl)amino)pyrimidin-4-yl)benzyl)azetidine-1-carboxamide (I-238), 3-(tert-butoxy)-N-(2-methyl-4-(6-((5-methyl-6-oxo-4,5,6,7-tetrahydropyrazolo-[1,5-a]pyrazin-2-yl)amino)pyrimidin-4-yl)benzyl)azetidine-1-carboxamide (I-239), 1-(tert-butyl)-N-(2-chloro-4-(6-((5-methyl-4,5,6,7-tetrahydropyrazolo[1,5-a]-pyrazin-2-yl)amino)pyrimidin-4-yl)benzyl)-1H-pyrazole-4-carboxamide (I-240), 1-(tert-butyl)-N-(4-(6-((5-methyl-4,5,6,7-tetrahydropyrazolo[1,5-a]pyrazin-2-yl)amino)pyrimidin-4-yl)-2-(trifluoromethyl)benzyl)-1H-pyrazole-4-carboxamide (I-241), 1-(tert-butyl)-N-(4-(6-((5,5-dioxido-6,7-dihydro-4H-pyrazolo[5,1-c][1,4]thiazin-2-yl)amino)pyrimidin-4-yl)-2-methylbenzyl)-1H-pyrazole-4-carboxamide (I-242), 3-isopropoxy-N-(2-methyl-4-(6-((1-d3-methyl-1H-pyrazol-4-yl)amino)pyrimidin-4-yl)benzyl)azetidine-1-carboxamide (I-243), (S)-3-(tert-butyl)-N-(2-methyl-4-(6-((5-methyl-4,5,6,7-tetrahydropyrazolo[1,5-a]pyrazin-2-yl)amino)pyrimidin-4-yl)benzyl)pyrrolidine-1-carboxamide (I-244), (R)-3-(tert-butyl)-N-(2-methyl-4-(6-((5-methyl-4,5,6,7-tetrahydropyrazolo[1,5-a]pyrazin-2-yl)amino)pyrimidin-4-yl)benzyl)pyrrolidine-1-carboxamide (I-245), 3-(1,1,1,3,3,3-d6)isopropoxy-N-(2-methyl-4-(2-((1-methyl-1H-pyrazol-4-yl)amino)pyrimidin-4-yl)benzyl)azetidine-1-carboxamide (I-246), 1-(tert-butyl)-N-(4-(2-((1-ethyl-1H-pyrazol-4-yl)amino)pyrimidin-4-yl)-2-methylbenzyl)-1H-pyrazole-4-carboxamide (I-247), 3-(tert-butoxy)-N-(7-(2-((1-methyl-1H-pyrazol-4-yl)amino)pyrimidin-4-yl)-2,3,4,5-tetrahydro-1H-benzo[d]azepin-1-yl)azetidine-1-carboxamide (I-248), 4-isobutyl-1-(2-methyl-4-(2-((1-methyl-1H-pyrazol-4-yl)amino)pyrimidin-4-yl)benzyl)piperazin-2-one (I-249), 1-tert-butyl-N-[[4-[2-[[1-(2-hydroxyethyl)pyrazol-4-yl]amino]pyrimidin-4-yl]-2-methyl-phenyl]methyl]pyrazole-4-carboxamide (I-250), 3-tert-butoxy-N-[[2-methyl-4-[6-[[5-(4-methylpiperazin-1-yl)-2-pyridyl]amino]pyrimidin-4-yl]phenyl]methyl]azetidine-1-carboxamide (I-251), 1-tert-butyl-N-[[2-methyl-4-[2-[(1-methylpyrazol-4-yl)amino]pyrimidin-4-yl]phenyl]methyl]pyrazole-3-carboxamide (I-252), (3R)-3-tert-butyl-N-[[2-methyl-4-[2-[(1-methylpyrazol-4-yl)amino]pyrimidin-4-yl]phenyl]methyl]pyrrolidine-1-carboxamide (I-253), (3S)-3-tert-butyl-N-[[2-methyl-4-[2-[(1-methylpyrazol-4-yl)amino]pyrimidin-4-yl]phenyl]methyl]pyrrolidine-1-carboxamide (I-254), (3S)-3-isopropyl-N-[[2-methyl-4-[2-[(1-methylpyrazol-4-yl)amino]pyrimidin-4-yl]phenyl]methyl]pyrrolidine-1-carboxamide (I-255), 3-tert-butoxy-N-[[2-methyl-4-[6-[(5-methyl-6,7-dihydro-4H-pyrazolo[1,5-a]pyrazin-2-yl)amino]pyrimidin-4-yl]phenyl]methyl]azetidine-1-carboxamide (I-256), 1-tert-butyl-N-[2-[2-[(1-methylpyrazol-4-yl)amino]pyrimidin-4-yl]-6,7,8,9-tetrahydro-5H-benzo[7]annulen-5-yl]pyrazole-4-carboxamide (I-257), 1-tert-butyl-N-[[4-[2-[(1-isopropylpyrazol-4-yl)amino]pyrimidin-4-yl]-2-methyl-phenyl]methyl]pyrazole-4-carboxamide (I-258), 3-isopropoxy-N-[[4-[2-[(1-isopropylpyrazol-4-yl)amino]pyrimidin-4-yl]-2-methyl-phenyl]methyl]azetidine-1-carboxamide (I-259), 1-tert-butyl-N-[[4-[2-[(1-cyclopropylpyrazol-4-yl)amino]pyrimidin-4-yl]-2-methyl-phenyl]methyl]pyrazole-4-carboxamide (I-260), N-[[4-[2-[(1-ethylpyrazol-4-yl)amino]pyrimidin-4-yl]-2-methyl-phenyl]methyl]-3-(1,1,1,3,3,3-d6)isopropoxy-azetidine-1-carboxamide (I-262), N-[[2-methyl-4-[2-[(1-methylpyrazol-4-yl)amino]pyrimidin-4-yl]phenyl]methyl]-3-propyl-azetidine-1-carboxamide (I-263), 5-tert-butyl-N-[[2-methyl-4-[2-[(1-methylpyrazol-4-yl)amino]pyrimidin-4-yl]phenyl]methyl]-1,2,4-oxadiazole-3-carboxamide (I-264), 5-tert-butyl-N-[[2-methyl-4-[6-[(5-methyl-6,7-dihydro-4H-pyrazolo[1,5-a]pyrazin-2-yl)amino]pyrimidin-4-yl]phenyl]methyl]isoxazole-3-carboxamide (I-265), 2-tert-butyl-N-[[2-methyl-4-[6-(5,6,7,8-tetrahydro-1,6-naphthyridin-2-ylamino)pyrimidin-4-yl]phenyl]methyl]thiazole-5-carboxamide (I-266), 2-tert-butyl-N-[[2-methyl-4-[6-(5,6,7,8-tetrahydro-2,7-naphthyridin-3-ylamino)pyrimidin-4-yl]phenyl]methyl]thiazole-5-carboxamide (I-267), 2-tert-butyl-N-[[4-[6-[[7-(2-hydroxyethyl)-6,8-dihydro-5H-2,7-naphthyridin-3-yl]amino]pyrimidin-4-yl]-2-methyl-phenyl]methyl]thiazole-5-carboxamide (I-268), 2-tert-butyl-N-[[2-methyl-4-[6-[(7-methyl-6,8-dihydro-5H-2,7-naphthyridin-3-yl)amino]pyrimidin-4-yl]phenyl]methyl]thiazole-5-carboxamide (I-269), 2-tert-butyl-N-[[2-methyl-4-[6-(4,5,6,7-tetrahydropyrazolo[1,5-a]pyrazin-2-ylamino)pyrimidin-4-yl]phenyl]methyl]thiazole-5-carboxamide (I-270), 2-tert-butyl-N-[[4-[6-[[5-(2-hydroxyethyl)-6,7-dihydro-4H-pyrazolo[1,5-a]pyrazin-2-yl]amino]pyrimidin-4-yl]-2-methyl-phenyl]methyl]thiazole-5-carboxamide (I-271), 3-isopropoxy-N-[[2-methyl-4-[6-(4,5,6,7-tetrahydropyrazolo[1,5-a]pyrazin-2-ylamino)pyrimidin-4-yl]phenyl]methyl]azetidine-1-carboxamide (I-272), 3-isopropoxy-N-[[2-methyl-4-[6-(5,6,7,8-tetrahydro-4H-pyrazolo[1,5-a][1,4]diazepin-2-ylamino)pyrimidin-4-yl]phenyl]methyl]azetidine-1-carboxamide (I-273), N-[[4-[6-[[5-(2-hydroxyethyl)-4,6,7,8-tetrahydropyrazolo[1,5-a][1,4]diazepin-2-yl]amino]pyrimidin-4-yl]-2-methyl-phenyl]methyl]-3-isopropoxy-azetidine-1-carboxamide (I-274), 3-tert-butyl-N-[[2-methyl-4-[6-[(5-methyl-6,7-dihydro-4H-pyrazolo[1,5-a]pyrazin-2-yl)amino]pyrimidin-4-yl]phenyl]methyl]pyrrolidine-1-carboxamide (I-275), 2-tert-butyl-N-[[4-[6-(6,7-dihydro-4H-pyrazolo[5,1-c][1,4]oxazin-2-ylamino)pyrimidin-4-yl]-2-methyl-phenyl]methyl]thiazole-5-carboxamide (I-276), N-[[4-[6-(6,7-dihydro-4H-pyrazolo[5,1-c][1,4]oxazin-2-ylamino)pyrimidin-4-yl]-2-methyl-phenyl]methyl]-3-isopropoxy-azetidine-1-carboxamide (I-277), 2-tert-butyl-N-[[2-methyl-4-[6-[(5-methyl-4-oxo-6,7-dihydropyrazolo[1,5-a]pyrazin-2-yl)amino]pyrimidin-4-yl]phenyl]methyl]thiazole-5-carboxamide (I-278), 2-tert-butyl-N-[[4-[6-[(5,6-dimethyl-6,7-dihydro-4H-pyrazolo[1,5-a]pyrazin-2-yl)amino]pyrimidin-4-yl]-2-methyl-phenyl]methyl]thiazole-5-carboxamide (I-279), 1-tert-butyl-N-[[4-[6-[(5,6-dimethyl-6,7-dihydro-4H-pyrazolo[1,5-a]pyrazin-2-yl)amino]pyrimidin-4-yl]-2-methyl-phenyl]methyl]pyrazole-4-carboxamide (I-280), 3-tert-butyl-N-[[2-methyl-4-[6-[(5-methyl-6-oxo-4,7-dihydropyrazolo[1,5-a]pyrazin-2-yl)amino]pyrimidin-4-yl]phenyl]methyl]pyrrolidine-1-carboxamide (I-281), 1-tert-butyl-N-[[4-[6-[(4,5-dimethyl-6,7-dihydro-4H-pyrazolo[1,5-a]pyrazin-2-yl)amino pyrimidin-4-yl]-2-methyl-phenyl]methyl]pyrazole-4-carboxamide (I-282), 2-tert-butyl-N-[[4-[6-[(4,5-dimethyl-6,7-dihydro-4H-pyrazolo[1,5-a]pyrazin-2-yl)amino]pyrimidin-4-yl]-2-methyl-phenyl]methyl]thiazole-5-carboxamide (I-283), 3-tert-butyl-N-[[4-[6-[(4,5-dimethyl-6,7-dihydro-4H-pyrazolo[1,5-a]pyrazin-2-yl)amino]pyrimidin-4-yl]-2-methyl-phenyl]methyl]pyrrolidine-1-carboxamide (I-284), 2-tert-butyl-N-[[4-[6-[[5-(2-hydroxyethyl)-4,6,7,8-tetrahydropyrazolo[1,5-a][1,4]diazepin-2-yl]amino]pyrimidin-4-yl]-2-methyl-phenyl]methyl]thiazole-5-carboxamide (I-285), 2-tert-butyl-N-[[2-methyl-4-[6-[(5-methyl-6-oxo-4,7-dihydropyrazolo[1,5-a]pyrazin-2-yl)amino]pyrimidin-4-yl]phenyl]methyl]thiazole-5-carboxamide (I-286), 3-tert-butoxy-N-[[4-[6-(6,7-dihydro-4H-pyrazolo[5,1-c][1,4]oxazin-2-ylamino)pyrimidin-4-yl]-2-methyl-phenyl]methyl]azetidine-1-carboxamide (I-287), 3-tert-butyl-N-[[4-[6-(6,7-dihydro-4H-pyrazolo[5,1-c][1,4]oxazin-2-ylamino)pyrimidin-4-yl]-2-methyl-phenyl]methyl]pyrrolidine-1-carboxamide (I-288), 2-tert-butyl-5-[[2-methyl-4-[2-[[1-(1-methyl-4-piperidyl)pyrazol-4-yl]amino]pyrimidin-4-yl]phenyl]methyl]-4H-pyrrolo[3,4-d]thiazol-6-one (I-289), 3-isopropoxy-N-[[4-[2-[(1-methylpyrazol-4-yl)amino]pyrimidin-4-yl]-2-(trifluoromethyl)phenyl]methyl]azetidine-1-carboxamide (I-290), 1-tert-butyl-N-[[2-chloro-4-[2-[(1-methylpyrazol-4-yl)amino]pyrimidin-4-yl]phenyl]methyl]pyrazole-4-carboxamide (I-291), 4-[4-[[4-[[(1-tert-butylpyrazole-4-carbonyl)amino]methyl]-3-methyl-phenyl]pyrimidin-2-yl]amino]pyrazol-1-yl]cyclohexanecarboxylic acid (I-292), 3-tert-butyl-N-[[4-[2-[(1-isopropylpyrazol-4-yl)amino]pyrimidin-4-yl]-2-(trifluoromethyl)phenyl]methyl]pyrrolidine-1-carboxamide (I-293), 3-tert-butoxy-N-[[4-[2-[(1-cyclopropylpyrazol-4-yl)amino]pyrimidin-4-yl]-2-(trifluoromethyl)phenyl]methyl]azetidine-1-carboxamide (I-294), 3-tert-butyl-N-[[4-[2-[[1-(2-methoxyethyl)pyrazol-4-yl]amino]pyrimidin-4-yl]-2-(trifluoromethyl)phenyl]methyl]pyrrolidine-1-carboxamide (I-295), 3-tert-butyl-N-[[4-[2-[(1-cyclopropylpyrazol-4-yl)amino]pyrimidin-4-yl]-2-(trifluoromethyl)phenyl]methyl]pyrrolidine-1-carboxamide (I-296), 3-tert-butyl-N-[[4-[2-[(1-ethylpyrazol-4-yl)amino]pyrimidin-4-yl]-2-(trifluoromethyl)phenyl]methyl]pyrrolidine-1-carboxamide (I-297), 3-tert-butyl-N-[[4-[2-[[1-(1-methyl-4-piperidyl)pyrazol-4-yl]amino]pyrimidin-4-yl]-2-(trifluoromethyl)phenyl]methyl]pyrrolidine-1-carboxamide (I-298), 3-isopropoxy-N-[[4-[2-[(1-isopropylpyrazol-4-yl)amino]pyrimidin-4-yl]-2-(trifluoromethyl)phenyl]methyl]azetidine-1-carboxamide (I-299), 3-methoxy-N-[[2-methyl-4-[2-[(1-methylpyrazol-4-yl)amino]pyrimidin-4-yl]phenyl]methyl]azetidine-1-carboxamideacid (I-300), N-[[4-[2-[[1-(2-hydroxyethyl)pyrazol-4-yl]amino]pyrimidin-4-yl]-2-(trifluoromethyl)phenyl]methyl]-3-isopropoxy-azetidine-1-carboxamide (I-301), 3-tert-butoxy-N-[[2-methyl-4-[2-[[1-(1-methyl-4-piperidyl)pyrazol-4-yl]amino]pyrimidin-4-yl]phenyl]methyl]azetidine-1-carboxamide (I-302), 3-tert-butyl-N-[[4-[2-[[1-(2-methoxyethyl)pyrazol-4-yl]amino]pyrimidin-4-yl]-2-methyl-phenyl]methyl]pyrrolidine-1-carboxamide (I-303), 3-tert-butoxy-N-[[4-[2-[[1-(2-methoxyethyl)pyrazol-4-yl]amino]pyrimidin-4-yl]-2-methyl-phenyl]methyl]azetidine-1-carboxamide (I-304), 3-tert-butyl-N-[[4-[2-[(1-ethylpyrazol-4-yl)amino]pyrimidin-4-yl]-2-methyl-phenyl]methyl]pyrrolidine-1-carboxamide (I-305), 3-tert-butoxy-N-[[4-[2-[(1-isopropylpyrazol-4-yl)amino]pyrimidin-4-yl]-2-methyl-phenyl]methyl]azetidine-1-carboxamide (I-306), 3-(2-fluoroethoxy)-N-[[2-methyl-4-[2-[(1-methylpyrazol-4-yl)amino]pyrimidin-4-yl]phenyl]methyl]azetidine-1-carboxamide (I-307), 3-tert-butyl-N-[[4-[2-[(1-cyclopropylpyrazol-4-yl)amino]pyrimidin-4-yl]-2-methyl-phenyl]methyl]pyrrolidine-1-carboxamide (I-308), 1-tert-butyl-5-[[2-methyl-4-[6-[(5-methyl-6,7-dihydro-4H-pyrazolo[1,5-a]pyrazin-2-yl)amino]pyrimidin-4-yl]phenyl]methyl]-6,7-dihydropyrazolo[4,3-c]pyridin-4-one (I-309), 1-[[4-[2-[[1-(2-hydroxyethyl)pyrazol-4-yl]amino]pyrimidin-4-yl]-2-(trifluoromethyl)phenyl]methyl]-4-isobutyl-piperazin-2-one (I-310), 3-tert-butyl-N-[[4-[2-[[1-(1-methylazetidin-3-yl)pyrazol-4-yl]amino]pyrimidin-4-yl]-2-(trifluoromethyl)phenyl]methyl]pyrrolidine-1-carboxamide (I-311), N-[[4-[2-[[1-[1,1-dimethyl-2-oxo-2-(2,2,2-trifluoroethylamino)ethyl]pyrazol-4-yl]amino]pyrimidin-4-yl]-2-methyl-phenyl]methyl]-3-isopropoxy-azetidine-1-carboxamide (I-312), 3-isopropoxy-N-[[4-[2-[[1-[(3S)-tetrahydrofuran-3-yl]pyrazol-4-yl]amino]pyrimidin-4-yl]-2-(trifluoromethyl)phenyl]methyl]azetidine-1-carboxamide (I-313), 3-isopropoxy-N-[[4-[2-[[1-[(3R)-tetrahydrofuran-3-yl]pyrazol-4-yl]amino]pyrimidin-4-yl]-2-(trifluoromethyl)phenyl]methyl]azetidine-1-carboxamide (I-314), 2-tert-butyl-N-[[4-[2-(5,6-dihydro-4H-pyrrolo[1,2-b]pyrazol-3-ylamino)pyrimidin-4-yl]-2-methyl-phenyl]methyl]thiazole-5-carboxamide (I-315), 3-tert-butyl-N-[[4-[2-[[1-[(3S)-pyrrolidin-3-yl]pyrazol-4-yl]amino]pyrimidin-4-yl]-2-(trifluoromethyl)phenyl]methyl]pyrrolidine-1-carboxamide (I-316), 3-isopropyl-N-[[4-[2-[[1-(2-methoxyethyl)pyrazol-4-yl]amino]pyrimidin-4-yl]-2-(trifluoromethyl)phenyl]methyl]pyrrolidine-1-carboxamide (I-317), 3-tert-butyl-N-[[4-[2-[[1-[(3R)-pyrrolidin-3-yl]pyrazol-4-yl]amino]pyrimidin-4-yl]-2-(trifluoromethyl)phenyl]methyl]pyrrolidine-1-carboxamide (I-318), 3-tert-butoxy-N-[[2-(2-methoxyethyl)-4-[2-[(1-methylpyrazol-4-yl)amino]pyrimidin-4-yl]phenyl]methyl]azetidine-1-carboxamide (I-319), 3-tert-butyl-N-[[2-(2-methoxyethyl)-4-[2-[(1-methylpyrazol-4-yl)amino]pyrimidin-4-yl]phenyl]methyl]pyrrolidine-1-carboxamide (I-320), 3-tert-butyl-N-[[4-[2-[(1,5-dimethylpyrazol-4-yl)amino]pyrimidin-4-yl]-2-(2-hydroxyethyl)phenyl]methyl]pyrrolidine-1-carboxamide (I-321), 3-tert-butoxy-N-[[4-[2-(5,6-dihydro-4H-pyrrolo[1,2-b]pyrazol-3-ylamino)pyrimidin-4-yl]-2-methyl-phenyl]methyl]azetidine-1-carboxamide (I-322), 3-tert-butoxy-N-[[4-[2-(5,6-dihydro-4H-pyrrolo[1,2-b]pyrazol-3-ylamino)pyrimidin-4-yl]-2-(2-methoxyethyl)phenyl]methyl]azetidine-1-carboxamide (I-323), 3-tert-butyl-N-[[4-[2-(5,6-dihydro-4H-pyrrolo[1,2-b]pyrazol-3-ylamino)pyrimidin-4-yl]-2-(2-hydroxyethyl)phenyl]methyl]pyrrolidine-1-carboxamide (I-324), (3S)-3-tert-butyl-N-[[4-[2-(5,6-dihydro-4H-pyrrolo[1,2-b]pyrazol-3-ylamino)pyrimidin-4-yl]-2-(2-methoxyethyl)phenyl]methyl]pyrrolidine-1-carboxamide (I-325), 3-isopropoxy-N-[6-[2-[[1-(1-methyl-4-piperidyl)pyrazol-4-yl]amino]pyrimidin-4-yl]tetralin-1-yl]azetidine-1-carboxamide (I-326), 3-tert-butyl-N-[6-[2-[[1-(2-hydroxyethyl)pyrazol-4-yl]amino]pyrimidin-4-yl]tetralin-1-yl]pyrrolidine-1-carboxamide (I-327), 3-tert-butyl-N-[2-[2-[(1-ethylpyrazol-4-yl)amino]pyrimidin-4-yl]-6,7,8,9-tetrahydro-5H-benzo[7]annulen-5-yl]pyrrolidine-1-carboxamide (I-328), N-[2-formyl-8-[2-[(1-methylpyrazol-4-yl)amino]pyrimidin-4-yl]-1,3,4,5-tetrahydro-2-benzazepin-5-yl]-3-isopropoxy-azetidine-1-carboxamide (I-329), 3-tert-butyl-N-[2-[2-[(1-tetrahydropyran-4-ylpyrazol-4-yl)amino]pyrimidin-4-yl]-6,7,8,9-tetrahydro-5H-benzo[7]annulen-5-yl]pyrrolidine-1-carboxamide (I-330), 3-ethoxy-N-[2-[2-[(1-methylpyrazol-4-yl)amino]pyrimidin-4-yl]-6,7,8,9-tetrahydro-5H-benzo[7]annulen-5-yl]azetidine-1-carboxamide (I-331), 3-tert-butoxy-N-[2-[6-(6,7-dihydro-4H-pyrazolo[5,1-c][1,4]oxazin-2-ylamino)pyrimidin-4-yl]-6,7,8,9-tetrahydro-5H-benzo[7]annulen-5- yl]azetidine-1-carboxamide (I-332), 3-isopropoxy-N-[2-[2-[[1-[(3R)-tetrahydrofuran-3-yl]pyrazol-4-yl]amino]pyrimidin-4-yl]-6,7,8,9-tetrahydro-5H-benzo[7]annulen-5-yl]azetidine-1-carboxamide (I-333), 3-tert-butoxy-N-[2-[2-[[1-[(3S)-tetrahydrofuran-3-yl]pyrazol-4-yl]amino]pyrimidin-4-yl]-6,7,8,9-tetrahydro-5H-benzo[7]annulen-5-yl]azetidine-1-carboxamide (I-334), 3-isopropoxy-N-[8-[2-[(1-methylpyrazol-4-yl)amino]pyrimidin-4-yl]-2,3,4,5-tetrahydro-1-benzoxepin-5-yl]azetidine-1-carboxamide (I-335), N-[2-[2-[[1-(2-hydroxy-2-methyl-propyl)pyrazol-4-yl]amino]pyrimidin-4-yl]-6,7,8,9-tetrahydro-5H-benzo[7]annulen-5-yl]-3-isopropoxy-azetidine-1-carboxamide (I-336), 3-tert-butoxy-N-[2-[2-[[1-(2-hydroxy-2-methyl-propyl)pyrazol-4-yl]amino]pyrimidin-4-yl]-6,7,8,9-tetrahydro-5H-benzo[7]annulen-5-yl]azetidine-1-carboxamide (I-337), 3-isopropoxy-N-[2-[2-[[1-[(3S)-tetrahydrofuran-3-yl]pyrazol-4-yl]amino]pyrimidin-4-yl]-6,7,8,9-tetrahydro-5H-benzo[7]annulen-5-yl]azetidine-1-carboxamide (I-338), 3-methoxy-N-[2-[2-[(1-methylpyrazol-4-yl)amino]pyrimidin-4-yl]-6,7,8,9-tetrahydro-5H-benzo[7]annulen-5-yl]azetidine-1-carboxamide (I-339), 3-isopropyl-N-[2-[2-[(1-methylpyrazol-4-yl)amino]pyrimidin-4-yl]-6,7,8,9-tetrahydro-5H-benzo[7]annulen-5-yl]pyrrolidine-1-carboxamide (I-340), N-[2-[2-[(1-ethylpyrazol-4-yl)amino]pyrimidin-4-yl]-6,7,8,9-tetrahydro-5H-benzo[7]annulen-5-yl]-3-isopropyl-pyrrolidine-1-carboxamide (I-341), 3-isopropyl-N-[2-[2-[(1-tetrahydropyran-4-ylpyrazol-4-yl)amino]pyrimidin-4-yl]-6,7,8,9-tetrahydro-5H-benzo[7]annulen-5-yl]pyrrolidine-1-carboxamide (I-342), 3-tert-butoxy-N-[2-[2-[[1-(4-piperidyl)pyrazol-4-yl]amino]pyrimidin-4-yl]-6,7,8,9-tetrahydro-5H-benzo[7]annulen-5-yl]azetidine-1-carboxamide (I-343), 3-isopropyl-N-[2-[2-[[1-[(3R)-tetrahydrofuran-3-yl]pyrazol-4-yl]amino]pyrimidin-4-yl]-6,7,8,9-tetrahydro-5H-benzo[7]annulen-5-yl]pyrrolidine-1-carboxamide (I-344), 3-isopropyl-N-[2-[2-[[1-[(3S)-tetrahydrofuran-3-yl]pyrazol-4-yl]amino]pyrimidin-4-yl]-6,7,8,9-tetrahydro-5H-benzo[7]annulen-5-yl]pyrrolidine-1-carboxamide (I-345), N-[2-(2-hydroxyethyl)-8-[2-[(1-methylpyrazol-4-yl)amino]pyrimidin-4-yl]-1,3,4,5-tetrahydro-2-benzazepin-5-yl]-3-isopropoxy-azetidine-1-carboxamide (I-346), 3-tert-butoxy-N-[2-[2-[(1,5-dimethylpyrazol-4-yl)amino]pyrimidin-4-yl]-6,7,8,9-tetrahydro-5H-benzo[7]annulen-5-yl]azetidine-1-carboxamide (I-347), N-[2-[2-[[1-(3-fluoro-1-methyl-4-piperidyl)pyrazol-4-yl]amino]pyrimidin-4-yl]-6,7,8,9-tetrahydro-5H-benzo[7]annulen-5-yl]-3-isopropoxy-azetidine-1-carboxamide (I-348), 4-isobutyl-1-[[2-methyl-4-[2-[[1-(1-methylazetidin-3-yl)pyrazol-4-yl]amino]pyrimidin-4-yl]phenyl]methyl]piperazin-2-oneacid (I-349), 4-(2,2-dimethylpropyl)-1-[[4-[2-[[1-(2-hydroxyethyl)pyrazol-4-yl]amino]pyrimidin-4-yl]-2-(trifluoromethyl)phenyl]methyl]piperazin-2-oneacid (I-350), 3-isopropoxy-N-[[4-[2-[[1-(2-methoxyethyl)pyrazol-4-yl]amino]pyrimidin-4-yl]-2-(trifluoromethyl)phenyl]methyl]azetidine-1-carboxamide (I-351), 3-isopropoxy-N-[7-[2-[(1-methylpyrazol-4-yl)amino]pyrimidin-4-yl]-2,3,4,5-tetrahydro-1H-3-benzazepin-1-yl]azetidine-1-carboxamide (I-352), N-[[2-chloro-4-[2-[[1-(1-methylazetidin-3-yl)pyrazol-4-yl]amino]pyrimidin-4-yl]phenyl]methyl]-3-isopropoxy-azetidine-1-carboxamide (I-353), 5-tert-butyl-N-[[2-chloro-4-[2-[[1-(1-methylazetidin-3-yl)pyrazol-4-yl]amino]pyrimidin-4-yl]phenyl]methyl]isoxazole-3-carboxamide (I-354), 5-tert-butyl-N-[[4-[2-[[1-(1-methylazetidin-3-yl)pyrazol-4-yl]amino]pyrimidin-4-yl]-2-(trifluoromethyl)phenyl]methyl]isoxazole-3-carboxamide (I-355), 1-tert-butyl-N-[[2-chloro-4-[2-[[1-(1-methylazetidin-3-yl)pyrazol-4-yl]amino]pyrimidin-4-yl]phenyl]methyl]pyrazole-4-carboxamide (I-356), 2-tert-butyl-N-[[2-methyl-4-[6-[[1-[(3R)-tetrahydrofuran-3-yl]pyrazol-3-yl]amino]pyrimidin-4-yl]phenyl]methyl]thiazole-5-carboxamide (I-357), 2-tert-butyl-N-[[2-methyl-4-[6-[[1-(1-methyl-4-piperidyl)pyrazol-3-yl]amino]pyrimidin-4-yl]phenyl]methyl]thiazole-5-carboxamide (I-358), 3-tert-butoxy-N-[6-[2-[(1-methylpyrazol-4-yl)amino]pyrimidin-4-yl]tetralin-1-yl]azetidine-1-carboxamide (I-359), and N-[[4-[2-[(1-ethylpyrazol-4-yl)amino]pyrimidin-4-yl]-2-methyl-phenyl]methyl]-3-isopropoxy-azetidine-1-carboxamideacid (I-360).

General Methods of Providing the Present Compounds

Compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

In certain embodiments, the present compounds are generally prepared according to Scheme A set forth below:

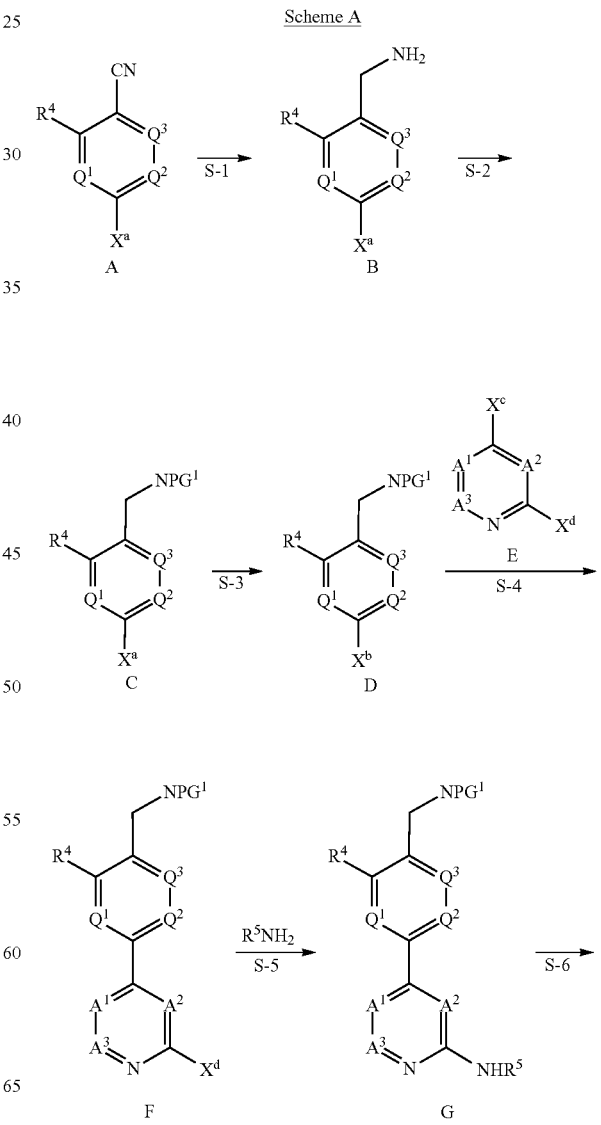

Scheme A

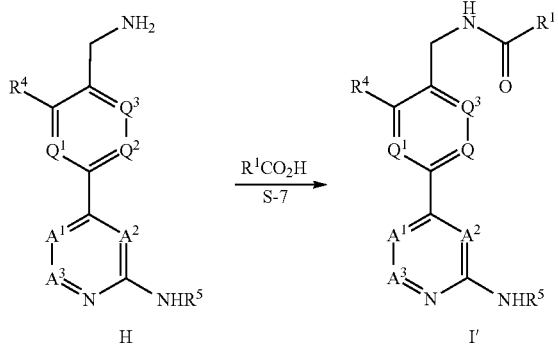

In one aspect, the present invention provides methods for preparing compounds of formula I, according to the steps depicted in Scheme A above wherein each variable is as defined and described herein and each $PG^1$ is a suitable protecting group. For compounds having an $X^a$ or $X^b$ group, $X^a$ and $X^b$ are defined as a moiety suitable for biaryl coupling with an aryl group of formula E, or a group capable of being converted to such a moiety. In some embodiments, $X^a$ and $X^b$ are the same. In some embodiments, $X^a$ is a group that is converted to $X^b$ in order to facilitate coupling with a compound of formula E. In some embodiments, $X^a$ is halogen. In some embodiments, $X^b$ is halogen, a boronic acid, or a boronic ester. In some embodiments, $X^c$ is halogen, a boronic acid, or a boronic ester. It will be appreciated that the reacting partners in a biaryl coupling will be complimentary, and therefore the identity of $X^b$ will depend upon the choice of $X^c$ in formula E. For example, in some embodiments, $X^b$ is a boronic acid or ester, and $X^c$ is halogen. In other embodiments, $X_c$ is a boronic acid or ester, and $X^b$ is halogen.

At step S-1, nitrile A is reduced under suitable conditions to form amine B. Suitable nitrile reduction conditions are well known in the art. In some embodiments, the conditions comprise borane.

At step S-2, amine B is protected using a suitable amino protecting group. Suitable amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable mono-protected amines include those defined herein. In some embodiments, $PG^1$ is a Boc protecting group.

At step S-3, protected amine C is optionally converted to protected amine D, depending upon the choice of biaryl couple chemistry as described above. In some embodiments, $X^a$ is halogen and is converted to a boronic ester in step S-3 in order to couple with a compound of formula E. Suitable conditions for the preparation of aryl boronic esters and acids are known in the art. In some embodiments, step S-3 comprises bis(pinacolato) diboron and catalytic palladium. In some embodiments, such as when formula E comprises a boronic ester, $X^a$ is halogen and step S-3 is omitted.

At step S-4, protected amine D is coupled with a compound of formula E to produce biaryl formula F. In some embodiments, step S-4 comprises a Suzuki coupling and $X^b$ and $X^a$ are selected accordingly. In some embodiments, $X^d$ is the same as $X^a$. It will be appreciated that $X^d$ will be selected as a moiety capable of undergoing amination in step S-5. In some embodiments, $X^d$ is halogen. Methods of carrying out Suzuki couplings are well known in the art and include those described by March (supra). Suitable conditions for the Suzuki reaction employ a palladium catalyst. In some embodiments, a palladium catalyst is $PdCl_2dppf$. Step S-4 typically employs a base. In some embodiments, the base is $K_2CO_3$.

At step S-5, formula F undergoes amination to form a compound of formula G. Suitable amination conditions are known in the art and include those described by March (supra). In certain embodiments, step S-5 comprises a palladium catalyst. In some embodiments, the palladium catalyst is $Pd_2(dba)_3$. In some embodiments, step S-5 comprises a base. In some embodiments, the base is t-BuONa.

At step S-6, the amine group of formula G is deprotected to provide amine H. Suitable conditions for the removal of an amino protecting group are known in the art and include those described by Greene (supra).

At step S-7, amine H is coupled with a carboxylic acid to provide a compound of formula I'. Suitable peptide coupling conditions are known in the art. In some embodiments, step S-7 comprises a peptide coupling reagent selected from a carbodiimide or triazole activating reagent, in the presence of a base such as DIEA or other bases familiar to one skilled in the art.

In certain embodiments, each of the aforementioned synthetic steps may be performed sequentially with isolation of each intermediate performed after each step. Alternatively, each of steps S-1, S-2, S-3, S-4, S-5, S-6, and S-7 as depicted in Scheme A above, may be performed in a manner whereby no isolation of one or more intermediates B, C, D, F, G, or H is performed.

In certain embodiments, all the steps of the aforementioned synthesis may be performed to prepare the desired final product. In other embodiments, two, three, four, five, or more sequential steps may be performed to prepare an intermediate or the desired final product.

In other embodiments, the present compounds are generally prepared according to Scheme B set forth below.

Scheme B

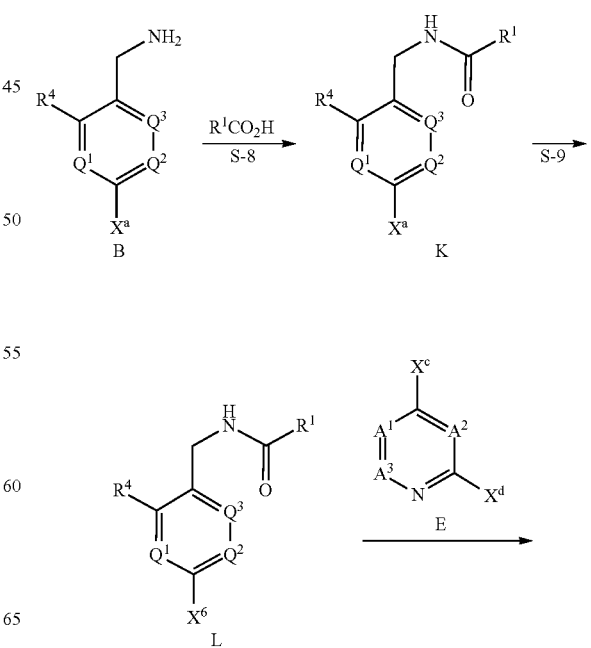

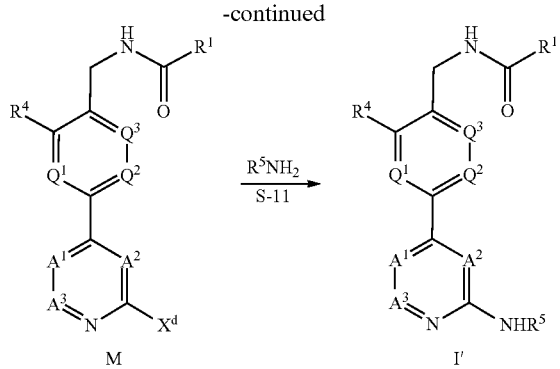

In one aspect, the present invention provides methods for preparing compounds of formula I, according to the steps depicted in Scheme B above wherein each variable is as defined and described herein.

At step S-8, amine B is coupled with a carboxylic acid to provide a compound of formula K. Suitable peptide coupling conditions are known in the art. In some embodiments, step S-8 comprises a peptide coupling reagent selected from a carbodiimide or triazole activating reagent, in the presence of a base such as DIPEA or other bases familiar to one skilled in the art.

At step S-9, formula K is optionally converted to formula L, depending upon the choice of biaryl couple chemistry to be performed in step S-10, as described above for Scheme A and step S-3.

At step S-10, formula L is coupled with amine E to provide formula M in a manner similar to that of step S-4 described above in Scheme A.

At step S-11, formula M undergoes amination to form a compound of formula I'. Suitable amination chemistries are known in the art and include those described in step S-5, above.

In certain embodiments, each of the aforementioned synthetic steps may be performed sequentially with isolation of each intermediate performed after each step. Alternatively, each of steps S-8, S-9, S-10, and S-11 as depicted in Scheme B above, may be performed in a manner whereby no isolation of one or more intermediates K, L, or M is performed.

In certain embodiments, all the steps of the aforementioned synthesis may be performed to prepare the desired final product. In other embodiments, two, three, or four sequential steps may be performed to prepare an intermediate or the desired final product.

Compounds of formula I may also be prepared according to Schemes 1-11 in the ensuing examples.

Methods of Use

In certain embodiments, compounds of the present invention are for use in medicine. In some embodiments, compounds of the present invention are useful as kinase inhibitors. In certain embodiments, compounds of the present invention are selective inhibitors of Btk. In some embodiments, the present invention provides methods of decreasing Btk enzymatic activity. Such methods include contacting a Btk with an effective amount of a Btk inhibitor. Therefore, the present invention further provides methods of inhibiting Btk enzymatic activity by contacting a Btk with a Btk inhibitor of the present invention.

In some embodiments, the present invention provides methods of decreasing Btk enzymatic activity. In some embodiments, such methods include contacting a Btk with an effective amount of a Btk inhibitor. Therefore, the present invention further provides methods of inhibiting Btk enzymatic activity by contacting a Btk with a Btk inhibitor of the present invention.

Btk enzymatic activity, as used herein, refers to Btk kinase enzymatic activity. For example, where Btk enzymatic activity is decreased, PIP3 binding and/or phosphorylation of PLCγ is decreased. In some embodiments, the half maximal inhibitory concentration ($IC_{50}$) of the Btk inhibitor against Btk is less than 1 uM. In some embodiments, the $IC_{50}$ of the Btk inhibitor against Btk is less than 500 nM. In some embodiments, the $IC_{50}$ of the Btk inhibitor against Btk is less than 100 nM. In some embodiments, the $IC_{50}$ of the Btk inhibitor against Btk is less than 10 nM. In some embodiments, the $IC_{50}$ of the Btk inhibitor against Btk is less than 1 nM. In some embodiments, the $IC_{50}$ of the Btk inhibitor against Btk is from 0.1 nM to 10 uM. In some embodiments, the $IC_{50}$ of the Btk inhibitor against Btk is from 0.1 nM to 1 uM. In some embodiments, the $IC_{50}$ of the Btk inhibitor against Btk is from 0.1 nM to 100 nM. In some embodiments, the $IC_{50}$ of the Btk inhibitor against Btk is from 0.1 nM to 10 nM.

In some embodiments, Btk inhibitors are useful for the treatment of diseases and disorders that may be alleviated by inhibiting (i.e., decreasing) Btk enzymatic activity. By "diseases" is meant diseases or disease symptoms. Thus, the present invention provides methods of treating autoimmune disorders, inflammatory disorders, and cancers in a subject in need thereof. Such methods include administering to the subject a therapeutically effective amount of a Btk inhibitor.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Coeliac disease, dermatomyositis, diabetes mellitus type 1, Goodpasture's syndrome, Graves' disease, Guillain-Barré syndrome (GBS), Hashimoto's disease, idiopathic thrombocytopenic purpura, lupus erythematosus, mixed connective tissue disease, multiple sclerosis, myasthenia gravis, pemphigus vulgaris, pernicious anaemia, polymyositis, primary biliary cirrhosis, Sjögren's syndrome, temporal arteritis, and Wegener's granulomatosis. The term "inflammatory disorders" includes diseases or disorders involving acute or chronic inflammation such as allergies, asthma, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection, and vasculitis. In some embodiments, the present invention provides a method of treating rheumatoid arthritis or lupus.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In some embodiments, the present invention provides a method of treating leukemia or lymphoma.

The term "subject," as used herein, refers to a mammal to whom a pharmaceutical composition is administered. Exemplary subjects include humans, as well as veterinary and laboratory animals such as horses, pigs, cattle, dogs, cats, rabbits, rats, mice, and aquatic mammals.

Assays

To develop useful Tec kinase family inhibitors, candidate inhibitors capable of decreasing Tec kinase family enzymatic activity may be identified in vitro. The activity of the inhibitor compounds can be assayed utilizing methods known in the art and/or those methods presented herein.

Compounds that decrease Tec kinase family members' enzymatic activity may be identified and tested using a biologically active Tec kinase family member, either recombinant or naturally occurring. Tec kinases can be found in native cells, isolated in vitro, or co-expressed or expressed in a cell. Measuring the reduction in the Tec kinase family member enzymatic activity in the presence of an inhibitor relative to the activity in the absence of the inhibitor may be performed using a variety of methods known in the art, such as the POLYGAT-LS assays described below in the Examples. Other methods for assaying the activity of Btk and other Tec kinases are known in the art. The selection of appropriate assay methods is well within the capabilities of those of skill in the art.

Once compounds are identified that are capable of reducing Tec kinase family members' enzymatic activity, the compounds may be further tested for their ability to selectively inhibit a Tec kinase family member relative to other enzymes. Inhibition by a compound of the invention is measured using standard in vitro or in vivo assays such as those well known in the art or as otherwise described herein.

Compounds may be further tested in cell models or animal models for their ability to cause a detectable changes in phenotype related to a Tec kinase family member activity. In addition to cell cultures, animal models may be used to test Tec kinase family member inhibitors for their ability to treat autoimmune disorders, inflammatory disorders, or cancer in an animal model.

Pharmaceutical Compositions

In another aspect, the present invention provides pharmaceutical compositions comprising a compound of formula I or a compound of formula I in combination with a pharmaceutically acceptable excipient (e.g., carrier).

The pharmaceutical compositions include optical isomers, diastereomers, or pharmaceutically acceptable salts of the inhibitors disclosed herein. The compound of formula I included in the pharmaceutical composition may be covalently attached to a carrier moiety, as described above. Alternatively, the compound of formula I included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethylcellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be coadministered to the subject. Coadministration is meant to include simultaneous or sequential administration of the compounds individually or in combination (more than one compound). The preparations can also be combined, when desired, with other active substances (e.g. to reduce metabolic degradation).

Formulations

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to Btk inhibition); presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of decreasing kinase enzymatic activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring kinase inhibition and adjusting the dosage upwards or downwards, as described above.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

EXAMPLES

The examples below are meant to illustrate certain embodiments of the invention, and not to limit the scope of the invention.

It will be appreciated that where an Example refers to another Example by referring to "Example I-XX", the reference is to the synthesis of the respective Compound I-XX, or the relevant portion of the synthesis.

Example 1: 2-(tert-butyl)-N-(2-methyl-4-(2-((1-methyl-1H-pyrazol-4-yl)amino)pyrimidin-4-yl)benzyl)thiazole-5-carboxamide (I-1)

Scheme 1

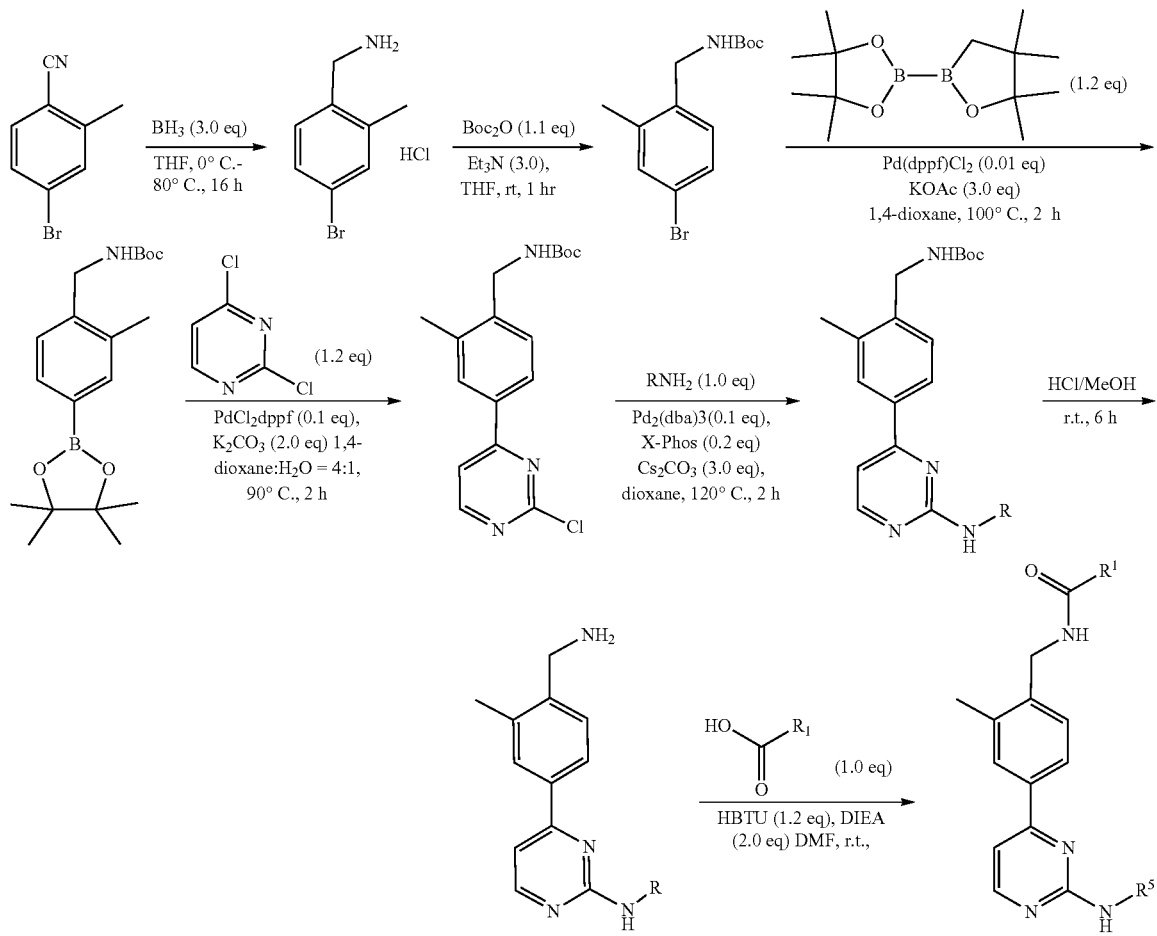

Preparation of (4-bromo-2-methylphenyl)methanamine

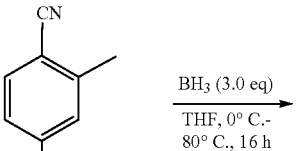

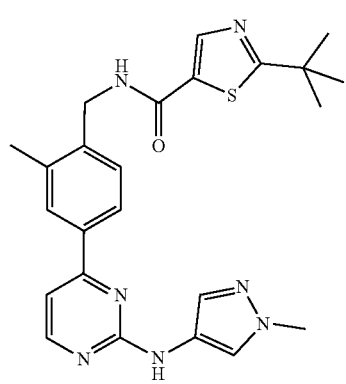

To a solution of 4-bromo-2-methylbenzonitrile (3 g, 15 mmol) in THF (20 mL), BH$_3$.THF (45 mL, 45 mmol) was added. The solution was stirred at 0° C. for 1 h and heated to 80° C. for 16 h. Then the mixture was quenched with MeOH. After concentrated, the residue was stirred with saturated HCl/EtOAc solution and filtered. The filter cake was rinsed with ether (20 mL×3) and dried under vacuum to afford (4-bromo-2-methylphenyl)methanamine (3.2 g, yield: 90%) as white solid. ESI-MS (M+H)+: 200.1

Preparation of tert-butyl 4-bromo-2-methylbenzylcarbamate

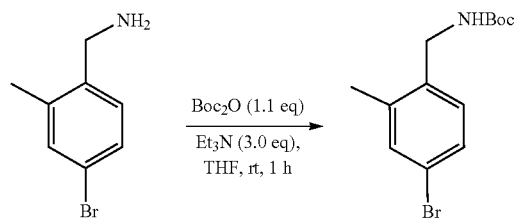

To a solution of (4-bromo-2-methylphenyl)methanamine (1.2 g, 6 mmol) in DCM (30 mL) were added TEA (1.82 g, 18 mmol) and Boc$_2$O (1.43 g, 6.6 mmol). The mixture was stirred at rt for 1 h. After diluted with water (50 mL), the mixture was extracted with DCM (50 mL×2). The combined organics were washed with brine (50 mL), dried (Na$_2$SO$_4$), filtered and concentrated to give crude title product (1.7 g, yield 95%) as a white solid, which was used directly in the next step without further purification. ESI-MS (M+H)+: 300.1.

Preparation of tert-butyl 2-methyl-4-(4,4,5,5-tetramethyl-1,3,2-dioxaborolan-2-yl)benzylcarbamate

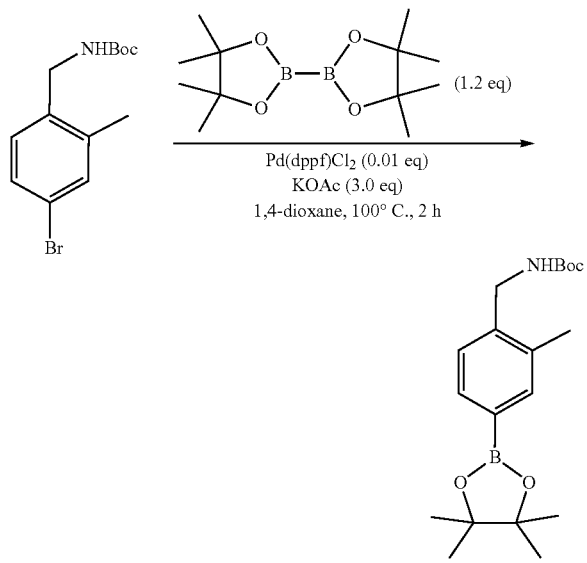

To a solution of tert-butyl 4-bromo-2-methylbenzylcarbamate (1.5 g, 5.0 mmol) in 1,4-dioxane (15 mL) were added 4,4,4',4',5,5,5',5'-octamethyl-2,2'-bi(1,3,2-dioxaborolane) (1.52 g, 6.0 mmol), KOAc (1.75 g, 18 mmol) and Pd(dppf)Cl$_2$DCM (407 mg, 0.5 mmol) under nitrogen. The mixture was stirred at 100° C. for 2 h. After cooling down to rt, the mixture was diluted with water (50 mL) and extracted with ethyl acetate (100 mL×3). The combined organic layer was washed with brine, dried, concentrated and purified by silica gel column (petroleum ether/EtOAc=10:1) to give tert-butyl 2-methyl-4-(4,4,5,5-tetramethyl-1,3,2-dioxaborolan-2-yl)benzylcarbamate (1.2 g, yield 69%) as white solid. ESI-MS (M+H)+: 348.2. $^1$H NMR (400 MHz, CDCl$_3$) δ: 7.61-7.59 (m, 2H), 7.26 (s, 1H), 4.68 (br, 1H), 4.33 (d, J=5.6 Hz, 2H), 2.32 (s, 3H), 1.45 (s, 9H), 1.34 (s, 12H).

Preparation of tert-butyl 4-(2-chloropyrimidin-4-yl)-2-methylbenzylcarbamate

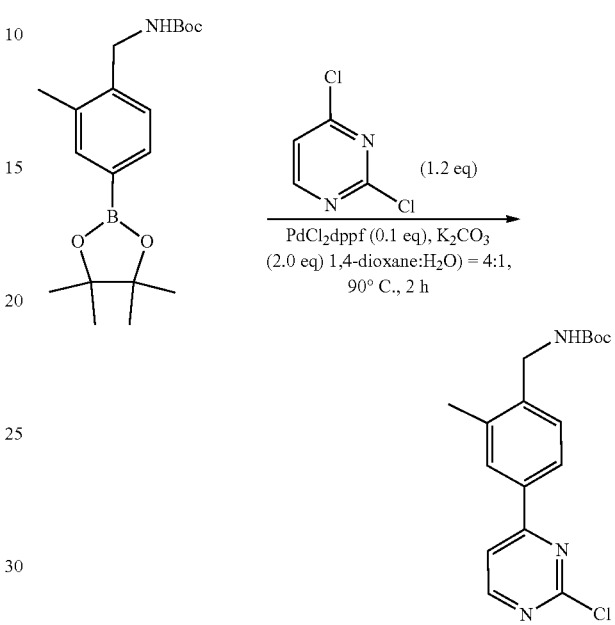

To a solution of tert-butyl 2-methyl-4-(4,4,5,5-tetramethyl-1,3,2-dioxaborolan-2-yl)benzylcarbamate (3.47 g, 10 mmol) and 2,4-dichloropyrimidine (1.79 g, 12 mmol) in 1,4-dioxane (28 mL) and H$_2$O (7 mL), Pd(dppf)Cl$_2$DCM (815 mg, 1.0 mmol) and K$_2$CO$_3$ (2.76 g, 20 mmol) were added under N$_2$. The mixture was stirred at 90° C. for 2 h. After cooling to rt, the mixture was diluted with H$_2$O (80 mL) and extracted with EA (80 mL×2). The organic layers were dried and concentrated. The residue was purified by column chromatography (silica, petroleum ether/EtOAc=5:1 to 2:1) to give tert-butyl 4-(2-chloropyrimidin-4-yl)-2-methylbenzylcarbamate (2.67 g, yield 80%) as white solid ESI-MS (M+H)+: 334.1. $^1$H NMR (400 MHz, CDCl$_3$) δ: 8.12 (d, J=5.2 Hz, 1H), 7.92 (s, 1H), 7.87 (d, J=8.0 Hz, 1H), 7.63 (d, J=5.6 Hz, 1H), 7.40 (d, J=7.6 Hz, 1H), 4.84 (br, 1H), 4.38 (d, J=5.2 Hz, 1H), 2.41 (s, 3H), 1.47 (s, 9H).

Preparation of tert-butyl 2-methyl-4-(2-((1-methyl-1H-pyrazol-4-yl)amino)pyrimidin-4-yl)benzylcarbamate

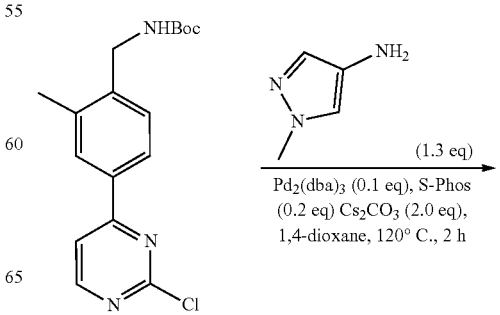

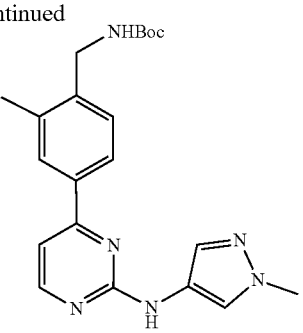

To a solution of tert-butyl 4-(2-chloropyrimidin-4-yl)-2-methylbenzylcarbamate (333 mg, 1.0 mmol) and 1-methyl-pyrazol-4-amine (126 mg, 1.3 mmol) in 1,4-dioxane (5 mL), Pd$_2$(dba)$_3$ (92 mg, 0.1 mmol), S-Phos (82 mg, 0.2 mmol) and Cs$_2$CO$_3$ (650 mg, 2.0 mmol) were added under N$_2$. The mixture was stirred at 120° C. for 2 h. After cooling to rt, the mixture was diluted with H$_2$O (40 mL) and extracted with EA (60 mL×2). The organic layers were dried and concentrated. The residue was purified by column chromatography (silica, petroleum ether/EtOAc=3:1 to 1:1) to give tert-butyl 2-methyl-4-(2-((1-methyl-1H-pyrazol-4-yl)amino)pyrimidin-4-yl)benzylcarbamate (248 mg, yield 63%) as white solid ESI-MS (M+H)$^+$: 395.1. $^1$H NMR (400 MHz, CD$_3$OD) δ: 8.38 (d, J=5.2 Hz, 1H), 7.97-7.93 (m, 3H), 7.65 (s, 1H), 7.38 (d, J=8.0 Hz, 1H), 7.20 (d, J=9.2 Hz, 1H), 4.30 (s, 2H), 3.85 (s, 3H), 2.42 (s, 3H), 1.48 (s, 9H).

Preparation of 4-(4-(aminomethyl)-3-methylphenyl)-N-(1-methyl-1H-pyrazol-4-yl)pyrimidin-2-amine

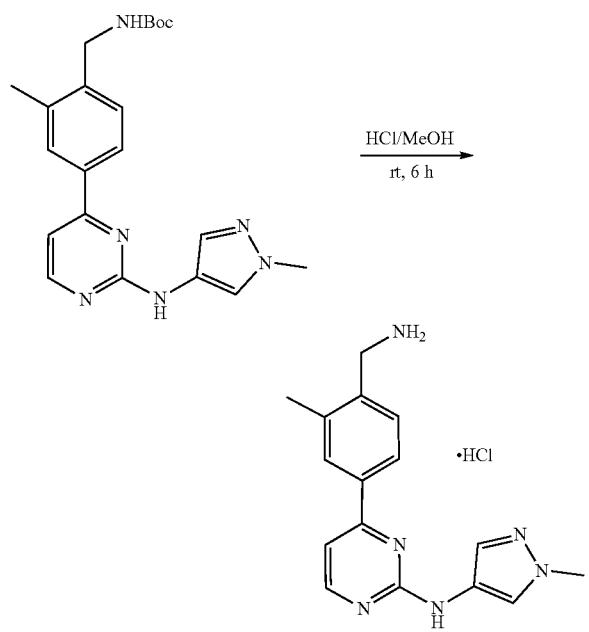

A mixture of tert-butyl 2-methyl-4-(2-((1-methyl-1H-pyrazol-4-yl)amino)pyrimidin-4-yl)benzylcarbamate (3.94 g, 10.0 mmol) in a solution of HCl in methanol (30 mL, prepared from gas HCl) was stirred at rt for 6 h. The solvent was removed and the solid was rinsed with cold diethyl ether (100 mL). The solid was dried under vacuum to give 4-(4-(aminomethyl)-3-methylphenyl)-N-(1-methyl-1H-pyrazol-4-yl)pyrimidin-2-amine (2.97 g, yield 90%) as a yellow solid ESI-MS (M+H)$^+$: 295.1. $^1$H NMR (400 MHz, D$_2$O) δ: 7.98-7.96 (m, 1H), 7.66-7.22 (m, 6H), 4.10 (s, 2H), 3.68 (s, 3H), 2.20 (s, 3H).

Preparation of 2-(tert-butyl)-N-(2-methyl-4-(2-((1-methyl-1H-pyrazol-4-yl)amino)pyrimidin-4-yl)benzyl)thiazole-5-carboxamide

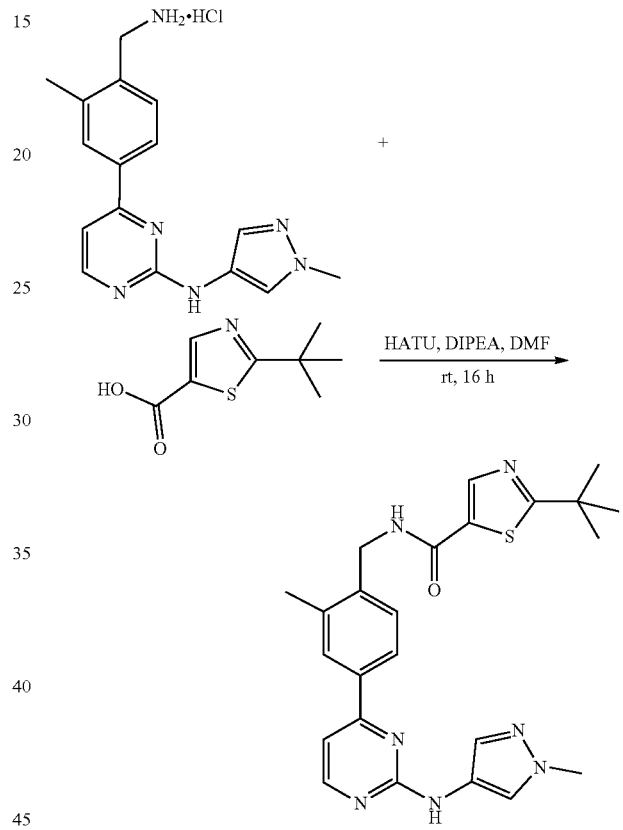

To a mixture of 4-(4-(aminomethyl)-3-methylphenyl)-N-(1-methyl-1H-pyrazol-4-yl)pyrimidin-2-amine (200 mg, 0.7 mmol), 2-(tert-butyl)thiazole-5-carboxylic acid (139 mg, 0.752 mmol), and N,N,N',N'-Tetramethyl-O-(7-azabenzotriazol-1-yl)uronium Hexafluorophosphate (0.32 g, 0.84 mmol) in N,N-Dimethylformamide (1.58 mL, 20.4 mmol) was added N,N-Diisopropylethylamine (0.355 mL, 2.04 mmol) slowly and stirred at room temperature overnight. The mixture was filtrate through celite and washed with DMF and purified by prep HPLC to give product, 2-(tert-butyl)-N-(2-methyl-4-(2-((1-methyl-1H-pyrazol-4-yl)amino)pyrimidin-4-yl)benzyl)thiazole-5-carboxamide as a solid (217.5 mg, yield 70%). LCMS: Rt=1.28 min, m/z 462.20. $^1$H NMR (300 MHz, DMSO-d6) δ: 9.57 (s, 1H), 9.10 (t, J=5.48 Hz, 1H), 8.46 (d, J=5.29 Hz, 1H), 8.33 (s, 1H), 7.95 (d, J=11.33 Hz, 3H), 7.56 (s, 1H), 7.40 (d, J=7.93 Hz, 1H), 7.28 (d, J=5.29 Hz, 1H), 4.50 (d, J=5.29 Hz, 2H), 3.65 (s, 3H), 2.42 (s, 3H), 1.39 (s, 9H).

Example 2: N-(2-methyl-4-(2-((1-methyl-1H-pyrazol-4-yl)amino)pyrimidin-4-yl)benzyl)-4,5,6,7-tetrahydrothieno[3,2-c]pyridine-2-carboxamide (I-2)

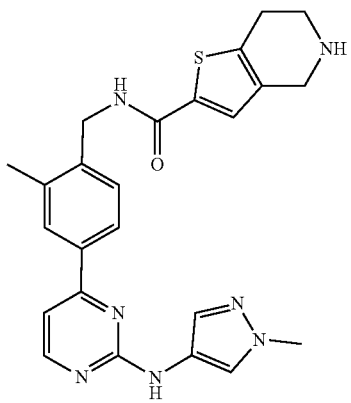

Synthesis of ethyl thieno[2,3-c]pyridine-2-carboxylate

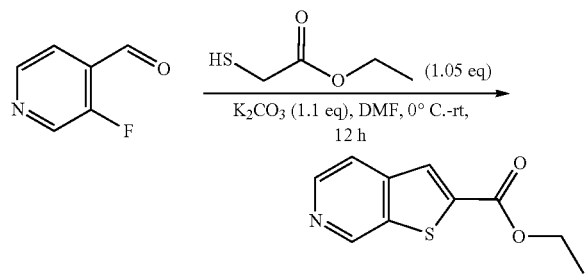

To a mixture of 3-fluoroisonicotinaldehyde (500 mg, 4.0 mmol) and ethyl 2-mercaptoacetate (504 mg, 4.2 mmol) in DMF (7 ml), K₂CO₃ (605 mg, 4.4 mmol) was added at 0° C. The mixture was stirred at rt for 12 h. The mixture was poured into water (30 mL), the precipitate was collected and dried to give ethyl thieno[2,3-c]pyridine-2-carboxylate (290 mg, yield: 35%) as a white solid. ¹H NMR (400 MHz, DMSO-d₆) δ: 9.37 (s, 1H), 8.56 (d, J=5.6 Hz, 1H), 8.26 (s, 1H), 7.98 (dd, J=5.2, 0.8 Hz, 1H), 4.39 (q, J=6.8 Hz, 2H), 1.35 (t, J=7.2 Hz, 3H).

Synthesis of ethyl 4,5,6,7-tetrahydrothieno[2,3-c]pyridine-2-carboxylate

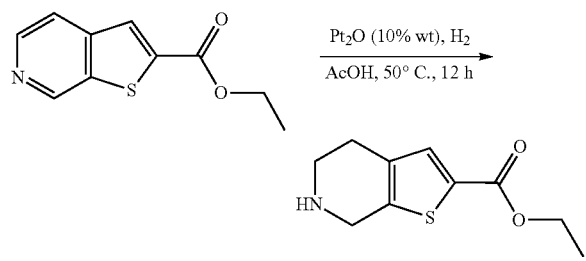

A mixture of ethyl thieno[2,3-c]pyridine-2-carboxylate (290 mg, 1.4 mmol, 1.0 eq) and Pt₂O (30 mg) in AcOH (5 mL) was stirred at 60° C. for 12 h under H₂ atmosphere. After cooling down, the catalyst was filtered out. The resulting filtrate was concentrated under reduced pressure to give ethyl 4,5,6,7-tetrahydrothieno[2,3-c]pyridine-2-carboxylate (290 mg, yield: 98%) as a yellow oil. ESI-MS (M+1)⁺: 212.1.

Synthesis of 6-tert-butyl 2-ethyl 4,5-dihydrothieno[2,3-c]pyridine-2,6(7H)-dicarboxylate

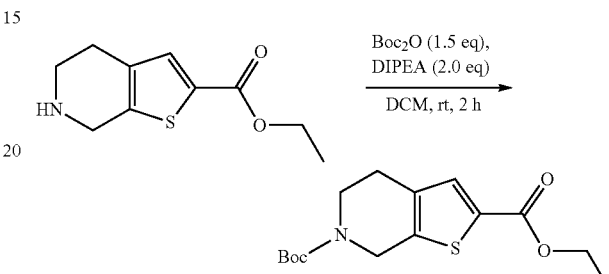

To a mixture of ethyl 4,5,6,7-tetrahydrothieno[2,3-c]pyridine-2-carboxylate (290 mg, 1.4 mmol, 1.0 equiv), DIPEA (361 mg, 2.8 mmol, 2.0 equiv) in DCM (10 mL), Boc₂O (460 mg, 2.1 mmol, 1.5 equiv) was added. The mixture was stirred at rt for 2 h. After diluted with DCM (50 mL), the mixture was washed with water (30 mL), brine (30 mL), dried over sodium sulfate and concentrated under reduced pressure. The residue was purified by silica gel column (PE:EA=10:1) to give 6-tert-butyl 2-ethyl 4,5-dihydrothieno[2,3-c]pyridine-2,6(7H)-dicarboxylate (350 mg, yield: 80%) as a colorless oil. ESI-MS (M+H-56)⁺: 256.1. ¹H NMR (400 MHz, CDCl₃) δ: 9.49 (s, 1H), 4.63 (s, 2H), 4.32 (q, J=7.2 Hz, 2H), 3.67 (t, J=5.2 Hz, 2H), 2.70 (t, J=5.2 Hz, 2H), 1.48 (s, 9H), 1.35 (t, J=6.8 Hz, 3H).

Synthesis of 6-(tert-butoxycarbonyl)-4,5,6,7-tetrahydrothieno[2,3-c]pyridine-2-carboxylic acid

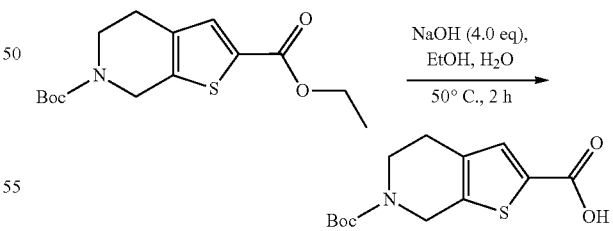

To a solution of 6-tert-butyl 2-ethyl 4,5-dihydrothieno[2,3-c]pyridine-2,6(7H)-dicarboxylate (350 mg, 1.12 mmol, 1.0 equiv) in EtOH (5 mL) and H₂O (5 mL) was added NaOH (180 mg, 4.5 mmol, 4.0 equiv). The reaction mixture was stirred at 50° C. for 2 h. Then the reaction was cooled to 0° C., and adjusted pH=5 with AcOH. The precipitate was collected and dried to give 6-(tert-butoxycarbonyl)-4,5,6,7-tetrahydrothieno[2,3-c]pyridine-2-carboxylic acid as a white solid (250 mg, yield: 78%). ESI-MS (M-55)⁺: 228.0

Synthesis of N-(2-methyl-4-(2-((1-methyl-1H-pyrazol-4-yl)amino)pyrimidin-4-yl)benzyl)-4,5,6,7-tetrahydrothieno[3,2-c]pyridine-2-carboxamide

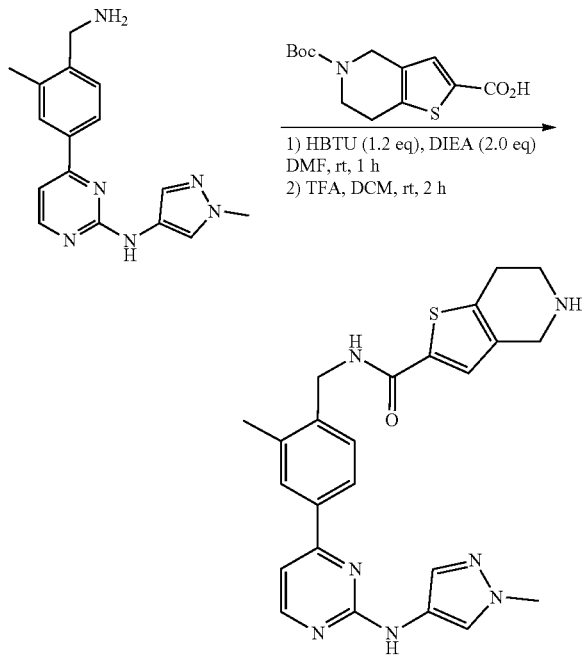

Synthesis of N-(2-methyl-4-(2-((1-methyl-1H-pyrazol-4-yl)amino)pyrimidin-4-yl)benzyl)-4,5,6,7-tetrahydrothieno[3,2-c]pyridine-2-carboxamide was similar to that of Example I-73, except 6-(tert-butoxycarbonyl)-4,5,6,7-tetrahydrothieno[2,3-c]pyridine-2-carboxylic acid was substituted for 2-(tert-butyl)thiazole-5-carboxylic acid. The crude was purified by prep-HPLC (CH$_3$CN/H$_2$O with 0.05% TFA as mobile phase) to get product N-(2-methyl-4-(2-((1-methyl-1H-pyrazol-4-yl)amino)pyrimidin-4-yl)benzyl)-4,5,6,7-tetrahydrothieno[3,2-c]pyridine-2-carboxamide as yellow solid (28 mg, yield 41%). ESI-MS (M+H)$^+$: 459.9. HPLC: (214 nm: 100%, 254 nm: 100%). $^1$H NMR (400 MHz, CD$_3$OD) δ: 8.38 (d, J=6.4 Hz, 1H), 7.98-7.93 (m, 3H), 7.66 (s, 1H), 7.54 (s, 1H), 7.42 (d, J=8.0 Hz, 1H), 7.22 (d, J=6.4 Hz, 1H), 4.61 (s, 2H), 4.31 (s, 2H), 3.89 (s, 3H), 3.58 (t, J=6.0 Hz, 2H), 3.21 (t, J=6.0 Hz, 2H), 2.47 (s, 3H).

Example 3: N-(2-methyl-4-(2-((1-methyl-1H-pyrazol-4-yl)amino)pyrimidin-4-yl)benzyl)-6,7-dihydro-4H-thieno[3,2-c]pyran-2-carboxamide (I-3)

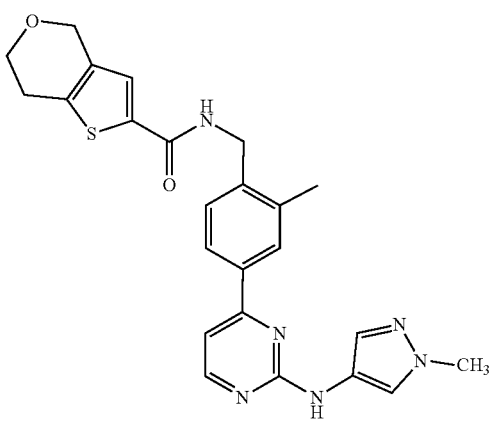

I-3

Preparation of ethyl 6,7-dihydro-4H-thieno[3,2-c]pyran-2-carboxylate

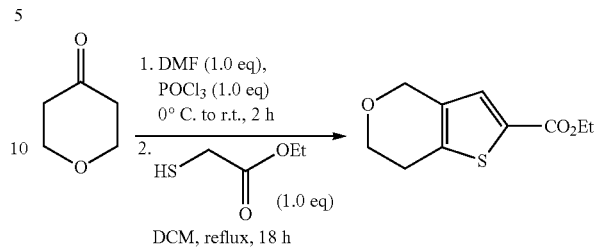

DMF (1.46 g, 20.0 mmol) was cooled at 0° C. and treated with POCl3 (1.46 g, 20.0 mmol) dropwise over 30 min. After addition, 10 mL DCM was added and stirred for another 1 h. Then dihydro-2H-pyran-4(3H)-one was added at 0° C. and the solution was allowed to warm up to room temperature for 2 h. After neutralized with potassium acetate, the mixture was extracted with DCM (60 mL×2), dried (Na$_2$SO$_4$), filtered and concentrated to give a yellow liquid. The liquid was dissolved in DCM (30 mL) and followed by addition of ethyl 2-mercaptoacetate (2.40 g, 20.0 mmol) and TEA (4.04 g, 40 mmol). Then the solution was heated at reflux for 16 h. The mixture was concentrated and purified by silica gel column chromatography (petroleum ether/EtOAc=1/4) to give ethyl 6,7-dihydro-4H-thieno[3,2-c]pyran-2-carboxylate as yellow oil (1.95 g, yield 46%). ESI-MS (M+H)$^+$: 213.0.

Preparation of 6,7-dihydro-4H-thieno[3,2-c]pyran-2-carboxylic acid

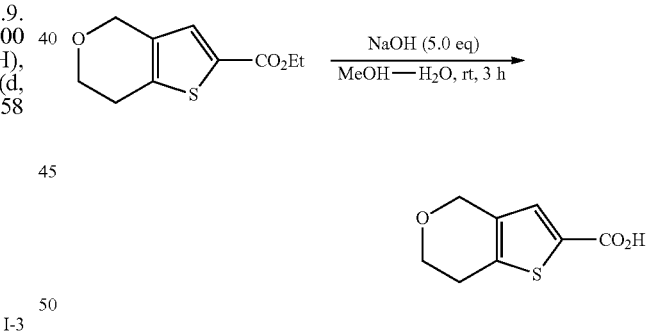

A mixture of ethyl 6,7-dihydro-4H-thieno[3,2-c]pyran-2-carboxylate (1.06 g, 5.0 mmol) and sodium hydroxide (1.0 g, 25 mmol) in methanol (15 mL) and water (5 mL) was stirred at room temperature for 3 h. After removal of methanol, the residue was diluted with water (15 ml) and the aqueous phase was adjusted to pH=5-6 with 1N HCl. The mixture was extracted with EtOAc (80 mL×2). The organic phase was dried (Na$_2$SO$_4$), filtered and concentrated to give product 6,7-dihydro-4H-thieno[3,2-c]pyran-2-carboxylic acid as a white solid (760 mg, yield 85%). ESI-MS (M+H)$^+$: 185.0. $^1$H NMR (400 MHz, CD$_3$OD) δ: 7.45 (s, 1H), 4.68 (s, 2H), 3.97 (t, J=5.6 Hz, 2H), 2.90 (t, J=5.6 Hz, 2H).

Preparation of N-(2-methyl-4-(2-((1-methyl-1H-pyrazol-4-yl)amino)pyrimidin-4-yl)benzyl)-6,7-dihydro-4H-thieno[3,2-c]pyran-2-carboxamide

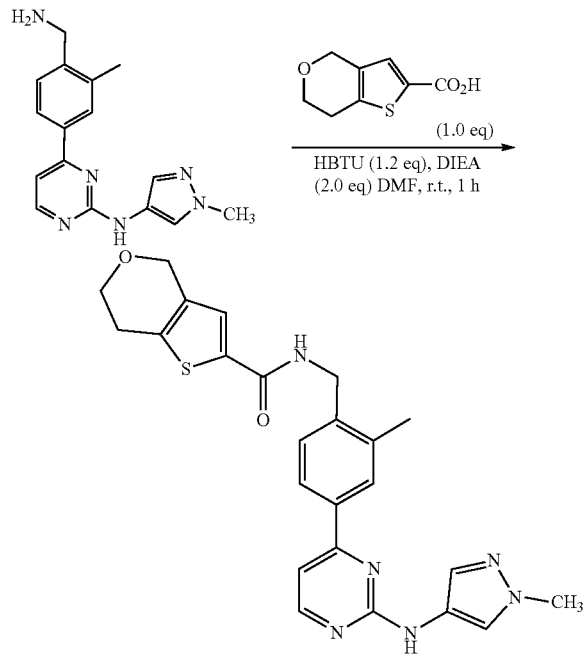

Synthesis of N-(2-methyl-4-(2-((1-methyl-1H-pyrazol-4-yl)amino)pyrimidin-4-yl)benzyl)-6,7-dihydro-4H-thieno[3,2-c]pyran-2-carboxamide was similar to that of Example 1, except 6,7-dihydro-4H-thieno[3,2-c]pyran-2-carboxylic acid was substituted for 2-(tert-butyl)thiazole-5-carboxylic acid. The crude was purified by prep-HPLC (CH$_3$CN/H$_2$O with 0.05% TFA as mobile phase) to give product N-(2-methyl-4-(2-((1-methyl-1H-pyrazol-4-yl)amino)pyrimidin-4-yl)benzyl)-6,7-dihydro-4H-thieno[3,2-c]pyran-2-carboxamide as pale yellow solid (21 mg, yield 43%). ESI-MS (M+H)$^+$: 461.0. HPLC: (214 nm: 97%, 254 nm: 92%). $^1$H NMR (400 MHz, CD$_3$OD) δ: 8.39 (d, J=5.2 Hz, 1H), 7.98-7.94 (m, 3H), 7.64 (s, 1H), 7.44-7.42 (m, 2H), 7.20 (d, J=5.2 Hz, 1H), 4.68 (s, 2H), 4.61 (s, 2H), 3.98 (d, J=5.6 Hz, 2H), 3.89 (s, 3H), 2.90 (d, J=5.6 Hz, 2H), 2.47 (s, 3H).

Example 4: N-(2-methyl-4-(2-((1-methyl-1H-pyrazol-4-yl)amino)pyrimidin-4-yl)benzyl)-2-(trifluoromethyl)thiazole-5-carboxamide (I-4)

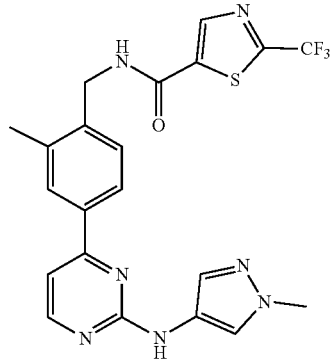

Synthesis of N-(2-methyl-4-(2-((1-methyl-1H-pyrazol-4-yl)amino)pyrimidin-4-yl)benzyl)-2-(trifluoromethyl)thiazole-5-carboxamide was similar to that of Example 1 except 2-(trifluoromethyl)thiazole-5-carboxylic acid was substituted for 2-(tert-butyl)thiazole-5-carboxylic acid. The residue was purified by prep-HPLC (CH$_3$CN/H$_2$O with 0.05% TFA as mobile phase) to give N-(2-methyl-4-(2-((1-methyl-1H-pyrazol-4-yl)amino)pyrimidin-4-yl)benzyl)-2-(trifluoromethyl)thiazole-5-carboxamide as a white solid (25 mg, yield 22%). ESI-MS (M+H)$^+$: 474.1. HPLC: (214 nm: 100%, 254 nm: 100%). $^1$H NMR (400 MHz, CD$_3$OD) δ: 8.41 (s, 1H), 8.26 (d, J=5.6 Hz, 1H), 7.94 (s, 1H), 7.92 (d, J=8.0 Hz, 1H), 7.86 (s, 1H), 7.56 (s, 1H), 7.40 (d, J=8.0 Hz, 1H), 7.27 (d, J=6.0 Hz, 1H), 4.56 (s, 2H), 3.81 (s, 3H), 2.39 (s, 3H).

Example 5: N-(2-methyl-4-(2-((1-methyl-1H-pyrazol-4-yl)amino)pyrimidin-4-yl)benzyl)-4,5,6,7-tetrahydrobenzo[b]thiophene-2-carboxamide (I-5)

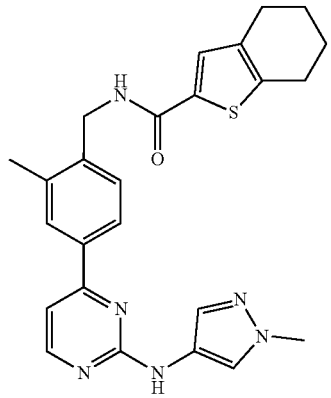

Synthesis of N-(2-methyl-4-(2-((1-methyl-1H-pyrazol-4-yl)amino)pyrimidin-4-yl)benzyl)-4,5,6,7-tetrahydrobenzo[b]thiophene-2-carboxamide was similar to that of Example 1 except 4,5,6,7-tetrahydrobenzo[b]thiophene-2-carboxylic acid was substituted for 2-(tert-butyl)thiazole-5-carboxylic acid. The residue was purified by prep-HPLC (CH$_3$CN/H$_2$O with 0.05% NH$_3$H$_2$O as mobile phase) to give N-(2-methyl-4-(2-((1-methyl-1H-pyrazol-4-yl)amino)pyrimidin-4-yl)benzyl)-4,5,6,7-tetrahydrobenzo[b]thiophene-2-carboxamide as a white solid (17 mg, yield 15%). ESI-MS (M+H)$^+$: 459.1. HPLC: (214 nm: 99%, 254 nm: 100%). $^1$H NMR (400 MHz, CD$_3$OD) δ: 8.25 (d, J=5.6 Hz, 1H), 7.89-7.86 (m, 3H), 7.55 (s, 1H), 7.35 (d, J=8.0 Hz, 1H), 7.30 (s, 1H), 7.20 (d, J=6.0 Hz, 1H), 4.48 (s, 2H), 3.80 (s, 3H), 2.69 (t, J=6.0 Hz, 2H), 2.53 (t, J=6.0 Hz, 2H), 2.36 (s, 3H), 1.77-1.70 (m, 4H).

Example 6: 5-(tert-butyl)-N-(2-methyl-4-(2-((1-methyl-1H-pyrazol-4-yl)amino)pyrimidin-4-yl)benzyl)picolinamide (I-6)

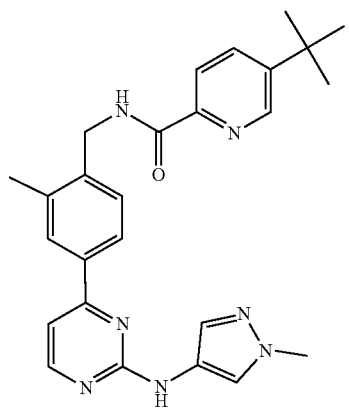

I-6

Synthesis of 5-(tert-butyl)-N-(2-methyl-4-(2-((1-methyl-1H-pyrazol-4-yl)amino)pyrimidin-4-yl)benzyl)picolinamide was similar to that of Example 1 except 5-(tert-butyl)picolinic acid was substituted for 2-(tert-butyl)thiazole-5-carboxylic acid. The crude product was purified by prep-HPLC (CH$_3$CN/H$_2$O with 0.05% NH$_3$.H$_2$O as mobile phase) to give 5-(tert-butyl)-N-(2-methyl-4-(2-((1-methyl-1H-pyrazol-4-yl)amino)pyrimidin-4-yl)benzyl)picolinamide as a yellow solid (35 mg, yield 32%). ESI-MS (M+H)$^+$: 456.1. $^1$H NMR (400 MHz, CDCl$_3$) δ: 8.58 (d, J=2.4 Hz, 1H), 8.41 (d, J=5.2 Hz, 1H), 8.27 (s, 1H), 8.16-8.14 (m, 1H), 7.89-7.84 (m, 4H), 7.54 (s, 1H), 7.44 (d, J=8.0 Hz, 1H), 7.06 (d, J=5.2 Hz, 1H), 6.84 (s, 1H), 4.72 (d, J=5.6 Hz, 2H), 3.91 (s, 3H), 2.47 (s, 3H), 1.37 (s, 9H).

Example 7: 4-(tert-butyl)-N-(2-methyl-4-(2-((1-methyl-1H-pyrazol-4-yl)amino)pyrimidin-4-yl)benzyl)benzamide (I-7)

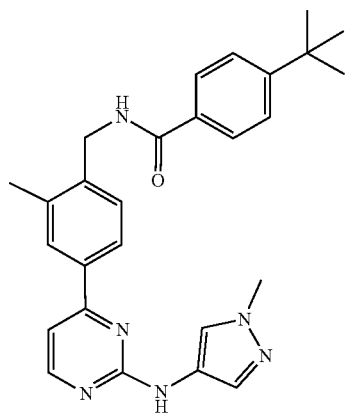

I-7

To a solution of 4-(4-(aminomethyl)-3-methylphenyl)-N-(1-methyl-1H-pyrazol-4-yl)pyrimidin-2-amine (60 mg, 0.2 mmol) and DIPEA (52 mg, 0.4 mmol) in DCM (5 mL) was added 4-tert-butylbenzoyl chloride (47 mg, 0.24 mmol). The mixture was stirred at rt for 2 h. After concentrated, the residue was purified by column chromatography (petroleum ether/EtOAc 1:1 to 1:4) to give compound 4-(tert-butyl)-N-(2-methyl-4-(2-((1-methyl-1H-pyrazol-4-yl)amino)pyrimidin-4-yl)benzyl)benzamide (60 mg, yield: 66%) as a light yellow liquid. ESI-MS (M+H)$^+$: 455.1. $^1$H NMR (400 MHz, CD$_3$OD) δ: 8.36 (d, J=5.2 Hz, 1H), 7.93-7.92 (m, 2H), 7.90 (d, J=8.0 Hz, 1H), 7.82 (d, J=8.6 Hz, 2H), 7.63 (s, 1H), 7.50 (d, J=8.6 Hz, 2H), 7.42 (d, J=8.0 Hz, 1H), 7.15 (d, J=5.2 Hz, 1H), 4.64 (s, 2H), 3.88 (s, 3H), 2.47 (s, 3H), 1.34 (s, 9H).

Example 8: 3,4-dichloro-N-(2-methyl-4-(2-((1-methyl-1H-pyrazol-4-yl)amino)pyrimidin-4-yl)benzyl)benzamide (I-8)

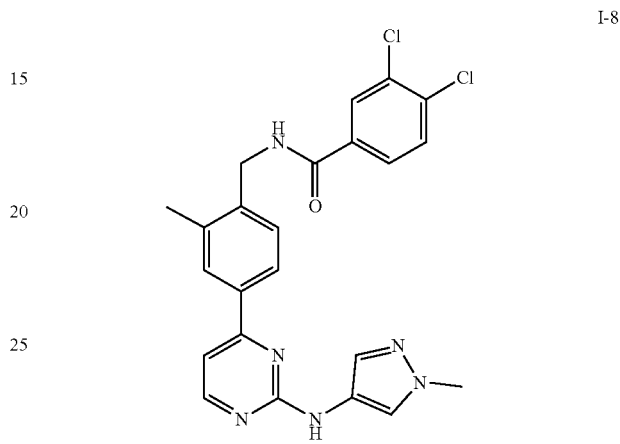

I-8

Synthesis of 3,4-dichloro-N-(2-methyl-4-(2-((1-methyl-1H-pyrazol-4-yl)amino)pyrimidin-4-yl)benzyl)benzamide was similar to that of Example 1, except 3,4-dichlorobenzoic acid was substituted for 2-(tert-butyl)thiazole-5-carboxylic acid. The residue was purified by prep-HPLC (MeCN/H$_2$O with 0.05% NH$_3$.H$_2$O as mobile phase) to give the compound 3,4-dichloro-N-(2-methyl-4-(2-((1-methyl-1H-pyrazol-4-yl)amino)pyrimidin-4-yl)benzyl)benzamide (39 mg, yield: 35%) as a straw yellow solid. ESI-MS (M+H)$^+$: 467.1. $^1$H NMR (400 MHz, DMSO-d$_6$) δ: 9.48 (s, 1H), 9.17 (t, J=5.6 Hz, 1H), 8.46 (d, J=5.2 Hz, 1H), 8.17 (d, J=2.0 Hz, 1H), 7.97 (s, 1H), 7.96-7.88 (m, 3H), 7.79 (d, J=8.4 Hz, 1H), 7.55 (s, 1H), 7.41 (d, J=8.0 Hz, 1H), 7.25 (d, J=5.2 Hz, 1H), 4.53 (d, J=5.6 Hz, 2H), 3.82 (s, 3H), 2.43 (s, 3H).

Example 9: N-(2-methyl-4-(2-((1-methyl-1H-pyrazol-4-yl)amino)pyrimidin-4-yl)benzyl)-4,5,6,7-tetrahydrobenzo[d]thiazole-2-carboxamide (I-9)

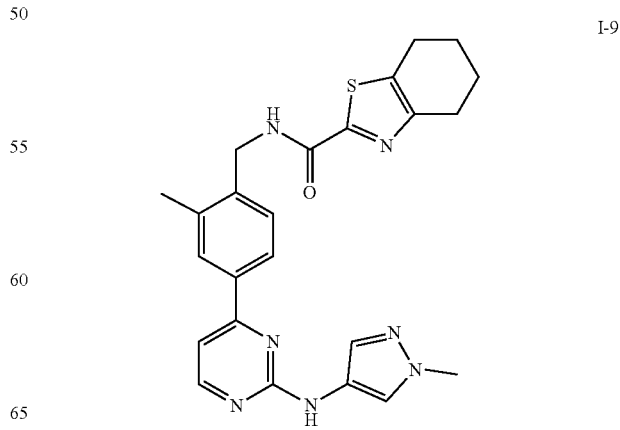

I-9

Synthesis of N-(2-methyl-4-(2-((1-methyl-1H-pyrazol-4-yl)amino)pyrimidin-4-yl)benzyl)-4,5,6,7-tetrahydrobenzo[d]thiazole-2-carboxamide was similar to that of Example 1 except 4,5,6,7-tetrahydrobenzo[d]thiazole-2-carboxylic acid was substituted for 2-(tert-butyl)thiazole-5-carboxylic acid. The crude was purified by prep-HPLC (CH$_3$CN/H$_2$O with 0.05% NH$_3$.H$_2$O as mobile phase) to give compound N-(2-methyl-4-(2-((1-methyl-1H-pyrazol-4-yl)amino)pyrimidin-4-yl)benzyl)-4,5,6,7-tetrahydrobenzo[d]thiazole-2-carboxamide (82 mg, yield: 89%) as a straw yellow solid. ESI-MS (M+H)$^+$: 460.0. $^1$H NMR (400 MHz, DMSO-d$_6$) δ: 9.47 (s, 1H), 9.25 (t, J=5.6 Hz, 1H), 8.45 (d, J=5.2 Hz, 1H), 7.94-7.92 (m, 3H), 7.54 (s, 1H), 7.37 (d, J=8.0 Hz, 1H), 7.24 (d, J=5.2 Hz, 1H), 4.48 (d, J=6.0 Hz, 2H), 3.82 (s, 3H), 2.84 (t, J=5.6 Hz, 2H), 2.78 (t, J=5.6 Hz, 2H), 2.42 (s, 3H), 1.83-1.80 (m, 4H).

Example 10: N-(2-methyl-4-(2-((1-methyl-1H-pyrazol-4-yl)amino)pyrimidin-4-yl)benzyl)-5,6-dihydro-4H-cyclopenta[d]thiazole-2-carboxamide (I-10)

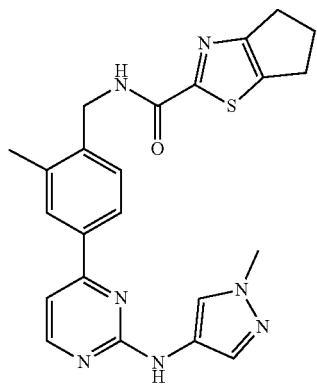

I-10

Synthesis of N-(2-methyl-4-(2-((1-methyl-1H-pyrazol-4-yl)amino)pyrimidin-4-yl)benzyl)-5,6-dihydro-4H-cyclopenta[d]thiazole-2-carboxamide was similar to that of Example 1, except 5,6-dihydro-4H-cyclopenta[d]thiazole-2-carboxylic acid was substituted for 2-(tert-butyl)thiazole-5-carboxylic acid. The crude product was purified by prep-HPLC (CH$_3$CN/H$_2$O with 0.05% NH$_3$.H$_2$O as mobile phase) to give N-(2-methyl-4-(2-((1-methyl-1H-pyrazol-4-yl)amino)pyrimidin-4-yl)benzyl)-5,6-dihydro-4H-cyclopenta[d]thiazole-2-carboxamide as a yellow solid (58 mg, yield 54%). ESI-MS (M+H)$^+$: 446.1. HPLC: (214 nm: 97%, 254 nm: 99%). $^1$H NMR (400 MHz, CDCl$_3$) δ: 8.42 (d, J=5.2 Hz, 1H), 7.89 (s, 1H), 7.86 (s, 1H), 7.84 (d, J=7.6 Hz, 1H), 7.55 (s, 1H), 7.44 (d, J=7.6 Hz, 1H), 7.35 (s, 1H), 7.07 (d, J=5.2 Hz, 1H), 6.86 (s, 1H), 4.69 (d, J=5.6 Hz, 2H), 3.91 (s, 3H), 2.98 (t, J=6.8 Hz, 2H), 2.85 (t, J=7.6 Hz, 2H), 2.57-2.51 (m, 2H), 2.46 (s, 3H).

Example 11: trans-N-(2-methyl-4-(2-((1-methyl-1H-pyrazol-4-yl)amino)pyrimidin-4-yl)benzyl)-4-(trifluoromethyl)cyclohexanecarboxamide (I-11)

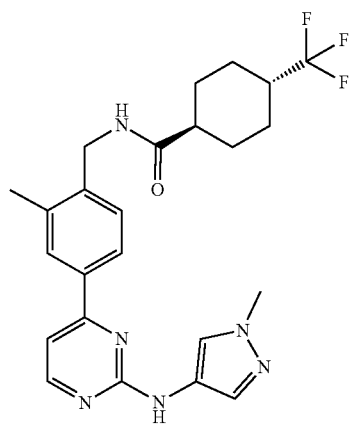

I-11

Synthesis trans-N-(2-methyl-4-(2-((1-methyl-1H-pyrazol-4-yl)amino)pyrimidin-4-yl)benzyl)-4-(trifluoromethyl)cyclohexanecarboxamide was similar to that of Example 1, except trans-4-(trifluoromethyl)cyclohexanecarboxylic acid was substituted for 2-(tert-butyl)thiazole-5-carboxylic acid. The crude product was purified by prep-HPLC to give product as a solid (17 mg, yield 10%). LCMS: Rt=1.33 min, m/z 473.2. 1H NMR (400 MHz, METHANOL-d4) δ 8.34 (d, J=5.77 Hz, 1H), 7.99-8.08 (m, 2H), 7.97 (s, 1H), 7.69 (s, 1H), 7.42 (d, J=7.78 Hz, 2H), 4.41-4.51 (m, 2H), 3.94 (s, 3H), 2.45 (s, 3H), 1.24-2.39 (m, 10H).

Example 12: 2-(tert-butyl)-5-(2-methyl-4-(2-((1-methyl-1H-pyrazol-4-yl)amino)pyrimidin-4-yl)benzyl)-4H-pyrrolo[3,4-d]thiazol-6(5H)-one (I-12)

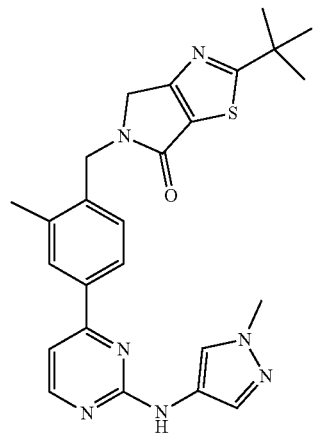

I-12

Synthesis of methyl 4-(bromomethyl)-2-(tert-butyl)thiazole-5-carboxylate

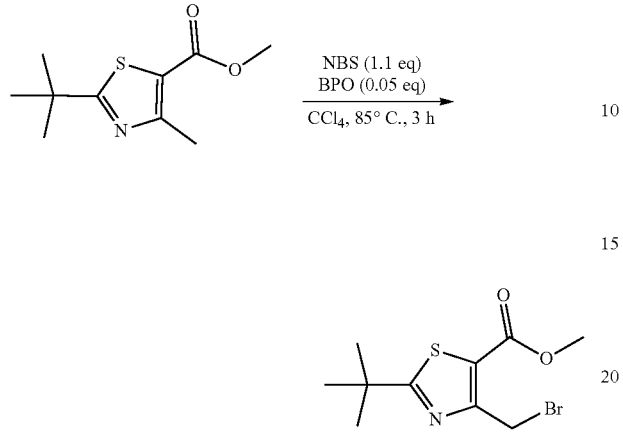

A mixture of methyl 2-(tert-butyl)-4-methylthiazole-5-carboxylate (90 mg, 0.42 mmol), N-bromosuccinimide (83 g, 0.46 mmol) and benzoyl peroxide (10 mg, 0.04 mmol) in CCl₄ (10 mL) was stirred at 85° C. for 3 h. After concentrated, the residue was diluted with EtOAc (60 mL), washed by saturated aqueous Na₂S₂O₃ (20 mL) and brine (20 mL). The organic phase was dried over MgSO₄ and concentrated to give methyl 4-(bromomethyl)-2-(tert-butyl)thiazole-5-carboxylate (89 mg, yield: 72%) as a light yellow liquid. ESI-MS (M+H)⁺: 291.9.

Synthesis of methyl 2-(tert-butyl)-4-(((2-methyl-4-(2-((1-methyl-1H-pyrazol-4-yl)amino)pyrimidin-4-yl)benzyl)amino)methyl)thiazole-5-carboxylate

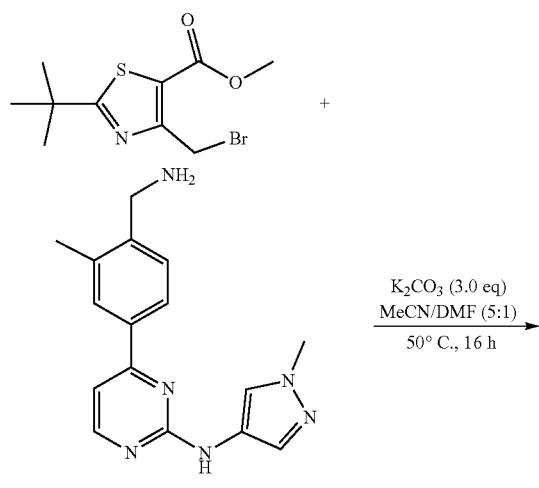

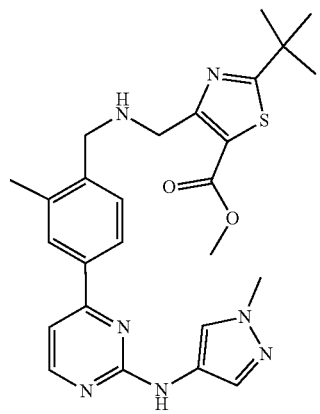

To a mixture of methyl 4-(bromomethyl)-2-(tert-butyl)thiazole-5-carboxylate (89 mg, 0.30 mmol) and 4-(4-(aminomethyl)-3-methylphenyl)-N-(1-methyl-1H-pyrazol-4-yl)pyrimidin-2-amine (202 mg, 0.61 mmol) in MeCN/DMF (12 mL, 5:1) was added K₂CO₃ (126 mg, 0.91 mmol). The reaction was kept at 50° C. for 16 h. After filtration, the filtrate was concentrated to give a crude residue which was purified by prep-HPLC (MeCN/H₂O with 10 mmol/L NH₄HCO₃ as mobile phase) to give compound methyl 2-(tert-butyl)-4-(((2-methyl-4-(2-((1-methyl-1H-pyrazol-4-yl)amino)pyrimidin-4-yl)benzyl)amino)methyl)thiazole-5-carboxylate (98 mg, yield: 64%) as a brown solid. ESI-MS (M+H)⁺: 506.1.

Synthesis of 2-(tert-butyl)-4-(((2-methyl-4-(2-((1-methyl-1H-pyrazol-4-yl)amino)pyrimidin-4-yl)benzyl)amino)methyl)thiazole-5-carboxylic acid

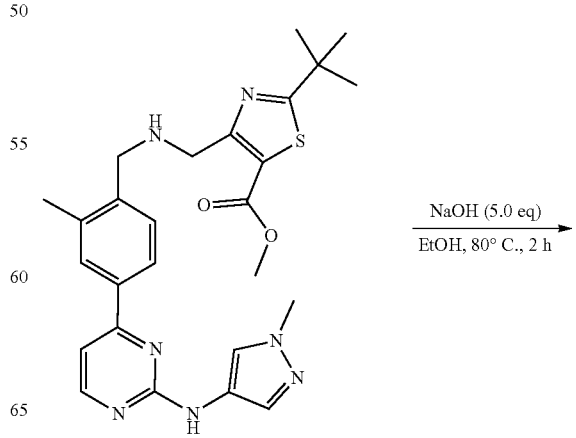

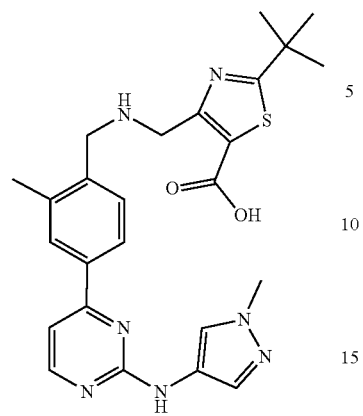

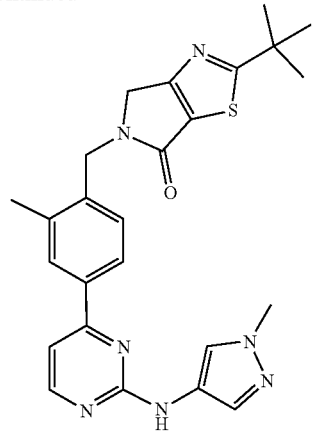

A mixture of methyl 2-(tert-butyl)-4-(((2-((1-methyl-1H-pyrazol-4-yl)amino)pyrimidin-4-yl)benzyl)amino)methyl)thiazole-5-carboxylate (86 mg, 0.17 mmol) and NaOH (34 mg, 0.85 mmol) in EtOH (10 mL) was stirred at 80° C. for 4 h. The resulting solution was concentrated and diluted with water (6 mL), adjusted to pH=5.0-6.0 with 3N HCl and extracted with EtOAc (30 mL×3). The combined organic phase was dried over MgSO₄ and concentrated to give 2-(tert-butyl)-4-(((2-methyl-4-(2-((1-methyl-1H-pyrazol-4-yl)amino)pyrimidin-4-yl)benzyl)amino)methyl)thiazole-5-carboxylic acid (82 mg, yield: 98%) as a straw yellow solid. ESI-MS (M+H)⁺: 492.3.

Synthesis of 2-(tert-butyl)-5-(2-methyl-4-(2-((1-methyl-1H-pyrazol-4-yl)amino)pyrimidin-4-yl)benzyl)-4H-pyrrolo[3,4-d]thiazol-6(5H)-one To a well-stirred solution of 2-(tert-butyl)-4-(((2-methyl-4-(2-((1-methyl-1H-pyrazol-4-yl)amino)pyrimidin-4-yl)benzyl)amino)methyl)thiazole-5-carboxylic acid (82 mg, 0.17 mmol) and TEA (116 µL, 0.84 mmol) in DMF/DCM (8 mL, 3:1) was added HATU (76 mg, 0.2 mmol) at 0° C. The reaction was kept at 0° C. for 2 h and stirred at rt for another 14 h. After diluted with EtOAc (80 mL), the mixture was washed with brine (20 mL×2). The organic phase was dried and concentrated to give a crude residue which was purified by prep-HPLC (MeOH/H₂O with 0.05% NH₃.H₂O as mobile phase) to give the compound 2-(tert-butyl)-5-(2-methyl-4-(2-((1-methyl-1H-pyrazol-4-yl)amino)pyrimidin-4-yl)benzyl)-4H-pyrrolo[3,4-d]thiazol-6(5H)-one (40 mg, yield: 51%) as a straw yellow solid. ESI-MS (M+H)⁺: 474.1. ¹H NMR (400 MHz, CDCl₃) δ: 8.42 (d, J=5.2 Hz, 1H), 7.89-7.86 (m, 2H), 7.84 (d, J=7.6 Hz, 1H), 7.54 (s, 1H), 7.30 (d, J=7.6 Hz, 1H), 7.16 (br, 1H), 7.06 (d, J=5.2 Hz, 1H), 4.84 (s, 2H), 4.25 (s, 2H), 3.91 (s, 3H), 2.44 (s, 3H), 1.47 (s, 9H).

Example 13: 2-cyclopropyl-5-(2-methyl-4-(2-((1-methyl-1H-pyrazol-4-yl)amino)pyrimidin-4-yl)benzyl)-4H-thieno[2,3-c]pyrrol-6(5H)-one (I-13)



Synthesis of methyl 3-(bromomethyl)thiophene-2-carboxylate

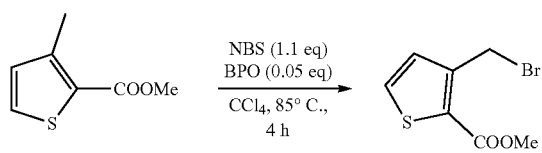

Synthesis of methyl 3-(bromomethyl)thiophene-2-carboxylate was similar to that of methyl 4-(bromomethyl)-2-(tert-butyl)thiazole-5-carboxylate in Example 12, except methyl 3-methylthiophene-2-carboxylate was substituted for methyl 2-(tert-butyl)-4-methylthiazole-5-carboxylate. The organic phase was dried and concentrated to give a crude residue which was purified by column chromatography (petroleum ether/EtOAc, 80:1 to 30:1) to give compound methyl 3-(bromomethyl)thiophene-2-carboxylate (3.6 g, yield: 59%) as a light yellow liquid. ESI-MS (M+H)$^+$: 234.9.

Synthesis of methyl 3-(aminomethyl)thiophene-2-carboxylate

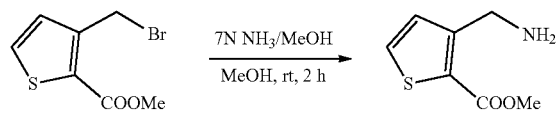 [SMILES: COC(=O)c1sccc1CBr ; COC(=O)c1sccc1CN]

A mixture of methyl 3-(bromomethyl)thiophene-2-carboxylate (1.9 g, 8.1 mmol) in 7N NH$_3$/MeOH (23 mL) and MeOH (20 mL) was stirred at rt for 2 h. After concentrated, the residue was purified by silica gel column chromatography (DCM/MeOH, 40:1 to 10:1) to give compound methyl 3-(aminomethyl)thiophene-2-carboxylate (1.3 g, yield: 94%) as a white solid. ESI-MS (M+H)$^+$: 172.1.

Synthesis of 4H-thieno[2,3-c]pyrrol-6(5H)-one

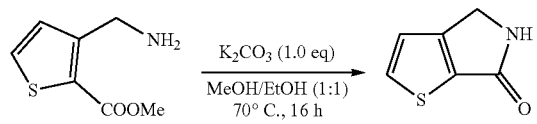

A mixture of methyl 3-(aminomethyl)thiophene-2-carboxylate (1.3 mg, 7.6 mmol) and K$_3$CO$_3$ (1.1 g, 7.6 mmol) in EtOH/MeOH (20 mL, 1:1) was stirred at 70° C. for 16 h. After concentrated, the residue was purified by silica gel column chromatography (DCM/MeOH, 100:1 to 60:1) to give compound 4H-thieno[2,3-c]pyrrol-6(5H)-one (580 g, yield: 55%) as a white solid. ESI-MS (M+H)$^+$: 140.1.

Synthesis of 2-bromo-4H-thieno[2,3-c]pyrrol-6(5H)-one

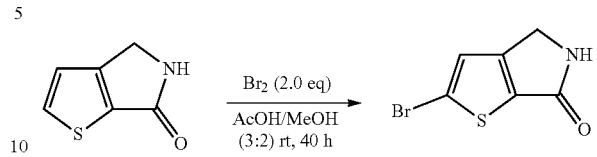

Br$_2$ (1.3 g, 8.4 mmol) was added dropwise to the solution of 4H-thieno[2,3-c]pyrrol-6(5H)-one (580 mg, 4.2 mmol) in AcOH/MeOH (10 mL, 3:2) at 0° C. The mixture was stirred at rt for 40 h. After concentrated, the residue was diluted with EtOAc (160 mL), washed with brine (60 mL). The organic phase was dried and concentrated to give a crude residue which was purified by column chromatography (DCM/MeOH, 100:1 to 80:1) to give the compound 2-bromo-4H-thieno[2,3-c]pyrrol-6(5H)-one (616 mg, yield: 68%) as a white solid. ESI-MS (M+H)$^+$: 217.8.

Synthesis of 2-cyclopropyl-4H-thieno[2,3-c]pyrrol-6(5H)-one

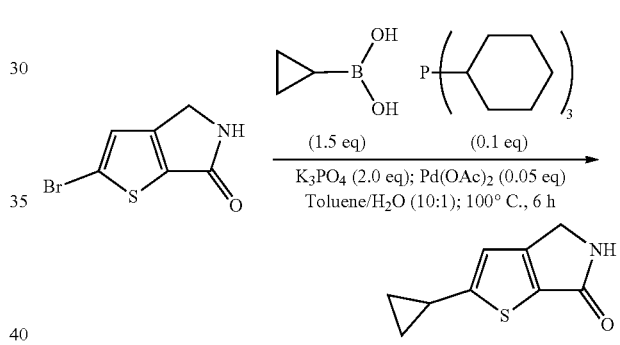

A mixture of 2-bromo-4H-thieno[2,3-c]pyrrol-6(5H)-one (202 mg, 0.9 mmol), cyclopropyl boronic acid (120 mg, 1.4 mmol), tricyclohexyl phosphine (25 mg, 0.1 mmol) and K$_3$PO$_4$ (393 mg, 1.9 mmol) in toluene/H$_2$ (17 mL, 16:1) was stirred at 100° C. for 5 min, followed by addition of Pd(OAc)$_2$ (11 mg, 0.05 mmol). The reaction was kept at 100° C. for 6 h. After concentrated, the residue was purified by silica gel column chromatography (DCM/MeOH, 100:1 to 80:1) to give the compound 2-cyclopropyl-4H-thieno[2,3-c]pyrrol-6(5H)-one (205 mg, yield: 65%) as a light yellow solid. ESI-MS (M+H)$^+$: 180.1.

Synthesis of 5-(4-bromo-2-methylbenzyl)-2-cyclopropyl-4H-thieno[2,3-c]pyrrol-6(5H)-one

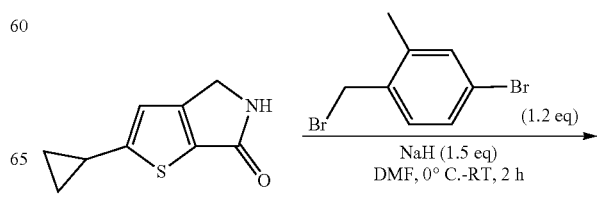

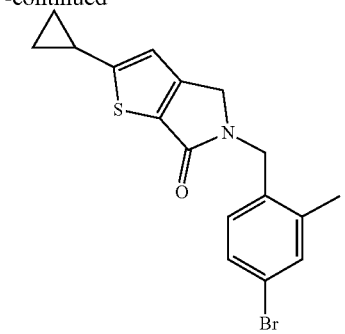

To a mixture of 2-cyclopropyl-4H-thieno[2,3-c]pyrrol-6 (5H)-one (150 mg, 0.8 mmol) in dry DMF (6 ml) was added 60% NaH (50 mg, 1.3 mmol) at 0° C. The mixture was stirred at rt for 10 min after which 4-bromo-1-(bromomethyl)-2-methylbenzene (264 mg, 1.0 mmol) was added. The mixture was stirred at rt for 1 h. Then the reaction was quenched by water (5 mL) and diluted EtOAc (100 mL), washed by brine (40 mL). The organic phase was dried and concentrated to give a crude residue which was purified by silica gel column chromatography (petroleum ether/EtOAc, 8:1 to 5:1) to give the compound 5-(4-bromo-2-methylbenzyl)-2-cyclopropyl-4H-thieno[2,3-c]pyrrol-6(5H)-one (35 mg, yield: 12%) as a light yellow solid. ESI-MS (M+H)$^+$: 362.1.

The preparation of 2-chloro-4-methoxypyrimidine

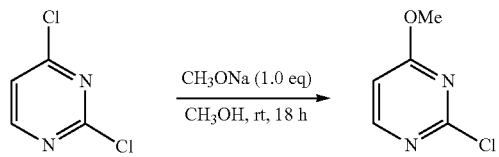 [SMILES: Clc1ccnc(Cl)n1 ; COc1ccnc(Cl)n1]

To a solution of 2,4-dichloropyrimidine (41.8 g, 280 mmol) in methanol (900 mL) was added a solution of CH$_3$ONa (15.2 g, 280 mmol) in 100 mL methanol at 0° C. The mixture was stirred at rt for overnight. The mixture was concentrated under reduce pressure to give a white solid, which was diluted with water (400 mL) and extracted with ethyl acetate (500 mL×3). The combined organic layer was washed with brine, dried, concentrated to give 2-chloro-4-methoxypyrimidine (40 g, yield: 98%) as white solid. ESI-MS (M+H)$^+$: 145.0. $^1$H NMR (400 MHz, CDCl$_3$) δ: 8.30 (d, J=5.6 Hz, 1H), 6.68 (s, J=5.6 Hz, 1H), 4.02 (s, 3H).

The preparation of 4-methoxy-N-(1-methyl-1H-pyrazol-4-yl)pyrimidin-2-amine

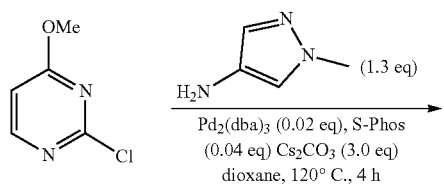

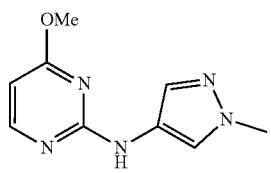

To a solution of 2-chloro-4-methoxypyrimidine (36.0 g, 250 mmol), 1-methyl-1H-pyrazol-4-amine (32 g, 325 mmol) in 1,4-dioxane (1000 mL) were added Cs$_2$CO$_3$ (244 g, 750 mmol), S-phos (4.0 g, 10.0 mmol) and Pd$_2$(dba)$_3$ (5.0 g, 5.0 mmol) under N$_2$. The mixture was stirred at 120° C. for 4 h. After cooling down to rt, the mixture was filtered to remove the insoluble matter by silica gel and washed with EA (500 mL). The organic phase was concentrated and purified by silica gel column (PE:EA=5:1 to 1:1) to give 4-methoxy-N-(1-methyl-1H-pyrazol-4-yl)pyrimidin-2-amine (25.0 g, yield: 44%) as gray powder. ESI-MS (M+H)$^+$: 206.1. $^1$H NMR (400 MHz, CDCl$_3$) δ: 8.06 (d, J=5.6 Hz, 1H), 7.89 (s, 1H), 7.57 (s, 1H), 6.15 (d, J=5.6 Hz, 1H), 3.97 (s, 3H), 3.88 (s, 3H).

The preparation of 4-chloro-N-(1-methyl-1H-pyrazol-4-yl)pyrimidin-2-amine

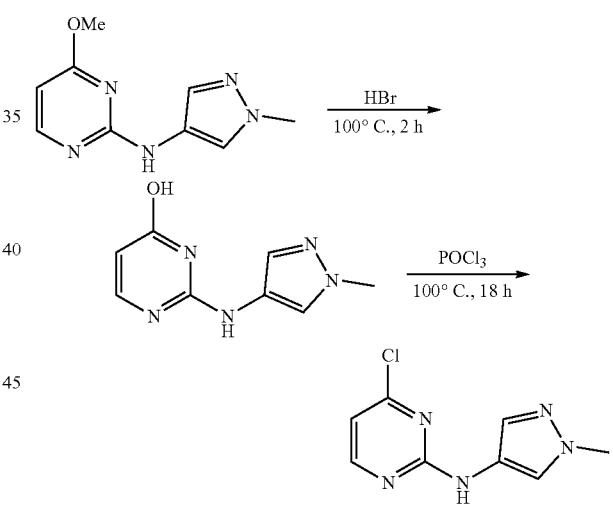

A mixture of 4-methoxy-N-(1-methyl-1H-pyrazol-4-yl)pyrimidin-2-amine (25.0 g, 122 mmol) in HBr (200 mL, 48%) was stirred at 100° C. for 2 h. The mixture was concentrated under reduced pressure to give crude 2-((1-methyl-1H-pyrazol-4-yl)amino)pyrimidin-4-ol as gray solid. The solid was dissolved in POCl$_3$ (200 mL) and stirred at 100° C. for 16 h. The mixture was concentrated under reduced pressure to remove excess POCl$_3$ and the residue was purified by silica gel column (PE:EA=5:1 to 2:1) and crystallized from EtOAc to give 4-chloro-N-(1-methyl-1H-pyrazol-4-yl)pyrimidin-2-amine (18.0 g, yield: 68% for 2 steps) as white powder. ESI-MS (M+H)$^+$: 210.1. $^1$H NMR (400 MHz, CDCl$_3$) δ: 8.29 (d, J=5.2 Hz, 1H), 7.94 (s, 1H), 7.56 (s, 1H), 6.75 (d, J=5.2 Hz, 1H), 3.89 (s, 3H).

Synthesis of 2-cyclopropyl-5-(2-methyl-4-(2-((1-methyl-1H-pyrazol-4-yl)amino)pyrimidin-4-yl)benzyl)-4H-thieno[2,3-c]pyrrol-6(5H)-one

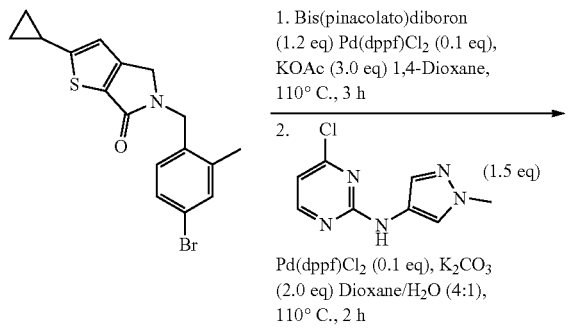

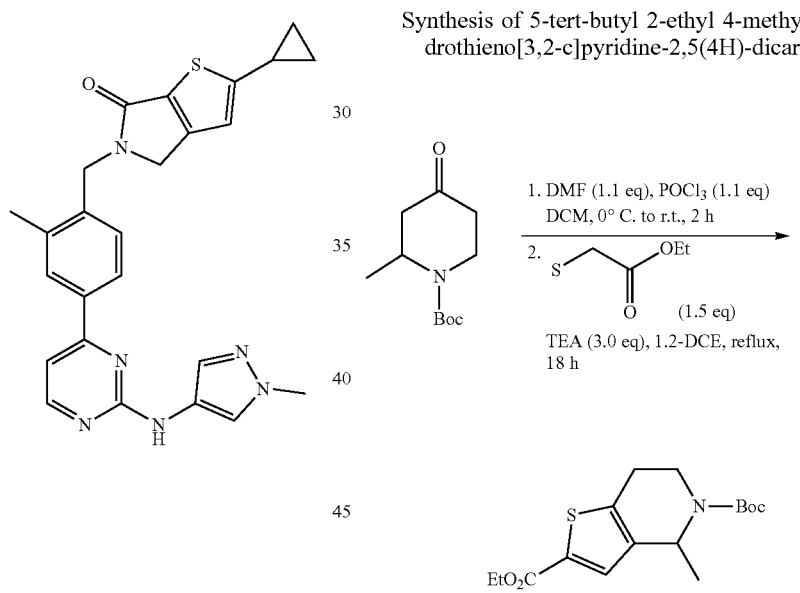

Synthesis of 2-cyclopropyl-5-(2-methyl-4-(2-((1-methyl-1H-pyrazol-4-yl)amino)pyrimidin-4-yl)benzyl)-4H-thieno[2,3-c]pyrrol-6(5H)-one was similar to that of tert-butyl 4-(2-chloropyrimidin-4-yl)-2-methylbenzylcarbamate in Example 1. The residue was purified by prep-HPLC (MeCN/H₂O with 10 mmol/L NH₄HCO₃ as mobile phase) to give the compound 2-cyclopropyl-5-(2-methyl-4-(2-((1-methyl-1H-pyrazol-4-yl)amino)pyrimidin-4-yl)benzyl)-4H-thieno[2,3-c]pyrrol-6(5H)-one (4 mg, yield: 9%) as a light yellow solid. ESI-MS (M+H)⁺: 457.1. ¹H NMR (400 MHz, CDCl₃) δ: 8.42 (d, J=4.8 Hz, 1H), 7.88 (s, 1H), 7.85 (s, 1H), 7.82 (d, J=7.6 Hz, 1H), 7.55 (s, 1H), 7.28 (d, J=8.0 Hz, 1H), 7.06 (d, J=4.8 Hz, 1H), 6.90 (s, 1H), 6.66 (s, 1H), 4.79 (s, 2H), 4.07 (s, 2H), 3.91 (s, 3H), 2.42 (s, 3H), 2.16-2.10 (m, 1H), 1.11-1.06 (m, 2H), 0.82-0.78 (m, 2H).

Example 14: 4-methyl-N-(2-methyl-4-(2-((1-methyl-1H-pyrazol-4-yl)amino)pyrimidin-4-yl)benzyl)-4,5,6,7-tetrahydrothieno[3,2-c]pyridine-2-carboxamide (I-14)

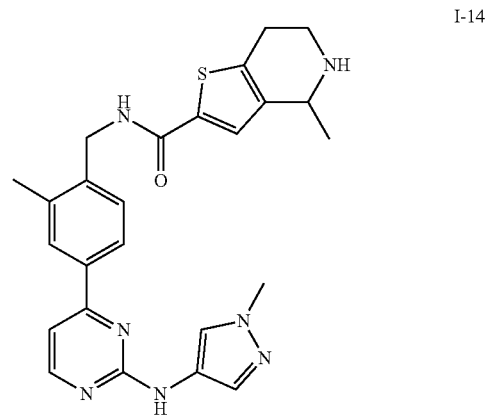 [SMILES: Cc1cc(-c2ccnc(Nc3cnn(C)c3)n2)ccc1CNC(=O)c1cc2c(s1)CCNC2C]

Synthesis of 5-tert-butyl 2-ethyl 4-methyl-6,7-dihydrothieno[3,2-c]pyridine-2,5(4H)-dicarboxylate Synthesis of 5-tert-butyl 2-ethyl 4-methyl-6,7-dihydrothieno[3,2-c]pyridine-2,5(4H)-dicarboxylate was similar to that of ethyl 6,7-dihydro-4H-thieno[3,2-c]pyran-2-carboxylate in Example 3, except tert-butyl 2-methyl-4-oxopiperidine-1-carboxylate was substituted for dihydro-2H-pyran-4(3H)-one. The mixture was purified by column chromatography (silica, petroleum ether/EtOAc=8:1) to give product (336 mg, yield: 44%) as a white liquid. ESI-MS (M+H-56)⁺: 270.1.

Synthesis of 5-(tert-butoxycarbonyl)-4-methyl-4,5,6,7-tetrahydrothieno[3,2-c]pyridine-2-carboxylic acid

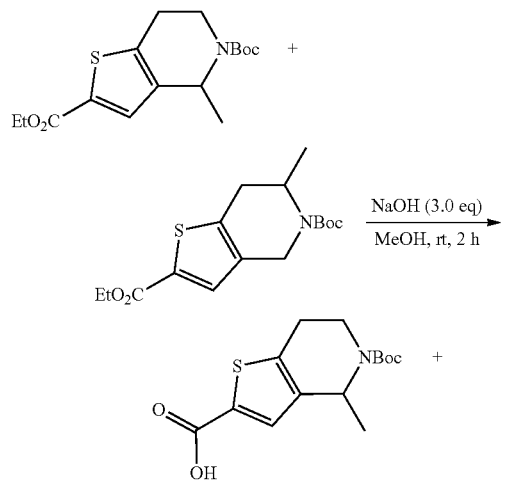

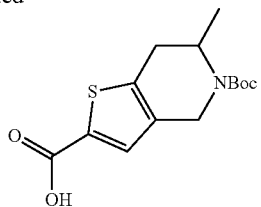

Synthesis of 5-(tert-butoxycarbonyl)-4-methyl-4,5,6,7-tetrahydrothieno[3,2-c]pyridine-2-carboxylic acid was similar to that of 6,7-dihydro-4H-thieno[3,2-c]pyran-2-carboxylic acid in Example 3. The crude product (240 mg, yield: 55%, white solid) was used in next step without further purification. ESI-MS (M+H-56)$^+$: 242.0. $^1$H NMR (400 MHz, CDCl$_3$) δ: 7.37 (s, 1H), 4.72-4.67 (m, 1H), 3.95-3.91 (m, 0.5H), 3.73-3.66 (m, 0.5H), 2.99-2.93 (m, 1H), 2.78-2.49 (m, 2H), 1.40-1.39 (m, 9H), 1.35 (d, J=6.8 Hz, 1.5H), 1.26 (d, J=6.8 Hz, 1.5H).

Synthesis of 4-methyl-N-(2-methyl-4-(2-((1-methyl-1H-pyrazol-4-yl)amino)pyrimidin-4-yl)benzyl)-4,5,6,7-tetrahydrothieno[3,2-c]pyridine-2-carboxamide

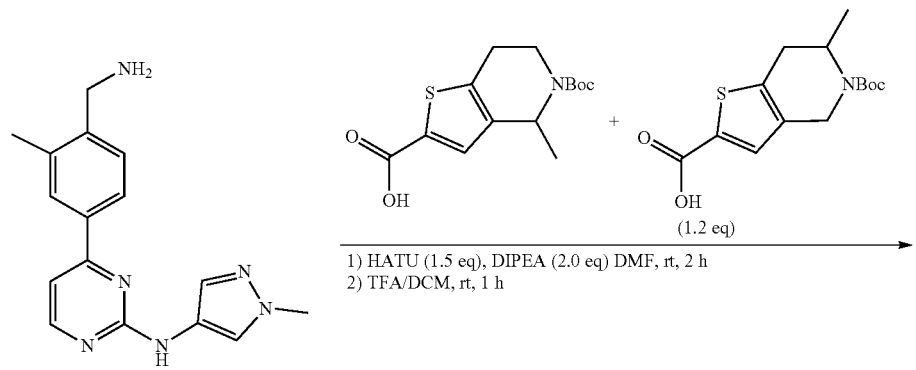

1) HATU (1.5 eq), DIPEA (2.0 eq) DMF, rt, 2 h
2) TFA/DCM, rt, 1 h

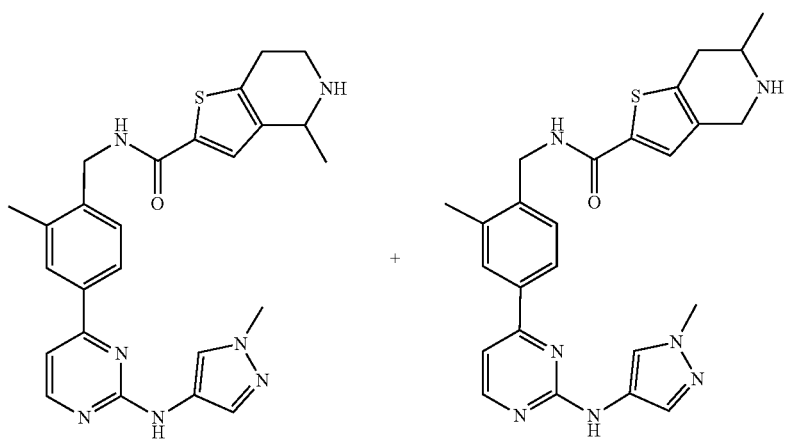

Synthesis of 4-methyl-N-(2-methyl-4-(2-((1-methyl-1H-pyrazol-4-yl)amino)pyrimidin-4-yl)benzyl)-4,5,6,7-tetrahydrothieno[3,2-c]pyridine-2-carboxamide was similar to that of Example I-73, except 5-(tert-butoxycarbonyl)-4-methyl-4,5,6,7-tetrahydrothieno[3,2-c]pyridine-2-carboxylic acid was substituted for 2-(tert-butyl)thiazole-5-carboxylic acid. The residue was purified by prep-HPLC (CH₃CN/H₂O with 0.05% NH₃.H₂O as mobile phase) to give 4-methyl-N-(2-methyl-4-(2-((1-methyl-1H-pyrazol-4-yl)amino)pyrimidin-4-yl)benzyl)-4,5,6,7-tetrahydrothieno[3,2-c]pyridine-2-carboxamide as a white solid (58 mg, yield: 77%). ESI-MS (M+H)$^+$: 474.1. HPLC: (214 nm: 97%, 254 nm: 100%). $^1$H NMR (400 MHz, DMSO-$d_6$) δ: 9.48 (s, 1H), 8.84-8.78 (m, 1H), 8.46-8.44 (m, 1H), 7.95-7.92 (m, 3H), 7.64 (s, 0.5), 7.54-7.53 (m, 1H), 7.52 (s, 0.5H), 7.39-7.36 (m, 1H), 7.25 (d, J=5.2 Hz, 1H), 4.48-4.46 (m, 2H), 3.82 (s, 3H), 3.81-3.71 (m, 1H), 3.23-3.09 (m, 1H), 2.92-2.61 (m, 2H), 2.41 (s, 3H), 2.39-2.31 (m, 1H), 1.28 (d, J=6.8 Hz, 1.5H), 1.15 (d, J=6.4 Hz, 1.5H).

Example 15: N-(2-methyl-4-(2-((1-methyl-1H-pyrazol-4-yl)amino)pyrimidin-4-yl)benzyl)-6,7-dihydro-5H-thieno[3,2-b]pyran-2-carboxamide (I-15)

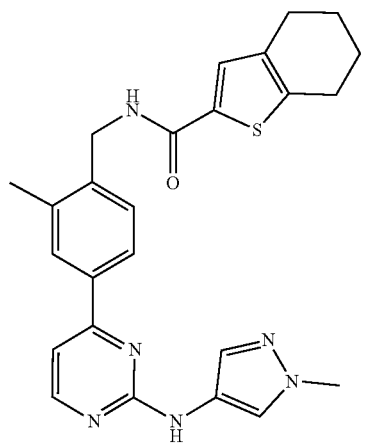

I-15

Synthesis of ethyl 6,7-dihydro-5H-thieno[3,2-b]pyran-2-carboxylate

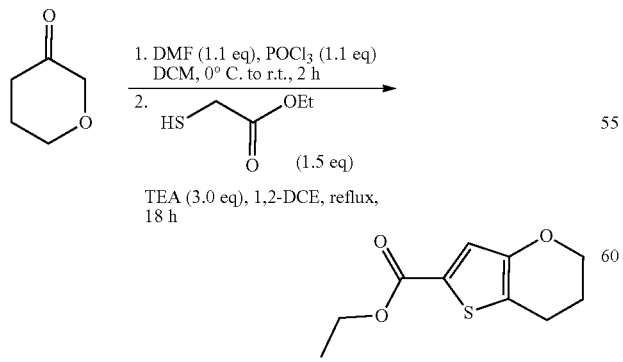

Synthesis of ethyl 6,7-dihydro-5H-thieno[3,2-b]pyran-2-carboxylate was similar to that of ethyl 6,7-dihydro-4H-thieno[3,2-c]pyran-2-carboxylate in Example 3, except dihydro-2H-pyran-3(4H)-one was substituted for dihydro-2H-pyran-4(3H)-one. The residue was purified by column chromatography (silica, petroleum ether/EtOAc=8:1) to give product ethyl 6,7-dihydro-5H-thieno[3,2-b]pyran-2-carboxylate (319 mg, yield: 30%) as a white liquid. ESI-MS (M+H)$^+$: 213.1. $^1$H NMR (400 MHz, CDCl₃) δ: 7.26 (s, 1H), 4.31 (q, J=7.2 Hz, 2H), 4.17 (t, J=5.2 Hz, 2H), 2.79 (t, J=6.8 Hz, 2H), 2.08-2.02 (m, 2H), 1.35 (t, J=6.8 Hz, 3H).

Synthesis of 6,7-dihydro-5H-thieno[3,2-b]pyran-2-carboxylic acid

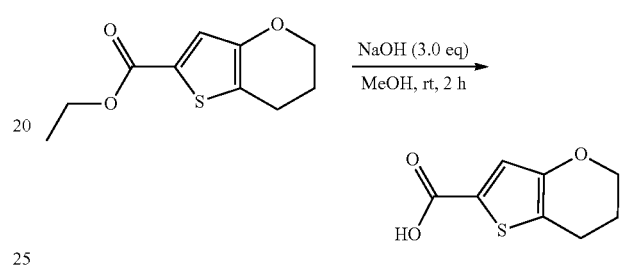

Synthesis of 6,7-dihydro-5H-thieno[3,2-b]pyran-2-carboxylic acid was similar to that of 6,7-dihydro-4H-thieno[3,2-c]pyran-2-carboxylic acid in Example 3. Crude product 6,7-dihydro-5H-thieno[3,2-b]pyran-2-carboxylic acid (225 mg, yield: 82%, white solid), which was used in next step without further purification. ESI-MS (M+H)$^+$: 185.0.

Synthesis of N-(2-methyl-4-(2-((1-methyl-1H-pyrazol-4-yl)amino)pyrimidin-4-yl)benzyl)-6,7-dihydro-5H-thieno[3,2-b]pyran-2-carboxamide

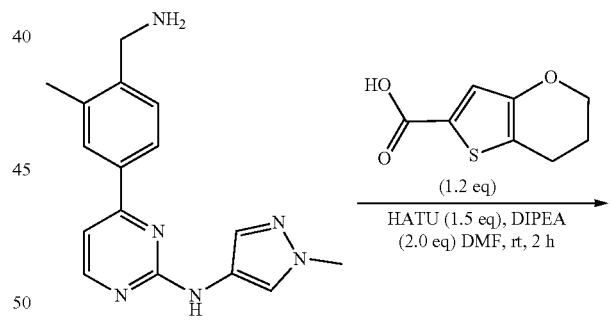

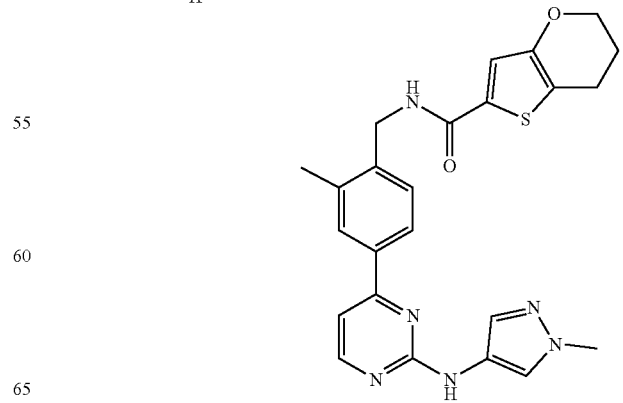

Synthesis of N-(2-methyl-4-(2-((1-methyl-1H-pyrazol-4-yl)amino)pyrimidin-4-yl)benzyl)-6,7-dihydro-5H-thieno[3,2-b]pyran-2-carboxamide was similar to that of Example 1, except 6,7-dihydro-5H-thieno[3,2-b]pyran-2-carboxylic acid was substituted for 2-(tert-butyl)thiazole-5-carboxylic acid. The residue was purified by prep-HPLC (CH$_3$CN/H$_2$O with 0.05% NH$_3$.H$_2$O as mobile phase) to give N-(2-methyl-4-(2-((1-methyl-1H-pyrazol-4-yl)amino)pyrimidin-4-yl)benzyl)-6,7-dihydro-5H-thieno[3,2-b]pyran-2-carboxamide as a white solid (44 mg, yield: 46%). ESI-MS (M+H)$^+$: 461.1. HPLC: (214 nm: 100%, 254 nm: 100%). $^1$H NMR (400 MHz, DMSO-d$_6$) δ: 9.47 (s, 1H), 8.86-8.83 (m, 1H), 8.45 (d, J=5.2 Hz, 1H), 7.95-7.92 (m, 3H), 7.54 (s, 1H), 7.40-7.36 (m, 2H), 7.25 (d, J=5.2 Hz, 1H), 4.47 (d, J=5.2 Hz, 2H), 4.13-4.11 (m, 2H), 3.82 (s, 3H), 2.74-2.71 (m, 2H), 2.41 (s, 3H), 1.98-1.93 (m, 2H).

Example 16: 1-methyl-N-(2-methyl-4-(2-((1-methyl-1H-pyrazol-4-yl)amino)pyrimidin-4-yl)benzyl)piperidine-4-carboxamide (I-16)

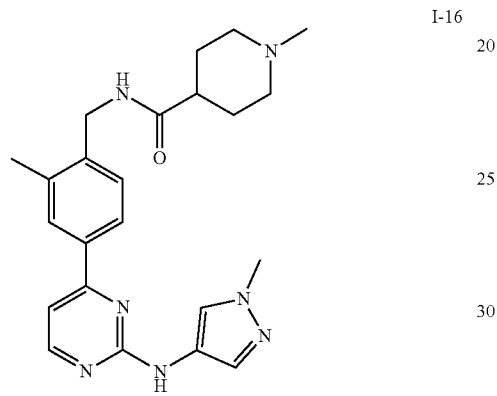

I-16

Synthesis of 1-methyl-N-(2-methyl-4-(2-((1-methyl-1H-pyrazol-4-yl)amino)pyrimidin-4-yl)benzyl)piperidine-4-carboxamide was similar to that of Example 1, except 1-methylpiperidine-4-carboxylic acid was substituted for 2-(tert-butyl)thiazole-5-carboxylic acid. The crude was filtrate through celite and washed with DMF and purified by prep HPLC to give product as a solid (118 mg, yield: 83%). LCMS: Rt=0.75, m/z 420.3. 1H NMR (400 MHz, DMSO-d6) δ: 9.49 (s, 1H), 8.32-8.57 (m, 2H), 7.78-8.11 (m, 3H), 7.58 (br. s., 1H), 7.11-7.42 (m, 2H), 4.32 (d, J=5.52 Hz, 2H), 3.82 (s, 3H), 2.61-3.71 (m, 6H), 2.54 (s, 3H), 2.37 (s, 3H), 1.56-2.14 (m, 3H).

Example 17: cis-N-(2-methyl-4-(2-((1-methyl-1H-pyrazol-4-yl)amino)pyrimidin-4-yl)benzyl)-4-(trifluoromethyl)cyclohexanecarboxamide (I-17)

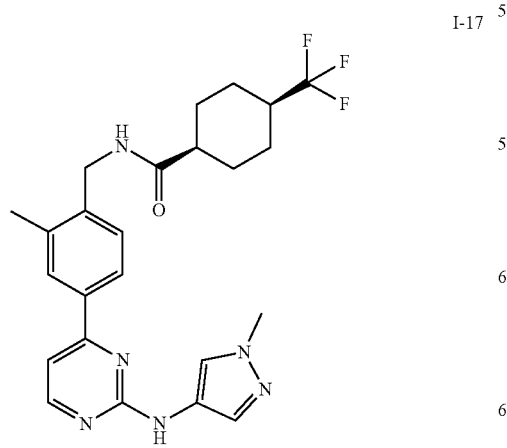

I-17

Synthesis of cis-N-(2-methyl-4-(2-((1-methyl-1H-pyrazol-4-yl)amino)pyrimidin-4-yl)benzyl)-4-(trifluoromethyl)cyclohexanecarboxamide was similar to that of Example 1, except cis-4-(trifluoromethyl)cyclohexanecarboxylic acid was substituted for 2-(tert-butyl)thiazole-5-carboxylic acid. The crude was purified by prep HPLC to give product as a solid (154 mg, yield:96%). LCMS: Rt=1.32 min, m/z 473.3. 1H NMR (400 MHz, DMSO-d$_6$) δ 9.48 (s, 1H), 8.45 (d, J=5.27 Hz, 1H), 8.24 (s, 1H), 7.82-8.00 (m, 3H), 7.55 (br. s., 1H), 7.32 (d, J=7.78 Hz, 1H), 7.26 (d, J=5.27 Hz, 1H), 4.31 (d, J=5.52 Hz, 2H), 3.80 (s, 3H), 2.54-2.74 (m, 1H), 2.37 (s, 3H), 1.11-2.29 (m, 9H).

Example 18. 5-methyl-N-(2-methyl-4-(2-((1-methyl-1H-pyrazol-4-yl)amino)pyrimidin-4-yl)benzyl)isoxazole-4-carboxamide (I-18)

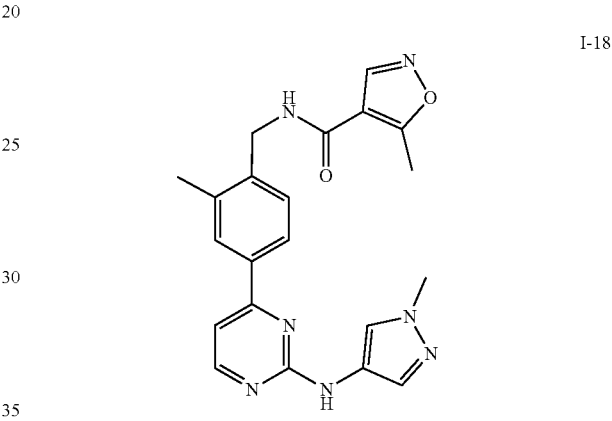

I-18

Synthesis of 5-methyl-N-(2-methyl-4-(2-((1-methyl-1H-pyrazol-4-yl)amino)pyrimidin-4-yl)benzyl)isoxazole-4-carboxamide was similar to that of Example 1, except 5-methylisoxazole-4-carboxylic acid was substituted for 2-(tert-butyl)thiazole-5-carboxylic acid. The crude was purified by prep HPLC to give product as a solid (62.1 mg, yield: 40%). LCMS: Rt=1.24 min, m/z 404.20. 1H NMR (300 MHz, DMSO-d6) δ: 9.49 (s, 1H), 8.46 (d, J=5.29 Hz, 1H), 7.94 (d, J=7.55 Hz, 3H), 7.55 (s, 1H), 7.33 (d, J=8.31 Hz, 1H), 7.25 (d, J=5.29 Hz, 1H), 4.43 (s, 2H), 3.83 (s, 3H), 2.40 (s, 3H), 2.26 (s, 3H).

Example 19: N-(2-methyl-4-(2-((1-methyl-1H-pyrazol-4-yl)amino)pyrimidin-4-yl)benzyl)-4-(trifluoromethyl)piperidine-1-carboxamide (I-19)

Scheme 2

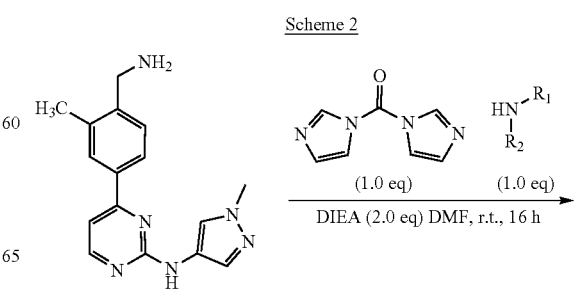

85

-continued

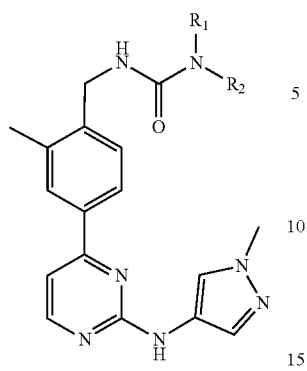

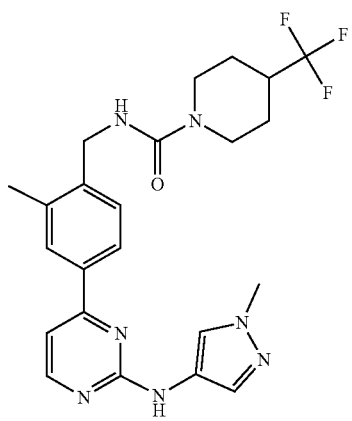

Synthesis of N-(2-methyl-4-(2-((1-methyl-1H-pyrazol-4-yl)amino)pyrimidin-4-yl)benzyl)-4-(trifluoromethyl)piperidine-1-carboxamide

86

-continued

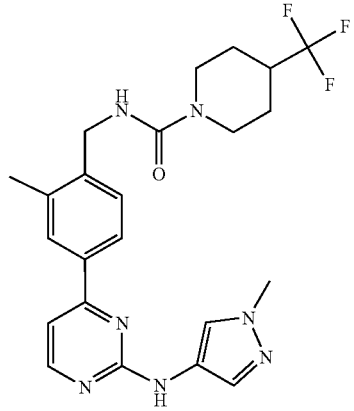

To a solution of 4-(4-(aminomethyl)-3-methylphenyl)-N-(1-methyl-1H-pyrazol-4-yl)pyrimidin-2-amine (80 mg, 0.24 mmol, 1.0 equiv) in DMF (2 mL) was added TEA (48 mg, 0.48 mmol, 2.0 equiv), the mixture was stirred at rt for 10 min. Then CDI (39 mg, 0.24 mmol, 1.0 eq) was added and the reaction mixture was stirred at rt for 1 h before 4-(trifluoromethyl)piperidine (48 mg, 0.48 mmol, 2.0 eq) was added. The mixture was stirred at room temperature for another 12 h. The mixture was purified by prep-HPLC (Gradient: 5% B increase to 95% B, A: 0.5% $NH_3$ in water, B: $CH_3CN$) to give N-(2-methyl-4-(2-((1-methyl-1H-pyrazol-4-yl)amino)pyrimidin-4-yl)benzyl)-4-(trifluoromethyl)piperidine-1-carboxamide (68 mg, yield: 52%) as a yellow solid. ESI-MS (M+H)$^+$:474.2. $^1$H NMR (400 MHz, $CDCl_3$) δ: 8.41 (d, J=5.2 Hz, 1H), 7.86-7.82 (m, 3H), 7.53 (s, 1H), 7.36 (d, J=7.6 Hz, 1H), 7.06-7.05 (m, 2H), 4.67 (t, J=5.2 Hz, 1H), 4.47 (d, J=5.6 Hz, 2H), 4.10-4.06 (m, 2H), 3.90 (s, 3H), 2.85-2.78 (m, 2H), 2.43 (s, 3H), 2.22-2.16 (m, 1H), 1.91-1.88 (m, 2H), 1.61-1.51 (m, 2H).

Example 20: 4-(tert-butyl)-N-(2-methyl-4-(2-((1-methyl-1H-pyrazol-4-yl)amino)pyrimidin-4-yl)benzyl)piperidine-1-carboxamide (I-20)

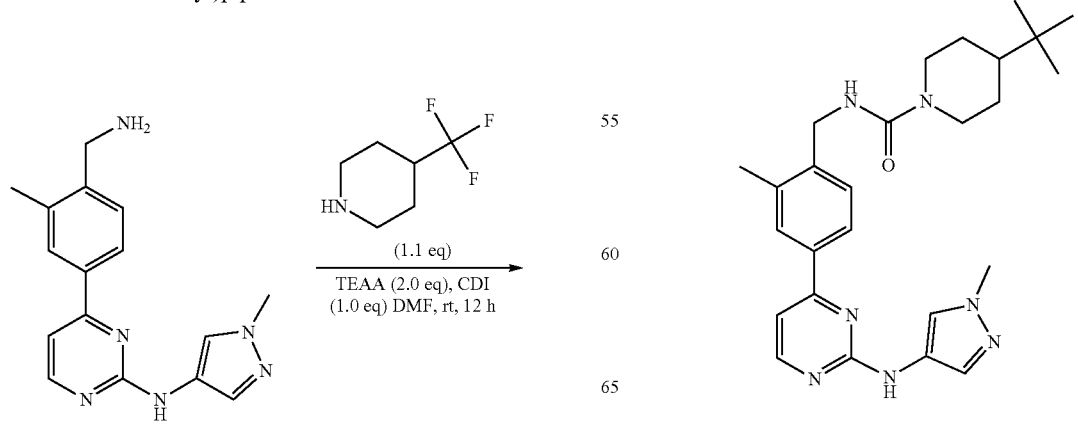

Synthesis of 4-(tert-butyl)piperidine

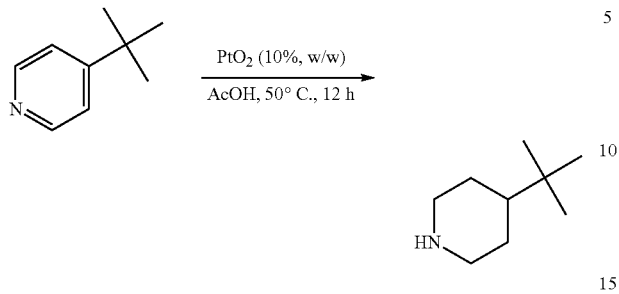

To a mixture of 4-(tert-butyl)pyridine (270 mg, 2 mmol, 1.0 equiv) in AcOH (5 mL) was added PtO₂ (27 mg, 10%). The mixture was stirred at 50° C. for 12 h under hydrogen atmosphere. The catalyst was filtered out and the resulting filtrate was concentrated to give 4-(tert-butyl)piperidine (130 mg, yield: 48%) as a yellow oil. ESI-MS (M+H): 142.2.

Synthesis of 4-(tert-butyl)-N-(2-methyl-4-(2-((1-methyl-1H-pyrazol-4-yl)amino)pyrimidin-4-yl)benzyl)piperidine-1-carboxamide

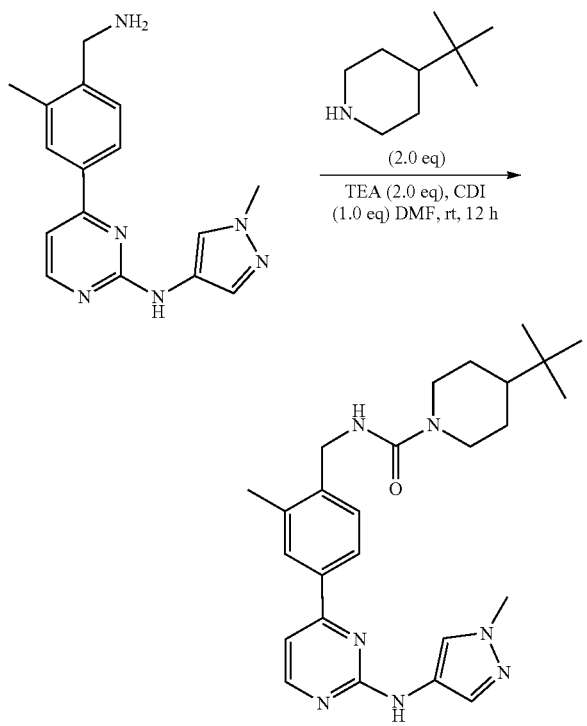

Synthesis of 4-(tert-butyl)-N-(2-methyl-4-(2-((1-methyl-1H-pyrazol-4-yl)amino)pyrimidin-4-yl)benzyl)piperidine-1-carboxamide was similar to that of Example 19, except 4-(tert-butyl)-piperidine was substituted for 4-(trifluoromethyl)piperidine. The mixture was purified by prep-HPLC (Gradient: 5% B increase to 95% B, A: 0.5% NH₃ in water, B: CH₃CN) to give 4-(tert-butyl)-N-(2-methyl-4-(2-((1-methyl-1H-pyrazol-4-yl)amino)pyrimidin-4-yl)benzyl)piperidine-1-carboxamide (73 mg, yield: 65%) as a white solid. ESI-MS (M+H)⁺:462.3. ¹H NMR (400 MHz, CDCl₃) δ: 8.41 (d, J=5.2 Hz, 1H), 7.88 (s, 1H), 7.84-7.82 (m, 2H), 7.55 (s, 1H), 7.38 (d, J=7.6 Hz, 1H), 7.06 (d, J=5.2 Hz, 1H), 6.87 (s, 1H), 4.61 (t, J=4.4 Hz, 1H), 4.48 (d, J=5.2 Hz, 2H), 4.03-4.00 (m, 2H), 3.91 (s, 3H), 2.76-2.71 (m, 2H), 2.43 (s, 3H), 1.71-1.68 (m, 2H), 1.24-1.14 (m, 3H), 0.86 (s, 9H).

Example 21: 3-isopropoxy-N-(2-methyl-4-(2-((1-methyl-1H-pyrazol-4-yl)amino)pyrimidin-4-yl)benzyl)azetidine-1-carboxamide (I-21)

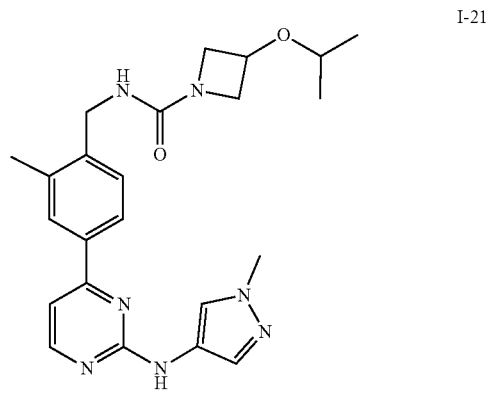 [SMILES: Cc1cc(-c2ccnc(Nc3cnn(C)c3)n2)ccc1CNC(=O)N1CC(OC(C)C)C1]

I-21

4-(4-(aminomethyl)-3-methylphenyl)-N-(1-methyl-1H-pyrazol-4-yl)pyrimidin-2-amine hydrochloride (prepared in Example 1) (200 mg, 0.7 mmol), 3-isopropoxy azetidine (113 mg, 0.747 mmol), and N,N-carbonyldiimidazole (0.110 g, 0.679 mmol) in N,N-dimethylformamide (1.58 mL, 20.4 mmol) was added N,N-diisopropylethylamine (0.473 mL, 2.72 mmol) slowly and stirred at room temperature overnight. The mixture was filtrate through celite and washed with DMF and purified by prep HPLC to give product as a solid (82 mg, yield: 30%). LCMS: Rt=1.05 min, m/z 436.3. 1H NMR (400 MHz, DMSO-d6) δ: 9.48 (s, 1H), 8.45 (d, J=5.02 Hz, 1H), 7.92 (s, 3H), 7.55 (br. s., 1H), 7.35 (d, J=8.53 Hz, 1H), 7.25 (d, J=5.27 Hz, 1H), 6.84 (s, 1H), 4.15-4.48 (m, 3H), 3.90-4.13 (m, 2H), 3.83 (s, 3H), 3.46-3.69 (m, 3H), 2.36 (s, 3H), 1.08 (d, J=6.27 Hz, 6H).

Example 21a: 3-((2-d-propan-2-yl)oxy)-N-(2-methyl-4-(2-((1-methyl-1H-pyrazol-4-yl)amino)pyrimidin-4-yl)benzyl)azetidine-1-carboxamide To a solution of N,N-carbonyldiimidazole (66.1 mg, 0.4077 mmol) in tetrahydrofuran (5 mL, 60 mmol) was added 4-(4-(aminomethyl)-3-methylphenyl)-N-(1-methyl-1H-pyrazol-4-yl)pyrimidin-2-amine (120.0 mg, 0.4077 mmol) and triethylamine (0.17 mL, 1.223 mmol). The mixture was stirred at RT for 2 h. 3-((2-d-propan-2-yl)oxy) azetidine hydrochloride (124.4 mg, 0.8153 mmol) was then added. The reaction mixture was stirred at rt overnight. The reaction mixture was diluted with EtOAc, washed with water. The organic phase was separated, dried and concentrated. The crude was purified by HPLC to give 3-((2-D-propan-2-yl)oxy)-N-(2-methyl-4-(2-((1-methyl-1H-pyrazol-4-yl)amino)pyrimidin-4-yl)benzyl)azetidine-1-carboxamide as a yellow powder (155 mg, TFA salt, yield: 87%). LCMS: RT 1.06 min.; MH+437.2; ¹H NMR (400 MHz, DMSO-d6) δ 9.53 (s, 1H), 8.45 (d, J=5.27 Hz, 1H), 7.93 (s, 3H), 7.56 (br. s., 1H), 7.36 (d, J=8.28 Hz, 1H), 7.26 (d, J=5.27 Hz, 1H), 6.85 (t, J=5.27 Hz, 1H), 4.27-4.38 (m, 1H), 4.23 (d, J=4.77 Hz, 2H), 3.98-4.09 (m, 2H), 3.83 (s, 3H), 3.62 (dd, J=4.64, 8.66 Hz, 2H), 2.37 (s, 3H), 1.07 (s, 6H).

Example 21b: 3-isopropoxy-N-(2-methyl-4-(2-((1-d₃-methyl-1H-pyrazol-4-yl)amino)pyrimidin-4-yl)benzyl)azetidine-1-carboxamide 1. Synthesis of 1-(d₃-methyl-1H-pyrazol-4-amine

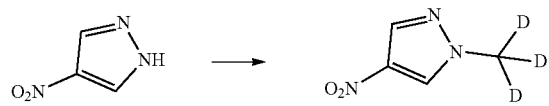 [SMILES: O=[N+]([O-])c1cn[nH]c1 ; [2H]C([2H])([2H])n1cc([N+](=O)[O-])cn1]

A mixture of 4-nitro-1H-pyrazole (5.0 g, 44 mmol) and d₆-dimethyl sulfate (10.0 g, 75.7 mmol) in 1 M solution of NaOH in water (50.0 mL) was heated at 35° C. overnight. The solid formed was filtered, washed with water, and dried (Na₂SO₄) to give 1-d₃-methyl-4-nitro-1H-pyrazole as a white crystal (3.9 g, yield: 68%). LCMS: RT 0.36 min.; MH+131.1; ¹H NMR (400 MHz, DMSO-d6) δ: 8.84 (s, 1H), 8.23 (s, 1H).

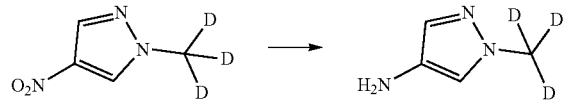 [SMILES: [2H]C([2H])([2H])n1cc([N+](=O)[O-])cn1 ; [2H]C([2H])([2H])n1cc(N)cn1]

A solution of 1-d₃-methyl-4-nitro-1H-pyrazole (3.9 g, 30 mmol) in EtOH (50.0 mL) was degassed with nitrogen, followed by the addition of 10% palladium on carbon (0.32 g, 0.30 mmol). The mixture was placed under an atmosphere of H₂ and stirred at rt for 2 h. The mixture was filtered and the filtrate was concentrated in vacuo to give 1-(d₃-methyl-1H-pyrazol-4-amine as an oil (2.9 g, yield: 96%) which was used in the next step without further purification.

2. Synthesis of N-(4-(2-chloropyrimidin-4-yl)-2-methylbenzyl)-3-isopropoxyazetidine-1-carboxamide

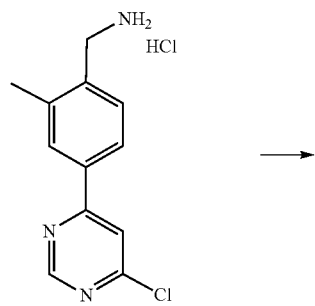

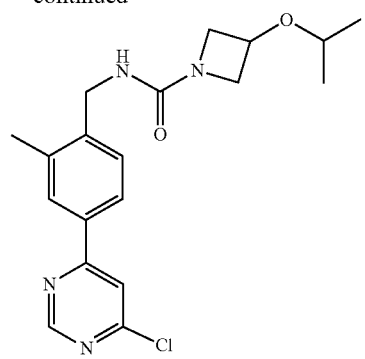

To solution of N,N-carbonyldiimidazole (1.20 g, 7.40 mmol) in THF (100 mL) was added a solution of (4-(2-chloropyrimidin-4-yl)-2-methylphenyl)methanamine hydrochloride (2.0 g, 7.40 mmol) and Et₃N (1.0 mL, 7.40 mmol). The mixture was stirred at rt for 12 h, followed by the addition of 3-isopropoxyazetidine hydrochloride (1.12 g, 7.40 mmol) and Et₃N (2.1 mL, 14.8 mmol), and then stirred at rt for 12 h. The solvent was removed in vacuo to afford the crude which was purified by silica gel chromatography (EtOAc/heptane gradient) to give N-(4-(2-chloropyrimidin-4-yl)-2-methylbenzyl)-3-isopropoxyazetidine-1-carboxamide as a white powder (1.68 g, yield: 60%). LCMS: RT 1.40 min.; MH+375.1; ¹H NMR (400 MHz, DMSO-d6) δ: 9.06 (d, J=0.75 Hz, 1H), 8.28 (s, 1H), 7.99-8.13 (m, 2H), 7.36 (d, J=8.53 Hz, 1H), 6.87 (t, J=5.77 Hz, 1H), 4.16-4.41 (m, 3H), 4.04 (dd, J=6.78, 8.53 Hz, 2H), 3.51-3.69 (m, 3H), 2.36 (s, 3H), 1.08 (d, J=6.27 Hz, 6H).

A mixture of N-(4-(2-chloropyrimidin-4-yl)-2-methylbenzyl)-3-isopropoxyazetidine-1-carboxamide (150 mg, 0.40 mmol) and 1-methyl-d3-1H-pyrazol-4-amine (52 mg, 0.52 mmol) in PhCH₃ (4 mL) was degassed with nitrogen for 5 min, then 2-dicyclohexylphosphino-2',6'-dimethoxybiphenyl (16 mg, 0.04 mmol) and tris(dibenzylideneacetone)dipalladium(0) (18 mg, 0.02 mmol) and sodium tert-butoxide (77 mg, 0.80 mmol) were added and degassed for another 5 min, and the reaction was heated in a sealed tube at 100° C. for 1 h. The reaction was then cooled to rt, diluted with EtOAc, and washed with water and the organic phase was separated, dried (Na₂SO₄), and concentrated in vacuo to afford the crude which was purified by HPLC to give 3-isopropoxy-N-(2-methyl-4-(2-((1-d₃-methyl-1H-pyrazol-4-yl)amino)pyrimidin-4-yl)benzyl)azetidine-1-carboxamide as a light yellow powder (78 mg, yield: 43%). LCMS: RT 1.05 min.; MH+439.1; ¹H NMR (400 MHz, DMSO-d6) δ: 9.48 (s, 1H), 8.45 (d, J=5.02 Hz, 1H), 7.92 (s, 3H), 7.55 (br. s., 1H), 7.35 (d, J=8.28 Hz, 1H), 7.25 (d, J=5.27 Hz, 1H), 6.84 (t, J=5.65 Hz, 1H), 4.27-4.37 (m, 1H), 4.23 (d, J=5.52 Hz, 2H), 3.99-4.09 (m, 2H), 3.51-3.68 (m, 3H), 2.37 (s, 3H), 1.08 (d, J=6.02 Hz, 6H).

Example 21c: 3-(1,1,1,3,3,3-d6)isopropoxy-N-(2-methyl-4-(2-((1-methyl-1H-pyrazol-4-yl)amino)pyrimidin-4-yl)benzyl)azetidine-1-carboxamide 1. Synthesis of 3-(1,1,1,3,3,3-d6)isopropoxyazetidine Hydrochloride

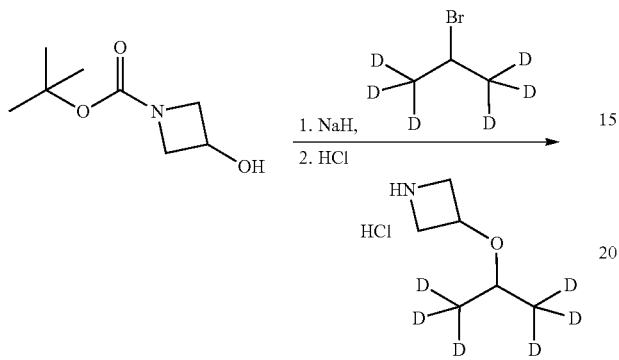

Sodium hydride (1.4 g, 35 mmol) was added to a solution of tert-butyl 3-hydroxyazetidine-1-carboxylate (2.0 g, 12 mmol) in DMF (50 mL, 600 mmol) and stirred at rt for 3 h before 2-bromopropane-1,1,1,3,3,3-d6 (1.6 mL, 2.2 g, 17 mmol) was added and heated at 80° C. for 12 h. LC-MS showed the formation of the desired product (1.45 min, very weak at 214 nM and no absorption at 254 nM, ES+/166.2 (M-Boc), 244.1 (M+Na), 267.2 (M+2Na), and 465.4 (2M+Na)) and remaining starting material (0.84 min, ES+/369.2 (2M+Na)). Another portion of 2-bromopropane-1,1,1,3,3,3-d6 (1.6 mL, 2.2 g, 17 mmol) was added and the reaction was heated for 3 h until reaction was shown to be completed by LCMS. The reaction was cooled down to rt, and diluted with diethyl ether and water. The organic phase was separated, dried (MgSO$_4$), concentrated in vacuo and purified by silica gel chromatography (EtOAc/Heptane) to give the product as a colorless liquid. 1H NMR (400 MHz, CDCl$_3$) δ: 1.43 (s, 9H), 3.80 (d, J=4.52 Hz, 2H), 3.88-3.97 (m, 1H), 4.12 (s, 2H), 4.46-4.62 (m, 1H).

To a solution of 3-(1,1,1,3,3,3-d6)isopropoxyazetidine-1 (2.5 g, 11 mmol) in 1,4-dioxane (50 mL, 600 mmol) was added a solution of 4 M of HCl in 1,4-Dioxane (12 mL, 46 mmol) and stirred for 12 h. The solvent was removed and the residue was triturated with diethyl ether to afford a solid which was filtered, washed with diethyl ether and dried to give the product as a white solid (1.5 g, yield: 84% as HCl salt). 1H NMR (400 MHz, DMSO-d6) δ: 3.60 (s, 1H) 3.66-3.82 (m, 2H) 4.09 (dd, J=11.55, 6.78 Hz, 2H) 4.40 (quin, J=6.46 Hz, 1H) 9.17 (br. s., 1H).

2. Synthesis of 3-(1,1,1,3,3,3-d6)isopropoxy-N-(2-methyl-4-(2-((1-methyl-1H-pyrazol-4-yl)amino)pyrimidin-4-yl)benzyl)azetidine-1-carboxamide To a solution of 4-(4-(aminomethyl)-3-methylphenyl)-N-(1-methyl-1H-pyrazol-4-yl)pyrimidin-2-amine hydrochloride (0.2 g, 0.6 mmol) and DIEA (0.53 mL, 3.0 mmol) in DMF (10 mL, 100 mmol) was added dropwise to a solution of CDI (0.11 g, 0.66 mmol) in DMF (2 mL, 20 mmol) at rt. To the solution was added 3-(1,1,1,3,3,3-d6)isopropoxyazetidine (0.081 g, 0.66 mmol) HCl salt and stirred at rt for 48 h. The reaction was diluted with water and extracted with EtOAc, dried (MgSO$_4$), and concentrated in vacuo to afford the crude which was purified with prep HPLC (CH$_3$CN/H$_2$O with 0.05% TFA as mobile phase) to give the desired product as a yellow solid (80 mg, yield: 30% as TFA salt). MS ES+/442.1; 1H NMR (400 MHz, DMSO-d6) δ: 9.46 (s, 1H) 8.45 (d, J=5.02 Hz, 1H) 7.92 (s, 3H) 7.55 (br. s., 1H) 7.35 (d, J=8.03 Hz, 1H) 7.24 (d, J=5.02 Hz, 1H) 6.84 (t, J=5.77 Hz, 1H) 4.27-4.38 (m, 1H) 4.23 (d, J=5.52 Hz, 2H) 4.00-4.09 (m, 2H) 3.83 (s, 3H) 3.62 (dd, J=8.78, 4.52 Hz, 2H) 3.56 (s, 1H) 2.37 (s, 3H).

Example 22: 1-(bicyclo[2.2.2]octan-1-yl)-3-(2-methyl-4-(2-((1-methyl-1H-pyrazol-4-yl)amino)pyrimidin-4-yl)benzyl)urea (I-22)

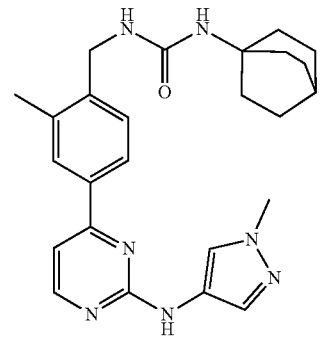

I-22

Synthesis of 1-(bicyclo[2.2.2]octan-1-yl)-3-(2-methyl-4-(2-((1-methyl-1H-pyrazol-4-yl)amino)pyrimidin-4-yl)benzyl)urea was similar to that of Example 19, except bicyclo[2.2.2]octan-1-amine was substituted for 4-(trifluoromethyl)piperidine. The mixture was filtrate through celite and washed with DMF and purified by prep HPLC to give product as a solid (17 mg, yield: 6%). LCMS: Rt=1.32 min, m/z 446.2. 1H NMR (400 MHz, DMSO-d6) δ: 9.49 (s, 1H), 8.45 (d, J=5.27 Hz, 1H), 7.93 (br. s., 3H), 7.55 (br. s., 1H), 7.33 (d, J=8.03 Hz, 1H), 7.25 (d, J=5.27 Hz, 1H), 4.19 (br. s., 2H), 3.82 (s, 3H), 2.35 (s, 3H), 1.73 (d, J=11.55 Hz, 6H), 1.58 (d, J=7.28 Hz, 6H), 1.49 (br. s., 1H).

Example 23: 4-(tert-butyl)-N-(2-methyl-4-(2-((1-methyl-1H-pyrazol-4-yl)amino)pyrimidin-4-yl)benzyl)piperazine-1-carboxamide (I-23)

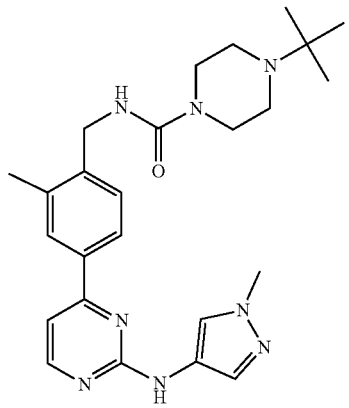

I-23

Synthesis of 4-(tert-butyl)-N-(2-methyl-4-(2-((1-methyl-1H-pyrazol-4-yl)amino)pyrimidin-4-yl)benzyl)piperazine-1-carboxamide was similar to that of Example 19, except 1-(tert-butyl)piperazine was substituted for 4-(trifluoromethyl)piperidine. The mixture was filtrate through celite and washed with DMF and purified by prep HPLC to give product as a solid (39.7 mg, yield: 10%). LCMS: Rt=0.8 min, m/z 463.3. 1H NMR (400 MHz, DMSO-d6) δ: 9.47 (s, 1H), 8.46 (d, J=5.27 Hz, 1H), 7.81-8.02 (m, 3H), 7.03-7.51 (m, 3H), 4.30 (d, J=5.27 Hz, 2H), 4.21 (d, J=13.80 Hz, 2H), 3.38-3.73 (m, 2H), 2.81-3.24 (m, 4H), 2.26-2.44 (m, 3H), 1.09-1.43 (m, 9H).

Example 24: 2-isopropyl-N-(2-methyl-4-(2-((1-methyl-1H-pyrazol-4-yl)amino)pyrimidin-4-yl)benzyl)morpholine-4-carboxamide (I-24)

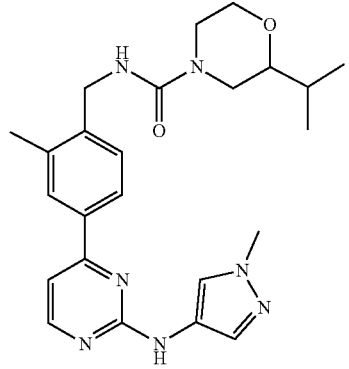

I-24

Synthesis of 2-isopropyl-N-(2-methyl-4-(2-((1-methyl-1H-pyrazol-4-yl)amino)pyrimidin-4-yl)benzyl)morpholine-4-carboxamide was similar to that of Example 19, except 2-isopropylmorpholine was substituted for 4-(trifluoromethyl)piperidine. The mixture was filtrate through celite and washed with DMF and purified by prep HPLC to give product as a solid (69 mg, yield: 20%). LCMS: Rt=1.17 min, m/z 450.3. 1H NMR (400 MHz, DMSO-d6) δ: 9.48 (s, 1H), 8.45 (d, J=5.27 Hz, 1H), 7.92 (s, 3H), 7.56 (br. s., 1H), 7.35 (d, J=8.28 Hz, 1H), 7.25 (d, J=5.27 Hz, 1H), 7.08 (t, J=5.27 Hz, 1H), 4.29 (d, J=5.02 Hz, 2H), 3.70-4.03 (m, 6H), 3.41 (d, J=2.51 Hz, 1H), 2.90-3.08 (m, 1H), 2.69-2.88 (m, 1H), 2.52-2.62 (m, 1H), 2.38 (s, 3H), 1.64 (qd, J=6.78, 13.55 Hz, 1H), 0.91 (dd, J=6.78, 10.54 Hz, 6H).

Example 25: 2-(tert-butyl)-N-(2-methyl-4-(2-((1-methylpiperidin-4-yl)amino)pyrimidin-4-yl)benzyl)thiazole-5-carboxamide (I-25)

Scheme 3

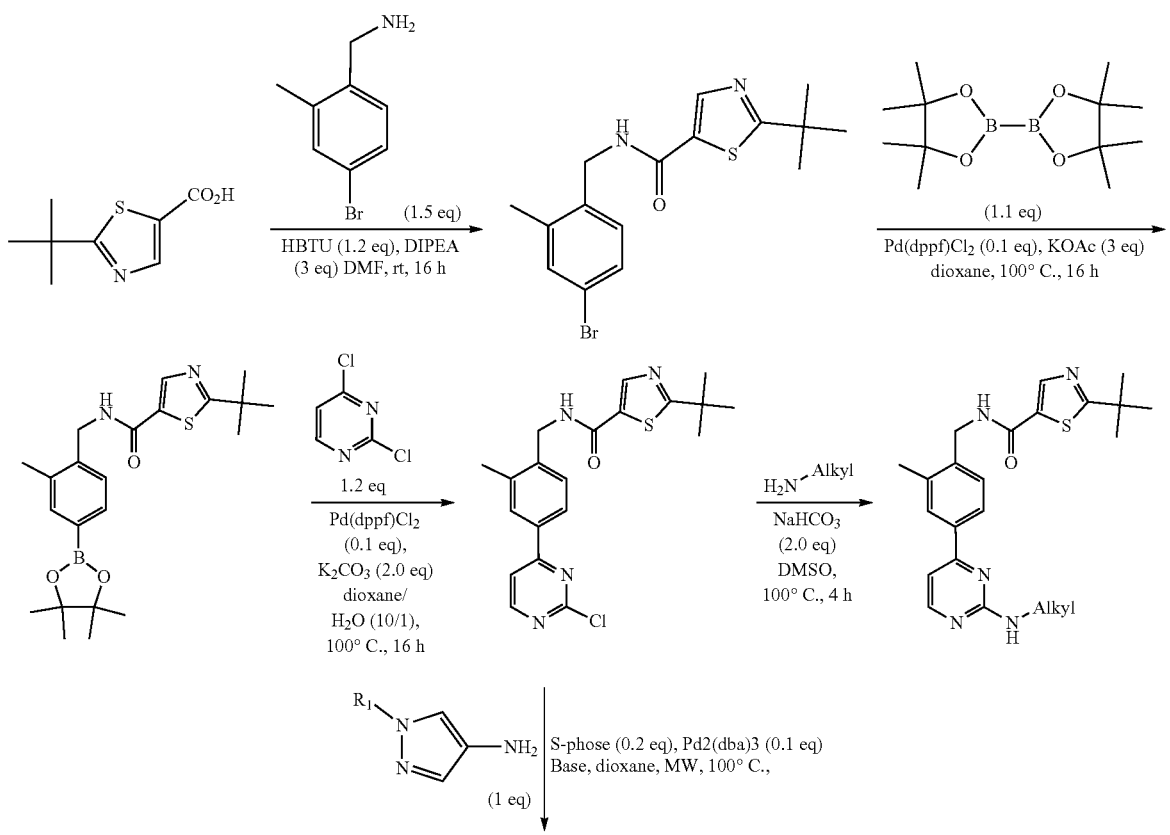

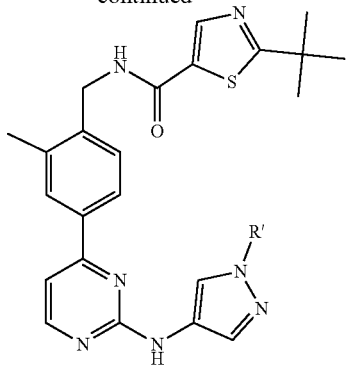

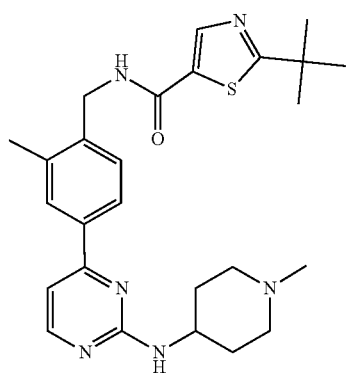

I-25

Synthesis of N-(4-bromo-2-methylbenzyl)-2-(tert-butyl)thiazole-5-carboxamide

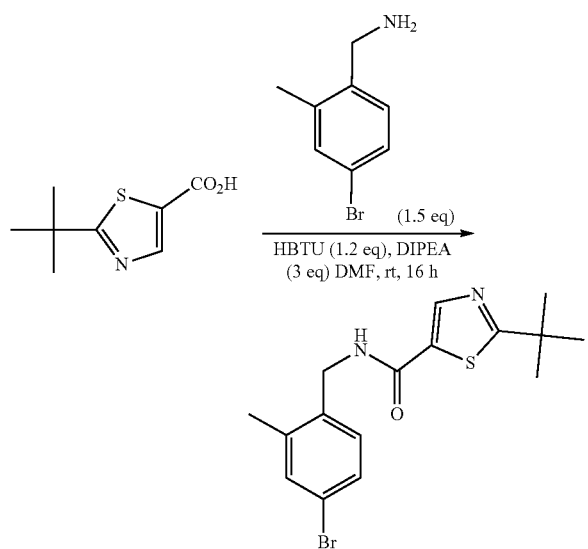

A mixture of 2-(tert-butyl)thiazole-5-carboxylic acid (185 mg, 1.0 mmol), HBTU (455 mg, 1.2 mmol) and DIPEA (387 mg, 3.0 mmol) in DMF (5 mL) was stirred at rt for 15 min. Then (4-bromo-2-methylphenyl)methanamine (300 mg, 1.5 mmol) was added. The resulting mixture was stirred at rt for 16 h. After diluted with water (40 mL), the mixture was extracted with EtOAc (80 mL×2). The organic phase was concentrated and the residue was purified by silica gel column chromatography (petroleum ether/EtOAc=10:1-4:1) to give N-(4-bromo-2-methylbenzyl)-2-(tert-butyl)thiazole-5-carboxamide (220 mg, yield: 60%) as a yellow solid. ESI-MS (M+H)$^+$: 367.1. $^1$H NMR (400 MHz, CDCl$_3$) δ: 8.20 (s, 1H), 7.35 (d, J=1.6 Hz, 1H), 7.32 (dd, J=8.0, 1.6 Hz, 1H), 7.17 (d, J=8.4 Hz, 1H), 4.55 (d, J=5.6 Hz, 2H), 2.34 (s, 3H), 1.47 (s, 9H).

Synthesis of 2-(tert-butyl)-N-(2-methyl-4-(4,4,5,5-tetramethyl-1,3,2-dioxaborolan-2-yl)benzyl)thiazole-5-carboxamide

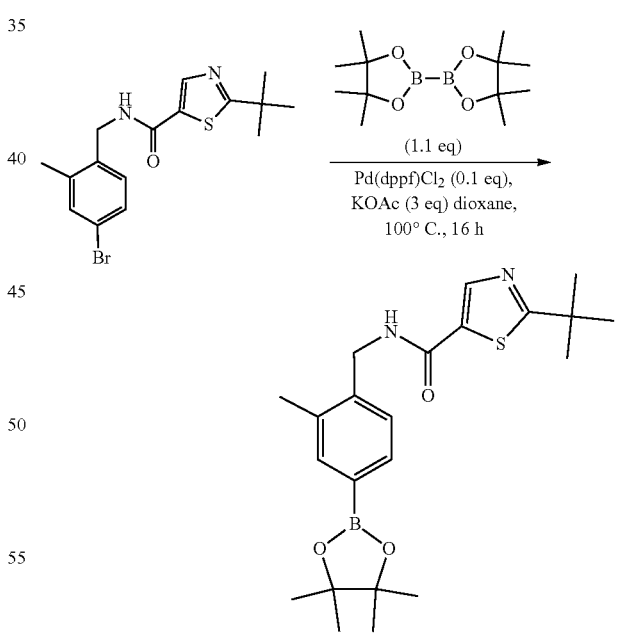

A mixture of N-(4-bromo-2-methylbenzyl)-2-(tert-butyl)thiazole-5-carboxamide (220 mg, 0.6 mmol), KOAc (176 mg, 1.8 mmol) and Pd(dppf)Cl$_2$DCM (130 mg, 0.06 mmol), bis(pinacolato)diboron (168 mg, 0.66 mmol) in dry 1,4-dioxane (6 mL) was stirred at 100° C. for 16 h under nitrogen. After cooling down to rt, the mixture was diluted with water (20 mL) and extracted with ethyl acetate (50 mL×2). The combined organic layer was washed with brine, dried, concentrated and purified by silica gel column (petroleum ether/EtOAc=4:1) to give 2-(tert-butyl)-N-(2-methyl-4-(4,4,5,5-tetramethyl-1,3,2-dioxaborolan-2-yl)benzyl)thiazole-5-carboxamide (188 mg, yield: 75%) as a white solid. ESI-MS (M+H)+: 415.0. ¹H NMR (400 MHz, CDCl₃) δ: 8.02 (s, 1H), 7.66 (s, 1H), 7.64 (d, J=8.0 Hz, 1H), 7.29 (d, J=8.0, 1H), 6.00 (br, 1H), 4.62 (d, J=5.6 Hz, 2H), 2.36 (s, 3H), 1.44 (s, 9H), 1.35 (s, 12H).

Synthesis of 2-(tert-butyl)-N-(4-(2-chloropyrimidin-4-yl)-2-methylbenzyl)thiazole-5-carboxamide

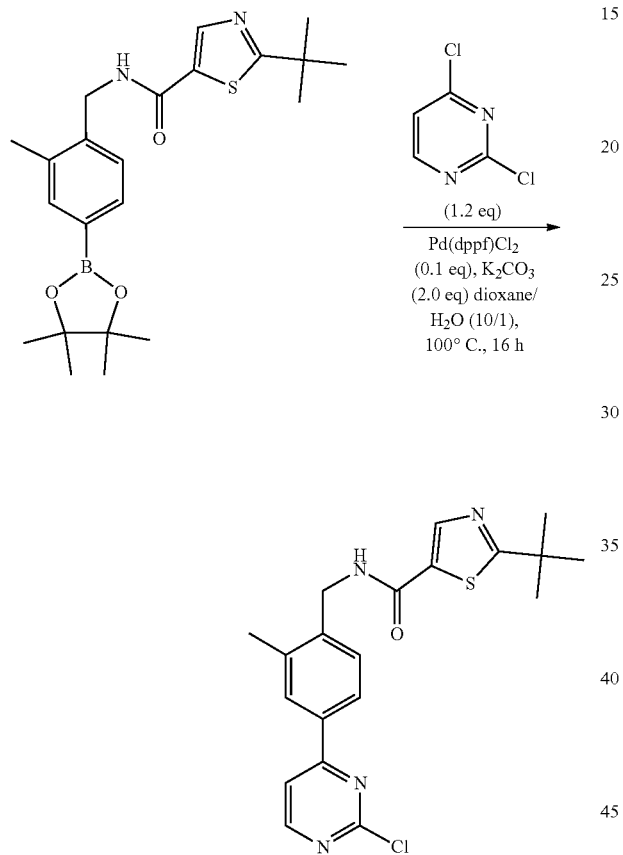

To a solution of 2-(tert-butyl)-N-(2-methyl-4-(4,4,5,5-tetramethyl-1,3,2-dioxaborolan-2-yl)benzyl)thiazole-5-carboxamide (188 mg, 0.45 mmol) in dioxane/H₂O (4:1) (5 mL) was added 2,4-dichloropyrimidine (80 mg, 0.54 mmol) followed by Pd(dppf)Cl₂ DCM (44 mg, 0.045 mmol) and K₂CO₃ (124 mg, 0.9 mmol) under nitrogen. The mixture was stirred at 100° C. for 16 h. After cooling to rt, the mixture was diluted with water and extracted with EtOAc (60 mL×2). The organic layer was washed with brine (40 mL), dried (Na₂SO₄), filtered and concentrated. The residue was purified by column chromatography (silica, petroleum ether/EtOAc=3:1) to give 2-(tert-butyl)-N-(4-(2-chloropyrimidin-4-yl)-2-methylbenzyl)thiazole-5-carboxamide as a light yellow solid (144 mg, yield: 80%). ESI-MS (M+H)+: 401.2

The preparation of 2-(tert-butyl)-N-(2-methyl-4-(2-((1-methylpiperidin-4-yl)amino)pyrimidin-4-yl)benzyl)thiazole-5-carboxamide

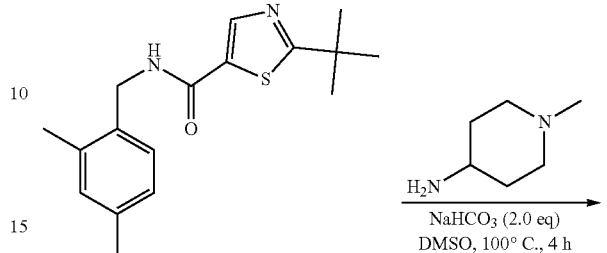

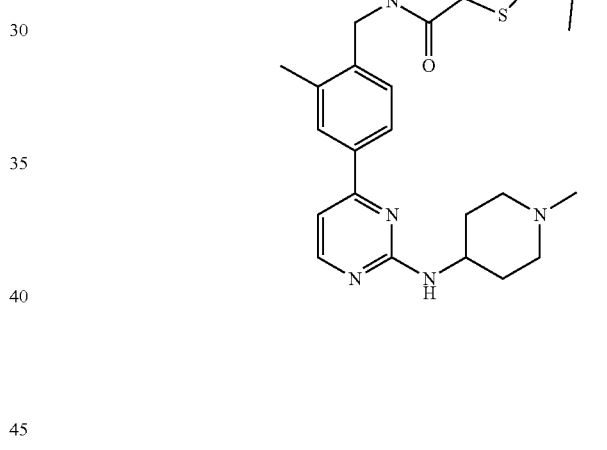

A mixture of 2-(tert-butyl)-N-(4-(2-chloropyrimidin-4-yl)-2-methylbenzyl)thiazole-5-carboxamide (60 mg, 0.15 mmol), 1-methylpiperidin-4-amine (0.3 mmol) and sodium bicarbonate (26 mg, 0.3 mmol) in DMSO (2 mL) was stirred at 100° C. for 4 h. The solid was filtered off and the filtrate was purified by prep-HPLC (CH₃CN/H₂O with 0.05% NH₃.H₂O as mobile phase) to give 2-(tert-butyl)-N-(2-methyl-4-(2-((1-methylpiperidin-4-yl)amino)pyrimidin-4-yl)benzyl)thiazole-5-carboxamide (40 mg, yield: 56%) as a yellow solid. ESI-MS (M+H)+: 479.3. ¹H NMR (400 MHz, CD₃OD) δ: 8.16 (d, J=5.2 Hz, 1H), 8.13 (s, 1H), 7.82 (s, 1H), 7.79 (d, J=7.6 Hz, 1H), 7.29 (d, J=8.0 Hz, 1H), 6.98 (d, J=5.6 Hz, 1H), 4.50 (s, 2H), 3.81-3.79 (m, 1H), 2.82-2.79 (m, 2H), 2.35 (s, 3H), 2.22 (s, 3H), 2.19-2.13 (m, 2H), 1.99-1.96 (m, 2H), 1.58-1.50 (m, 2H), 1.35 (s, 9H).

Example 26: 2-(tert-butyl)-N-(2-methyl-4-(2-((tetrahydro-2H-pyran-4-yl)amino)pyrimidin-4-yl)benzyl)thiazole-5-carboxamide (I-26)

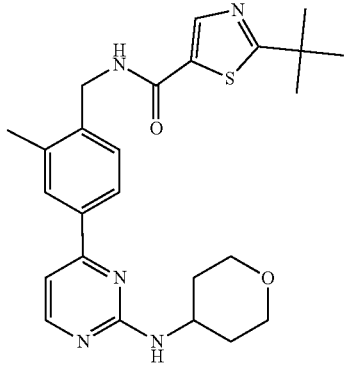

I-26

Synthesis of 2-(tert-butyl)-N-(2-methyl-4-(2-((tetrahydro-2H-pyran-4-yl)amino)pyrimidin-4-yl)benzyl)thiazole-5-carboxamide was similar to that of Example 25, except tetrahydro-2H-pyran-4-amine was substituted for 1-methylpiperidin-4-amine. The crude was purified by prep-HPLC (MeOH/H$_2$O with 0.05% NH$_3$.H$_2$O as mobile phase) to give the compound 2-(tert-butyl)-N-(2-methyl-4-(2-((tetrahydro-2H-pyran-4-yl)amino)pyrimidin-4-yl)benzyl)thiazole-5-carboxamide (80 mg, yield: 63%) as a yellow solid. ESI-MS (M+H)$^+$: 466.2. $^1$H NMR (400 MHz, CD$_3$OD) δ: 8.27 (d, J=5.2 Hz, 1H), 8.24 (s, 1H), 7.92-7.89 (m, 2H), 7.40 (d, J=8.0 Hz, 1H), 7.09 (d, J=5.6 Hz, 1H), 4.61 (s, 2H), 4.10-4.01 (m, 1H), 4.01-3.98 (m, 2H), 3.60-3.56 (m, 2H), 2.45 (s, 3H), 2.04-2.01 (m, 2H), 1.65-1.61 (m, 2H), 1.46 (s, 9H).

Example 27: (R)-2-(tert-butyl)-N-(4-(2-((1-cyclohexylethyl)amino)pyrimidin-4-yl)-2-methylbenzyl)thiazole-5-carboxamide (I-27)

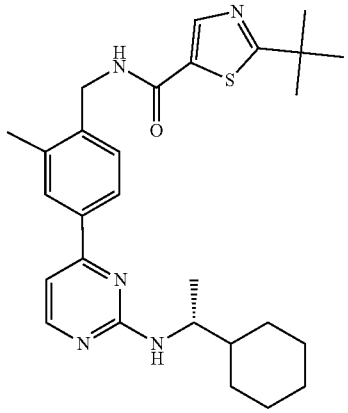

I-27

Synthesis of (R)-2-(tert-butyl)-N-(4-(2-((1-cyclohexylethyl)amino)pyrimidin-4-yl)-2-methylbenzyl)thiazole-5-carboxamide was similar to that of Example 25, except (R)-1-cyclohexylethyl)amine was substituted for 1-methylpiperidin-4-amine. The crude was purified by prep-HPLC (MeOH/H$_2$O with 0.05% NH$_3$.H$_2$O as mobile phase) to give the compound (R)-2-(tert-butyl)-N-(4-(2-((1-cyclohexylethyl)amino)pyrimidin-4-yl)-2-methylbenzyl)thiazole-5-carboxamide (35 mg, yield: 52%) as a yellow solid. ESI-MS (M+H)$^+$: 492.1. $^1$H NMR (400 MHz, CD$_3$OD) δ: 8.13-8.12 (m, 2H), 7.82 (s, 1H), 7.78 (d, J=8.0 Hz, 1H), 7.29 (d, J=8.0 Hz, 1H), 6.93 (d, J=5.6 Hz, 1H), 4.50 (s, 2H), 3.95-3.87 (m, 1H), 2.35 (s, 3H), 1.80-1.41 (m, 6H), 1.36 (s, 9H), 1.22-0.93 (m, 8H).

Example 28: (S)-2-(tert-butyl)-N-(4-(2-((1-cyclohexylethyl)amino)pyrimidin-4-yl)-2-methylbenzyl)thiazole-5-carboxamide (I-28)

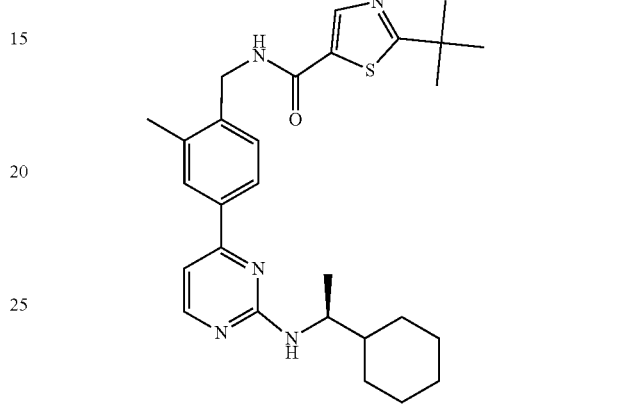

I-28

Synthesis of (S)-2-(tert-butyl)-N-(4-(2-((1-cyclohexylethyl)amino)pyrimidin-4-yl)-2-methylbenzyl)thiazole-5-carboxamide was similar to that of Example 25, except (S)-1-cyclohexylethyl)amine was substituted for 1-methylpiperidin-4-amine. The residue was purified by prep-HPLC (CH$_3$CN/H$_2$O with 0.05% NH$_3$.H$_2$O as mobile phase) to give (S)-2-(tert-butyl)-N-(4-(2-((1-cyclohexylethyl)amino)pyrimidin-4-yl)-2-methylbenzyl)thiazole-5-carboxamide as a yellow solid (73 mg, yield: 63%). ESI-MS (M+H)$^+$: 491.9. $^1$H NMR (400 MHz, DMSO-d$_6$) δ: 9.09 (t, J=4.8 Hz, 1H), 8.34-8.28 (m, 2H), 7.90-7.86 (m, 2H), 7.35 (d, J=8.0 Hz, 1H), 7.04 (d, J=4.8 Hz, 1H), 6.95 (d, J=8.4 Hz, 1H), 4.48 (d, J=5.6 Hz, 2H), 3.95-3.93 (m, 1H), 2.38 (s, 3H), 1.75-1.46 (m, 6H), 1.39 (s, 9H), 1.23-0.97 (m, 8H).

Example 29: 2-(tert-butyl)-N-(2-methyl-4-(2-((1-(pyridin-4-yl)ethyl)amino)pyrimidin-4-yl)benzyl)thiazole-5-carboxamide (I-291

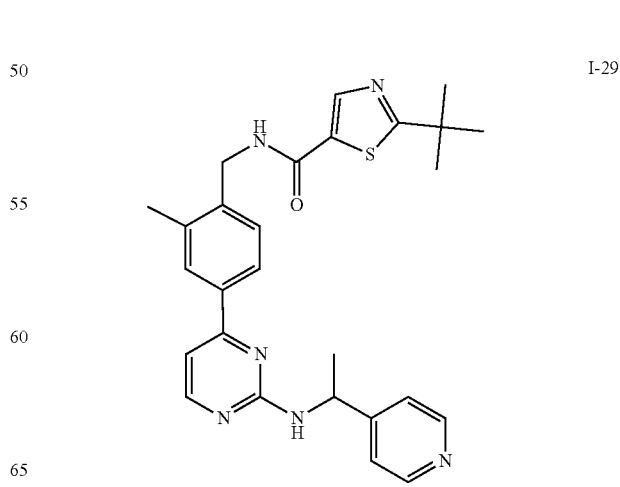

I-29

Synthesis of 2-(tert-butyl)-N-(2-methyl-4-(2-((1-(pyridin-4-yl)ethyl)amino)pyrimidin-4-yl)benzyl)thiazole-5-carboxamide was similar to that of Example 25, except 1-(pyridin-4-yl)ethanamine was substituted for 1-methylpiperidin-4-amine. The crude was purified by prep-HPLC (MeOH/H$_2$O with 0.05% NH$_3$.H$_2$O as mobile phase) to give the compound 2-(tert-butyl)-N-(2-methyl-4-(2-((1-(pyridin-4-yl)ethyl)amino)pyrimidin-4-yl)benzyl)thiazole-5-carboxamide (40 mg, yield: 45%) as a yellow solid. ESI-MS (M+H)$^+$: 487.2. $^1$H NMR (400 MHz, CD$_3$OD) δ: 8.46-8.45 (m, 2H), 8.25 (d, J=5.2 Hz, 1H), 8.23 (s, 1H), 7.76-7.75 (m, 2H), 7.52-7.50 (m, 2H), 7.35 (d, J=8.8 Hz, 1H), 7.09 (d, J=5.2 Hz, 1H), 5.18-5.15 (m, 1H), 4.58 (s, 2H), 2.41 (s, 3H), 1.58 (d, J=6.8 Hz, 3H), 1.47 (s, 9H).

Example 30: 2-(tert-butyl)-N-(4-(2-((1,1-dioxidotetrahydro-2H-thiopyran-4-yl)amino)pyrimidin-4-yl)-2-methylbenzyl)thiazole-5-carboxamide (I-30)

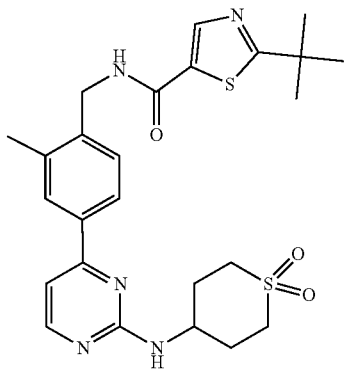

I-30

Synthesis of 2-(tert-butyl)-N-(4-(2-((1,1-dioxidotetrahydro-2H-thiopyran-4-yl)amino)pyrimidin-4-yl)-2-methylbenzyl)thiazole-5-carboxamide was similar to that of Example 32, except 4-aminotetrahydro-2H-thiopyran 1,1-dioxide was substituted for 1-methylpiperidin-4-amine. The crude was purified by prep-HPLC (MeOH/H$_2$O with 0.05% NH$_3$.H$_2$O as mobile phase) to give the compound 2-(tert-butyl)-N-(4-(2-((1,1-dioxidotetrahydro-2H-thiopyran-4-yl)amino)pyrimidin-4-yl)-2-methylbenzyl)thiazole-5-carboxamide (40 mg, yield: 45%) as a yellow solid. ESI-MS (M+H)$^+$: 514.2. $^1$H NMR (400 MHz, CD$_3$OD) δ: 8.31 (d, J=5.6 Hz, 1H), 8.24 (s, 1H), 7.96-7.92 (m, 2H), 7.41 (d, J=8.0 Hz, 1H), 7.14 (d, J=5.2 Hz, 1H), 4.61 (s, 2H), 4.25-4.23 (m, 1H), 3.26-3.14 (m, 4H), 2.46 (s, 3H), 2.45-2.16 (m, 4H), 2.16 (s, 9H).

Example 31: 2-(tert-butyl)-N-(4-(2-(((1,1-dioxido-tetrahydro-2H-thiopyran-4-yl)methyl)amino)pyrimidin-4-yl)-2-methylbenzyl)thiazole-5-carboxamide (I-31)

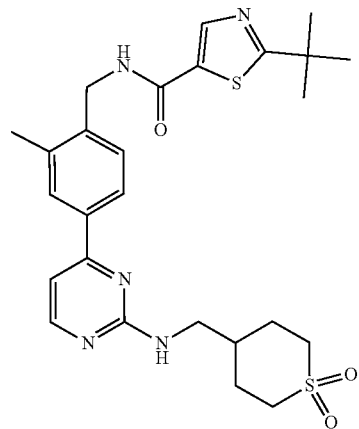

I-31

Synthesis of 2-(tert-butyl)-N-(4-(2-(((1,1-dioxidotetrahydro-2H-thiopyran-4-yl)methyl)amino)pyrimidin-4-yl)-2-methylbenzyl)thiazole-5-carboxamide was similar to that of Example 25, except 4-(aminomethyl)tetrahydro-2H-thiopyran 1,1-dioxide was substituted for 1-methylpiperidin-4-amine. The crude was purified by prep-HPLC (MeOH/H$_2$O with 0.05% NH$_3$.H$_2$O as mobile phase) to give the compound 2-(tert-butyl)-N-(4-(2-(((1,1-dioxidotetrahydro-2H-thiopyran-4-yl)methyl)amino)pyrimidin-4-yl)-2-methylbenzyl)thiazole-5-carboxamide (37 mg, yield: 42%) as a yellow solid. ESI-MS (M+H)$^+$: 528.2. $^1$HNMR (400 MHz, CDCl$_3$) δ: 8.30 (d, J=5.2 Hz, 1H), 8.05 (s, 1H), 7.82-7.80 (m, 2H), 7.03 (d, J=8.0 Hz, 1H), 6.98 (d, J=4.8 Hz, 1H), 6.19-6.18 (m, 1H), 5.42 (t, J=5.2 Hz, 1H), 4.66 (d, J=5.2 Hz, 2H), 3.52-3.50 (m, 2H), 3.10-3.07 (m, 2H), 3.00-2.93 (m, 2H), 2.44 (s, 3H), 2.24-2.21 (m, 2H), 1.94-1.91 (m, 3H), 1.45 (s, 9H).

Example 32: 2-(tert-butyl)-N-(2-methyl-4-(2-((pyridin-4-ylmethyl)amino)pyrimidin-4-yl)benzyl)thiazole-5-carboxamide (I-32)

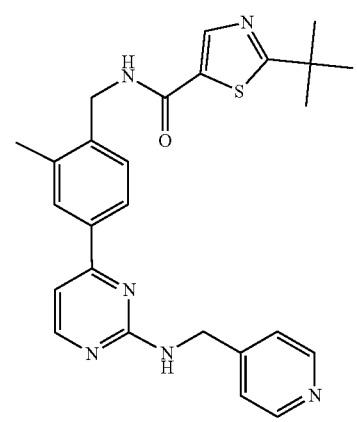

I-32

Synthesis of 2-(tert-butyl)-N-(2-methyl-4-(2-((pyridin-4-ylmethyl)amino)pyrimidin-4-yl)benzyl)thiazole-5-carboxamide was similar to that of Example 25, except pyridin-4-ylmethanamine was substituted for 1-methylpiperidin-4-amine. The residue was purified by prep-HPLC (CH$_3$CN/H$_2$O with 0.05% NH$_3$.H$_2$O as mobile phase) to give 2-(tert-butyl)-N-(2-methyl-4-(2-((pyridin-4-ylmethyl)amino)pyrimidin-4-yl)benzyl)thiazole-5-carboxamide as a pale yellow solid (40 mg, yield: 72%). ESI-MS (M+H)$^+$: 473.1. $^1$H NMR (400 MHz, CD$_3$OD) δ: 8.49 (d, J=5.2 Hz, 1H), 8.27 (d, J=5.2 Hz, 1H), 8.22 (s, 1H), 7.81-7.73 (m, 3H), 7.46 (d, J=7.6 Hz, 1H), 7.34 (d, J=8.0 Hz, 1H), 7.28 (dd, J=5.6, 1.6 Hz, 1H), 7.10 (d, J=5.2 Hz, 1H), 4.76 (s, 2H), 4.57 (s, 2H), 2.40 (s, 3H), 1.45 (s, 9H).

Example 33: Synthesis of 2-(tert-butyl)-N-(2-methyl-4-(2-(methylamino)pyrimidin-4-yl)benzyl)thiazole-5-carboxamide (I-33)

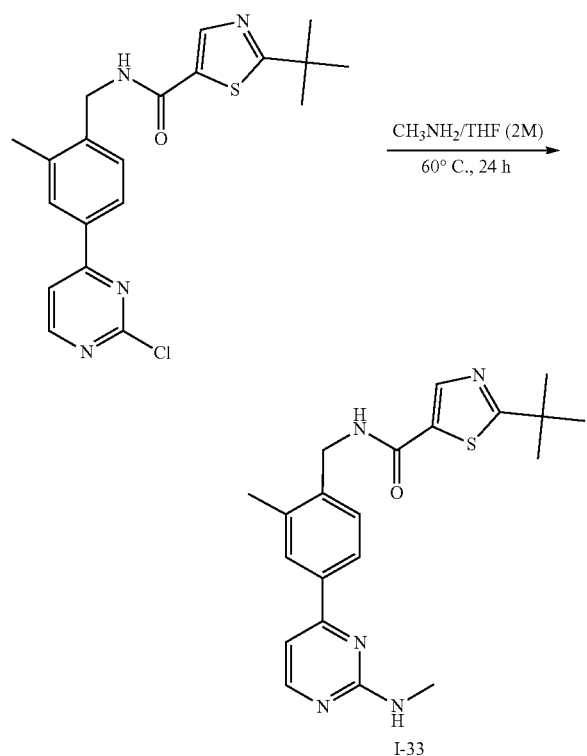

A solution of 2-(tert-butyl)-N-(4-(2-chloropyrimidin-4-yl)-2-methylbenzyl)thiazole-5-carboxamide (65 mg, 0.16 mmol) in methylamine/THF (2M, 4 mL) was placed in a sealed tube which was heated at 60° C. for 24 h. Then the solvent was removed. The crude was purified through silica gel column chromatography (petroleum ether/EtOAc=1/1) to give 2-(tert-butyl)-N-(2-methyl-4-(2-(methylamino)pyrimidin-4-yl)benzyl)thiazole-5-carboxamide as a white solid (30 mg, yield: 47%). ESI-MS (M+H)$^+$: 395.9. HPLC: (214 nm: 96.80%, 254 nm: 98.36%). $^1$H NMR (400 MHz, CD$_3$OD) δ: 8.16 (d, J=5.6 Hz, 1H), 8.15 (s, 1H), 7.84 (s, 1H), 7.80 (d, J=7.6 Hz, 1H), 7.30 (d, J=7.6 Hz, 1H), 6.97 (d, J=5.6 Hz, 1H), 4.51 (s, 2H), 2.91 (s, 3H), 2.35 (s, 3H), 1.37 (s, 9H).

Example 34: Synthesis of 2-(tert-butyl)-N-(4-(2-(ethylamino)pyrimidin-4-yl)-2-methylbenzyl)thiazole-5-carboxamide (I-34)

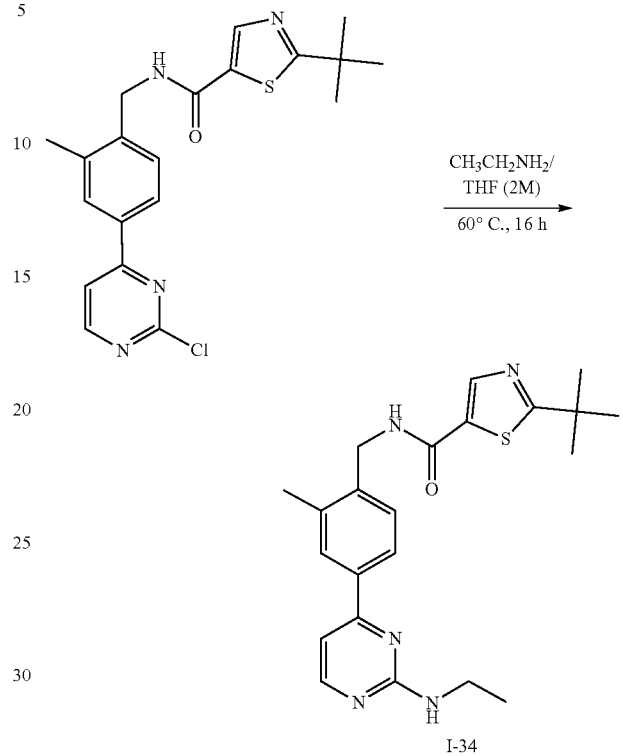

Synthesis of 2-(tert-butyl)-N-(4-(2-(ethylamino)pyrimidin-4-yl)-2-methylbenzyl)thiazole-5-carboxamide was similar to that of Example 33, except ethylamine was substituted for methyl amine. Obtained 2-(tert-butyl)-N-(4-(2-(ethylamino)pyrimidin-4-yl)-2-methylbenzyl)thiazole-5-carboxamide (51 mg, yield: 75%) as a white solid. ESI-MS (M+H)$^+$: 409.9. HPLC: (214 nm: 98.10%, 254 nm: 98.67%). $^1$H NMR (400 MHz, CD$_3$OD) δ: 8.27 (d, J=4.4 Hz, 1H), 8.24 (s, 1H), 7.95 (s, 1H), 7.92 (d, J=8.0 Hz, 1H), 7.41 (d, J=8.4 Hz, 1H), 7.09 (d, J=4.4 Hz, 1H), 4.62 (s, 2H), 3.49 (q, J=5.6 Hz, 2H), 2.47 (s, 3H), 1.48 (s, 9H), 1.27 (t, J=5.6 Hz, 3H).

Example 35: Synthesis of 2-(tert-butyl)-N-(4-(2-(isopropylamino)pyrimidin-4-yl)-2-methylbenzyl)thiazole-5-carboxamide (I-35)

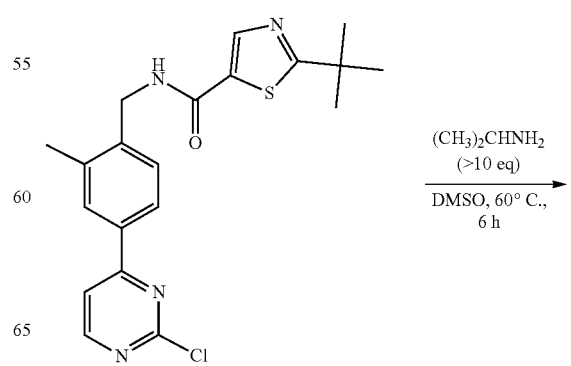

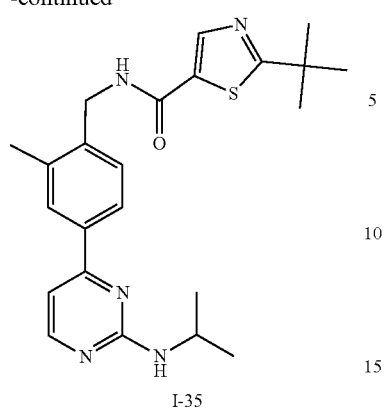

I-35

Synthesis of 2-(tert-butyl)-N-(4-(2-(isopropylamino)pyrimidin-4-yl)-2-methylbenzyl)thiazole-5-carboxamide was similar to that of Example 33, except isopropylamine was substituted for methyl amine. 2-(tert-butyl)-N-(4-(2-(isopropylamino)pyrimidin-4-yl)-2-methylbenzyl)thiazole-5-carboxamide (53 mg, yield: 76%) was obtained as a white solid. ESI-MS (M+H)$^+$: 423.9. HPLC: (214 nm: 95.52%, 254 nm: 95.83%). $^1$H NMR (400 MHz, CD$_3$OD) δ: 8.16 (d, J=5.2 Hz, 1H), 8.15 (s, 1H), 7.83 (s, 1H), 7.79 (d, J=7.6 Hz, 1H), 7.30 (d, J=8.0 Hz, 1H), 6.95 (d, J=5.2 Hz, 1H), 4.51 (s, 2H), 4.14-4.10 (m, 1H), 2.37 (s, 3H), 1.37 (s, 9H), 1.18 (d, J=6.4 Hz, 6H).

Example 36: N-(4-(2-((1H-pyrazol-4-yl)amino)pyrimidin-4-yl)-2-methylbenzyl)-2-(tert-butyl)thiazole-5-carboxamide (I-36)

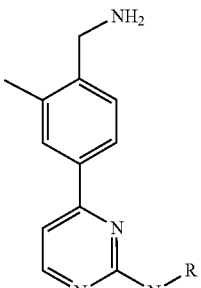

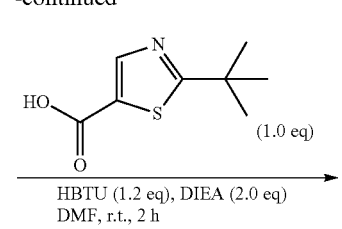

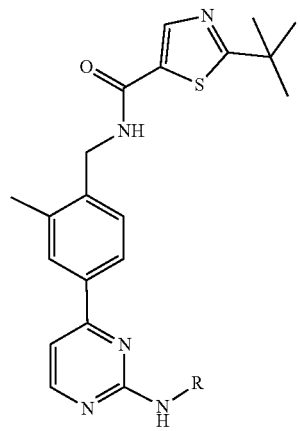

I-36

Preparation of tert-butyl 4-nitro-1H-pyrazole-1-carboxylate

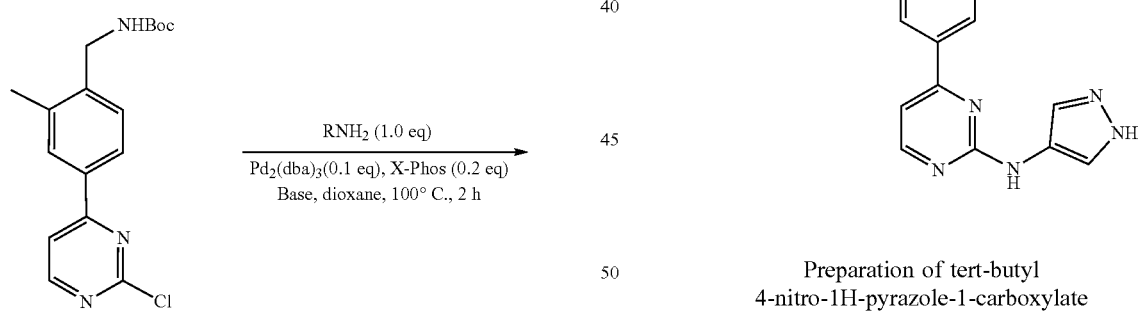

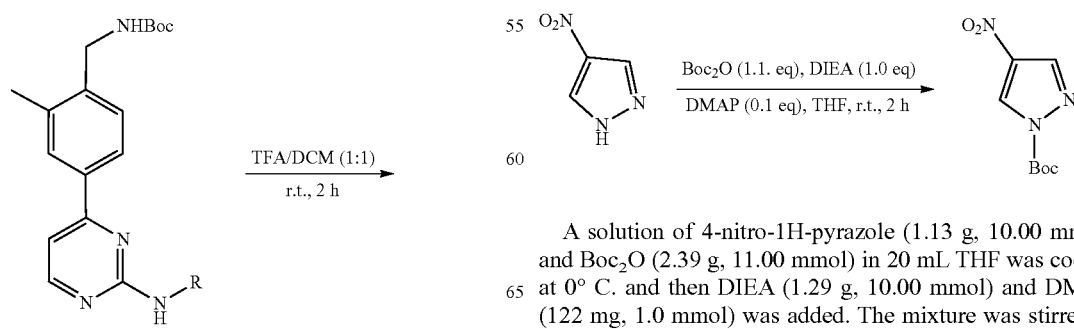

A solution of 4-nitro-1H-pyrazole (1.13 g, 10.00 mmol) and Boc$_2$O (2.39 g, 11.00 mmol) in 20 mL THF was cooled at 0° C. and then DIEA (1.29 g, 10.00 mmol) and DMAP (122 mg, 1.0 mmol) was added. The mixture was stirred at rt for 2 h. After diluted with EtOAc (120 mL), the mixture was washed with 0.5 N HCl (30 mL) and water (50 mL). The organic phase was dried (Na$_2$SO$_4$), filtered and concentrated to give crude product tert-butyl 4-nitro-1H-pyrazole-1-carboxylate as a yellow solid (2.4 g, yield: 100%) which was used directly in the next step. ESI-MS (M+H-56)$^+$: 158.0.

Preparation of tert-butyl 4-amino-1H-pyrazole-1-carboxylate

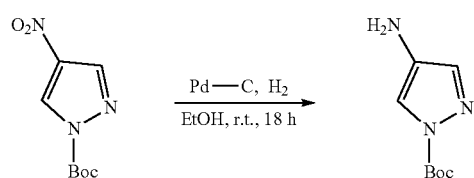

A mixture of tert-butyl 4-nitro-1H-pyrazole-1-carboxylate (3.00 g, 14.08 mmol) and palladium on charcoal (300 mg, 10% wt) in ethanol (30 mL) was stirred at rt under H$_2$ atmosphere (balloon pressure) for 16 h. The catalyst was filtered off and the filtrate was concentrated. The residue was purified by silica gel column chromatography (petroleum ether/EtOAc=1/1 with 0.01% TEA) to give product tert-butyl 4-amino-1H-pyrazole-1-carboxylate as a white solid (2.30 g, yield: 89%). ESI-MS (M+H)$^+$: 129.0. $^1$H NMR (400 MHz, CDCl$_3$) δ: 7.59 (s, 1H), 7.43 (s, 1H), 1.63 (s, 9H).

Preparation of tert-butyl 4-((4-(4-(((tert-butoxycarbonyl)amino)methyl)-3-methylphenyl)pyrimidin-2-yl)amino)-1H-pyrazole-1-carboxylate

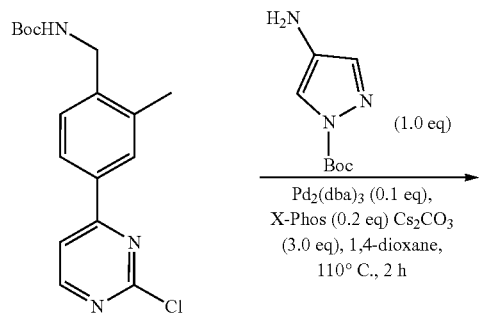

Synthesis of tert-butyl 4-((4-(4-(((tert-butoxycarbonyl)amino)methyl)-3-methylphenyl)pyrimidin-2-yl)amino)-1H-pyrazole-1-carboxylate was similar to that of tert-butyl 4-(2-chloropyrimidin-4-yl)-2-methylbenzylcarbamate. The crude was purified by silica gel column chromatography (petroleum ether/EtOAc=1/2 to 1/1) to give product tert-butyl 4-((4-(4-(((tert-butoxycarbonyl)amino)methyl)-3-methylphenyl)pyrimidin-2-yl)amino)-1H-pyrazole-1-carboxylate as pale yellow solid (90 mg, yield: 31%). ESI-MS (M+H)$^+$: 481.0.

Preparation of N-(4-(2-((1H-pyrazol-4-yl)amino)pyrimidin-4-yl)-2-methylbenzyl)-2-(tert-butyl)thiazole-5-carboxamide

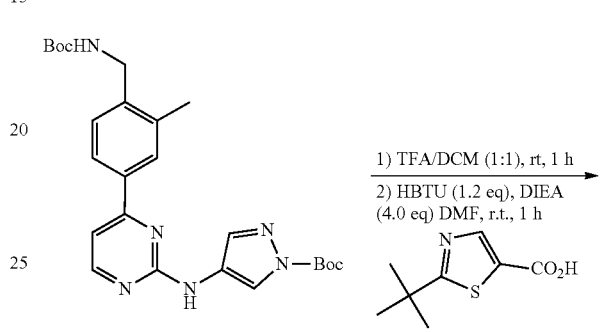

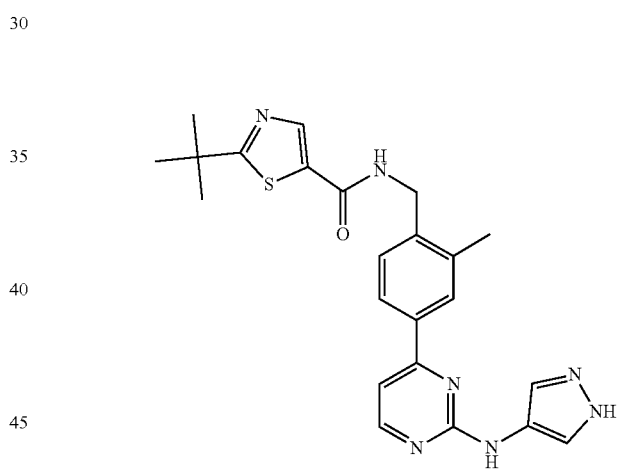

Synthesis of N-(4-(2-((1H-pyrazol-4-yl)amino)pyrimidin-4-yl)-2-methylbenzyl)-2-(tert-butyl)thiazole-5-carboxamide was similar to that of Example 1. The crude product was purified by silica gel column chromatography (petroleum ether/EtOAc=2/1) to give product N-(4-(2-((1H-pyrazol-4-yl)amino)pyrimidin-4-yl)-2-methylbenzyl)-2-(tert-butyl)thiazole-5-carboxamide as a pale yellow solid (37 mg, yield: 46%). ESI-MS (M+H)$^+$: 447.9. HPLC: (214 nm: 93%, 254 nm: 98%). $^1$H NMR (400 MHz, DMSO-d6) δ: 12.47 (s, 1H), 9.48 (s, 1H), 9.10 (t, J=5.2 Hz, 1H), 8.46 (d, J=5.2 Hz, 1H), 8.33 (s, 1H), 7.96-7.93 (m, 3H), 7.60 (s, 1H), 7.39 (d, J=8.4 Hz, 1H), 7.24 (d, J=5.2 Hz, 1H), 4.50 (d, J=5.2 Hz, 2H), 2.41 (s, 3H), 1.39 (s, 9H).

Example 37: 2-(tert-butyl)-N-(4-(2-((1-(2-hydroxy-ethyl)-1H-pyrazol-4-yl)amino)pyrimidin-4-yl)-2-methylbenzyl)thiazole-5-carboxamide (I-37)

I-37

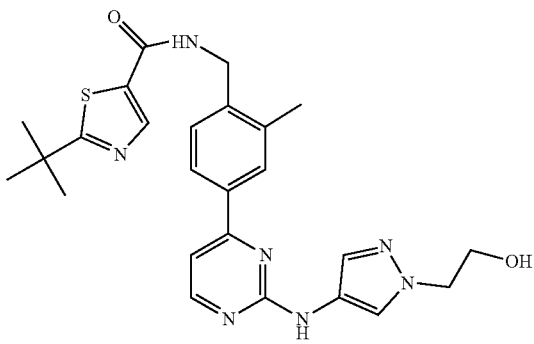

Preparation of 2-(4-nitro-1H-pyrazol-1-yl)ethanol

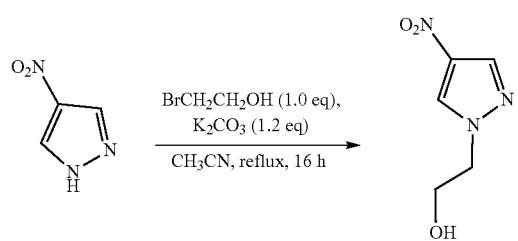 [SMILES: O=[N+]([O-])c1cn[nH]c1 ; O=[N+]([O-])c1cnn(CCO)c1]

A mixture of 2-bromoethanol (3.75 g, 30.00 mmol), 4-nitropyrazzole (3.39 g, 30.00 mmol) and K₂CO₃ (4.97 g, 36.00 mmol) in acetonitrile (30 mL) was refluxed for 16 h. Then the mixture was filtered and the filtrate was concentrated to dryness to give crude product 2-(4-nitro-1H-pyrazol-1-yl)ethanol as a white solid (4.70 g, yield: 100%), which was used directly in the next step. ESI-MS (M+H)⁺: 158.0.

Preparation of 4-nitro-1-(2-((tetrahydro-2H-pyran-2-yl)oxy)ethyl)-1H-pyrazole

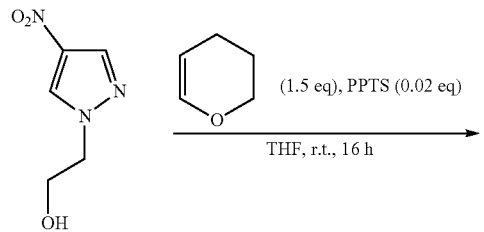

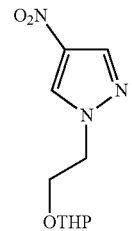

A solution of 2-(4-nitro-1H-pyrazol-1-yl)ethanol (2.00 g, 12.73 mmol), 3,4-dihydro-2H-pyran (1.60 g, 19.10 mmol) and p-toluenesulfonic acid (87 mg, 0.51 mmol) in THF (20 mL) was stirred at room temperature for 2 h. Then the mixture was diluted with EtOAc (150 mL), washed with sat. aqueous sodium carbonate (50 mL) and water 60 mL. The organic phase was dried (Na₂SO₄), filtered and concentrated to give crude product 4-nitro-1-(2-((tetrahydro-2H-pyran-2-yl)oxy)ethyl)-1H-pyrazole as colorless oil (2.00 g, yield: 67%). ESI-MS (M+H)⁺: 242.0.

Preparation of 1-(2-((tetrahydro-2H-pyran-2-yl)oxy)ethyl)-1H-pyrazol-4-amine

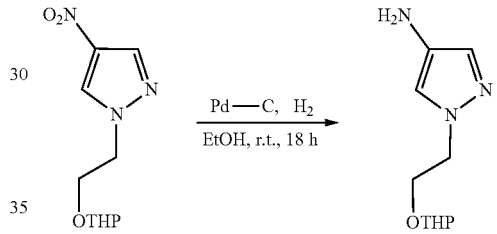

Synthesis of 1-(2-((tetrahydro-2H-pyran-2-yl)oxy)ethyl)-1H-pyrazol-4-amine was similar to that of tert-butyl 4-amino-1H-pyrazole-1-carboxylate. The crude was purified by silica gel column chromatography (petroleum ether/EtOAc=1/8 to 1/4) to give product 1-(2-((tetrahydro-2H-pyran-2-yl)oxy)ethyl)-1H-pyrazol-4-amine as a red oil (1.20 g, yield: 69%). ESI-MS (M+H)⁺: 212.0. ¹H NMR (400 MHz, CDCl₃) δ: 7.15 (s, 1H), 7.13 (s, 1H), 4.54-4.52 (m, 1H), 4.22-4.19 (m, 2H), 4.04-3.99 (m, 1H), 3.75-3.68 (m, 2H), 3.49-3.44 (m, 1H), 2.87 (br, 2H), 1.81-1.76 (m, 1H), 1.71-1.65 (m, 1H), 1.58-1.49 (m, 4H).

Preparation of tert-butyl 2-methyl-4-(2-((1-(2-((tetrahydro-2H-pyran-2-yl)oxy)ethyl)-1H-pyrazol-4-yl)amino)pyrimidin-4-yl)benzylcarbamate

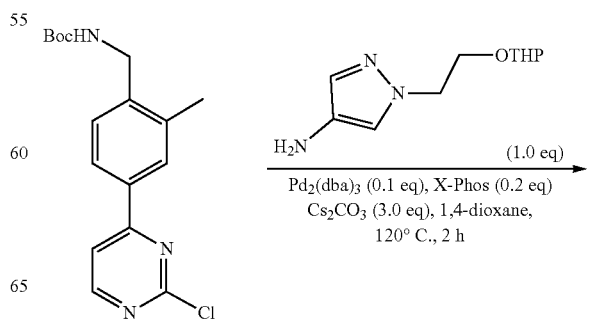

-continued

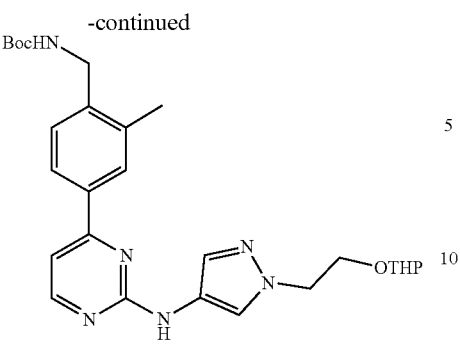

Synthesis of tert-butyl 2-methyl-4-(2-((1-(2-((tetrahydro-2H-pyran-2-yl)oxy)ethyl)-1H-pyrazol-4-yl)amino)pyrimidin-4-yl)benzylcarbamate was similar to that of tert-butyl 4-(2-chloropyrimidin-4-yl)-2-methylbenzylcarbamate. The crude was purified by silica gel column chromatography (petroleum ether/EtOAc=1/2 to 1/1) to give product tert-butyl 2-methyl-4-(2-((1-(2-((tetrahydro-2H-pyran-2-yl)oxy)ethyl)-1H-pyrazol-4-yl)amino)pyrimidin-4-yl)benzylcarbamate as a pale yellow solid (105 mg, yield: 28%). ESI-MS (M+H)+: 508.9.

Preparation of 2-(tert-butyl)-N-(4-(2-((1-(2-hydroxyethyl)-1H-pyrazol-4-yl)amino)pyrimidin-4-yl)-2-methylbenzyl)thiazole-5-carboxamide

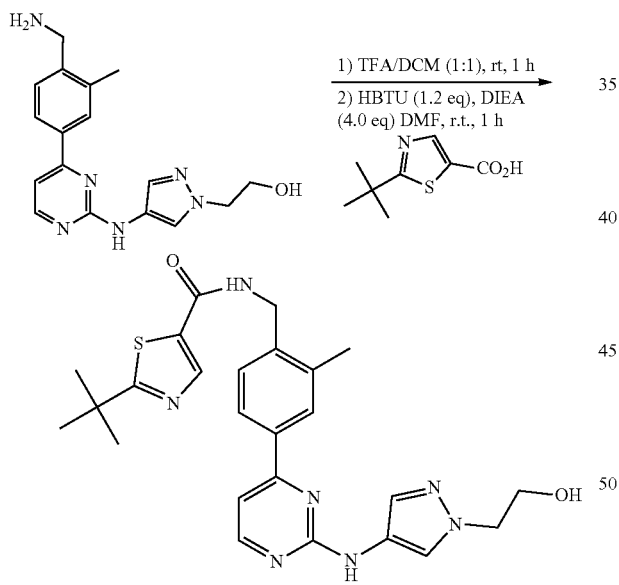

Synthesis of 2-(tert-butyl)-N-(4-(2-((1-(2-hydroxyethyl)-1H-pyrazol-4-yl)amino)pyrimidin-4-yl)-2-methylbenzyl)thiazole-5-carboxamide was similar to that of Example 1. The crude was purified by prep-HPLC (CH$_3$CN/H$_2$O with 0.01% ammonia as mobile phase) to give product 2-(tert-butyl)-N-(4-(2-((1-(2-hydroxyethyl)-1H-pyrazol-4-yl)amino)pyrimidin-4-yl)-2-methylbenzyl)thiazole-5-carboxamide as a yellow solid (56 mg, yield: 56%). ESI-MS (M+H)+: 492.0. HPLC: (214 nm: 100%, 254 nm: 94%). $^1$H NMR (400 MHz, DMSO-d6) δ: 9.50 (s, 1H), 9.11 (t, J=5.2 Hz, 1H), 8.46 (d, J=5.2 Hz, 1H), 8.34 (s, 1H), 8.01 (s, 1H), 7.99 (s, 1H), 7.94 (d, J=7.6 Hz, 1H), 7.57 (s, 1H), 7.39 (d, J=7.6 Hz, 1H), 7.26 (d, J=5.2 Hz, 1H), 4.92 (br, 1H), 4.50 (d, J=5.2 Hz, 2H), 4.12 (t, J=5.2 Hz, 2H), 3.75-3.70 (m, 2H), 2.42 (s, 3H), 1.39 (s, 9H).

Example 38: 2-(tert-butyl)-N-(2-methyl-4-(2-((1-(tetrahydro-2H-pyran-4-yl)-1H-pyrazol-4-yl)amino)pyrimidin-4-yl)benzyl)thiazole-5-carboxamide (I-38)

I-38

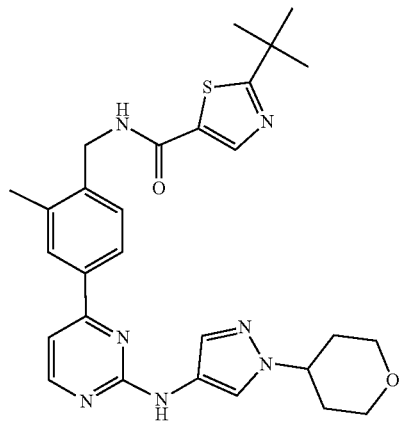

Preparation of 4-nitro-1-(tetrahydro-2H-pyran-4-yl)-1H-pyrazole

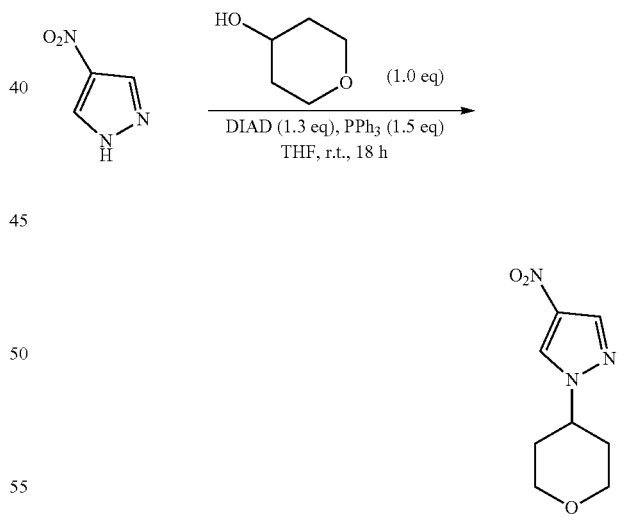

To a solution of 4-nitro-1H-pyrazole (1.00 g, 9.80 mmol), tetrahydro-2H-pyran-4-ol (1.10 g, 9.80 mmol), triphenylphosphine (3.34 g, 12.74 mmol) in 20 mL dry THF was added DIAD (2.57 g, 12.74 mmol) in one portion under N$_2$. After addition, the solution was stirred at rt for 16 h. Then the mixture was concentrated and purified by silica gel column chromatography (EA/PE=1/4) to give product 4-nitro-1-(tetrahydro-2H-pyran-4-yl)-1H-pyrazole as a white solid (950 mg, yield: 54%). ESI-MS (M+H)+: 198.0.

113
Preparation of 1-(tetrahydro-2H-pyran-4-yl)-1H-pyrazol-4-amine

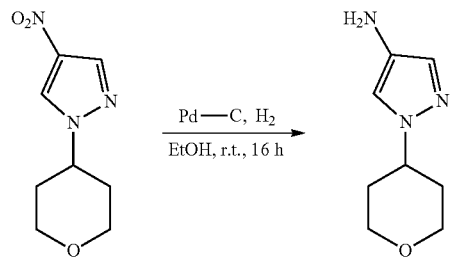

Synthesis of 1-(tetrahydro-2H-pyran-4-yl)-1H-pyrazol-4-amine was similar to that of tert-butyl 4-amino-1H-pyrazole-1-carboxylate. The crude product 1-(tetrahydro-2H-pyran-4-yl)-1H-pyrazol-4-amine as a pink solid (614 mg, yield: 76%) which was used directly in the next step. ESI-MS (M+H)$^+$: 168.0. $^1$H NMR (400 MHz, CD$_3$OD) δ: 7.28 (s, 1H), 7.16 (s, 1H), 4.29-4.21 (m, 1H), 4.06-4.02 (m, 2H), 3.58-3.52 (m, 2H), 2.02-1.96 (m, 4H).

Preparation of tert-butyl 2-methyl-4-(2-((1-(tetra-hydro-2H-pyran-4-yl)-1H-pyrazol-4-yl)amino)pyrimidin-4-yl)benzylcarbamate

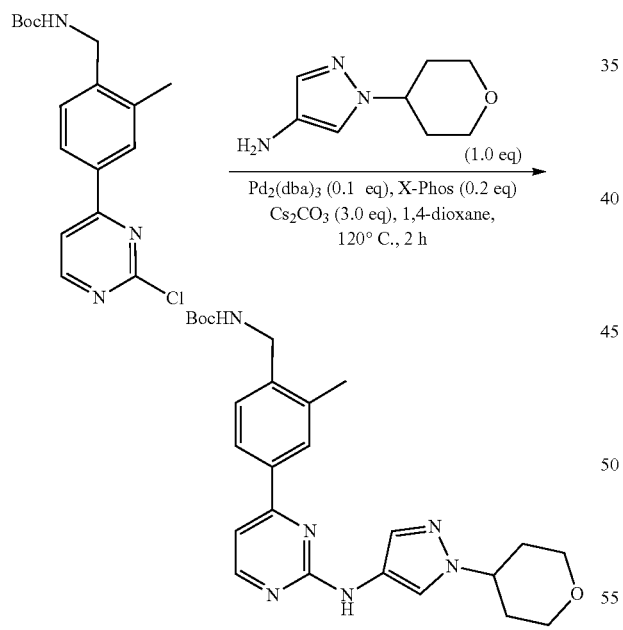

Synthesis of tert-butyl 2-methyl-4-(2-((1-(tetrahydro-2H-pyran-4-yl)-1H-pyrazol-4-yl)amino)pyrimidin-4-yl)benzylcarbamate was similar to that of tert-butyl 4-(2-chloropyrimidin-4-yl)-2-methylbenzylcarbamate. The crude was purified by silica gel column chromatography (petroleum ether/EtOAc=1/2 to 1/1) to give product tert-butyl 2-methyl-4-(2-((1-(tetrahydro-2H-pyran-4-yl)-1H-pyrazol-4-yl)amino)pyrimidin-4-yl)benzylcarbamate as a pale yellow solid (75 mg, yield: 33%). ESI-MS (M+H)$^+$: 468.1.

114
Preparation of 2-(tert-butyl)-N-(2-methyl-4-(2-((1-(tetrahydro-2H-pyran-4-yl)-1H-pyrazol-4-yl)amino)pyrimidin-4-yl)benzyl)thiazole-5-carboxamide

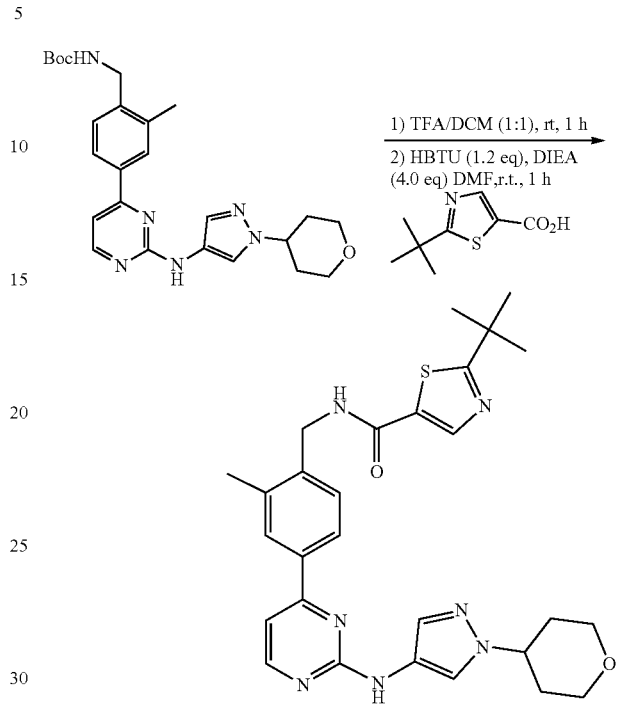

Synthesis of 2-(tert-butyl)-N-(2-methyl-4-(2-((1-(tetrahydro-2H-pyran-4-yl)-1H-pyrazol-4-yl)amino)pyrimidin-4-yl)benzyl)thiazole-5-carboxamide was similar to that of Example 1. The crude was purified by prep-HPLC (CH$_3$CN/H$_2$O with 0.05% TFA as mobile phase) to give product 2-(tert-butyl)-N-(2-methyl-4-(2-((1-(tetrahydro-2H-pyran-4-yl)-1H-pyrazol-4-yl)amino)pyrimidin-4-yl)benzyl)thiazole-5-carboxamide as a pale yellow solid (32 mg, yield: 36%). ESI-MS (M+H)$^+$: 532.0. HPLC: (214 nm: 97%, 254 nm: 98%). $^1$H NMR (400 MHz, DMSO-d6) δ: 9.52 (s, 1H), 9.11 (t, J=5.2 Hz, 1H), 8.46 (d, J=4.8 Hz, 1H), 8.33 (s, 1H), 8.04 (s, 1H), 7.99 (s, 1H), 7.94 (d, J=8.0 Hz, 1H), 7.59 (s, 1H), 7.39 (d, J=8.0 Hz, 1H), 7.26 (d, J=4.8 Hz, 1H), 4.50 (d, J=6.0 Hz, 2H), 4.39-4.37 (m, 1H), 3.97-3.94 (m, 2H), 3.48-3.46 (m, 2H), 2.42 (s, 3H), 2.00-1.90 (m, 4H), 1.39 (s, 9H).

Example 39: 2-(tert-butyl)-N-(4-(2-((1-(2-methoxyethyl)-1H-pyrazol-4-yl)amino)pyrimidin-4-yl)-2-methylbenzyl)thiazole-5-carboxamide (I-39)

I-39

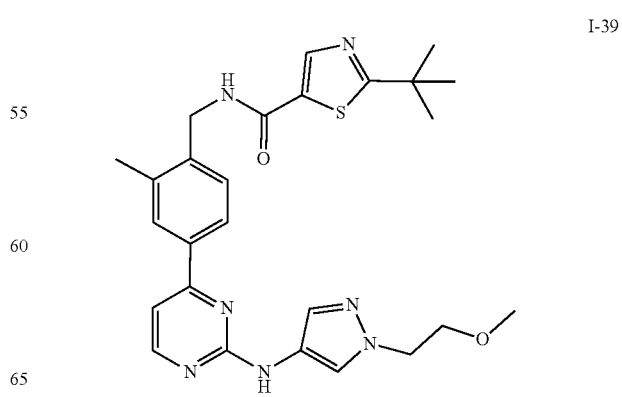

Synthesis of 1-(2-methoxyethyl)-4-nitro-1H-pyrazole

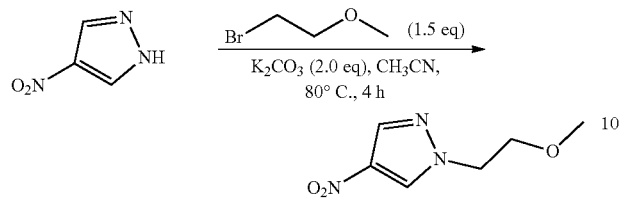

To a mixture of 4-nitro-1H-pyrazole (113 mg, 1 mmol, 1.0 eq) in CH₃CN (5 mL), 1-bromo-2-methoxyethane (138 mg, 1 mmol, 1.0 equiv) and K₂CO₃ (276 mg, 2 mmol, 2.0 equiv) was added. The mixture was stirred at 80° C. for 4 h. After diluted with EtOAc (100 mL), the mixture was washed with water (50 mL×2). The organic layer was concentrated and purified by silica gel column (petroleum ether/EtOAc=10:1) to give 1-(2-methoxyethyl)-4-nitro-1H-pyrazole (170 mg, yield: 100%) as a colorless oil. ESI-MS (M+H)⁺: 172.1. ¹H NMR (400 MHz, CDCl₃) δ: 8.23 (s, 1H), 8.07 (s, 1H), 4.31 (t, J=5.2 Hz, 2H), 3.74 (t, J=5.2 Hz, 2H), 3.35 (s, 3H).

Synthesis of 1-(2-methoxyethyl)-1H-pyrazol-4-amine

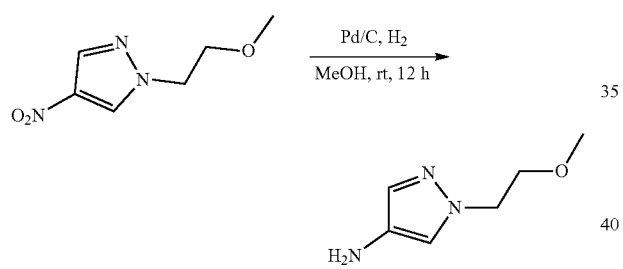

Synthesis of 1-(2-methoxyethyl)-1H-pyrazol-4-amine was similar to that of tert-butyl 4-amino-1H-pyrazole-1-carboxylate. Compound 1-(2-methoxyethyl)-1H-pyrazol-4-amine (140 mg, yield: 100%) was obtained as a red oil. ESI-MS (M+H)⁺: 142.1.

Synthesis of tert-butyl 4-(2-((1-(2-methoxyethyl)-1H-pyrazol-4-yl)amino)pyrimidin-4-yl)-2-methylbenzylcarbamate

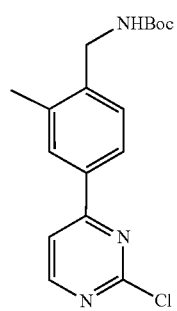

+

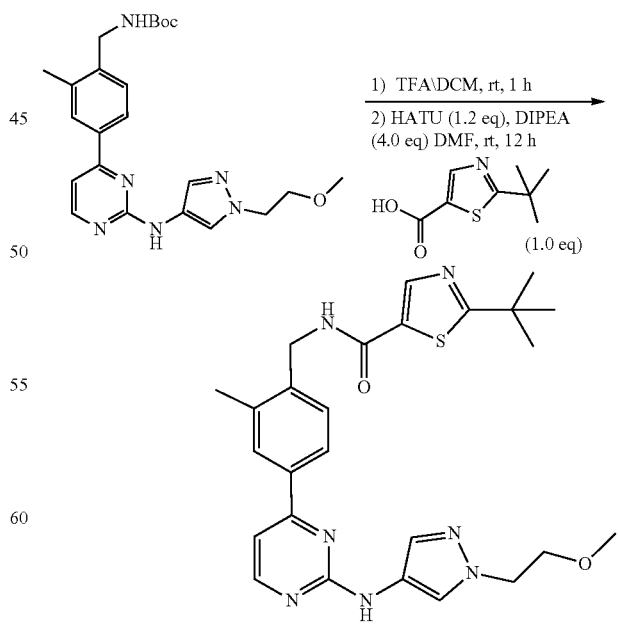

Synthesis of tert-butyl 4-(2-((1-(2-methoxyethyl)-1H-pyrazol-4-yl)amino)pyrimidin-4-yl)-2-methylbenzylcarbamate was similar to that of tert-butyl 4-(2-chloropyrimidin-4-yl)-2-methylbenzylcarbamate. The mixture was concentrated and purified by prep-HPLC (Gradient: 5% B increase to 95% B, A: 0.5% NH₃ in water, B: CH₃CN) to give tert-butyl 4-(2-((1-(2-methoxyethyl)-1H-pyrazol-4-yl)amino)pyrimidin-4-yl)-2-methylbenzylcarbamate (160 mg, yield: 90%) as a yellow solid. ESI-MS (M+H)⁺: 439.3. ¹H NMR (400 MHz, CDCl₃) δ: 8.41 (d, J=5.2 Hz, 1H), 7.98 (s, 1H), 7.85-7.83 (m, 2H), 7.60 (s, 1H), 7.36 (d, J=8.4 Hz, 1H), 7.05 (d, J=5.2 Hz, 1H), 7.03 (s, 1H), 4.87 (br, 1H), 4.37 (d, J=5.6 Hz, 2H), 4.29 (t, J=5.2 Hz, 2H), 3.78 (t, J=5.2 Hz, 2H), 3.35 (s, 3H), 2.41 (s, 3H), 1.47 (s, 9H).

Synthesis of 2-(tert-butyl)-N-(4-(2-((1-(2-methoxyethyl)-1H-pyrazol-4-yl)amino)pyrimidin-4-yl)-2-methylbenzyl)thiazole-5-carboxamide Synthesis of 2-(tert-butyl)-N-(4-(2-((1-(2-methoxyethyl)-1H-pyrazol-4-yl)amino)pyrimidin-4-yl)-2-methylbenzyl)

thiazole-5-carboxamide was similar to that of Example 1. The mixture was purified by prep-HPLC (Gradient: 5% B increase to 95% B, A: 0.5% NH$_3$ in water, B: CH$_3$CN) to give 2-(tert-butyl)-N-(4-(2-((1-(2-methoxyethyl)-1H-pyrazol-4-yl)amino)pyrimidin-4-yl)-2-methylbenzyl)thiazole-5-carboxamide (55 mg, yield: 27%) as a yellow solid. ESI-MS (M+H)$^+$: 506.1. $^1$H NMR (400 MHz, CDCl$_3$) δ: 8.42 (d, J=5.2 Hz, 1H), 8.04 (s, 1H), 7.97 (s, 1H), 7.89 (s, 1H), 7.86 (d, J=8.4 Hz, 1H), 7.61 (s, 1H), 7.40 (d, J=8.0 Hz, 1H), 7.06 (d, J=5.2 Hz, 1H), 6.93 (s, 1H), 6.09 (t, J=7.2 Hz, 1H), 4.67 (d, J=5.6 Hz, 2H), 4.28 (t, J=5.6 Hz, 2H), 3.78 (t, J=5.6 Hz, 2H), 3.35 (s, 3H), 2.45 (s, 3H), 1.45 (s, 9H).

Example 40: 2-(tert-butyl)-N-(4-(2-((1-ethyl-1H-pyrazol-4-yl)amino)pyrimidin-4-yl)-2-methylbenzyl) thiazole-5-carboxamide (I-40)

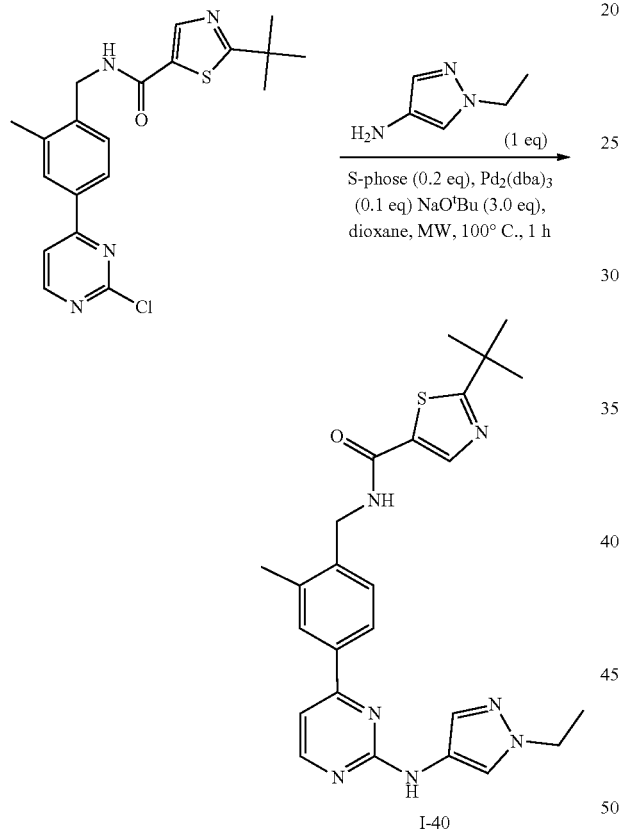

I-40

A mixture of 2-(tert-butyl)-N-(4-(2-chloropyrimidin-4-yl)-2-methylbenzyl)thiazole-5-carboxamide (100 mg, 0.25 mmol), 1-ethyl-1H-pyrazol-4-amine (28 mg, 0.25 mmol), t-BuONa (72 mg, 0.75 mmol), Pd$_2$(dba)$_3$ (27 mg, 0.03 mmol), S-Phos (25 mg, 0.06 mmol) in 5 mL 1,4-dioxane was heated at 100° C. for 1 h under microwave and nitrogen. After cooling to rt and diluted with EtOAc (120 mL), the mixture was washed with water (60 mL). The organic phase was dried and concentrated. The residue was purified by pre-TLC (MeOH/DCM=1/20) to give product 2-(tert-butyl)-N-(4-(2-((1-ethyl-1H-pyrazol-4-yl)amino)pyrimidin-4-yl)-2-methylbenzyl)thiazole-5-carboxamide as a yellow solid (50 mg, yield: 44%). ESI-MS (M+H)$^+$: 476.2. $^1$H NMR (400 MHz, CDCl$_3$) δ: 8.43 (d, J=4.4 Hz, 1H), 8.05 (s, 1H), 7.92-7.84 (m, 3H), 7.56 (s, 1H), 7.14 (d, J=8.0 Hz, 1H), 7.07 (d, J=8.0 Hz, 1H), 6.99 (m, 1H), 6.05 (br, 1H), 4.68 (d, J=5.6 Hz, 2H), 4.17 (q, J=7.2 Hz, 2H), 2.45 (s, 3H), 1.52 (t, J=7.2 Hz, 3H), 1.45 (s, 9H).

Example 41: 2-(tert-butyl)-N-(4-(2-((1-isopropyl-1H-pyrazol-4-yl)amino)pyrimidin-4-yl)-2-methylbenzyl)thiazole-5-carboxamide (I-41)

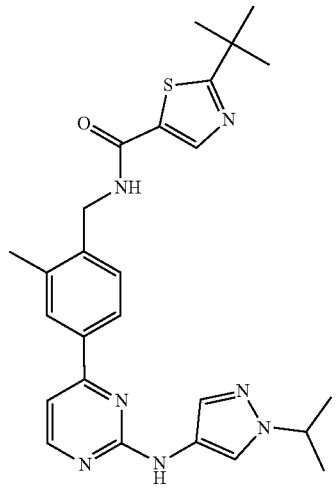

I-41

Synthesis of 2-(tert-butyl)-N-(4-(2-((1-isopropyl-1H-pyrazol-4-yl)amino)pyrimidin-4-yl)-2-methylbenzyl)thiazole-5-carboxamide was similar to that of Example 37, except 1-isopropyl-1H-pyrazol-4-amine was substituted for 1-ethyl-1H-pyrazol-4-amine. The residue was purified by prep-HPLC (CH$_3$CN/H$_2$O with 0.05% ammonia as mobile phase) to give product 2-(tert-butyl)-N-(4-(2-((1-isopropyl-1H-pyrazol-4-yl)amino)pyrimidin-4-yl)-2-methylbenzyl) thiazole-5-carboxamide as a pale yellow solid (45 mg, yield: 55%). ESI-MS (M+H)$^+$: 490.2. $^1$H NMR (400 MHz, CD$_3$OD) δ: 8.39 (d, J=4.8 Hz, 1H), 8.24 (s, 1H), 8.06 (s, 1H), 7.99 (s, 1H), 7.93 (d, J=8.0 Hz, 1H), 7.66 (s, 1H), 7.43 (d, J=8.0 Hz, 1H), 7.20 (d, J=5.2 Hz, 1H), 4.62 (s, 2H), 4.52-4.48 (m, 1H), 2.47 (s, 3H), 1.52 (d, J=6.8 Hz, 6H), 1.46 (s, 9H).

Example 42: N-(4-(2-((1-(azetidin-3-yl)-1H-pyrazol-4-yl)amino)pyrimidin-4-yl)-2-methylbenzyl)-2-(tert-butyl)thiazole-5-carboxamide (I-42)

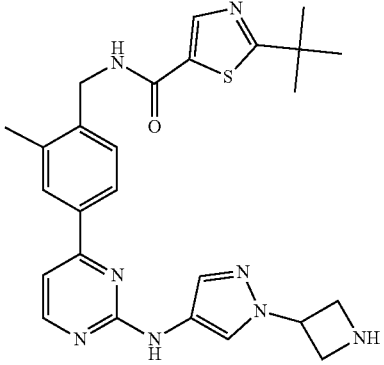

I-42

Synthesis of tert-butyl 3-(4-nitro-1H-pyrazol-1-yl)azetidine-1-carboxylate

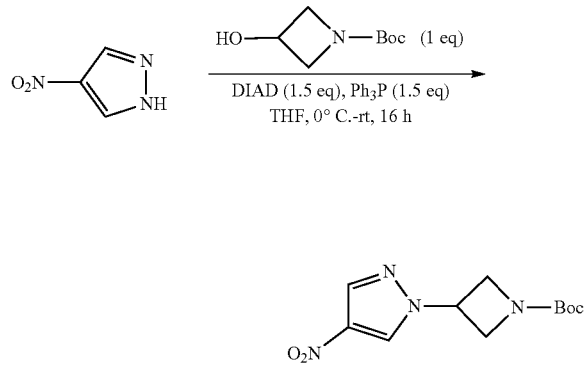

DIAD (3.92 mL, 19.9 mmmol, 1.5 equiv) was added dropwise to a stirred solution of 4-nitro-1H-pyrazole (1.5 g, 13.27 mmol), 1-Boc-3-Hydroxyazetidine (2.3 g, 13.27 mmol, 1 equiv) and triphenylphosphine (5.22 g, 19.9 mmol, 1.5 equiv) in THF (30 mL) placed an ice-bath under $N_2$. The mixture was stirred at 0° C. for 10 min and allowed to warm to rt and stirred for 16 h. After diluted with EA (100 mL), the mixture was washed with water (40 mL), brine (30 mL×2). The combined organic layer was dried, concentrated. The crude was purified through silica gel column chromatography (petroleum ether/EtOAc=1/10) to give tert-butyl 3-(4-nitro-1H-pyrazol-1-yl)azetidine-1-carboxylate as light yellow solid (3 g, yield: 85%). ESI-MS (M+56)⁺: 213.1. $^1$H NMR (400 MHz, CDCl$_3$) δ: 8.28 (s, 1H), 8.16 (s, 1H), 5.07-5.04 (m, 1H), 4.44-4.40 (m, 2H), 4.34-4.30 (m, 2H), 1.47 (s, 9H).

Synthesis of tert-butyl 3-(4-amino-1H-pyrazol-1-yl)azetidine-1-carboxylate

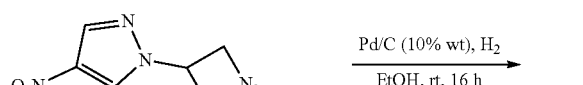

Synthesis of tert-butyl 3-(4-amino-1H-pyrazol-1-yl)azetidine-1-carboxylate was similar to that of tert-butyl 4-amino-1H-pyrazole-1-carboxylate. Obtained tert-butyl 3-(4-amino-1H-pyrazol-1-yl)azetidine-1-carboxylate (1 g, yield: 95%) as purple red oil. ESI-MS (M+H-56)⁺: 183.1. $^1$H NMR (400 MHz, CDCl$_3$) δ: 7.22 (s, 1H), 7.14 (s, 1H), 4.93-4.89 (m, 1H), 4.35-4.31 (m, 2H), 4.25-4.22 (m, 2H), 2.94 (br, 2H), 1.45 (s, 9H).

Synthesis of tert-butyl 3-(4-((4-(4-((2-(tert-butyl)thiazole-5-carboxamido)methyl)-3-methylphenyl)pyrimidin-2-yl)amino)-1H-pyrazol-1-yl)azetidine-1-carboxylate

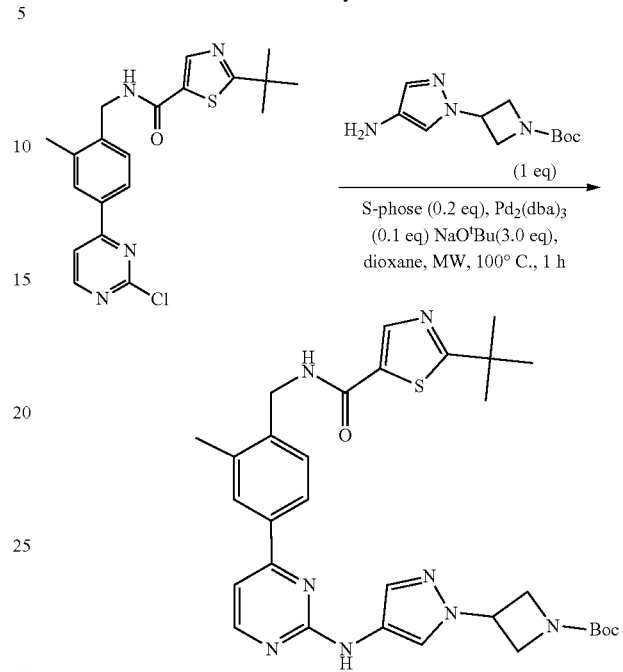

Synthesis of tert-butyl 3-(4-((4-(4-((2-(tert-butyl)thiazole-5-carboxamido)methyl)-3-methylphenyl)pyrimidin-2-yl)amino)-1H-pyrazol-1-yl)azetidine-1-carboxylate was similar to that of tert-butyl 4-(2-chloropyrimidin-4-yl)-2-methylbenzylcarbamate. Purified through silica gel column chromatography with (MeOH/DCM=1/20) to give tert-butyl 3-(4-((4-(4-((2-(tert-butyl)thiazole-5-carboxamido)methyl)-3-methylphenyl)pyrimidin-2-yl)amino)-1H-pyrazol-1-yl)azetidine-1-carboxylate (150 mg, yield: 69%) as a yellow solid. ESI-MS (M+H)⁺: 603.2. $^1$H NMR (400 MHz, CDCl$_3$) δ: 8.45 (d, J=5.2 Hz, 1H), 8.12 (s, 1H), 8.05 (s, 1H), 7.88 (s, 1H), 7.85 (d, J=8.0 Hz, 1H), 7.64 (s, 1H), 7.42 (d, J=8.0 Hz, 1H), 7.10 (d, J=5.6 Hz, 1H), 6.94 (s, 1H), 6.11-6.09 (m, 1H), 5.08-5.01 (m, 1H), 4.68 (d, J=5.2 Hz, 2H), 4.42-4.33 (m, 4H), 2.46 (s, 3H), 1.56 (s, 9H), 1.45 (s, 9H).

Synthesis of N-(4-(2-((1-(azetidin-3-yl)-1H-pyrazol-4-yl)amino)pyrimidin-4-yl)-2-methylbenzyl)-2-(tert-butyl)thiazole-5-carboxamide

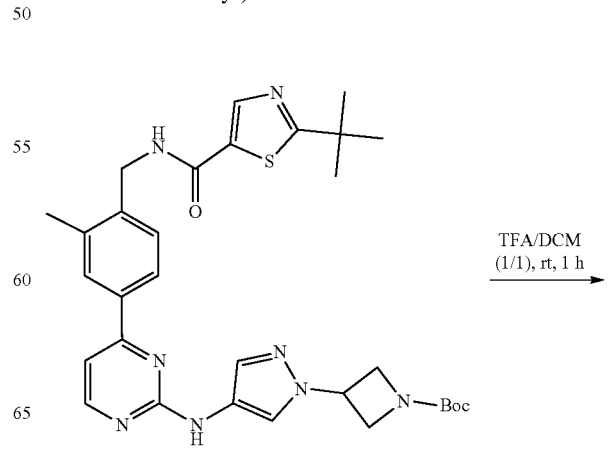

121

-continued

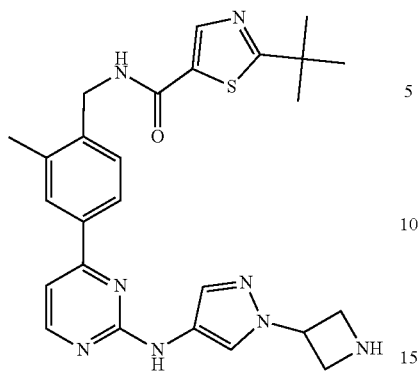

To a solution of tert-butyl 3-(4-((4-(4-((2-(tert-butyl)thiazole-5-carboxamido)methyl)-3-methylphenyl)pyrimidin-2-yl)amino)-1H-pyrazol-1-yl)azetidine-1-carboxylate (150 mg, 0.25 mmol) in DCM (2 mL) was added TFA (2 mL). The mixture was stirred at rt for 1 h. The solvent was removed. The crude was purified through prep-HPLC (CH$_3$CN/H$_2$O with 0.05% NH$_3$.H$_2$O as mobile phase) to give N-(4-(2-((1-(azetidin-3-yl)-1H-pyrazol-4-yl)amino)pyrimidin-4-yl)-2-methylbenzyl)-2-(tert-butyl)thiazole-5-carboxamide as a yellow solid (125 mg, yield: 100%). ESI-MS (M+H)$^+$: 503.1. HPLC: (214 nm: 97.49%, 254 nm: 98.23%). $^1$H NMR (400 MHz, CD$_3$OD) δ: 8.41 (d, J=5.2 Hz, 1H), 8.24 (s, 1H), 8.12 (s, 1H), 7.97 (s, 1H), 7.96 (d, J=8.0 Hz, 1H), 7.85 (s, 1H), 7.44 (d, J=8.0 Hz, 1H), 7.24 (d, J=5.6 Hz, 1H), 5.45-5.37 (m, 1H), 4.63 (s, 2H), 4.57-4.54 (m, 4H), 2.48 (s, 3H), 1.47 (s, 9H).

Example 43: 2-(tert-butyl)-N-(2-methyl-4-(2-((1-(1-methylazetidin-3-yl)-1H-pyrazol-4-yl)amino)pyrimidin-4-yl)benzyl)thiazole-5-carboxamide (I-43)

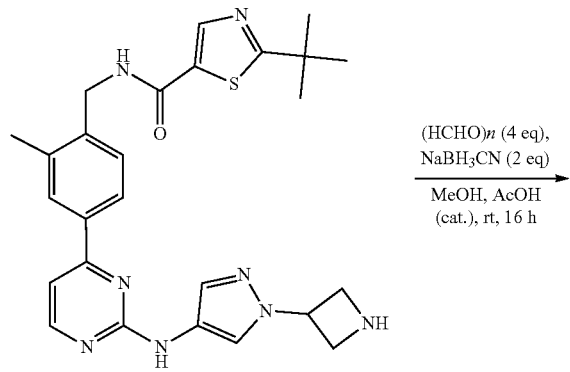

(HCHO)n (4 eq), NaBH$_3$CN (2 eq)
MeOH, AcOH (cat.), rt, 16 h

122

-continued

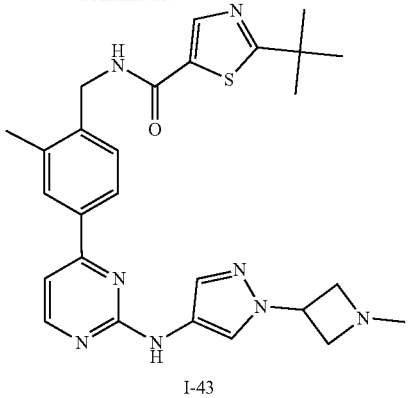

I-43

To a solution of N-(4-(2-((1-(azetidin-3-yl)-1H-pyrazol-4-yl)amino)pyrimidin-4-yl)-2-methylbenzyl)-2-(tert-butyl)thiazole-5-carboxamide (95 mg, 0.189 mmol) in MeOH (4 mL) were added paraformaldehyde (24 mg, 0.757 mmol, 4 equiv), NaBH$_3$CN (24 mg, 0.378 mmol, 2 equiv) and AcOH (cat.). The mixture was stirred at rt for 16 h. After diluted with EtOAc (80 mL), the mixture was washed with water (20 mL), dried and concentrated. The crude was purified through prep-TLC (MeOH/DCM=1/15) to give 2-(tert-butyl)-N-(2-methyl-4-(2-((1-(1-methylazetidin-3-yl)-1H-pyrazol-4-yl)amino)pyrimidin-4-yl)benzyl)thiazole-5-carboxamide as a yellow solid (42 mg, yield: 43%). ESI-MS (M+H)$^+$: 517.3. HPLC: (214 nm: 97.38%, 254 nm: 97.27%). $^1$H NMR (400 MHz, CD$_3$OD) δ: 8.41 (d, J=5.6 Hz, 1H), 8.25 (s, 1H), 8.20 (s, 1H), 7.98 (s, 1H), 7.96 (d, J=8.0 Hz, 1H), 7.73 (s, 1H), 7.43 (d, J=8.0 Hz, 1H), 7.21 (d, J=5.2 Hz, 1H), 5.02-4.95 (m, 1H), 4.63 (s, 2H), 3.89-3.85 (m, 2H), 3.61-3.57 (m, 2H), 2.48 (s, 3H), 2.47 (s, 3H), 1.47 (s, 9H).

Example 44: The preparation of 3-(4-((4-(4-((2-(tert-butyl)thiazole-5-carboxamido)methyl)-3-methylphenyl)pyrimidin-2-yl)amino)-1H-pyrazol-1-yl)cyclobutanecarboxylic acid (I-44)

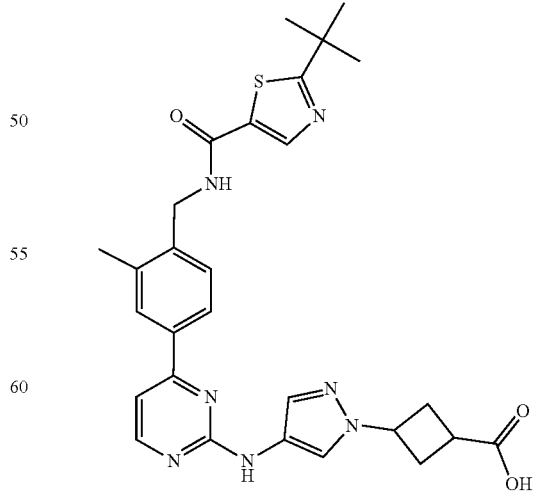

I-44

Synthesis of 3-(4-((4-(4-((2-(tert-butyl)thiazole-5-carboxamido)methyl)-3-methylphenyl)pyrimidin-2-yl)amino)-1H- pyrazol-1-yl)cyclobutanecarboxylic acid was similar to that of Example 37 starting from methyl 3-hydroxycyclobutanecarboxylate. The residue was purified by prep-HPLC (CH$_3$CN/H$_2$O with 0.05% ammonia as mobile phase) to give product 3-(4-((4-(4-((2-(tert-butyl)thiazole-5-carboxamido)methyl)-3-methylphenyl)pyrimidin-2-yl)amino)-1H-pyrazol-1-yl)cyclobutanecarboxylic acid as a pale yellow solid (25 mg, yield: 12%). ESI-MS (M+H)$^+$: 546.1. $^1$H NMR (400 MHz, CD$_3$OD) δ: 8.35 (d, J=5.2 Hz, 1H), 8.25 (s, 1H), 8.09 (s, 1H), 8.04 (s, 1H), 7.99 (d, J=8.4 Hz, 1H), 7.75 (s, 1H), 7.46 (d, J=8.0 Hz, 1H), 7.37 (d, J=5.6 Hz, 1H), 5.52-5.47 (m, 1H), 4.62 (s, 2H), 3.20-3.16 (m, 1H), 2.91-2.75 (m, 4H), 2.48 (s, 3H), 1.46 (s, 9H).

Example 45: 2-(tert-butyl)-N-(2-methyl-4-(2-((1-(piperidin-4-yl)-1H-pyrazol-4-yl)amino)pyrimidin-4-yl)benzyl)thiazole-5-carboxamide (I-45)

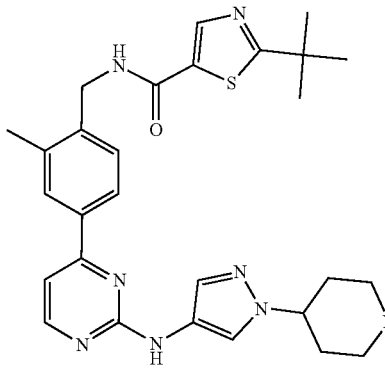

Synthesis of tert-butyl 4-(4-nitro-1H-pyrazol-1-yl)piperidine-1-carboxylate

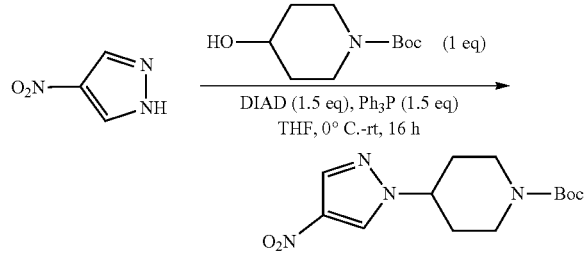

Synthesis of tert-butyl 4-(4-nitro-1H-pyrazol-1-yl)piperidine-1-carboxylate was similar to that of tert-butyl 3-(4-nitro-1H-pyrazol-1-yl)azetidine-1-carboxylate. The crude product was purified through silica gel column chromatography with (petroleum ether/EtOAc=1/10) to give tert-butyl 4-(4-nitro-1H-pyrazol-1-yl)piperidine-1-carboxylate as light yellow solid (3.2 g, yield: 84%). ESI-MS (M+H-56)$^+$: 241.1. $^1$H NMR (400 MHz, CDCl$_3$) δ: 8.17 (s, 1H), 8.08 (s, 1H), 5.00-4.94 (m, 1H), 4.33-4.26 (m, 2H), 2.93-2.87 (m, 2H), 2.18-2.15 (m, 2H), 1.96-1.86 (m, 2H), 1.48 (s, 9H).

Synthesis of tert-butyl 4-(4-amino-1H-pyrazol-1-yl)piperidine-1-carboxylate

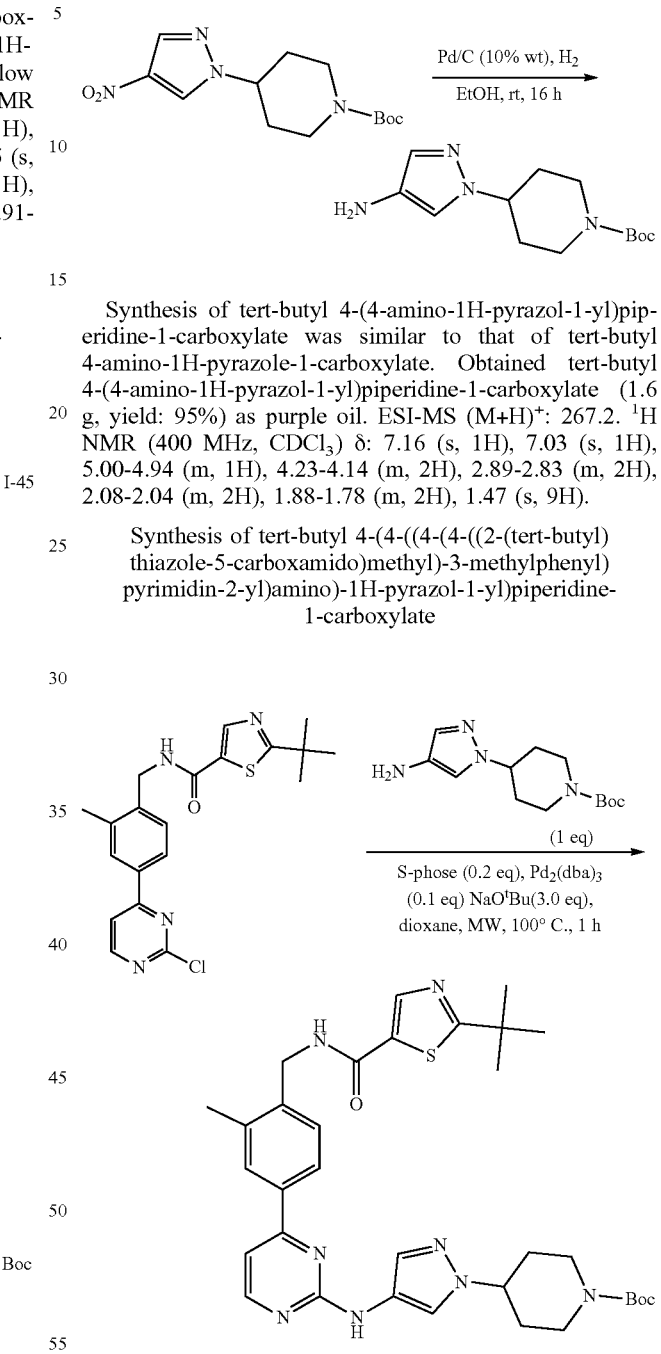

Synthesis of tert-butyl 4-(4-amino-1H-pyrazol-1-yl)piperidine-1-carboxylate was similar to that of tert-butyl 4-amino-1H-pyrazole-1-carboxylate. Obtained tert-butyl 4-(4-amino-1H-pyrazol-1-yl)piperidine-1-carboxylate (1.6 g, yield: 95%) as purple oil. ESI-MS (M+H)$^+$: 267.2. $^1$H NMR (400 MHz, CDCl$_3$) δ: 7.16 (s, 1H), 7.03 (s, 1H), 5.00-4.94 (m, 1H), 4.23-4.14 (m, 2H), 2.89-2.83 (m, 2H), 2.08-2.04 (m, 2H), 1.88-1.78 (m, 2H), 1.47 (s, 9H).

Synthesis of tert-butyl 4-(4-((4-(4-((2-(tert-butyl)thiazole-5-carboxamido)methyl)-3-methylphenyl)pyrimidin-2-yl)amino)-1H-pyrazol-1-yl)piperidine-1-carboxylate Synthesis of tert-butyl 4-(4-((4-(4-((2-(tert-butyl)thiazole-5-carboxamido)methyl)-3-methylphenyl)pyrimidin-2-yl)amino)-1H-pyrazol-1-yl)piperidine-1-carboxylate was similar to that of tert-butyl 4-(2-chloropyrimidin-4-yl)-2-methylbenzylcarbamate. The crude product was purified through silica gel column chromatography with (MeOH/DCM=1/25) to give tert-butyl 4-(4-((4-(4-((2-(tert-butyl)thiazole-5-carboxamido)methyl)-3-methylphenyl)pyrimidin-2-yl)amino)-1H-pyrazol-1-yl)piperidine-1-carboxylate (270 mg, yield: 84%) as a yellow solid. ESI-MS (M+H)$^+$: 631.2.

125

Synthesis of 2-(tert-butyl)-N-(2-methyl-4-(2-((1-(piperidin-4-yl)-1H-pyrazol-4-yl)amino)pyrimidin-4-yl)benzyl)thiazole-5-carboxamide

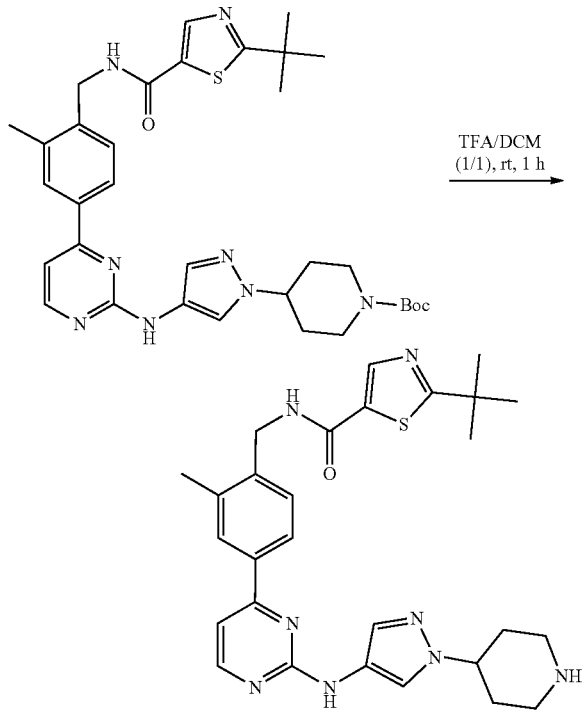

Synthesis of 2-(tert-butyl)-N-(2-methyl-4-(2-((1-(piperidin-4-yl)-1H-pyrazol-4-yl)amino)pyrimidin-4-yl)benzyl)thiazole-5-carboxamide was similar to that of Example 42. Purified through prep-HPLC (CH$_3$CN/H$_2$O with 0.05% NH$_3$.H$_2$O as mobile phase) to give 2-(tert-butyl)-N-(2-methyl-4-(2-((1-(piperidin-4-yl)-1H-pyrazol-4-yl)amino)pyrimidin-4-yl)benzyl)thiazole-5-carboxamide (220 mg, yield: 95%) as a yellow solid. ESI-MS (M+H)$^+$: 531.0. HPLC: (214 nm: 99.77%, 254 nm: 100%). $^1$H NMR (400 MHz, CD$_3$OD) δ: 8.37 (d, J=5.6 Hz, 1H), 8.25 (s, 1H), 8.08 (s, 1H), 7.99 (s, 1H), 7.96 (d, J=8.4 Hz, 1H), 7.75 (s, 1H), 7.44 (d, J=8.0 Hz, 1H), 7.29 (d, J=6.0 Hz, 1H), 4.61 (s, 2H), 4.57-4.50 (m, 1H), 3.59-3.56 (m, 2H), 3.26-3.19 (m, 2H), 2.47 (s, 3H), 2.38-2.23 (m, 4H), 1.46 (s, 9H).

Example 46: 2-(tert-butyl)-N-(2-methyl-4-(2-((1-(1-methylpiperidin-4-yl)-1H-pyrazol-4-yl)amino)pyrimidin-4-yl)benzyl)thiazole-5-carboxamide (I-46)

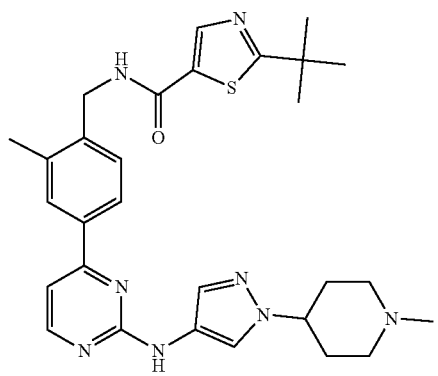

I-46

126

Synthesis of 2-(tert-butyl)-N-(2-methyl-4-(2-((1-(1-methylpiperidin-4-yl)-1H-pyrazol-4-yl)amino)pyrimidin-4-yl)benzyl)thiazole-5-carboxamide was similar to that of Example 43. Purified through prep-TLC (MeOH/DCM=1/15) to give 2-(tert-butyl)-N-(2-methyl-4-(2-((1-(1-methylpiperidin-4-yl)-1H-pyrazol-4-yl)amino)pyrimidin-4-yl)benzyl)thiazole-5-carboxamide (20 mg, yield: 55%) as a yellow solid. ESI-MS (M+H)$^+$: 545.2. HPLC: (214 nm: 99.51%, 254 nm: 98.97%). $^1$H NMR (400 MHz, CD$_3$OD) δ: 8.40 (d, J=5.2 Hz, 1H), 8.24 (s, 1H), 8.10 (s, 1H), 7.99 (s, 1H), 7.95 (d, J=8.4 Hz, 1H), 7.67 (s, 1H), 7.44 (d, J=8.0 Hz, 1H), 7.21 (d, J=5.6 Hz, 1H), 4.63 (s, 2H), 4.20-4.15 (m, 1H), 3.04-3.01 (m, 2H), 2.48 (s, 3H), 2.35 (s, 3H), 2.31-2.26 (m, 2H), 2.19-2.07 (m, 4H), 1.47 (s, 9H).

Example 47: Synthesis of 2-(tert-butyl)-N-(2-methyl-4-(2-((1-(1-(methylsulfonyl)piperidin-4-yl)-1H-pyrazol-4-yl)amino)pyrimidin-4-yl)benzyl)thiazole-5-carboxamide (I-47)

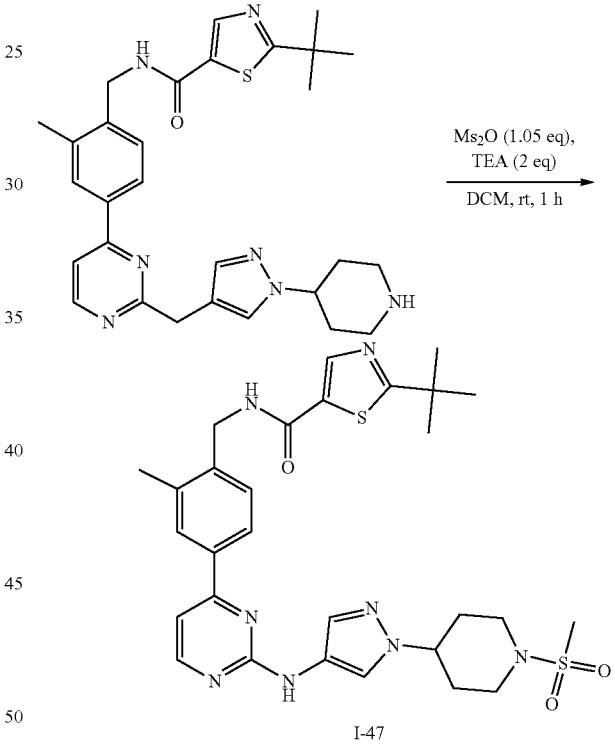

I-47

To a solution of 2-(tert-butyl)-N-(2-methyl-4-(2-((1-(piperidin-4-yl)-1H-pyrazol-4-yl)amino)pyrimidin-4-yl)benzyl)thiazole-5-carboxamide (63 mg, 0.119 mmol) in DCM (5 mL) were added Ms$_2$O (22 mg, 0.125 mmol, 1.05 equiv) and TEA (24 mg, 0.238 mmol, 2 equiv). The mixture was stirred at rt for 1 h. After diluted with DCM (80 mL), the mixture was washed with brine (30 mL), dried and concentrated. The crude was purified through silica gel column chromatography (MeOH/DCM=1/20) to give 2-(tert-butyl)-N-(2-methyl-4-(2-((1-(1-(methylsulfonyl)piperidin-4-yl)-1H-pyrazol-4-yl)amino)pyrimidin-4-yl)benzyl)thiazole-5-carboxamide as a yellow solid (30 mg, yield: 40%). ESI-MS (M+H)$^+$: 609.2. HPLC: (214 nm: 100%, 254 nm: 100%). $^1$H NMR (400 MHz, CDCl$_3$) δ: 8.44 (d, J=5.2 Hz, 1H), 8.05 (s, 1H), 8.02 (s, 1H), 7.88 (s, 1H), 7.85 (d, J=8.0 Hz, 1H), 7.57

(s, 1H), 7.40 (d, J=8.0 Hz, 1H), 7.09 (d, J=5.2 Hz, 1H), 6.95 (s, 1H), 6.12 (br, 1H), 4.68 (d, J=5.6 Hz, 2H), 4.30-4.23 (m, 1H), 3.93-3.89 (m, 2H), 2.99-2.93 (m, 2H), 2.84 (s, 3H), 2.46 (s, 3H), 2.32-2.27 (m, 2H), 2.23-2.13 (m, 2H), 1.45 (s, 9H).

Example 48: cis-4-(4-((4-(4-((2-(tert-butyl)thiazole-5-carboxamido)methyl)-3-methylphenyl)pyrimidin-2-yl)amino)-1H-pyrazol-1-yl)cyclohexanecarboxylic acid (I-48) and trans-4-(4-((4-(4-((2-(tert-butyl)thiazole-5-carboxamido)methyl)-3-methylphenyl)pyrimidin-2-yl)amino)-1H-pyrazol-1-yl)cyclohexanecarboxylic acid (I-49)

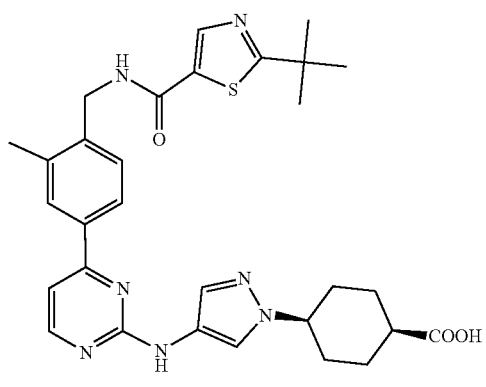

I-48

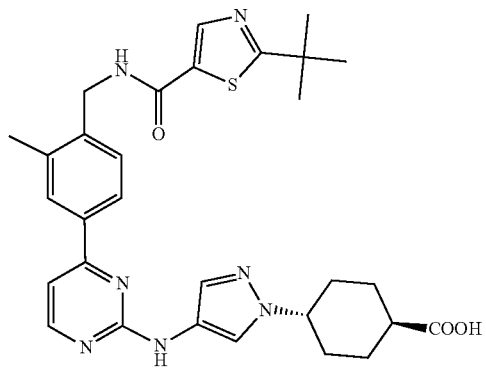

I-49

Synthesis of methyl 4-(tosyloxy)cyclohexanecarboxylate

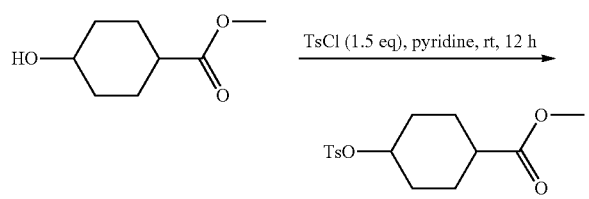

To a mixture of methyl 4-hydroxycyclohexanecarboxylate (172 mg, 1 mmol, 1.0 equiv) in pyridine (2 mL), TsCl (285 mg, 1.5 mmol, 1.5 equiv) was added. The mixture was stirred rt for 12 h. After diluted with EtOAc (100 mL), the mixture was washed with HCl (1 N, 50 mL), water (50 mL). The organic layer was dried and concentrated to give methyl 4-(tosyloxy)cyclohexanecarboxylate (326 mg, yield: 100%) as a colorless oil and used for next step without further purification. ESI-MS (M+Na)$^+$: 355.1.

Synthesis of methyl 4-(4-nitro-1H-pyrazol-1-yl)cyclohexanecarboxylate

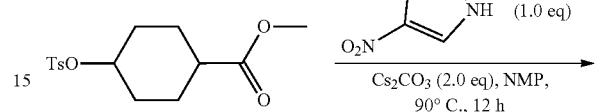

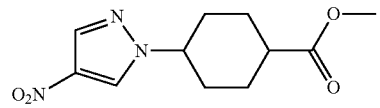

Synthesis of methyl 4-(4-nitro-1H-pyrazol-1-yl)cyclohexanecarboxylate was similar to that of 2-(4-nitro-1H-pyrazol-1-yl)ethanol. The organic layer was concentrated and purified by silica gel column (petroleum ether/EtOAc=3:1) to give methyl 4-(4-nitro-1H-pyrazol-1-yl)cyclohexanecarboxylate (110 mg, yield: 49%) as a colorless oil. ESI-MS (M+H)$^+$: 254.1.

Synthesis of methyl 4-(4-amino-1H-pyrazol-1-yl)cyclohexanecarboxylate

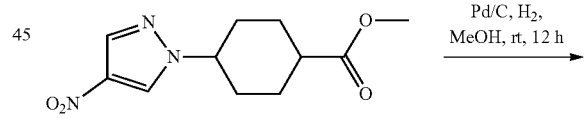

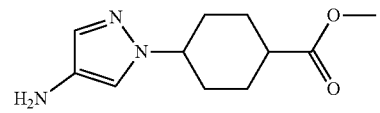

Synthesis of methyl 4-(4-amino-1H-pyrazol-1-yl)cyclohexanecarboxylate was similar to that of tert-butyl 4-amino-1H-pyrazole-1-carboxylate. The catalyst was filtered out and the resulting filtrate was concentrated to give target compound methyl 4-(4-amino-1H-pyrazol-1-yl)cyclohexanecarboxylate (93 mg, yield: 97%) as a yellow oil. ESI-MS (M+H)$^+$: 224.1.

129

Synthesis of methyl 4-(4-((4-(4-(((tert-butoxycarbonyl)amino)methyl)-3-methylphenyl)pyrimidin-2-yl)amino)-1H-pyrazol-1-yl)cyclohexanecarboxylate

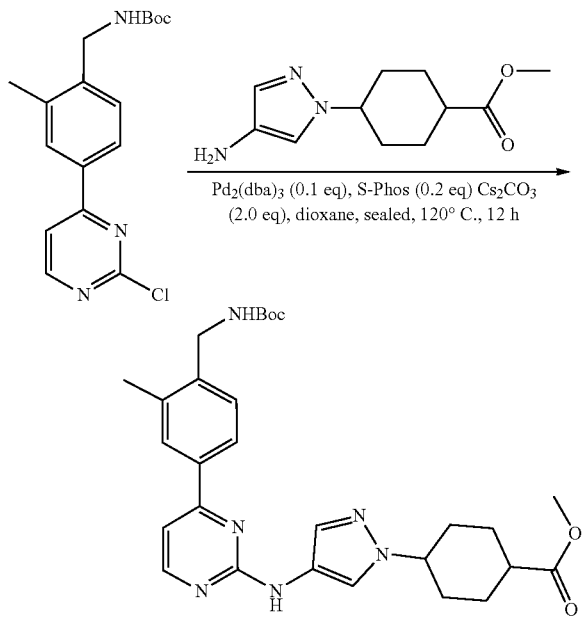

Synthesis of methyl 4-(4-((4-(4-(((tert-butoxycarbonyl)amino)methyl)-3-methylphenyl)pyrimidin-2-yl)amino)-1H-pyrazol-1-yl)cyclohexanecarboxylate was similar to that of tert-butyl 4-(2-chloropyrimidin-4-yl)-2-methylbenzylcarbamate. The residue was purified by prep-HPLC (Gradient: 5% B increase to 95% B, A: 0.5% NH₃ in water, B: CH₃CN) to give methyl 4-(4-((4-(4-(((tert-butoxycarbonyl)amino)methyl)-3-methylphenyl)pyrimidin-2-yl)amino)-1H-pyrazol-1-yl)cyclohexanecarboxylate (94 mg, yield: 50%) as a yellow solid. ESI-MS (M+H)⁺: 521.2. ¹H NMR (400 MHz, CDCl₃) δ: 8.41 (d, J=4.8 Hz, 1H), 7.98 (s, 1H), 7.88-7.83 (m, 2H), 7.58 (s, 1H), 7.38-7.31 (m, 1H), 7.07-7.06 (m, 1H), 6.96-6.95 (m, 1H), 4.79 (br, 1H), 4.37 (d, J=5.2 Hz, 2H), 4.18-4.09 (m, 1H), 3.71 (s, 3H), 2.41 (s, 3H), 2.32-2.17 (m, 3H), 2.10-1.99 (m, 3H), 1.76-1.69 (m, 3H), 1.47 (s, 9H).

Synthesis of methyl 4-(44(4-(4-((2-(tert-butyl)thiazole-5-carboxamido)methyl)-3-methylphenyl)pyrimidin-2-yl)amino)-1H-pyrazol-1-yl)cyclohexanecarboxylate

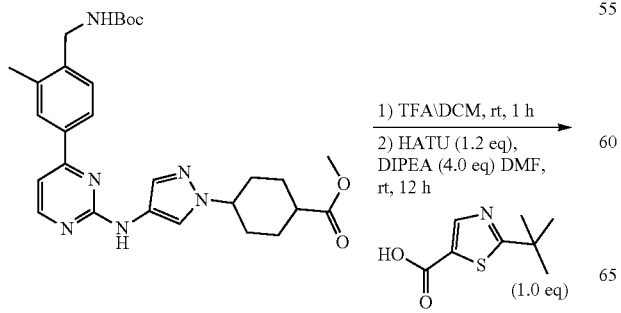

130

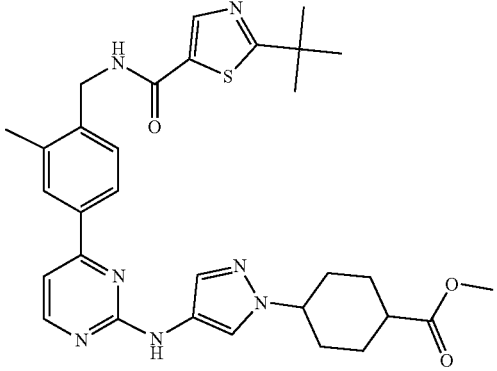

Synthesis of methyl 4-(4-((4-(4-((2-(tert-butyl)thiazole-5-carboxamido)methyl)-3-methylphenyl)pyrimidin-2-yl)amino)-1H-pyrazol-1-yl)cyclohexanecarboxylate was similar to that of Example 1. The mixture was purified by prep-HPLC (Gradient: 5% B increase to 95% B, A: 0.5% NH₃ in water, B: CH₃CN) to give methyl 4-(4-((4-(4-((2-(tert-butyl)thiazole-5-carboxamido)methyl)-3-methylphenyl)pyrimidin-2-yl)amino)-1H-pyrazol-1-yl)cyclohexanecarboxylate (40 mg, yield: 38%) as a yellow solid. ESI-MS (M+H)⁺: 588.3.

Synthesis of cis-4-(4-((4-(4-((2-(tert-butyl)thiazole-5-carboxamido)methyl)-3-methylphenyl)pyrimidin-2-yl)amino)-1H-pyrazol-1-yl)cyclohexanecarboxylic acid and trans-4-(4-((4-(4-((2-(tert-butyl)thiazole-5-carboxamido)methyl)-3-methylphenyl)pyrimidin-2-yl)amino)-1H-pyrazol-1-yl)cyclohexanecarboxylic acid

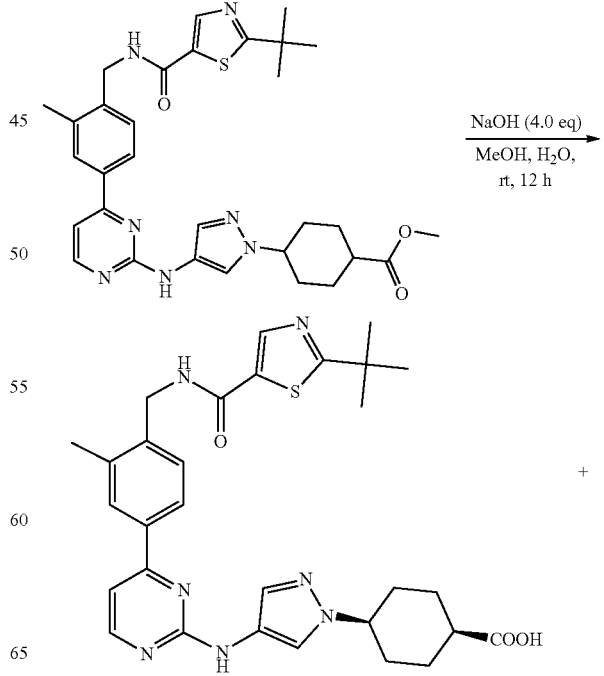

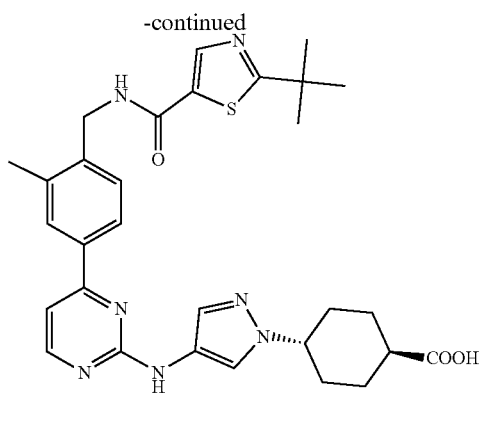

To a mixture of methyl 4-(4-((4-(4-((2-(tert-butyl)thiazole-5-carboxamido)methyl)-3-methylphenyl)pyrimidin-2-yl)amino)-1H-pyrazol-1-yl)cyclohexanecarboxylate (40 mg, 0.07 mmol, 1.0 equiv) in MeOH (3 mL)/H$_2$O (1 mL), NaOH (11 mg, 0.28 mmol, 4.0 equiv) was added. The mixture was stirred at rt for 12 h. After concentrated and diluted with water (5 mL), the mixture was acidified to pH=5 with HCl (1 N), the precipitate was collected and purified by prep-HPLC (Gradient: 5% B increase to 95% B, A: 0.5% NH$_3$ in water, B: CH$_3$CN) to give cis-4-(4-((4-(4-((2-(tert-butyl)thiazole-5-carboxamido)methyl)-3-methylphenyl)pyrimidin-2-yl)amino)-1H-pyrazol-1-yl)cyclohexanecarboxylic acid (9 mg, yield: 23%) and trans-4-(4-((4-(4-((2-(tert-butyl)thiazole-5-carboxamido)methyl)-3-methylphenyl)pyrimidin-2-yl)amino)-1H-pyrazol-1-yl)cyclohexanecarboxylic acid (13 mg, yield: 33%) as yellow solid. ESI-MS (M+H)$^+$: 574.2.

cis-4-(4-((4-(4-((2-(tert-butyl)thiazole-5-carboxamido)methyl)-3-methylphenyl)pyrimidin-2-yl)amino)-1H-pyrazol-1-yl)cyclohexanecarboxylic acid: $^1$H NMR (400 MHz, CD$_3$OD) δ: 8.29 (d, J=5.2 Hz, 1H), 8.07 (s, 1H), 8.04 (s, 1H), 7.80-7.78 (m, 2H), 7.50 (s, 1H), 7.41 (d, J=7.6 Hz, 1H), 7.01 (d, J=5.2 Hz, 1H), 4.56 (s, 2H), 4.14-4.05 (m, 1H), 2.64-2.61 (m, 1H), 2.41 (s, 3H), 2.24-2.19 (m, 2H), 2.04-1.91 (m, 4H), 1.70-1.62 (m, 2H), 1.39 (s, 9H).

trans-4-(4-((4-(4-((2-(tert-butyl)thiazole-5-carboxamido)methyl)-3-methylphenyl)pyrimidin-2-yl)amino)-1H-pyrazol-1-yl)cyclohexanecarboxylic acid: $^1$H NMR (400 MHz, CD$_3$OD) δ: 8.31 (d, J=5.2 Hz, 1H), 8.02 (s, 1H), 7.91 (s, 1H), 7.81 (s, 1H), 7.76 (d, J=8.0 Hz, 1H), 7.56 (s, 1H), 7.35 (d, J=8.0 Hz, 1H), 7.00 (d, J=5.2 Hz, 1H), 4.56 (s, 2H), 4.07-4.00 (m, 1H), 2.39 (s, 3H), 2.33-2.26 (m, 1H), 2.23-2.11 (m, 4H), 1.81-1.71 (m, 2H), 1.63-1.53 (m, 2H), 1.39 (s, 9H).

Example 49: N-(4-(2-((1-(2-aminoethyl)-1H-pyrazol-4-yl)amino)pyrimidin-4-yl)-2-methylbenzyl)-2-(tert-butyl)thiazole-5-carboxamide (I-50)

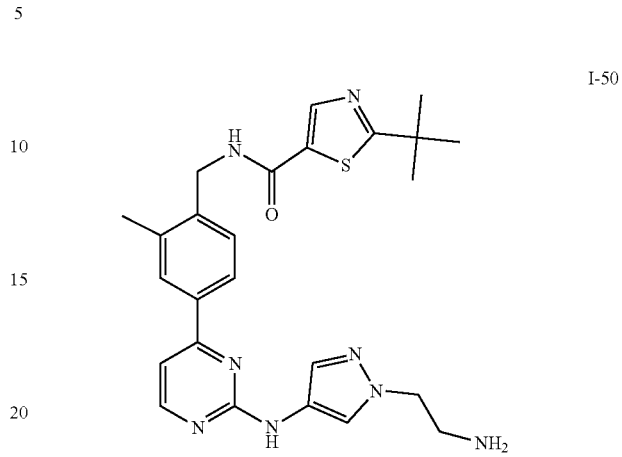

I-50

Preparation of tert-butyl (2-(4-amino-1H-pyrazol-1-yl)ethyl)carbamate

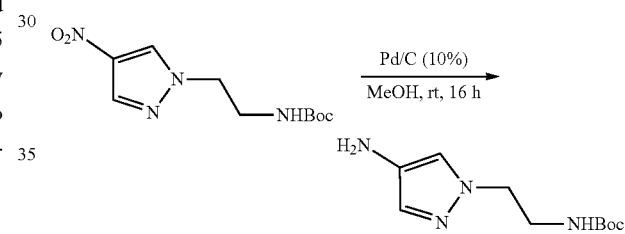

Synthesis of tert-butyl (2-(4-amino-1H-pyrazol-1-yl)ethyl)carbamate was similar to that of tert-butyl 4-amino-1H-pyrazole-1-carboxylate. The crude product (470 mg, yield: 98%) was used in the next step without further purification. ESI-MS (M+H)$^+$: 227.1.

Preparation of tert-butyl (2-(4-((4-(4-((2-(tert-butyl)thiazole-5-carboxamido)methyl)-3-methylphenyl)pyrimidin-2-yl)amino)-1H-pyrazol-1-yl)ethyl)carbamate

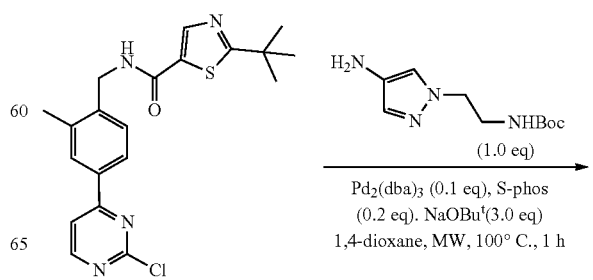

-continued

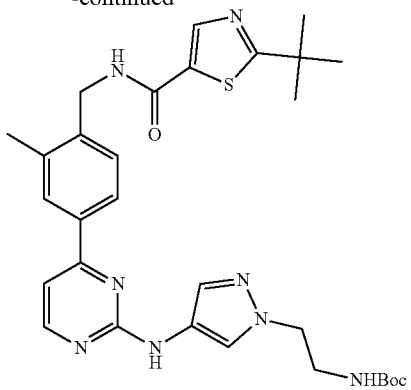

Synthesis of tert-butyl (2-(4-((4-(4-((2-(tert-butyl)thiazole-5-carboxamido)methyl)-3-methylphenyl)pyrimidin-2-yl)amino)-1H-pyrazol-1-yl)ethyl)carbamate was similar to that of tert-butyl 4-(2-chloropyrimidin-4-yl)-2-methylbenzylcarbamate. The residue was purified by prep-HPLC (CH$_3$CN/H$_2$O with 0.05% NH$_3$.H$_2$O as mobile phase) to give tert-butyl (2-(4-((4-(4-((2-(tert-butyl)thiazole-5-carboxamido)methyl)-3-methylphenyl)pyrimidin-2-yl)amino)-1H-pyrazol-1-yl)ethyl)carbamate as a white solid (62 mg, yield: 53%). ESI-MS (M+H)$^+$: 591.2.

Preparation of N-(4-(2-((1-(2-aminoethyl)-1H-pyrazol-4-yl)amino)pyrimidin-4-yl)-2-methylbenzyl)-2-(tert-butyl)thiazole-5-carboxamide

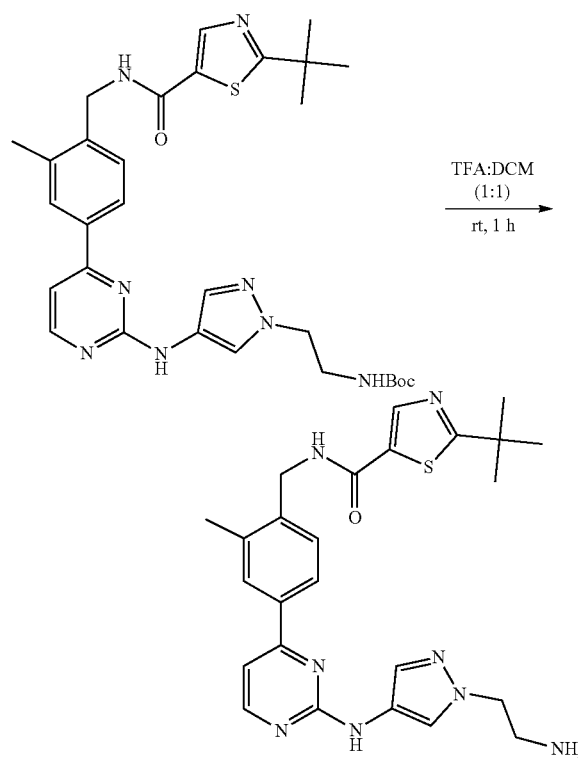

A mixture of tert-butyl (2-(4-((4-(4-((2-(tert-butyl)thiazole-5-carboxamido)methyl)-3-methylphenyl)pyrimidin-2-yl)amino)-1H-pyrazol-1-yl)ethyl)carbamate (78 mg, 0.13 mmol) in TFA/DCM (10 mL, 1:1) was stirred at rt for 1 h. Then the solvent was removed. The crude product was purified by prep-HPLC (CH$_3$CN/H$_2$O with 0.05% TFA as mobile phase) to give N-(4-(2-((1-(2-aminoethyl)-1H-pyrazol-4-yl)amino)pyrimidin-4-yl)-2-methylbenzyl)-2-(tert-butyl)thiazole-5-carboxamide as a yellow solid (36 mg, yield: 56%). ESI-MS (M+H)$^+$: 491.1. HPLC: (214 nm: 100%, 254 nm: 100%). $^1$H NMR (400 MHz, CD$_3$OD) δ: 8.39 (d, J=5.2 Hz, 1H), 8.23 (s, 1H), 8.07 (s, 1H), 7.98-7.95 (m, 2H), 7.74 (s, 1H), 7.44 (d, J=8.4 Hz, 1H), 7.28-7.26 (m, 1H), 4.61 (s, 2H), 4.44 (t, J=5.6 Hz, 2H), 3.44 (t, J=5.6 Hz, 2H), 2.48 (s, 3H), 1.46 (s, 9H).

Example 50: 2-(tert-butyl)-N-(4-(2-((1,3-dimethyl-1H-pyrazol-4-yl)amino)pyrimidin-4-yl)-2-methylbenzyl)thiazole-5-carboxamide (I-51)

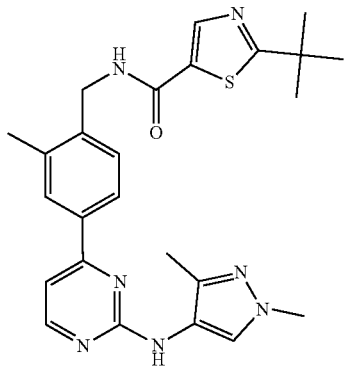

I-51

Preparation of tert-butyl 4-(2-((1,3-dimethyl-1H-pyrazol-4-yl)amino)pyrimidin-4-yl)-2-methylbenzylcarbamate and tert-butyl 4-(2-((1,5-dimethyl-1H-pyrazol-4-yl)amino)pyrimidin-4-yl)-2-methylbenzylcarbamate

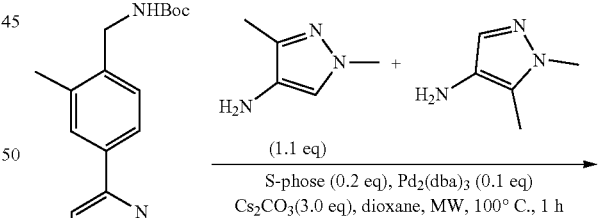

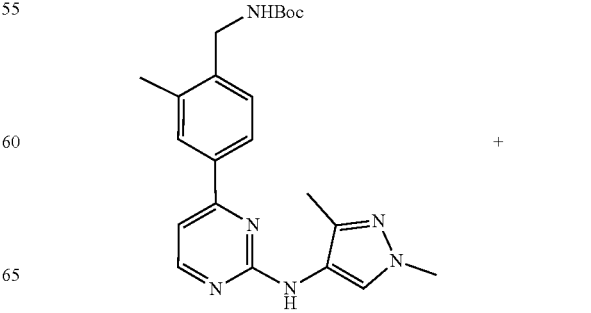

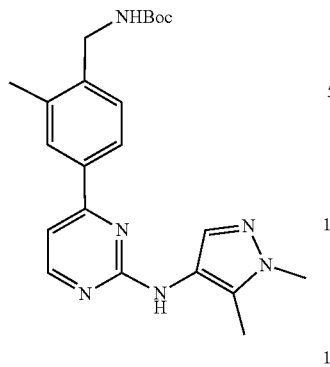

Synthesis of tert-butyl 4-(2-((1,3-dimethyl-1H-pyrazol-4-yl)amino)pyrimidin-4-yl)-2-methylbenzylcarbamate was similar to that of tert-butyl 4-(2-chloropyrimidin-4-yl)-2-methylbenzylcarbamate. The resulting product was purified by column chromatography (petroleum ether/EtOAc=5:1 to 1:2) to give tert-butyl 4-(2-((1,3-dimethyl-1H-pyrazol-4-yl)amino)pyrimidin-4-yl)-2-methylbenzylcarbamate (116 mg) and tert-butyl 4-(2-((1,5-dimethyl-1H-pyrazol-4-yl)amino)pyrimidin-4-yl)-2-methylbenzylcarbamate as a yellow solid (218 mg, yield: 86%). ESI-MS (M+H)+: 409.3.

tert-butyl 4-(2-((1,3-dimethyl-1H-pyrazol-4-yl)amino)pyrimidin-4-yl)-2-methylbenzylcarbamate: $^1$H NMR (400 MHz, CDCl$_3$) δ: 8.41 (d, J=5.2 Hz, 1H), 7.87 (s, 1H), 7.83 (s, 1H), 7.81 (s, 1H), 7.37 (d, J=7.6 Hz, 1H), 7.05 (d, J=5.6 Hz, 1H), 6.59 (s, 1H), 4.38 (d, J=5.2 Hz, 2H), 3.85 (s, 3H), 2.41 (s, 3H), 2.27 (s, 3H), 1.47 (s, 9H).

tert-butyl 4-(2-((1,5-dimethyl-1H-pyrazol-4-yl)amino)pyrimidin-4-yl)-2-methylbenzylcarbamate: $^1$H NMR (400 MHz, CDCl$_3$) δ: 8.37 (d, J=5.2 Hz, 1H), 7.83 (s, 1H), 7.81 (s, 1H), 7.69 (s, 1H), 7.34 (d, J=7.6 Hz, 1H), 7.05 (d, J=5.2 Hz, 1H), 6.42 (s, 1H), 4.36 (d, J=5.2 Hz, 2H), 3.81 (s, 3H), 2.40 (s, 3H), 2.27 (s, 3H), 1.47 (s, 9H).

Preparation of 2-(tert-butyl)-N-(4-(2-((1,3-dimethyl-1H-pyrazol-4-yl)amino)pyrimidin-4-yl)-2-methylbenzyl)thiazole-5-carboxamide

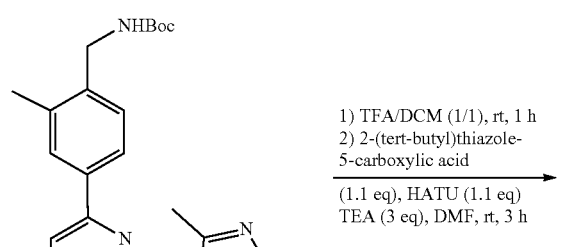

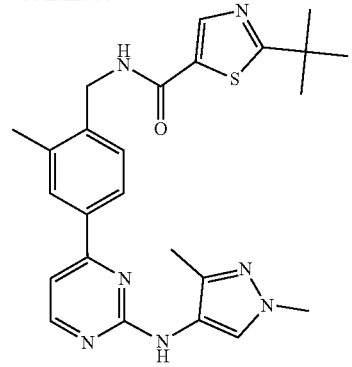

Synthesis of 2-(tert-butyl)-N-(4-(2-((1,3-dimethyl-1H-pyrazol-4-yl)amino)pyrimidin-4-yl)-2-methylbenzyl)thiazole-5-carboxamide was similar to that of Example 1. The resulting product was purified by prep-HPLC (CH$_3$CN/H$_2$O with 0.05% NH$_3$.H$_2$O as mobile phase) to give 2-(tert-butyl)-N-(4-(2-((1,3-dimethyl-1H-pyrazol-4-yl)amino)pyrimidin-4-yl)-2-methylbenzyl)thiazole-5-carboxamide (88 mg, yield: 45%) as a yellow solid. ESI-MS (M+H)+: 476.3. $^1$H NMR (400 MHz, DMSO-d$_6$) δ: 8.76 (t, J=6.4 Hz, 1H), 8.40 (d, J=4.8 Hz, 1H), 8.30 (s, 1H), 7.88-7.83 (m, 3H), 7.72-7.69 (m, 1H), 7.43 (d, J=7.6 Hz, 1H), 7.07 (d, J=4.8 Hz, 1H), 4.57 (d, J=5.2 Hz, 2H), 3.84 (s, 3H), 2.59 (s, 3H), 2.26 (s, 3H), 1.45 (s, 9H).

Example 51: The preparation of 2-(tert-butyl)-N-(4-(2-((1,5-dimethyl-1H-pyrazol-4-yl)amino)pyrimidin-4-yl)-2-methylbenzyl)thiazole-5-carboxamide (I-52)

I-52

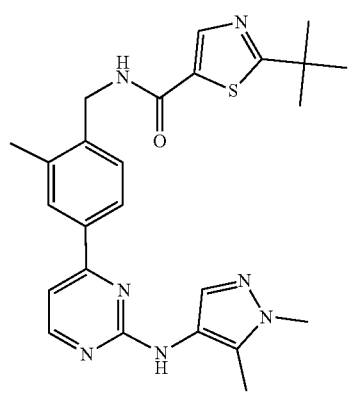

Synthesis of 2-(tert-butyl)-N-(4-(2-((1,5-dimethyl-1H-pyrazol-4-yl)amino)pyrimidin-4-yl)-2-methylbenzyl)thiazole-5-carboxamide was similar to that of Example 50. The resulting product was purified by prep-HPLC (CH$_3$CN/H$_2$O with 0.05% NH$_3$.H$_2$O as mobile phase) to give 2-(tert-butyl)-N-(4-(2-((1,5-dimethyl-1H-pyrazol-4-yl)amino)pyrimidin-4-yl)-2-methylbenzyl)thiazole-5-carboxamide (135 mg, yield: 50%) as a yellow solid. ESI-MS (M+H)+: 476.3. $^1$H NMR (400 MHz, CDCl$_3$) δ: 8.35 (d, J=5.2 Hz, 1H), 8.16 (s, 1H), 7.78 (s, 1H), 7.74 (d, J=7.6 Hz, 1H), 7.57 (s, 1H), 7.31 (d, J=8.0 Hz, 1H), 7.11 (br, 1H), 6.99 (d, J=5.2 Hz, 1H), 6.80 (br, 1H), 4.61 (d, J=5.2 Hz, 2H), 3.73 (s, 3H), 2.39 (s, 3H), 2.13 (s, 3H), 1.44 (s, 9H).

Example 52: 2-(tert-butyl)-N-(2-methyl-4-(2-((1,3,5-trimethyl-1H-pyrazol-4-yl)amino)pyrimidin-4-yl)benzyl)thiazole-5-carboxamide (I-53)

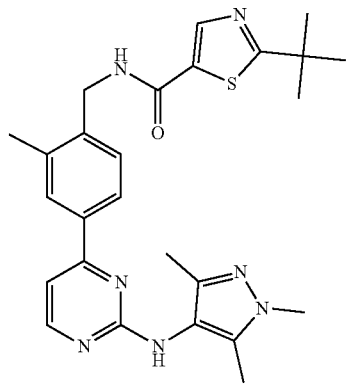

I-53

Synthesis of 2-(tert-butyl)-N-(2-methyl-4-(2-((1,3,5-trimethyl-1H-pyrazol-4-yl)amino)pyrimidin-4-yl)benzyl)thiazole-5-carboxamide was similar to that of Example 50 starting from 1,3,5-trimethyl-1H-pyrazol-4-amine. The residue was purified by prep-HPLC (CH$_3$CN/H$_2$O with 0.05% NH$_3$.H$_2$O as mobile phase) to give a yellow solid (15 mg, yield: 25%). ESI-MS (M+H)$^+$: 490.2. HPLC: (214 nm: 98.13%, 254 nm: 97.13%). $^1$H NMR (400 MHz, CD$_3$OD) δ: 8.14-8.12 (m, 2H), 7.81-7.75 (m, 2H), 7.27 (d, J=7.6 Hz, 1H), 7.07 (d, J=5.6 Hz, 1H), 4.48 (s, 2H), 3.62 (s, 3H), 2.32 (s, 3H), 2.03 (s, 3H), 1.98 (s, 3H), 1.34 (s, 9H).

Example 53: 2-(tert-butyl)-N-(2-methyl-4-(2-((4,5,6,7-tetrahydropyrazolo[1,5-a]pyrazin-2-yl)amino)pyrimidin-4-yl)benzyl)thiazole-5-carboxamide (I-54)

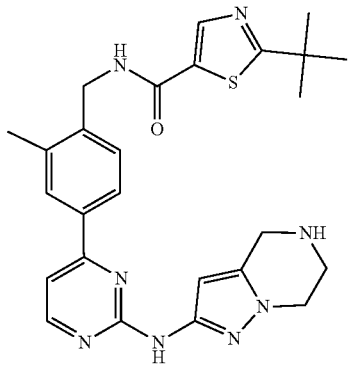

I-54

Synthesis of 2-nitro-4,5,6,7-tetrahydropyrazolo[1,5-a]pyrazine

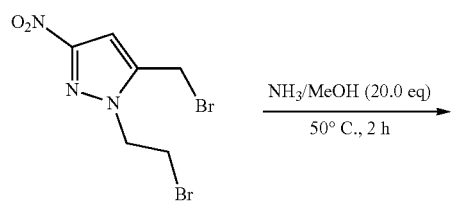

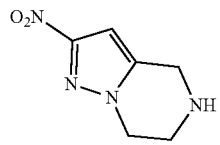

A mixture of 1-(2-bromoethyl)-5-(bromomethyl)-3-nitro-1H-pyrazole (625 mg, 2 mmol) and ammonia in methanol (5.73 mL, 40 mmol, 20 eq) in a sealed tube was stirred at 50° C. for 2 h. Then the solvent was removed. The crude was purified through silica gel column chromatography (MeOH/DCM=1/20) to give 2-nitro-4,5,6,7-tetrahydropyrazolo[1,5-a]pyrazine as a white solid (270 mg, yield: 80%).

Synthesis of tert-butyl 2-nitro-6,7-dihydropyrazolo[1,5-a]pyrazine-5(4H)-carboxylate

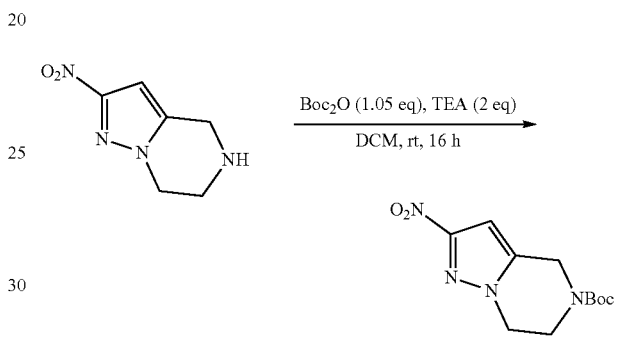

To a solution of 2-nitro-4,5,6,7-tetrahydropyrazolo[1,5-a]pyrazine (270 mg, 1.61 mmol) in DCM (20 mL) was added Boc$_2$O (368 mg, 1.69 mmol, 1.05 equiv) and TEA (324 mg, 3.2 mmol, 2 equiv). The mixture was stirred at rt for 16 h. After diluted with DCM (20 mL), the mixture was washed with water (40 mL) and brine (20 mL). The organic layer was dried and concentrated. The crude was purified through silica gel column chromatography (petroleum ether/EtOAc=1/3) to give tert-butyl 2-nitro-6,7-dihydropyrazolo[1,5-a]pyrazine-5(4H)-carboxylate as a white solid (380 mg, yield: 88%).

Synthesis of tert-butyl 2-amino-6,7-dihydropyrazolo[1,5-a]pyrazine-5(4H)-carboxylate

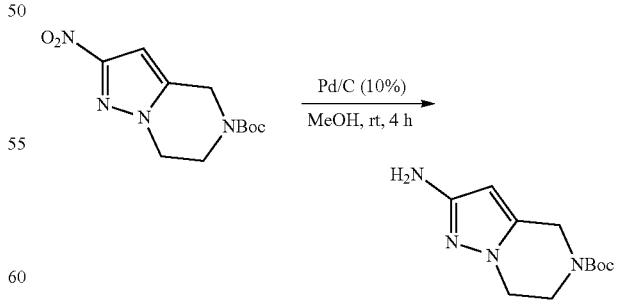

To a solution of tert-butyl 2-nitro-6,7-dihydropyrazolo[1,5-a]pyrazine-5(4H)-carboxylate (380 mg, 1.42 mmol) in methanol (20 mL) was added Pd/C (38 mg, 10% wt). The mixture was stirred at rt for 16 h under H$_2$ atmosphere (balloon pressure). The mixture was filtered through Celite.

The filtrate was concentrated to give tert-butyl 2-amino-6,7-dihydropyrazolo[1,5-a]pyrazine-5(4H)-carboxylate as a white solid (330 mg, yield: 90%). $^1$H NMR (400 MHz, CDCl$_3$) δ: 5.41 (s, 1H), 4.53 (s, 2H), 3.95 (t, J=5.2 Hz, 2H), 3.83 (t, J=5.2 Hz, 2H), 3.60 (s, 2H), 1.48 (s, 9H).

Synthesis of tert-butyl 2-((4-(4-((2-(tert-butyl)thiazole-5-carboxamido)methyl)-3-methylphenyl)pyrimidin-2-yl)amino)-6,7-dihydropyrazolo[1,5-a]pyrazine-5(4H)-carboxylate

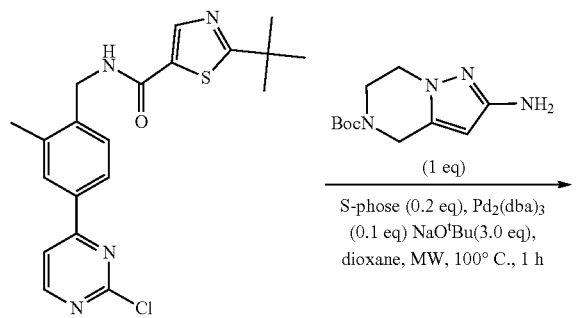

Synthesis of tert-butyl 2-((4-(4-((2-(tert-butyl)thiazole-5-carboxamido)methyl)-3-methylphenyl)pyrimidin-2-yl)amino)-6,7-dihydropyrazolo[1,5-a]pyrazine-5(4H)-carboxylate was similar to that of tert-butyl 2-methyl-4-(2-(((1-methyl-1H-pyrazol-4-yl)amino)pyrimidin-4-yl)benzylcarbamate. Obtained tert-butyl 2-((4-(4-((2-(tert-butyl)thiazole-5-carboxamido)methyl)-3-methylphenyl)pyrimidin-2-yl)amino)-6,7-dihydropyrazolo[1,5-a]pyrazine-5(4H)-carboxylate (140 mg, yield: 60%) as a yellow solid. $^1$H NMR (400 MHz, DMSO-d$_6$) δ: 9.77 (s, 1H), 9.11 (t, J=5.2 Hz, 1H), 8.47 (d, J=5.2 Hz, 1H), 8.34 (s, 1H), 7.97 (s, 1H), 7.96 (d, J=8.0 Hz, 1H), 7.39 (d, J=8.0 Hz, 1H), 7.33 (d, J=5.6 Hz, 1H), 6.60 (s, 1H), 4.61 (s, 2H), 4.50 (d, J=5.2 Hz, 2H), 3.98 (t, J=5.2 Hz, 2H), 3.82 (t, J=5.2 Hz, 2H), 2.41 (s, 3H), 1.44 (s, 9H), 1.39 (s, 9H).

Synthesis of 2-(tert-butyl)-N-(2-methyl-4-(2-((4,5,6,7-tetrahydropyrazolo[1,5-a]pyrazin-2-yl)amino)pyrimidin-4-yl)benzyl)thiazole-5-carboxamide

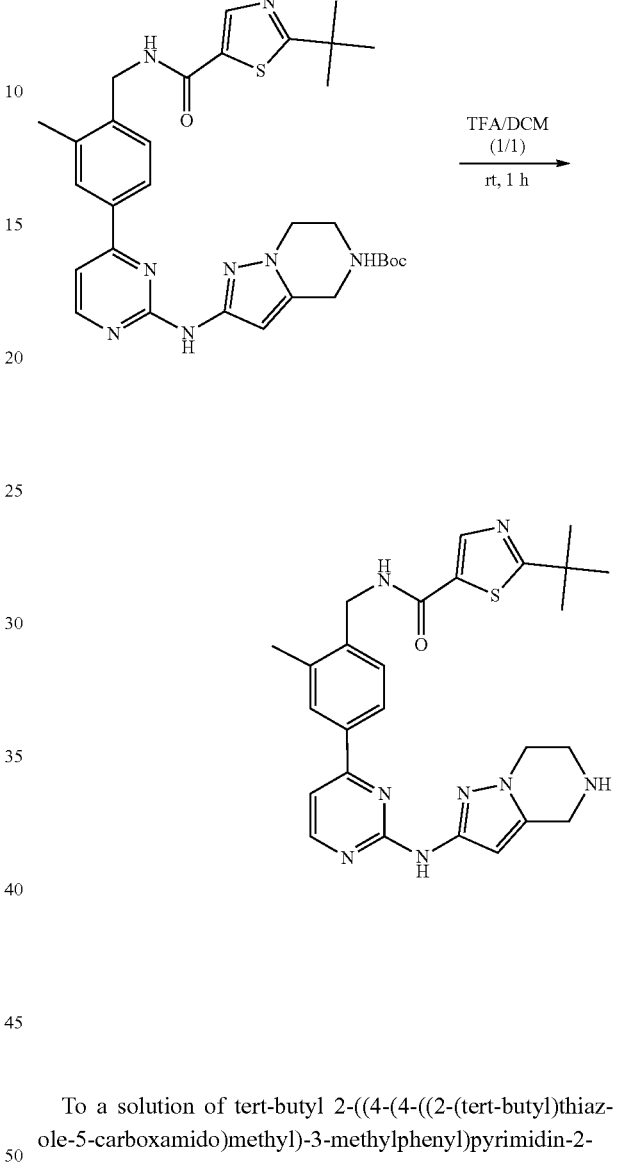

To a solution of tert-butyl 2-((4-(4-((2-(tert-butyl)thiazole-5-carboxamido)methyl)-3-methylphenyl)pyrimidin-2-yl)amino)-6,7-dihydropyrazolo[1,5-a]pyrazine-5(4H)-carboxylate (120 mg, 0.2 mmol) in DCM (1.5 mL) was added TFA (1.5 mL). The mixture was stirred at rt for 1 h. The solvent was removed. The crude was dissolved in water and adjusted pH to 7-8 with NH$_3$H$_2$O. Then the formed solid was filtered to give 2-(tert-butyl)-N-(2-methyl-4-(2-((4,5,6,7-tetrahydropyrazolo[1,5-a]pyrazin-2-yl)amino)pyrimidin-4-yl)benzyl)thiazole-5-carboxamide (70 mg, yield: 70%) as a light yellow solid. ESI-MS (M+H)$^+$: 502.8. HPLC: (214 nm: 97.70%, 254 nm: 96.52%). $^1$H NMR (400 MHz, DMSO-d$_6$) δ: 9.66 (s, 1H), 9.11 (t, J=5.2 Hz, 1H), 8.44-8.33 (m, 2H), 7.97-7.96 (m, 2H), 7.39-7.31 (m, 2H), 6.46 (s, 1H), 4.50 (s, 2H), 3.89-3.87 (m, 4H), 3.10-3.08 (s, 2H), 2.36 (s, 3H), 1.39 (s, 9H).

Example 54: 2-(tert-butyl)-N-(2-methyl-4-(2-((5-methyl-4,5,6,7-tetrahydropyrazolo[1,5-a]pyrazin-2-yl)amino)pyrimidin-4-yl)benzyl)thiazole-5-carboxamide (I-55)

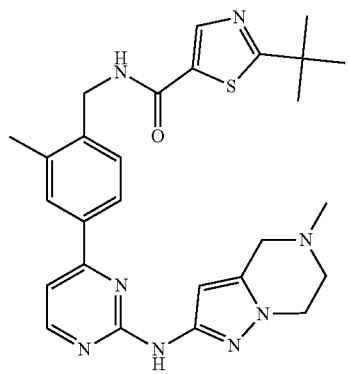

I-55

Preparation of tert-butyl 2-methyl-4-(2-((5-methyl-4,5,6,7-tetrahydropyrazolo[1,5-a]pyrazin-2-yl)amino)pyrimidin-4-yl)benzylcarbamate

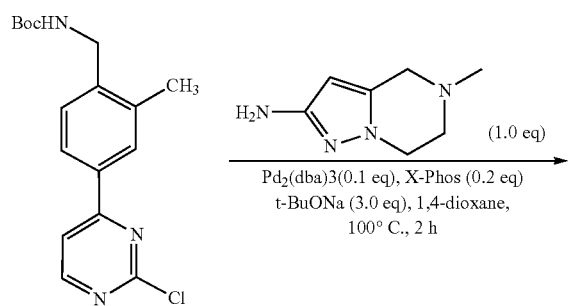

Synthesis of tert-butyl 2-methyl-4-(2-((5-methyl-4,5,6,7-tetrahydropyrazolo[1,5-a]pyrazin-2-yl)amino)pyrimidin-4-yl)benzylcarbamate was similar to that of tert-butyl 2-methyl-4-(2-((1-methyl-1H-pyrazol-4-yl)amino)pyrimidin-4-yl)benzylcarbamate. The crude was purified by pre-TLC (MeOH/DCM=1/20) to give product tert-butyl 2-methyl-4-(2-((5-methyl-4,5,6,7-tetrahydropyrazolo[1,5-a]pyrazin-2-yl)amino)pyrimidin-4-yl)benzylcarbamate as a yellow solid (50 mg, yield: 37%). ESI-MS (M+H)+: 449.9.

Preparation of 2-(tert-butyl)-N-(2-methyl-4-(2-((5-methyl-4,5,6,7-tetrahydropyrazolo[1,5-a]pyrazin-2-yl)amino)pyrimidin-4-yl)benzyl)thiazole-5-carboxamide

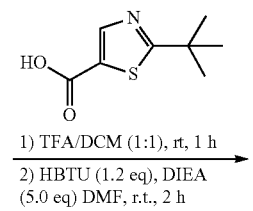

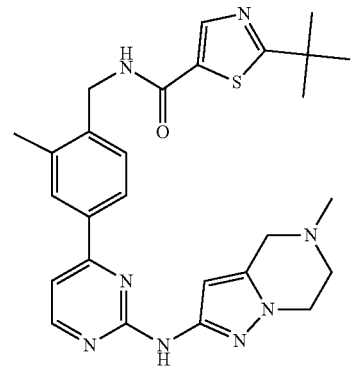

Synthesis of 2-(tert-butyl)-N-(2-methyl-4-(2-((5-methyl-4,5,6,7-tetrahydropyrazolo[1,5-a]pyrazin-2-yl)amino)pyrimidin-4-yl)benzyl)thiazole-5-carboxamide was similar to that of Example 1. The crude was purified by prep-HPLC (CH$_3$CN/H$_2$O with 0.05% ammonia as mobile phase) to give product 2-(tert-butyl)-N-(2-methyl-4-(2-((5-methyl-4,5,6,7-tetrahydropyrazolo[1,5-a]pyrazin-2-yl)amino)pyrimidin-4-yl)benzyl)thiazole-5-carboxamide as a white solid (31 mg, yield: 54%). ESI-MS (M+H)+: 516.9. HPLC: (214 nm: 100%, 254 nm: 96%). $^1$H NMR (400 MHz, DMSO-d$_6$) δ: 9.69 (s, 1H), 9.11 (t, J=5.6 Hz, 1H), 8.46 (d, J=5.2 Hz, 1H), 8.34 (s, 1H), 7.97 (s, 1H), 7.95 (d, J=8.0 Hz, 1H), 7.38 (d, J=8.0 Hz, 1H), 7.32 (d, J=5.2 Hz, 1H), 6.50 (s, 1H), 4.49 (d, J=5.6 Hz, 2H), 3.96 (t, J=5.6 Hz, 2H), 3.57 (s, 2H), 2.82 (t, J=5.6 Hz, 2H), 2.41 (s, 3H), 2.38 (s, 3H), 1.39 (s, 9H).

Example 55: 2-(tert-butyl)-N-(4-(2-((5-ethyl-4,5,6,7-tetrahydropyrazolo[1,5-a]pyrazin-2-yl)amino)pyrimidin-4-yl)-2-methylbenzyl)thiazole-5-carboxamide (I-56)

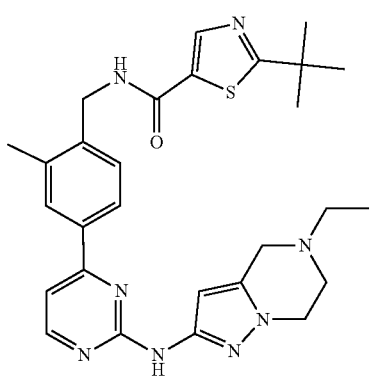

I-56

Preparation of tert-butyl 4-(2-((5-ethyl-4,5,6,7-tetrahydropyrazolo[1,5-a]pyrazin-2-yl)amino)pyrimidin-4-yl)-2-methylbenzylcarbamate

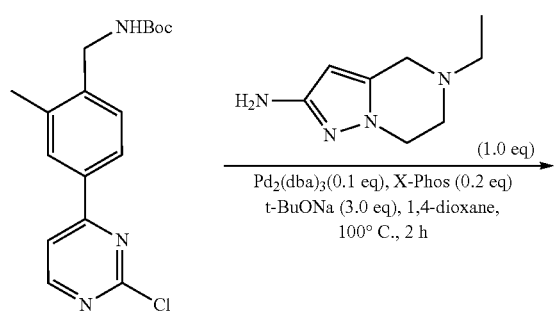

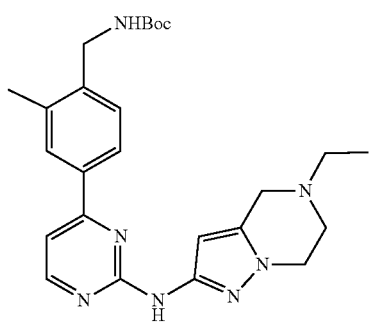

A mixture of tert-butyl 4-(2-chloropyrimidin-4-yl)-2-methylbenzylcarbamate (100 mg, 0.30 mmol), 5-ethyl-4,5,6,7-tetrahydropyrazolo[1,5-a]pyrazin-2-amine (50 mg, 0.30 mmol), t-BuONa (86 mg, 0.90 mmol), Pd₂(dba)₃ (27 mg, 0.03 mmol), X-Phos (28 mg, 0.06 mmol) in 5 mL 1,4-dioxane was heated at 100° C. for 2 h under nitrogen. After cooling to rt and diluted with EtOAc (120 mL), the mixture was washed with water (60 mL). The organic phase was dried and concentrated. The residue was purified by pre-TLC (MeOH/DCM=1/20) to give title product as a yellow solid (40 mg, yield: 29%). ESI-MS (M+H)⁺: 464.0.

Preparation of 2-(tert-butyl)-N-(4-(2-((5-ethyl-4,5,6,7-tetrahydropyrazolo[1,5-a]pyrazin-2-yl)amino)pyrimidin-4-yl)-2-methylbenzyl)thiazole-5-carboxamide

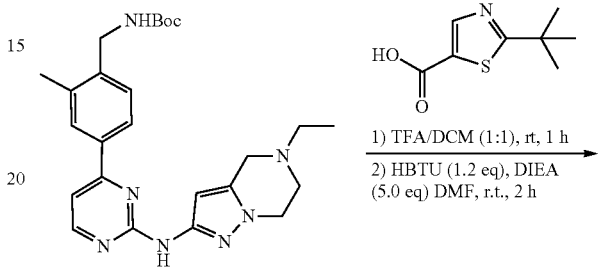

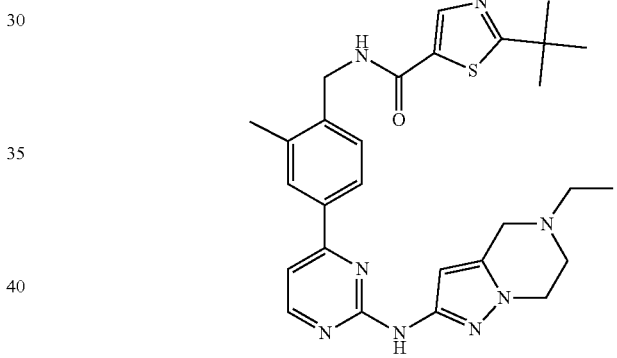

Synthesis of 2-(tert-butyl)-N-(4-(2-((5-ethyl-4,5,6,7-tetrahydropyrazolo[1,5-a]pyrazin-2-yl)amino)pyrimidin-4-yl)-2-methylbenzyl)thiazole-5-carboxamide was similar to that of Example 1. The residue was purified by prep-HPLC (CH₃CN/H₂O with 0.05% ammonia as mobile phase) to give product 2-(tert-butyl)-N-(4-(2-((5-ethyl-4,5,6,7-tetrahydropyrazolo[1,5-a]pyrazin-2-yl)amino)pyrimidin-4-yl)-2-methylbenzyl)thiazole-5-carboxamide as a pale yellow solid (15 mg, yield: 36%). ESI-MS (M+H)⁺: 530.9. HPLC: (214 nm: 100%, 254 nm: 100%). ¹H NMR (400 MHz, DMSO-d₆) δ: 9.69 (s, 1H), 9.10 (t, J=5.6 Hz, 1H), 8.46 (d, J=5.2 Hz, 1H), 8.34 (s, 1H), 7.96-7.94 (m, 2H), 7.39 (d, J=8.0 Hz, 1H), 7.31 (d, J=5.2 Hz, 1H), 6.50 (s, 1H), 4.50 (d, J=6.0 Hz, 2H), 3.96 (t, J=5.6 Hz, 2H), 3.62 (s, 2H), 2.87 (t, J=5.6 Hz, 2H), 2.56 (q, J=7.2 Hz, 2H), 2.41 (s, 3H), 1.39 (s, 9H), 1.07 (t, J=7.2 Hz, 3H).

Example 56: 2-(tert-butyl)-N-(2-methyl-4-(2-((3-methylisoxazol-4-yl)amino)pyrimidin-4-yl)benzyl)thiazole-5-carboxamide (I-57)

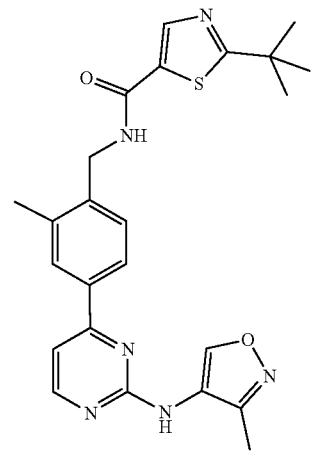

I-57

Preparation of tert-butyl (3-methylisoxazol-4-yl)carbamate

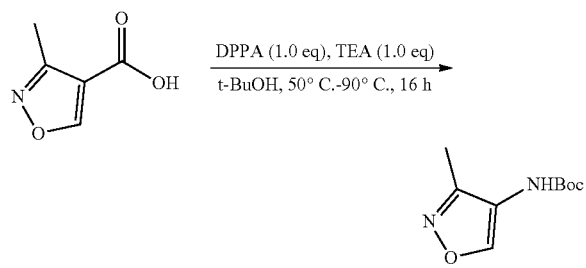

Diphenyl phosphorazidate (642 mg, 2.34 mmol) and TEA (236 mg, 2.34 mmol) were added to a solution of 3-methylisoxazole-4-carboxylic acid (300 mg, 2.34 mmol) in tert-butanol (10 mL) at 50° C. The mixture was stirred at 90° C. for 16 h. After concentrated, the residue was purified by silica gel column chromatography (petroleum ether/EtOAc=1:4) to give tert-butyl (3-methylisoxazol-4-yl)carbamate (412 mg, yield: 66%) as a yellow solid. ESI-MS (M+H)+: 199.1.

Preparation of 3-methylisoxazol-4-amine

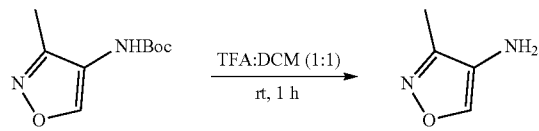

A mixture of tert-butyl (3-methylisoxazol-4-yl)carbamate (150 mg, 0.75 mmol) in TFA/DCM (10 mL, 1:1) was stirred at rt for 1 h. After concentrated, the residue was dissolved in DCM (20 mL) and solid K$_2$CO$_3$ (1 g) was added. The solid was filtered off and the filtrate was concentrated to give crude title product (96 mg, yield: 93%), which was used in nest step without further purification.

Preparation of tert-butyl 2-methyl-4-(2-((3-methylisoxazol-4-yl)amino)pyrimidin-4-yl)benzylcarbamate

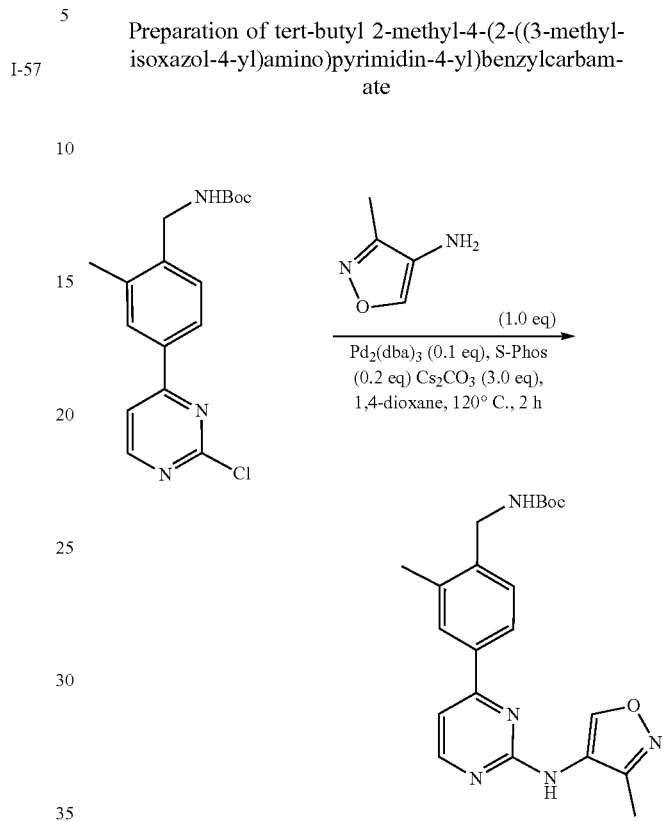

Synthesis of tert-butyl 2-methyl-4-(2-((3-methylisoxazol-4-yl)amino)pyrimidin-4-yl)benzylcarbamate was similar to that of tert-butyl 2-methyl-4-(2-((1-methyl-1H-pyrazol-4-yl)amino)pyrimidin-4-yl)benzylcarbamate. The residue was purified by silica gel chromatography column (petroleum ether/EtOAc=1:2) to give tert-butyl 2-methyl-4-(2-((3-methylisoxazol-4-yl)amino)pyrimidin-4-yl)benzylcarbamate as a yellow solid (234 mg, yield: 59%). ESI-MS (M+H)+: 396.1.

Preparation of 2-(tert-butyl)-N-(2-methyl-4-(2-((3-methylisoxazol-4-yl)amino)pyrimidin-4-yl)benzyl)thiazole-5-carboxamide

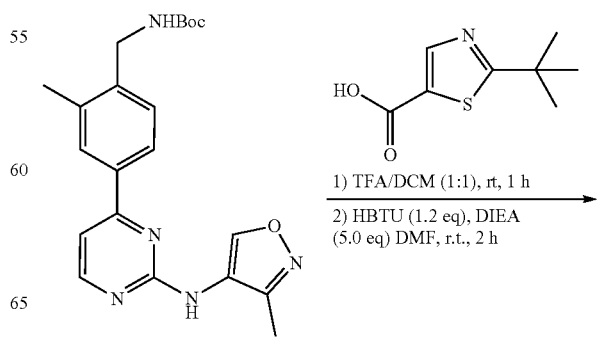

-continued

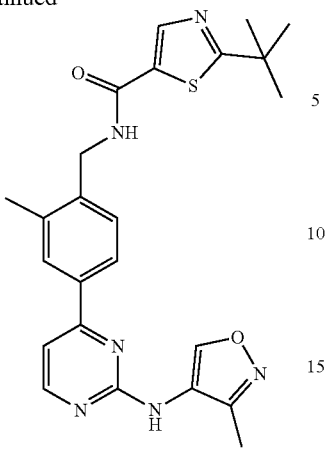

Synthesis of 2-(tert-butyl)-N-(2-methyl-4-(2-((3-methyl-isoxazol-4-yl)amino)pyrimidin-4-yl)benzyl)thiazole-5-carboxamide was similar to that of Example 1. The residue was purified by prep-HPLC (CH$_3$CN/H$_2$O with 0.05% NH$_3$.H$_2$O as mobile phase) to give 2-(tert-butyl)-N-(2-methyl-4-(2-((3-methylisoxazol-4-yl)amino)pyrimidin-4-yl)benzyl)thiazole-5-carboxamide as a white solid (54 mg, yield: 59%). ESI-MS: (M+H)$^+$:463.0. HPLC: (214 nm: 100%, 254 nm: 100%). $^1$H NMR (400 MHz, CD$_3$OD) δ: 8.95 (s, 1H), 8.36 (d, J=5.6 Hz, 1H), 8.13 (s, 1H), 7.85 (s, 1H), 7.83 (d, J=8.0 Hz, 1H), 7.33 (d, J=8.0 Hz, 1H), 7.19 (d, J=5.6 Hz, 1H), 4.50 (s, 2H), 2.36 (s, 3H), 2.26 (s, 3H), 1.35 (s, 9H).

Example 57: 2-(tert-butyl)-N-(2-methyl-4-(2-((1-methyl-1H-1,2,3-triazol-4-yl)amino)pyrimidin-4-yl)benzyl)thiazole-5-carboxamide (I-58)

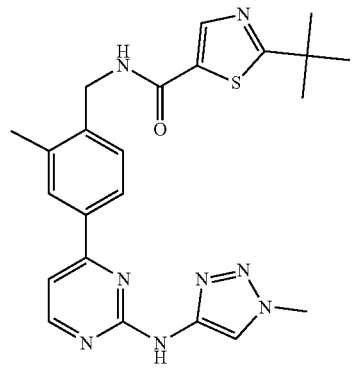

I-58

Synthesis of 2-(tert-butyl)-N-(2-methyl-4-(2-((1-methyl-1H-1,2,3-triazol-4-yl)amino)pyrimidin-4-yl)benzyl)thiazole-5-carboxamide was similar to that of Example 56, starting from 1-methyl-1H-1,2,3-triazol-4-amine. The residue was purified by prep-HPLC (CH$_3$CN/H$_2$O with 0.05% NH$_3$.H$_2$O as mobile phase) to give a yellow solid (35 mg, yield: 25%). ESI-MS (M+H)$^+$: 463.2. HPLC: (214 nm: 100%, 254 nm: 100%). $^1$H NMR (400 MHz, DMSO-d$_6$) δ: 10.25 (s, 1H), 9.11-9.08 (m, 1H), 8.54 (d, J=5.2 Hz, 1H), 8.33 (s, 1H), 8.04 (s, 1H), 7.98-7.95 (m, 2H), 7.42-7.39 (m, 2H), 4.50 (d, J=5.2 Hz, 1H), 4.06 (s, 3H), 2.42 (s, 3H), 1.39 (s, 9H).

Example 58: 2-(tert-butyl)-N-(2-methyl-4-(2-((5-methyl-1,3,4-thiadiazol-2-yl)amino)pyrimidin-4-yl)benzyl)thiazole-5-carboxamide (I-59)

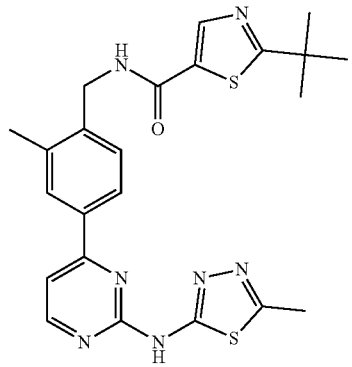

I-59

Synthesis of 2-(tert-butyl)-N-(2-methyl-4-(2-((5-methyl-1,3,4-thiadiazol-2-yl)amino)pyrimidin-4-yl)benzyl)thiazole-5-carboxamide was similar to that of Example 56, starting from 5-methyl-1,3,4-thiadiazol-2-amine. The crude was purified by prep-HPLC (CH$_3$CN/H$_2$O with 0.05% ammonia as mobile phase) to give product 2-(tert-butyl)-N-(2-methyl-4-(2-((5-methyl-1,3,4-thiadiazol-2-yl)amino)pyrimidin-4-yl)benzyl)thiazole-5-carboxamide as a white solid (100 mg, yield: 54%). ESI-MS (M+H)$^+$: 479.9. HPLC: (214 nm: 93%, 254 nm: 96%). $^1$H NMR (400 MHz, DMSO-d$_6$) δ: 9.16 (t, J=5.6 Hz, 1H), 8.63 (d, J=4.4 Hz, 1H), 8.35 (s, 1H), 8.09 (s, 1H), 8.08 (d, J=8.0 Hz, 1H), 7.51 (s, 1H), 7.43 (d, J=8.0 Hz, 1H), 6.51 (d, J=5.2 Hz, 1H), 4.51 (d, J=5.6 Hz, 2H), 2.61 (s, 3H), 2.44 (s, 3H), 1.38 (s, 9H).

Example 59: 2-(tert-butyl)-N-(2-methyl-4-(2-(pyridin-2-ylamino)pyrimidin-4-yl)benzyl)thiazole-5-carboxamide. (I-60)

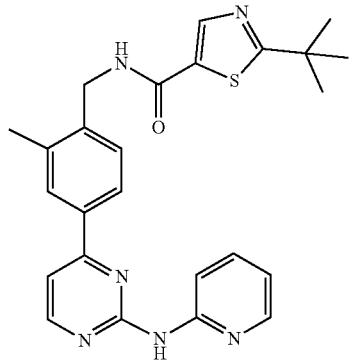

I-60

Synthesis of 2-(tert-butyl)-N-(2-methyl-4-(2-(pyridin-2-ylamino)pyrimidin-4-yl)benzyl)thiazole-5-carboxamide was similar to that of Example 56, starting from pyridin-2-amine. The residue was purified by prep-HPLC (CH$_3$CN/H$_2$O with 0.05% NH$_3$.H$_2$O as mobile phase) to give 2-(tert-butyl)-N-(2-methyl-4-(2-(pyridin-2-ylamino)pyrimidin-4-yl)benzyl)thiazole-5-carboxamide as a pale yellow solid (17 mg, yield: 53%). ESI-MS (M+H)$^+$: 459.3. HPLC: (214 nm:

100%, 254 nm: 100%). ¹H NMR (400 MHz, DMSO-d₆) δ: 9.76 (s, 1H), 9.12 (t, J=5.6 Hz, 1H), 8.60 (d, J=4.2 Hz, 1H), 8.36 (d, J=8.4 Hz, 1H), 8.34 (s, 1H), 8.29 (dd, J=8.4, 1.2 Hz, 1H), 8.02 (s, 1H), 7.99 (s, 1H), 7.83-7.78 (m, 1H), 7.50 (d, J=4.2 Hz, 1H), 7.40 (d, J=8.4 Hz, 1H), 7.00 (dd, J=4.2, 1.2 Hz, 1H), 4.50 (d, J=5.6 Hz, 2H), 2.42 (s, 3H), 1.39 (s, 9H).

Example 60: 2-(tert-butyl)-N-(4-(2-((5-(dimethylamino)pyridin-2-yl)amino)pyrimidin-4-yl)-2-methylbenzyl)thiazole-5-carboxamide (I-61)

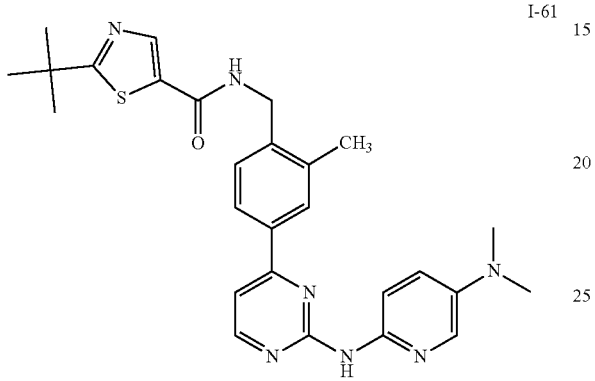

Synthesis of 2-(tert-butyl)-N-(4-(2-((5-(dimethylamino)pyridin-2-yl)amino)pyrimidin-4-yl)-2-methylbenzyl)thiazole-5-carboxamide was similar to that of Example 56. The residue was purified by prep-HPLC (CH₃CN/H₂O with 0.05% NH₃.H₂O as mobile phase) to give 2-(tert-butyl)-N-(4-(2-((5-(dimethylamino)pyridin-2-yl)amino)pyrimidin-4-yl)-2-methylbenzyl)thiazole-5-carboxamide as a pale yellow solid (39 mg, yield: 78%). ESI-MS (M+H)⁺: 502.2. HPLC: (214 nm: 100%, 254 nm: 98%). ¹H NMR (400 MHz, CD₃OD) δ: 8.45 (d, J=5.6 Hz, 1H), 8.25 (s, 1H), 8.15 (d, J=9.2 Hz, 1H), 7.99 (s, 1H), 7.91 (s, 1H), 7.82 (d, J=2.8 Hz, 1H), 7.43 (d, J=8.0 Hz, 1H), 7.37 (dd, J=9.2, 3.2 Hz, 1H), 7.33 (d, J=5.6 Hz, 1H), 4.62 (s, 2H), 2.96 (s, 6H), 2.48 (s, 3H), 1.47 (s, 9H).

Example 61: 2-(tert-butyl)-N-(2-methyl-4-(2-((5-(4-methylpiperazin-1-yl)pyridin-2-yl)amino)pyrimidin-4-yl)benzyl)thiazole-5-carboxamide (I-62)

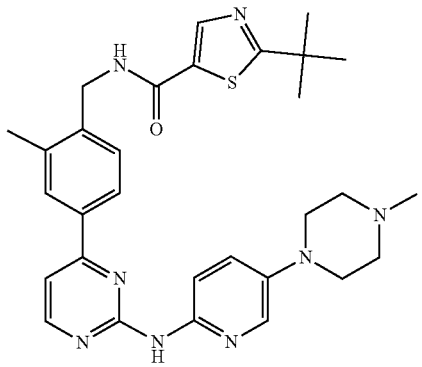

Synthesis of 2-(tert-butyl)-N-(2-methyl-4-(2-((5-(4-methylpiperazin-1-yl)pyridin-2-yl)amino)pyrimidin-4-yl)benzyl)thiazole-5-carboxamide was similar to that of Example 56, starting from 5-(4-methylpiperazin-1-yl)pyridin-2-amine. The residue was purified by prep-HPLC (CH₃CN/H₂O with 0.05% NH₃H₂O as mobile phase) to give 2-(tert-butyl)-N-(2-methyl-4-(2-((5-(4-methylpiperazin-1-yl)pyridin-2-yl)amino)pyrimidin-4-yl)benzyl)thiazole-5-carboxamide as a white solid (18 mg, yield: 17%). ESI-MS: (M+H)⁺:557.0. HPLC: (214 nm: 89%, 254 nm: 96%). ¹H NMR (400 MHz, CDCl₃) δ: 8.40 (d, J=4.8 Hz, 1H), 8.29 (d, J=9.2 Hz, 1H), 8.21 (s, 1H), 8.01-7.97 (m, 2H), 7.78 (s, 1H), 7.76 (d, J=5.6 Hz, 1H), 7.33-7.26 (m, 2H), 7.05 (d, J=5.2 Hz, 1H), 6.41 (br, 1H), 4.57 (d, J=5.6 Hz, 2H), 3.10 (t, J=4.0 Hz, 4H), 2.54 (t, J=4.4 Hz, 4H), 2.36 (s, 3H), 2.29 (s, 3H), 1.37 (s, 9H).

Example 62: 2-(tert-butyl)-N-(2-methyl-4-(6-((5-methyl-4,5,6,7-tetrahydropyrazolo[1,5-a]pyrazin-2-yl)amino)pyrimidin-4-yl)benzyl)thiazole-5-carboxamide (I-63)

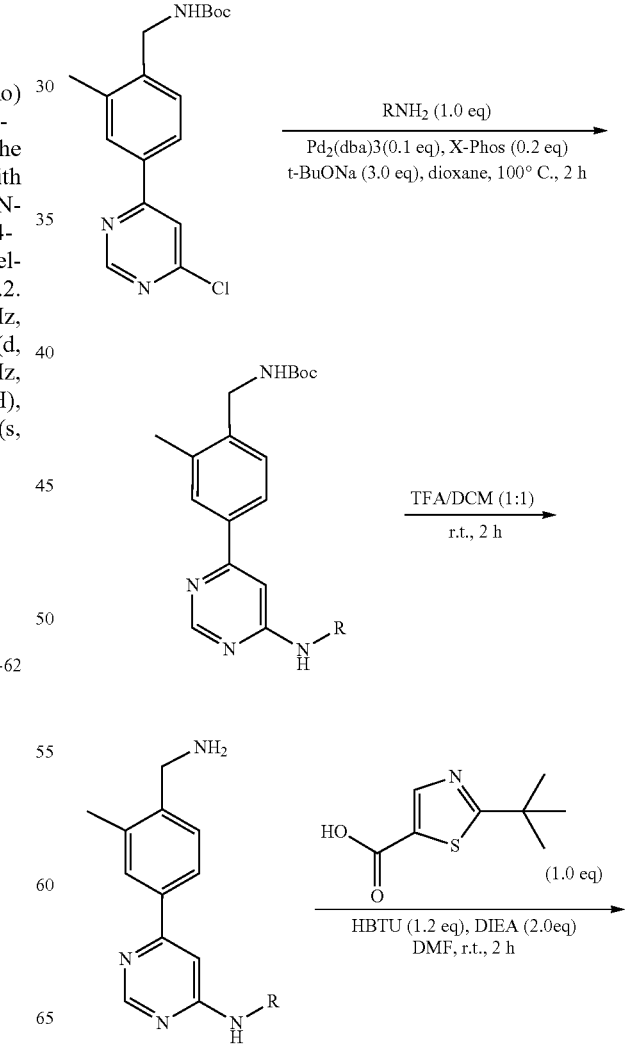

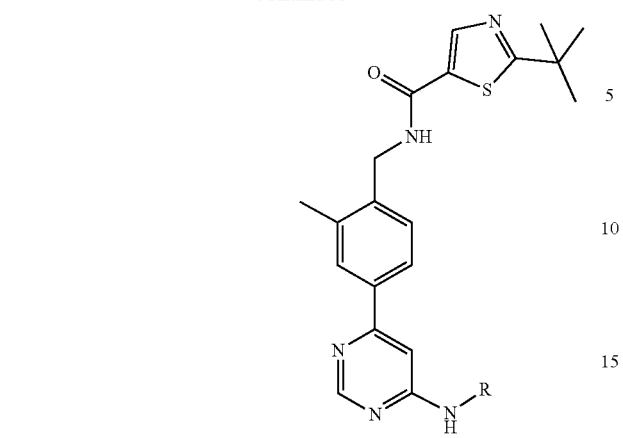

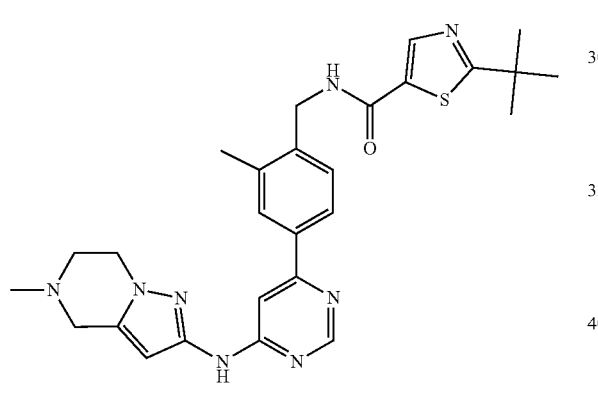

I-63

Synthesis of tert-butyl
4-(6-chloropyrimidin-4-yl)-2-methylbenzylcarbamate

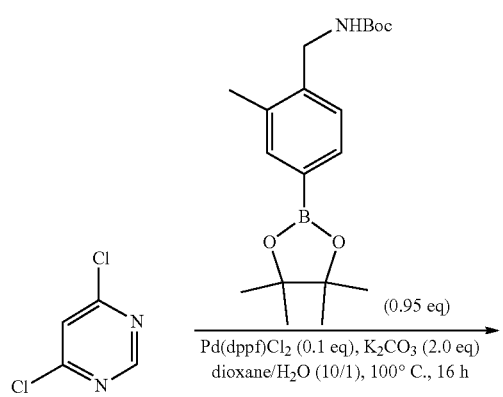

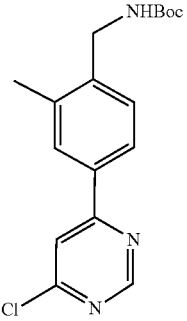

Synthesis of tert-butyl 4-(6-chloropyrimidin-4-yl)-2-methylbenzylcarbamate was similar to that of tert-butyl 4-(2-chloropyrimidin-4-yl)-2-methylbenzylcarbamate in Example 1, except that 4,6-dichloropyrimidine was substituted for 2,4-dichloropyrimidine. Obtained tert-butyl 4-(6-chloropyrimidin-4-yl)-2-methylbenzylcarbamate (327 mg, yield: 48%) as a white solid. ESI-MS (M+H)⁺: 333.9. ¹H NMR (400 MHz, CDCl₃) δ: 9.02 (s, 1H), 7.89 (s, 1H), 7.86 (d, J=7.6 Hz, 1H), 7.73 (s, 1H), 7.40 (d, J=8.4 Hz, 1H), 4.81 (br, 1H), 4.38 (d, J=5.6 Hz, 2H), 2.42 (s, 3H), 1.47 (s, 9H).

Synthesis of tert-butyl 2-methyl-4-(6-((5-methyl-4,5,6,7-tetrahydropyrazolo[1,5-a]pyrazin-2-yl)amino)pyrimidin-4-yl)benzylcarbamate

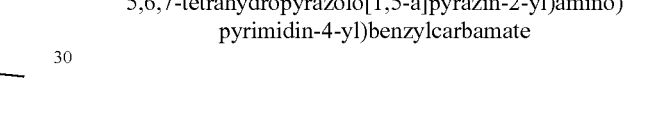

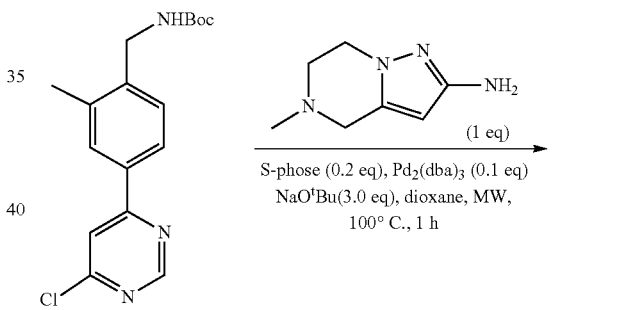

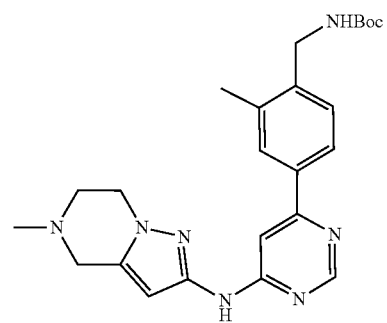

Synthesis of tert-butyl 2-methyl-4-(6-((5-methyl-4,5,6,7-tetrahydropyrazolo[1,5-a]pyrazin-2-yl)amino)pyrimidin-4-yl)benzylcarbamate was similar to that of tert-butyl 2-methyl-4-(2-((1-methyl-1H-pyrazol-4-yl)amino)pyrimidin-4-yl)benzylcarbamate in Example 1, except that the bicyclic amine shown above was substituted for 1-methyl-pyrazol-4-amine, and tert-butyl 4-(6-chloropyrimidin-4-yl)-2-methylbenzylcarbamate was substituted for tert-butyl 4-(2-chloropyrimidin-4-yl)-2-methylbenzylcarbamate. Obtained tert-butyl 2-methyl-4-(6-((5-methyl-4,5,6,7-tetrahydropyrazolo[1,5-a]pyrazin-2-yl)amino)pyrimidin-4-yl)benzylcarbamate (40 mg, yield: 15%) as a yellow solid. ESI-MS (M+H)+: 450.1.

Synthesis of 2-(tert-butyl)-N-(2-methyl-4-(6-((5-methyl-4,5,6,7-tetrahydropyrazolo[1,5-a]pyrazin-2-yl)amino)pyrimidin-4-yl)benzyl)thiazole-5-carboxamide

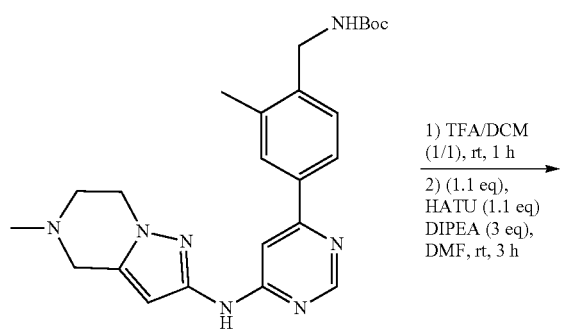

Synthesis of 2-(tert-butyl)-N-(2-methyl-4-(6-((5-methyl-4,5,6,7-tetrahydropyrazolo[1,5-a]pyrazin-2-yl)amino)pyrimidin-4-yl)benzyl)thiazole-5-carboxamide was similar to that of 2-(tert-butyl)-N-(2-methyl-4-(2-((1-methyl-1H-pyrazol-4-yl)amino)pyrimidin-4-yl)benzyl)thiazole-5-carboxamide in Example 1, except that tert-butyl 2-methyl-4-(6-((5-methyl-4,5,6,7-tetrahydropyrazolo[1,5-a]pyrazin-2-yl)amino)pyrimidin-4-yl)benzylcarbamate was substituted for tert-butyl 2-methyl-4-(2-((1-methyl-1H-pyrazol-4-yl)amino)pyrimidin-4-yl)benzylcarbamate. Obtained 2-(tert-butyl)-N-(2-methyl-4-(6-((5-methyl-4,5,6,7-tetrahydropyrazolo[1,5-a]pyrazin-2-yl)amino)pyrimidin-4-yl)benzyl)thiazole-5-carboxamide (20 mg, yield: 43%) as a yellow solid. ESI-MS (M+H)+: 516.8. HPLC: (214 nm: 99.33%, 254 nm: 97.39%). $^1$H NMR (400 MHz, CD$_3$OD) δ: 8.48 (s, 1H), 8.13 (s, 1H), 7.68 (s, 1H), 7.64 (d, J=8.0 Hz, 1H), 7.42 (s, 1H), 7.30 (d, J=8.0 Hz, 1H), 6.15 (s, 1H), 4.49 (s, 2H), 4.01 (t, J=5.6 Hz, 2H), 3.57 (s, 2H), 2.87 (t, J=5.6 Hz, 2H), 2.40 (s, 3H), 2.34 (s, 3H), 1.35 (s, 9H).

Example 63: 2-(tert-butyl)-N-(2-methyl-4-(6-((1-methyl-1H-pyrazol-4-yl)amino)pyrimidin-4-yl)benzyl)thiazole-5-carboxamide (I-64)

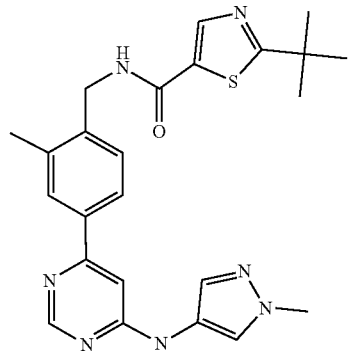

Synthesis of 2-(tert-butyl)-N-(2-methyl-4-(6-((1-methyl-1H-pyrazol-4-yl)amino)pyrimidin-4-yl)benzyl)thiazole-5-carboxamide was similar to that of Example 62. Obtained 2-(tert-butyl)-N-(2-methyl-4-(6-((1-methyl-1H-pyrazol-4-yl)amino)pyrimidin-4-yl)benzyl)thiazole-5-carboxamide (50 mg, yield: 48%) as a white solid. ESI-MS (M+H)+: 461.9. HPLC: (214 nm: 99.47%, 254 nm: 99.16%). $^1$H NMR (400 MHz, CD$_3$OD) δ: 8.60 (s, 1H), 8.24 (s, 1H), 8.05 (s, 1H), 7.77 (s, 1H), 7.74 (d, J=8.0 Hz, 1H), 7.56 (s, 1H), 7.42 (d, J=8.0 Hz, 1H), 6.99 (s, 1H), 4.61 (s, 2H), 3.90 (s, 3H), 2.46 (s, 3H), 1.47 (s, 9H).

Example 64: 2-(tert-butyl)-N-(2-methyl-4-(6-((1-methyl-1H-imidazol-4-yl)amino)pyrimidin-4-yl)benzyl)thiazole-5-carboxamide (I-65)

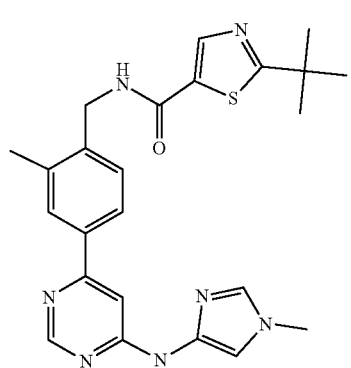

Preparation of 1-methyl-1H-imidazol-4-amine

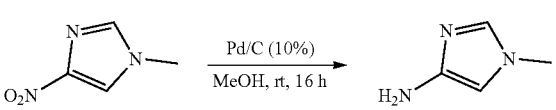

To a solution of 1-methyl-4-nitro-1H-imidazole (500 mg, 3.94 mmol) in MeOH (10 mL) was added Pd/C (50 mg). The mixture was stirred at rt for 16 h under hydrogen atmosphere. Then the mixture was filtered and the filtrate was concentrated in vacuo. The crude product (340 mg. yield: 89%) was used in the next step without further purification. ESI-MS (M+H)⁺: 98.1.

Preparation of 6-chloro-N-(1-methyl-1H-imidazol-4-yl)pyrimidin-4-amine

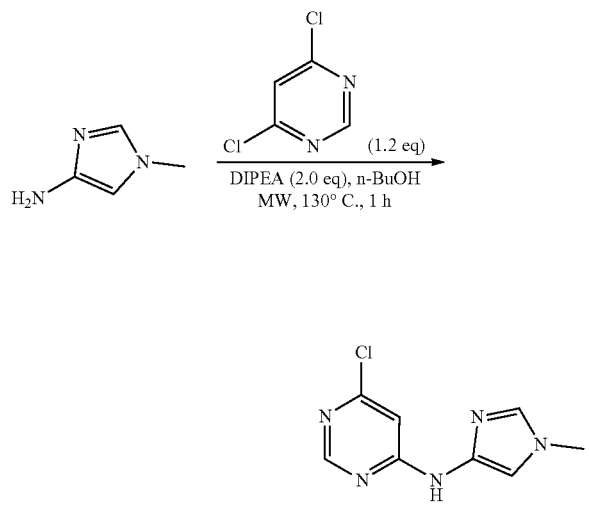

To a solution of 1-methyl-1H-imidazol-4-amine (80 mg, 0.80 mmol) in n-BuOH (4 mL) were added 4,6-dichloropyrimidine (140 mg, 0.96 mmol) and DIPEA (205 mg, 1.60 mmol). The mixture was stirred at 130° C. for 1 h under microwave. After removal of solution, the residue was purified by silica gel column chromatography (petroleum ether/EtOAc=2:1) to give compound 6-chloro-N-(1-methyl-1H-imidazol-4-yl)pyrimidin-4-amine (70 mg, yield: 41%) as a white solid. ESI-MS (M+H)⁺: 210.2. ¹H NMR (400 MHz, CDCl₃) δ: 8.51 (s, 1H), 7.30 (s, 1H), 7.26 (s, 1H), 6.71 (s, 1H), 3.73 (s, 3H).

Preparation of 2-(tert-butyl)-N-(2-methyl-4-(6-((1-methyl-1H-imidazol-4-yl)amino)pyrimidin-4-yl)benzyl)thiazole-5-carboxamide

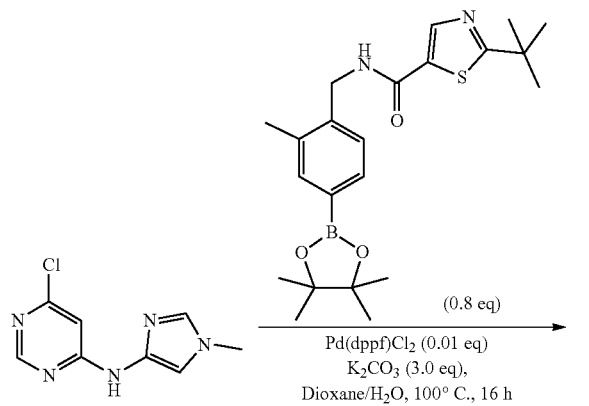

Synthesis of 2-(tert-butyl)-N-(2-methyl-4-(6-((1-methyl-1H-imidazol-4-yl)amino)pyrimidin-4-yl)benzyl)thiazole-5-carboxamide was similar to that of tert-butyl 4-(2-chloropyrimidin-4-yl)-2-methylbenzylcarbamate. The crude product was purified by prep-HPLC (CH₃CN/H₂O with 0.05% NH₃.H₂O as mobile phase) to give 2-(tert-butyl)-N-(2-methyl-4-(6-((1-methyl-1H-imidazol-4-yl)amino)pyrimidin-4-yl)benzyl)thiazole-5-carboxamide as a yellow solid (40 mg, yield: 26%). ESI-MS (M+H)⁺: 462.1. HPLC: (214 nm: 100%, 254 nm: 100%). ¹H NMR (400 MHz, CD₃OD) δ: 8.50 (s, 1H), 8.12 (s, 1H), 7.68 (s, 1H), 7.64 (d, J=8.0 Hz, 1H), 7.35 (s, 1H), 7.32 (d, J=8.4 Hz, 1H), 7.25 (s, 1H), 7.06 (s, 1H), 4.60 (s, 2H), 3.74 (s, 3H), 2.45 (s, 3H), 1.46 (s, 9H).

Example 65: 2-(tert-butyl)-N-(2-methyl-4-(6-((1-methyl-1H-pyrazol-3-yl)amino)pyrimidin-4-yl)benzyl)thiazole-5-carboxamide (I-66)

I-66

Synthesis of 2-(tert-butyl)-N-(2-methyl-4-(6-((1-methyl-1H-pyrazol-3-yl)amino)pyrimidin-4-yl)benzyl)thiazole-5-carboxamide was similar to that of Example 62, starting from 1-methyl-1H-pyrazol-3-amine. The crude product was purified by column chromatography on silica gel column eluting with petroleum ether/EtOAc (1/4) to give 2-(tert-butyl)-N-(2-methyl-4-(6-((1-methyl-1H-pyrazol-3-yl)amino)pyrimidin-4-yl)benzyl)thiazole-5-carboxamide (48 mg, yield: 52%) as a yellow solid. ESI-MS (M+1)⁺: 462.2. ¹H NMR (400 MHz, CD₃OD) δ: 8.56 (s, 1H), 8.21 (s, 1H), 7.75 (s, 1H), 7.74 (d, J=7.6 Hz, 1H), 7.48-7.37 (m, 3H), 6.37 (s, 1H), 4.57 (s, 2H), 3.82 (s, 3H), 2.42 (s, 3H), 1.43 (s, 9H).

Example 66: 2-(tert-butyl)-N-(2-methyl-4-(6-((2-methyl-2H-1,2,3-triazol-4-yl)amino)pyrimidin-4-yl)benzyl)thiazole-5-carboxamide (I-67)

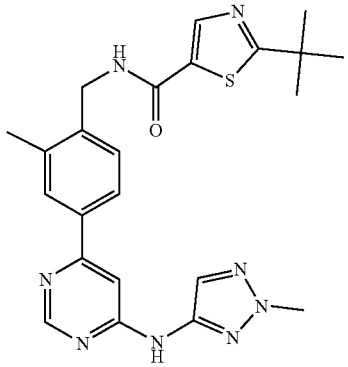

I-67

Synthesis of 2-(tert-butyl)-N-(2-methyl-4-(6-((2-methyl-2H-1,2,3-triazol-4-yl)amino)pyrimidin-4-yl)benzyl)thiazole-5-carboxamide was similar to that of Example 62, starting from 2-methyl-2H-1,2,3-triazol-4-amine. The residue was purified by prep-HPLC (CH$_3$CN/H$_2$O with 0.05% NH$_3$.H$_2$O as mobile phase) to give a yellow solid (47 mg, yield: 41%). ESI-MS (M+H)$^+$: 463.2. HPLC: (214 nm: 100%, 254 nm: 100%). $^1$H NMR (400 MHz, DMSO-d6) δ: 10.36 (s, 1H), 9.09 (t, J=5.2 Hz, 1H), 8.74 (s, 1H), 8.34 (s, 1H), 7.97 (s, 1H), 7.87 (s, 1H), 7.82 (d, J=7.6 Hz, 1H), 7.41-7.39 (m, 2H), 4.50 (d, J=5.2 Hz, 2H), 4.10 (s, 3H), 2.41 (s, 3H), 1.40 (s, 9H).

Example 67: 2-(tert-butyl)-N-(2-methyl-4-(6-((2-methyl-2H-tetrazol-5-yl)amino)pyrimidin-4-yl)benzyl)thiazole-5-carboxamide (I-68)

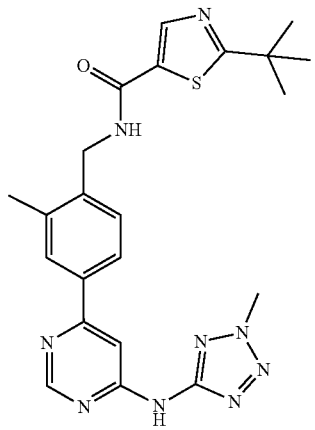

I-68

Synthesis of 2-(tert-butyl)-N-(2-methyl-4-(6-((2-methyl-2H-tetrazol-5-yl)amino)pyrimidin-4-yl)benzyl)thiazole-5-carboxamide was similar to that of Example 62, starting from 2-methyl-2H-tetrazol-5-amine. The residue was purified by prep-HPLC (CH$_3$CN/H$_2$O with 0.05% NH$_3$.H$_2$O as mobile phase) to give a yellow solid (7 mg, yield: 11%). ESI-MS (M+H)$^+$: 464.2. $^1$HNMR (400 MHz, DMSO-d$_6$) δ: 11.01 (s, 1H), 9.10 (t, J=5.6 Hz, 1H), 8.78 (s, 1H), 8.32 (s, 1H), 8.05 (s, 1H), 7.89 (s, 1H), 7.86 (d, J=8.0 Hz, 1H), 7.40 (d, J=8.0 Hz, 1H), 4.49 (d, J=5.2 Hz, 2H), 4.34 (s, 3H), 2.41 (s, 3H), 1.38 (s, 9H).

Example 68: 2-(tert-butyl)-N-(2-methyl-4-(6-((5-(4-methylpiperazin-1-yl)pyridin-2-yl)amino)pyrimidin-4-yl)benzyl)thiazole-5-carboxamide (I-69)

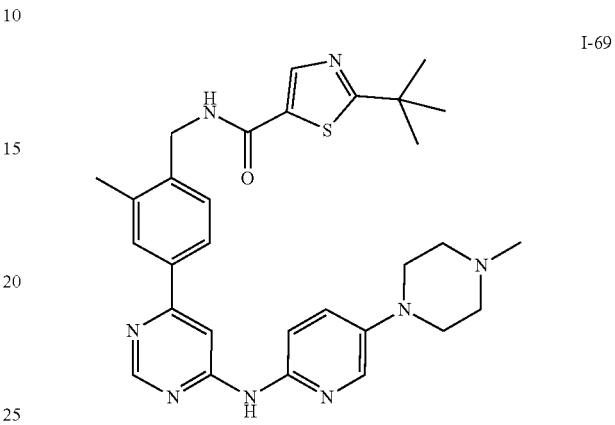

I-69

Synthesis of tert-butyl 4-(6-aminopyrimidin-4-yl)-2-methylbenzylcarbamate

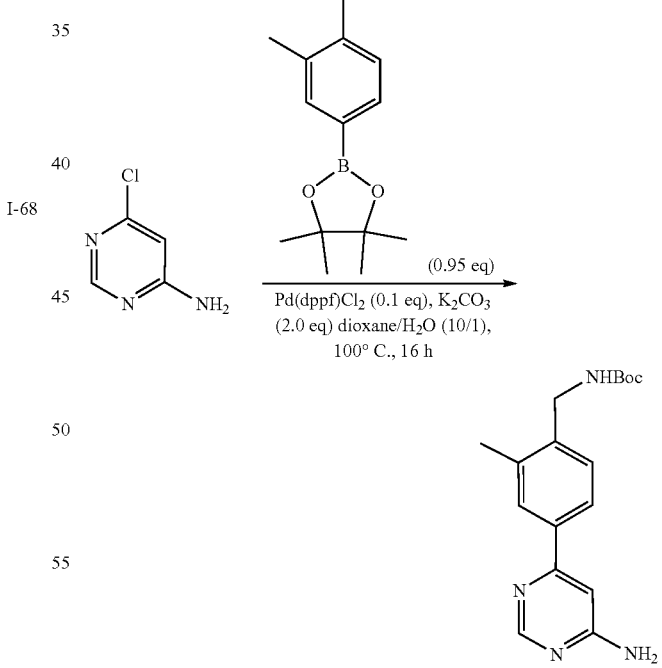

Synthesis of tert-butyl 4-(6-aminopyrimidin-4-yl)-2-methylbenzylcarbamate was similar to that of tert-butyl 4-(2-chloropyrimidin-4-yl)-2-methylbenzylcarbamate. Obtained tert-butyl 4-(6-aminopyrimidin-4-yl)-2-methylbenzylcarbamate (170 mg, yield: 52%) as a white solid. ESI-MS (M+H)$^+$: 315.1. $^1$H NMR (400 MHz, CDCl$_3$) δ: 8.66 (s, 1H), 7.81 (s, 1H), 7.74 (d, J=8.0 Hz, 1H), 7.34 (d, J=8.4 Hz, 1H), 6.81 (s, 1H), 4.95 (br, 2H), 4.78 (br, 1H), 4.36 (d, J=5.2 Hz, 2H), 2.39 (s, 3H), 1.47 (s, 9H).

Synthesis of tert-butyl 2-methyl-4-(6-((5-(4-methylpiperazin-1-yl)pyridin-2-yl)amino)pyrimidin-4-yl)benzylcarbamate

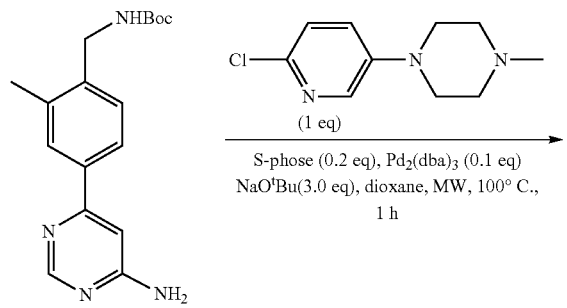

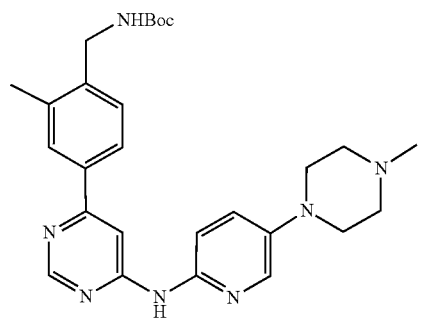

Synthesis of tert-butyl 2-methyl-4-(6-((5-(4-methylpiperazin-1-yl)pyridin-2-yl)amino)pyrimidin-4-yl)benzylcarbamate was similar to that of tert-butyl 2-methyl-4-(2-((1-methyl-1H-pyrazol-4-yl)amino)pyrimidin-4-yl)benzylcarbamate. Obtained tert-butyl 2-methyl-4-(6-((5-(4-methylpiperazin-1-yl)pyridin-2-yl)amino)pyrimidin-4-yl)benzylcarbamate (30 mg, yield: 21%) as a yellow solid. ESI-MS (M+H)⁺: 490.1.

Synthesis of 2-(tert-butyl)-N-(2-methyl-4-(6-((5-(4-methylpiperazin-1-yl)pyridin-2-yl)amino)pyrimidin-4-yl)benzyl)thiazole-5-carboxamide

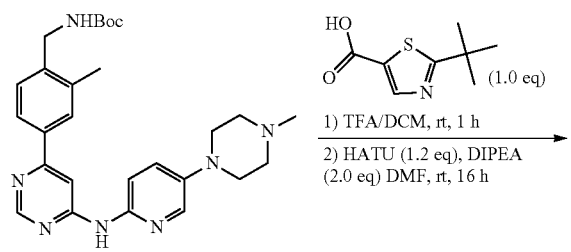

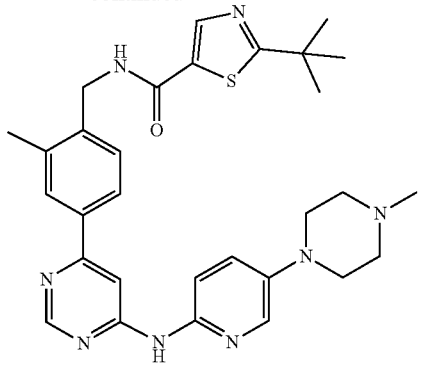

Synthesis of 2-(tert-butyl)-N-(2-methyl-4-(6-((5-(4-methylpiperazin-1-yl)pyridin-2-yl)amino)pyrimidin-4-yl)benzyl)thiazole-5-carboxamide was similar to that of Example 1. The residue was purified by prep-HPLC (CH₃CN/H₂O with 0.05% NH₃H₂O as mobile phase) to give 2-(tert-butyl)-N-(2-methyl-4-(6-((5-(4-methylpiperazin-1-yl)pyridin-2-yl)amino)pyrimidin-4-yl)benzyl)thiazole-5-carboxamide as a white solid (28 mg, yield: 39%). ESI-MS (M+H)⁺: 556.9. HPLC: (214 nm: 93%, 254 nm: 93%). ¹H NMR (400 MHz, CD₃OD) δ: 8.53 (s, 1H), 8.13 (s, 1H), 7.95 (d, J=2.8 Hz, 1H), 7.77 (s, 1H), 7.72 (s, 1H), 7.69 (d, J=8.0 Hz, 1H), 7.55 (d, J=8.8 Hz, 1H), 7.37 (dd, J=8.8, 3.2 Hz, 1H), 7.33 (d, J=8.0 Hz, 1H), 4.50 (s, 2H), 3.12 (t, J=4.8 Hz, 4H), 3.55 (t, J=5.2 Hz, 4H), 2.36 (s, 3H), 2.27 (s, 3H), 1.36 (s, 9H).

Example 69: 2-(tert-butyl)-N-(2-methyl-4-(2-((5-(4-methylpiperazin-1-yl)pyridin-2-yl)amino)pyridin-4-yl)benzyl)thiazole-5-carboxamide (I-70)

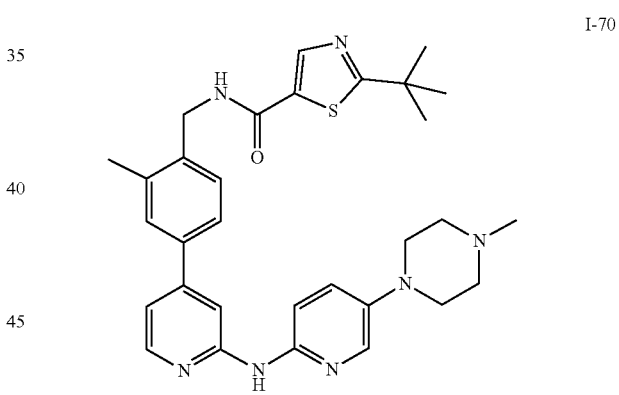

I-70

Synthesis of tert-butyl 4-(2-aminopyridin-4-yl)-2-methylbenzylcarbamate

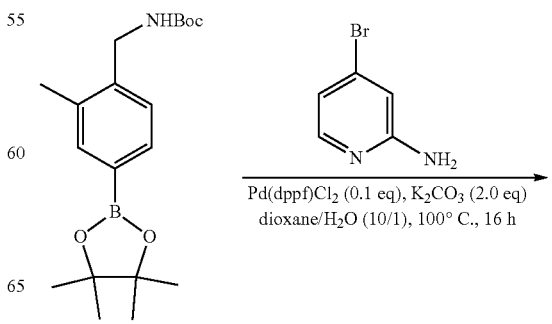

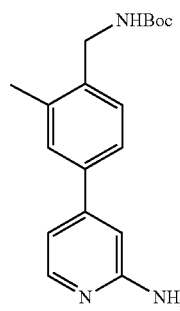

To a solution of tert-butyl 2-methyl-4-(4,4,5,5-tetramethyl-1,3,2-dioxaborolan-2-yl)benzylcarbamate (347 mg, 1.0 mmol) in 1,4-dioxane (4 mL) and H$_2$O (1 mL), 4-bromopyridin-2-amine (172 mg, 1.0 mmol), Pd(dppf)Cl$_2$.DCM (81 mg, 0.1 mmol) and K$_2$CO$_3$ (276 mg, 2.0 mmol) were added under N$_2$. The mixture was stirred at 110° C. for 16 h. After cooling to rt, the mixture was diluted with H$_2$O (20 mL) and extracted with EA (60 mL×2). The organic layers were collected, concentrated. The residue was purified by column chromatography (silica, petroleum ether/EtOAc=4:1 to 2:1) to give tert-butyl 4-(2-aminopyridin-4-yl)-2-methylbenzylcarbamate (210 mg, yield: 65%) as a yellow solid. ESI-MS (M+H)$^+$: 314.1. $^1$H NMR (400 MHz, CDCl$_3$) δ: 8.09 (d, J=6.0 Hz, 1H), 7.40-7.38 (m, 2H), 7.32 (d, J=8.4 Hz, 1H), 6.87 (dd, J=5.6, 1.2 Hz, 1H), 6.70 (s, 1H), 4.76 (br, 1H), 4.62 (br, 2H), 4.36 (d, J=5.6 Hz, 2H), 2.38 (s, 3H), 1.47 (s, 9H).

Synthesis of tert-butyl 2-methyl-4-(2-((5-(4-methylpiperazin-1-yl)pyridin-2-yl)amino)pyridin-4-yl)benzylcarbamate

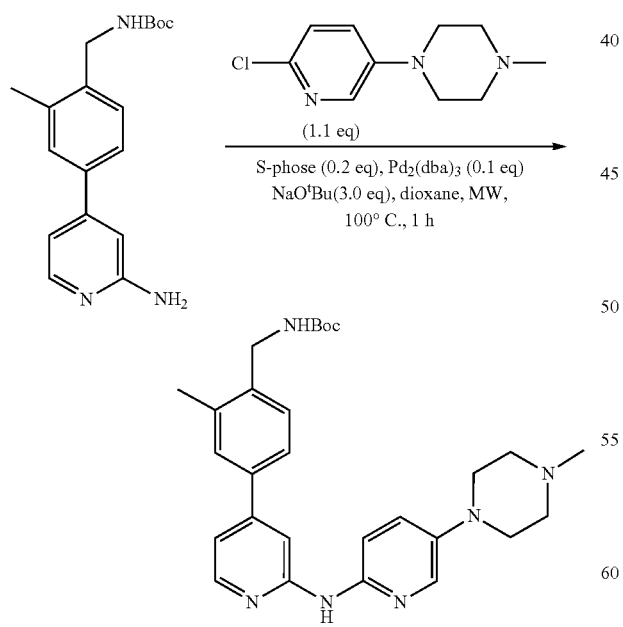

Synthesis of tert-butyl 2-methyl-4-(2-((5-(4-methylpiperazin-1-yl)pyridin-2-yl)amino)pyridin-4-yl)benzylcarbamate was similar to that of tert-butyl 2-methyl-4-(2-((1-methyl-1H-pyrazol-4-yl)amino)pyrimidin-4-yl)benzylcarbamate.

Obtained tert-butyl 2-methyl-4-(2-((5-(4-methylpiperazin-1-yl)pyridin-2-yl)amino)pyridin-4-yl)benzylcarbamate (75 mg, yield: 51%) as a yellow solid. ESI-MS (M+H)$^+$: 489.1.

Synthesis of 2-(tert-butyl)-N-(2-methyl-4-(2-((5-(4-methylpiperazin-1-yl)pyridin-2-yl)amino)pyridin-4-yl)benzyl)thiazole-5-carboxamide

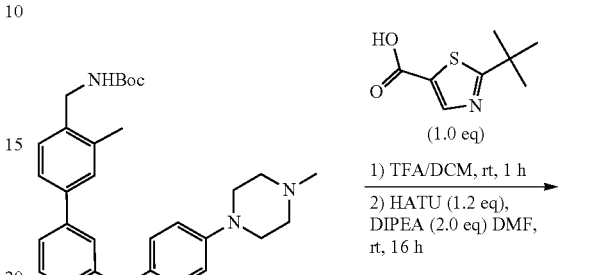

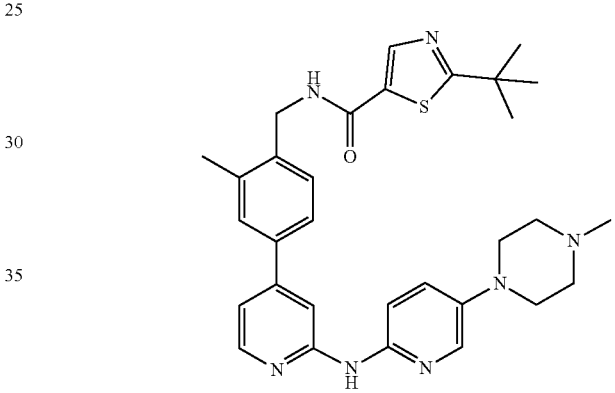

A mixture of tert-butyl 2-methyl-4-(2-((5-(4-methylpiperazin-1-yl)pyridin-2-yl)amino)pyridin-4-yl)benzylcarbamate (123 mg, 0.25 mmol) in TFA/DCM (4 mL, 1:1) was stirred at rt for 1 h. After concentration, the residue was dissolved in 4 mL DMF and 2-(tert-butyl)thiazole-5-carboxylic acid (46 mg, 0.25 mmol), HATU (114 mg, 0.30 mmol) and DIPEA (65 mg, 0.50 mmol) were added. After stirring at rt for 16 h, the mixture was diluted with water (20 mL) and extracted with EtOAc (50 mL×2). The combined organic layer was washed with H$_2$O (20 mL×2), dried (Na$_2$SO$_4$), filtered and concentrated. The residue was purified by prep-HPLC (CH$_3$CN/H$_2$O with 0.05% NH$_3$H$_2$O as mobile phase) to give 2-(tert-butyl)-N-(2-methyl-4-(2-((5-(4-methylpiperazin-1-yl)pyridin-2-yl)amino)pyridin-4-yl)benzyl)thiazole-5-carboxamide as a white solid (61 mg, yield: 43%). ESI-MS (M+H)$^+$: 556.3. HPLC: (214 nm: 99%, 254 nm: 96%). $^1$H NMR (400 MHz, CD$_3$OD) δ: 8.12 (s, 1H), 8.05 (d, J=5.2 Hz, 1H), 7.82 (s, 1H), 7.59 (s, 1H), 7.43-7.39 (m, 3H), 7.32-7.27 (m, 2H), 6.97-6.96 (m, 1H), 4.48 (s, 2H), 3.05 (t, J=4.8 Hz, 4H), 2.51 (t, J=4.8 Hz, 4H), 2.33 (s, 3H), 2.24 (s, 3H), 1.34 (s, 9H).

Example 70: 2-(tert-butyl)-N-(2-methyl-4-(2-(1-methylpiperidine-4-carboxamido)pyridin-4-yl)benzyl)thiazole-5-carboxamide. (I-71)

Synthesis of 2-(tert-butyl)-N-(2-methyl-4-(2-(1-methylpiperidine-4-carboxamido)pyridin-4-yl)benzyl)thiazole-5-carboxamide

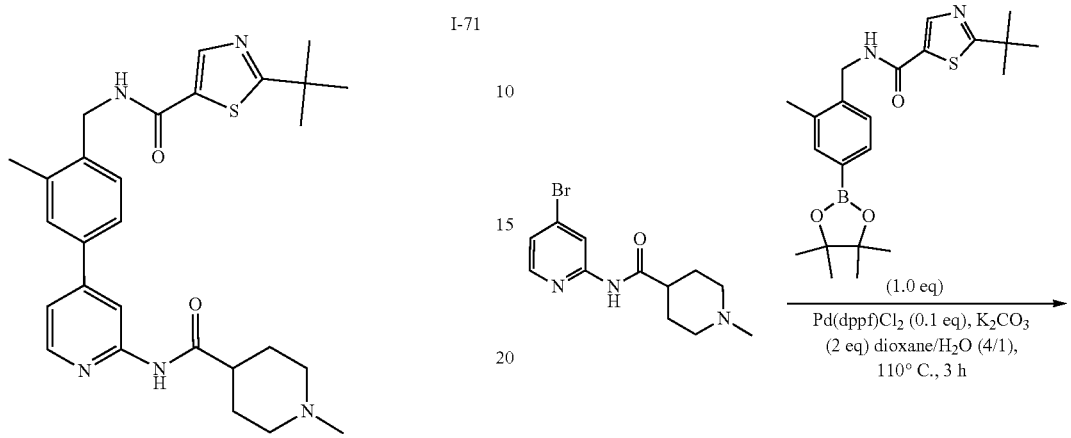

Synthesis of N-(4-bromopyridin-2-yl)-1-methylpiperidine-4-carboxamide

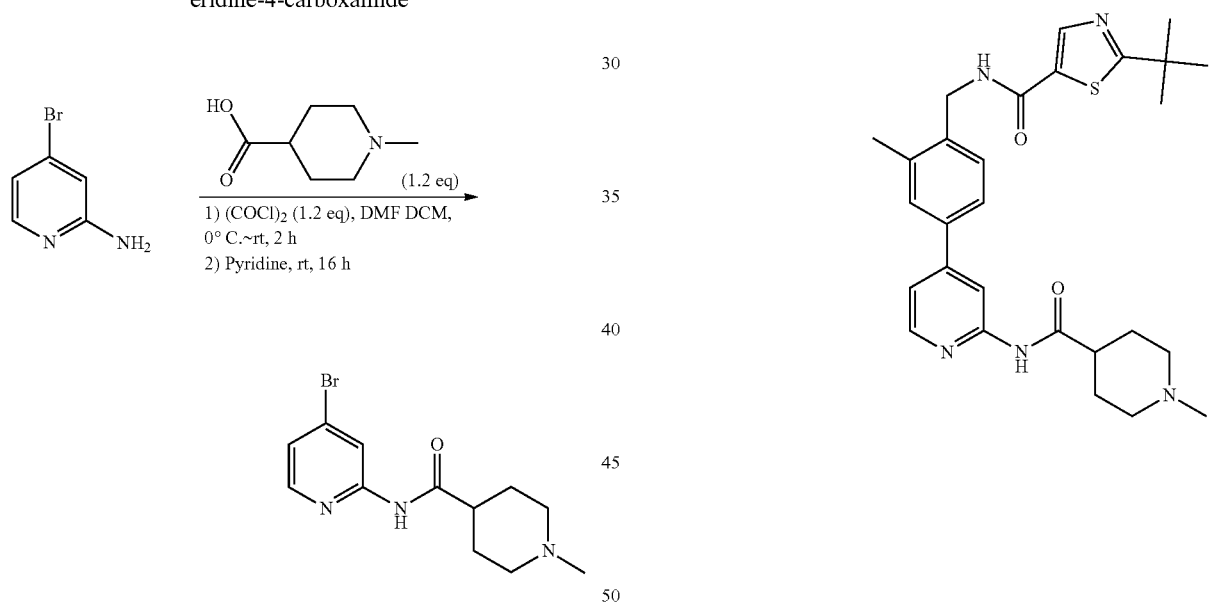

To a solution of 1-methylpiperidine-4-carboxylic acid (207 mg, 1.45 mmol) and DMF (cat) in DCM (5 mL) was added (COCl)$_2$ (182 mg, 1.45 mmol) at 0° C. The mixture was stirred at rt for 2 h, then the solvent was removed. The residue was dissolved in pyridine (5 mL), 4-bromopyridin-2-amine (207 mg, 1.2 mmol) was added. The mixture was stirred at rt for another 16 h. After the solvent was removed, the residue was purified by prep-HPLC (CH$_3$CN/H$_2$O with 0.05% NH$_3$H$_2$O as mobile phase) to give N-(4-bromopyridin-2-yl)-1-methylpiperidine-4-carboxamide (270 mg, yield: 75%) as a white solid. ESI-MS (M+H)$^+$: 297.9.

Synthesis of 2-(tert-butyl)-N-(2-methyl-4-(2-(1-methylpiperidine-4-carboxamido)pyridin-4-yl)benzyl)thiazole-5-carboxamide was similar to that of tert-butyl 4-(2-chloropyrimidin-4-yl)-2-methylbenzylcarbamate. The crude product was purified by prep-HPLC (CH$_3$CN/H$_2$O with 0.05% NH$_3$.H$_2$O as mobile phase) to give 2-(tert-butyl)-N-(2-methyl-4-(2-(1-methylpiperidine-4-carboxamido)pyridin-4-yl)benzyl)thiazole-5-carboxamide as a white solid (40 mg, yield: 26%). ESI-MS (M+H)$^+$: 506.3. HPLC: (214 nm: 100%, 254 nm: 100%). $^1$H NMR (400 MHz, CD$_3$OD) δ: 8.26 (s, 1H), 8.19 (d, J=5.2 Hz, 1H), 8.13 (s, 1H), 7.44-7.40 (m, 2H), 7.30 (d, J=7.6 Hz, 1H), 7.24 (dd, J=5.2, 1.6 Hz, 1H), 4.48 (s, 2H), 2.87-2.82 (m, 2H), 2.39-2.35 (m, 1H), 2.32 (s, 3H), 2.17 (s, 3H), 2.02-1.96 (m, 2H), 1.82-1.74 (m, 4H), 1.34 (s, 9H).

Example 71: The preparation of N-(4-(2-aminopyrimidin-4-yl)-2-methylbenzyl)-5,6,7,8-tetrahydro-4H-pyrazolo[1,5-a][1,4]diazepine-2-carboxamide (I-72)

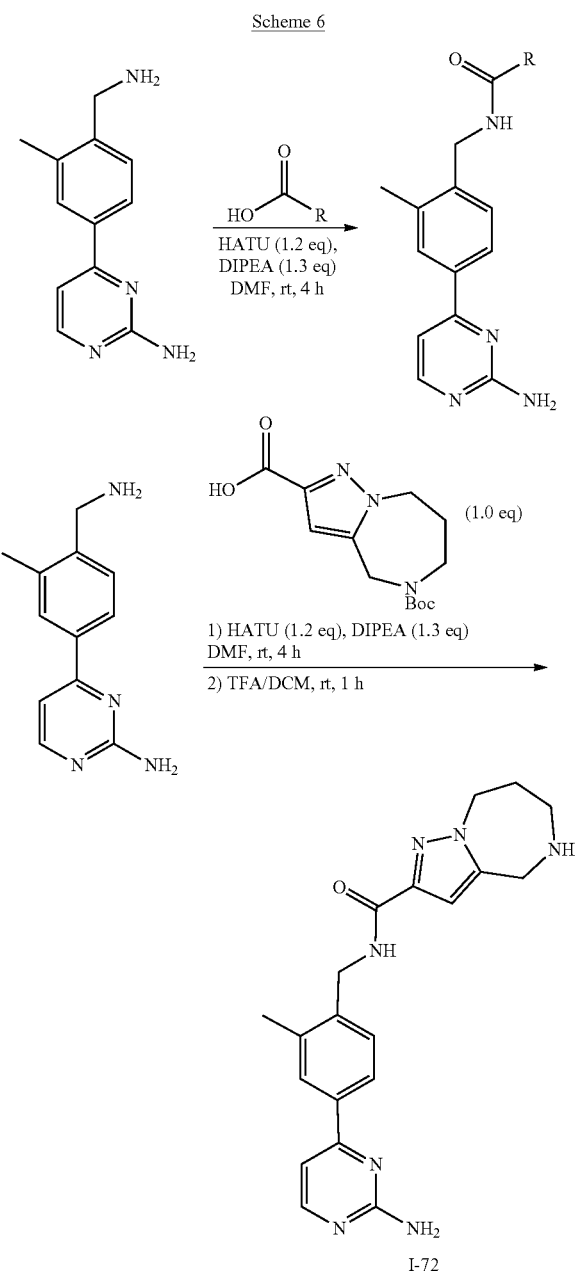

A mixture of 4-(4-(aminomethyl)-3-methylphenyl)pyrimidin-2-amine (56 mg, 0.2 mmol 5-(tert-butoxycarbonyl)-5,6,7,8-tetrahydro-4H-pyrazolo[1,5-a][1,4]diazepine-2-carboxylic acid (44 mg, 0.2 mmol), HATU (81 mg, 0.24 mmol) and TEA (34 mg, 2.6 mmol) in DMF (3 mL) was stirred at rt for 4 h. After diluted with EtOAc (60 mL), the mixture was washed with water (30 mL) and brine (30 mL). The organic phase was dried and concentrated. The residue was dissolved in DCM/TFA (4 mL, 1:1) and the mixture was stirred at rt for 1 h. After concentrated, the residue was purified by prep-HPLC (MeOH/H$_2$O with 0.05% NH$_3$.H$_2$O as mobile phase) to give the compound N-(4-(2-aminopyrimidin-4-yl)-2-methylbenzyl)-5,6,7,8-tetrahydro-4H-pyrazolo[1,5-a][1,4]diazepine-2-carboxamide (40 mg, yield: 54%) as a white solid. ESI-MS (M+H)$^+$: 378.2. $^1$H NMR (400 MHz, CD$_3$OD) δ: 8.25 (d, J=5.2 Hz, 1H), 7.90 (s, 1H), 7.85 (d, J=8.4 Hz, 1H), 7.39 (d, J=8.0 Hz, 1H), 7.12 (d, J=5.6 Hz, 1H), 6.63 (s, 1H), 4.60 (s, 2H), 4.47-4.45 (m, 2H), 3.94 (s, 2H), 3.18 (t, J=5.2 Hz, 2H), 2.45 (s, 3H), 1.90-1.88 (m, 2H).

Example 72: N-(4-(2-aminopyrimidin-4-yl)-2-methylbenzyl)-5,6,7,8-tetrahydro-4H-thiazolo[4,5-d]azepine-2-carboxamide (I-73)

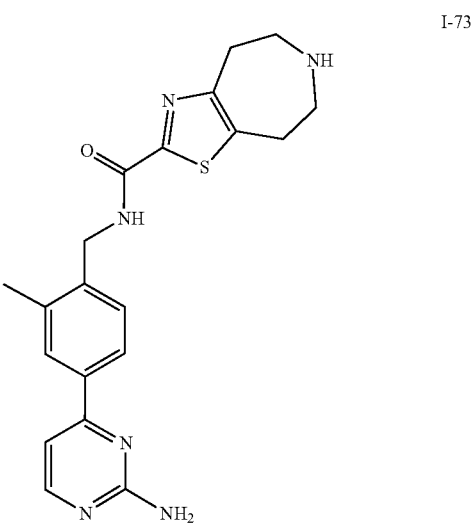 [SMILES: Cc1cc(-c2ccnc(N)n2)ccc1CNC(=O)c1nc2c(s1)CCNCC2]

Synthesis of N-(4-(2-aminopyrimidin-4-yl)-2-methylbenzyl)-5,6,7,8-tetrahydro-4H-thiazolo[4,5-d]azepine-2-carboxamide was similar to that of Example 71, starting from 6-(tert-butoxycarbonyl)-5,6,7,8-tetrahydro-4H-thiazolo[4,5-d]azepine-2-carboxylic. The crude was purified by prep-HPLC (MeOH/H$_2$O with 0.05% NH$_3$.H$_2$O as mobile phase) to give the compound N-(4-(2-aminopyrimidin-4-yl)-2-methylbenzyl)-5,6,7,8-tetrahydro-4H-thiazolo[4,5-d]azepine-2-carboxamide (40 mg, yield: 55%) as a white solid. ESI-MS (M+H)$^+$: 395.2. $^1$H NMR (400 MHz, CD$_3$OD) δ: 8.26 (d, J=5.6 Hz, 1H), 7.91-7.84 (m, 2H), 7.40 (d, J=8.0 Hz, 1H), 7.12 (d, J=5.2 Hz, 1H), 4.61 (s, 2H), 3.14-2.98 (m, 8H), 2.46 (s, 3H).

Example 73: N-(4-(2-aminopyrimidin-4-yl)-2-methylbenzyl)-5,6,7,8-tetrahydroimidazo[1,2-a]pyrazine-2-carboxamide (I-74)

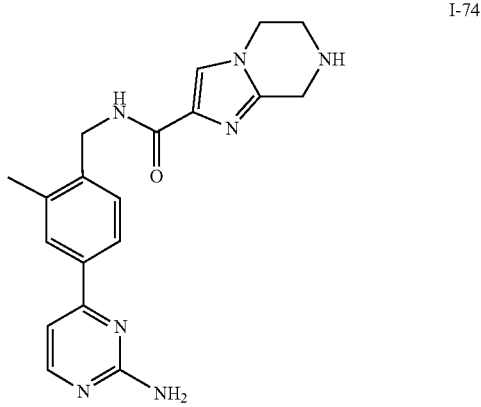 [SMILES: Cc1cc(-c2ccnc(N)n2)ccc1CNC(=O)c1cn2c(n1)CNCC2]

Synthesis of N-(4-(2-aminopyrimidin-4-yl)-2-methylbenzyl)-5,6,7,8-tetrahydroimidazo[1,2-a]pyrazine-2-carboxamide was similar to that of Example 71, starting from 7-(tert-butoxycarbonyl)-5,6,7,8-tetrahydroimidazo[1,2-a]pyrazine-2-carboxylic acid. The crude was purified by prep-HPLC (CH$_3$CN/H$_2$O with 0.05% NH$_3$.H$_2$O as mobile phase) to give compound N-(4-(2-aminopyrimidin-4-yl)-2-methylbenzyl)-5,6,7,8-tetrahydroimidazo[1,2-a]pyrazine-2-carboxamide (18 mg, yield:51%) as a white solid. ESI-MS (M+H)$^+$: 364.1. $^1$H NMR (400 MHz, CD$_3$OD) δ: 8.16 (d, J=5.6 Hz, 1H), 7.08 (s, 1H), 7.56 (d, J=8.0 Hz, 1H), 7.50 (s, 1H), 7.30 (d, J=7.6 Hz, 1H), 7.02 (d, J=5.2 Hz, 1H), 4.50 (s, 2H), 3.97 (t, J=5.6 Hz, 2H), 3.88 (s, 2H), 3.11 (t, J=5.6 Hz, 2H), 2.34 (s, 3H).

Example 74: N-(4-(2-aminopyrimidin-4-yl)-2-methylbenzyl)-4,5,6,7-tetrahydrothiazolo[5,4-c]pyridine-2-carboxamide (I-75)

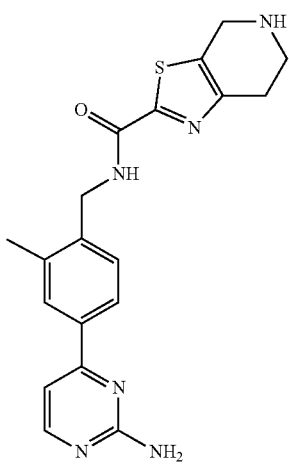

I-75

Synthesis of N-(4-(2-aminopyrimidin-4-yl)-2-methylbenzyl)-4,5,6,7-tetrahydrothiazolo[5,4-c]pyridine-2-carboxamide was similar to that of Example 71, starting from 5-(tert-butoxycarbonyl)-4,5,6,7-tetrahydrothiazolo[5,4-c]pyridine-2-carboxylic acid. The crude was purified by prep-HPLC (MeOH/H$_2$O with 0.05% NH$_3$.H$_2$O as mobile phase) to give the compound N-(4-(2-aminopyrimidin-4-yl)-2-methylbenzyl)-4,5,6,7-tetrahydrothiazolo[5,4-c]pyridine-2-carboxamide (36 mg, yield: 42%) as a white solid. ESI-MS (M+H)$^+$: 381.1. $^1$H NMR (400 MHz, CD$_3$OD) δ: 8.25 (d, J=5.2 Hz, 1H), 7.91 (s, 1H), 7.86 (d, J=8.0 Hz, 1H), 7.40 (d, J=8.0 Hz, 1H), 7.12 (d, J=6.0 Hz, 1H), 4.33 (s, 2H), 4.09 (s, 2H), 3.16 (t, J=5.6 Hz, 2H), 2.89 (t, J=6.0 Hz, 2H), 2.46 (s, 3H).

Example 75: N-(4-(2-aminopyrimidin-4-yl)-2-methylbenzyl)-4,5,6,7-tetrahydro pyrazolo[1,5-a]pyrazine-2-carboxamide (I-76)

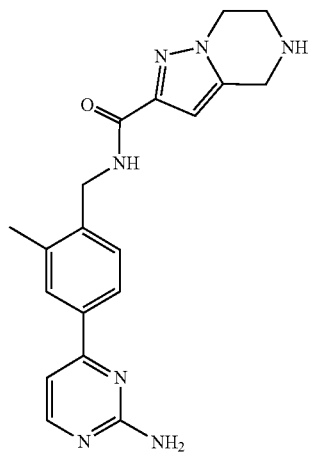

I-76

Synthesis of N-(4-(2-aminopyrimidin-4-yl)-2-methylbenzyl)-4,5,6,7-tetrahydropyrazolo[1,5-a]pyrazine-2-carboxamide was similar to that of Example 71, starting from 5-(tert-butoxycarbonyl)-4,5,6,7-tetrahydropyrazolo[1,5-a]pyrazine-2-carboxylic acid. The crude was purified by prep-HPLC (MeOH/H$_2$O with 0.05% NH$_3$.H$_2$O as mobile phase) to give the compound N-(4-(2-aminopyrimidin-4-yl)-2-methylbenzyl)-4,5,6,7-tetrahydropyrazolo[1,5-a]pyrazine-2-carboxamide (28 mg, yield: 45%) as a white solid. ESI-MS (M+H)$^+$: 364.2. $^1$H NMR (400 MHz, CD$_3$OD) δ: 8.25 (d, J=5.6 Hz, 1H), 7.90-7.84 (m, 2H), 7.39 (d, J=8.0 Hz, 1H), 7.12 (d, J=5.2 Hz, 1H), 6.54 (s, 1H), 4.61 (s, 2H), 4.19 (t, J=5.2 Hz, 2H), 4.09 (s, 2H), 3.34-3.33 (m, 2H), 2.45 (s, 3H).

Example 76: N-(4-(2-aminopyrimidin-4-yl)-2-methylbenzyl)-1,2,3,4-tetrahydroisoquinoline-6-carboxamide (I-77)

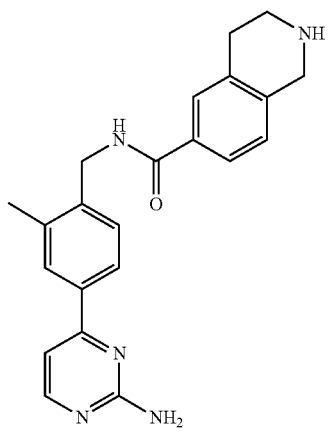

I-77

Synthesis of N-(4-(2-aminopyrimidin-4-yl)-2-methylbenzyl)-1,2,3,4-tetrahydroisoquinoline-6-carboxamide was similar to that of Example 71, starting from 2-(tert-butoxycarbonyl)-1,2,3,4-tetrahydroisoquinoline-6-carboxylic acid. The crude was purified by prep-HPLC (MeOH/H$_2$O with 0.05% NH$_3$.H$_2$O as mobile phase) to give the compound N-(4-(2-aminopyrimidin-4-yl)-2-methylbenzyl)-1,2,3,4-tetrahydroisoquinoline-6-carboxamide (38 mg, yield: 47%) as a white solid. ESI-MS (M+H)$^+$: 374.2. $^1$H NMR (400 MHz, DMSO-d$_6$) δ: 8.86 (t, J=5.6 Hz, 1H), 8.27 (d, J=5.2 Hz, 1H), 7.90 (s, 1H), 7.83 (d, J=8.0 Hz, 1H), 7.65-7.64 (m, 2H), 7.32 (d, J=8.0 Hz, 1H), 7.11-7.09 (m, 2H), 6.64 (s, 2H), 4.48 (d, J=5.2 Hz, 2H), 3.87 (s, 2H), 2.95 (t, J=5.6 Hz, 2H), 2.73 (t, J=5.6 Hz, 2H), 2.40 (s, 3H).

Example 77: N-(4-(2-aminopyrimidin-4-yl)-2-methylbenzyl)-5,6,7,8-tetrahydro-1,6-naphthyridine-2-carboxamide (I-78)

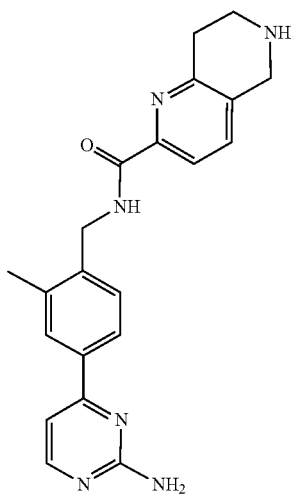

I-78

Synthesis of N-(4-(2-aminopyrimidin-4-yl)-2-methylbenzyl)-5,6,7,8-tetrahydro-1,6-naphthyridine-2-carboxamide was similar to that of Example 71, starting from 6-(tert-butoxycarbonyl)-5,6,7,8-tetrahydro-1,6-naphthyridine-2-carboxylic acid. The crude was purified by prep-HPLC (MeOH/H$_2$O with 0.05% NH$_3$.H$_2$O as mobile phase) to give the compound N-(4-(2-aminopyrimidin-4-yl)-2-methylbenzyl)-5,6,7,8-tetrahydro-1,6-naphthyridine-2-carboxamide (15 mg, yield: 23%) as a white solid. ESI-MS (M+H)$^+$: 375.1. $^1$H NMR (400 MHz, CD$_3$OD) δ: 8.14 (d, J=5.6 Hz, 1H), 7.81-7.78 (m, 2H), 7.73 (d, J=8.0 Hz, 1H), 7.55 (d, J=7.6 Hz, 1H), 7.27 (d, J=8.0 Hz, 1H), 7.00 (d, J=6.0 Hz, 1H), 4.55 (s, 2H), 3.97 (s, 2H), 3.12 (t, J=6.0 Hz, 2H), 2.91 (t, J=6.0 Hz, 2H), 2.33 (s, 3H).

Example 78: (7R,9aR)—N-(4-(2-aminopyrimidin-4-yl)-2-methylbenzyl)octahydro-1H-pyrido[1,2-a]pyrazine-7-carboxamide (I-79)

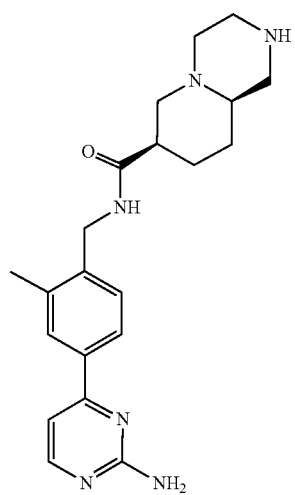

I-79

Synthesis of (7R,9aR)—N-(4-(2-aminopyrimidin-4-yl)-2-methylbenzyl)octahydro-1H-pyrido[1,2-a]pyrazine-7-carboxamide was similar to that of Example 71, starting from (7R,9aR)-2-(tert-butoxycarbonyl)octahydro-1H-pyrido[1,2-a]pyrazine-7-carboxylic acid. The crude was purified by prep-HPLC (MeOH/H$_2$O with 0.05% NH$_3$.H$_2$O as mobile phase) to give the compound (7R,9aR)—N-(4-(2-aminopyrimidin-4-yl)-2-methylbenzyl)octahydro-1H-pyrido[1,2-a]pyrazine-7-carboxamide (43 mg, yield: 52%) as a white solid. ESI-MS (M+H)$^+$: 381.3. $^1$H NMR (400 MHz, CD$_3$OD) δ: 8.27 (d, J=5.2 Hz, 1H), 7.93-7.88 (m, 2H), 7.43 (d, J=8.0 Hz, 1H), 7.14 (d, J=5.2 Hz, 1H), 4.50 (ABq, J=80.0, 15.2 Hz, 2H), 3.11-2.79 (m, 5H), 2.58-2.57 (m, 1H), 2.47 (s, 3H), 2.41-2.08 (m, 5H), 1.79-1.22 (m, 3H).

Example 79: N-(4-(2-aminopyrimidin-4-yl)-2-methylbenzyl)-1-methyl-1H-pyrazole-4-carboxamide (I-80)

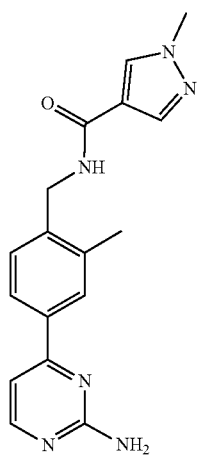

I-80

Synthesis of N-(4-(2-aminopyrimidin-4-yl)-2-methylbenzyl)-1-methyl-1H-pyrazole-4-carboxamide was similar to that of Example 71, starting from 1-methyl-1H-pyrazole-4-carboxylic acid. The residue was purified by prep-HPLC (CH$_3$CN/H$_2$O with 0.05% NH$_3$H$_2$O as mobile phase) to give N-(4-(2-aminopyrimidin-4-yl)-2-methylbenzyl)-1-methyl-1H-pyrazole-4-carboxamide as a white solid (30 mg, yield: 58%). ESI-MS (M+H)$^+$: 323.3. HPLC: (214 nm: 100%, 254 nm: 100%). $^1$H NMR (400 MHz, CD$_3$OD) δ: 8.15 (d, J=5.2 Hz, 1H), 7.97 (s, 1H), 7.82 (s, 1H), 7.79 (s, 1H), 7.75 (dd, J=8.0, 1.2 Hz, 1H), 7.28 (d, J=8.0 Hz, 1H), 7.01 (d, J=5.2 Hz, 1H), 4.47 (s, 2H), 3.81 (s, 3H), 2.33 (s, 3H).

Example 80: N-(4-(2-aminopyrimidin-4-yl)-2-methylbenzyl)octahydrocyclopenta[c]pyrrole-5-carboxamide (I-81)

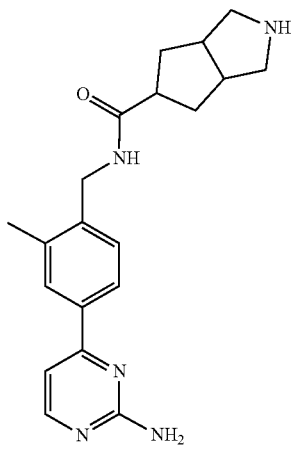

I-81

Synthesis of N-(4-(2-aminopyrimidin-4-yl)-2-methylbenzyl)octahydrocyclopenta[c]pyrrole-5-carboxamide was similar to that of Example 71, starting from 2-(tert-butoxycarbonyl)octahydrocyclopenta[c]pyrrole-5-carboxylic acid. The crude was purified by prep-HPLC (CH$_3$CN/H$_2$O with 0.05% NH$_3$.H$_2$O as mobile phase) to give compound N-(4-(2-aminopyrimidin-4-yl)-2-methylbenzyl)octahydrocyclopenta[c]pyrrole-5-carboxamide (20 mg, yield: 43%) as a white solid. ESI-MS (M+H)$^+$: 352.1. $^1$HNMR (400 MHz, CD$_3$OD) δ: 8.26 (d, J=5.6 Hz, 1H), 7.90 (s, 1H), 7.85 (d, J=8.0 Hz, 1H), 7.33 (d, J=8.0 Hz, 1H), 7.11 (d, J=5.6 Hz, 1H), 4.43 (s, 2H), 3.31-3.19 (m, 1H), 2.94-2.85 (m, 2H), 2.74-2.73 m, 3H), 2.52-2.47 (m, 1H), 2.41 (s, 3H), 2.24-2.21 (m, 1H), 2.05-1.94 (m, 1H), 1.74-1.71 (m, 1H), 1.60-1.55 (m, 1H).

Example 81: N-(4-(2-aminopyrimidin-4-yl)-2-methylbenzyl)-4,5,6,7-tetrahydrothieno[2,3-c]pyridine-2-carboxamide (I-82)

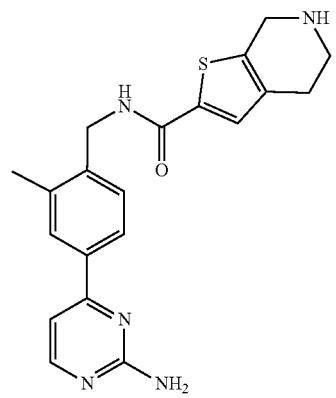

I-82

Synthesis of N-(4-(2-aminopyrimidin-4-yl)-2-methylbenzyl)-4,5,6,7-tetrahydrothieno[2,3-c]pyridine-2-carboxamide was similar to that of Example 71, starting from 6-(tert-butoxycarbonyl)-4,5,6,7-tetrahydrothieno[2,3-c]pyridine-2-carboxylic acid. The crude was purified by prep-HPLC (CH$_3$CN/H$_2$O with 0.05% NH$_3$.H$_2$O as mobile phase) to give compound N-(4-(2-aminopyrimidin-4-yl)-2-methylbenzyl)-4,5,6,7-tetrahydrothieno[2,3-c]pyridine-2-carboxamide (40 mg, yield: 50%) as a white solid. ESI-MS (M+H)$^+$: 379.9. $^1$H NMR (400 MHz, CD$_3$OD) δ: 8.25 (d, J=5.2 Hz, 1H), 7.90 (s, 1H), 7.85 (d, J=9.2 Hz, 1H), 7.45 (s, 1H), 7.39 (d, J=8.0 Hz, 1H), 7.12 (d, J=5.6 Hz, 1H), 4.58 (s, 2H), 4.01 (s, 2H), 3.08 (t, J=5.6 Hz, 2H), 2.71 (t, J=6.0 Hz, 2H), 2.44 (s, 3H).

Example 82: N-(4-(2-aminopyrimidin-4-yl)-2-methylbenzyl)-2-(trifluoromethyl)thiazole-5-carboxamide (I-83)

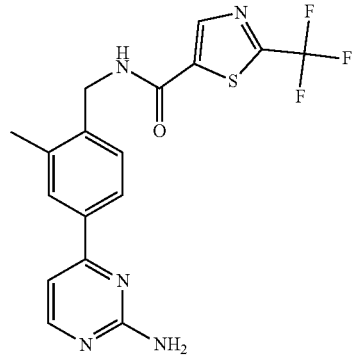

I-83

Synthesis of N-(4-(2-aminopyrimidin-4-yl)-2-methylbenzyl)-2-(trifluoromethyl)thiazole-5-carboxamide was similar to that of Example 71, starting from 2-(trifluoromethyl)thiazole-5-carboxylic acid. The crude was purified by prep-HPLC (CH$_3$CN/H$_2$O with 0.05% NH$_3$.H$_2$O as mobile phase) to give compound N-(4-(2-aminopyrimidin-4-yl)-2-methylbenzyl)-2-(trifluoromethyl)thiazole-5-carboxamide (15 mg, yield: 33%) as a white solid. ESI-MS (M+H)+: 394.0. ¹H NMR (400 MHz, CD₃OD) δ: 8.41 (s, 1H), 8.16 (d, J=5.6 Hz, 1H), 7.82 (s, 1H), 7.78 (d, J=8.0 Hz, 1H), 7.33 (d, J=8.0 Hz, 1H), 7.02 (d, J=5.2 Hz, 1H), 4.54 (s, 2H), 2.36 (s, 3H).

Example 83: N-(4-(2-aminopyrimidin-4-yl)-2-methylbenzyl)thiazole-5-carboxamide (I-84)

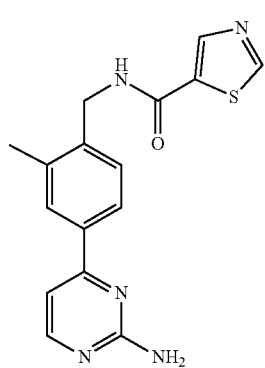

Synthesis of N-(4-(2-aminopyrimidin-4-yl)-2-methylbenzyl)thiazole-5-carboxamide was similar to that of Example 71, starting from thiazole-5-carboxylic acid. The crude was purified by prep-HPLC (CH₃CN/H₂O with 0.05% NH₃.H₂O as mobile phase) to give compound N-(4-(2-aminopyrimidin-4-yl)-2-methylbenzyl)thiazole-5-carboxamide (51 mg, yield: 53%) as a white solid. ESI-MS (M+H)+: 326.0. ¹H NMR (400 MHz, DMSO-d₆) δ: 9.24 (s, 1H), 9.21 (t, J=5.6 Hz, 1H), 8.56 (s, 1H), 8.28 (d, J=5.2 Hz, 1H), 7.91 (s, 1H), 7.86 (d, J=7.6 Hz, 1H), 7.36 (d, J=8.0 Hz, 1H), 7.10 (d, J=5.2 Hz, 1H), 6.67 (s, 2H), 4.50 (d, J=5.2 Hz, 2H), 2.39 (s, 3H).

Example 84: N-(4-(2-aminopyrimidin-4-yl)-2-methylbenzyl)-2-cyclopropylthiazole-5-carboxamide (I-85)

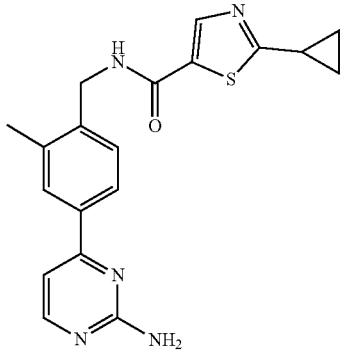

Synthesis of N-(4-(2-aminopyrimidin-4-yl)-2-methylbenzyl)-2-cyclopropylthiazole-5-carboxamide was similar to that of Example 71, starting from 2-cyclopropylthiazole-5-carboxylic acid. A white solid (62 mg, yield: 53%) was obtained. ESI-MS (M+H)+: 366.0. HPLC: (214 nm: 100%, 254 nm: 94%). ¹H NMR (400 MHz, CD₃OD) δ: 8.26 (d, J=5.6 Hz, 1H), 8.14 (s, 1H), 7.92 (s, 1H), 7.87 (d, J=8.0 Hz, 1H), 7.39 (d, J=8.0 Hz, 1H), 7.12 (d, J=5.6 Hz, 1H), 4.59 (s, 2H), 2.45-2.41 (m, 4H), 1.25-1.21 (m, 2H), 1.11-1.09 (m, 2H).

Example 85: N-(4-(2-aminopyrimidin-4-yl)-2-methylbenzyl)-2-isopropylthiazole-5-carboxamide (I-86)

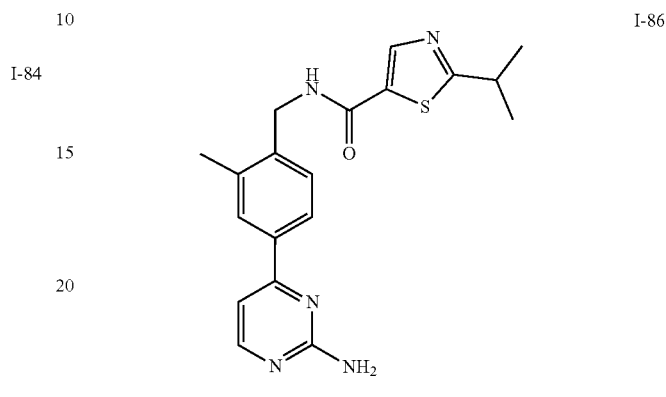

Synthesis of N-(4-(2-aminopyrimidin-4-yl)-2-methylbenzyl)-2-isopropylthiazole-5-carboxamide was similar to that of Example 71, starting from 2-isopropylthiazole-5-carboxylic acid. Obtained N-(4-(2-aminopyrimidin-4-yl)-2-methylbenzyl)-2-isopropylthiazole-5-carboxamide (70 mg, yield: 63%) as a light yellow solid. ESI-MS (M+H)+: 368.0. HPLC: (214 nm: 100%, 254 nm: 99.60%). ¹H NMR (400 MHz, CD₃OD) δ: 8.26 (d, J=5.2 Hz, 1H), 8.23 (s, 1H), 7.91 (s, 1H), 7.87 (d, J=8.4 Hz, 1H), 7.40 (d, J=8.0 Hz, 1H), 7.12 (d, J=5.2 Hz, 1H), 4.61 (s, 2H), 3.38-3.32 (m, 1H), 2.45 (s, 3H), 1.42 (d, J=6.8 Hz, 6H).

Example 86: N-(4-(2-aminopyrimidin-4-yl)-2-methylbenzyl)-2-(1-methoxyethyl)thiazole-5-carboxamide (I-87)

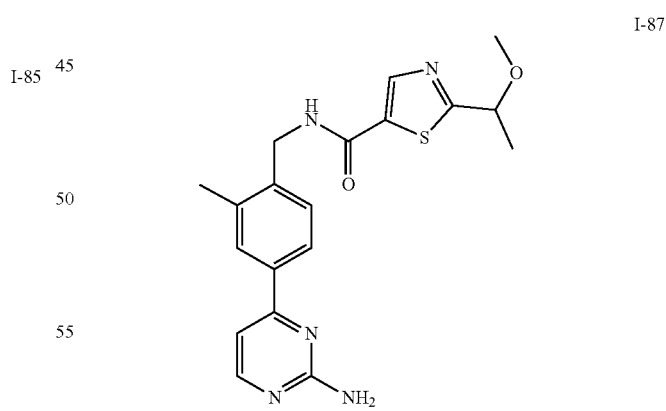

Synthesis of N-(4-(2-aminopyrimidin-4-yl)-2-methylbenzyl)-2-(1-methoxyethyl)thiazole-5-carboxamide was similar to that of Example 71, starting from 2-(1-methoxyethyl)thiazole-5-carboxylic acid. Obtained N-(4-(2-aminopyrimidin-4-yl)-2-methylbenzyl)-2-(1-methoxyethyl)thiazole-5-carboxamide (75 mg, yield: 65%) as a light yellow solid. ESI-MS (M+H)+: 384.0. HPLC: (214 nm: 100%, 254 nm: 100%). ¹H NMR (400 MHz, CD₃OD) δ: 8.27 (s, 1H), 8.26

(d, J=5.6 Hz, 1H), 7.92 (s, 1H), 7.87 (d, J=8.0 Hz, 1H), 7.41 (d, J=8.0 Hz, 1H), 7.13 (d, J=5.6 Hz, 1H), 4.67 (q, J=6.4 Hz, 1H), 4.62 (s, 2H), 3.44 (s, 3H), 2.46 (s, 3H), 1.54 (d, J=6.0 Hz, 3H).

Example 87: N-(4-(2-aminopyrimidin-4-yl)-2-methylbenzyl)-2-(tetrahydrofuran-2-yl)thiazole-5-carboxamide (I-88)

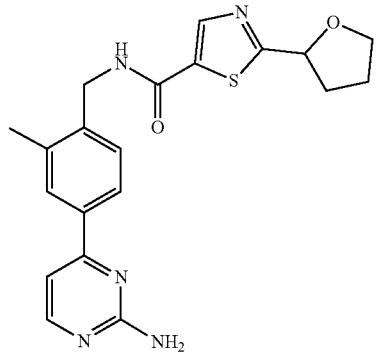

I-88

Synthesis of N-(4-(2-aminopyrimidin-4-yl)-2-methylbenzyl)-2-(tetrahydrofuran-2-yl)thiazole-5-carboxamide was similar to that of Example 71, starting from 2-(tetrahydrofuran-2-yl)thiazole-5-carboxylic acid. A white solid (56 mg, yield: 44%) was obtained. ESI-MS (M+H)$^+$: 396.1. HPLC: (214 nm: 100%, 254 nm: 100%). $^1$H NMR (400 MHz, CD$_3$OD) δ: 8.28 (s, 1H), 8.25 (d, J=6.4 Hz, 1H), 7.91 (s, 1H), 7.86 (d, J=8.0 Hz, 1H), 7.39 (d, J=8.0 Hz, 1H), 7.12 (d, J=6.4 Hz, 1H), 5.21-5.17 (m, 1H), 4.60 (s, 2H), 4.12-4.08 (m, 1H), 3.98-3.93 (m, 1H), 2.49-2.44 (m, 4H), 2.12-1.99 (m, 3H).

Example 88: 2-(tert-butyl)-N-(2-(2-((1-methyl-1H-pyrazol-4-yl)amino)pyrimidin-4-yl)-6,7,8,9-tetrahydro-5H-benzo[7]annulen-5-yl)thiazole-5-carboxamide (I-89)

Scheme 7

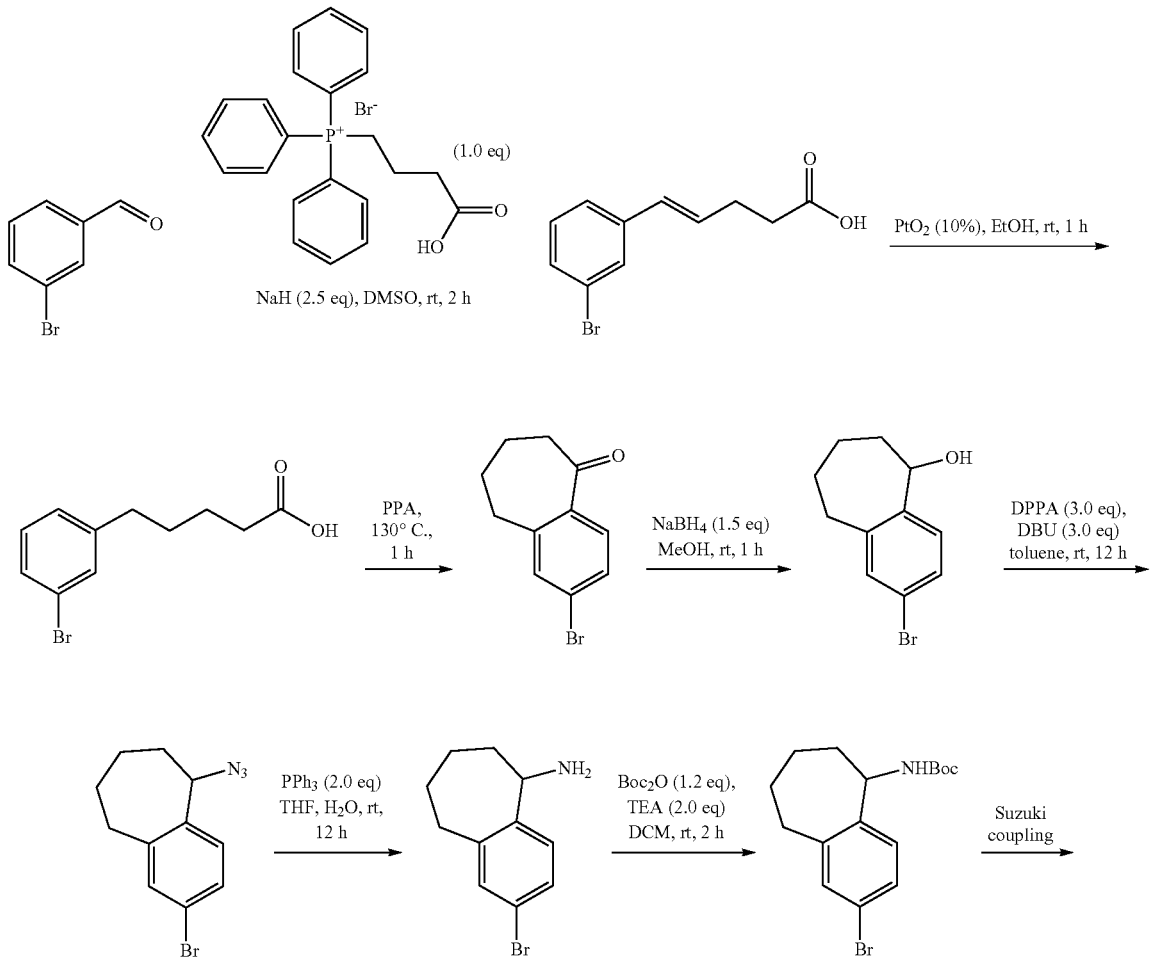

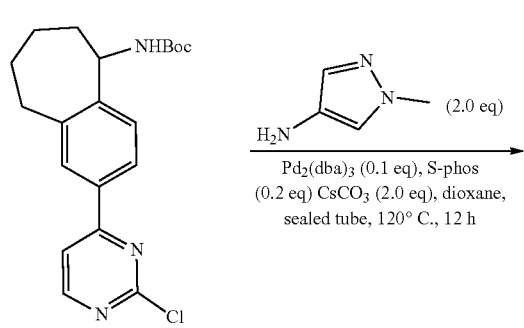

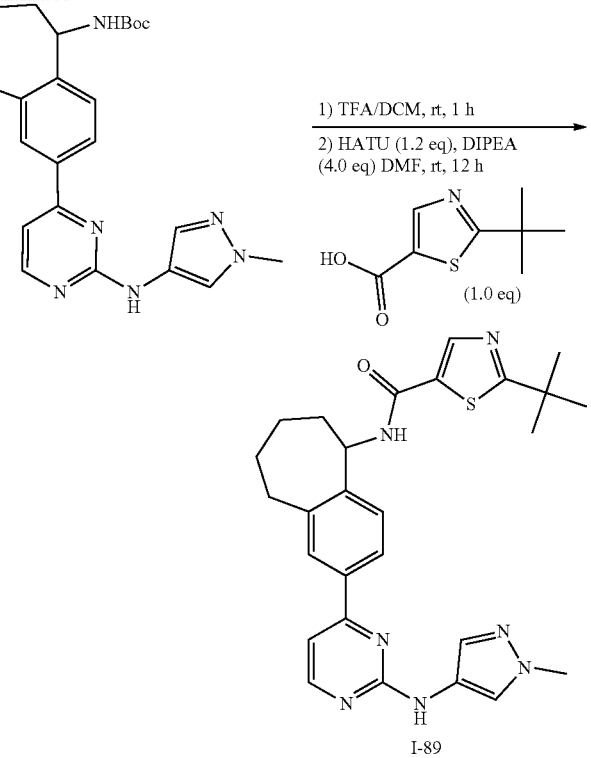

I-89

Synthesis of (E)-5-(3-bromophenyl)pent-4-enoic acid

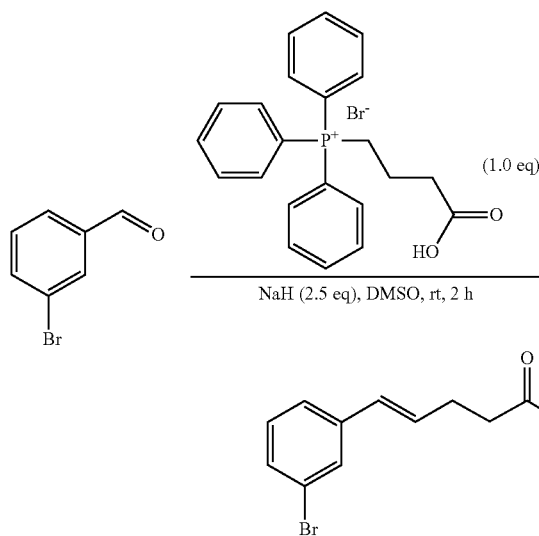

To a solution of (3-carboxypropyl)triphenylphosphonium bromide (12.87 g, 30 mmol, 1.0 equiv) in dry DMSO (50 mL) was added NaH (3 g, 75 mmol, 2.5 equiv) by portions at 0° C. The reaction was stirred at room temperature for 30 min before 3-bromobenzaldehyde (5.5 g, 30 mmol, 1.0 equiv) was dropwise added. The mixture was stirred at room temperature for another 2 h and then poured into water (200 mL) and extracted with EA (100 mL). The aqueous solution was acidified with concentrated HCl and extracted with EA (200 mL×3). The combined organic layer was washed with brine (100 mL×3). The organic layer was dried over sodium sulfate and concentrated under reduced pressure. The residue was purified by silica gel column (petroleum ether/EtOAc=2:1) to give (E)-5-(3-bromophenyl)pent-4-enoic acid (4.4 g, yield: 58%) as a yellow oil. ESI-MS (M+1)$^+$: 254.9. $^1$H NMR (400 MHz, CDCl$_3$) δ: 7.48 (s, 1H), 7.33 (d, J=7.6 Hz, 1H), 7.23 (d, J=8.0 Hz, 1H), 7.15 (t, J=8.0 Hz, 1H), 6.39-6.35 (m, 1H), 6.23-6.19 (m, 1H), 2.55-2.53 (m, 4H).

Synthesis of 5-(3-bromophenyl)pentanoic acid

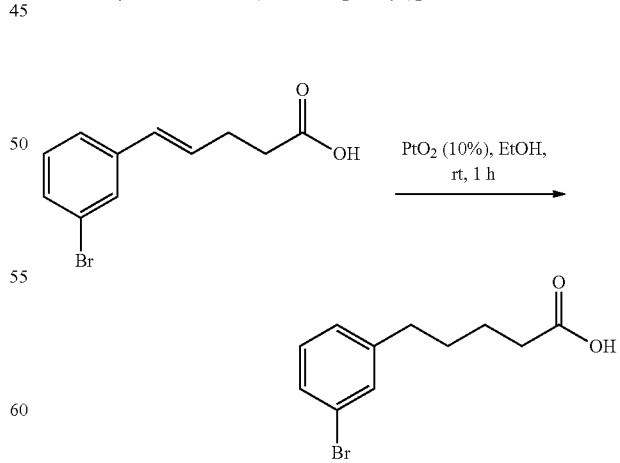

To a solution of (E)-5-(3-bromophenyl)pent-4-enoic acid (2.4 g, 9.4 mmol, 1.0 equiv) in ethanol (20 mL) was added PtO$_2$ (200 mg, 10%). The mixture was stirred for 1 h under hydrogen atmosphere. The catalyst was filtered out and the resulting filtrate was concentrated to give target compound 5-(3-bromophenyl)pentanoic acid (2.1 g, yield: 87%) as a yellow solid, which was used to next step without further purification. ESI-MS (M+1)⁺: 256.9. ¹H NMR (400 MHz, CD₃OD) δ: 7.24 (s, 1H), 7.21-7.18 (m, 1H), 7.06-7.03 (m, 2H), 2.50 (t, J=6.8 Hz, 2H), 2.20 (t, J=6.8 Hz, 2H), 1.53-1.51 (m, 4H).

Synthesis of 2-bromo-6,7,8,9-tetrahydro-5H-benzo[7]annulen-5-one

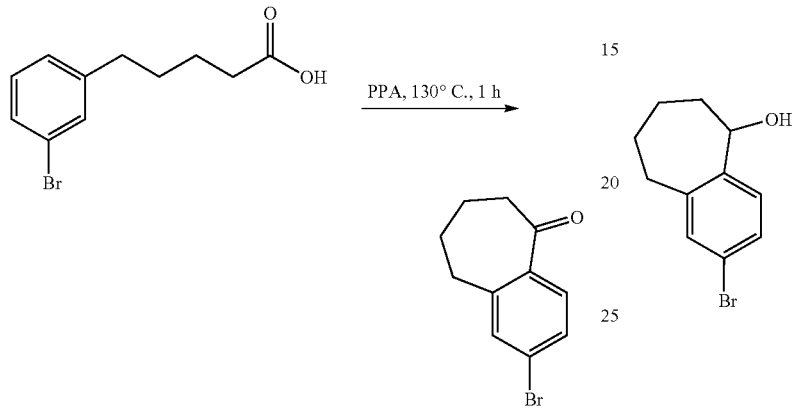

A mixture of 5-(3-bromophenyl)pentanoic acid (2.1 g, 8.2 mmol, 1.0 equiv) in PPA (5 ml) was stirred at 130° C. for 1 h. After cooling down, the mixture was basified to pH=7~8 with NaOH (1 N). The mixture was extracted with EtOAc (200 mL×2). The combined organic layers was concentrated and purified by prep-HPLC (Gradient: 5% B increase to 95% B, A: 0.5% NH₃ in water, B: CH₃CN) to give 2-bromo-6,7,8,9-tetrahydro-5H-benzo[7]annulen-5-one (1.1 g, yield: 56%) as a colorless oil. ESI-MS (M+H)⁺: 239.0. ¹H NMR (400 MHz, CDCl₃) δ: 7.59 (d, J=8.4 Hz, 1H), 7.43 (dd, J=8.4, 2.0 Hz, 1H), 7.38 (s, 1H), 2.89 (t, J=6.8 Hz, 2H), 2.72 (t, J=6.0 Hz, 2H), 1.90-1.79 (m, 4H).

Synthesis of 2-bromo-6,7,8,9-tetrahydro-5H-benzo[7]annulen-5-ol

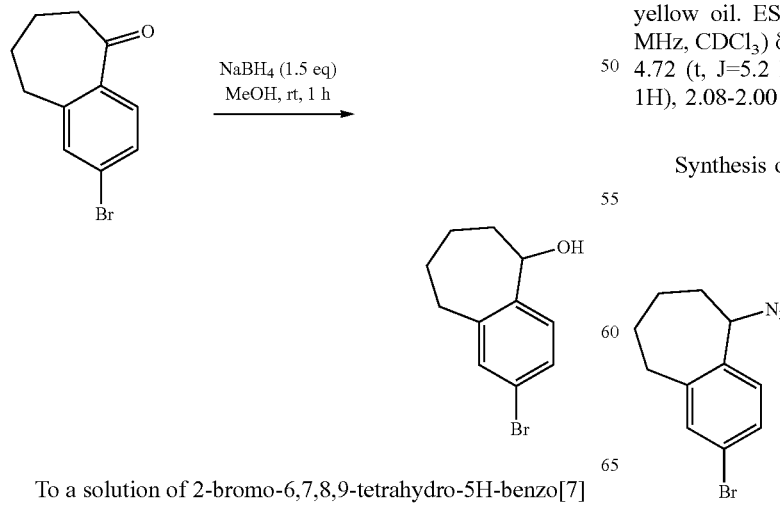

To a solution of 2-bromo-6,7,8,9-tetrahydro-5H-benzo[7]annulen-5-one (600 mg, 2.5 mmol, 1.0 equiv) in MeOH (10 mL) was added NaBH₄ (144 mg, 3.8 mmol, 1.5 equiv) and then stirred at room temperature for 1 h. After evaporation of the solvent, the residue was purified by silica gel column (EtOAc/hexane=1:5) to give 2-bromo-6,7,8,9-tetrahydro-5H-benzo[7]annulen-5-ol (600 mg, yield: 99%) as a white solid. ESI-MS (M+H-17)⁺: 222.9. ¹H NMR (400 MHz, CDCl₃) δ: 7.34-7.30 (m, 2H), 7.24 (s, 1H), 4.88-4.86 (m, 1H), 2.88-8.82 (m, 1H), 2.70-2.63 (m, 1H), 2.08-2.00 (m, 2H), 1.81-1.72 (m, 4H).

Synthesis of 5-azido-2-bromo-6,7,8,9-tetrahydro-5H-benzo[7]annulene

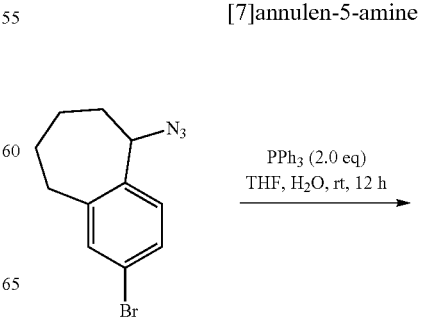

A solution of 2-bromo-6,7,8,9-tetrahydro-5H-benzo[7]annulen-5-ol (600 mg, 2.5 mmol, 1.0 equiv) in toluene (10 mL) was cooled in an ice bath under N₂ and treated with DPPA (2.06 g, 7.5 mmol, 3.0 equiv) in one portion followed by DBU (1.14 g, 7.5 mmol, 3.0 equiv). The reaction temperature was kept at 0° C. for 1 h and then was warmed to room temperature for 12 h. The mixture was diluted with EtOAc (100 mL), washed with 2N HCl (2×50 mL), brine and the organic layer was dried over Na₂SO₄, filtered then concentrated. The crude product was purified by silica gel column (eluted with PE) to give 5-azido-2-bromo-6,7,8,9-tetrahydro-5H-benzo[7]annulene (350 mg, yield: 45%) as a yellow oil. ESI-MS (M+H—N₃)⁺: 223.0. ¹H NMR (400 MHz, CDCl₃) δ: 7.31-7.29 (m, 2H), 7.15 (d, J=8.0 Hz, 1H), 4.72 (t, J=5.2 Hz, 1H), 2.99-2.92 (m, 1H), 2.70-2.64 (m, 1H), 2.08-2.00 (m, 1H), 1.90-1.59 (m, 5H).

Synthesis of 2-bromo-6,7,8,9-tetrahydro-5H-benzo[7]annulen-5-amine

182

Synthesis of tert-butyl (2-(2-chloropyrimidin-4-yl)-6,7,8,9-tetrahydro-5H-benzo[7]annulen-5-yl)carbamate

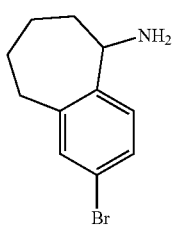

To a mixture of 5-azido-2-bromo-6,7,8,9-tetrahydro-5H-benzo[7]annulene (375 mg, 1.4 mmol, 1.0 equiv) in THF (5 mL) and H₂O (0.5 mL) was added PPh₃ (741 mg, 2.8 mmol, 2.0 equiv). The mixture was stirred at room temperature for 12 h. The mixture was acidified to pH=1 with HCl (1 N) and extracted with EA (100 mL). The separated aqueous layer was basified to pH=10 with NaOH (1 N). The resulting precipitate was collected and dried to give 2-bromo-6,7,8,9-tetrahydro-5H-benzo[7]annulen-5-amine (360 mg, yield: 100%) as a white solid. ESI-MS (M+H-17)⁺: 222.9.

Synthesis of tert-butyl (2-bromo-6,7,8,9-tetrahydro-5H-benzo[7]annulen-5-yl)carbamate

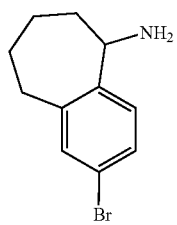

Boc₂O (1.2 eq), TEA (2.0 eq)
DCM, rt, 2 h
→

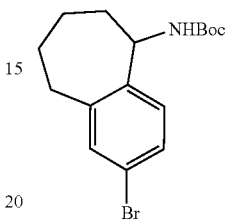

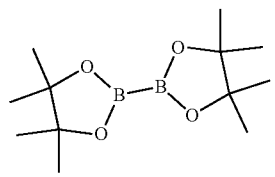
(1.0 eq)

1) KOAc (3.0 eq), Pd(dppf)Cl₂ (0.05 eq) dioxane, 100° C., 12 h

2) K₂CO₃ (2.0 eq), Pd(dppf)Cl₂ (0.05 eq) dioxane, H₂O, 100° C., 12 h

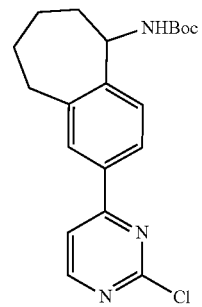

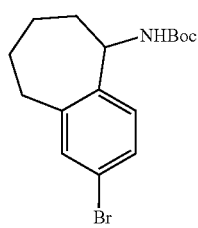

Synthesis of tert-butyl (2-(2-chloropyrimidin-4-yl)-6,7,8,9-tetrahydro-5H-benzo[7]annulen-5-yl)carbamate was similar to that of tert-butyl 4-(2-chloropyrimidin-4-yl)-2-methylbenzylcarbamate. The mixture was concentrated and purified by silica gel column (PE:EA=4:1) to give tert-butyl (2-(2-chloropyrimidin-4-yl)-6,7,8,9-tetrahydro-5H-benzo[7]annulen-5-yl)carbamate (200 mg, yield: 66%) as a white solid. ESI-MS (M+H)⁺: 374.1.

Synthesis of tert-butyl (2-(2-((1-methyl-1H-pyrazol-4-yl)amino)pyrimidin-4-yl)-6,7,8,9-tetrahydro-5H-benzo[7]annulen-5-yl)carbamate To a mixture of tert-butyl (2-bromo-6,7,8,9-tetrahydro-5H-benzo[7]annulen-5-yl)carbamate (360 mg, 1.5 mmol, 1.0 equiv) in DCM (5 mL) and TEA (303 mg, 3.0 mmol, 2.0 equiv) was added Boc₂O (394 mg, 1.8 mmol, 1.2 equiv). The mixture was stirred at room temperature for 2 h. After diluted with EtOAc (100 mL), the mixture was washed with water (100 mL×2). The organic layer was concentrated and purified by silica gel column (PE:EA=30:1) to give tert-butyl (2-bromo-6,7,8,9-tetrahydro-5H-benzo[7]annulen-5-yl)carbamate (310 mg, yield: 61%) as a white solid. ESI-MS (M-55): 284.0. ¹H NMR (400 MHz, CDCl₃) δ: 7.29-7.23 (m, 2H), 7.10 (d, J=8.0 Hz, 1H), 4.92-4.82 (m, 2H), 2.84-2.75 (m, 2H), 1.88-1.83 (m, 5H), 1.44 (s, 9H).

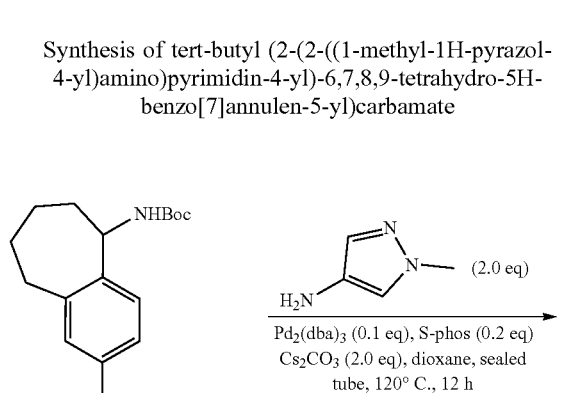

Pd₂(dba)₃ (0.1 eq), S-phos (0.2 eq)
Cs₂CO₃ (2.0 eq), dioxane, sealed tube, 120° C., 12 h

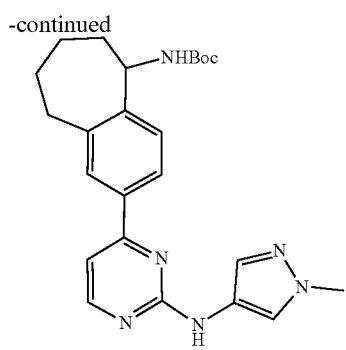

Synthesis of tert-butyl (2-(2-((1-methyl-1H-pyrazol-4-yl)amino)pyrimidin-4-yl)-6,7,8,9-tetrahydro-5H-benzo[7]annulen-5-yl)carbamate was similar to that of tert-butyl 2-methyl-4-(2-((1-methyl-1H-pyrazol-4-yl)amino)pyrimidin-4-yl)benzylcarbamate. The mixture was concentrated and purified by silica gel column (DCM:MeOH=30:1) to give tert-butyl (2-(2-((1-methyl-1H-pyrazol-4-yl)amino)pyrimidin-4-yl)-6,7,8,9-tetrahydro-5H-benzo[7]annulen-5-yl)carbamate (80 mg, yield: 34%) as a yellow solid. ESI-MS (M+H)⁺: 435.2.

Synthesis of 2-(tert-butyl)-N-(2-(2-((1-methyl-1H-pyrazol-4-yl)amino)pyrimidin-4-yl)-6,7,8,9-tetrahydro-5H-benzo[7]annulen-5-yl)thiazole-5-carboxamide

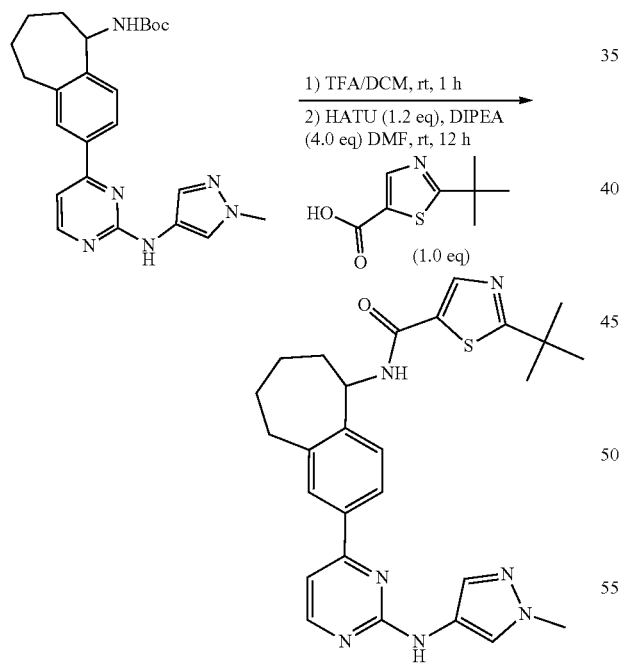

Synthesis of 2-(tert-butyl)-N-(2-(2-((1-methyl-1H-pyrazol-4-yl)amino)pyrimidin-4-yl)-6,7,8,9-tetrahydro-5H-benzo[7]annulen-5-yl)thiazole-5-carboxamide was similar to that of Example 1. The mixture was purified by prep-HPLC (Gradient: 5% B increase to 95% B, A: 0.5% NH₃ in water, B: CH₃CN) to give 2-(tert-butyl)-N-(2-(2-((1-methyl-1H-pyrazol-4-yl)amino)pyrimidin-4-yl)-6,7,8,9-tetrahydro-5H-benzo[7]annulen-5-yl)thiazole-5-carboxamide (32 mg, yield: 69%) as a yellow solid. ESI-MS (M+1)⁺: 502.2. ¹H NMR (400 MHz, CD₃OD) δ: 8.39 (s, 1H), 8.37 (d, J=5.6 Hz, 1H), 7.95 (s, 1H), 7.92-7.91 (m, 2H), 7.64 (s, 1H), 7.36 (d, J=8.4 Hz, 1H), 7.18 (d, J=5.2 Hz, 1H), 5.38-5.35 (m, 1H), 3.87 (s, 3H), 3.10-2.95 (m, 2H), 2.10-1.77 (m, 5H), 1.48 (s, 9H), 1.43-1.38 (m, 1H).

Example 89: 2-(tert-butyl)-N-(5-(2-((1-methyl-1H-pyrazol-4-yl)amino)pyrimidin-4-yl)-2,3-dihydro-1H-inden-1-yl)thiazole-5-carboxamide (I-90)

I-90

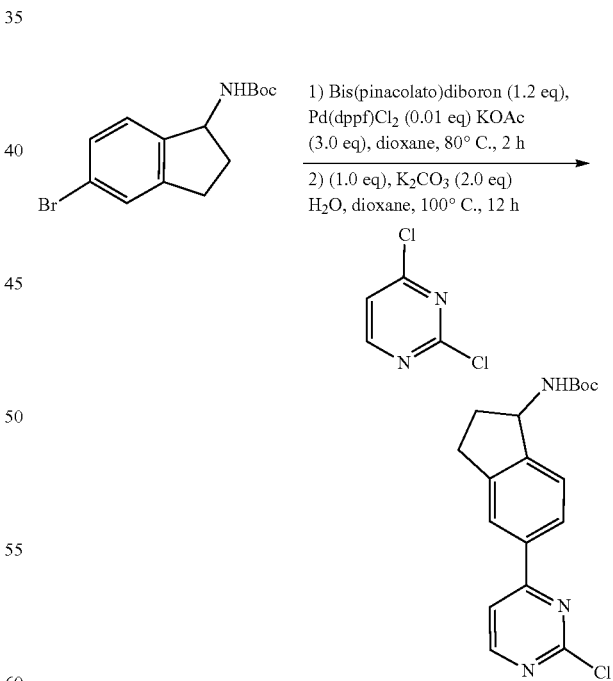

Synthesis of tert-butyl (5-(2-chloropyrimidin-4-yl)-2,3-dihydro-1H-inden-1-yl)carbamate Synthesis of tert-butyl (5-(2-chloropyrimidin-4-yl)-2,3-dihydro-1H-inden-1-yl)carbamate was similar to that of tert-butyl 4-(2-chloropyrimidin-4-yl)-2-methylbenzylcarbamate. The mixture was concentrated and purified by silica gel column (petroleum ether/EtOAc=4:1) to give tert-butyl (5-(2-chloropyrimidin-4-yl)-2,3-dihydro-1H-inden-1-yl)

carbamate (790 mg, yield: 49%) as a yellow solid. ESI-MS (M+H)⁺: 346.0. ¹H NMR (400 MHz, CDCl₃) δ: 8.62 (d, J=5.6 Hz, 1H), 7.98 (s, 1H), 7.91 (d, J=7.6 Hz, 1H), 7.62 (d, J=5.2 Hz, 1H), 7.45 (d, J=8.0 Hz, 1H), 5.27-5.21 (m, 1H), 4.81-4.79 (m, 1H), 3.07-3.00 (m, 1H), 2.95-2.87 (m, 1H), 2.66-2.63 (m, 1H), 1.90-1.85 (m, 1H), 1.50 (s, 9H).

Synthesis of tert-butyl (5-(2-((1-methyl-1H-pyrazol-4-yl)amino)pyrimidin-4-yl)-2,3-dihydro-1H-inden-1-yl)carbamate

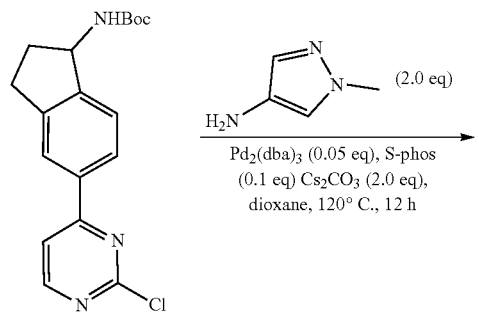

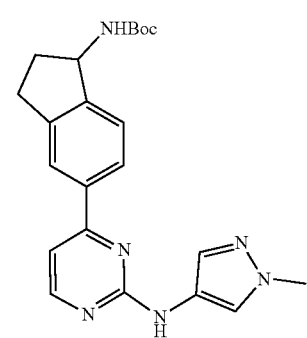

Synthesis of tert-butyl (5-(2-((1-methyl-1H-pyrazol-4-yl)amino)pyrimidin-4-yl)-2,3-dihydro-1H-inden-1-yl)carbamate was similar to that of tert-butyl 2-methyl-4-(2-((1-methyl-1H-pyrazol-4-yl)amino)pyrimidin-4-yl)benzylcarbamate. The mixture was purified by silica gel column (petroleum ether/EtOAc=1:1) to give tert-butyl (5-(2-((1-methyl-1H-pyrazol-4-yl)amino)pyrimidin-4-yl)-2,3-dihydro-1H-inden-1-yl)carbamate (80 mg, yield: 45%) as a yellow solid. ESI-MS (M+H)⁺: 406.9. ¹H NMR (400 MHz, CDCl₃) δ: 8.42 (d, J=5.2 Hz, 1H), 7.88-7.87 (m, 3H), 7.54 (s, 1H), 7.42 (d, J=7.6 Hz, 1H), 7.06-7.05 (m, 2H), 5.27-5.21 (m, 1H), 4.81-4.78 (m, 1H), 3.07-2.88 (m, 2H), 2.65-2.59 (m, 1H), 1.95-1.80 (m, 1H), 1.50 (s, 9H).

Synthesis of 2-(tert-butyl)-N-(5-(2-((1-methyl-1H-pyrazol-4-yl)amino)pyrimidin-4-yl)-2,3-dihydro-1H-inden-1-yl)thiazole-5-carboxamide

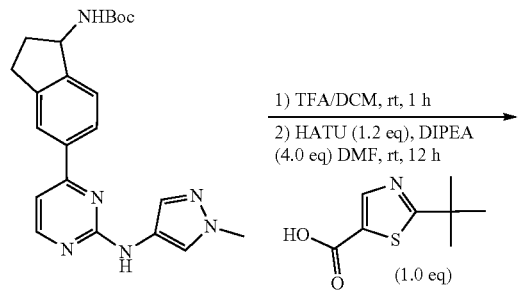

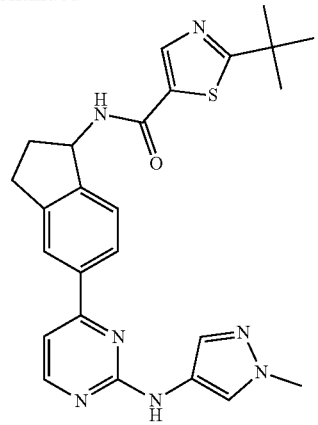

Synthesis of 2-(tert-butyl)-N-(5-(2-((1-methyl-1H-pyrazol-4-yl)amino)pyrimidin-4-yl)-2,3-dihydro-1H-inden-1-yl)thiazole-5-carboxamide was similar to that of Example 1. The mixture was purified by prep-HPLC (Gradient: 5% B increase to 95% B, A: 0.5% NH₃ in water, B: CH₃CN) to give 2-(tert-butyl)-N-(5-(2-((1-methyl-1H-pyrazol-4-yl)amino)pyrimidin-4-yl)-2,3-dihydro-1H-inden-1-yl)thiazole-5-carboxamide (48 mg, yield: 43%) as a yellow solid. ESI-MS (M+H)⁺: 474.0. ¹H NMR (400 MHz, CDCl₃) δ: 8.42 (d, J=5.6 Hz, 1H), 8.06 (s, 1H), 7.93 (s, 1H), 7.89 (d, J=8.0 Hz, 1H), 7.86 (s, 1H), 7.50 (s, 1H), 7.45 (d, J=8.0 Hz, 1H), 7.07-7.06 (m, 2H), 6.21 (d, J=8.0 Hz, 1H), 5.75-5.68 (m, 1H), 3.90 (s, 3H), 3.13-2.95 (m, 2H), 2.79-2.70 (m, 1H), 2.00-1.95 (m, 1H), 1.45 (s, 9H).

Example 90: 2-(tert-butyl)-N-(6-(2-((1-methyl-1H-pyrazol-4-yl)amino)pyrimidin-4-yl)-1,2,3,4-tetrahydronaphthalen-1-yl)thiazole-5-carboxamide (I-91)

I-91

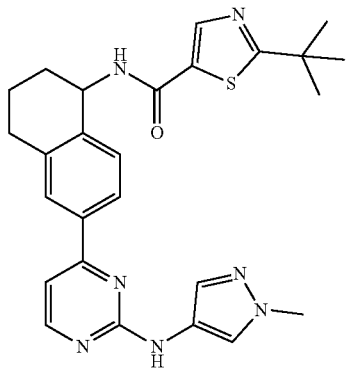

Synthesis of 2-(tert-butyl)-N-(6-(2-((1-methyl-1H-pyrazol-4-yl)amino)pyrimidin-4-yl)-1,2,3,4-tetrahydronaphthalen-1-yl)thiazole-5-carboxamide was similar to that of Example 89. The residue was purified by prep-HPLC (CH₃CN/H₂O with 0.05% NH₃.H₂O as mobile phase) to give 2-(tert-butyl)-N-(6-(2-((1-methyl-1H-pyrazol-4-yl)amino)pyrimidin-4-yl)-1,2,3,4-tetrahydronaphthalen-1-yl)thiazole-5-carboxamide as yellow solid (90 mg, yield: 76%). ESI-MS (M+H)⁺: 488.2. ¹H NMR (400 MHz, DMSO-d₆) δ: 9.53 (s, 1H), 9.01 (d, J=8.4 Hz, 1H), 8.46 (d, J=5.2 Hz, 1H), 8.33 (s, 1H), 7.93-7.92 (m, 3H), 7.53 (s, 1H), 7.36 (d, J=8.4

Hz, 1H), 7.26 (d, J=5.2 Hz, 1H), 5.24-5.22 (m, 1H), 3.82 (s, 3H), 2.89-2.88 (m, 2H), 2.02-2.00 (m, 2H), 1.83-1.81 (m, 2H), 1.39 (s, 9H).

Example 91: 2-(tert-butyl)-N-(6-(6-((1-methyl-1H-pyrazol-4-yl)amino)pyrimidin-4-yl)-1,2,3,4-tetrahydronaphthalen-1-yl)thiazole-5-carboxamide (I-92)

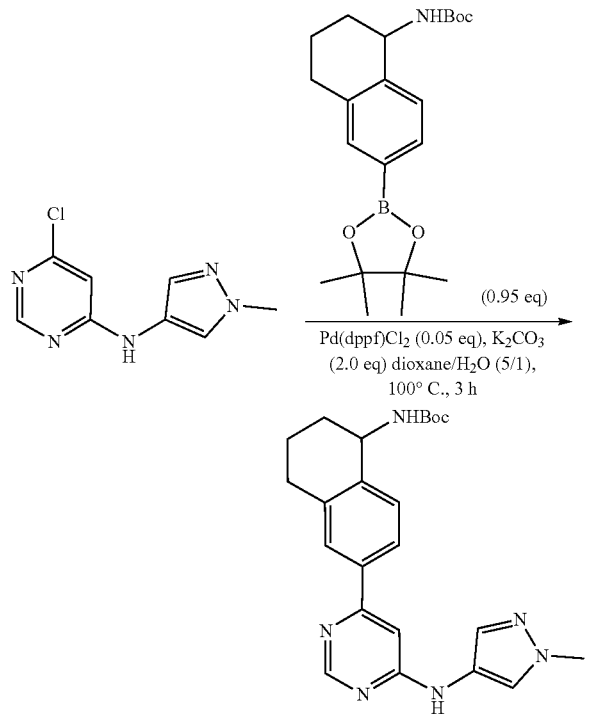

Synthesis of tert-butyl (6-(6-((1-methyl-1H-pyrazol-4-yl)amino)pyrimidin-4-yl)-1,2,3,4-tetrahydronaphthalen-1-yl)carbamate

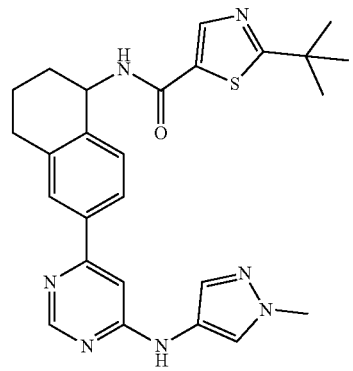

Synthesis of tert-butyl (6-(6-((1-methyl-1H-pyrazol-4-yl) amino)pyrimidin-4-yl)-1,2,3,4-tetrahydronaphthalen-1-yl) carbamate was similar to that of tert-butyl 4-(2-chloropyrimidin-4-yl)-2-methylbenzylcarbamate. Obtained tert-butyl (6-(6-((1-methyl-1H-pyrazol-4-yl)amino)pyrimidin-4-yl)-1,2,3,4-tetrahydronaphthalen-1-yl)carbamate (170 mg, yield: 47%) as a white solid. ESI-MS (M+H)⁺: 421.1. ¹H NMR (400 MHz, CDCl₃) δ: 8.71 (s, 1H), 7.71 (s, 1H), 7.68-7.65 (m, 2H), 7.50 (s, 1H), 7.42 (d, J=8.0 Hz, 1H), 6.82 (s, 1H), 6.45 (s, 1H), 4.91-4.87 (m, 1H), 4.80-4.77 (m, 1H), 3.94 (s, 3H), 2.85-2.80 (m, 2H), 2.12-2.07 (m, 1H), 1.86-1.77 (m, 3H), 1.48 (s, 9H).

Synthesis of 2-(tert-butyl)-N-(6-(6-((1-methyl-1H-pyrazol-4-yl)amino)pyrimidin-4-yl)-1,2,3,4-tetrahydronaphthalen-1-yl)thiazole-5-carboxamide

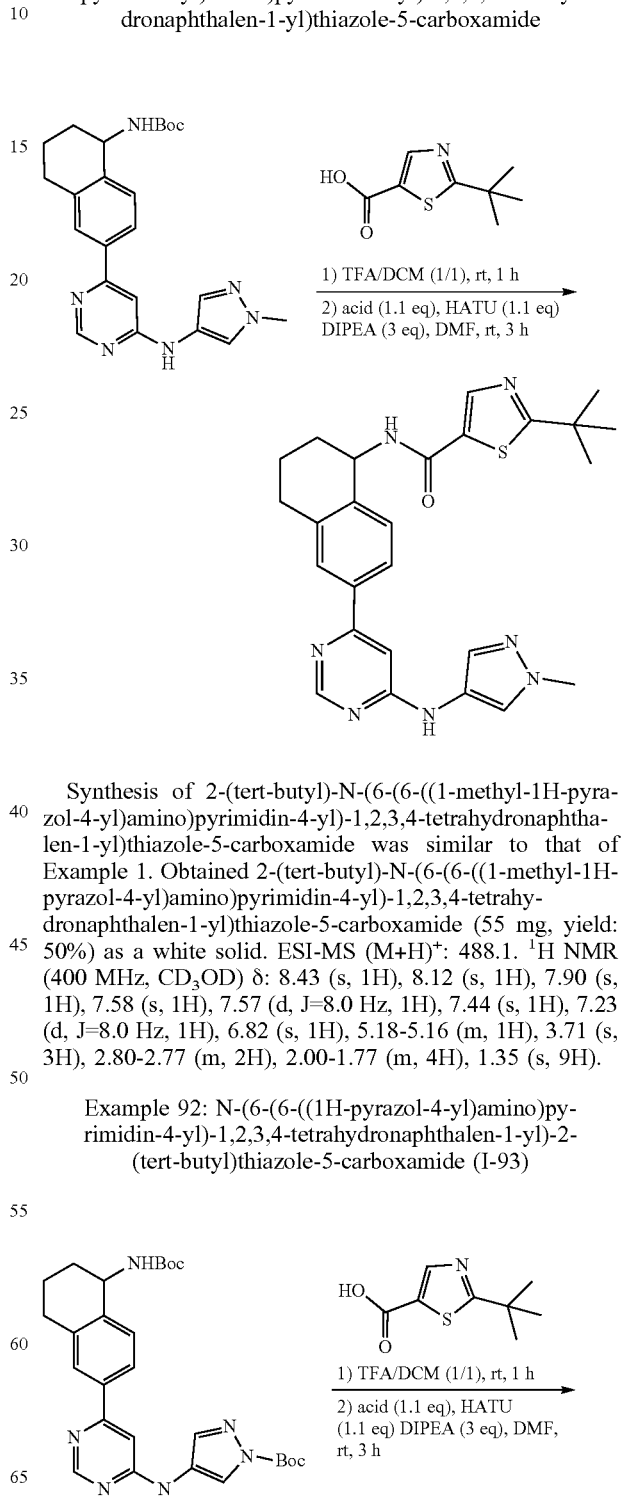

Synthesis of 2-(tert-butyl)-N-(6-(6-((1-methyl-1H-pyrazol-4-yl)amino)pyrimidin-4-yl)-1,2,3,4-tetrahydronaphthalen-1-yl)thiazole-5-carboxamide was similar to that of Example 1. Obtained 2-(tert-butyl)-N-(6-(6-((1-methyl-1H-pyrazol-4-yl)amino)pyrimidin-4-yl)-1,2,3,4-tetrahydronaphthalen-1-yl)thiazole-5-carboxamide (55 mg, yield: 50%) as a white solid. ESI-MS (M+H)⁺: 488.1. ¹H NMR (400 MHz, CD₃OD) δ: 8.43 (s, 1H), 8.12 (s, 1H), 7.90 (s, 1H), 7.58 (s, 1H), 7.57 (d, J=8.0 Hz, 1H), 7.44 (s, 1H), 7.23 (d, J=8.0 Hz, 1H), 6.82 (s, 1H), 5.18-5.16 (m, 1H), 3.71 (s, 3H), 2.80-2.77 (m, 2H), 2.00-1.77 (m, 4H), 1.35 (s, 9H).

Example 92: N-(6-(6-((1H-pyrazol-4-yl)amino)pyrimidin-4-yl)-1,2,3,4-tetrahydronaphthalen-1-yl)-2-(tert-butyl)thiazole-5-carboxamide (I-93)

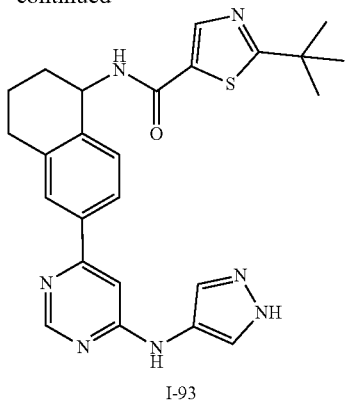

I-93

Synthesis of N-(6-(6-((1H-pyrazol-4-yl)amino)pyrimidin-4-yl)-1,2,3,4-tetrahydronaphthalen-1-yl)-2-(tert-butyl)thiazole-5-carboxamide was similar to that of Example 89. Obtained N-(6-(6-((1H-pyrazol-4-yl)amino)pyrimidin-4-yl)-1,2,3,4-tetrahydronaphthalen-1-yl)-2-(tert-butyl)thiazole-5-carboxamide (32 mg, yield: 26%) as a white solid. ESI-MS (M+H)$^+$: 474.1. $^1$H NMR (400 MHz, CD$_3$OD) δ: 8.84 (s, 1H), 8.23 (s, 1H), 8.06-8.04 (m, 2H), 7.66-7.63 (m, 2H), 7.51 (d, J=8.4 Hz, 1H), 7.14 (s, 1H), 5.34-5.32 (m, 1H), 3.00-2.90 (m, 2H), 2.17-1.93 (m, 4H), 1.46 (s, 9H).

Example 93: Synthesis of N-(6-(6-((1-methyl-1H-pyrazol-4-yl)amino)pyrimidin-4-yl)-1,2,3,4-tetrahydronaphthalen-1-yl)-6,7-dihydro-4H-thieno[3,2-c]pyran-2-carboxamide (I-94)

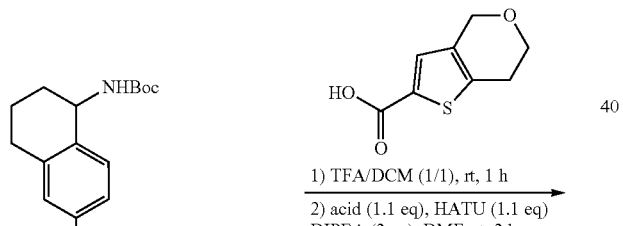

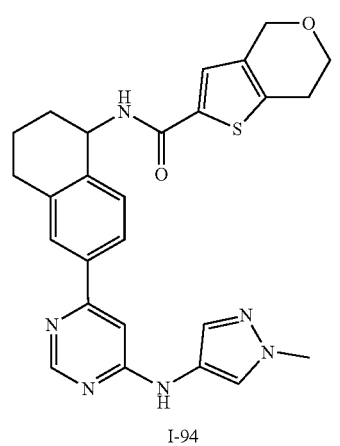

I-94

Synthesis of N-(6-(6-((1-methyl-1H-pyrazol-4-yl)amino)pyrimidin-4-yl)-1,2,3,4-tetrahydronaphthalen-1-yl)-6,7-dihydro-4H-thieno[3,2-c]pyran-2-carboxamide was similar to that of Example 89, starting from 6,7-dihydro-4H-thieno[3,2-c]pyran-2-carboxylic acid. Obtained N-(6-(6-((1-methyl-1H-pyrazol-4-yl)amino)pyrimidin-4-yl)-1,2,3,4-tetrahydronaphthalen-1-yl)-6,7-dihydro-4H-thieno[3,2-c]pyran-2-carboxamide (45 mg, yield: 43%) as a white solid. ESI-MS (M+H)$^+$: 486.8. HPLC: (214 nm: 100%, 254 nm: 100%). $^1$H NMR (400 MHz, DMSO-d$_6$) δ: 9.56 (br, 1H), 8.76 (d, J=8.8 Hz, 1H), 8.63 (s, 1H), 8.00 (s, 1H), 7.80 (s, 1H), 7.57 (d, J=8.0 Hz, 1H), 7.54 (s, 1H), 7.50 (s, 1H), 7.29 (d, J=8.4 Hz, 1H), 7.04 (s, 1H), 5.22-5.17 (m, 1H), 4.58 (s, 2H), 3.87 (t, J=5.6 Hz, 2H), 3.83 (s, 3H), 2.86-2.82 (m, 4H), 2.03-1.98 (m, 2H), 1.86-1.79 (m, 2H).

Example 94: N-(6-(2-((1-methyl-1H-pyrazol-4-yl)amino)pyrimidin-4-yl)-1,2,3,4-tetrahydronaphthalen-1-yl)-6,7-dihydro-4H-thieno[3,2-c]pyran-2-carboxamide (I-95)

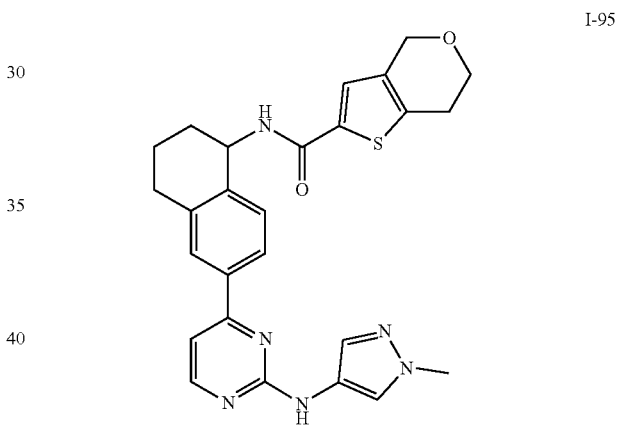

I-95

Synthesis of N-(6-(2-((1-methyl-1H-pyrazol-4-yl)amino)pyrimidin-4-yl)-1,2,3,4-tetrahydronaphthalen-1-yl)-6,7-dihydro-4H-thieno[3,2-c]pyran-2-carboxamide was similar to that of Example 89 starting from 6,7-dihydro-4H-thieno[3,2-c]pyran-2-carboxylic acid. The residue was purified by prep-HPLC (CH$_3$CN/H$_2$O with 0.05% NH$_3$.H$_2$O as mobile phase) to give title product as a yellow solid (23 mg, yield: 24%). ESI-MS (M+H)$^+$: 487.2. HPLC: (214 nm: 100%, 254 nm: 100%). $^1$H NMR (400 MHz, CD$_3$OD) δ: 8.44 (d, J=4.8 Hz, 1H), 7.98-7.93 (m, 3H), 7.60 (s, 1H), 7.46 (s, 1H), 7.38 (d, J=8.0 Hz, 1H), 7.22 (d, J=5.2 Hz, 1H), 5.30-5.26 (m, 1H), 4.62 (s, 2H), 3.94-3.91 (m, 2H), 3.86 (s, 3H), 2.94-2.86 (m, 4H), 2.10-1.84 (m, 4H), 1.28-1.27 (m, 2H).

Example 95: 2-(tert-butyl)-N-(6-(2-((5-(4-methylpiperazin-1-yl)pyridin-2-yl)amino)pyrimidin-4-yl)-1,2,3,4-tetrahydronaphthalen-1-yl)thiazole-5-carboxamide (I-96)

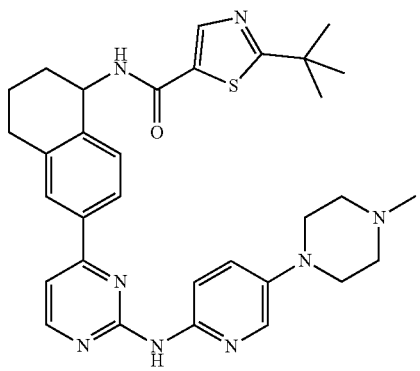

I-96

Synthesis of 2-(tert-butyl)-N-(6-(2-((5-(4-methylpiperazin-1-yl)pyridin-2-yl)amino)pyrimidin-4-yl)-1,2,3,4-tetrahydronaphthalen-1-yl)thiazole-5-carboxamide was similar to that of Example 89. The residue was purified by prep-HPLC ($CH_3CN/H_2O$ with 0.05% $NH_3H_2O$ as mobile phase) to give 2-(tert-butyl)-N-(6-(2-((5-(4-methylpiperazin-1-yl)pyridin-2-yl)amino)pyrimidin-4-yl)-1,2,3,4-tetrahydronaphthalen-1-yl)thiazole-5-carboxamide as a white solid (10 mg, yield: 18%). ESI-MS $(M+H)^+$: 582.9. HPLC: (214 nm: 100%, 254 nm: 100%). $^1$H NMR (400 MHz, $CD_3OD$) δ: 9.50 (s, 1H), 9.00 (d, J=6.8 Hz, 1H), 8.53 (d, J=4.4 Hz, 1H), 8.33 (s, 1H), 8.17 (d, J=7.2 Hz, 1H), 8.00 (d, J=2.0 Hz, 1H), 7.97-7.95 (m, 2H), 7.48 (dd, J=7.6, 2.4 Hz, 1H), 7.41 (d, J=4.0 Hz, 1H), 7.36 (d, J=6.0 Hz, 1H), 5.24-5.21 (m, 1H), 3.12 (t, J=3.2 Hz, 4H), 2.89 (s, 2H), 2.46 (t, J=4.0 Hz, 4H), 2.22 (s, 3H), 2.02-1.97 (m, 2H), 1.86-1.83 (m, 2H), 1.37 (s, 9H).

Example 96: 2-(tert-butyl)-N-(7-(2-((1-methyl-1H-pyrazol-4-yl)amino)pyrimidin-4-yl)chroman-4-yl)thiazole-5-carboxamide (I-97)

Scheme 8

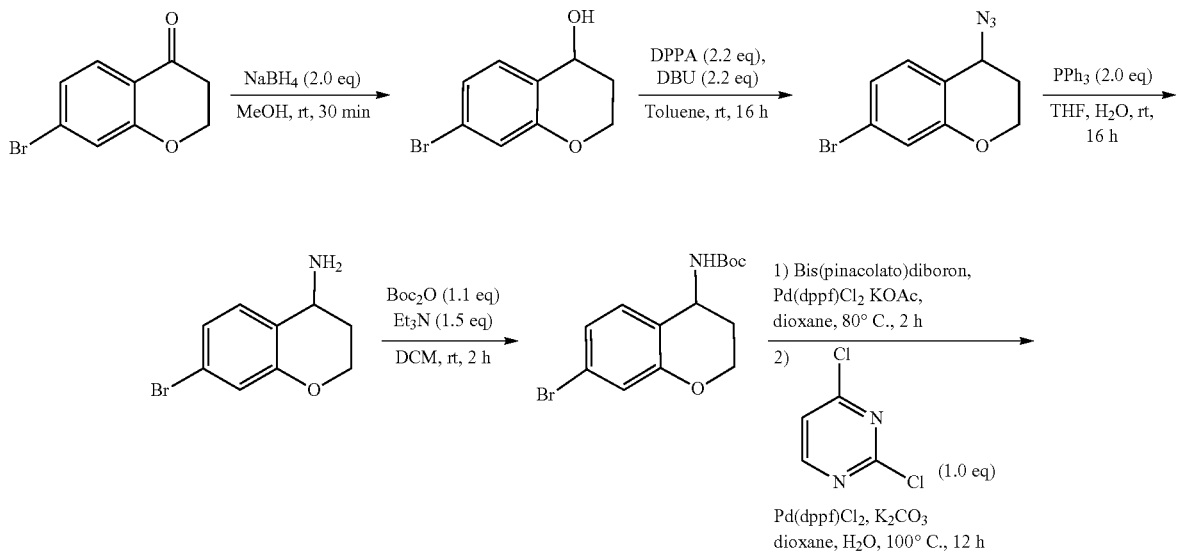

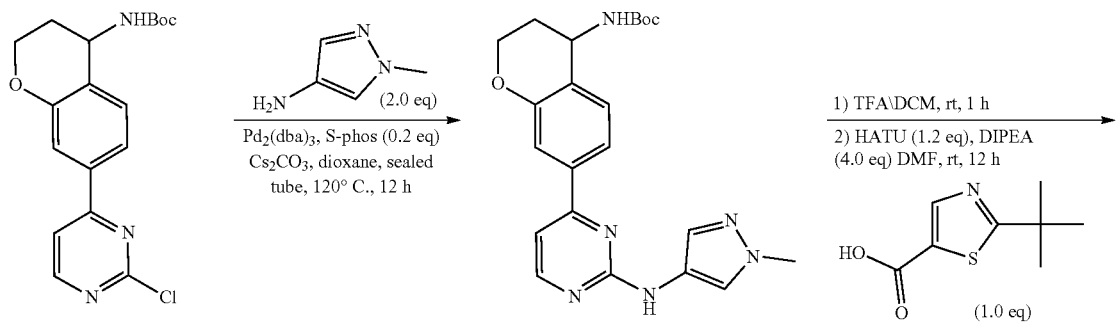

-continued

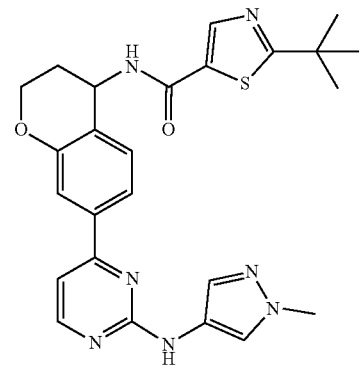

Synthesis of 4-azido-7-bromochroman

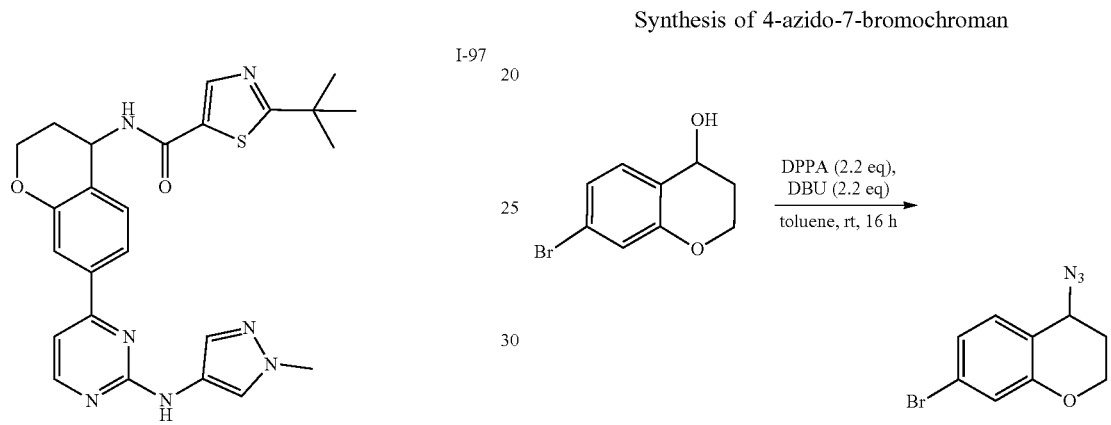

I-97

A solution of 7-bromochroman-4-ol (200 mg, 0.88 mmol, 1.0 equiv) in toluene (5 mL) was cooled in an ice bath under N$_2$ and treated with DPPA (532 mg, 1.93 mmol, 2.2 equiv) in one portion followed by DBU (293 mg, 1.93 mmol, 2.2 equiv). The reaction temperature was kept at 0° C. for 1 h and then was warmed to room temperature for 16 h. The mixture was diluted with EtOAc (50 mL), washed with 2N HCl (2×30 mL), brine and the organic layer was dried over Na$_2$SO$_4$, filtered then concentrated. The crude product was purified by silica gel column (eluted with PE). 4-azido-7-bromochroman (188 mg, yield: 90%) was obtained as a white solid. $^1$H NMR (400 MHz, CDCl$_3$) δ: 7.07-7.06 (m, 3H), 4.56 (t, J=3.6 Hz, 1H), 4.30-4.17 (m, 2H), 2.19-1.99 (m, 2H).

Synthesis of 7-bromochroman-4-amine

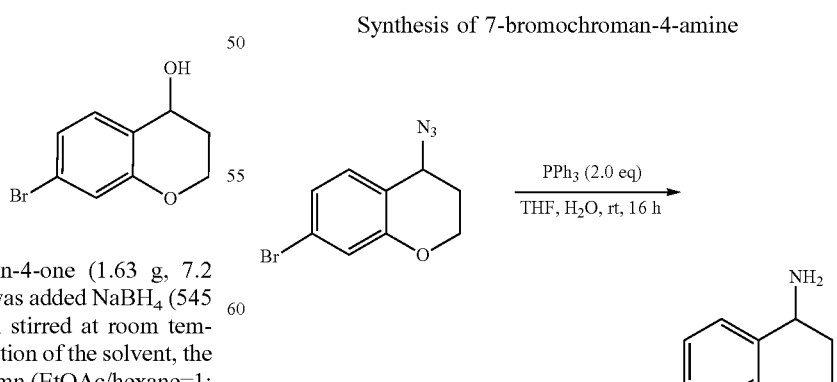

Synthesis of 7-bromochroman-4-ol

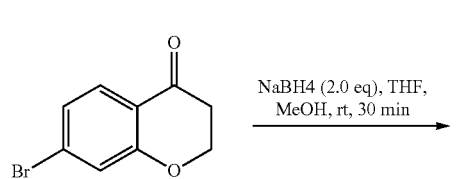

To a solution of 7-bromochroman-4-one (1.63 g, 7.2 mmol, 1.0 equiv) in MeOH (10 mL) was added NaBH$_4$ (545 mg, 14.4 mmol, 2.0 equiv) and then stirred at room temperature for 30 minutes. After evaporation of the solvent, the residue was purified by silica gel column (EtOAc/hexane=1:2) to give 7-bromochroman-4-ol (1.61 g, yield: 98%) as a white solid. ESI-MS (M+H-18)$^+$: 211.0. $^1$H NMR (400 MHz, CDCl$_3$) δ: 7.17 (d, J=8.0 Hz, 1H), 7.05-7.01 (m, 2H), 4.76-4.73 (m, 1H), 4.27-4.24 (m, 2H) 2.14-1.99 (m, 2H).

A solution of 4-azido-7-bromochroman (2.2 g, 8.7 mmol, 1.0 equiv) in THF (50 mL) and H$_2$O (10 mL) was treated with PPh₃ (4.5 g, 17 mmol, 2.0 equiv). The mixture was stirred at room temperature for 16 h. After concentrated to dryness, the residue was diluted with 1N HCl (100 mL), extracted with EA (100 mL). The aqueous was basified to pH=10 with 2N NaOH, extracted with EtOAc (50 mL×2). The combined organic extracts were dried over Na₂SO₄, filtered then concentrated. 7-bromochroman-4-amine (1.4 g, yield: 71%) was obtained as a colorless oil. ESI-MS (M+H-17)⁺: 210.9.

Synthesis of tert-butyl (7-bromochroman-4-yl)carbamate

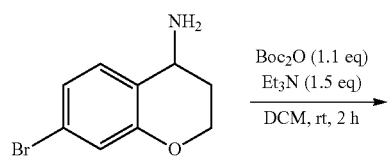

To a solution of 7-bromochroman-4-amine (1.4 g, 6.16 mmol, 1.0 equiv) in dichloromethane (30 mL) were added Et₃N (933 mg, 9.24 mmol, 1.5 equiv) and Boc₂O (1.5 g, 6.8 mmol, 1.1 equiv). The reaction solution was stirred at room temperature for 2 h. The mixture was concentrated and purified by silica gel column (petroleum ether/EtOAc=30:1). tert-butyl (7-bromochroman-4-yl)carbamate (1.5 g, yield: 74%) was obtained as a white solid. ESI-MS (M+H-56)⁺: 272.0. ¹H NMR (400 MHz, CDCl₃) δ: 7.14-7.12 (m, 1H), 7.03-6.98 (m, 2H), 4.78-4.77 (m, 1H), 4.27-4.11 (m, 2H) 2.19-1.99 (m, 2H), 1.48 (s, 9H).

Synthesis of tert-butyl (7-(2-chloropyrimidin-4-yl)chroman-4-yl)carbamate

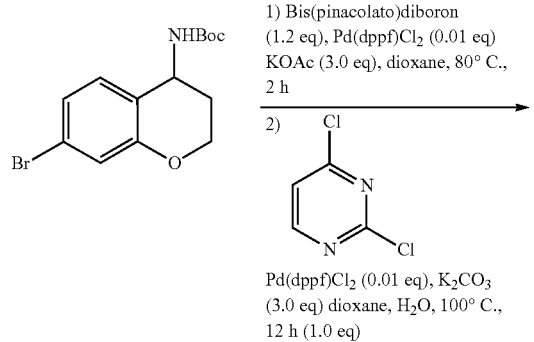

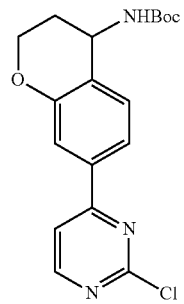

The synthesis of tert-butyl (7-(2-chloropyrimidin-4-yl)chroman-4-yl)carbamate was similar to that of tert-butyl 4-(2-chloropyrimidin-4-yl)-2-methylbenzylcarbamate. The residue was purified by silica gel column column (petroleum ether/EtOAc=4:1) to give tert-butyl (7-(2-chloropyrimidin-4-yl)chroman-4-yl)carbamate (500 mg, yield: 70%) as a white solid. ESI-MS (M+H)⁺: 362.0. ¹H NMR (400 MHz, CDCl₃) δ:8.62 (d, J=5.2 Hz, 1H), 7.78 (d, J=5.2 Hz, 1H), 7.65-7.63 (m, 1H), 7.56 (s, 1H), 7.42 (d, J=7.6 Hz, 1H), 4.86 (t, J=5.2 Hz, 1H), 4.31-4.27 (m, 2H), 2.24-2.05 (m, 2H), 1.21 (s, 9H).

Synthesis of tert-butyl (7-(2-((1-methyl-1H-pyrazol-4-yl)amino)pyrimidin-4-yl)chroman-4-ylcarbamate

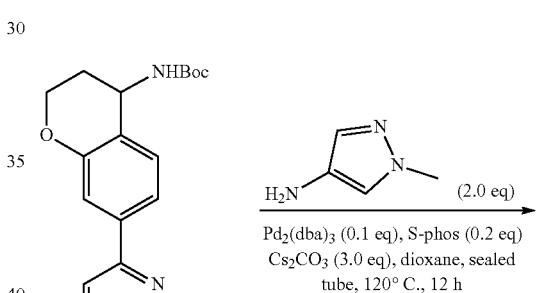

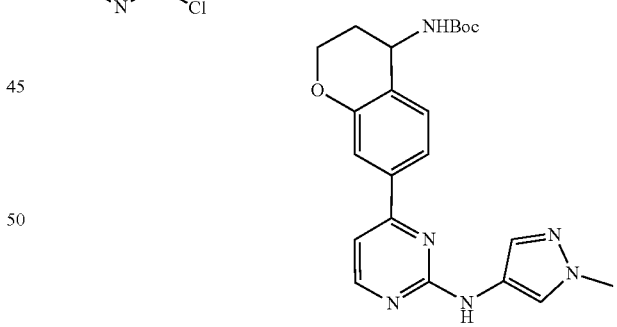

To a mixture of tert-butyl (7-(2-chloropyrimidin-4-yl)chroman-4-yl)carbamate (180 mg, 0.5 mmol) and 1-methyl-pyrazol-4-amine (97 mg, 1.0 mmol, 2.0 equiv) in dioxane (5 mL), Cs₂CO₃ (489 mg, 1.5 mmol), Pd₂(dba)₃ (46 mg, 0.05 mmol) and S-Phos (41 mg, 0.1 mmol) were added under N₂. The mixture was stirred at 120° C. for 12 h. After diluted with EtOAc (150 mL), the mixture was washed with brine and the organic layer was dried over Na₂SO₄, filtered then concentrated. The residue was purified by silica gel column (petroleum ether/EtOAc=1:1) to give tert-butyl (7-(2-((1-methyl-1H-pyrazol-4-yl)amino)pyrimidin-4-yl)chroman-4-yl)carbamate (120 mg, yield: 57%) as a yellow solid.

ESI-MS (M+H)⁺: 423.1. ¹H NMR (400 MHz, DMSO-d₆) δ: 9.46 (s, 1H), 8.45-8.44 (m, 1H), 7.89 (s, 1H), 7.65 (d, J=8.0 Hz, 1H), 7.57 (s, 1H), 7.50 (s, 1H), 7.43 (d, J=8.8 Hz, 1H), 7.32-7.30 (m, 1H), 7.23-7.21 (m, 1H), 4.83-4.74 (m, 1H), 4.31-4.21 (m, 2H), 3.82 (s, 3H), 2.11-1.87 (m, 2H), 1.44 (s, 9H).

Synthesis of 2-(tert-butyl)-N-(7-(2-((1-methyl-1H-pyrazol-4-yl)amino)pyrimidin-4-yl)chroman-4-yl)thiazole-5-carboxamide

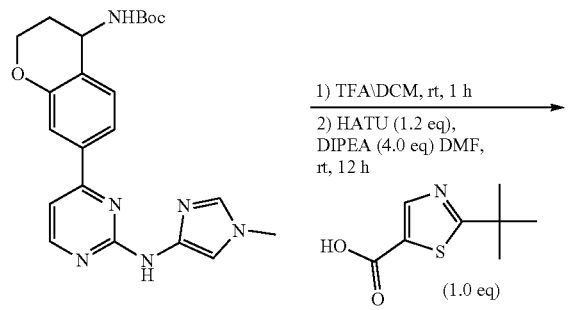

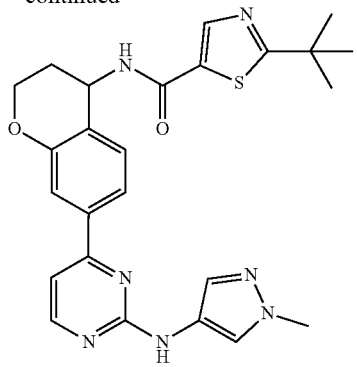

Synthesis of 2-(tert-butyl)-N-(7-(2-((1-methyl-1H-pyrazol-4-yl)amino)pyrimidin-4-yl)chroman-4-yl)thiazole-5-carboxamide was similar to that of Example 1. The mixture was purified by prep-HPLC (Gradient: 5% B increase to 95% B, A: 0.5% NH₃ in water, B: CH₃CN) to give 2-(tert-butyl)-N-(7-(2-((1-methyl-1H-pyrazol-4-yl)amino)pyrimidin-4-yl)chroman-4-yl)thiazole-5-carboxamide (48 mg, yield: 43%) as a yellow solid. ESI-MS (M+H)⁺: 490.0. ¹H NMR (400 MHz, DMSO-d₆) δ: 9.49 (s, 1H), 9.06 (d, J=8.0 Hz, 1H), 8.45 (d, J=5.2 Hz, 1H), 8.32-8.31 (m, 1H), 7.88 (s, 1H), 7.67 (d, J=8.0 Hz, 1H), 7.58-7.57 (m, 2H), 7.34 (d, J=8.0 Hz, 1H), 7.24 (d, J=5.2 Hz, 1H), 5.28-5.26 (m, 1H), 4.33-4.31 (m, 2H), 3.82 (s, 3H), 2.19-1.99 (m, 2H), 1.39 (s, 9H).

Example 97: 2-(tert-butyl)-N-(7-(2-((1-methyl-1H-pyrazol-4-yl)amino)pyrimidin-4-yl)isochroman-4-yl)thiazole-5-carboxamide (I-98)

Scheme 9

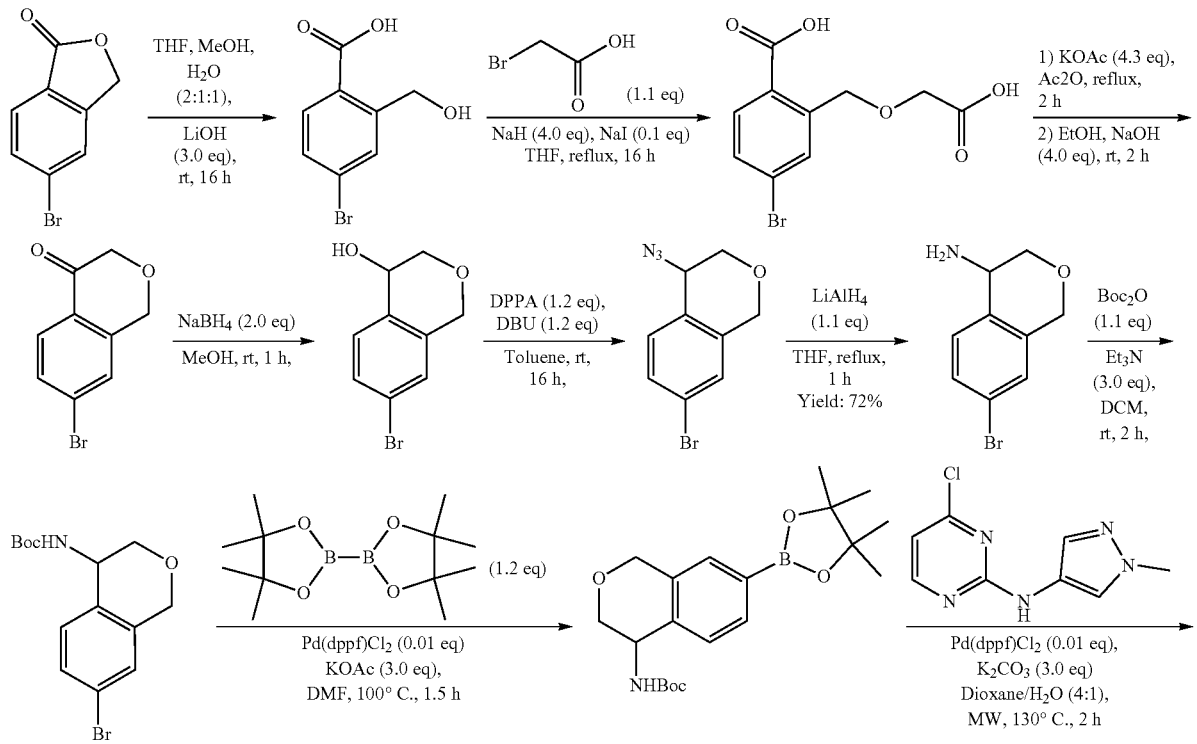

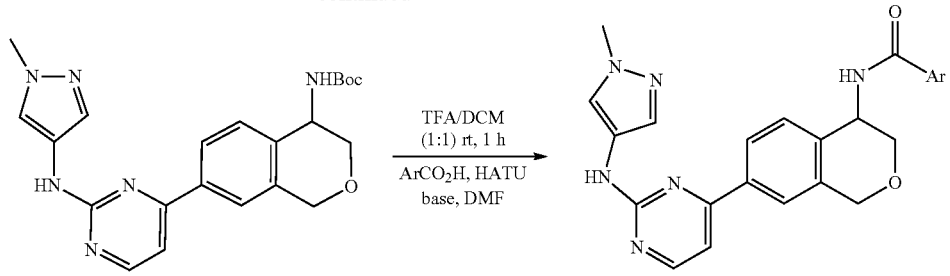

I-98

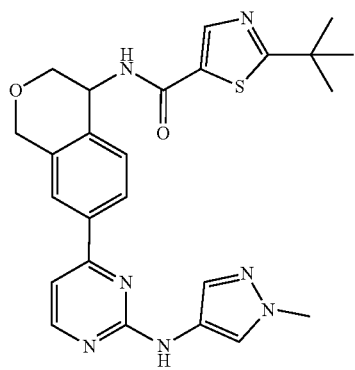

Synthesis of 4-bromo-2-(hydroxymethyl)benzoic acid

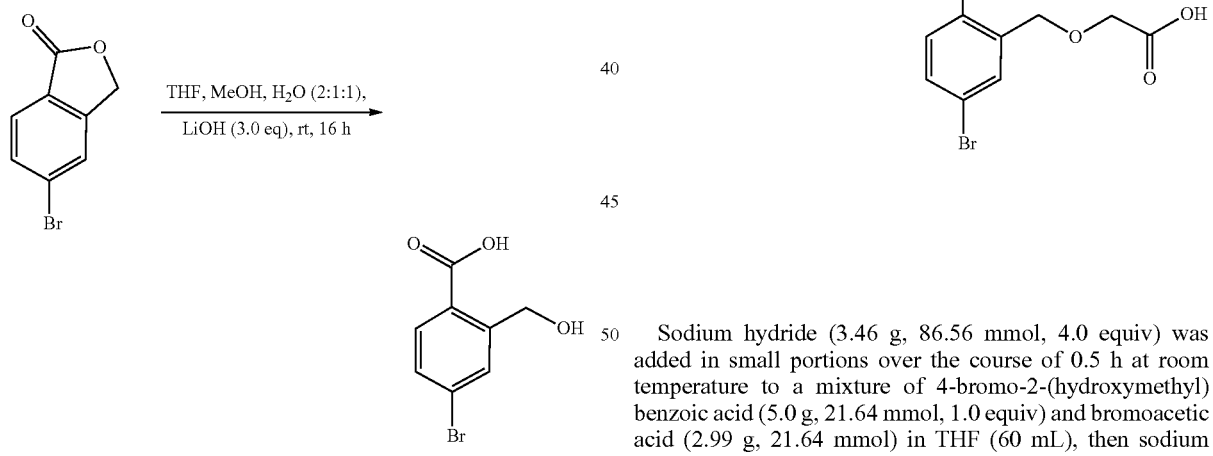

Lithium hydroxide (3.45 g, 70.42 mmol, 3.0 equiv) was added at room temperature over several minutes to a solution of 5-bromophthalide (5.0 g, 23.47 mmol, 1.0 equiv) in a 2:1:1 solution of THF/MeOH/H$_2$O (80 mL) and the reaction mixture was stirred at room temperature for 16 h. After removal of the solvent, the residue was diluted with water (100 mL), adjusted to pH=3 with HCl (2 N) and extracted with EtOAc (100 mL×3). The organic layers were collected, dried (Na$_2$SO$_4$), filtered, and concentrated via rotary evaporator to give title product (3.47 g, yield: 94%) as a white solid, which was used in the next step without further purification. ESI-MS (M+H)$^+$: 231.1. $^1$H NMR (400 MHz, CD$_3$OD) δ: 7.88-7.86 (m, 2H), 7.45 (dd, J=8.4, 2.0 Hz, 1H), 4.90 (s, 2H).

Synthesis of 4-bromo-2-((carboxymethoxy)methyl)benzoic acid

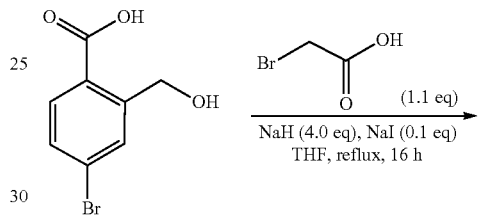

Sodium hydride (3.46 g, 86.56 mmol, 4.0 equiv) was added in small portions over the course of 0.5 h at room temperature to a mixture of 4-bromo-2-(hydroxymethyl) benzoic acid (5.0 g, 21.64 mmol, 1.0 equiv) and bromoacetic acid (2.99 g, 21.64 mmol) in THF (60 mL), then sodium iodide (324.6 mg, 2.164 mmol, 0.1 equiv) was added. The reaction mixture was heated at reflux for 16 h. The reaction mixture was cooled to room temperature and poured into water (150 mL) and then extracted with diethyl ether (100 mL×3). The aqueous phase was acidified with 10% hydrochloric acid to pH=3-4 and extracted with ethyl acetate (200 mL×3). The combined ethyl acetate phases were washed with water (150 mL) and brine, dried (sodium sulfate), filtered, and concentrated to yield 4-bromo-2-((carboxymethoxy)methyl)benzoic acid as a white solid (4.37 g, yield: 70%), which was used for next step without further purification. $^1$H NMR (400 MHz, CD$_3$OD) δ: 7.93-7.87 (m, 2H), 7.55-7.52 (m, 1H), 4.98 (s, 2H), 4.23 (s, 2H).

Synthesis of 7-bromoisochroman-4-one

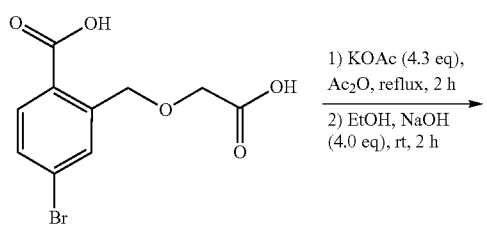

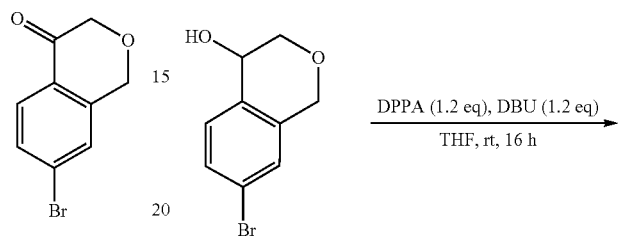

A solution of 4-bromo-2-((carboxymethoxy)methyl)benzoic acid (5.2 g, 18.06 mmol, 1.0 equiv) in acetic anhydride (100 mL) containing potassium acetate (7.61 g, 77.64 mmol, 4.3 equiv) was heated at reflux for 2 h. The reaction mixture was cooled to room temperature and concentrated under reduced pressure and the residue partitioned between ethyl acetate (200 mL) and water (100 mL). The phases were separated and the aqueous phase was extracted with ethyl acetate (100 mL×3). The combined ethyl acetate phases were then washed with brine, dried (sodium sulfate), filtered and concentrated. The residue was dissolved in EtOH (50 mL), NaOH (2.89 g, 72.24 mmol, 4.0 eq) was added. The reaction mixture was stirred at rt for 2 h. After concentration, the residue was portioned between ethyl acetate (200 mL) and water (100 mL), washed with saturated brine, dried (sodium sulfate), filtered and concentrated. The residue was purified by column chromatography (silica, petroleum ether/EtOAc=1:1) to give 7-bromoisochroman-4-one (725 mg, yield: 18%) as a slight yellow solid. ESI-MS (M+H)$^+$: 227.0. $^1$H NMR (400 MHz, CDCl$_3$) δ: 7.90 (d, J=8.4 Hz, 1H), 7.56 (dd, J=8.4, 2.0 Hz, 1H), 7.42 (s, 1H), 4.86 (s, 2H), 4.36 (s, 2H).

Synthesis of 7-bromoisochroman-4-ol

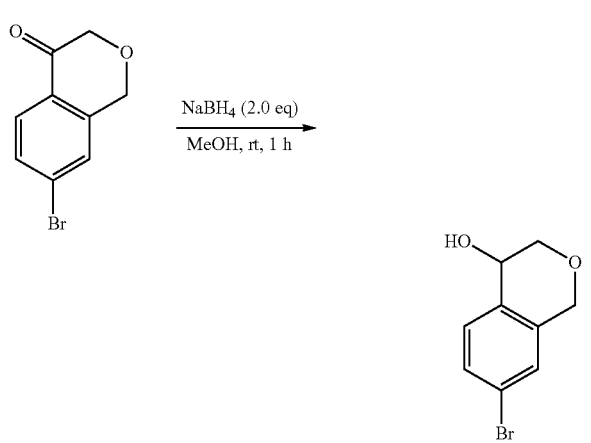

Synthesis of 7-bromoisochroman-4-ol was similar to that of 7-bromochroman-4-ol. The crude (1.3 g, yield: 89%) was used directly in the next step without further purification. ESI-MS (M+H)$^+$: 229.0. $^1$H NMR (400 MHz, CDCl$_3$) δ: 7.42-7.40 (m, 1H), 7.34-7.32 (m, 1H), 7.17 (s, 1H), 4.66 (ABq, J=20.4, 15.2 Hz, 2H), 4.51-4.50 (m, 1H), 4.12-4.10 (m, 1H), 3.84-3.80 (m, 1H).

Synthesis of 4-azido-7-bromoisochroman

Synthesis of 4-azido-7-bromoisochroman was similar to that of 4-azido-7-bromochroman. The residue was purified by column chromatography (silica, petroleum ether/EtOAc=50:1) to give 4-azido-7-bromoisochroman (568 mg, yield: 39%) as a white solid. ESI-MS (M+H-28)$^+$: 226.0. $^1$H NMR (400 MHz, CDCl$_3$) δ: 7.47-7.44 (m, 1H), 7.28-7.24 (m, 2H), 4.77 (ABq, J=20.4, 15.6 Hz, 2H), 4.22-4.16 (m, 2H), 3.96-3.92 (m, 1H).

Synthesis of 7-bromoisochroman-4-amine

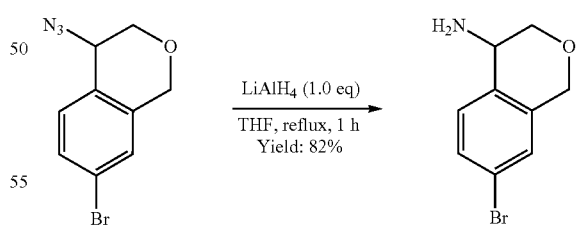

To a solution of 4-azido-7-bromoisochroman (207 mg, 0.82 mmol, 1.0 eq) in THF (5 mL), 1N LiAlH$_4$ (0.82 mL, 0.82 mmol, 1.0 equiv) was added at 0° C. Then the mixture was refluxed for 1 h. After cooling down to rt, Na$_2$SO$_4$.10H$_2$O was added and the mixture was stirred for another 0.5 h. The solid was filtered off and the filtrate was concentrated to give title product (153 mg, yield: 82%), which was used directly for next step without further purification. ESI-MS (M+H)$^+$: 228.0.

Synthesis of tert-butyl (7-bromoisochroman-4-yl)carbamate

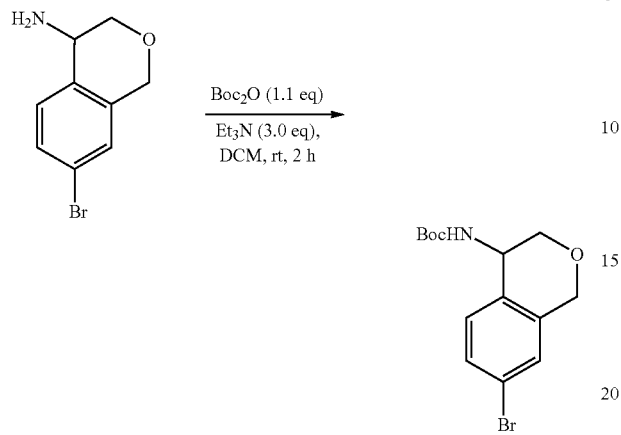

Synthesis of tert-butyl (7-bromoisochroman-4-yl)carbamate was similar to that of tert-butyl (7-bromochroman-4-yl) carbamate. The crude was purified by prep-HPLC (MeOH/H$_2$O with 0.05% NH$_3$.H$_2$O as mobile phase) to give compound tert-butyl (7-bromoisochroman-4-yl)carbamate (332 mg, yield: 55%) as a white solid. ESI-MS (M+H-56)$^+$: 272.05. $^1$H NMR (400 MHz, CDCl$_3$) δ: 7.38-7.30 (m, 2H), 7.15 (s, 1H), 5.11-5.09 (m, 1H), 4.75-4.63 (m, 3H), 4.04-4.00 (m, 1H), 3.86-3.82 (m, 1H), 1.45 (s, 9H).

Synthesis of tert-butyl (7-(4,4,5,5-tetramethyl-1,3,2-dioxaborolan-2-yl)isochroman-4-yl)carbamate

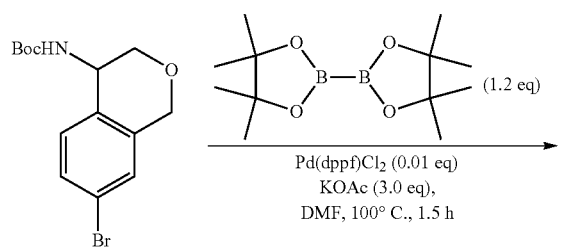

Synthesis of tert-butyl (7-(4,4,5,5-tetramethyl-1,3,2-dioxaborolan-2-yl)isochroman-4-yl)carbamate was similar to that of tert-butyl 2-methyl-4-(4,4,5,5-tetramethyl-1,3,2-dioxaborolan-2-yl)benzylcarbamate. The residue was purified by column chromatography (silica, petroleum ether/EtOAc=10:1) to give tert-butyl (7-(4,4,5,5-tetramethyl-1,3,2-dioxaborolan-2-yl)isochroman-4-yl)carbamate (310 mg, yield: 81%) as a white solid. ESI-MS (M+H-56)$^+$: 320.2.

Preparation of tert-butyl (7-(2-((1-methyl-1H-pyrazol-4-yl)amino)pyrimidin-4-yl)isochroman-4-yl)carbamate Synthesis of tert-butyl (7-(2-((1-methyl-1H-pyrazol-4-yl)amino)pyrimidin-4-yl)isochroman-4-yl)carbamate was similar to that of tert-butyl 2-methyl-4-(2-((1-methyl-1H-pyrazol-4-yl)amino)pyrimidin-4-yl)benzylcarbamate. The residue was purified by column chromatography (silica, petroleum ether/EtOAc=1:2) to give title compound as a yellow solid (272 mg, yield: 79%). ESI-MS (M+H-56)$^+$: 367.2.

Preparation of 2-(tert-butyl)-N-(7-(2-((1-methyl-1H-pyrazol-4-yl)amino)pyrimidin-4-yl)isochroman-4-yl) thiazole-5-carboxamide

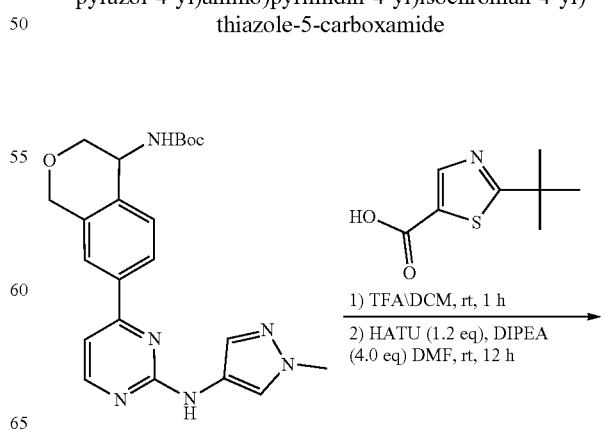

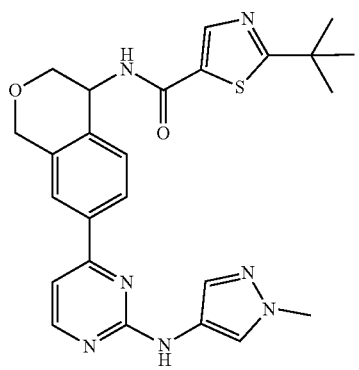

Synthesis of 2-(tert-butyl)-N-(7-(2-((1-methyl-1H-pyrazol-4-yl)amino)pyrimidin-4-yl)isochroman-4-yl)thiazole-5-carboxamide was similar to that of Example 1. The residue was purified by prep-HPLC (CH$_3$CN/H$_2$O with 0.05% NH$_3$.H$_2$O as mobile phase) to give a yellow solid (105 mg, yield: 61%). ESI-MS (M+H)$^+$: 490.2. HPLC: (214 nm: 100%, 254 nm: 100%). $^1$H NMR (400 MHz, DMSO-d$_6$) δ: 9.52 (s, 1H), 9.07 (d, J=8.4 Hz, 1H), 8.48 (d, J=5.2 Hz, 1H), 8.35 (s, 1H), 8.03 (d, J=8.0 Hz, 1H), 7.92-7.91 (m, 2H), 7.54 (s, 1H), 7.47 (d, J=8.8 Hz, 1H), 7.26 (d, J=5.2 Hz, 1H), 5.25-5.21 (m, 1H), 4.92-4.83 (m, 2H), 4.09-4.01 (m, 1H), 3.85-3.80 (m, 4H), 1.39 (s, 9H).

Example 98: 2-(tert-butyl)-N-(7-(2-((1-methyl-1H-pyrazol-4-yl)amino)pyrimidin-4-yl)-1,2,3,4-tetrahydroquinolin-4-yl)thiazole-5-carboxamide (I-99)

I-99

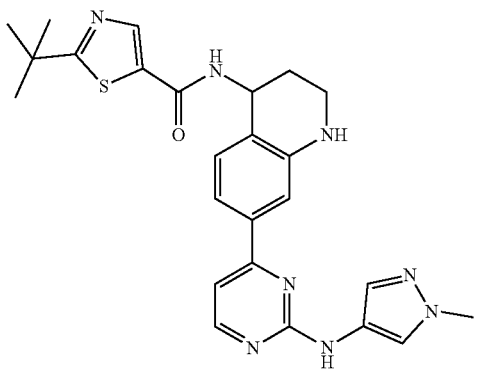

Preparation of methyl 3-((3-bromophenyl)amino)propanoate

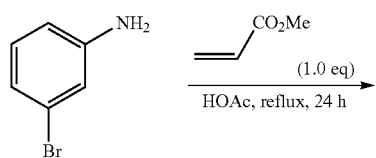

A mixture of 3-bromoaniline (10.00 g, 58.14 mmol) and methyl acrylate (5.30 mL, 58.14 mmol) in acetic acid (0.4 mL) was refluxed for 16 h. Then the solution was concentrated, and the residue was purified by silica gel column chromatography (petroleum ether/EtOAc=1/10 to 1/6) to give product methyl 3-((3-bromophenyl)amino)propanoate (11.92 g, yield: 80%) as red liquid. ESI-MS (M+H)$^+$: 257.8

Preparation of methyl 3-(N-(3-bromophenyl)-4-methylphenylsulfonamido)propanoate

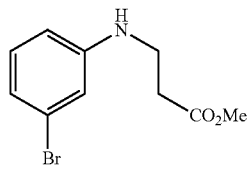

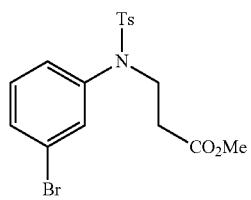

To a solution of methyl 3-((3-bromophenyl)amino)propanoate (11.90 g, 46.30 mmol) in pyridine (10 mL) was added p-tosyl chloride (10.58 g, 55.56 mmol) portionwise at room temperature. The mixture was stirred for another 2 h. The mixture was concentrated and the residue was diluted with EtOAc (20 mL). The organic phase was washed with 1N HCl (60 mL) and brine (60 mL×2). After drying over Na$_2$SO$_4$, filtered and concentrated, the residue was purified by silica gel column chromatography (petroleum ether/EtOAc=1/10 to 1/4) to give product methyl 3-(N-(3-bromophenyl)-4-methylphenylsulfonamido)propanoate (15.30 g, yield: 80%) as brown sticky oil. ESI-MS (M+H)$^+$: 411.9.

Preparation of 3-(N-(3-bromophenyl)-4-methylphenylsulfonamido)propanoic acid

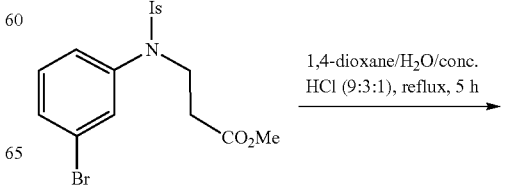

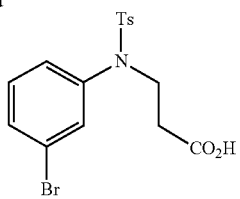

A solution of methyl 3-(N-(3-bromophenyl)-4-methylphenylsulfonamido)propanoate (15.23 g, 37.06 mmol) in concentrated HCl (21.80 mL), water (68.6 mL) and 1,4-dioxane (192.6 mL) was heated at reflux for 5 h. Then the solution was concentrated to half volume (~130 mL), neutralized with saturated NaHCO$_3$ solution to pH=8-9 and extracted with EtOAc (80 mL×3). The combined organic phase was back-extracted with water (80 mL). The combined aqueous phase was acidified by conc. HCl solution (pH=3), extracted with EtOAc (80 mL×3). The organic phase was combined and dried over Na$_2$SO$_4$, filtered and concentrated to dryness to give 3-(N-(3-bromophenyl)-4-methylphenylsulfonamido)propanoic acid (7.00 g, yield: 48%) as brown oil. ESI-MS (M+H)$^+$: 397.9.

Preparation of
7-bromo-2,3-dihydroquinolin-4(1H)-one

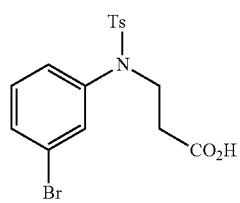

A solution of 3-(N-(3-bromophenyl)-4-methylphenylsulfonamido)propanoic acid (5.00 g, 12.59 mmol), SOCl$_2$ (4.60 mL, 62.97 mmol) and one drop of DMF in DCM (20 mL) was refluxed for 2 h. Then the solution was concentrated to dryness to give carboxylic chloride which was used for next step. A mixture of AlCl$_3$ (3.40 g, 25.18 mmol) in DCM (20 mL) was cooled at 5° C., and then a solution of carboxylic chloride prepared above in DCM (10 mL) was added dropwise over 30 min. After addition, the solution was stirred at room temperature for 3 h. Then the solution was quenched with ice water, neutralized with NaOH solution, and extracted with EtOAc (50 mL×3). The combined organic phase was dried (Na$_2$SO$_4$) and concentrated. The residue was purified by silica gel column chromatography (petroleum ether/EtOAc=1/4) to give product 7-bromo-2,3-dihydroquinolin-4(1H)-one as a yellow solid (1.86 g, yield: 54%). ESI-MS (M+H)$^+$: 226.0

Preparation of
7-bromo-1-tosyl-2,3-dihydroquinolin-4(1H)-one

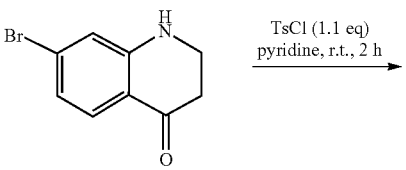

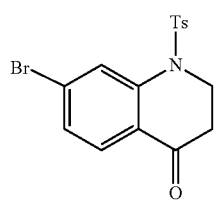

Synthesis of 7-bromo-1-tosyl-2,3-dihydroquinolin-4(1H)-one was similar to that of methyl 3-(N-(3-bromophenyl)-4-methylphenylsulfonamido)propanoate. The residue was purified by silica gel column chromatography (petroleum ether/EtOAc=1/6) to give product 7-bromo-1-tosyl-2,3-dihydroquinolin-4(1H)-one as a yellow solid (2.57 g, yield: 85%). ESI-MS (M+H)$^+$: 380.0. $^1$H NMR (400 MHz, CD$_3$OD) δ: 8.02 (d, J=1.6 Hz, 1H), 7.78 (d, J=8.4 Hz, 1H), 7.63 (d, J=8.4 Hz, 2H), 7.47 (dd, J=8.4, 1.6 Hz, 1H), 7.37 (d, J=8.4 Hz, 2H), 4.25 (t, J=6.4 Hz, 2H), 2.42 (s, 3H), 2.38 (t, J=6.4 Hz, 2H).

Preparation of (E)-N-(7-bromo-1-tosyl-2,3-dihydroquinolin-4(1H)-ylidene)-2-methylpropane-2-sulfinamide

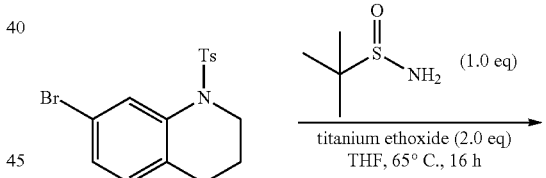

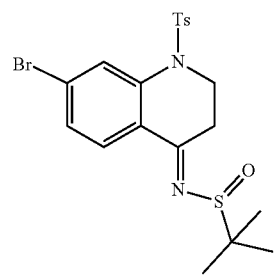

A solution of 7-bromo-1-tosyl-2,3-dihydroquinolin-4(1H)-one (700 mg, 1.84 mmol), t-butylsulfinamide (245 mg, 2.02 mmol) and titanium ethoxide (890 mg, 3.68 mmol) in dry THF (10 mL) was heated at reflux for 16 h. Then the mixture was diluted with EA (150 mL) and washed with brine (60 mL), water (60 mL). The organic phase was dried (Na$_2$SO$_4$) and concentrated to give crude product (E)-N-(7-bromo-1-tosyl-2,3-dihydroquinolin-4(1H)-ylidene)-2-methylpropane-2-sulfinamide as a white solid (740 mg, yield: 83%) which was used directly in the next step. ESI-MS (M+H)⁺: 482.9.

Preparation of 7-bromo-1-tosyl-1,2,3,4-tetrahydroquinolin-4-amine

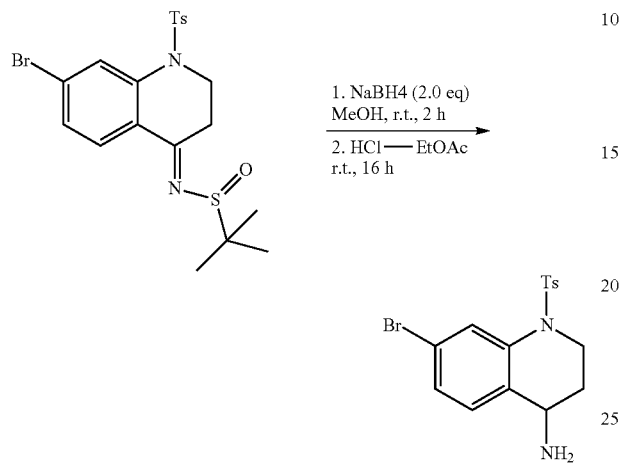

To a solution of (E)-N-(7-bromo-1-tosyl-2,3-dihydroquinolin-4(1H)-ylidene)-2-methylpropane-2-sulfinamide (740 mg, 1.53 mmol) in methanol (7 mL) was added sodium borohydride (117 mg, 3.07 mmol) portionwise at 0° C. Then the mixture was stirred at room temperature for 2 h. The organic solvent was removed under reduced pressure, and the residue was dissolved in EtOAc (7 mL) and treated with conc. HCl (3 mL). The mixture was stirred at room temperature for 16 h. Then the mixture was adjusted to pH=8 with solid sodium bicarbonate and extracted with EtOAc (10 mL). The organic phase was washed with water (40 mL), dried (Na₂SO₄) and concentrated to give crude product 7-bromo-1-tosyl-1,2,3,4-tetrahydroquinolin-4-amine as a white solid (400 mg crude) which was used directly in the next step. ESI-MS (M+H)⁺: 381.0

Preparation of tert-butyl (7-bromo-1-tosyl-1,2,3,4-tetrahydroquinolin-4-yl)carbamate

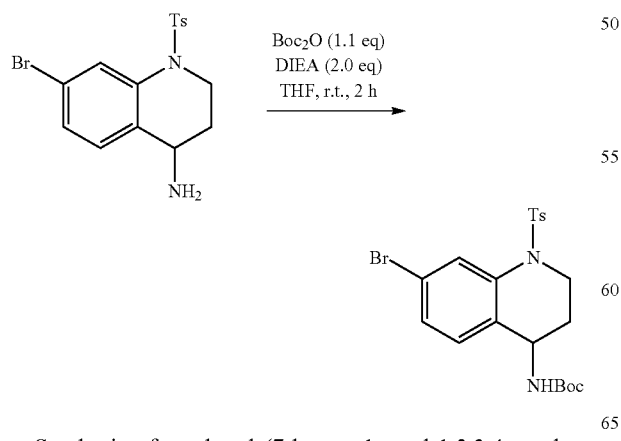

Synthesis of tert-butyl (7-bromo-1-tosyl-1,2,3,4-tetrahydroquinolin-4-yl)carbamate was similar to that of tert-butyl (7-bromochroman-4-yl)carbamate. The residue was purified by silica gel column chromatography (petroleum ether/EtOAc=1/6) to give product tert-butyl (7-bromo-1-tosyl-1,2,3,4-tetrahydroquinolin-4-yl)carbamate as a white foam (438 mg, yield: 60% for two steps). ESI-MS (M+H)⁺: 480.9. ¹H NMR (400 MHz, CD₃OD) δ: 7.96 (d, J=1.6 Hz, 1H), 7.56 (d, J=8.4 Hz, 2H), 7.35 (d, J=8.4 Hz, 2H), 7.28 (dd, J=8.4, 1.6 Hz, 1H), 7.14 (d, J=8.4 Hz, 1H), 4.35-4.31 (m, 1H), 4.03-3.97 (m, 1H), 3.79-3.72 (m, 1H), 2.40 (s, 3H), 1.78-1.61 (m, 2H), 1.40 (s, 9H).

Preparation of tert-butyl (7-(2-chloropyrimidin-4-yl)-1-tosyl-1,2,3,4-tetrahydroquinolin-4-yl)carbamate

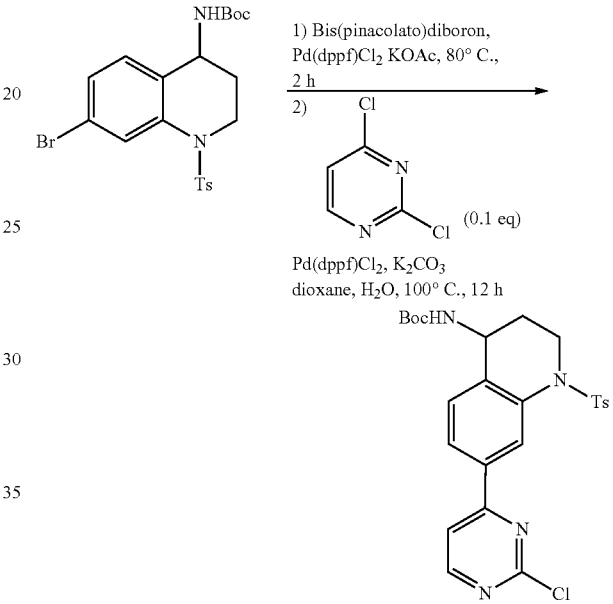

Synthesis of tert-butyl (7-(2-chloropyrimidin-4-yl)-1-tosyl-1,2,3,4-tetrahydroquinolin-4-yl)carbamate was similar to that of tert-butyl 4-(2-chloropyrimidin-4-yl)-2-methylbenzylcarbamate. The residue was purified by silica gel column chromatography (petroleum ether/EtOAc=1/6 to 1/4) to give product tert-butyl (7-(2-chloropyrimidin-4-yl)-1-tosyl-1,2,3,4-tetrahydroquinolin-4-yl)carbamate as a white solid (208 mg, yield: 61%). ESI-MS (M+H)⁺: 515.1.

Preparation of tert-butyl (7-(2-((1-methyl-1H-pyrazol-4-yl)amino)pyrimidin-4-yl)-1-tosyl-1,2,3,4-tetrahydroquinolin-4-yl)carbamate

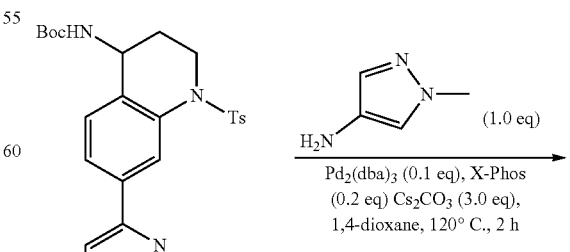

-continued

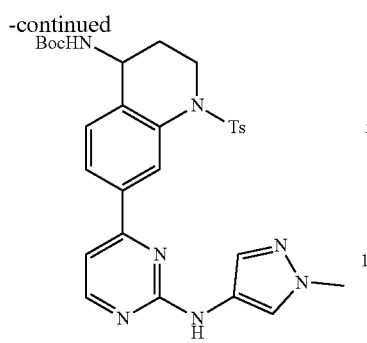

Synthesis of tert-butyl (7-(2-((1-methyl-1H-pyrazol-4-yl)amino)pyrimidin-4-yl)-1-tosyl-1,2,3,4-tetrahydroquinolin-4-yl)carbamate was similar to that of tert-butyl 4-(2-chloropyrimidin-4-yl)-2-methylbenzylcarbamate. The residue was purified by silica gel column chromatography (petroleum ether/EtOAc=1/2 to 2/1) to give product tert-butyl (7-(2-((1-methyl-1H-pyrazol-4-yl)amino)pyrimidin-4-yl)-1-tosyl-1,2,3,4-tetrahydroquinolin-4-yl)carbamate as a green solid (92 mg, yield: 40%). ESI-MS (M+H)$^+$: 576.2.

Preparation of 2-(tert-butyl)-N-(7-(2-((1-methyl-1H-pyrazol-4-yl)amino)pyrimidin-4-yl)-1-tosyl-1,2,3,4-tetrahydroquinolin-4-yl)thiazole-5-carboxamide

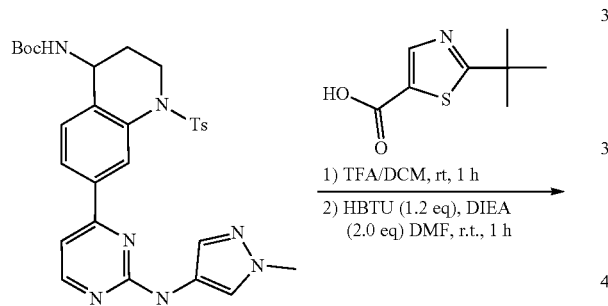

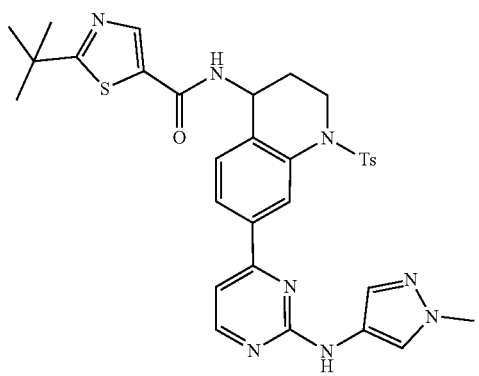

Synthesis of 2-(tert-butyl)-N-(7-(2-((1-methyl-1H-pyrazol-4-yl)amino)pyrimidin-4-yl)-1-tosyl-1,2,3,4-tetrahydroquinolin-4-yl)thiazole-5-carboxamide was similar to that of Example 1. The residue was purified silica gel column chromatography (petroleum ether/EtOAc=2/1) to give product 2-(tert-butyl)-N-(7-(2-((1-methyl-1H-pyrazol-4-yl)amino)pyrimidin-4-yl)-1-tosyl-1,2,3,4-tetrahydroquinolin-4-yl)thiazole-5-carboxamide as a yellow solid (70 mg, yield: 73%). ESI-MS (M+H)$^+$: 643.2.

Synthesis of 2-(tert-butyl)-N-(7-(2-((1-methyl-1H-pyrazol-4-yl)amino)pyrimidin-4-yl)-1,2,3,4-tetrahydroquinolin-4-yl)thiazole-5-carboxamide

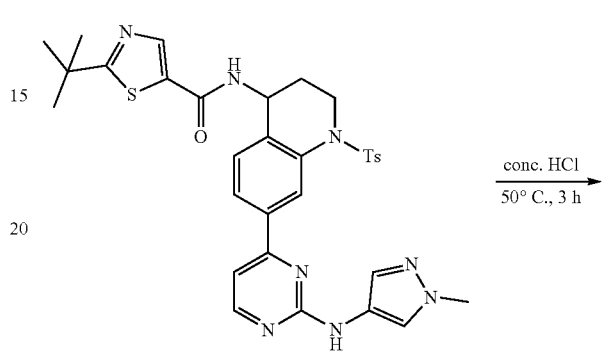

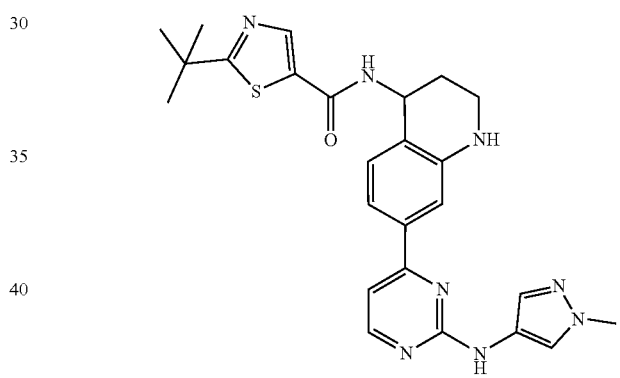

A solution of 2-(tert-butyl)-N-(7-(2-((1-methyl-1H-pyrazol-4-yl)amino)pyrimidin-4-yl)-1-tosyl-1,2,3,4-tetrahydroquinolin-4-yl)thiazole-5-carboxamide (60 mg, 0.09 mmol) in conc. HCl solution (1.5 mL) was heated at 50° C. for 3 h. Then the mixture was concentrated and the residue was dissolved in EtOAc (50 mL). The organic phase was washed with saturated Na$_2$CO$_3$, dried (Na$_2$SO$_4$), filtered and concentrated. The residue was purified by prep-HPLC (MeCN/H$_2$O with 0.05% NH$_3$.H$_2$O as mobile phase) to give product 2-(tert-butyl)-N-(7-(2-((1-methyl-1H-pyrazol-4-yl)amino)pyrimidin-4-yl)-1,2,3,4-tetrahydroquinolin-4-yl)thiazole-5-carboxamide as a pale yellow solid (12 mg, yield: 27%). ESI-MS (M+H)$^+$: 489.0. HPLC: (214 nm: 100%, 254 nm: 100%). $^1$H NMR (400 MHz, CD$_3$OD) δ: 8.35 (d, J=5.6 Hz, 1H), 8.25 (s, 1H), 7.98 (s, 1H), 7.63 (s, 1H), 7.35 (d, J=1.6 Hz, 1H), 7.32 (dd, J=8.0, 1.6 Hz, 1H), 7.20 (d, J=8.0 Hz, 1H), 7.11 (d, J=5.6 Hz, 1H), 5.30 (t, J=5.6 Hz, 1H), 3.89 (s, 3H), 3.40 (t, J=5.6 Hz, 2H), 2.14-2.09 (m, 2H), 1.46 (s, 9H).

Example 99: 2-(tert-butyl)-N-((3-methyl-5-(2-((1-methyl-1H-pyrazol-4-yl)amino)pyrimidin-4-yl)pyridin-2-yl)methyl)thiazole-5-carboxamide (I-100)

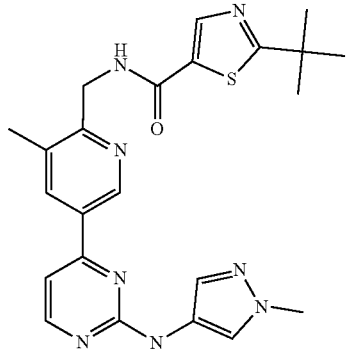

I-100

Scheme 10

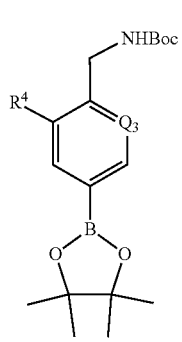 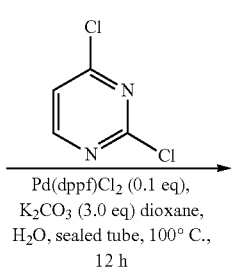

Pd(dppf)Cl$_2$ (0.1 eq), K$_2$CO$_3$ (3.0 eq) dioxane, H$_2$O, sealed tube, 100° C., 12 h

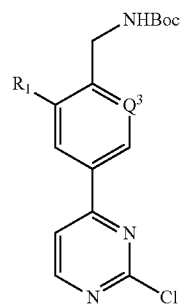

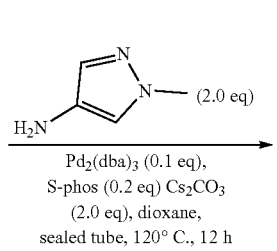  (2.0 eq)

Pd$_2$(dba)$_3$ (0.1 eq), S-phos (0.2 eq) Cs$_2$CO$_3$ (2.0 eq), dioxane, sealed tube, 120° C., 12 h

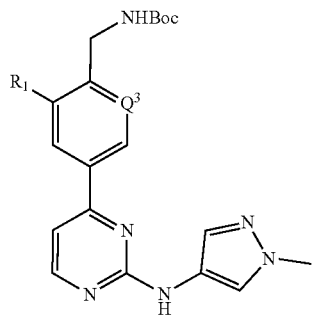

1) TFA\DCM, rt, 1 h
2) R$^1$CO$_2$H, HATU (1.2 eq), DIPEA (4.0 eq) DMF, rt, 12 h

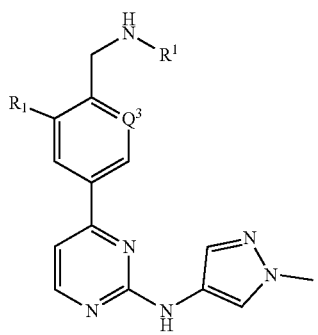

Synthesis of tert-butyl ((3-methyl-5-(2-((1-methyl-1H-pyrazol-4-yl)amino)pyrimidin-4-yl)pyridin-2-yl)methyl)carbamate

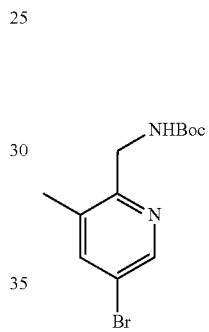 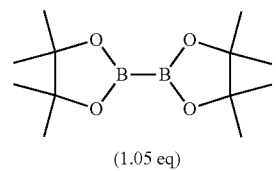 (1.05 eq)

1) Pd(dppf)Cl$_2$ (0.1 eq), KOAc (3 eq) dioxane, 110° C., 1 h
2) Pd(dppf)Cl$_2$ (0.05 eq), K$_2$CO$_3$ (2 eq) dioxane/H$_2$O (5/1), 100° C., 2 h

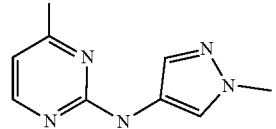

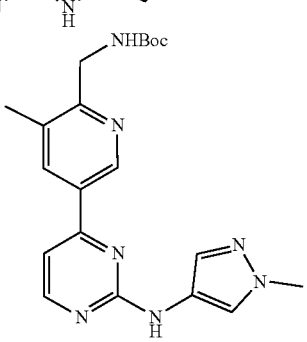

To a solution of tert-butyl ((5-bromo-3-methylpyridin-2-yl)methyl)carbamate (150 mg, 0.5 mmmol) in dioxane (2 mL) were added 4,4,4',4',5,5,5',5'-octamethyl-2,2'-bi(1,3,2-dioxaborolane) (140 mg, 0.55 mmol, 1.1 equiv), Pd(dppf)Cl$_2$.DCM (20 mg, 0.025 mmol, 0.05 equiv) and KOAc (147 mg, 1.5 mmol, 3 equiv). The mixture was heated to 110° C. for 1 h under N$_2$. After cooled to rt, 4-chloro-N-(1-methyl-1H-pyrazol-4-yl)pyrimidin-2-amine (100 mg, 0.5 mmol, 1 equiv), Pd(dppf)Cl$_2$.DCM (20 mg, 0.025 mmol, 0.05 equiv) and K$_2$CO$_3$ (138 mg, 1 mmol, 2 equiv) were added. The mixture was heated to 100° C. for another 2 h. After diluted with EA (150 mL), the mixture was washed with water (50 mL×2). The organic phase was concentrated and the crude was purified through silica gel column chromatography (petroleum ether/EtOAc=2/1) to give tert-butyl ((3-methyl-5-(2-((1-methyl-1H-pyrazol-4-yl)amino)pyrimidin-4-yl)pyridin-2-yl)methyl)carbamate as a yellow solid (145 mg, yield: 70%). ESI-MS (M+H)+: 396.1. ¹H NMR (400 MHz, CDCl₃) δ: 8.99 (s, 1H), 8.45 (d, J=4.8 Hz, 1H), 8.07 (s, 1H), 7.88 (s, 1H), 7.55 (s, 1H), 7.45 (br, 1H), 7.06 (d, J=5.2 Hz, 1H), 6.24 (s, 1H), 4.48 (d, J=4.0 Hz, 2H), 3.91 (s, 3H), 2.37 (s, 3H), 1.49 (s, 9H).

Synthesis of 2-(tert-butyl)-N-((3-methyl-5-(2-((1-methyl-1H-pyrazol-4-yl)amino)pyrimidin-4-yl)pyridin-2-yl)methyl)thiazole-5-carboxamide

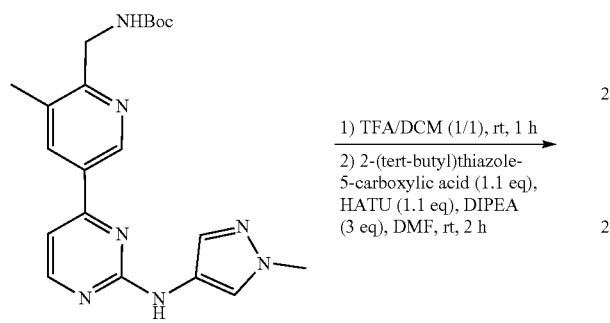

Synthesis of 2-(tert-butyl)-N-((3-methyl-5-(2-((1-methyl-1H-pyrazol-4-yl)amino)pyrimidin-4-yl)pyridin-2-yl)methyl)thiazole-5-carboxamide was similar to that of Example 1. The crude was purified through prep-TLC (MeOH/DCM=1/25) to give 2-(tert-butyl)-N-((3-methyl-5-(2-((1-methyl-1H-pyrazol-4-yl)amino)pyrimidin-4-yl)pyridin-2-yl)methyl)thiazole-5-carboxamide as a yellow solid (50 mg, yield: 65%). ESI-MS (M+H)+: 463.2. HPLC: (214 nm: 98.74%, 254 nm: 98.43%). ¹H NMR (400 MHz, CDCl₃) δ: 9.04 (s, 1H), 8.48 (d, J=5.2 Hz, 1H), 8.19 (s, 1H), 8.13 (s, 1H), 8.00 (br, 1H), 7.85 (s, 1H), 7.58 (s, 1H), 7.14 (s, 1H), 7.09 (d, J=5.2 Hz, 1H), 4.72 (d, J=4.0 Hz, 2H), 3.93 (s, 3H), 2.42 (s, 3H), 1.48 (s, 9H).

Example 100: N-((3-methyl-5-(2-((1-methyl-1H-pyrazol-4-yl)amino)pyrimidin-4-yl)pyridin-2-yl)methyl)-6,7-dihydro-4H-thieno[3,2-c]pyran-2-carboxamide (I-101)

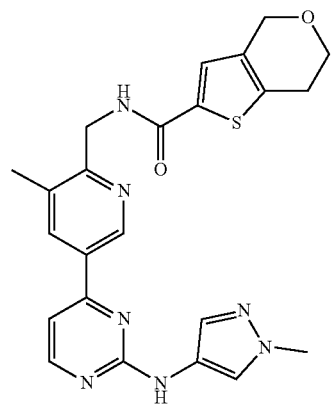

Synthesis of N-((3-methyl-5-(2-((1-methyl-1H-pyrazol-4-yl)amino)pyrimidin-4-yl)pyridin-2-yl)methyl)-6,7-dihydro-4H-thieno[3,2-c]pyran-2-carboxamide was similar to that of Example 99. Purified through prep-TLC (MeOH/DCM=1/20) to give N-((3-methyl-5-(2-((1-methyl-1H-pyrazol-4-yl)amino)pyrimidin-4-yl)pyridin-2-yl)methyl)-6,7-dihydro-4H-thieno[3,2-c]pyran-2-carboxamide (40 mg, yield: 45%) as a yellow solid. ESI-MS (M+H)+: 462.1. HPLC: (214 nm: 94.50%, 254 nm: 95.27%). ¹H NMR (400 MHz, CDCl₃) δ: 9.04 (s, 1H), 8.47 (d, J=4.8 Hz, 1H), 8.12 (s, 1H), 7.96 (br, 1H), 7.83 (s, 1H), 7.61 (s, 1H), 7.33 (s, 1H), 7.09 (d, J=5.2 Hz, 1H), 6.99 (s, 1H), 4.73 (s, 2H), 4.72 (d, J=4.0 Hz, 2H), 4.00 (t, J=5.2 Hz, 2H), 3.93 (s, 3H), 2.92 (t, J=5.2 Hz, 2H), 2.43 (s, 3H).

Example 101: 2-(tert-butyl)-N-((6-methyl-2'-((1-methyl-1H-pyrazol-4-yl)amino)-[2,4'-bipyridin]-5-yl)methyl)thiazole-5-carboxamide (I-102)

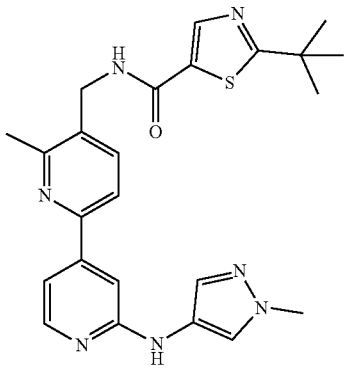

217

Synthesis of N-((6-bromo-2-methylpyridin-3-yl)methyl)-2-(tert-butyl)thiazole-5-carboxamide

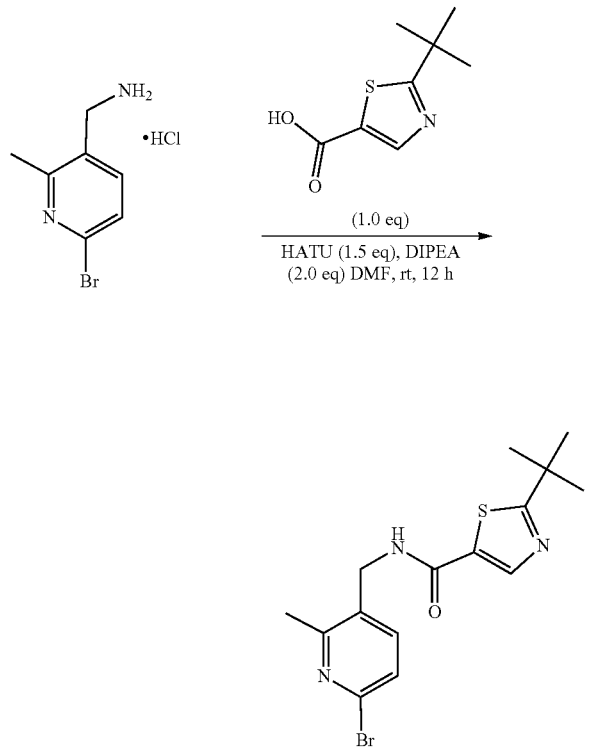

Synthesis of N-((6-bromo-2-methylpyridin-3-yl)methyl)-2-(tert-butyl)thiazole-5-carboxamide was similar to that of Example 1. The residue was purified by silica gel column (petroleum ether/EtOAc=2:1) to give N-((6-bromo-2-methylpyridin-3-yl)methyl)-2-(tert-butyl)thiazole-5-carboxamide (140 mg, yield: 38%) as a yellow solid. ESI-MS (M+1)$^+$: 368.0. $^1$H NMR (400 MHz, CD$_3$OD) δ: 8.21 (s, 1H), 7.59 (d, J=8.0 Hz, 1H), 7.42 (d, J=8.0 Hz, 1H), 4.52 (s, 2H), 2.55 (s, 3H), 1.45 (s, 9H).

Synthesis of 2-(tert-butyl)-N-((2'-chloro-6-methyl-[2,4'-bipyridin]-5-yl)methyl)thiazole-5-carboxamide

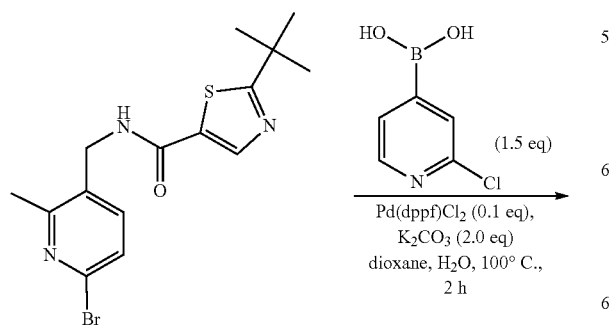

218

-continued

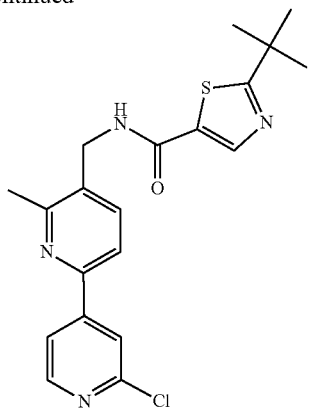

Synthesis of 2-(tert-butyl)-N-((2'-chloro-6-methyl-[2,4'-bipyridin]-5-yl)methyl)thiazole-5-carboxamide was similar to that of tert-butyl 4-(2-chloropyrimidin-4-yl)-2-methylbenzylcarbamate. The mixture was purified by silica gel column (petroleum ether/EtOAc=1:1) to give 2-(tert-butyl)-N-((2'-chloro-6-methyl-[2,4'-bipyridin]-5-yl)methyl)thiazole-5-carboxamide (80 mg, yield: 52%) as a yellow solid. ESI-MS (M+H)$^+$: 400.9. $^1$H NMR (400 MHz, CDCl$_3$) δ: 8.43 (d, J=4.8 Hz, 1H), 8.09 (s, 1H), 7.95 (s, 1H), 7.78 (dd, J=5.2, 0.8 Hz, 1H), 7.21 (d, J=8.0 Hz, 1H), 7.59 (d, J=7.6 Hz, 1H), 6.36 (t, J=5.6 Hz, 1H), 4.67 (d, J=5.6 Hz, 2H), 2.67 (s, 3H), 1.45 (s, 9H).

Synthesis of 2-(tert-butyl)-N-((6-methyl-2'-((1-methyl-1H-pyrazol-4-yl)amino)-[2,4'-bipyridin]-5-yl)methyl)thiazole-5-carboxamide

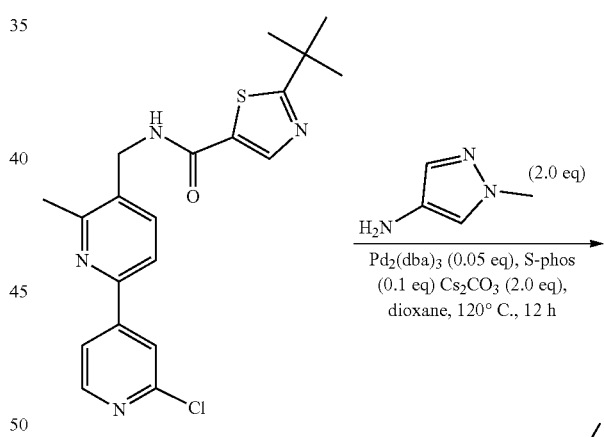

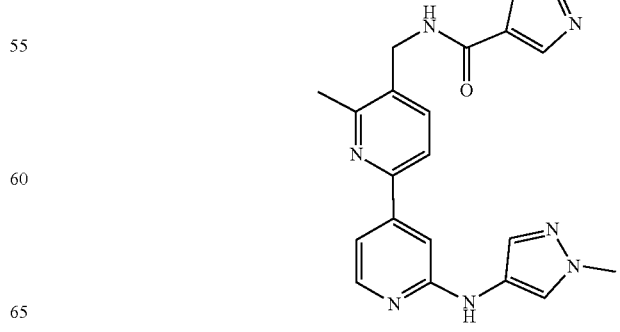

Synthesis of 2-(tert-butyl)-N-((6-methyl-2'-((1-methyl-1H-pyrazol-4-yl)amino)-[2,4'-bipyridin]-5-yl)methyl)thiazole-5-carboxamide was similar to that of 4-(4-(aminomethyl)-3-methylphenyl)-N-(1-methyl-1H-pyrazol-4-yl)pyrimidin-2-amine. The mixture was purified by prep-HPLC (Gradient: 5% B increase to 95% B, A: 0.5% $NH_3$ in water, B: $CH_3CN$) to give 2-(tert-butyl)-N-((6-methyl-2'-((1-methyl-1H-pyrazol-4-yl)amino)-[2,4'-bipyridin]-5-yl)methyl)thiazole-5-carboxamide (20 mg, yield: 22%) as a brown solid. ESI-MS (M+H)$^+$: 462.1. $^1$H NMR (400 MHz, $CDCl_3$) δ: 8.20 (d, J=6.4 Hz, 1H), 8.10 (s, 1H), 7.67 (s, 1H), 7.69 (d, J=0.8 Hz, 1H), 7.45-7.43 (m, 2H), 7.16 (dd, J=5.2, 0.8 Hz, 1H), 7.13 (s, 1H), 6.78 (t, J=5.6 Hz, 1H), 6.38 (s, 1H), 4.60 (d, J=5.6 Hz, 2H), 3.87 (s, 3H), 2.59 (s, 3H), 1.45 (s, 9H).

Example 102: 2-(tert-butyl)-N-((2-methyl-6-(2-((1-methyl-1H-pyrazol-4-yl)amino)pyrimidin-4-yl)pyridin-3-yl)methyl)thiazole-5-carboxamide (I-103)

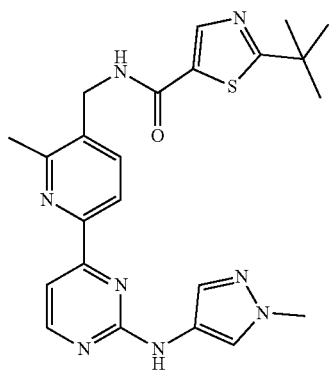

I-103

Synthesis of 1-(1-methyl-1H-pyrazol-4-yl)guanidine

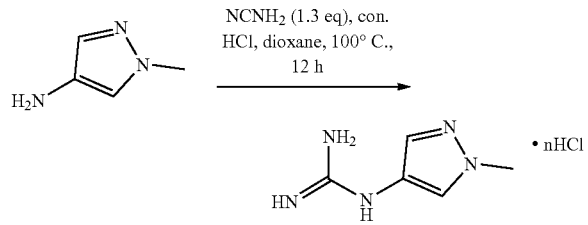

To a solution of 1-methyl-1H-pyrazol-4-amine (500 mg, 5 mmol, 1.0 equiv) in dioxane (10 mL) was added $NCNH_2$ (273 g, 6.5 mmol, 1.3 equiv) and conc. HCl (1 mL). The reaction was stirred at 100° C. for 12 h. The solvent was removed under reduced pressure. The residue was recrystallized from the co-solvent of MeOH and $Et_2O$. 1-(1-methyl-1H-pyrazol-4-yl)guanidine (600 mg, yield: 55%) was obtained as a yellow solid. ESI-MS (M+H)$^+$: 140.1. $^1$H NMR (400 MHz, $CD_3OD$) δ: 7.78 (s, 1H), 7.48 (s, 1H), 3.91 (s, 3H).

Synthesis of tert-butyl ((6-bromo-2-methylpyridin-3-yl)methyl)carbamate

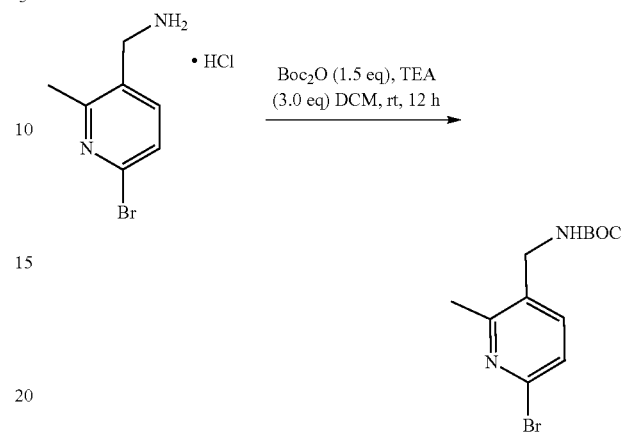

To a mixture of 1-(1-methyl-1H-pyrazol-4-yl)guanidine (709 mg, 3 mmol, 1.0 equiv) in DCM (10 mL) and TEA (909 mg, 9.0 mmol, 3.0 equiv) was added $Boc_2O$ (981 mg, 4.5 mmol, 1.5 equiv). The mixture was stirred at room temperature for 12 h. After concentrated, the residue was purified by silica gel column (petroleum ether/EtOAc=8:1) to give tert-butyl ((6-bromo-2-methylpyridin-3-yl)methyl)carbamate (728 mg, yield: 82%) as a white solid. ESI-MS (M+H)$^+$: 301.2. $^1$H NMR (400 MHz, $CDCl_3$) δ: 7.41 (d, J=8.0 Hz, 1H), 7.30 (d, J=8.0 Hz, 1H), 4.26 (d, J=5.6 Hz, 2H), 2.52 (s, 3H), 1.45 (s, 9H).

Synthesis of tert-butyl ((6-acetyl-2-methylpyridin-3-yl)methyl)carbamate

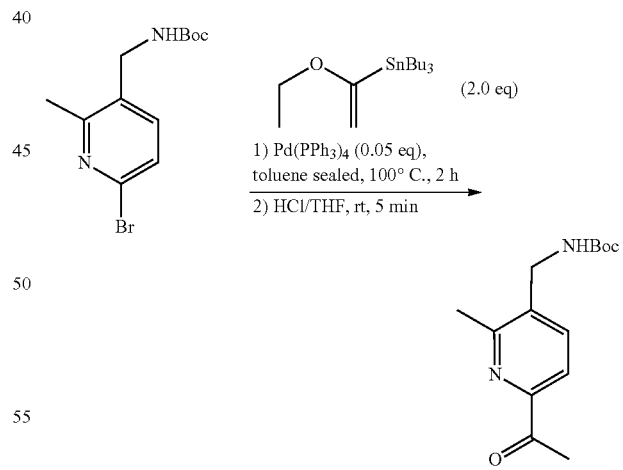

To a mixture of tert-butyl ((6-bromo-2-methylpyridin-3-yl)methyl)carbamate (1.49 g, 5 mmol, 1.0 equiv) and tributyl(1-ethoxyvinyl)stannane (2.7 g, 7.5 mmol, 2.0 equiv) in toluene (20 ml), $Pd(PPh_3)_4$ (288 mg, 0.25 mmol, 0.05 equiv) was added quickly under $N_2$. The mixture was stirred at 120° C. for 2 h. After cooling down, the mixture was concentrated and purified by silica gel column (petroleum ether/EtOAc=4:1) to give the intermediate, which was dissolved in 5 mL THF and followed by addition of a solution of HCl (0.6 N, 1 mL, 6 mmol, 1.2 equiv). After stirred at rt for 5 m and basified to pH=8 with sat. sodium bicarbonate, the mixture was extracted with EA (100 mL), washed with water (50 mL), brine (50 mL) and the organic layer was dried over Na₂SO₄, filtered then concentrated to give tert-butyl ((6-acetyl-2-methylpyridin-3-yl)methyl)carbamate (550 mg, yield: 42%) as a yellow solid. ESI-MS (M+H)⁺: 265.0. ¹H NMR (400 MHz, CDCl₃) δ: 7.85 (d, J=7.2 Hz, 1H), 7.66 (d, J=8.0 Hz, 1H), 4.93 (br, 1H), 4.36 (d, J=5.6 Hz, 2H), 2.70 (s, 3H), 2.59 (s, 3H), 1.46 (s, 9H).

Synthesis of (E)-tert-butyl ((6-(3-(dimethylamino)acryloyl)-2-methylpyridin-3-yl)methyl)carbamate

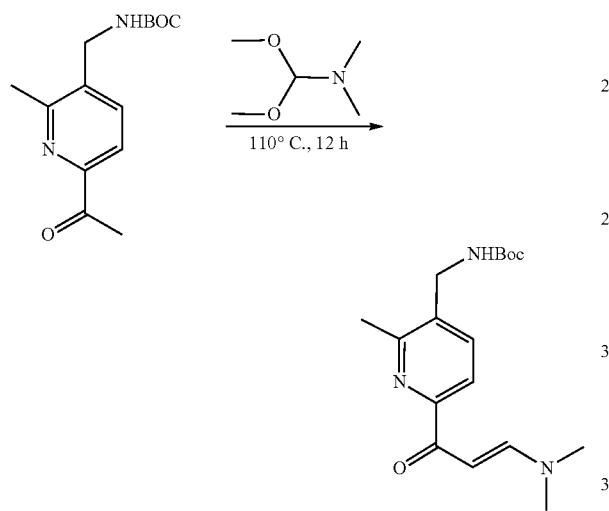

A solution of tert-butyl ((6-acetyl-2-methylpyridin-3-yl)methyl)carbamate (550 mg, 2.1 mmol, 1.0 equiv) in DMF-DMA (5 mL) was stirred at 110° C. for 12 h. After evaporation of the solvent, the residue was purified by silica gel column (DCM:MeOH=20:1) to give (E)-tert-butyl ((6-(3-(dimethylamino)acryloyl)-2-methylpyridin-3-yl)methyl)carbamate (600 mg, yield: 90%) as a yellow oil. ESI-MS (M+H)⁺: 320.2. ¹H NMR (400 MHz, CDCl₃) δ:7.94 (d, J=8.0 Hz, 1H), 7.90-7.86 (m, 1H), 7.62 (d, J=8.0 Hz, 1H), 6.47 (d, J=12.0 Hz, 1H), 4.85 (br, 1H), 4.36 (d, J=5.2 Hz, 2H), 3.16 (s, 3H), 2.99 (s, 3H), 2.59 (s, 3H), 1.46 (s, 9H).

Synthesis of tert-butyl ((2-methyl-6-(2-((1-methyl-1H-pyrazol-4-yl)amino)pyrimidin-4-yl)pyridin-3-yl)methyl)carbamate

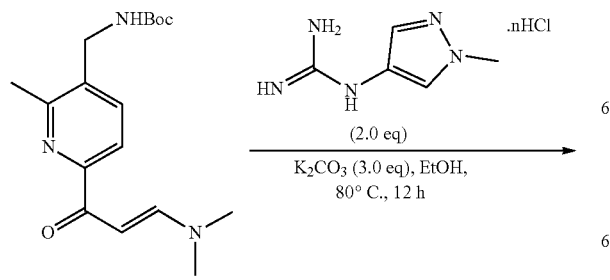

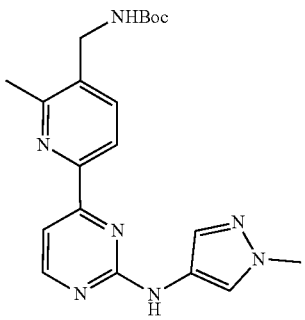

A solution of (E)-tert-butyl ((6-(3-(dimethylamino)acryloyl)-2-methylpyridin-3-yl)methyl)carbamate (300 mg, 0.95 mmol, 1.0 equiv) in EtOH (10 mL) was treated with 1-(1-methyl-1H-pyrazol-4-yl)guanidine (400 mg, 1.89 mmol, 2.0 equiv) and K₂CO₃ (393 g, 2.85 mmol, 3.0 equiv). The reaction was stirred at 80° C. for 12 h. After cooling down, the crude product was purified by prep-HPLC (Gradient: 5% B increase to 95% B, A: 0.5% NH₃ in water, B: CH₃CN) to give tert-butyl ((2-methyl-6-(2-((1-methyl-1H-pyrazol-4-yl)amino)pyrimidin-4-yl)pyridin-3-yl)methyl)carbamate (120 mg, yield: 32%) as a yellow solid. ESI-MS (M+H)⁺: 396.1. ¹H NMR (400 MHz, CDCl₃) δ: 8.50 (d, J=5.2 Hz, 1H), 8.17 (d, J=8.4 Hz, 1H), 7.86 (s, 1H), 7.72-7.68 (m, 2H), 7.57 (s, 1H), 6.91 (s, 1H), 4.85 (br, 1H), 4.38 (d, J=5.2 Hz, 2H), 3.92 (s, 3H), 2.62 (s, 3H), 1.47 (s, 9H).

Synthesis of 2-(tert-butyl)-N-((2-methyl-6-(2-((1-methyl-1H-pyrazol-4-yl)amino)pyrimidin-4-yl)pyridin-3-yl)methyl)thiazole-5-carboxamide

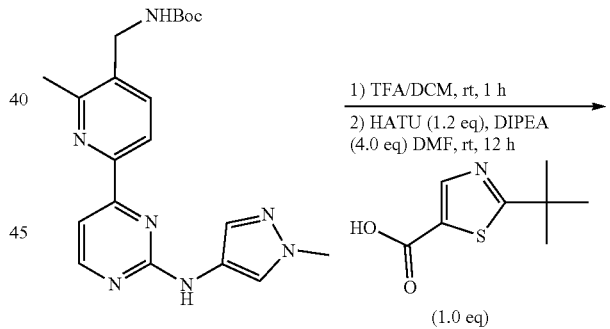

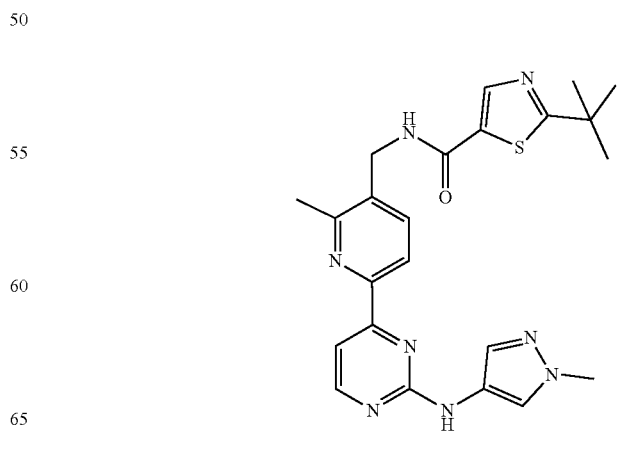

Synthesis of 2-(tert-butyl)-N-((2-methyl-6-(2-((1-methyl-1H-pyrazol-4-yl)amino)pyrimidin-4-yl)pyridin-3-yl)methyl)thiazole-5-carboxamide was similar to that of Example 1. The mixture was purified by prep-HPLC (Gradient: 5% B increase to 95% B, A: 0.5% NH₃ in water, B: CH₃CN) to give 2-(tert-butyl)-N-((2-methyl-6-(2-((1-methyl-1H-pyrazol-4-yl)amino)pyrimidin-4-yl)pyridin-3-yl)methyl)thiazole-5-carboxamide (35 mg, yield: 54%) as a yellow solid. ESI-MS (M+H)⁺:463.1. ¹H NMR (400 MHz, CD₃OD) δ: 8.49 (d, J=5.2 Hz, 1H), 8.25-8.23 (m, 2H), 7.99 (s, 1H), 7.83 (d, J=8.0 Hz, 1H), 7.66 (d, J=5.2 Hz, 1H), 7.62 (s, 1H), 4.64 (s, 2H), 3.89 (s, 3H), 2.67 (s, 3H), 1.47 (s, 9H).

Example 103: N-((2-methyl-6-(2-((1-methyl-1H-pyrazol-4-yl)amino)pyrimidin-4-yl)pyridin-3-yl)methyl)-6,7-dihydro-4H-thieno[3,2-c]pyran-2-carboxamide (I-104)

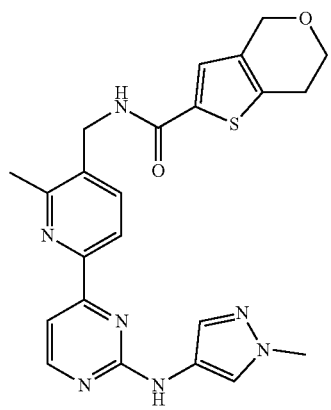

I-104

Synthesis of N-((2-methyl-6-(2-((1-methyl-1H-pyrazol-4-yl)amino)pyrimidin-4-yl)pyridin-3-yl)methyl)-6,7-dihydro-4H-thieno[3,2-c]pyran-2-carboxamide was similar to that of Example 102 starting from 6,7-dihydro-4H-thieno[3,2-c]pyran-2-carboxylic acid. The mixture was stirred at room temperature for 12 h. The mixture was purified by prep-HPLC (Gradient: 5% B increase to 95% B, A: 0.5% NH₃ in water, B: CH₃CN) to give N-((2-methyl-6-(2-((1-methyl-1H-pyrazol-4-yl)amino)pyrimidin-4-yl)pyridin-3-yl)methyl)-6,7-dihydro-4H-thieno[3,2-c]pyran-2-carboxamide (20 mg, yield: 29%) as a yellow solid. ESI-MS (M+H)⁺:462.1. ¹H NMR (400 MHz, CDCl₃) δ: 8.51 (d, J=5.2 Hz, 1H), 8.16 (d, J=7.6 Hz, 1H), 7.85 (s, 1H), 7.72-7.70 (m, 2H), 7.55 (s, 1H), 7.22 (s, 1H), 6.95 (s, 1H), 6.21 (t, J=5.6 Hz, 1H), 4.67-4.66 (m, 4H), 3.98 (t, J=5.6 Hz, 2H), 3.91 (s, 3H), 2.90 (t, J=5.6 Hz, 2H), 2.66 (s, 3H).

Example 104: N-(1-(2-methyl-4-(2-((1-methyl-1H-pyrazol-4-yl)amino)pyrimidin-4-yl)phenyl)ethyl)-6,7-dihydro-4H-thieno[3,2-c]pyran-2-carboxamide (I-105)

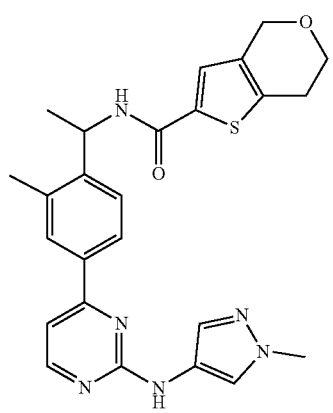

I-105

Preparation of tert-butyl (1-(4-(2-chloropyrimidin-4-yl)-2-methylphenyl)ethyl)carbamate

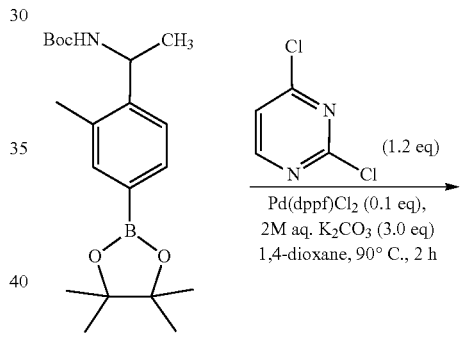

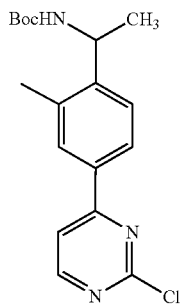

Synthesis of tert-butyl (1-(4-(2-chloropyrimidin-4-yl)-2-methylphenyl)ethyl)carbamate was similar to that of tert-butyl 4-(2-chloropyrimidin-4-yl)-2-methylbenzylcarbamate. The crude was purified by silica gel column chromatography (petroleum ether/EtOAc=1/4) to give product tert-butyl (1-(4-(2-chloropyrimidin-4-yl)-2-methylphenyl)ethyl)carbamate as green oil (460 mg, yield: 60%). ESI-MS (M+H)⁺: 347.9.

Preparation of tert-butyl (1-(2-methyl-4-(2-((1-methyl-1H-pyrazol-4-yl)amino)pyrimidin-4-yl)phenyl)ethyl)carbamate

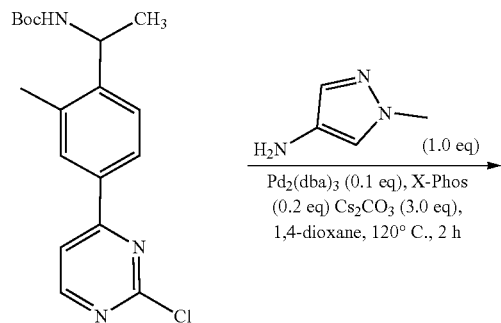

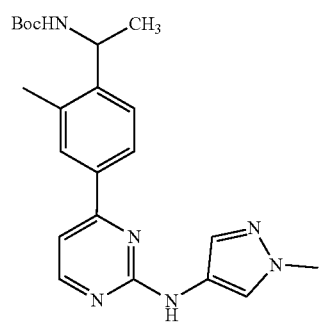

Synthesis of tert-butyl (1-(2-methyl-4-(2-((1-methyl-1H-pyrazol-4-yl)amino)pyrimidin-4-yl)phenyl)ethyl)carbamate was similar to that of tert-butyl 2-methyl-4-(2-((1-methyl-1H-pyrazol-4-yl)amino)pyrimidin-4-yl)benzylcarbamate. The crude was purified by silica gel column chromatography (petroleum ether/EtOAc=4/1 to 1/2) to give product tert-butyl (1-(2-methyl-4-(2-((1-methyl-1H-pyrazol-4-yl)amino)pyrimidin-4-yl)phenyl)ethyl)carbamate as green oil (165 mg, yield: 30%). ESI-MS (M+H)+: 408.9.

Preparation of N-(1-(2-methyl-4-(2-((1-methyl-1H-pyrazol-4-yl)amino)pyrimidin-4-yl)phenyl)ethyl)-6,7-dihydro-4H-thieno[3,2-c]pyran-2-carboxamide

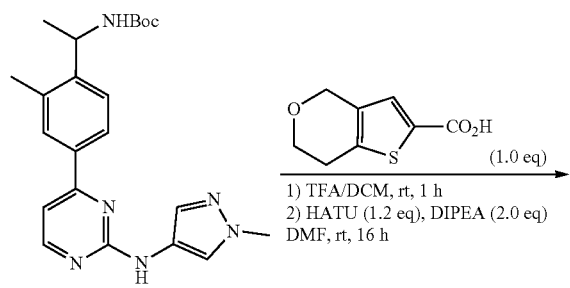

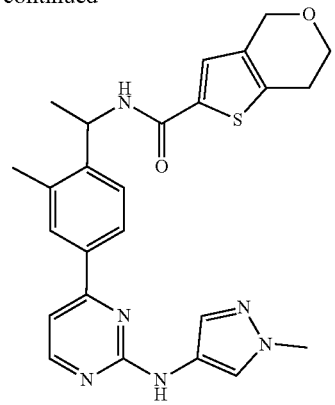

Synthesis of N-(1-(2-methyl-4-(2-((1-methyl-1H-pyrazol-4-yl)amino)pyrimidin-4-yl)phenyl)ethyl)-6,7-dihydro-4H-thieno[3,2-c]pyran-2-carboxamide was similar to that of Example 1. The crude was purified by prep-HPLC (CH$_3$CN/H$_2$O with 0.01% ammonia as mobile phase) to give product N-(1-(2-methyl-4-(2-((1-methyl-1H-pyrazol-4-yl)amino)pyrimidin-4-yl)phenyl)ethyl)-6,7-dihydro-4H-thieno[3,2-c]pyran-2-carboxamide as a white solid (77 mg, yield: 81%). ESI-MS (M+H)+: 475.0. HPLC: (214 nm: 93%, 254 nm: 94%). $^1$H NMR (400 MHz, CD$_3$OD) δ: 8.34 (d, J=4.8 Hz, 1H), 7.94-7.89 (m, 3H), 7.63 (s, 1H), 7.50 (d, J=8.0 Hz, 1H), 7.43 (s, 1H), 7.13 (d, J=5.2 Hz, 1H), 5.40-5.37 (m, 1H), 4.64 (s, 2H), 3.93 (t, J=5.6 Hz, 2H), 3.86 (s, 3H), 2.84 (t, J=5.6 Hz, 2H), 2.49 (s, 3H), 1.53 (d, J=6.8 Hz, 3H).

Example 105: 2-(tert-butyl)-N-(1-(2-methyl-4-(2-((1-methyl-1H-pyrazol-4-yl)amino)pyrimidin-4-yl)phenyl)ethyl)thiazole-5-carboxamide (I-106)

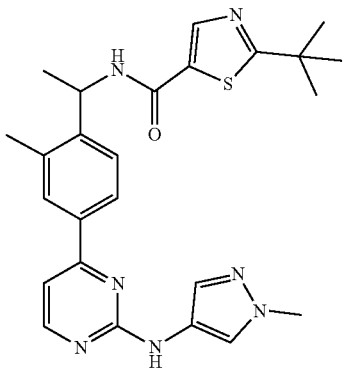

I-106

Synthesis of 2-(tert-butyl)-N-(1-(2-methyl-4-(2-((1-methyl-1H-pyrazol-4-yl)amino)pyrimidin-4-yl)phenyl)ethyl)thiazole-5-carboxamide was similar to that of Example 1. ESI-MS (M+H)+: 476.0. $^1$H NMR (400 MHz, CD$_3$OD) δ: 8.32 (d, J=5.2 Hz, 1H), 8.28 (s, 1H), 7.93-7.88 (m, 3H), 7.62 (s, 1H), 7.49 (d, J=8.0 Hz, 1H), 7.10 (d, J=5.2 Hz, 1H), 5.39-5.37 (m, 1H), 3.85 (s, 3H), 2.48 (s, 3H), 1.53 (d, J=7.2 Hz, 3H), 1.42 (s, 9H).

Example 106: N-(1-(4-(2-aminopyrimidin-4-yl)-2-methylphenyl)ethyl)-2-(trifluoromethyl)thiazole-5-carboxamide (I-107)

Preparation of 2-(tert-butyl)-N-(2-((tert-butyldimethylsilyl)oxy)-1-(2-methyl-4-(2-((1-methyl-M-pyrazol-4-yl)amino)pyrimidin-4-yl)phenyl)ethyl)thiazole-5-carboxamide

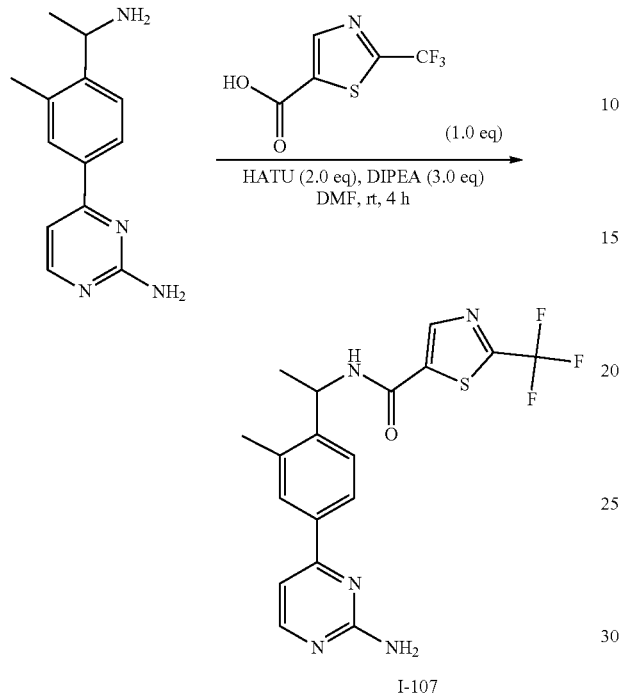

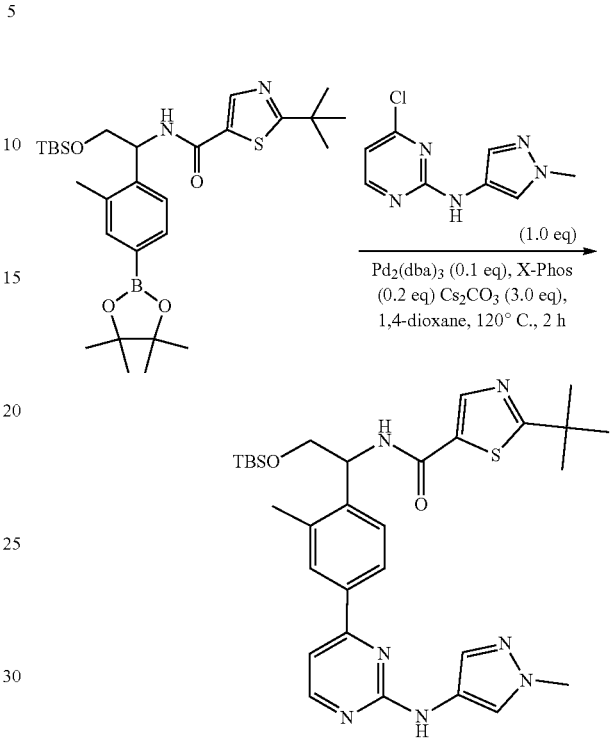

Synthesis of N-(1-(4-(2-aminopyrimidin-4-yl)-2-methylphenyl)ethyl)-2-(trifluoromethyl)thiazole-5-carboxamide was similar to that of Example 1. The crude product was purified by prep-HPLC (CH₃CN/H₂O with 0.05% NH₃.H₂O as mobile phase) to give N-(1-(4-(2-aminopyrimidin-4-yl)-2-methylphenyl)ethyl)-2-(trifluoromethyl)thiazole-5-carboxamide as a white solid (20 mg, yield: 57%). ESI-MS (M+H)⁺: 408.0. HPLC: (214 nm: 96%, 254 nm: 100%). ¹H NMR (400 MHz, CD₃OD) δ: 8.46 (s, 1H), 8.15 (d, J=5.2 Hz, 1H), 7.79-7.78 (m, 2H), 7.47 (d, J=8.8 Hz, 1H), 7.47 (d, J=5.2 Hz, 1H), 5.36-5.31 (m, 1H), 2.41 (s, 3H), 1.48 (d, J=7.2 Hz, 3H).

Synthesis of 2-(tert-butyl)-N-(2-((tert-butyldimethylsilyl)oxy)-1-(2-methyl-4-(2-((1-methyl-1H-pyrazol-4-yl)amino)pyrimidin-4-yl)phenyl)ethyl)thiazole-5-carboxamide was similar to that of tert-butyl 4-(2-chloropyrimidin-4-yl)-2-methylbenzylcarbamate. The crude was purified by silica gel column chromatography (EtOAc/petroleum ether=1/2 to 2/1) to give product 2-(tert-butyl)-N-(2-((tert-butyldimethylsilyl)oxy)-1-(2-methyl-4-(2-((1-methyl-1H-pyrazol-4-yl)amino)pyrimidin-4-yl)phenyl)ethyl)thiazole-5-carboxamide as a yellow solid (64 mg, yield: 50%). ESI-MS (M+H)⁺: 606.2.

Example 107: 2-(tert-butyl)-N-(2-hydroxy-1-(2-methyl-4-(2-((1-methyl-1H-pyrazol-4-yl)amino)pyrimidin-4-yl)phenyl)ethyl)thiazole-5-carboxamide (I-108)

Preparation of 2-(tert-butyl)-N-(2-hydroxy-1-(2-methyl-4-(2-((1-methyl-M-pyrazol-4-yl)amino)pyrimidin-4-yl)phenyl)ethyl)thiazole-5-carboxamide

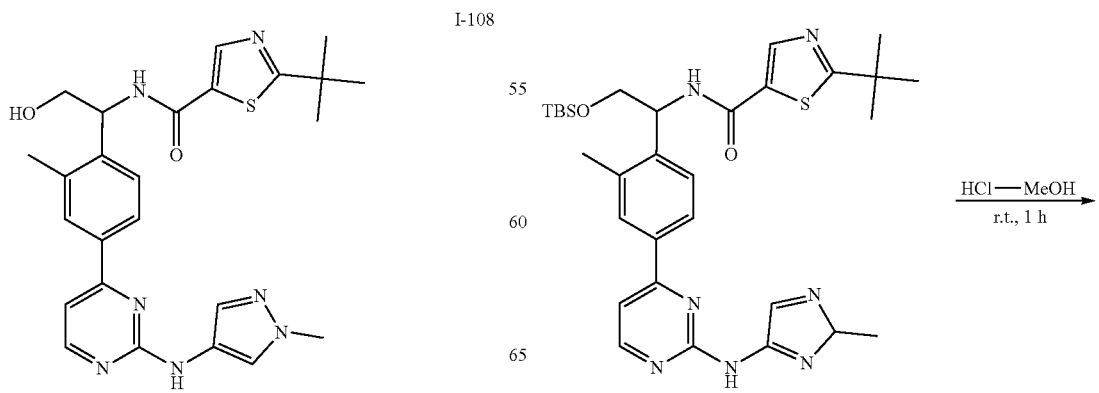

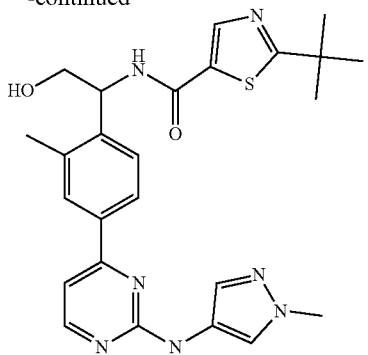

A mixture of 2-(tert-butyl)-N-(2-((tert-butyldimethylsilyl)oxy)-1-(2-methyl-4-(2-((1-methyl-1H-pyrazol-4-yl)amino)pyrimidin-4-yl)phenyl)ethyl)thiazole-5-carboxamide (64 mg, 0.10 mmol) in HCl (3M solution in methanol) was stirred at room temperature for 1 h. Then the solution was concentrated and the residue was purified by prep-HPLC (CH$_3$CN/water as mobile phase) to give product 2-(tert-butyl)-N-(2-hydroxy-1-(2-methyl-4-(2-((1-methyl-1H-pyrazol-4-yl)amino)pyrimidin-4-yl)phenyl)ethyl)thiazole-5-carboxamide as a yellow solid (27 mg, yield: 55%). ESI-MS (M+H)$^+$: 492.0. HPLC: (214 nm: 97%, 254 nm: 97%). $^1$H NMR (400 MHz, CD$_3$OD) δ: 8.37 (d, J=5.6 Hz, 1H), 8.33 (s, 1H), 7.94-7.93 (m, 3H), 7.64 (s, 1H), 7.51 (d, J=8.0 Hz, 1H), 7.16 (d, J=5.6 Hz, 1H), 5.47-5.44 (m, 1H), 3.88 (s, 3H), 3.86-3.83 (m, 2H), 2.57 (s, 3H), 1.45 (s, 9H).

Example 108: N-(2-hydroxy-1-(2-methyl-4-(2-((1-methyl-1H-pyrazol-4-yl)amino)pyrimidin-4-yl)phenyl)ethyl)-6,7-dihydro-4H-thieno[3,2-c]pyran-2-carboxamide (I-109)

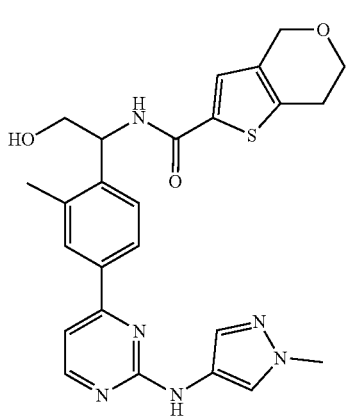

I-109

Synthesis of N-(2-hydroxy-1-(2-methyl-4-(2-((1-methyl-1H-pyrazol-4-yl)amino)pyrimidin-4-yl)phenyl)ethyl)-6,7-dihydro-4H-thieno[3,2-c]pyran-2-carboxamide was similar to that of Example 107, except 6,7-dihydro-4H-thieno[3,2-c]pyran-2-carboxylic acid was substituted for 2-(tert-butyl)thiazole-5-carboxylic acid. The crude was purified by prep-HPLC (CH$_3$CN/water as mobile phase) to give product N-(2-hydroxy-1-(2-methyl-4-(2-((1-methyl-1H-pyrazol-4-yl)amino)pyrimidin-4-yl)phenyl)ethyl)-6,7-dihydro-4H-thieno[3,2-c]pyran-2-carboxamide as a yellow solid (40 mg, yield: 51%). ESI-MS (M+H)$^+$: 491.0. HPLC: (214 nm: 98%, 254 nm: 98%). $^1$H NMR (400 MHz, CD$_3$OD) δ: 8.38 (d, J=5.2 Hz, 1H), 7.96-7.93 (m, 3H), 7.64 (s, 1H), 7.52 (d, J=7.6 Hz, 1H), 7.49 (s, 1H), 7.19 (d, J=5.2 Hz, 1H), 5.44 (t, J=6.8 Hz, 1H), 4.69 (s, 2H), 3.96 (t, J=5.6 Hz, 2H), 3.89 (s, 3H), 3.84 (d, J=6.8 Hz, 2H), 2.88 (t, J=5.6 Hz, 2H), 2.58 (s, 3H).

Scheme 11

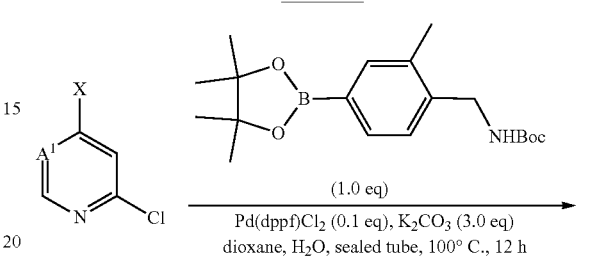

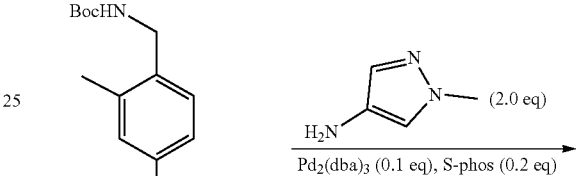

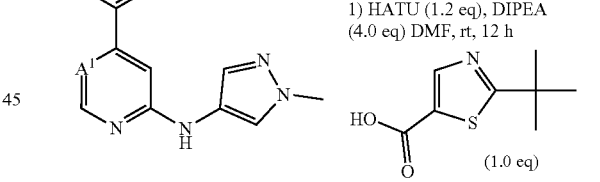

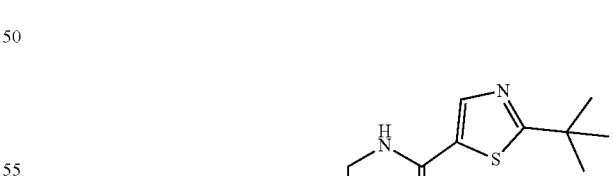

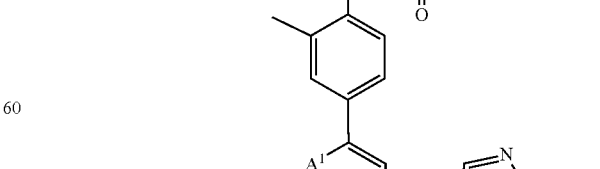

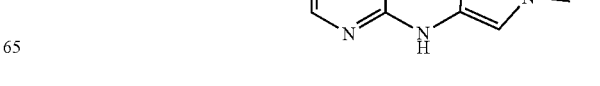

Example 109: N-(4-(2-amino-5-fluoropyrimidin-4-yl)-2-methylbenzyl)-2-(tert-butyl)thiazole-5-carboxamide (I-110)

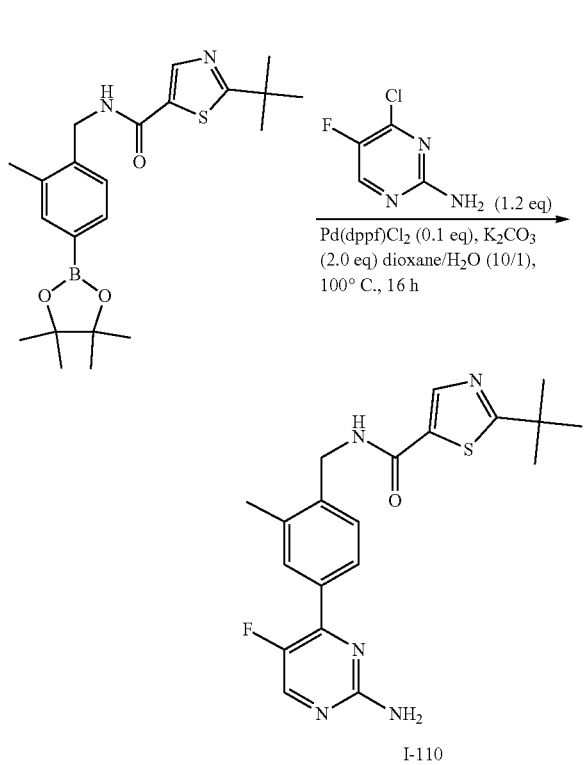

I-110

Synthesis of N-(4-(2-amino-5-fluoropyrimidin-4-yl)-2-methylbenzyl)-2-(tert-butyl)thiazole-5-carboxamide was similar to that of tert-butyl 4-(2-chloropyrimidin-4-yl)-2-methylbenzylcarbamate, starting from 4-chloro-5-fluoropyrimidin-2-amine. Purified through silica gel column chromatography with (MeOH/DCM=1/20) to give N-(4-(2-amino-5-fluoropyrimidin-4-yl)-2-methylbenzyl)-2-(tert-butyl)thiazole-5-carboxamide (45 mg, yield: 59%) as a white solid. ESI-MS (M+H)$^+$: 400.1. HPLC: (214 nm: 98.20%, 254 nm: 97.80%). $^1$H NMR (400 MHz, CD$_3$OD) δ: 8.24 (s, 1H), 8.23 (d, J=4.0 Hz, 1H), 7.88 (s, 1H), 7.85 (d, J=8.4 Hz, 1H), 7.42 (d, J=8.0 Hz, 1H), 4.61 (s, 2H), 2.45 (s, 3H), 1.46 (s, 9H).

Example 110: 2-(tert-butyl)-N-(4-(5-fluoro-2-((1-methyl-1H-pyrazol-4-yl)amino)pyrimidin-4-yl)-2-methylbenzyl)thiazole-5-carboxamide (I-111)

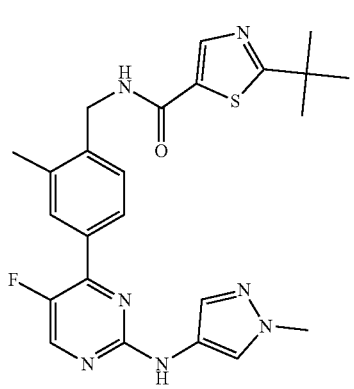

I-111

Synthesis of tert-butyl 4-(2-chloro-5-fluoropyrimidin-4-yl)-2-methylbenzylcarbamate

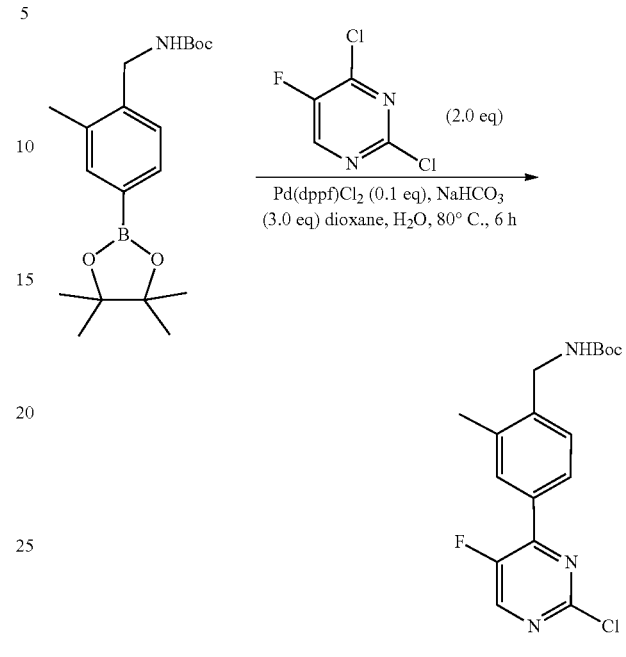

To a mixture of tert-butyl 2-methyl-4-(4,4,5,5-tetramethyl-1,3,2-dioxaborolan-2-yl)benzylcarbamate (220 mg, 0.63 mmol, 1.0 equiv) and 2,4-dichloro-5-fluoropyrimidine (209 mg, 1.26 mmol, 2.0 equiv) in dioxane (5 ml) and H$_2$O (0.5 mL), NaHCO$_3$ (159 mg, 1.89 mmol, 3.0 equiv), Pd(dppf)Cl$_2$.DCM (46 mg, 0.06 mmol, 0.1 equiv) were added quickly under N$_2$. The mixture was stirred at 80° C. for 6 h. After cooling down and diluted with water (20 mL), the mixture was extracted with EtOAc (80 mL×2). The organic phase was concentrated and purified by silica gel column (petroleum ether/EtOAc=4:1) to give tert-butyl 4-(2-chloro-5-fluoropyrimidin-4-yl)-2-methylbenzylcarbamate (180 mg, yield: 71%) as a white solid. ESI-MS (M+H)$^+$: 352.0. $^1$H NMR (400 MHz, CDCl$_3$) δ: 8.49 (d, J=3.2 Hz, 1H), 7.95-7.93 (m, 2H), 7.40 (d, J=8.4 Hz, 1H), 4.81 (br, 1H), 4.38 (d, J=4.8 Hz, 2H), 2.41 (s, 3H), 1.47 (s, 9H).

Synthesis of tert-butyl 4-(5-fluoro-2-((1-methyl-1H-pyrazol-4-yl)amino)pyrimidin-4-yl)-2-methylbenzylcarbamate

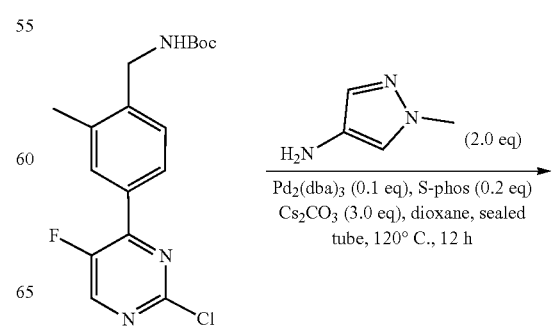

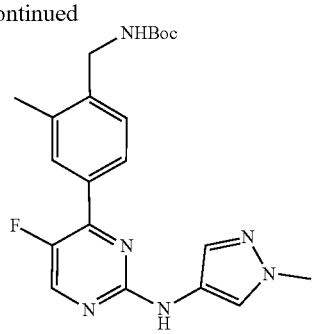

Synthesis of tert-butyl 4-(5-fluoro-2-((1-methyl-1H-pyrazol-4-yl)amino)pyrimidin-4-yl)-2-methylbenzylcarbamate was similar to that of tert-butyl 2-methyl-4-(2-((1-methyl-1H-pyrazol-4-yl)amino)pyrimidin-4-yl)benzylcarbamate, starting from 1-methyl-1H-pyrazol-4-amine. The mixture was purified by silica gel column (DCM:MeOH=40:1) to give tert-butyl 4-(5-fluoro-2-((1-methyl-1H-pyrazol-4-yl)amino)pyrimidin-4-yl)-2-methylbenzylcarbamate (200 mg, yield: 94%) as a yellow solid. ESI-MS (M+H)$^+$: 413.1. $^1$H NMR (400 MHz, CDCl$_3$) δ: 8.29 (d, J=3.2 Hz, 1H), 7.91-7.87 (m, 2H), 7.82 (s, 1H), 7.52 (s, 1H), 7.39-7.37 (m, 1H), 6.88 (s, 1H), 4.83-4.76 (m, 1H), 4.38 (d, J=4.8 Hz, 2H), 3.90 (s, 3H), 2.41 (s, 3H), 1.47 (s, 9H).

Synthesis of 2-(tert-butyl)-N-(4-(5-fluoro-2-((1-methyl-1H-pyrazol-4-yl)amino)pyrimidin-4-yl)-2-methylbenzyl)thiazole-5-carboxamide

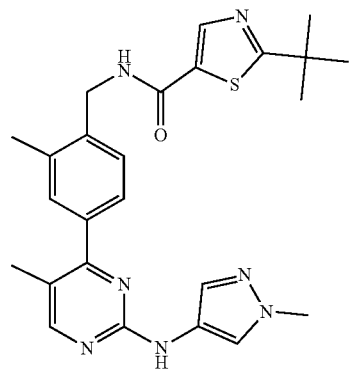

Synthesis of 2-(tert-butyl)-N-(4-(5-fluoro-2-((1-methyl-1H-pyrazol-4-yl)amino)pyrimidin-4-yl)-2-methylbenzyl)thiazole-5-carboxamide was similar to that of Example 1. The mixture was purified by prep-HPLC (Gradient: 5% B increase to 95% B, A: 0.5% NH$_3$ in water, B: CH$_3$CN) to give 2-(tert-butyl)-N-(4-(5-fluoro-2-((1-methyl-1H-pyrazol-4-yl)amino)pyrimidin-4-yl)-2-methylbenzyl)thiazole-5-carboxamide (38 mg, yield: 45%) as a yellow solid. ESI-MS (M+H)$^+$: 480.0. $^1$H NMR (400 MHz, CDCl$_3$) δ: 8.30 (d, J=2.8 Hz, 1H), 8.06 (s, 1H), 7.90-7.87 (m, 2H), 7.81 (s, 1H), 7.48 (s, 1H), 7.41 (d, J=8.0 Hz, 1H), 6.94 (s, 1H), 6.18 (t, J=5.6 Hz, 1H), 4.67 (d, J=5.6 Hz, 2H), 3.89 (s, 3H), 2.45 (s, 3H), 1.45 (s, 9H).

Example 111: 2-(tert-butyl)-N-(2-methyl-4-(5-methyl-2-((1-methyl-1H-pyrazol-4-yl)amino)pyrimidin-4-yl)benzyl)thiazole-5-carboxamide (I-112)

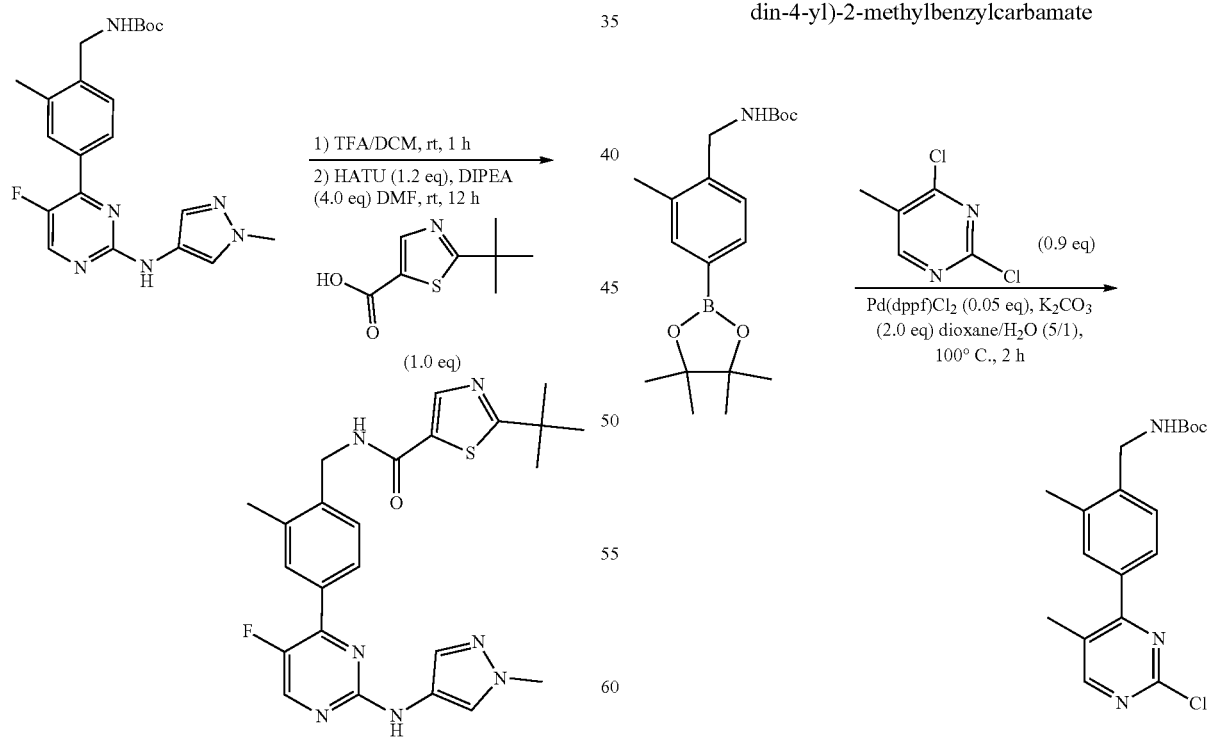

Synthesis of tert-butyl 4-(2-chloro-5-methylpyrimidin-4-yl)-2-methylbenzylcarbamate was similar to that of tert-butyl 4-(2-chloropyrimidin-4-yl)-2-methylbenzylcarbamate, starting from 2,4-dichloro-5-methylpyrimidine. Purified through silica gel column chromatography with (petroleum ether/EtOAc=6/1) to give tert-butyl 4-(2-chloro-5-methylpyrimidin-4-yl)-2-methylbenzylcarbamate (200 mg, yield: 44%) as a white solid. ESI-MS (M+H)+: 348.2.

Synthesis of tert-butyl 2-methyl-4-(5-methyl-2-((1-methyl-1H-pyrazol-4-yl)amino)pyrimidin-4-yl)benzylcarbamate

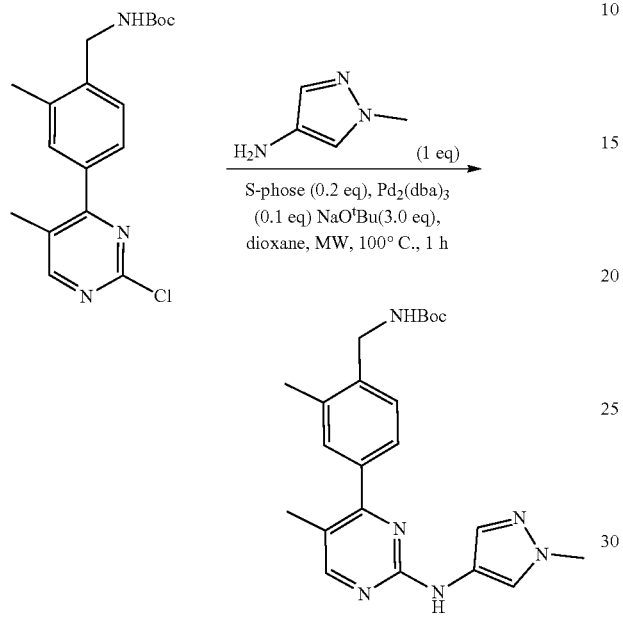

Synthesis of tert-butyl 2-methyl-4-(5-methyl-2-((1-methyl-1H-pyrazol-4-yl)amino)pyrimidin-4-yl)benzylcarbamate was similar to that of tert-butyl 4-(2-((1-methyl-1H-pyrazol-4-yl)amino)pyrimidin-4-yl)benzylcarbamate, starting from 1-methyl-1H-pyrazol-4-amine. Purified through silica gel column chromatography with (petroleum ether/EtOAc=1/1) to give tert-butyl 2-methyl-4-(5-methyl-2-((1-methyl-1H-pyrazol-4-yl)amino)pyrimidin-4-yl)benzylcarbamate (230 mg, yield: 78%) as a yellow solid. ESI-MS (M+H)+: 409.1. ¹H NMR (400 MHz, DMSO-d₆) δ: 9.30 (s, 1H), 8.31 (s, 1H), 7.83 (s, 1H), 7.47-7.45 (m, 3H), 7.38 (t, J=6.0 Hz, 1H), 7.30 (d, J=7.2 Hz, 1H), 4.18 (d, J=5.6 Hz, 2H), 3.77 (s, 3H), 2.33 (s, 3H), 2.18 (s, 3H), 1.41 (s, 9H).

Synthesis of 2-(tert-butyl)-N-(2-methyl-4-(5-methyl-2-((1-methyl-1H-pyrazol-4-yl)amino)pyrimidin-4-yl)benzyl)thiazole-5-carboxamide

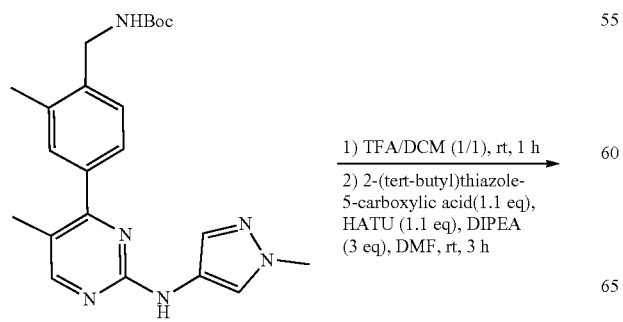

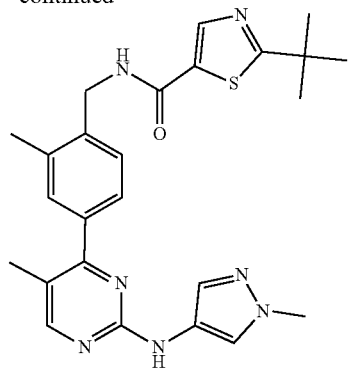

Synthesis of 2-(tert-butyl)-N-(2-methyl-4-(5-methyl-2-((1-methyl-1H-pyrazol-4-yl)amino)pyrimidin-4-yl)benzyl)thiazole-5-carboxamide was similar to that of Example 1. Purified through silica gel column chromatography with (petroleum ether/EtOAc=2/1) to give 2-(tert-butyl)-N-(2-methyl-4-(5-methyl-2-((1-methyl-1H-pyrazol-4-yl)amino)pyrimidin-4-yl)benzyl)thiazole-5-carboxamide (60 mg, yield: 52%) as a yellow solid. ESI-MS (M+H)+: 476.1. HPLC: (214 nm: 97.05%, 254 nm: 97.87%). ¹H NMR (400 MHz, CD₃OD) δ: 8.27 (s, 1H), 8.24 (s, 1H), 7.90 (s, 1H), 7.57 (s, 1H), 7.49-7.46 (m, 2H), 7.43 (d, J=7.6 Hz, 1H), 4.63 (s, 2H), 3.84 (s, 3H), 2.46 (s, 3H), 2.22 (s, 3H), 1.46 (s, 9H).

Example 112: N-((5-(2-aminopyrimidin-4-yl)-3-fluoropyridin-2-yl)methyl)-4,5,6,7-tetrahydrobenzo[b]thiophene-2-carboxamide (I-113)

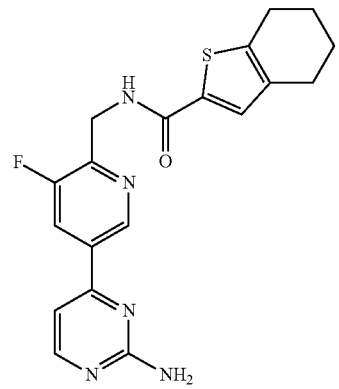

I-113

Synthesis of N-((5-bromo-3-fluoropyridin-2-yl)methyl)-4,5,6,7-tetrahydrobenzo[b]thiophene-2-carboxamide

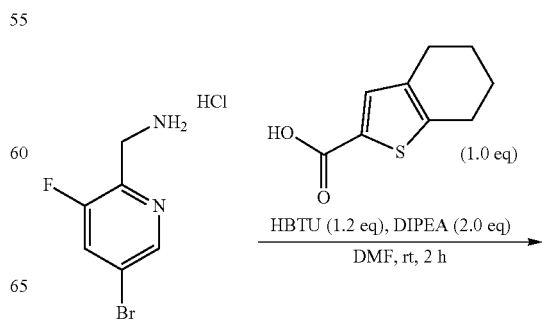

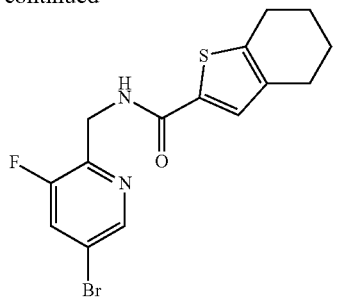

To a solution of (5-bromo-3-fluoropyridin-2-yl)methanamine (480 mg, 2 mmol) in DMF (10 mL) were added 4,5,6,7-tetrahydrobenzo[b]thiophene-2-carboxylic acid (364 mg, 2 mmol), HBTU (909 mg, 2.4 mmol) and TEA (606 mg, 6 mmol). The mixture was stirred at rt for 16 h. After diluted with EtOAc (180 mL), the mixture was washed with H$_2$O (60 mL×2) and brine (60 mL), dried (Na$_2$SO$_4$), filtered and concentrated. The residue was purified by silica gel column chromatography (petroleum ether/EtOAc=2:1) to give N-((5-bromo-3-fluoropyridin-2-yl)methyl)-4,5,6,7-tetrahydrobenzo[b]thiophene-2-carboxamide as a white solid (496 mg, yield: 77%). ESI-MS (M+H)$^+$: 369.0. $^1$H NMR (400 MHz, DMSO-d$_6$) δ: 8.85 (t, J=5.6 Hz, 1H), 8.54 (s, 1H), 8.16 (dd, J=9.6, 1.6 Hz, 1H), 7.47 (s, 1H), 4.52 (d, J=4.8 Hz, 2H), 2.71 (t, J=5.6 Hz, 2H), 2.55 (t, J=5.6 Hz, 2H), 1.76-1.70 (m, 4H).

Synthesis of (5-fluoro-6-((4,5,6,7-tetrahydrobenzo[b]thiophene-2-carboxamido)methyl)pyridin-3-yl)boronic acid

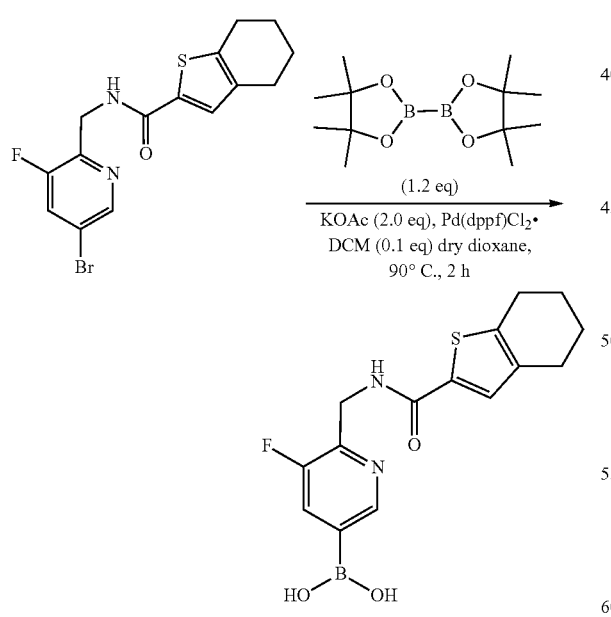

To a solution of N-((5-bromo-3-fluoropyridin-2-yl)methyl)-4,5,6,7-tetrahydrobenzo[b]thiophene-2-carboxamide (147 mg, 0.4 mmol) in dry dioxane (5 mL,) were added 4,4,4',4',5,5,5',5'-octamethyl-2,2'-bi(1,3,2-dioxaborolane) (116 mg, 0.48 mmol), KOAc (78 mg, 0.8 mmol) and Pd(dppf)Cl$_2$DCM (33 mg, 0.04 mmol) under nitrogen. The mixture was stirred at 90° C. for 2 h. After cooling down to rt, the mixture was filtered through Celite pad and the filtrate was purified by prep-HPLC (CH$_3$CN/H$_2$O with 0.05% TFA as mobile phase) to give compound (5-fluoro-6-((4,5,6,7-tetrahydrobenzo[b]thiophene-2-carboxamido)methyl)pyridin-3-yl)boronic acid (115 mg, yield: 86%) as light yellow solid ESI-MS (M+H)$^+$: 335.1. $^1$H NMR (400 MHz, DMSO-d$_6$) δ: 8.83 (t, J=5.6 Hz, 1H), 8.64 (s, 1H), 7.84 (d, J=10.4 Hz, 1H), 7.60 (s, 1H), 4.57 (d, J=5.2 Hz, 2H), 2.71 (t, J=5.6 Hz, 2H), 2.55 (t, J=5.6 Hz, 2H), 1.76-1.72 (m, 4H).

Synthesis of N-((5-(2-aminopyrimidin-4-yl)-3-fluoropyridin-2-yl)methyl)-4,5,6,7-tetrahydrobenzo[b]thiophene-2-carboxamide

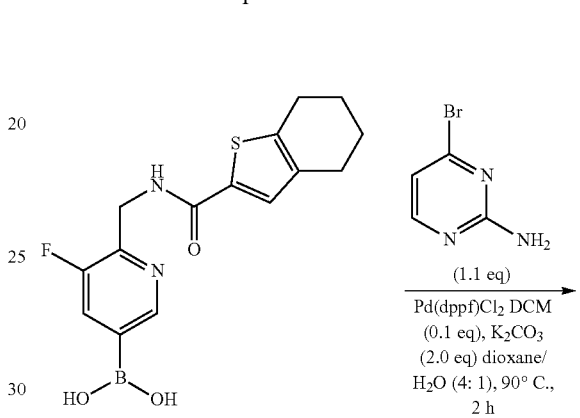

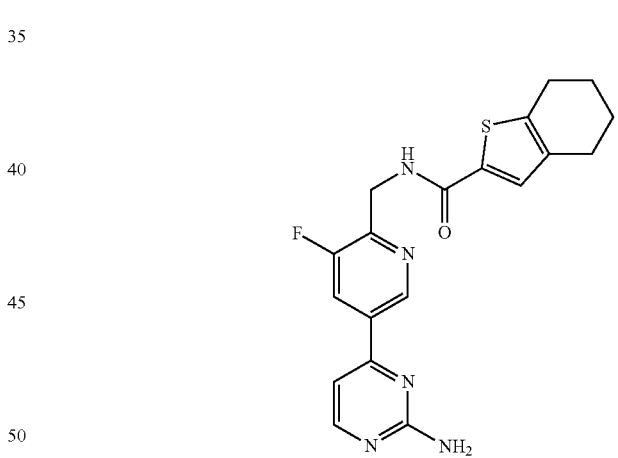

Synthesis of N-((5-(2-aminopyrimidin-4-yl)-3-fluoropyridin-2-yl)methyl)-4,5,6,7-tetrahydrobenzo[b]thiophene-2-carboxamide was similar to that of tert-butyl 4-(2-chloropyrimidin-4-yl)-2-methylbenzylcarbamate. The crude product was purified by prep-HPLC (CH$_3$CN/H$_2$O with 0.05% NH$_3$.H$_2$O as mobile phase) to give compound N-((5-(2-aminopyrimidin-4-yl)-3-fluoropyridin-2-yl)methyl)-4,5,6,7-tetrahydrobenzo[b]thiophene-2-carboxamide (23 mg, yield: 12%) as light yellow solid. ESI-MS (M+H)$^+$: 384.2. HPLC: (214 nm: 95.06%, 254 nm: 99.27%). $^1$H NMR (400 MHz, DMSO-d$_6$) δ: 9.05 (s, 1H), 8.89 (t, J=4.8 Hz, 1H), 8.37 (d, J=4.8 Hz, 1H), 8.26-8.23 (m, 1H), 7.50 (s, 1H), 7.25 (d, J=4.8 Hz, 1H), 6.84 (s, 2H), 4.62 (d, J=5.2 Hz, 2H), 2.72 (t, J=5.6 Hz, 2H), 2.57 (t, J=5.6 Hz, 2H), 1.78-1.72 (m, 4H).

Example 113: 2-(tert-butyl)-N-(2-methyl-4-(6-((1-methyl-1H-pyrazol-4-yl)amino)pyridazin-4-yl)benzyl)thiazole-5-carboxamide (I-114)

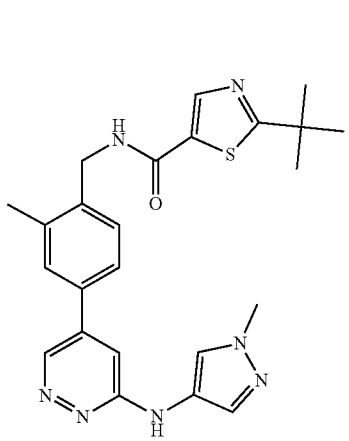

I-114

Synthesis of 2-(tert-butyl)-N-(4-(6-hydroxypyridazin-4-yl)-2-methylbenzyl)thiazole-5-carboxamide

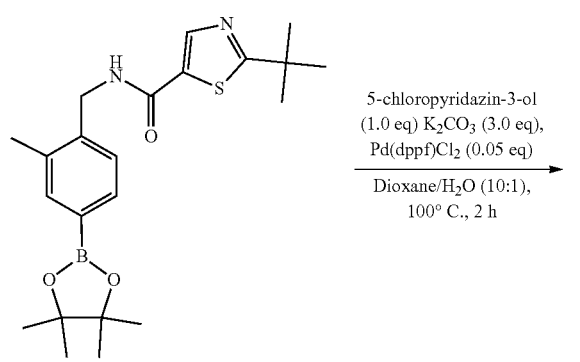

Synthesis of 2-(tert-butyl)-N-(4-(6-hydroxypyridazin-4-yl)-2-methylbenzyl)thiazole-5-carboxamide was similar to that of tert-butyl 4-(2-chloropyrimidin-4-yl)-2-methylbenzylcarbamate, starting from 5-chloropyridazin-3-ol. The residue was purified by prep-HPLC ($CH_3CN/H_2O$ with 0.05% $NH_3 \cdot H_2O$ as mobile phase) to give compound 2-(tert-butyl)-N-(4-(6-hydroxypyridazin-4-yl)-2-methylbenzyl)thiazole-5-carboxamide (200 mg, yield: 87%) as a white solid. ESI-MS (M+H)$^+$: 383.2.

Synthesis of 2-(tert-butyl)-N-(4-(6-chloropyridazin-4-yl)-2-methylbenzyl)thiazole-5-carboxamide

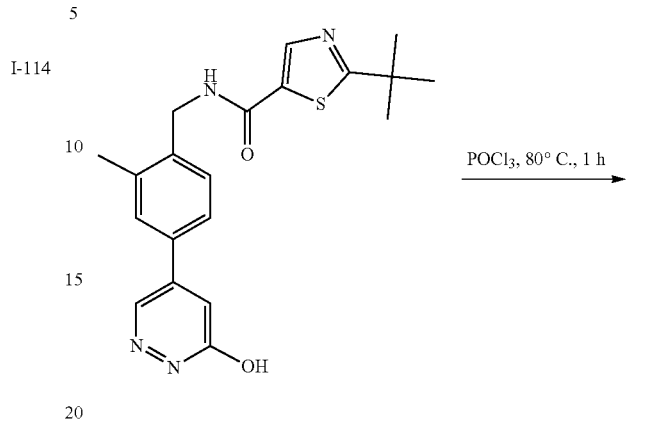

A mixture of 2-(tert-butyl)-N-(4-(6-chloropyridazin-4-yl)-2-methylbenzyl)thiazole-5-carboxamide (200 mg, 0.52 mmol) in $POCl_3$ (10 mL) was stirred at 80° C. for 1 h. The mixture was evaporated and the residue was purified by pre-TLC (petroleum ether/EtOAc=1:1) to give 2-(tert-butyl)-N-(4-(6-chloropyridazin-4-yl)-2-methylbenzyl)thiazole-5-carboxamide (90 mg, yield: 43%) as a white solid. ESI-MS (M+H)$^+$: 401.1.

Synthesis of 2-(tert-butyl)-N-(2-methyl-4-(6-((1-methyl-1H-pyrazol-4-yl)amino)pyridazin-4-yl)benzyl)thiazole-5-carboxamide

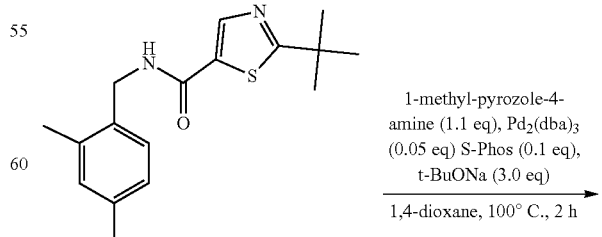

-continued

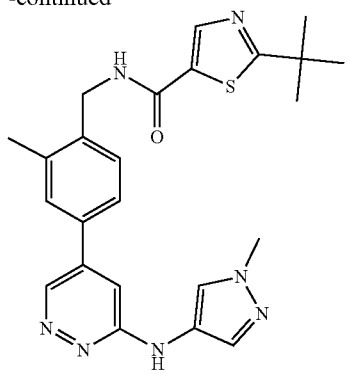

Synthesis of 2-(tert-butyl)-N-(2-methyl-4-(6-((1-methyl-1H-pyrazol-4-yl)amino)pyridazin-4-yl)benzyl)thiazole-5-carboxamide was similar to that of tert-butyl 2-methyl-4-(2-((1-methyl-1H-pyrazol-4-yl)amino)pyrimidin-4-yl)benzylcarbamate, starting from 1-methyl-1H-pyrazol-4-amine. The residue was purified by prep-HPLC (CH$_3$CN/H$_2$O with 0.05% NH$_3$.H$_2$O as mobile phase) to give compound 2-(tert-butyl)-N-(2-methyl-4-(6-((1-methyl-1H-pyrazol-4-yl)amino)pyridazin-4-yl)benzyl)thiazole-5-carboxamide (7 mg, yield: 7%) as a yellow solid. ESI-MS (M+H)$^+$: 462.2. $^1$HNMR (400 MHz, CD$_3$OD) δ:8.72 (d, J=2.0 Hz, 1H), 8.13 (s, 1H), 7.96 (s, 1H), 7.47-7.45 (m, 3H), 7.34 (d, J=7.6 Hz, 1H), 7.06 (d, J=2.0 Hz, 1H), 4.51 (s, 2H), 3.79 (s, 3H), 2.37 (s, 3H), 1.36 (s, 9H).

Example 114: N-(4-(2-((1-methyl-1H-pyrazol-4-yl)amino)pyrimidin-4-yl)-2-(trifluoromethyl)benzyl)-6,7-dihydro-4H-thieno[3,2-c]pyran-2-carboxamide (I-115)

I-115

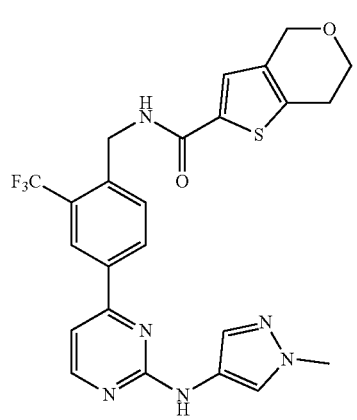

Synthesis of tert-butyl 4-bromo-2-(trifluoromethyl)benzylcarbamate

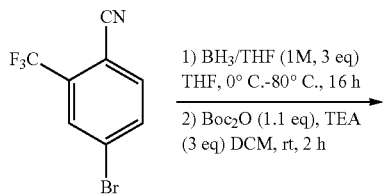

-continued

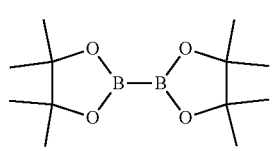

To a solution of 4-bromo-2-(trifluoromethyl)benzonitrile (2.5 g, 10 mmol) in THF (10 mL) in an ice/water bath was added BH$_3$/THF (1M, 30 mL, 30 mmol, 3 equiv) slowly under nitrogen. After addition, the mixture was heated to 80° C. for 16 h. The mixture was cooled to rt and quenched with methanol, acidized with a solution of HCl (conc.) in EA. The formed precipitate was collected through filtering to give a white solid. The solid was dissolved in DCM (20 mL) followed by addition of Boc$_2$O (2.38 g, 11 mmol) and TEA (3.03 g, 30 mmol, 3 equiv). The mixture was stirred at rt for 2 h. The solvent was diluted with DCM (80 mL), washed with brine (20 mL×2). The organic layer was dried, concentrated. The crude was purified through silica gel column chromatography (EtOAc/petroleum ether=1/10) to give tert-butyl 4-bromo-2-(trifluoromethyl)benzylcarbamate as a white solid (1.76 g, yield: 50%). ESI-MS (M+H-56)$^+$: 298.0. $^1$H NMR (400 MHz, CDCl$_3$) δ: 7.76 (s, 1H), 7.66 (d, J=8.4 Hz, 1H), 7.47 (d, J=7.6 Hz, 1H), 4.91 (br, 1H), 4.44 (d, J=6.4 Hz, 2H), 1.45 (s, 9H).

Synthesis of tert-butyl 4-(4,4,5,5-tetramethyl-1,3,2-dioxaborolan-2-yl)-2-(trifluoromethyl)benzylcarbamate

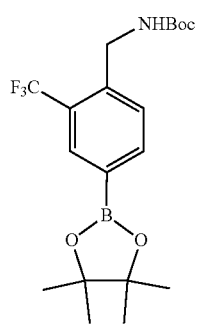

Synthesis of tert-butyl 4-(4,4,5,5-tetramethyl-1,3,2-dioxaborolan-2-yl)-2-(trifluoromethyl)benzylcarbamate was similar to that of tert-butyl 2-methyl-4-(4,4,5,5-tetramethyl-1,3,2-dioxaborolan-2-yl)benzylcarbamate. Purified through silica gel column chromatography with (EtOAc/petroleum ether=1/10) to give tert-butyl 4-(4,4,5,5-tetramethyl-1,3,2-

Synthesis of tert-butyl 4-(2-chloropyrimidin-4-yl)-2-(trifluoromethyl)benzylcarbamate

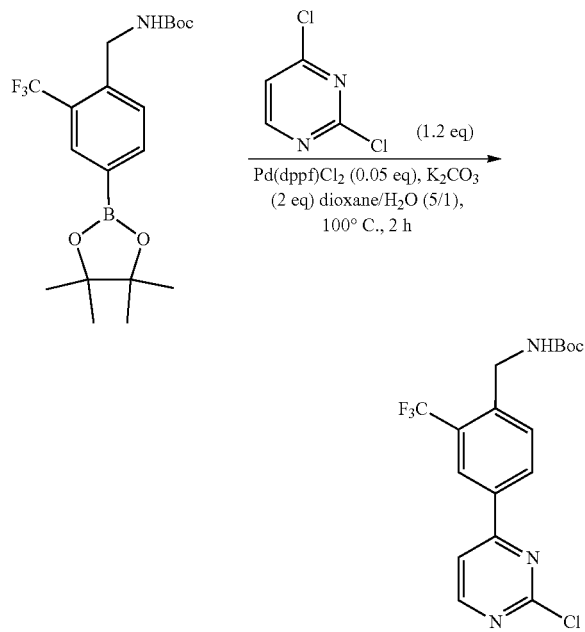

Synthesis of tert-butyl 4-(2-chloropyrimidin-4-yl)-2-(trifluoromethyl)benzylcarbamate was similar to that of tert-butyl 4-(2-chloropyrimidin-4-yl)-2-methylbenzylcarbamate. Purified through silica gel column chromatography with (EtOAc/petroleum ether=1/5) to give tert-butyl 4-(2-chloropyrimidin-4-yl)-2-(trifluoromethyl)benzylcarbamate (175 mg, yield: 70%) as a while solid. ESI-MS (M+H)$^+$: 388.1. $^1$H NMR (400 MHz, CDCl$_3$) δ: 8.70 (d, J=5.2 Hz, 1H), 8.37 (s, 1H), 8.25 (d, J=8.4 Hz, 1H), 7.75 (d, J=8.0 Hz, 1H), 7.67 (d, J=5.2 Hz, 1H), 5.00 (br, 1H), 4.57 (d, J=6.0 Hz, 2H), 1.47 (s, 9H).

Synthesis of tert-butyl 4-(2-((1-methyl-1H-pyrazol-4-yl)amino)pyrimidin-4-yl)-2-(trifluoromethyl)benzylcarbamate

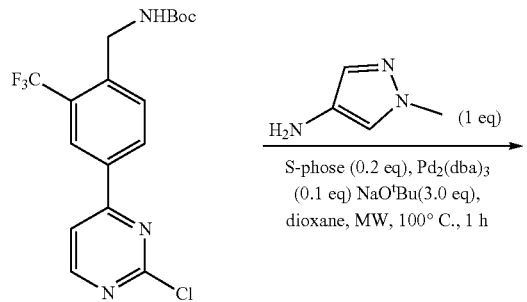

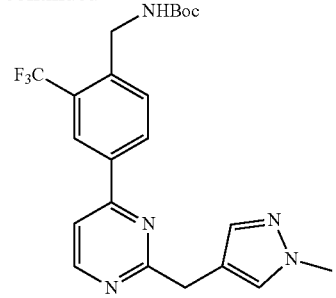

Synthesis of tert-butyl 4-(2-((1-methyl-1H-pyrazol-4-yl)amino)pyrimidin-4-yl)-2-(trifluoromethyl)benzylcarbamate was similar to that of tert-butyl 2-methyl-4-(2-((1-methyl-1H-pyrazol-4-yl)amino)pyrimidin-4-yl)benzylcarbamate. The crude was purified through silica gel column chromatography (EtOAc/petroleum ether=3/2) to give tert-butyl 4-(2-((1-methyl-1H-pyrazol-4-yl)amino)pyrimidin-4-yl)-2-(trifluoromethyl)benzylcarbamate as a yellow solid (105 mg, yield: 60%). ESI-MS (M+H)$^+$: 449.1. $^1$H NMR (400 MHz, DMSO-d$_6$) δ: 9.58 (s, 1H), 8.53 (d, J=5.2 Hz, 1H), 8.47 (s, 1H), 8.41 (d, J=8.0 Hz, 1H), 7.92 (s, 1H), 7.66 (d, J=8.4 Hz, 1H), 7.59 (t, J=6.0 Hz, 1H), 7.55 (s, 1H), 7.38 (d, J=5.2 Hz, 1H), 4.39 (d, J=5.2 Hz, 2H), 3.82 (s, 3H), 1.46 (s, 9H).

Synthesis of N-(4-(2-((1-methyl-1H-pyrazol-4-yl)amino)pyrimidin-4-yl)-2-(trifluoromethyl)benzyl)-6,7-dihydro-4H-thieno[3,2-c]pyran-2-carboxamide

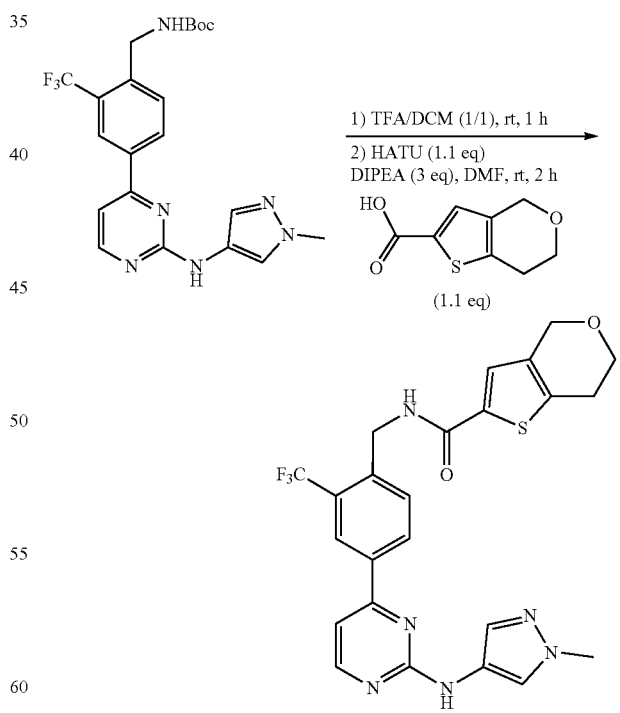

Synthesis of N-(4-(2-((1-methyl-1H-pyrazol-4-yl)amino)pyrimidin-4-yl)-2-(trifluoromethyl)benzyl)-6,7-dihydro-4H-thieno[3,2-c]pyran-2-carboxamide was similar to that of Example 1. Purified through prep-TLC (MeOH/DCM=1/25) to give N-(4-(2-((1-methyl-1H-pyrazol-4-yl)amino)pyrimidin-4-yl)-2-(trifluoromethyl)benzyl)-6,7-dihydro-4H-thieno[3,2-c]pyran-2-carboxamide (45 mg, yield: 75%) as a yellow solid. ESI-MS (M+H)$^+$: 515.0. HPLC: (214 nm: 100%, 254 nm: 99.25%). $^1$H NMR (400 MHz, CDCl$_3$) δ: 8.47 (d, J=5.2 Hz, 1H), 8.41 (s, 1H), 8.15 (d, J=8.0 Hz, 1H), 7.90 (s, 1H), 7.77 (d, J=8.0 Hz, 1H), 7.52 (s, 1H), 7.18 (s, 1H), 7.09 (d, J=5.2 Hz, 1H), 7.00 (s, 1H), 6.31 (t, J=6.0 Hz, 1H), 4.84 (d, J=5.6 Hz, 2H), 4.67 (s, 2H), 3.97 (t, J=5.6 Hz, 2H), 3.92 (s, 3H), 2.89 (t, J=5.6 Hz, 2H).

Example 115: 2-(tert-butyl)-N-(4-(2-((1-methyl-1H-pyrazol-4-yl)amino)pyrimidin-4-yl)-2-(trifluoromethyl)benzyl)thiazole-5-carboxamide. (I-116)

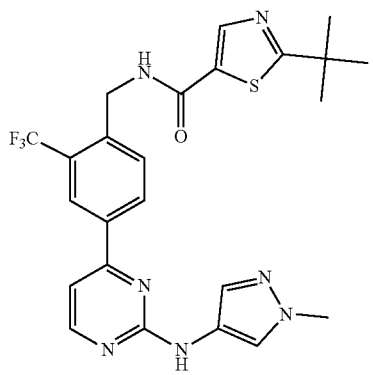

I-116

Synthesis of 2-(tert-butyl)-N-(4-(2-((1-methyl-1H-pyrazol-4-yl)amino)pyrimidin-4-yl)-2-(trifluoromethyl)benzyl)thiazole-5-carboxamide was similar to that of Example 1. Purified through prep-TLC (MeOH/DCM=1/20) to give 2-(tert-butyl)-N-(4-(2-((1-methyl-1H-pyrazol-4-yl)amino)pyrimidin-4-yl)-2-(trifluoromethyl)benzyl)thiazole-5-carboxamide (30 mg, yield: 57%) as a yellow solid. ESI-MS (M+H)$^+$: 516.2. HPLC: (214 nm: 100%, 254 nm: 98.40%). $^1$H NMR (400 MHz, DMSO-d$_6$) δ: 9.59 (s, 1H), 9.30 (t, J=6.0 Hz, 1H), 8.54 (d, J=5.2 Hz, 1H), 8.50 (s, 1H), 8.39 (d, J=8.0 Hz, 1H), 8.36 (s, 1H), 7.92 (s, 1H), 7.70 (d, J=8.4 Hz, 1H), 7.55 (s, 1H), 7.38 (d, J=5.2 Hz, 1H), 4.70 (d, J=5.6 Hz, 2H), 3.81 (s, 3H), 1.40 (s, 9H).

Example 116: N-(2-fluoro-4-(2-((1-methyl-1H-pyrazol-4-yl)amino)pyrimidin-4-yl)benzyl)-6,7-dihydro-4H-thieno[3,2-c]pyran-2-carboxamide (I-117)

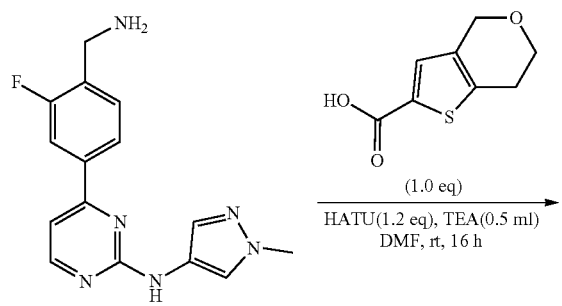

-continued

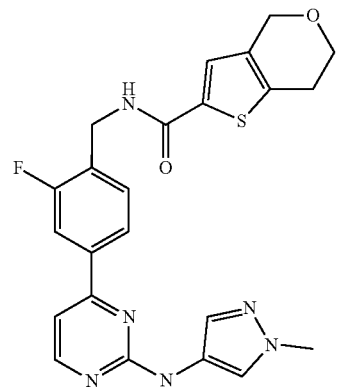

I-117

Synthesis of N-(2-fluoro-4-(2-((1-methyl-1H-pyrazol-4-yl)amino)pyrimidin-4-yl)benzyl)-6,7-dihydro-4H-thieno[3,2-c]pyran-2-carboxamide was similar to that of Example 115, starting from (4-bromo-2-fluorophenyl)methanamine. The resulting product is purified by column chromatography on silica gel (PE/EA=2:1-1:2) to give N-(2-fluoro-4-(2-((1-methyl-1H-pyrazol-4-yl)amino)pyrimidin-4-yl)benzyl)-6,7-dihydro-4H-thieno[3,2-c]pyran-2-carboxamide (22 mg, yield: 24%) as a white solid. ESI-MS (M+H)$^+$: 465.2. $^1$H NMR (400 MHz, CDCl$_3$) δ: 8.44 (d, J=5.2 Hz, 1H), 7.85 (s, 1H), 7.77-7.74 (m, 2H), 7.53-7.50 (m, 2H), 7.20 (s, 1H), 7.05-7.02 (m, 2H), 6.40 (t, J=5.2 Hz, 1H), 4.69 (d, J=5.6 Hz, 2H), 4.67 (s, 2H), 3.97 (t, J=5.6 Hz, 2H), 3.92 (s, 3H), 2.89 (t, J=5.6 Hz, 2H).

Example 117: 2-(tert-butyl)-N-(2-chloro-5-fluoro-4-(2-((1-methyl-1H-pyrazol-4-yl)amino)pyrimidin-4-yl)benzyl)thiazole-5-carboxamide (I-118)

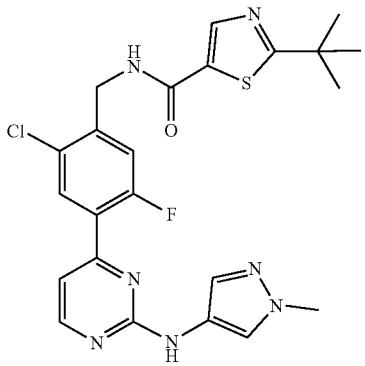

I-118

Preparation of N-(4-bromo-2-chloro-5-fluorobenzyl)-2-(tert-butyl)thiazole-5-carboxamide

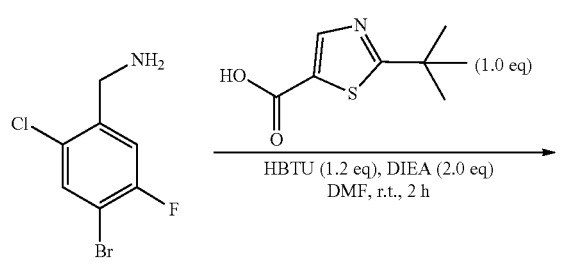

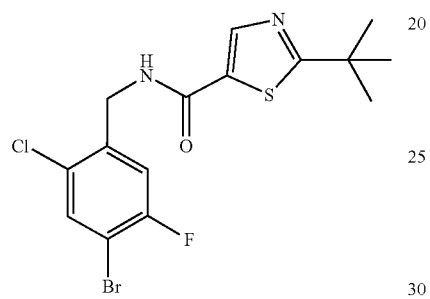

To a solution of (4-bromo-2-chloro-5-fluorophenyl)methanamine (427 mg, 2.31 mmol) in 4 mL DMF were added 2-(tert-butyl)thiazole-5-carboxylic acid (500 mg, 2.10 mmol), HBTU (955 mg, 2.52 mmol) and DIEA (542 mg, 4.20 mmol). The mixture was stirred at rt for 1.5 h. After diluted with water (30 mL), the mixture was extracted with EtOAc (60 mL×2). The combined organic layer was dried (Na$_2$SO$_4$), filtered and concentrated. The residue was purified by silica gel column chromatography (EtOAc/petroleum ether=1/4) to give product N-(4-bromo-2-chloro-5-fluorobenzyl)-2-(tert-butyl)thiazole-5-carboxamide as a pale yellow solid (540 mg, yield: 72%). ESI-MS (M+H)$^+$: 405.0.

Synthesis of 2-(tert-butyl)-N-(2-chloro-5-fluoro-4-(2-((1-methyl-1H-pyrazol-4-yl)amino)pyrimidin-4-yl)benzyl)thiazole-5-carboxamide

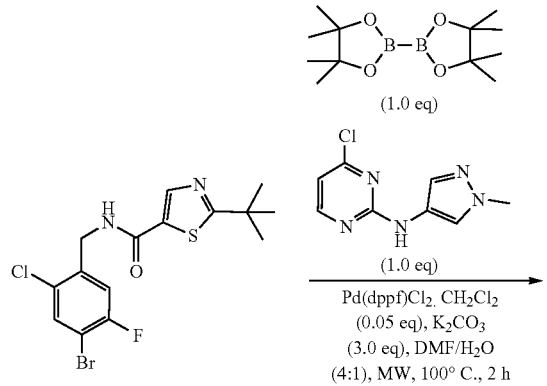

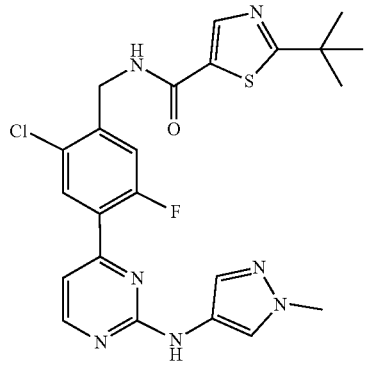

A mixture of N-(4-bromo-2-chloro-5-fluorobenzyl)-2-(tert-butyl)thiazole-5-carboxamide (240 mg, 0.60 mmol), Bis(pinacolato)diboron (156 mg, 0.60 mmol), 4-chloro-N-(1-methyl-1H-pyrazol-4-yl)pyrimidin-2-amine (136 mg, 0.60 mmol), Pd(dppf)Cl$_2$.CH$_2$Cl$_2$ (48 mg, 0.06 mmol), K$_2$CO$_3$ (246 mg, 1.80 mmol) in DMF (8 mL) and water (2 mL) was heated at 100° C. by microwave for 2 h under nitrogen. The mixture was diluted with water (20 mL) and extracted with EtOAc (60 mL×2). The organic layer was dried (Na$_2$SO$_4$), filtered and concentrated. The residue was purified by prep-HPLC(CH$_3$CN/H$_2$O with 0.05% NH$_3$H$_2$O as mobile phase) to give product 2-(tert-butyl)-N-(2-chloro-5-fluoro-4-(2-((1-methyl-1H-pyrazol-4-yl)amino)pyrimidin-4-yl)benzyl)thiazole-5-carboxamide as a pale yellow solid (26 mg, yield: 9%). ESI-MS (M+H)$^+$: 500.1. HPLC: (214 nm: 100%, 254 nm: 100%). $^1$H NMR (400 MHz, DMSO-d$_6$) δ: 9.61 (s, 1H), 9.25 (t, J=6.0 Hz, 1H), 8.51 (d, J=4.8 Hz, 1H), 8.34 (s, 1H), 8.10 (d, J=7.2 Hz, 1H), 7.87 (s, 1H), 7.53 (s, 1H), 7.36-7.34 (m, 1H), 7.13-7.10 (m, 1H), 5.54 (d, J=5.6 Hz, 2H), 3.82 (s, 3H), 1.39 (s, 9H).

Example 118: N-(2-methyl-4-(2-((5-(4-methylpiperazin-1-yl)pyridin-2-yl)amino)pyrimidin-4-yl)benzyl)-4,5,6,7-tetrahydrothieno[3,2-c]pyridine-2-carboxamide (I-119)

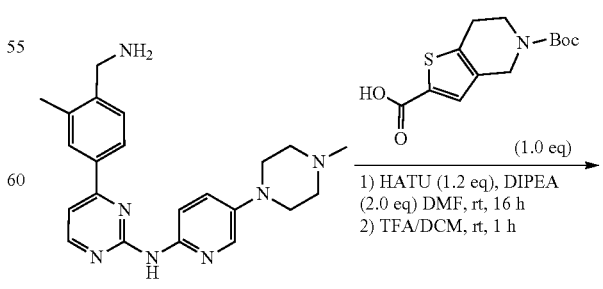

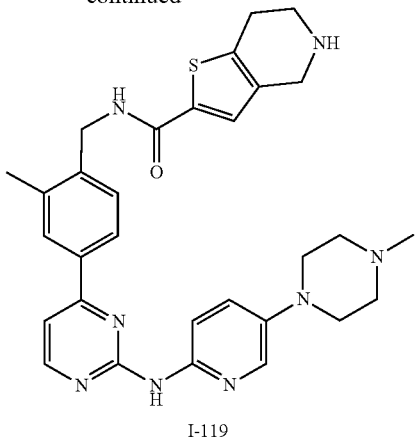

I-119

Synthesis of N-(2-methyl-4-(2-((5-(4-methylpiperazin-1-yl)pyridin-2-yl)amino)pyrimidin-4-yl)benzyl)-4,5,6,7-tetrahydrothieno[3,2-c]pyridine-2-carboxamide was similar to that of Example 1-72. The residue was purified by prep-HPLC (CH₃CN/H₂O with 0.05% TFA as mobile phase) to get product N-(2-methyl-4-(2-((5-(4-methylpiperazin-1-yl)pyridin-2-yl)amino)pyrimidin-4-yl)benzyl)-4,5,6,7-tetrahydrothieno[3,2-c]pyridine-2-carboxamide as pale yellow oil (12 mg, yield: 27%). ESI-MS (M+H)⁺: 555.2. HPLC: (214 nm: 100%, 254 nm: 100%). ¹H NMR (400 MHz, CD₃OD) δ: 8.61 (d, J=5.6 Hz, 1H), 8.07-7.94 (m, 3H), 7.96 (d, J=5.6 Hz, 1H), 7.88 (d, J=2.8 Hz, 1H), 7.45-7.36 (m, 3H), 4.52 (s, 2H), 4.21 (s, 2H), 3.95-3.49 (m, 2H), 3.47 (t, J=6.0 Hz, 4H), 3.45-3.35 (m, 2H), 3.10 (t, J=6.0 Hz, 4H), 2.90 (s, 3H), 2.39 (s, 3H).

Example 119: N-(4-(2-((1-(2-hydroxyethyl)-1H-pyrazol-4-yl)amino)pyrimidin-4-yl)-2-methylbenzyl)-6,7-dihydro-4H-thieno[3,2-c]pyran-2-carboxamide (I-120)

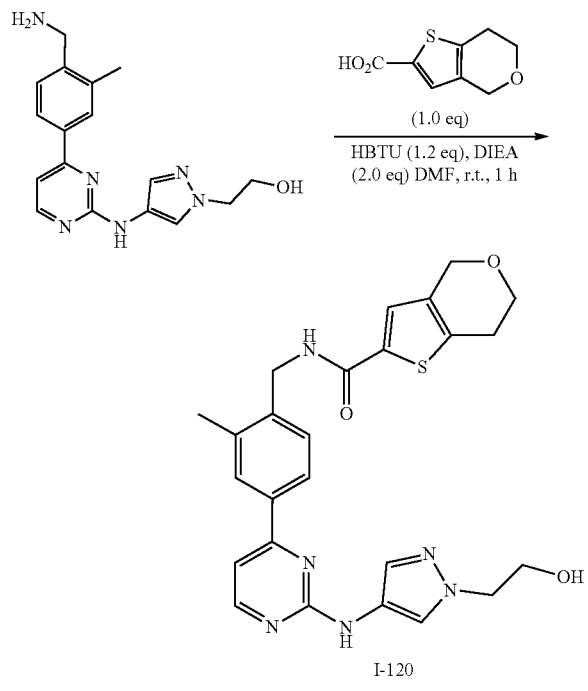

I-120

Synthesis of N-(4-(2-((1-(2-hydroxyethyl)-1H-pyrazol-4-yl)amino)pyrimidin-4-yl)-2-methylbenzyl)-6,7-dihydro-4H-thieno[3,2-c]pyran-2-carboxamide was similar to that of Example 1. The crude product was purified by silica gel column chromatography (EtOAc/petroleum ether=1/2 then EA) to give product N-(4-(2-((1-(2-hydroxyethyl)-1H-pyrazol-4-yl)amino)pyrimidin-4-yl)-2-methylbenzyl)-6,7-dihydro-4H-thieno[3,2-c]pyran-2-carboxamide as a yellow solid (70 mg, yield: 56%). ESI-MS (M+H)⁺: 491.1. HPLC: (214 nm: 94%, 254 nm: 96%). ¹H NMR (400 MHz, DMSO-d₆) δ: 9.48 (s, 1H), 8.89 (t, J=5.2 Hz, 1H), 8.45 (d, J=4.4 Hz, 1H), 8.01-7.92 (m, 3H), 7.55 (d, J=8.0 Hz, 1H), 7.54 (s, 1H), 7.37 (d, J=8.0 Hz, 1H), 7.25 (d, J=4.4 Hz, 1H), 4.90 (s, 1H), 4.61 (s, 2H), 4.47 (d, J=5.6 Hz, 2H), 4.11 (t, J=5.6 Hz, 2H), 3.88 (t, J=5.6 Hz, 2H), 3.75-3.71 (m, 2H), 2.84 (t, J=5.2 Hz, 2H), 2.41 (s, 3H).

Example 120: 3-isopropoxy-N-(2-methyl-4-(6-((5-methyl-4,5,6,7-tetrahydropyrazolo[1,5-a]pyrazin-2-yl)amino)pyrimidin-4-yl)benzyl)azetidine-1-carboxamide (I-121)

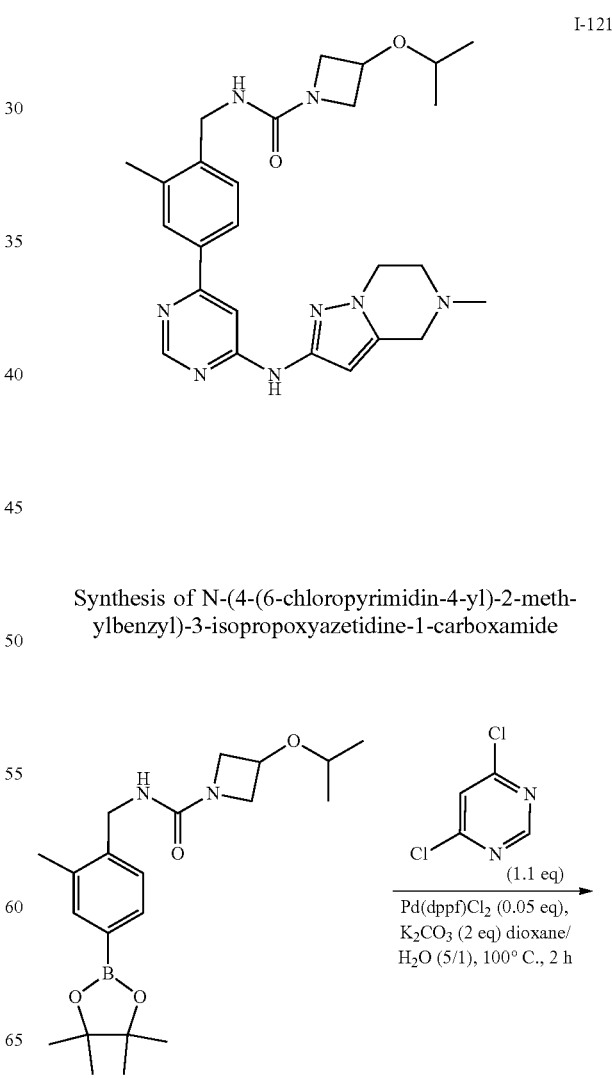

Synthesis of N-(4-(6-chloropyrimidin-4-yl)-2-methylbenzyl)-3-isopropoxyazetidine-1-carboxamide

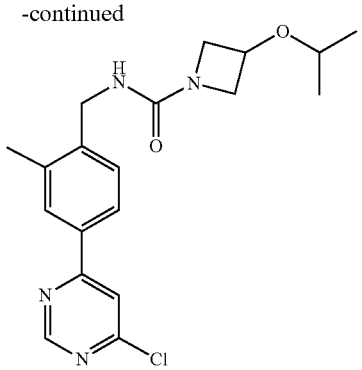

Synthesis of N-(4-(6-chloropyrimidin-4-yl)-2-methylbenzyl)-3-isopropoxyazetidine-1-carboxamide was similar to that of tert-butyl 4-(2-chloropyrimidin-4-yl)-2-methylbenzylcarbamate. The crude was purified through silica gel column chromatography (MeOH/DCM=1/30) to give N-(4-(6-chloropyrimidin-4-yl)-2-methylbenzyl)-3-isopropoxyazetidine-1-carboxamide (130 mg, yield: 77%) as yellow oil. ESI-MS (M+H)$^+$: 375.0.

Synthesis of 3-isopropoxy-N-(2-methyl-4-(6-((5-methyl-4,5,6,7-tetrahydropyrazolo[1,5-a]pyrazin-2-yl)amino)pyrimidin-4-yl)benzyl)azetidine-1-carboxamide

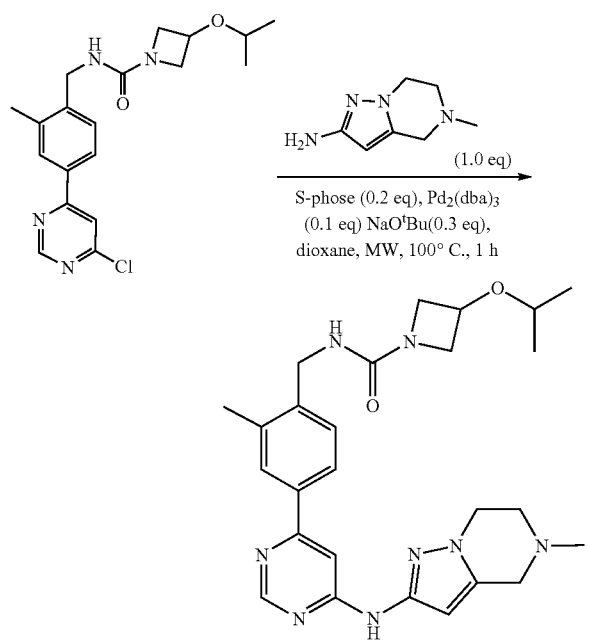

Synthesis of 3-isopropoxy-N-(2-methyl-4-(6-((5-methyl-4,5,6,7-tetrahydropyrazolo[1,5-a]pyrazin-2-yl)amino)pyrimidin-4-yl)benzyl)azetidine-1-carboxamide was similar to that of tert-butyl 2-methyl-4-(2-((1-methyl-1H-pyrazol-4-yl)amino)pyrimidin-4-yl)benzylcarbamate. The crude was purified through silica gel column chromatography (MeOH/DCM=1/20) to give 3-isopropoxy-N-(2-methyl-4-(6-((5-methyl-4,5,6,7-tetrahydropyrazolo[1,5-a]pyrazin-2-yl)amino)pyrimidin-4-yl)benzyl)azetidine-1-carboxamide (30 mg, yield: 18%) as a yellow solid. ESI-MS (M+H)$^+$: 491.2.

HPLC: (214 nm: 95.69%, 254 nm: 97.57%). $^1$H NMR (400 MHz, CD$_3$OD) δ: 8.48 (s, 1H), 7.64 (s, 1H), 7.63 (d, J=7.6 Hz, 1H), 7.41 (s, 1H), 7.26 (d, J=7.6 Hz, 1H), 6.14 (s, 1H), 4.32-4.29 (m, 1H), 4.26 (s, 2H), 4.08-4.01 (m, 4H), 3.71-3.67 (m, 2H), 3.57 (s, 2H), 3.56-3.52 (m, 1H), 2.87 (t, J=6.0 Hz, 2H), 2.40 (s, 3H), 2.30 (s, 3H), 1.05 (d, J=6.0 Hz, 6H).

Example 121: (R)-2-(tert-butyl)-N-(2-methyl-4-(2-((1-(pyrrolidin-3-yl)-1H-pyrazol-4-yl)amino)pyrimidin-4-yl)benzyl)thiazole-5-carboxamide (I-122)

I-122

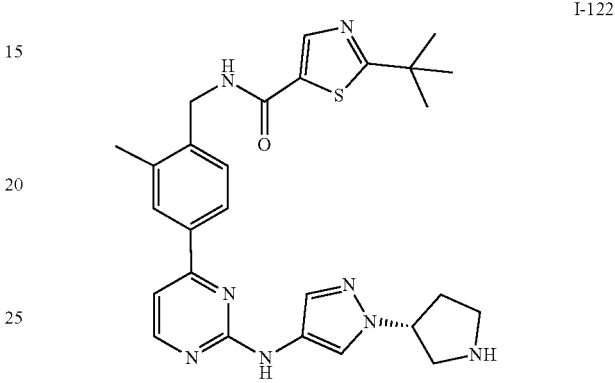

Synthesis of (S)-tert-butyl 3-(tosyloxy)pyrrolidine-1-carboxylate

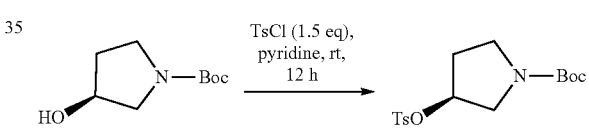

To a mixture of (S)-tert-butyl 3-hydroxypyrrolidine-1-carboxylate (1 g, 5.3 mmol, 1.0 equiv) in pyridine (20 mL), TsCl (1.53 g, 7.95 mmol, 1.5 equiv) was added. The mixture was stirred at rt for 12 h. After concentrated, the residue was diluted with EtOAc (200 mL) and washed with water (50 mL), HCl (1 N, 50 mL), brine (50 mL). The organic layer was dried and concentrated to give (S)-tert-butyl 3-(tosyloxy)pyrrolidine-1-carboxylate (1.3 g, yield: 71%) as a colorless oil, which was used for next step without further purification. ESI-MS (M+Na)$^+$: 364.0.

Synthesis of (R)-tert-butyl 3-(4-nitro-1H-pyrazol-1-yl)pyrrolidine-1-carboxylate

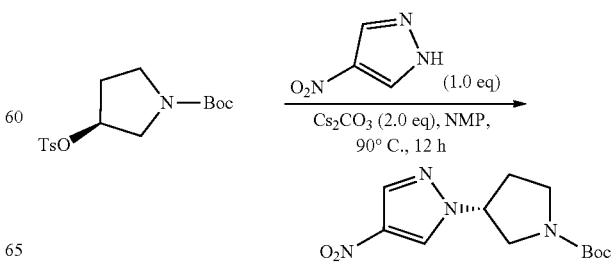

To a mixture of (S)-tert-butyl 3-(tosyloxy)pyrrolidine-1-carboxylate (1.3 g, 3.8 mmol, 1.0 equiv) in NMP (10 mL), 4-nitro-1H-pyrazole (429 mg, 3.8 mmol, 1.0 equiv) and $Cs_2CO_3$ (2.47 g, 7.6 mmol, 2.0 equiv) were added. The mixture was stirred at 90° C. for 12 h. After cooling down to rt, the mixture was diluted with EtOAc (150 mL) and washed with water (50 mL×4). The organic layer was concentrated and purified by silica gel column (PE:EA=3:1) to give (R)-tert-butyl 3-(4-nitro-1H-pyrazol-1-yl)pyrrolidine-1-carboxylate (500 mg, yield: 47%) as a yellow solid. ESI-MS (M+Na)+:305.1. $^1$H NMR (400 MHz, $CDCl_3$) δ: 8.17 (s, 1H), 8.09 (s, 1H), 4.91-4.89 (m, 1H), 3.89-3.85 (m, 2H), 3.56-3.50 (m, 2H), 2.43-2.41 (m, 2H), 1.48 (s, 9H).

Synthesis of (R)-tert-butyl 3-(4-amino-1H-pyrazol-1-yl)pyrrolidine-1-carboxylate A mixture of Pd/C (29 mg, 10% wt) and (R)-tert-butyl 3-(4-nitro-1H-pyrazol-1-yl)pyrrolidine-1-carboxylate (290 mg, 1.1 mmol, 1.0 equiv) in MeOH (5 mL) was stirred for at rt 12 h under hydrogen atmosphere (balloon pressure). The catalyst was filtered out and the resulting filtrate was concentrated to give target compound (R)-tert-butyl 3-(4-amino-1H-pyrazol-1-yl)pyrrolidine-1-carboxylate (260 mg, yield: 100%) as a yellow oil. ESI-MS (M+H)$^+$: 253.2.

Synthesis of (R)-tert-butyl 3-(44(4-(44(2-(tert-butyl)thiazole-5-carboxamido)methyl)-3-methylphenyl)pyrimidin-2-yl)amino)-1H-pyrazol-1-yl)pyrrolidine-1-carboxylate

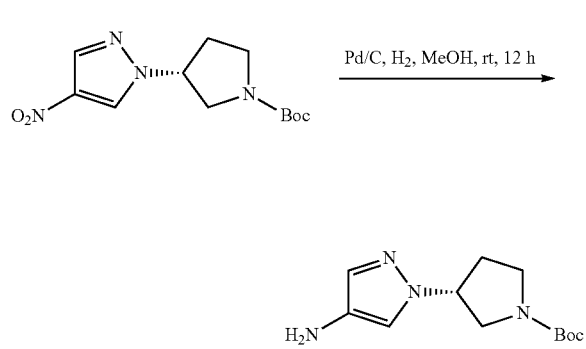

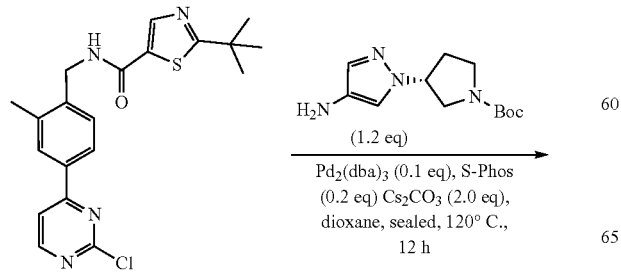

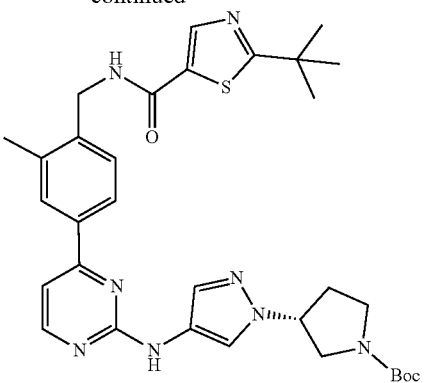

To a mixture of 2-(tert-butyl)-N-(4-(2-chloropyrimidin-4-yl)-2-methylbenzyl)thiazole-5-carboxamide (250 mg, 0.625 mmol, 1.0 equiv) and (R)-tert-butyl 3-(4-amino-1H-pyrazol-1-yl)pyrrolidine-1-carboxylate (189 mg, 0.75 mmol, 1.2 equiv) in 1,4-dioxane (10 mL), $Cs_2CO_3$ (407 mg, 1.25 mmol, 2.0 equiv), $Pd_2(dba)_3$ (57 mg, 0.063 mmol, 0.1 eq) and S-Phos (51 mg, 0.13 mmol, 0.2 equiv) were added quickly under $N_2$. The mixture was stirred at 120° C. for 12 h. After cooling down, the mixture was concentrated and diluted with EtOAc (150 mL). The organic phase was washed with brine, dried and purified by prep-HPLC (Gradient: 5% B increase to 95% B, A: 0.5% $NH_3$ in water, B: $CH_3CN$) to give (R)-tert-butyl 3-(4-((4-(4-((2-(tert-butyl)thiazole-5-carboxamido)methyl)-3-methylphenyl)pyrimidin-2-yl)amino)-1H-pyrazol-1-yl)pyrrolidine-1-carboxylate (200 mg, yield: 53%) as a yellow solid. ESI-MS (M+H)$^+$: 617.3

Synthesis of (R)-2-(tert-butyl)-N-(2-methyl-4-(2-((1-(pyrrolidin-3-yl)-1H-pyrazol-4-yl)amino)pyrimidin-4-yl)benzyl)thiazole-5-carboxamide

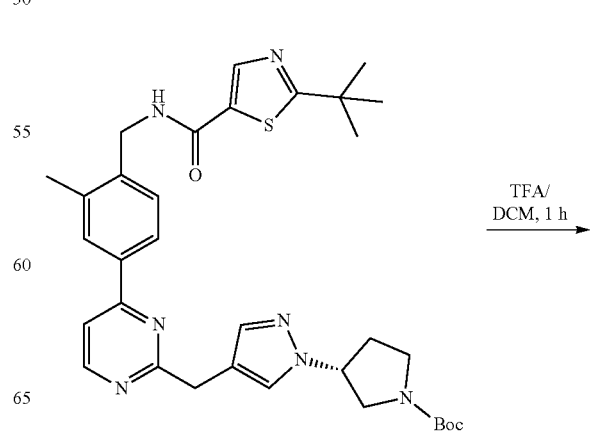

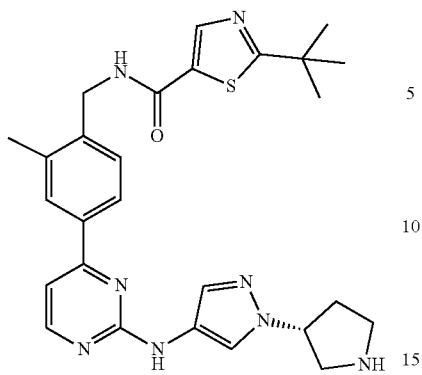

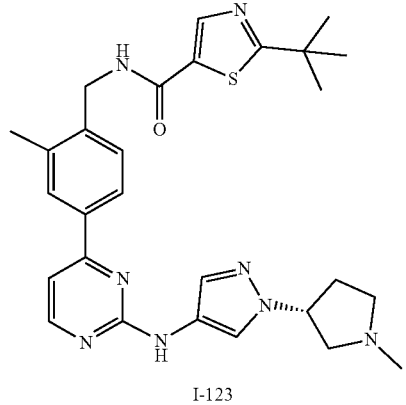

I-123

To a solution of (R)-2-(tert-butyl)-N-(2-methyl-4-(2-((1-(pyrrolidin-3-yl)-1H-pyrazol-4-yl)amino)pyrimidin-4-yl)benzyl)thiazole-5-carboxamide (170 mg, 0.32 mmol, 1.0 equiv) in MeOH (5 mL) was added (HCHO)$_n$ (20 mg, 0.64 mmol, 2.0 equiv) and NaBH$_3$CN (41 mg, 0.64 mmol, 2.0 equiv). The mixture was stirred at room temperature for 12 h. After concentrated, the residue was purified by pre-TLC (DCM:MeOH=10:1) to give (R)-2-(tert-butyl)-N-(2-methyl-4-(2-((1-(1-methylpyrrolidin-3-yl)-1H-pyrazol-4-yl)amino)pyrimidin-4-yl)benzyl)thiazole-5-carboxamide (53 mg, yield: 30%) as a yellow solid. ESI-MS (M+H)$^+$: 531.2. $^1$H NMR (400 MHz, CD$_3$OD) δ: 8.40 (d, J=5.2 Hz, 1H), 8.24 (s, 1H), 8.17 (s, 1H), 7.97-7.95 (m, 2H), 7.65 (s, 1H), 7.43 (d, J=8.0 Hz, 1H), 7.20 (d, J=5.2 Hz, 1H), 4.96-4.89 (m, 1H), 4.62 (s, 2H), 3.07-3.02 (m, 1H), 2.91-2.85 (m, 2H), 2.71-2.65 (m, 1H), 2.65-2.54 (m, 4H), 2.41 (s, 3H), 2.25-2.19 (m, 1H), 1.46 (s, 9H).

A solution of (R)-tert-butyl 3-(4-((4-(4-((2-(tert-butyl)thiazole-5-carboxamido)methyl)-3-methylphenyl)pyrimidin-2-yl)amino)-1H-pyrazol-1-yl)pyrrolidine-1-carboxylate (200 mg, 0.32 mmol, 1.0 equiv) in TFA/DCM (0.5 mL/2 mL) was stirred at rt for 1 h. The mixture was concentrated and purified by prep-HPLC (Gradient: 5% B increase to 95% B, A: 0.5% NH$_3$ in water, B: CH$_3$CN) to give (R)-2-(tert-butyl)-N-(2-methyl-4-(2-((1-(pyrrolidin-3-yl)-1H-pyrazol-4-yl)amino)pyrimidin-4-yl)benzyl)thiazole-5-carboxamide (130 mg, yield: 77%) as a yellow solid. ESI-MS (M+H)$^+$: 517.2. $^1$H NMR (400 MHz, CDCl$_3$) δ: 8.42 (d, J=5.2 Hz, 1H), 8.06 (s, 1H), 7.96 (s, 1H), 7.86 (s, 1H), 7.83 (d, J=7.6 Hz, 1H), 7.54 (s, 1H), 7.39 (d, J=8.4 Hz, 1H), 7.18 (s, 1H), 7.06 (d, J=5.2 Hz, 1H), 6.34 (t, J=4.4 Hz, 1H), 4.82-4.79 (m, 1H), 4.66 (d, J=5.2 Hz, 2H), 3.32-3.26 (m, 2H), 3.19-3.16 (m, 1H), 3.02-2.95 (m, 1H), 2.44 (s, 3H), 2.35-2.15 (m, 2H), 1.45 (s, 9H).

Example 122: (R)-2-(tert-butyl)-N-(2-methyl-4-(2-((1-(1-methylpyrrolidin-3-yl)-1H-pyrazol-4-yl)amino)pyrimidin-4-yl)benzyl)thiazole-5-carboxamide (I-123)

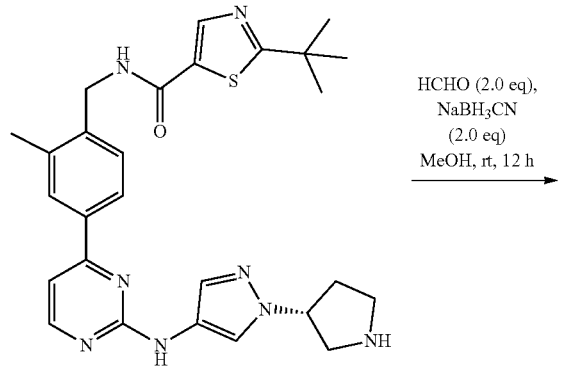

HCHO (2.0 eq),
NaBH$_3$CN
(2.0 eq)
MeOH, rt, 12 h

Example 123: (S)-2-(tert-butyl)-N-(2-methyl-4-(2-((1-(pyrrolidin-3-yl)-1H-pyrazol-4-yl)amino)pyrimidin-4-yl)benzyl)thiazole-5-carboxamide (I-124)

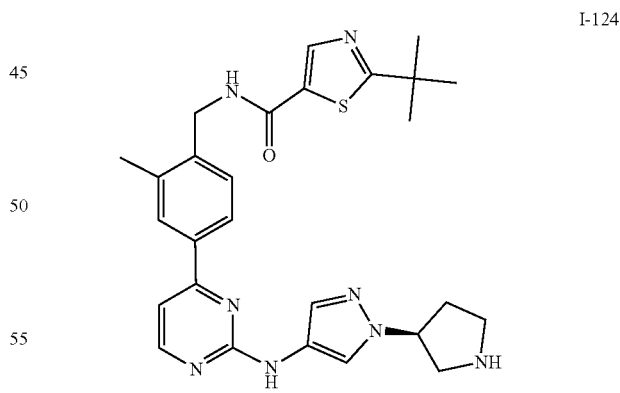

I-124

Synthesis of (S)-2-(tert-butyl)-N-(2-methyl-4-(2-((1-(pyrrolidin-3-yl)-1H-pyrazol-4-yl)amino)pyrimidin-4-yl)benzyl)thiazole-5-carboxamide was similar to that of Example 121. The mixture was concentrated and purified by prep-HPLC (Gradient: 5% B increase to 95% B, A: 0.5% TFA in water, B: CH$_3$CN) to give (S)-2-(tert-butyl)-N-(2-methyl-4-(2-((1-(pyrrolidin-3-yl)-1H-pyrazol-4-yl)amino)pyrimidin-4-yl)benzyl)thiazole-5-carboxamide (51 mg, yield: 64%) as a yellow solid. ESI-MS (M+H)$^+$: 517.2. $^1$H NMR (400 MHz, CD$_3$OD) δ: 8.37 (d, J=6.0 Hz, 1H), 8.25 (s, 1H), 8.11 (s, 1H), 8.01-7.99 (m, 2H), 7.79 (s, 1H), 7.46 (d, J=7.6 Hz, 1H), 7.39 (d, J=6.0 Hz, 1H), 5.26-5.23 (m, 1H), 4.62 (s, 2H), 3.81-3.78 (m, 1H), 3.73-3.64 (m, 2H), 3.55-3.49 (m, 1H), 2.61-2.51 (m, 1H), 2.48 (s, 3H), 2.44-2.37 (m, 1H), 1.46 (s, 9H).

Example 124: (S)-2-(tert-butyl)-N-(2-methyl-4-(2-((1-(1-methylpyrrolidin-3-yl)-1H-pyrazol-4-yl)amino)pyrimidin-4-yl)benzyl)thiazole-5-carboxamide (I-125)

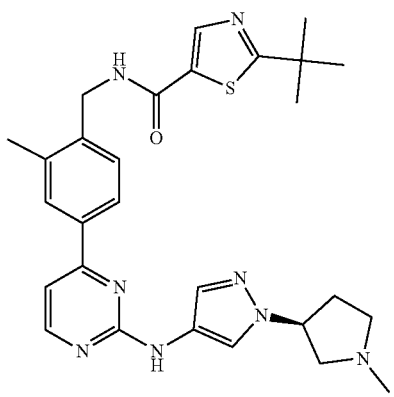

I-125

Synthesis of (S)-2-(tert-butyl)-N-(2-methyl-4-(2-((1-(1-methylpyrrolidin-3-yl)-1H-pyrazol-4-yl)amino)pyrimidin-4-yl)benzyl)thiazole-5-carboxamide was similar to that of Example 122. The mixture was concentrated and purified by silica gel column chromatography (DCM:MeOH=25:1 to 10:1) to give (S)-2-(tert-butyl)-N-(2-methyl-4-(2-((1-(1-methylpyrrolidin-3-yl)-1H-pyrazol-4-yl)amino)pyrimidin-4-yl)benzyl)thiazole-5-carboxamide (76 mg, yield: 69%) as a yellow solid. ESI-MS (M+H)$^+$: 531.2. $^1$H NMR (400 MHz, CD$_3$OD) δ: 8.38 (d, J=5.2 Hz, 1H), 8.25 (s, 1H), 8.11 (s, 1H), 7.94-7.91 (m, 2H), 7.74 (s, 1H), 7.41 (d, J=8.0 Hz, 1H), 7.18 (d, J=5.2 Hz, 1H), 5.21-5.16 (m, 1H), 4.60 (s, 2H), 3.66-3.61 (m, 3H), 3.34-3.33 (m, 1H), 2.92 (s, 3H), 2.71-2.61 (m, 1H), 2.45 (s, 3H), 2.39-2.32 (m, 1H), 1.45 (s, 9H).

Example 125: (S)-2-(tert-butyl)-N-(2-methyl-4-(2-((1-(morpholin-2-ylmethyl)-1H-pyrazol-4-yl)amino)pyrimidin-4-yl)benzyl)thiazole-5-carboxamide (I-126)

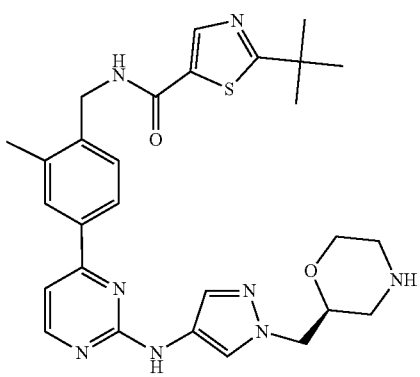

I-126

Preparation of (S)-tert-butyl 2-((4-nitro-1H-pyrazol-1-yl)methyl)morpholine-4-carboxylate

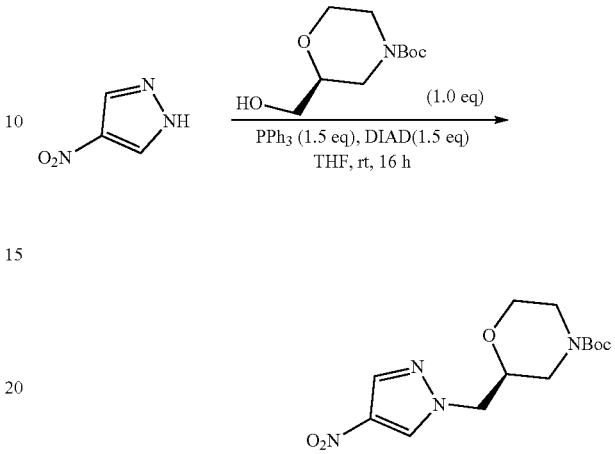

To a solution of 4-nitro-1H-pyrazole (1.0 g, 8.85 mmol) in THF (dry, 25 mL), (S)-4-Boc-2-(hydroxymethyl)morpholine (1.9 g, 8.85 mmol, 1 equiv) and PPh$_3$ (3.5 g, 13.3 mmol, 1.5 equiv) were added respectively. DIAD (2.69 g, 13.3 mmol, 1.5 equiv) was added at 0° C. under nitrogen. The mixture was stirred at rt for 16 h. Then the solvent was removed. The residue was purified by silica gel chromatography column (EtOAc/petroleum ether=1:3) to give (S)-tert-butyl 2-((4-nitro-1H-pyrazol-1-yl)methyl)morpholine-4-carboxylate as yellow oil (1.0 g, yield: 69%). ESI-MS (M+H-56)$^+$: 257.1. $^1$H NMR (400 MHz, CD$_3$OD) δ: 8.54 (s, 1H), 8.13 (s, 1H), 4.58-4.56 (m, 1H), 4.38-4.25 (m, 2H), 4.13-4.08 (m, 1H), 3.99-3.77 (m, 4H), 3.50-3.44 (m, 1H), 1.47 (s, 9H).

Preparation of (S)-tert-butyl 2-((4-amino-1H-pyrazol-1-yl)methyl)morpholine-4-carboxylate

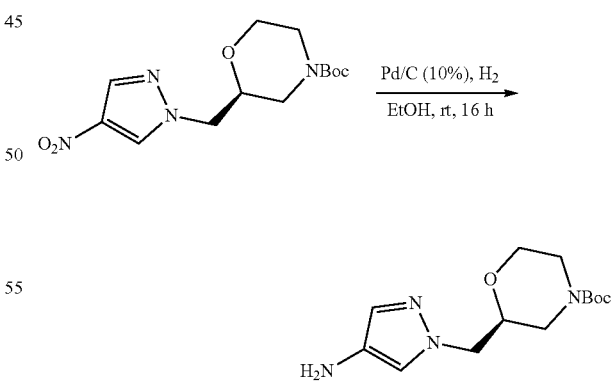

Synthesis of (S)-tert-butyl 2-((4-amino-1H-pyrazol-1-yl)methyl)morpholine-4-carboxylate was similar to that of (R)-tert-butyl 3-(4-amino-1H-pyrazol-1-yl)pyrrolidine-1-carboxylate. After the catalyst was removed, the filtrate was concentrated and the crude title product (870 mg, yield: 96%) was used to next step without further purification. ESI-MS (M+H)$^+$: 283.2.

Preparation of (S)-tert-butyl 2-((4-((4-(4-((2-(tert-butyl)thiazole-5-carboxamido)methyl)-3-methylphenyl)pyrimidin-2-yl)amino)-1H-pyrazol-1-yl)methyl)morpholine-4-carboxylate

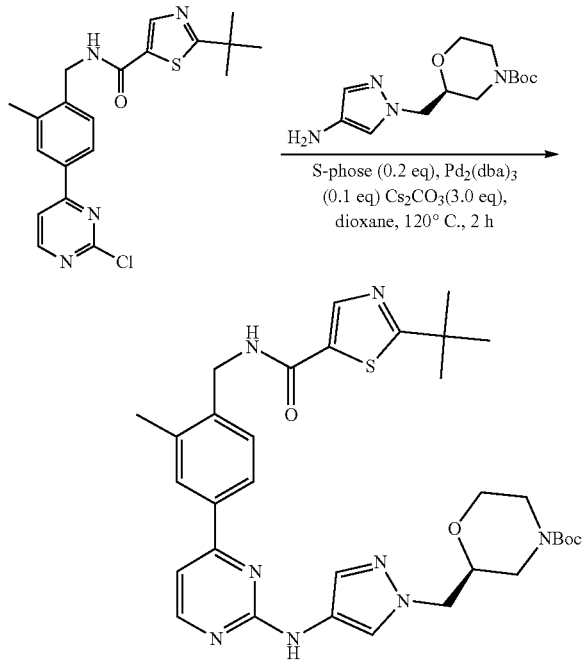 [SMILES: Cc1cc(-c2ccnc(Cl)n2)ccc1CNC(=O)c1cnc(C(C)(C)C)s1 ; CC(C)(C)OC(=O)N1CCO[C@H](Cn2cc(N)cn2)C1 ; Cc1cc(-c2ccnc(Nc3cnn(C[C@@H]4CN(C(=O)OC(C)(C)C)CCO4)c3)n2)ccc1CNC(=O)c1cnc(C(C)(C)C)s1]

Synthesis of (S)-tert-butyl 2-((4-((4-(4-((2-(tert-butyl)thiazole-5-carboxamido)methyl)-3-methylphenyl)pyrimidin-2-yl)amino)-1H-pyrazol-1-yl)methyl)morpholine-4-carboxylate was similar to that of (R)-tert-butyl 3-(4-((4-(4-((2-(tert-butyl)thiazole-5-carboxamido)methyl)-3-methylphenyl)pyrimidin-2-yl)amino)-1H-pyrazol-1-yl)pyrrolidine-1-carboxylate. The residue was purified by prep-HPLC (CH₃CN/H₂O with 0.05% NH₃.H₂O as mobile phase) to give title product as a yellow solid (73 mg, yield: 73%). ESI-MS (M+H)⁺: 647.3.

Preparation of (S)-2-(tert-butyl)-N-(2-methyl-4-(2-((1-(morpholin-2-ylmethyl)-1H-pyrazol-4-yl)amino)pyrimidin-4-yl)benzyl)thiazole-5-carboxamide

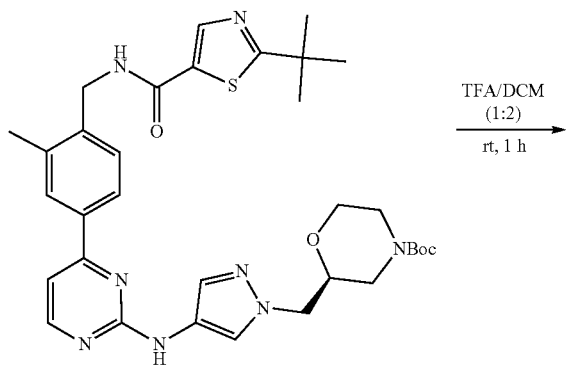

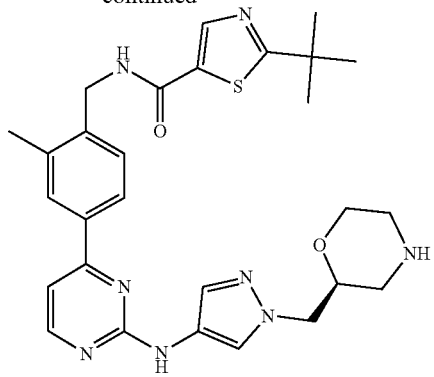

Synthesis of (S)-2-(tert-butyl)-N-(2-methyl-4-(2-((1-(morpholin-2-ylmethyl)-1H-pyrazol-4-yl)amino)pyrimidin-4-yl)benzyl)thiazole-5-carboxamide was similar to that of Example 121. The residue was purified by prep-HPLC (CH₃CN/H₂O with 0.05% NH₃.H₂O as mobile phase) to give (S)-2-(tert-butyl)-N-(2-methyl-4-(2-((1-(morpholin-2-ylmethyl)-1H-pyrazol-4-yl)amino)pyrimidin-4-yl)benzyl)thiazole-5-carboxamide as a yellow solid (58 mg, yield: 93%). ESI-MS (M+H)⁺: 547.3. HPLC: (214 nm: 100%, 254 nm: 100%). ¹H NMR (400 MHz, CD₃OD) δ: 8.34 (d, J=5.6 Hz, 1H), 8.26 (s, 1H), 8.06 (s, 1H), 7.99-7.97 (m, 2H), 7.75 (s, 1H), 7.45 (d, J=7.6 Hz, 1H), 7.39 (d, J=6.0 Hz, 1H), 4.61 (s, 2H), 4.38-4.29 (m, 2H), 4.15-4.07 (m, 2H), 3.86-3.79 (m, 1H), 3.40-3.37 (m, 1H), 3.27-3.24 (m, 1H), 3.14-3.10 (m, 1H), 2.89 (t, J=12.0 Hz, 1H), 2.46 (s, 3H), 1.46 (s, 9H).

Example 126: (R)-2-(tert-butyl)-N-(2-methyl-4-(2-((1-(morpholin-2-ylmethyl)-1H-pyrazol-4-yl)amino)pyrimidin-4-yl)benzyl)thiazole-5-carboxamide (I-128)

I-128

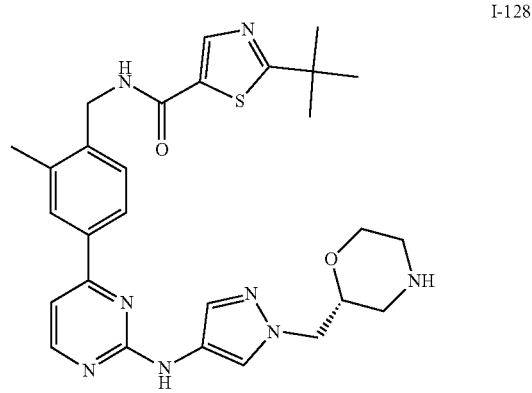

Synthesis of (R)-2-(tert-butyl)-N-(2-methyl-4-(2-((1-(morpholin-2-ylmethyl)-1H-pyrazol-4-yl)amino)pyrimidin-4-yl)benzyl)thiazole-5-carboxamide was similar to that of Example 121. The residue was purified by prep-HPLC (CH₃CN/H₂O with 0.05% NH₃.H₂O as mobile phase) to give (R)-2-(tert-butyl)-N-(2-methyl-4-(2-((1-(morpholin-2-ylmethyl)-1H-pyrazol-4-yl)amino)pyrimidin-4-yl)benzyl)thiazole-5-carboxamide as a yellow solid (103 mg, yield: 82%). ESI-MS (M+H)⁺: 547.3. HPLC: (214 nm: 100%, 254 nm: 100%). ¹H NMR (400 MHz, CD₃OD) δ: 8.39 (d, J=5.6 Hz, 1H), 8.25 (s, 1H), 8.09 (s, 1H), 8.02-7.99 (m, 2H), 7.73

(s, 1H), 7.46 (d, J=8.0 Hz, 1H), 7.35 (d, J=6.0 Hz, 1H), 4.63 (s, 2H), 4.36-4.33 (m, 2H), 4.12-4.08 (m, 2H), 3.83-3.81 (m, 1H), 3.39-3.35 (m, 1H), 3.29-3.24 (m, 1H), 3.12-3.10 (m, 1H), 2.88 (t, J=11.6 Hz, 1H), 2.49 (s, 3H), 1.47 (s, 9H).

Example 127: (R)—N-(4-(2-((1-(3-amino-2-hydroxypropyl)-1H-pyrazol-4-yl)amino)pyrimidin-4-yl)-2-methylbenzyl)-2-(tert-butyl)thiazole-5-carboxamide (I-127)

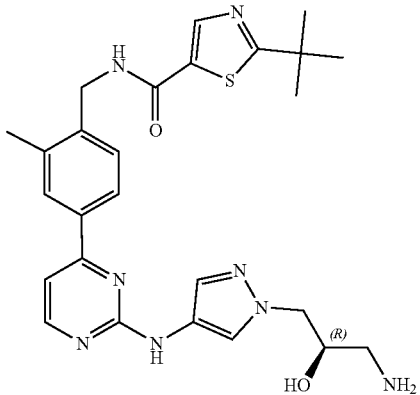

Synthesis of (S)-2-(tert-butyl)-N-(2-methyl-4-(2-((1-(oxiran-2-ylmethyl)-1H-pyrazol-4-yl)amino)pyrimidin-4-yl)benzyl)thiazole-5-carboxamide

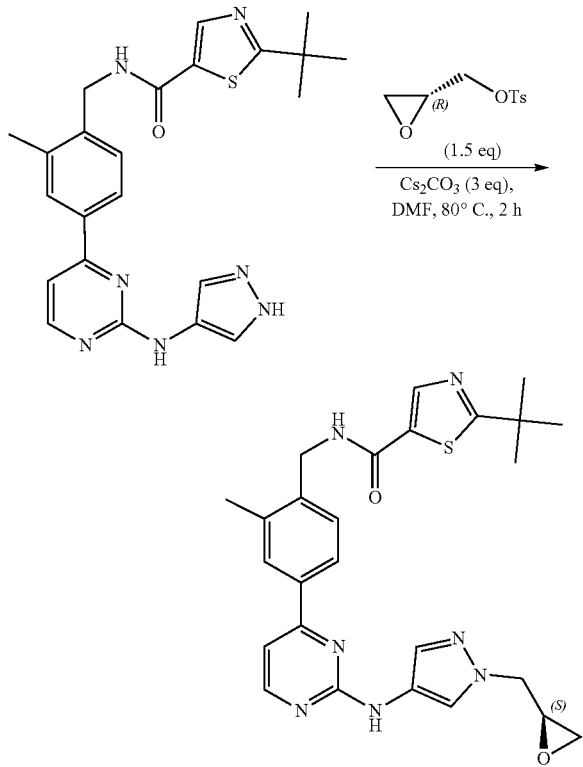

A mixture of N-(4-(2-((1H-pyrazol-4-yl)amino)pyrimidin-4-yl)-2-methylbenzyl)-2-(tert-butyl)thiazole-5-carboxamide (223 mg, 0.5 mmol) and Cs$_2$CO$_3$ (487 mg, 1.5 mmol, 3 equiv) in DMF (5 mL) was stirred at rt for 1 h. Then (R)-oxiran-2-ylmethyl 4-methylbenzenesulfonate (171 mg, 0.75 mmol, 1.5 equiv) was added. The mixture was stirred at rt for 30 min, then 80° C. for 2 h. After cooling down to rt, the mixture was diluted with EA (80 mL), washed with brine, dried, concentrated. The crude was purified through prep-TLC (MeOH/DCM=1/20) to give (S)-2-(tert-butyl)-N-(2-methyl-4-(2-((1-(oxiran-2-ylmethyl)-1H-pyrazol-4-yl)amino)pyrimidin-4-yl)benzyl)thiazole-5-carboxamide as a yellow solid (65 mg, yield: 26%). ESI-MS (M+H)$^+$: 504.1. $^1$H NMR (400 MHz, DMSO-d$_6$) δ: 9.54 (s, 1H), 9.10 (t, J=5.6 Hz, 1H), 8.47 (d, J=5.2 Hz, 1H), 8.33 (s, 1H), 8.04 (s, 1H), 7.99 (s, 1H), 7.95 (d, J=7.6 Hz, 1H), 7.60 (s, 1H), 7.39 (d, J=7.6 Hz, 1H), 7.27 (d, J=5.2 Hz, 1H), 4.50 (d, J=5.6 Hz, 2H), 4.45 (d, J=15.6 Hz, 1H), 4.10 (dd, J=14.8, 6.4 Hz, 1H), 2.81 (t, J=4.8 Hz, 1H), 2.58-2.56 (m, 1H), 2.42-2.41 (m, 4H), 1.39 (s, 9H).

Synthesis of (R)—N-(4-(2-((1-(3-amino-2-hydroxypropyl)-1H-pyrazol-4-yl)amino)pyrimidin-4-yl)-2-methylbenzyl)-2-(tert-butyl)thiazole-5-carboxamide

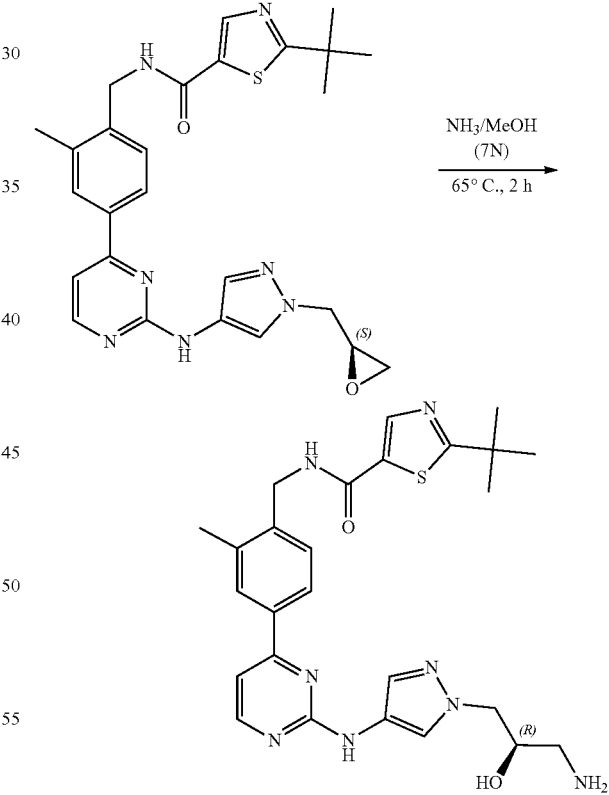

A solution of (S)-2-(tert-butyl)-N-(2-methyl-4-(2-((1-(oxiran-2-ylmethyl)-1H-pyrazol-4-yl)amino)pyrimidin-4-yl)benzyl)thiazole-5-carboxamide (80 mg, 0.16 mmol) in 7N NH$_3$/MeOH (4 mL) was heated to 65° C. for 2 h in a sealed tube. Then the mixture was cooled to rt and the solvent was removed. The crude was purified through prep-HPLC (TFA/MeCN/Water as a mobile phase) to give (R)—N-(4-(2-((1-(3-amino-2-hydroxypropyl)-1H-pyrazol-4-yl)

amino)pyrimidin-4-yl)-2-methylbenzyl)-2-(tert-butyl) thiazole-5-carboxamide (62 mg, yield: 75%) as a yellow solid. ESI-MS (M+H)+: 521.2. HPLC: (214 nm: 100%, 254 nm: 100%). $^1$H NMR (400 MHz, CD$_3$OD) δ: 8.35 (d, J=5.6 Hz, 1H), 8.26 (s, 1H), 8.08 (s, 1H), 8.04-8.01 (m, 2H), 7.77 (s, 1H), 7.48-7.43 (m, 2H), 4.62 (s, 2H), 4.29-4.22 (m, 3H), 3.12-3.10 (m, 1H), 2.88-2.83 (m, 1H), 2.48 (s, 3H), 1.46 (s, 9H).

Example 128: (S)—N-(4-(2-((1-(3-amino-2-hydroxypropyl)-1H-pyrazol-4-yl)amino)pyrimidin-4-yl)-2-methylbenzyl)-2-(tert-butyl)thiazole-5-carboxamide (I-129)

I-129

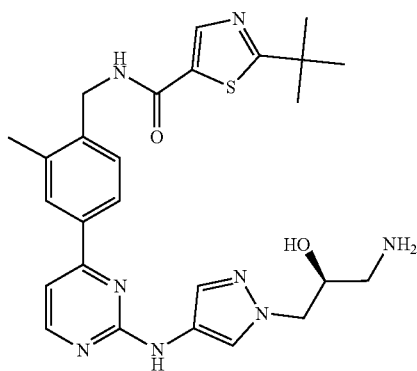

Synthesis of (S)—N-(4-(2-((1-(3-amino-2-hydroxypropyl)-1H-pyrazol-4-yl)amino)pyrimidin-4-yl)-2-methylbenzyl)-2-(tert-butyl)thiazole-5-carboxamide was similar to that of Example 127. After concentrated, the residue was purified by prep-HPLC (MeOH/H$_2$O with 0.05% TFA as mobile phase) to give compound (S)—N-(4-(2-((1-(3-amino-2-hydroxypropyl)-1H-pyrazol-4-yl)amino)pyrimidin-4-yl)-2-methylbenzyl)-2-(tert-butyl)thiazole-5-carboxamide (140 mg, yield: 92%) as a yellow solid. ESI-MS (M+H)+: 521.2. $^1$H NMR (400 MHz, CD$_3$OD) δ: 8.40 (d, J=5.6 Hz, 1H), 8.25 (s, 1H), 8.10 (s, 1H), 8.01 (s, 1H), 7.99 (d, J=8.0 Hz, 1H), 7.72 (s, 1H), 7.45 (d, J=8.0 Hz, 1H), 7.29 (d, J=5.6 Hz, 1H), 4.63 (s, 2H), 4.28-4.17 (m, 3H), 3.09-3.07 (m, 1H), 2.85-2.81 (m, 1H), 2.49 (s, 3H), 1.47 (s, 9H).

Example 129: (S)-2-amino-3-(4-((4-(4-((2-(tert-butyl)thiazole-5-carboxamido)methyl)-3-methylphenyl)pyrimidin-2-yl)amino)-1H-pyrazol-1-yl)propanoic acid (I-130)

I-130

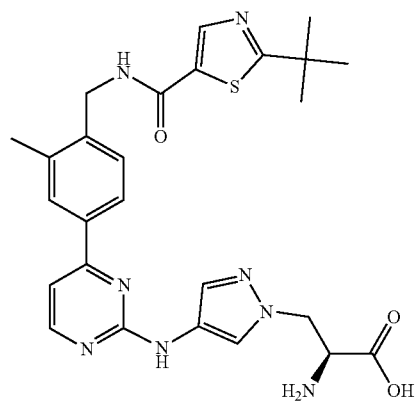

Preparation of (S)-methyl 2-((tert-butoxycarbonyl)amino)-3-(4-nitro-1H-pyrazol-1-yl)propanoate

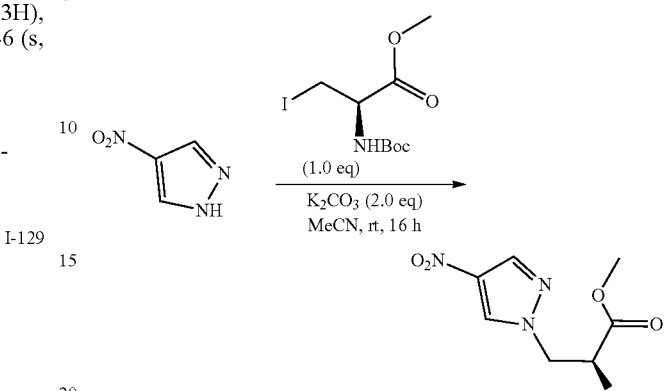

To a solution of 4-nitro-1H-pyrazole (1.5 g, 13.2 mmol) in MeCN (30 mL) were added (R)-methyl 2-((tert-butoxycarbonyl)amino)-3-iodopropanoate (2.7 g, 13.2 mmol) and K$_2$CO$_3$ (2.2 g, 15.8 mmol). The mixture was stirred at rt for 16 h. The solid was filtered off and the filtrate was concentrated and purified by column chromatography (silica, petroleum ether/EtOAc=4:1) to give product (S)-methyl 2-((tert-butoxycarbonyl)amino)-3-(4-nitro-1H-pyrazol-1-yl) propanoate (1.44 g, yield: 21%) as a yellow liquid. ESI-MS (M+H-56)+: 259.0. $^1$H NMR (400 MHz, CD$_3$OD) δ: 8.49 (s, 1H), 8.12 (s, 1H), 4.68-4.64 (m, 2H), 4.49-4.43 (m, 1H), 3.77 (s, 3H), 1.40 (s, 9H).

Preparation of (S)-methyl 3-(4-amino-1H-pyrazol-1-yl)-2-((tert-butoxycarbonyl)amino)propanoate

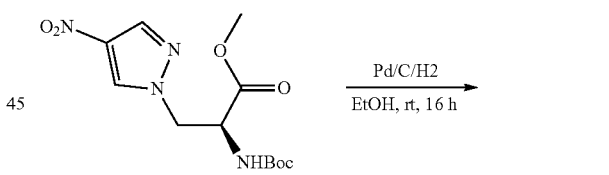

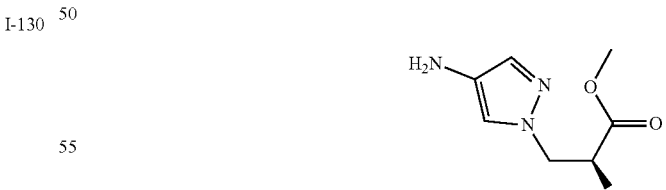

To a solution of (S)-methyl 2-((tert-butoxycarbonyl) amino)-3-(4-nitro-1H-pyrazol-1-yl)propanoate (1.44 g, 4.6 mmol) in MeOH (20 mL) was added Pd/C (144 mg, 10% wt). The mixture was stirred at rt for 16 h under hydrogen atmosphere (balloon pressure). Then the mixture was filtered and the filtrate was concentrated in vacuo. The crude product (1.29 g. yield: 99%) was used in the next step without further purification. ESI-MS (M+H)+: 285.1.

Preparation of (S)-2-((tert-butoxycarbonyl)amino)-3-(4-((4-(4-((2-(tert-butyl)thiazole-5-carboxamido)methyl)-3-methylphenyl)pyrimidin-2-yl)amino)-1H-pyrazol-1-yl)propanoic acid

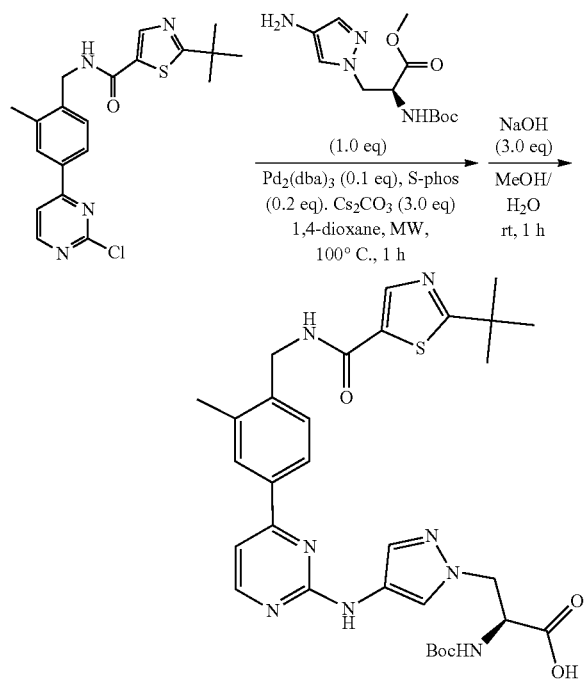

Synthesis of (S)-2-((tert-butoxycarbonyl)amino)-3-(4-((4-(4-((2-(tert-butyl)thiazole-5-carboxamido)methyl)-3-methylphenyl)pyrimidin-2-yl)amino)-1H-pyrazol-1-yl)propanoic acid was similar to that of (R)-tert-butyl 3-(4-((4-(4-((2-(tert-butyl)thiazole-5-carboxamido)methyl)-3-methylphenyl)pyrimidin-2-yl)amino)-1H-pyrazol-1-yl)pyrrolidine-1-carboxylate. The residue was purified by prep-HPLC (CH$_3$CN/H$_2$O with 0.05% NH$_3$.H$_2$O as mobile phase) to give (S)-2-((tert-butoxycarbonyl)amino)-3-(4-((4-(4-((2-(tert-butyl)thiazole-5-carboxamido)methyl)-3-methylphenyl)pyrimidin-2-yl)amino)-1H-pyrazol-1-yl)propanoic acid as a yellow solid (62 mg, yield: 56%). ESI-MS (M+H)$^+$: 635.2.

Preparation of (S)-2-amino-3-(4(4-(4-((2-(tert-butyl)thiazole-5-carboxamido)methyl)-3-methylphenyl)pyrimidin-2-yl)amino)-1H-pyrazol-1-yl)propanoic acid

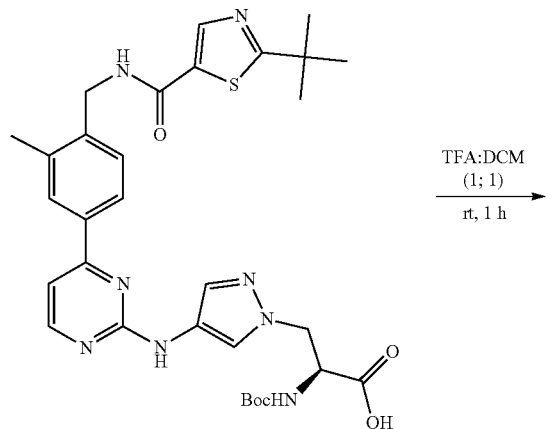

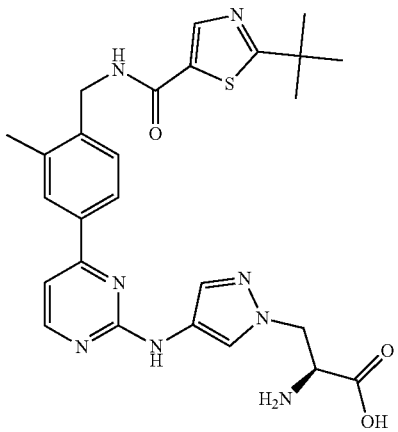

Synthesis of (S)-2-amino-3-(4-((4-(4-((2-(tert-butyl)thiazole-5-carboxamido)methyl)-3-methylphenyl)pyrimidin-2-yl)amino)-1H-pyrazol-1-yl)propanoic acid was similar to that of Example 129. The crude product was purified by prep-HPLC (CH$_3$CN/H$_2$O with 0.05% TFA as mobile phase) to give (S)-2-amino-3-(4-((4-(4-((2-(tert-butyl)thiazole-5-carboxamido)methyl)-3-methylphenyl)pyrimidin-2-yl)amino)-1H-pyrazol-1-yl)propanoic acid as a yellow solid (90 mg, yield: 54%). ESI-MS (M+H)$^+$: 535.2. HPLC: (214 nm: 100%, 254 nm: 100%). $^1$H NMR (400 MHz, DMSO-d$_6$) δ: 9.55 (s, 1H), 9.13 (t, J=5.6 Hz, 1H), 8.47 (d, J=5.2 Hz, 1H), 8.34 (s, 1H), 8.00-7.95 (m, 3H), 7.67 (br, 1H), 7.41 (d, J=8.0 Hz, 1H), 7.27 (d, J=5.2 Hz, 1H), 4.55-4.94 (m, 3H), 4.35-4.27 (m, 1H), 3.64-3.61 (m, 1H), 2.42 (s, 3H), 1.39 (s, 9H).

Example 130: (S)—N-(4-(2-((1-(2-amino-3-hydroxypropyl)-1H-pyrazol-4-yl)amino)pyrimidin-4-yl)-2-methylbenzyl)-2-(tert-butyl)thiazole-5-carboxamide (I-131)

I-131

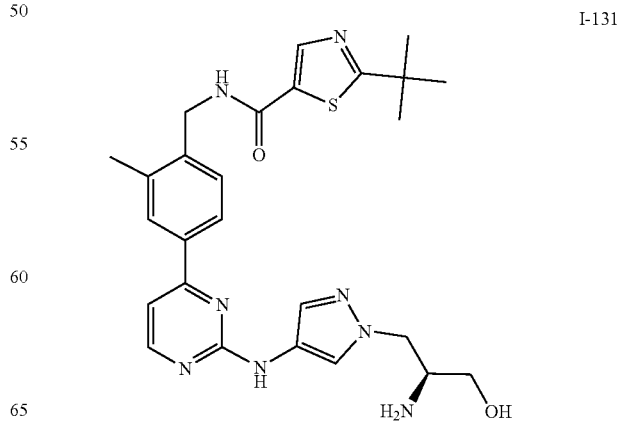

267

Preparation of (S)-tert-butyl (1-(44(4-(44(2-(tert-butyl)thiazole-5-carboxamido)methyl)-3-methylphenyl)pyrimidin-2-yl)amino)-1H-pyrazol-1-yl)-3-hydroxypropan-2-yl)carbamate

268

Preparation of (S)—N-(4-(2-((1-(2-amino-3-hydroxypropyl)-1H-pyrazol-4-yl)amino)pyrimidin-4-yl)-2-methylbenzyl)-2-(tert-butyl)thiazole-5-carboxamide

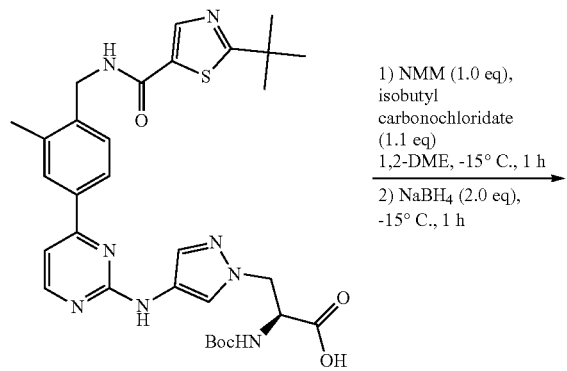

1) NMM (1.0 eq), isobutyl carbonochloridate (1.1 eq) 1,2-DME, -15° C., 1 h
2) NaBH₄ (2.0 eq), -15° C., 1 h

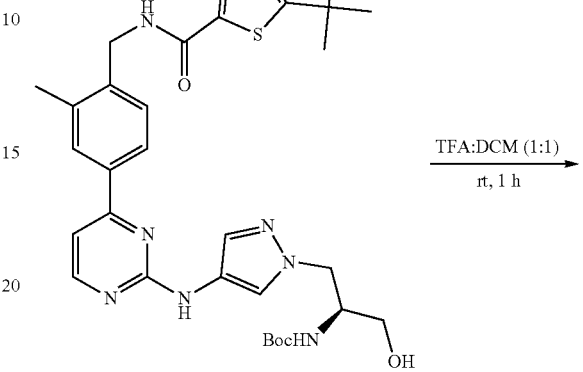

TFA:DCM (1:1)
rt, 1 h

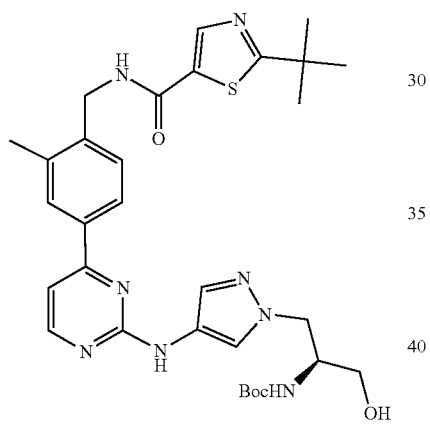

To a solution of (S)-2-(((tert-butoxycarbonyl)amino)-3-(4-((4-(4-((2-(tert-butyl)thiazole-5-carboxamido)methyl)-3-methylphenyl)pyrimidin-2-yl)amino)-1H-pyrazol-1-yl)propanoic acid (224 mg, 0.35 mmol) in 15 mL DME were added NMM (35 mg, 0.35 mmol), isobutyl carbonochloridate (53 mg, 0.39 mmol) at −15° C. The mixture was stirred at −15° C. for 20 min. The solid was filtered off and NaBH₄ (27 mg, 0.70 mmol) was added to the filtrate at −15° C. Then the mixture was stirred at −15° C. for another 1 h. After diluted with water (4 mL), the mixture was extracted with EtOAc (50 mL×2). The combined organic layer was washed with H₂O (40 mL), dried (Na₂SO₄), filtered and concentrated. The crude product (300 mg, yield: 80%) was used in the next step without further purification.

Synthesis of (S)—N-(4-(2-((1-(2-amino-3-hydroxypropyl)-1H-pyrazol-4-yl)amino)pyrimidin-4-yl)-2-methylbenzyl)-2-(tert-butyl)thiazole-5-carboxamide was similar to that of Example 121. The crude product was purified by prep-HPLC (CH₃CN/H₂O with 0.05% NH₃.H₂O as mobile phase) to give (S)—N-(4-(2-((1-(2-amino-3-hydroxypropyl)-1H-pyrazol-4-yl)amino)pyrimidin-4-yl)-2-methylbenzyl)-2-(tert-butyl)thiazole-5-carboxamide as a yellow solid (64 mg, yield: 25%). ESI-MS (M+H)⁺: 521.2. HPLC: (214 nm: 97%, 254 nm: 97%). ¹H NMR (400 MHz, DMSO-d₆) δ: 9.49 (s, 1H), 9.11 (t, J=5.6 Hz, 1H), 8.45 (d, J=5.2 Hz, 1H), 8.31 (s, 1H), 7.98-7.92 (m, 3H), 7.56 (br, 1H), 7.39 (d, J=8.0 Hz, 1H), 7.25 (d, J=5.2 Hz, 1H), 4.72-4.71 (m, 1H), 4.92 (d, J=5.6 Hz, 2H), 4.11-4.07 (m, 1H), 3.92-3.87 (m, 1H), 3.26-3.23 (m, 2H), 3.06-3.00 (m, 1H), 2.40 (s, 3H), 1.38 (s, 9H).

Example 131: (R)-2-amino-3-(4-((4-(4-((2-(tert-butyl)thiazole-5-carboxamido)methyl)-3-methylphenyl)pyrimidin-2-yl)amino)-1H-pyrazol-1-yl)propanoic acid (I-132)

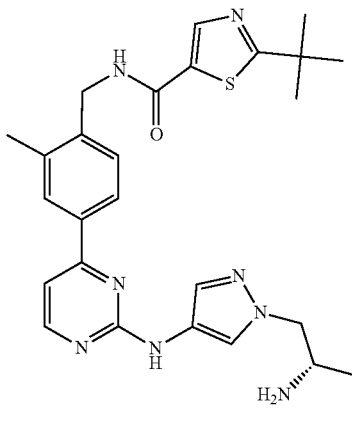

I-132

Synthesis of (R)-2-amino-3-(4-((4-(4-((2-(tert-butyl)thiazole-5-carboxamido)methyl)-3-methylphenyl)pyrimidin-2-yl)amino)-1H-pyrazol-1-yl)propanoic acid was similar to that of Example 129. The crude product was purified by prep-HPLC (CH₃CN/H₂O with 0.05% NH₃ as mobile phase) to give (R)-2-amino-3-(4-((4-(4-((2-(tert-butyl)thiazole-5-carboxamido)methyl)-3-methylphenyl)pyrimidin-2-yl)amino)-1H-pyrazol-1-yl)propanoic acid as a yellow solid (55 mg, yield: 54%). ESI-MS (M+H)⁺: 535.2. HPLC: (214 nm: 100%, 254 nm: 100%). ¹H NMR (400 MHz, DMSO-$d_6$) δ: 9.54 (s, 1H), 9.13 (br, 1H), 8.47 (d, J=4.4 Hz, 1H), 8.34 (s, 1H), 8.00-7.95 (m, 3H), 7.64 (s, 1H), 7.41 (d, J=8.0 Hz, 1H), 7.26 (d, J=5.2 Hz, 1H), 4.51-4.47 (m, 3H), 4.35-4.27 (m, 1H), 3.51-3.49 (m, 1H), 2.42 (s, 3H), 1.39 (s, 9H).

Example 132: (R)—N-(4-(2-((1-(2-amino-3-hydroxypropyl)-1H-pyrazol-4-yl)amino)pyrimidin-4-yl)-2-methylbenzyl)-2-(tert-butyl)thiazole-5-carboxamide (I-133)

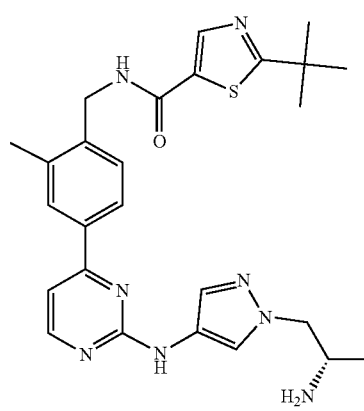

I-133

Synthesis of (R)—N-(4-(2-((1-(2-amino-3-hydroxypropyl)-1H-pyrazol-4-yl)amino)pyrimidin-4-yl)-2-methylbenzyl)-2-(tert-butyl)thiazole-5-carboxamide was similar to that of Example 130. The crude product was purified by prep-HPLC (CH₃CN/H₂O with 0.05% NH₃.H₂O as mobile phase) to give (R)—N-(4-(2-((1-(2-amino-3-hydroxypropyl)-1H-pyrazol-4-yl)amino)pyrimidin-4-yl)-2-methylbenzyl)-2-(tert-butyl)thiazole-5-carboxamide as a yellow solid (15 mg, yield: 8%). ESI-MS (M+H)⁺: 521.2. HPLC: (214 nm: 100%, 254 nm: 98%). ¹H NMR (400 MHz, DMSO-$d_6$) δ: 9.49 (s, 1H), 9.10 (t, J=5.6 Hz, 1H), 8.45 (d, J=4.8 Hz, 1H), 8.32 (s, 1H), 7.98-7.92 (m, 3H), 7.57 (br, 1H), 7.39 (d, J=8.0 Hz, 1H), 7.25 (d, J=5.2 Hz, 1H), 4.72-4.71 (m, 1H), 4.49 (d, J=5.2 Hz, 2H), 4.12-4.07 (m, 1H), 3.92-3.87 (m, 1H), 3.28-3.20 (m, 2H), 3.06-3.02 (m, 1H), 2.40 (s, 3H), 1.38 (s, 9H).

Example 133: 2-(tert-butyl)-N-(6-(6-((5-methyl-4,5,6,7-tetrahydropyrazolo[1,5-a]pyrazin-2-yl)amino)pyrimidin-4-yl)-1,2,3,4-tetrahydronaphthalen-1-yl)thiazole-5-carboxamide (I-134)

I-134

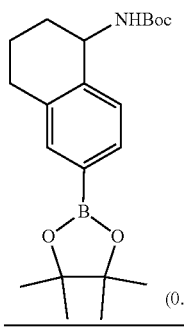

Synthesis of tert-butyl (6-(6-chloropyrimidin-4-yl)-1,2,3,4-tetrahydronaphthalen-1-yl)carbamate 271
-continued

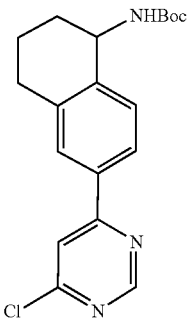

Synthesis of tert-butyl (6-(6-chloropyrimidin-4-yl)-1,2,3,4-tetrahydronaphthalen-1-yl)carbamate was similar to that of tert-butyl 4-(2-chloropyrimidin-4-yl)-2-methylbenzylcarbamate. Obtained tert-butyl (6-(6-chloropyrimidin-4-yl)-1,2,3,4-tetrahydronaphthalen-1-yl)carbamate (260 mg, yield: 68%) as a white solid. ESI-MS (M+H)$^+$: 359.9. $^1$H NMR (400 MHz, CDCl$_3$) δ: 9.01 (s, 1H), 7.84-7.82 (m, 2H), 7.72 (s, 1H), 7.50 (d, J=8.4 Hz, 1H), 4.94-4.90 (m, 1H), 4.81-4.79 (m, 1H), 2.92-2.81 (m, 2H), 2.11-2.04 (m, 1H), 1.88-1.74 (m, 3H), 1.49 (s, 9H).

Synthesis of tert-butyl (6-(6-((5-methyl-4,5,6,7-tetrahydropyrazolo[1,5-a]pyrazin-2-yl)amino)pyrimidin-4-yl)-1,2,3,4-tetrahydronaphthalen-1-yl) carbamate

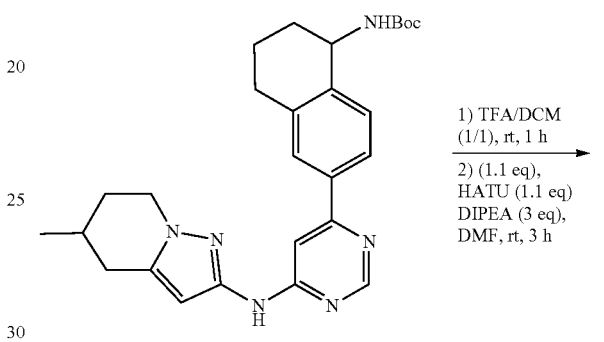

272

(6-(6-((5-methyl-4,5,6,7-tetrahydropyrazolo[1,5-a]pyrazin-2-yl)amino)pyrimidin-4-yl)-1,2,3,4-tetrahydronaphthalen-1-yl)carbamate (100 mg, yield: 28%) as a yellow solid. ESI-MS (M+H)$^+$: 476.1. $^1$H NMR (400 MHz, CDCl$_3$) δ: 8.74 (s, 1H), 8.15 (s, 1H), 7.77 (s, 1H), 7.74 (d, J=8.4 Hz, 1H), 7.49 (s, 1H), 7.44 (d, J=8.0 Hz, 1H), 6.09 (s, 1H), 4.89-4.87 (m, 2H), 4.13 (t, J=6.0 Hz, 2H), 3.64 (s, 2H), 2.92 (t, J=5.6 Hz, 2H), 2.85-2.82 (m, 2H), 2.50 (s, 3H), 2.08-2.05 (m, 1H), 1.84-1.80 (m, 3H), 1.49 (s, 9H).

Synthesis of 2-(tert-butyl)-N-(6-(6-((5-methyl-4,5,6,7-tetrahydropyrazolo[1,5-a]pyrazin-2-yl)amino)pyrimidin-4-yl)-1,2,3,4-tetrahydronaphthalen-1-yl) thiazole-5-carboxamide

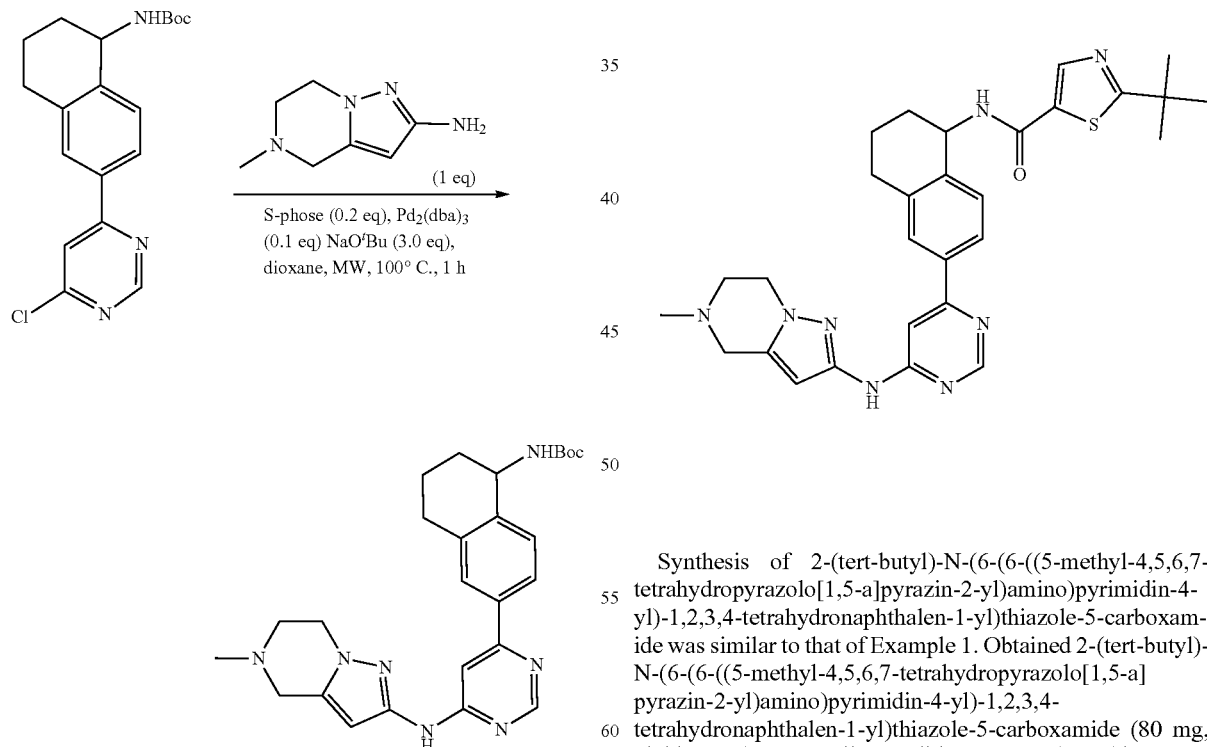

Synthesis of 2-(tert-butyl)-N-(6-(6-((5-methyl-4,5,6,7-tetrahydropyrazolo[1,5-a]pyrazin-2-yl)amino)pyrimidin-4-yl)-1,2,3,4-tetrahydronaphthalen-1-yl)thiazole-5-carboxamide was similar to that of Example 1. Obtained 2-(tert-butyl)-N-(6-(6-((5-methyl-4,5,6,7-tetrahydropyrazolo[1,5-a]pyrazin-2-yl)amino)pyrimidin-4-yl)-1,2,3,4-tetrahydronaphthalen-1-yl)thiazole-5-carboxamide (80 mg, yield: 70%) as a yellow solid. ESI-MS (M+H)$^+$: 542.8. HPLC: (214 nm: 99.33%, 254 nm: 97.39%). $^1$H NMR (400 MHz, CD$_3$OD) δ: 8.60 (s, 1H), 8.23 (s, 1H), 7.76-7.73 (m, 2H), 7.54 (s, 1H), 7.39 (d, J=8.0 Hz, 1H), 6.26 (s, 1H), 5.35-5.32 (m, 1H), 4.13 (t, J=5.6 Hz, 2H), 3.69 (s, 2H), 3.00-2.89 (m, 4H), 2.51 (s, 3H), 2.17-2.13 (m, 1H), 2.08-2.04 (m, 1H), 1.96-1.91 (m, 2H), 1.46 (s, 9H).

Example 134: N-(4-(2-aminopyrimidin-4-yl)-2-methylbenzyl)-2-(tert-butyl)thiazole-5-carboxamide (I-135)

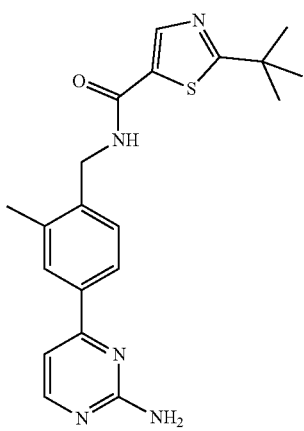

I-135

Synthesis of tert-butyl 4-(2-aminopyrimidin-4-yl)-2-methylbenzylcarbamate

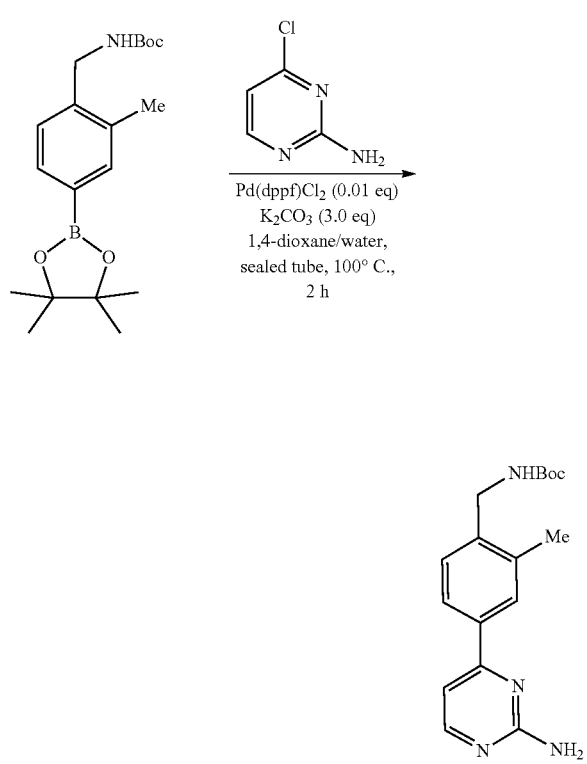

To a solution of tert-butyl 2-methyl-4-(4,4,5,5-tetramethyl-1,3,2-dioxaborolan-2-yl)benzylcarbamate (347 mg, 1.0 mmol) in dioxane (8 mL) and H$_2$O (2 mL), 4-chloropyrimidin-2-amine (129 mg, 1.0 mmol), Pd(dppf)Cl$_2$ (7.5 mg, 0.01 mmol) and K$_2$CO$_3$ (414 mg, 3.0 mmol) were added under N$_2$. The mixture was stirred at 100° C. for 2 h. Then the mixture was quenched with H$_2$O (60 mL) and extracted with EA (60 mL×3). The organic layers were collected, concentrated. The residue was purified by column chromatography (silica, petroleum ether/EtOAc=1:1 to 1:2) to give tert-butyl 4-(2-aminopyrimidin-4-yl)-2-methylbenzylcarbamate (257 mg, yield: 82%) as yellow solid ESI-MS (M+H)$^+$: 315.2. $^1$H NMR (400 MHz, CDCl$_3$) δ: 8.30 (d, J=4.8 Hz, 1H), 7.82 (s, 1H), 7.78 (d, J=8.0 Hz, 1H), 7.34 (d, J=7.6 Hz, 1H), 7.03 (d, J=5.6 Hz, 1H), 5.13 (br, 2H), 4.77 (br, 1H), 4.36 (d, J=6.0 Hz, 2H), 2.40 (s, 3H), 1.48 (s, 9H).

Synthesis of N-(4-(2-aminopyrimidin-4-yl)-2-methylbenzyl)-2-(tert-butyl)thiazole-5-carboxamide

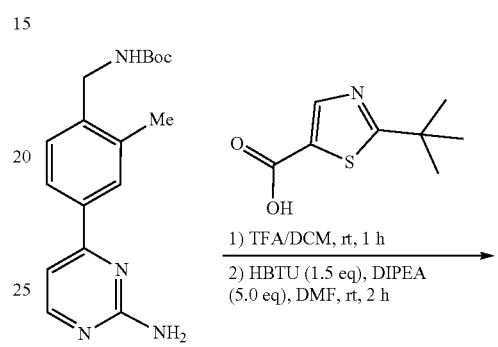

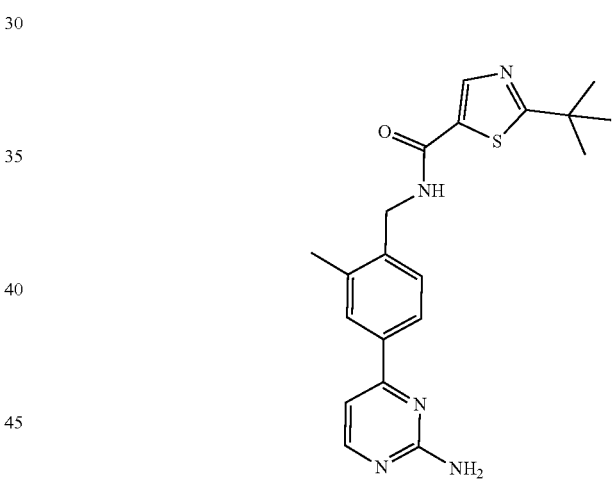

A mixture of tert-butyl 4-(2-aminopyrimidin-4-yl)-2-methylbenzylcarbamate (79 mg, 0.25 mmol) in TFA/DCM (6 mL, 1:1) was stirred at rt for 1 h. After removal of solvents, the residue was dissolved in DMF (4 mL), 2-(tert-butyl)thiazole-5-carboxylic acid (47 mg, 0.25 mmol), HBTU (143 mg, 0.38 mmol) and DIPEA (167 mg, 1.30 mmol) were added. The mixture was stirred at rt for further 16 h. After diluted with water (60 mL), the mixture was extracted with ethyl acetate (80 mL×2). The combined extracts were evaporated and the residue was purified by prep-HPLC (CH$_3$CN/H$_2$O with 0.05% NH$_3$.H$_2$O as mobile phase) to give compound N-(4-(2-aminopyrimidin-4-yl)-2-methylbenzyl)-2-(tert-butyl)thiazole-5-carboxamide (62 mg, yield: 65%) as a white solid. ESI-MS (M+H)$^+$: 382.2. $^1$H NMR (400 MHz, CD$_3$OD) δ: 8.28 (s, 1H), 8.27 (d, J=5.6 Hz, 1H), 7.93 (s, 1H), 7.87 (d, J=8.0 Hz, 1H), 7.38 (d, J=8.0 Hz, 1H), 7.10 (d, J=5.2 Hz, 1H), 4.55 (s, 2H), 2.42 (s, 3H), 1.42 (s, 9H).

Example 135: N-(6-(2-aminopyrimidin-4-yl)-1,2,3, 4-tetrahydronaphthalen-1-yl)-2-(tert-butyl)thiazole-5-carboxamide (I-136)

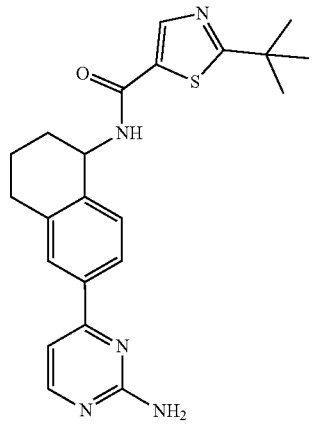

I-136

Synthesis of N-(6-(2-aminopyrimidin-4-yl)-1,2,3,4-tetrahydronaphthalen-1-yl)-2-(tert-butyl)thiazole-5-carboxamide was similar to that of Example 134. The residue was purified by prep-HPLC (MeCN/H₂O with 0.05% NH₃.H₂O as mobile phase) to give N-(6-(2-aminopyrimidin-4-yl)-1,2, 3,4-tetrahydronaphthalen-1-yl)-2-(tert-butyl)thiazole-5-carboxamide as a white solid (42 mg, yield: 26%). ESI-MS (M+H)⁺: 408.2. ¹H NMR (400 MHz, DMSO-d₆) δ: 8.98 (d, J=8.4 Hz, 1H), 8.32 (s, 1H), 8.28 (d, J=5.2 Hz, 1H), 7.88 (s, 1H), 7.85 (dd, J=8.4, 1.6 Hz, 1H), 7.30 (d, J=8.0 Hz, 1H), 7.10 (d, J=5.2 Hz, 1H), 6.66 (s, 2H), 5.22-5.20 (m, 1H), 2.86-2.84 (m, 2H), 2.02-1.95 (m, 2H), 1.82-1.79 (m, 2H), 1.39 (s, 9H).

Example 136: N-(6-(2-aminopyrimidin-4-yl)-1,2,3, 4-tetrahydronaphthalen-1-yl)-4,5,6,7-tetrahydrobenzo[b]thiophene-2-carboxamide (I-137)

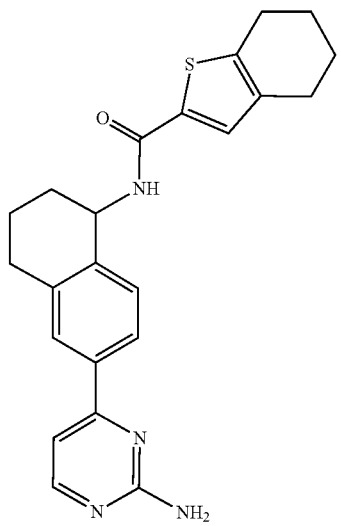

I-137

Synthesis of N-(6-(2-aminopyrimidin-4-yl)-1,2,3,4-tetrahydronaphthalen-1-yl)-4,5,6,7-tetrahydrobenzo[b]thiophene-2-carboxamide was similar to that of Example 134. The residue was purified by prep-HPLC (CH₃CN/H₂O with 0.05% NH₃H₂O as mobile phase) to give N-(6-(2-aminopyrimidin-4-yl)-1,2,3,4-tetrahydronaphthalen-1-yl)-4,5,6,7-tetrahydrobenzo[b]thiophene-2-carboxamide (50 mg, yield: 30%) as a white solid. ESI-MS (M+H)⁺: 405.1. HPLC: (214 nm: 100.00%, 254 nm: 100.00%). ¹H NMR (400 MHz, CDCl₃) δ: 8.32 (d, J=5.2 Hz, 1H), 7.79 (s, 1H), 7.77 (d, J=8.4 Hz, 1H), 7.45 (d, J=7.6 Hz, 1H), 7.18 (s, 1H), 7.05 (d, J=5.6 Hz, 1H), 6.03 (d, J=8.8 Hz, 1H), 5.40-5.38 (m, 1H), 5.29 (br, 2H), 2.91-2.88 (m, 2H), 2.77 (t, J=5.6 Hz, 2H), 2.59 (t, J=5.6 Hz, 2H), 2.20-2.14 (m, 1H), 1.94-1.77 (m, 7H).

Example 137: N-(4-(2-aminopyrimidin-4-yl)-2-methylbenzyl)-6,7-dihydro-4H-thieno[3,2-c]thiopyran-2-carboxamide 5,5-dioxide (I-138)

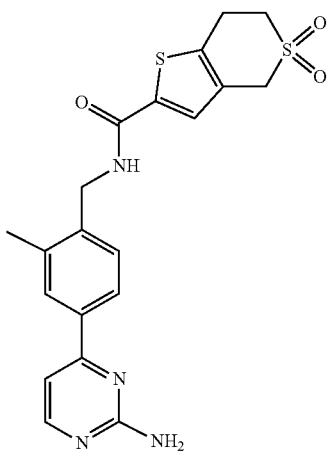

I-138

Synthesis of ethyl 6,7-dihydro-4H-thieno[3,2-c]thiopyran-2-carboxylate

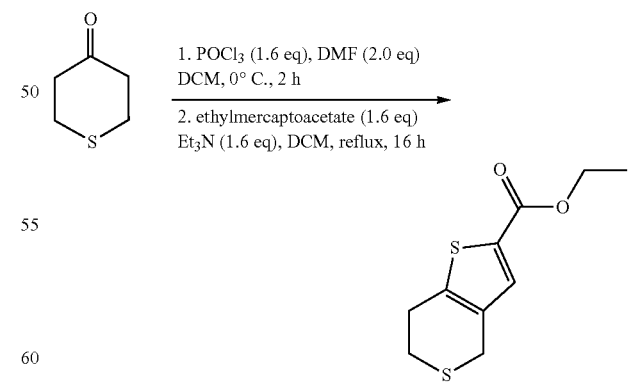

POCl₃ (2.12 g, 13.79 mmol) was dropwise added to DMF (1.13 g, 15.52 mmol) in ice bath. DCM (20 mL) was added and the bath was removed when the reaction media appeared to be pasty. The reaction was kept at room temperature for 2 h. Then it was cooled to 0° C. again. Tetrahydro-thiopyran- 4-one (1.0 g, 8.62 mmol) in 10 mL DCM was then dropwise added within 3 minutes. The reaction was kept at 0° C. for 2 h, dilute with DCM (250 ml) and then wash with ice cold saturated aqueous sodium acetate solution (100 mL). The organic layer was dried filtered, concentrated. The crude compound was dissolved in DCM (30 mL) then added ethyl 2-mercapto-acetate (1.66 g, 13.79 mmol) and 1 mL TEA. The mixture was refluxed for 16 h. Then it was washed with water and dried over magnesium sulfate. After filtered and concentrated, the residue was purified by silica gel column chromatography (EtOAc/petroleum ether=1:10) to give ethyl 6,7-dihydro-4H-thieno[3,2-c]thiopyran-2-carboxylate (900 mg, yield: 46%). ESI-MS (M+H)$^+$: 229.0. $^1$H NMR (400 MHz, CDCl$_3$) δ: 7.47 (s, 1H), 4.32 (q, J=7.2 Hz, 2H), 3.72 (s, 2H), 3.10 (t, J=5.6 Hz, 2H), 2.93 (t, J=5.6 Hz, 2H), 1.36 (t, J=7.2 Hz, 3H).

Synthesis of ethyl 6,7-dihydro-4H-thieno[3,2-c]thiopyran-2-carboxylate 5,5-dioxide

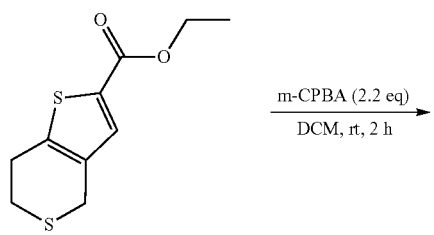

To a solution of ethyl 6,7-dihydro-4H-thieno[3,2-c]thiopyran-2-carboxylate (300 mg, 1.32 mmol) in DCM (30 mL) was added m-CPBA (500 mg, 2.89 mmol) in portions. The mixture was stirred at room temperature for 2 h. After washing with saturated aqueous sodium sulfite (40 mL), the organic phase was evaporated and the residue was purified by pre-TLC (EtOAc/petroleum ether=1:5) to give ethyl 6,7-dihydro-4H-thieno[3,2-c]thiopyran-2-carboxylate 5,5-dioxide as a brown oil. ESI-MS (M+H)$^+$: 261.0. $^1$H NMR (400 MHz, CDCl$_3$) δ: 7.42 (s, 1H), 4.34 (q, J=7.2 Hz, 2H), 4.24 (s, 2H), 3.48 (t, J=6.4 Hz, 2H), 3.30 (t, J=6.4 Hz, 2H), 1.35 (t, J=7.2 Hz, 3H).

Synthesis of 6,7-dihydro-4H-thieno[3,2-c]thiopyran-2-carboxylic acid 5,5-dioxide

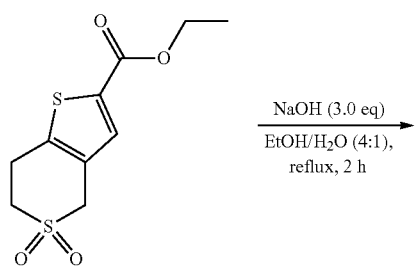

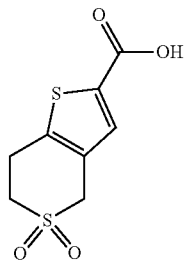

To a solution ethyl 6,7-dihydro-4H-thieno[3,2-c]thiopyran-2-carboxylate 5,5-dioxide (180 mg, 0.692 mmol) in EtOH/H$_2$O (4:1, 20 mL) was added sodium hydroxide (83 mg, 2.08 mmol). The mixture was refluxed for 2 h. After concentrated, the residue was diluted with water (10 mL), acidified with 1 N HCl to pH=4-5. The precipitate was collected by filtration and dried to give 6,7-dihydro-4H-thieno[3,2-c]thiopyran-2-carboxylic acid 5,5-dioxide (150 mg, yield: 93%) as a white solid. ESI-MS (M+H)$^+$: 233.0.

Synthesis of N-(4-(2-aminopyrimidin-4-yl)-2-methylbenzyl)-6,7-dihydro-4H-thieno[3,2-c]thiopyran-2-carboxamide 5,5-dioxide

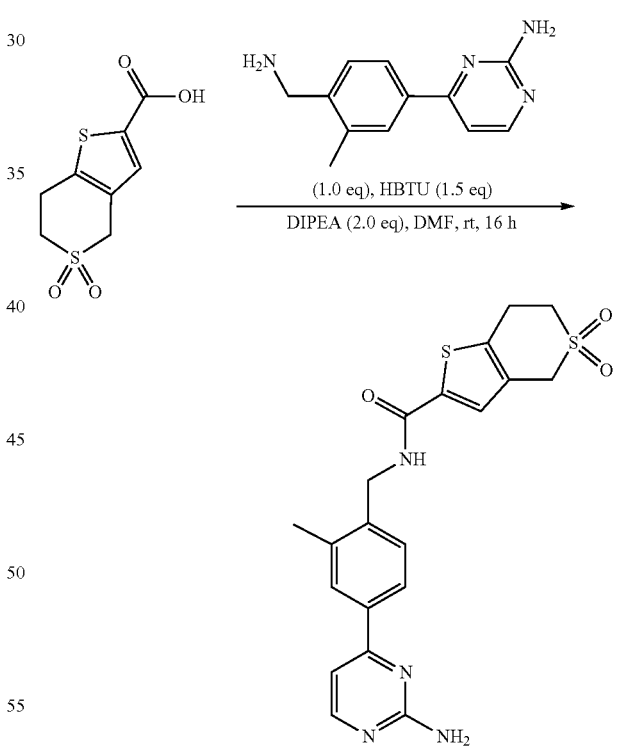

Synthesis of N-(4-(2-aminopyrimidin-4-yl)-2-methylbenzyl)-6,7-dihydro-4H-thieno[3,2-c]thiopyran-2-carboxamide 5,5-dioxide was similar to that of Example 134, starting from 6,7-dihydro-4H-thieno[3,2-c]thiopyran-2-carboxylic acid 5,5-dioxide. The residue was purified by prep-HPLC (CH$_3$CN/H$_2$O with 0.05% NH$_3$.H$_2$O as mobile phase) to give compound N-(4-(2-aminopyrimidin-4-yl)-2-methylbenzyl)-6,7-dihydro-4H-thieno[3,2-c]thiopyran-2-carboxamide 5,5-dioxide (80 mg, yield: 29%) as a white solid.

ESI-MS (M+H)+: 429.2. ¹H NMR (400 MHz, DMSO-d₆) δ: 8.99 (t, J=6.0 Hz, 1H), 8.28 (d, J=5.6 Hz, 1H), 7.90 (s, 1H), 7.84 (d, J=8.0 Hz, 1H), 7.52 (s, 1H), 7.32 (d, J=8.0 Hz, 1H), 7.09 (d, J=5.2 Hz, 1H), 6.64 (s, 2H), 4.44 (d, J=5.6 Hz, 2H), 4.43 (s, 2H), 3.46 (t, J=5.6 Hz, 2H), 3.35 (t, J=5.6 Hz, 2H), 2.37 (s, 3H).

Example 138: N-(4-(2-aminopyrimidin-4-yl)-2-methylbenzyl)-6,7-dihydro-4H-thieno[3,2-c]pyran-2-carboxamide (I-139)

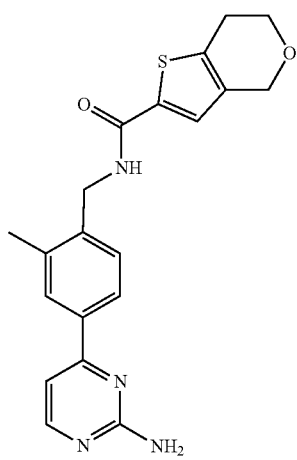

I-139

Synthesis of N-(4-(2-aminopyrimidin-4-yl)-2-methylbenzyl)-6,7-dihydro-4H-thieno[3,2-c]pyran-2-carboxamide was similar to that of Example 134, starting from 6,7-dihydro-4H-thieno[3,2-c]pyran-2-carboxylic acid. The residue was purified by prep-HPLC (MeCN/H₂O with 0.05% NH₃·H₂O as mobile phase) to give title product as a white solid (40 mg, yield: 44%). ESI-MS (M+H)+: 381.1. ¹H NMR (400 MHz, CD₃OD) δ: 8.27 (d, J=7.2 Hz, 1H), 8.08 (s, 1H), 8.04 (dd, J=9.2, 1.6 Hz, 1H), 7.49-7.46 (m, 2H), 7.41 (s, 1H), 4.68 (s, 2H), 4.61 (s, 2H), 3.98 (t, J=5.6 Hz, 2H), 2.91 (t, J=5.6 Hz, 2H), 2.48 (s, 3H).

Example 139: N-(4-(2-aminopyrimidin-4-yl)-2-methylbenzyl)-4,5,6,7-tetrahydrothieno[3,2-c]pyridine-2-carboxamide (I-140)

I-140

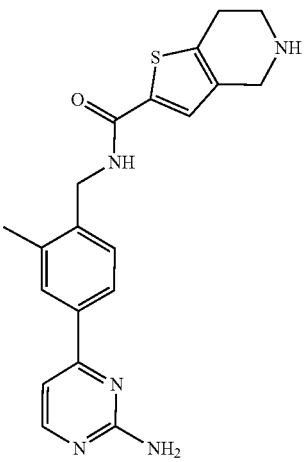

Synthesis of 5-tert-butyl 2-ethyl 6,7-dihydrothieno[3,2-c]pyridine-2,5(4H)-dicarboxylate

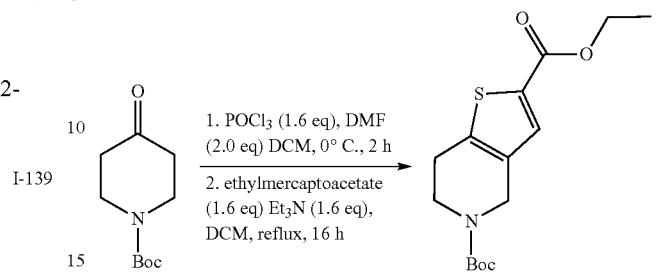

Synthesis of 5-tert-butyl 2-ethyl 6,7-dihydrothieno[3,2-c]pyridine-2,5(4H)-dicarboxylate was similar to that of ethyl 6,7-dihydro-4H-thieno[3,2-c]thiopyran-2-carboxylate, starting from tert-butyl 4-oxopiperidine-1-carboxylate. The crude product was purified by silica gel column chromatography (EtOAc/petroleum ether=1:10) to give 5-tert-butyl 2-ethyl 6,7-dihydrothieno[3,2-c]pyridine-2,5(4H)-dicarboxylate (4.1 g, yield: 52%) as an yellow oil. ESI-MS (M+H)+: 312.1. ¹H NMR (400 MHz, CDCl₃) δ: 7.49 (s, 1H), 4.48 (s, 2H), 4.33 (q, J=7.2 Hz, 2H), 3.72 (t, J=5.6 Hz, 2H), 2.86 (t, J=5.6 Hz, 2H), 1.49 (s, 9H) 1.36 (t, J=7.2 Hz, 3H).

Synthesis of 5-(tert-butoxycarbonyl)-4,5,6,7-tetrahydrothieno[3,2-c]pyridine-2-carboxylic acid

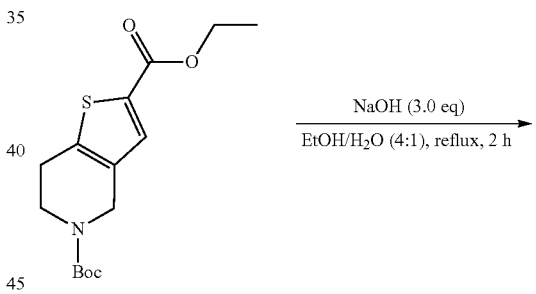

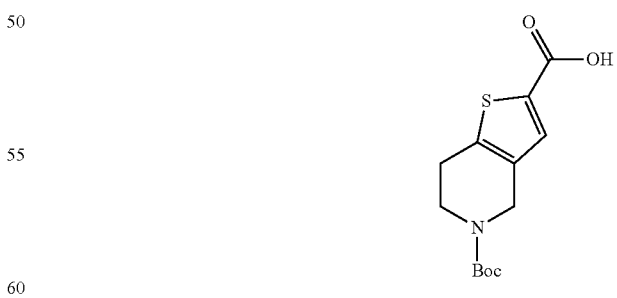

Synthesis of 5-(tert-butoxycarbonyl)-4,5,6,7-tetrahydrothieno[3,2-c]pyridine-2-carboxylic acid was similar to that of 6,7-dihydro-4H-thieno[3,2-c]thiopyran-2-carboxylic acid 5,5-dioxide. The crude product (500 mg, yield: 55%) was used in the next step without further purification. ESI-MS (M+H)+: 284.1.

281

Synthesis of tert-butyl 2-((4-(2-aminopyrimidin-4-yl)-2-methylbenzyl)carbamoyl)-6,7-dihydrothieno[3,2-c]pyridine-5(4H)-carboxylate

282

Synthesis of N-(4-(2-aminopyrimidin-4-yl)-2-methylbenzyl)-4,5,6,7-tetrahydrothieno[3,2-c]pyridine-2-carboxamide

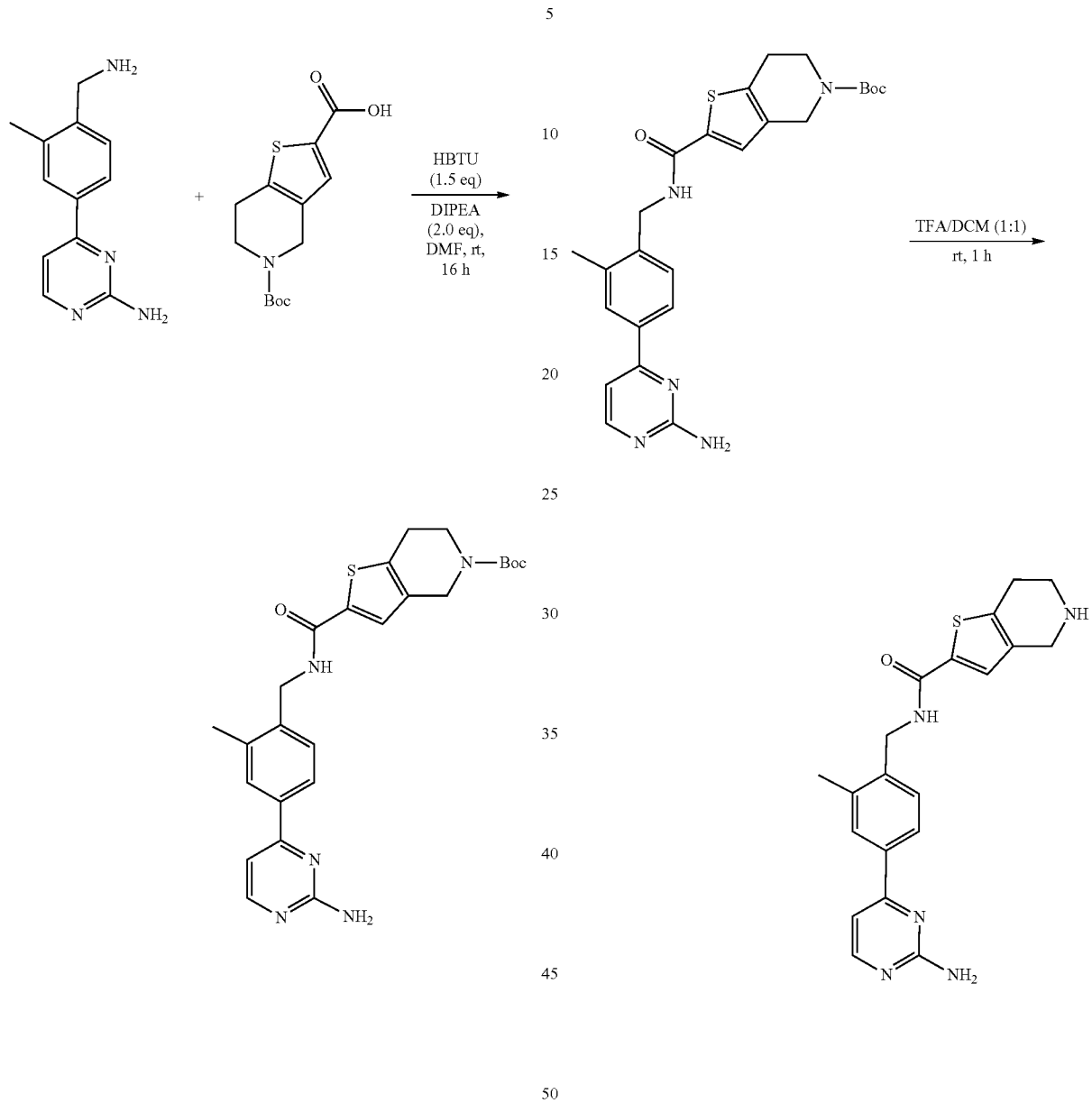

Synthesis of tert-butyl 2-((4-(2-aminopyrimidin-4-yl)-2-methylbenzyl)carbamoyl)-6,7-dihydrothieno[3,2-c]pyridine-5(4H)-carboxylate was similar to that of Example 134. The crude tert-butyl 2-((4-(2-aminopyrimidin-4-yl)-2-methylbenzyl)carbamoyl)-6,7-dihydrothieno[3,2-c]pyridine-5(4H)-carboxylate (200 mg, yield: 66%) was used in the next step without further purification. ESI-MS (M+H)$^+$: 480.2. $^1$H NMR (400 MHz, CDCl$_3$) δ: 8.34 (d, J=5.2 Hz, 1H), 8.01 (s, 1H), 7.85 (s, 1H), 7.78 (d, J=8.0 Hz, 1H), 7.37 (d, J=8.0 Hz, 1H), 7.23 (s, 1H), 7.03 (d, J=5.2 Hz, 1H), 6.07 (br, 1H), 5.09 (br, 2H), 4.65 (d, J=5.6 Hz, 2H), 4.46 (s, 2H), 3.72 (t, J=5.6 Hz, 2H), 2.85 (t, J=5.6 Hz, 2H), 2.43 (s, 3H), 1.48 (s, 9H).

A mixture of tert-butyl 2-((4-(2-aminopyrimidin-4-yl)-2-methylbenzyl)carbamoyl)-6,7-dihydrothieno[3,2-c]pyridine-5(4H)-carboxylate (200 mg, 0.418 mmol) in TFA/DCM (1:1, 20 mL) was stirred at room temperature for 1 h. After removal of solvent, the residue was adjusted to pH=8 with saturated aqueous sodium bicarbonate and purified by prep-HPLC (CH$_3$CN/H$_2$O with 0.05% NH$_3$.H$_2$O as mobile phase) to give compound N-(4-(2-aminopyrimidin-4-yl)-2-methylbenzyl)-4,5,6,7-tetrahydrothieno[3,2-c]pyridine-2-carboxamide (100 mg, yield: 63%) as yellow solid. ESI-MS (M+H)$^+$: 380.2. HPLC: (214 nm: 100%, 254 nm: 100%). $^1$H NMR (400 MHz, DMSO-d6) δ: 8.81 (t, J=6.0 Hz, 1H), 8.28 (d, J=5.6 Hz, 1H), 7.90 (s, 1H), 7.84 (d, J=8.0 Hz, 1H), 7.51 (s, 1H), 7.32 (d, J=8.0 Hz, 1H), 7.09 (d, J=5.6 Hz, 1H), 6.63 (s, 2H), 4.44 (d, J=5.6 Hz, 2H), 3.72 (s, 2H), 2.94 (t, J=5.6 Hz, 2H), 2.69 (t, J=5.6 Hz, 2H), 2.38 (s, 3H).

Example 140: N-(4-(2-aminopyrimidin-4-yl)-2-methylbenzyl)-5-methyl-4,5,6,7-tetrahydrothieno[3,2-c]pyridine-2-carboxamide (I-141)

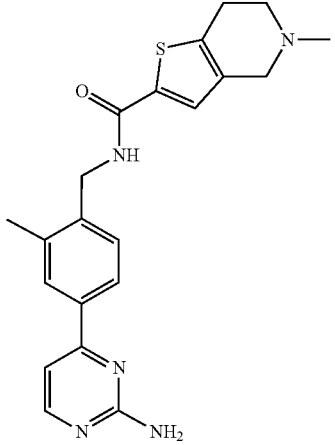

I-141

Synthesis of ethyl 4,5,6,7-tetrahydrothieno[3,2-c]pyridine-2-carboxylate

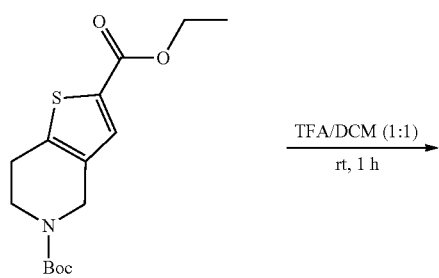

Synthesis of ethyl 4,5,6,7-tetrahydrothieno[3,2-c]pyridine-2-carboxylate was similar to that of N-(4-(2-aminopyrimidin-4-yl)-2-methylbenzyl)-4,5,6,7-tetrahydrothieno[3,2-c]pyridine-2-carboxamide. Crude ethyl 4,5,6,7-tetrahydrothieno[3,2-c]pyridine-2-carboxylate (678 mg, yield: 100%) was used in the next step without further purification. ESI-MS (M+H)⁺: 212.1.

Synthesis of ethyl 5-methyl-4,5,6,7-tetrahydrothieno[3,2-c]pyridine-2-carboxylate

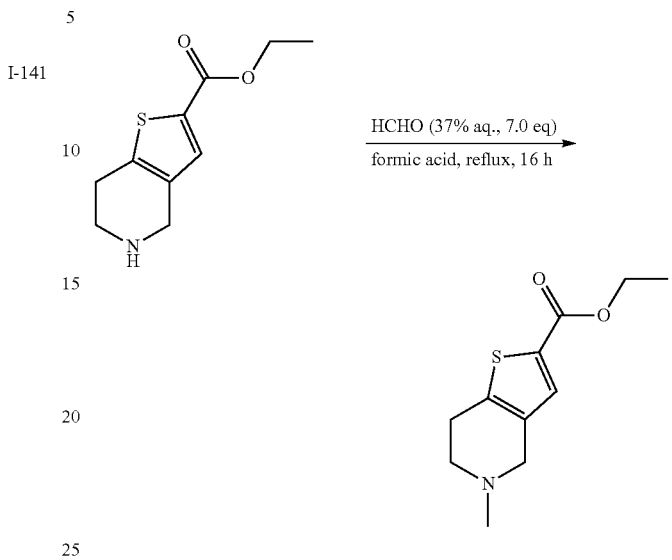

To a solution of ethyl 4,5,6,7-tetrahydrothieno[3,2-c]pyridine-2-carboxylate (678 mg, 3.22 mmol) in formic acid (30 mL) was added formalin (37%, 1.8 mL). The mixture was refluxed for 16 h. After cooling to rt, the mixture was concentrated under reduced pressure. The residue was adjusted to pH=8 with 1 N NaOH and extracted with EtOAc (80 mL×2). The combined extracts were washed with brine, dried, purified with pre-TLC (EtOAc/petroleum ether=1:1) to give ethyl 5-methyl-4,5,6,7-tetrahydrothieno[3,2-c]pyridine-2-carboxylate (130 mg, yield: 18%) as an yellow oil. ESI-MS (M+H)⁺: 226.1. ¹H NMR (400 MHz, CDCl₃) δ: 7.44 (s, 1H), 4.32 (q, J=7.2 Hz, 2H), 3.51 (s, 2H), 2.95 (t, J=5.6 Hz, 2H), 2.76 (t, J=5.6 Hz, 2H), 2.49 (s, 3H), 1.35 (t, J=7.2 Hz, 3H).

Synthesis of 5-methyl-4,5,6,7-tetrahydrothieno[3,2-c]pyridine-2-carboxylic acid

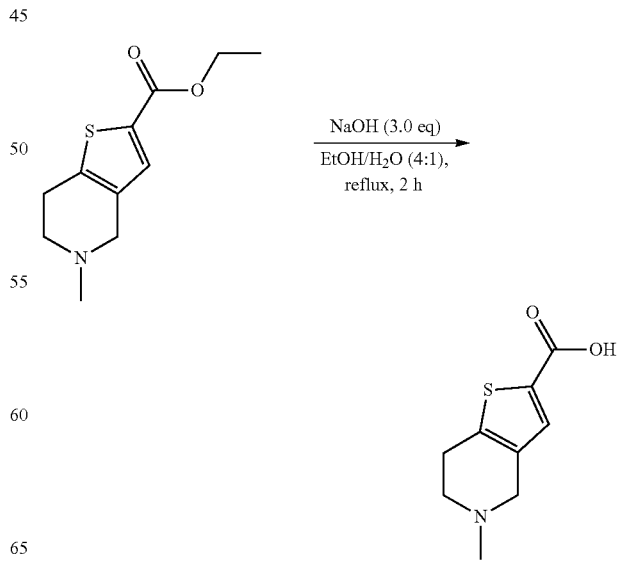

Synthesis of 5-methyl-4,5,6,7-tetrahydrothieno[3,2-c]pyridine-2-carboxylic acid was similar to that of 6,7-dihydro-4H-thieno[3,2-c]thiopyran-2-carboxylic acid 5,5-dioxide. The crude product (100 mg, yield: 88%) was used in the next step without further purification. ESI-MS (M+H)⁺: 198.1.

Synthesis of N-(4-(2-aminopyrimidin-4-yl)-2-methylbenzyl)-5-methyl-4,5,6,7-tetrahydrothieno[3,2-c]pyridine-2-carboxamide

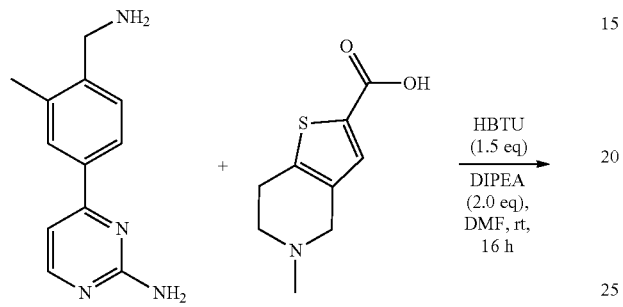

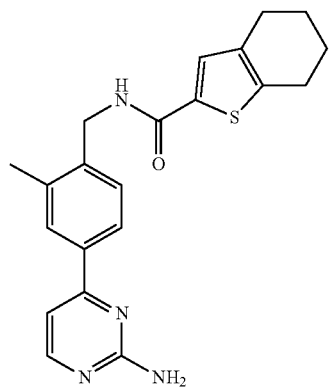

Synthesis of N-(4-(2-aminopyrimidin-4-yl)-2-methylbenzyl)-5-methyl-4,5,6,7-tetrahydrothieno[3,2-c]pyridine-2-carboxamide was similar to that of Example 134. The crude product was purified by prep-HPLC (CH₃CN/H₂O with 0.05% NH₃.H₂O as mobile phase) to give compound N-(4-(2-aminopyrimidin-4-yl)-2-methylbenzyl)-5-methyl-4,5,6,7-tetrahydrothieno[3,2-c]pyridine-2-carboxamide (53 mg, yield: 43%) as yellow solid. ESI-MS (M+H)⁺: 394.2. HPLC: (214 nm: 100%, 254 nm: 100%). ¹H NMR (400 MHz, DMSO-d₆) δ: 8.83 (t, J=5.2 Hz, 1H), 8.28 (d, J=5.2 Hz, 1H), 7.90 (s, 1H), 7.84 (d, J=8.0 Hz, 1H), 7.51 (s, 1H), 7.32 (d, J=8.0 Hz, 1H), 7.09 (d, J=5.2 Hz, 1H), 6.63 (s, 2H), 4.45 (d, J=5.2 Hz, 2H), 3.38 (s, 2H), 2.82 (t, J=5.2 Hz, 2H), 2.64 (t, J=5.2 Hz, 2H), 2.38 (s, 3H), 2.35 (s, 3H).

Example 141: N-(4-(2-aminopyrimidin-4-yl)-2-methylbenzyl)-4,5,6,7-tetrahydrobenzo[b]thiophene-2-carboxamide (I-142)

I-142

Synthesis of N-(4-(2-aminopyrimidin-4-yl)-2-methylbenzyl)-4,5,6,7-tetrahydrobenzo[b]thiophene-2-carboxamide was similar to that of Example 134. The residue was purified by prep-HPLC (CH₃CN/H₂O with 0.05% NH₃.H₂O as mobile phase) to give N-(4-(2-aminopyrimidin-4-yl)-2-methylbenzyl)-4,5,6,7-tetrahydrobenzo[b]thiophene-2-carboxamide as a white solid (120 mg, yield: 55%). ESI-MS (M+H)⁺: 379.1. HPLC: (214 nm: 98%, 254 nm: 99%). ¹H NMR (400 MHz, CDCl₃) δ: 8.34 (d, J=5.2 Hz, 1H), 7.85 (s, 1H), 7.79 (d, J=8.0 Hz, 1H), 7.39 (d, J=8.0 Hz, 1H), 7.20 (s, 1H), 7.04 (d, J=5.6 Hz, 1H), 5.97 (br, 1H), 5.13 (br, 2H), 4.65 (d, J=5.2 Hz, 2H), 2.79 (t, J=6.0 Hz, 2H), 2.61 (t, J=6.4 Hz, 2H), 2.43 (s, 3H), 1.86-1.71 (m, 4H).

Example 142: N-(4-(6-acetamidopyrimidin-4-yl)-2-methylbenzyl)-4,5,6,7-tetrahydrobenzo[b]thiophene-2-carboxamide (I-143)

I-143

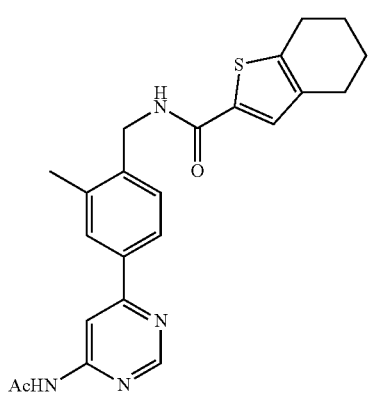

Synthesis of N-(4-bromo-2-methylbenzyl)-4,5,6,7-tetrahydrobenzo[b]thiophene-2-carboxamide

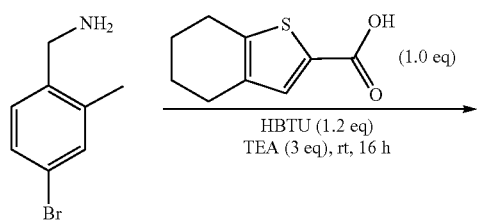

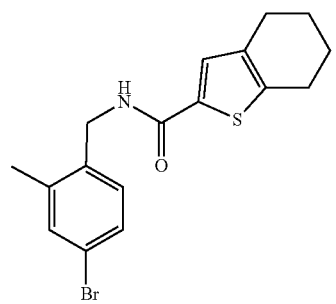

To a solution of 4,5,6,7-tetrahydrobenzo[b]thiophene-2-carboxylic acid (2.1 g, 12 mmol) in 30 mL DMF were added (4-bromo-2-methylphenyl)methanamine (2.4 g, 12 mmol), HBTU (5.4 g, 14.4 mmol) and TEA (3.6 g, 36 mmol). The mixture was stirred at rt for 16 h. After diluted with water (100 ml), the mixture was extracted with EtOAc (100 mL×2). The combined organic layer was washed with H$_2$O (80 mL×2), dried (Na$_2$SO$_4$), filtered and concentrated. The residue was purified by silica gel chromatography column (EtOAc/petroleum ether=1:5) to give N-(4-bromo-2-methylbenzyl)-4,5,6,7-tetrahydrobenzo[b]thiophene-2-carboxamide as a white solid (3.8 g, yield: 86%). ESI-MS: 364.1 (M+H)$^+$.

Synthesis of N-(2-methyl-4-(4,4,5,5-tetramethyl-1,3,2-dioxaborolan-2-yl)benzyl)-4,5,6,7-tetrahydrobenzo[b]thiophene-2-carboxamide

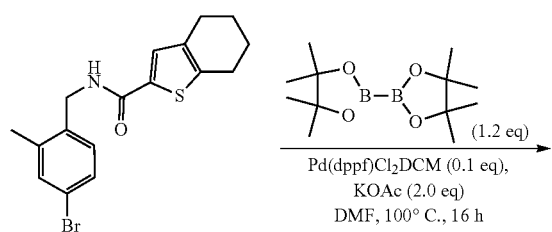

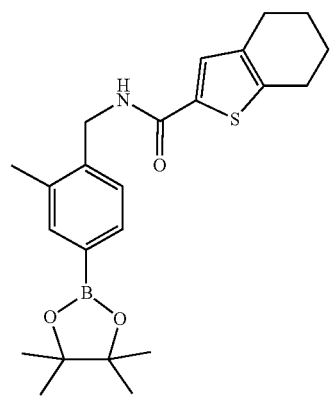

To a solution of N-(4-bromo-2-methylbenzyl)-4,5,6,7-tetrahydrobenzo[b]thiophene-2-carboxamide (1 g, 2.7 mmol) and bis(pinacolato)diboron (740 mg, 3.2 mmol) in DMF (15 mL) were added KOAc (544 mg, 5.4 mmol) and Pd(dppf)Cl$_2$DCM (112 mg, 0.14 mmol) respectively. The mixture was stirred at 100° C. for 16 h under N$_2$. After cooling to rt, the mixture was diluted with water (80 mL) and extracted with EtOAc (80 mL×2). The organic layer was washed with brine (80 mL), dried (Na$_2$SO$_4$), filtered and concentrated. The residue was purified by silica gel chromatography column (EtOAc/petroleum ether=1:4) to give N-(2-methyl-4-(4,4,5,5-tetramethyl-1,3,2-dioxaborolan-2-yl)benzyl)-4,5,6,7-tetrahydrobenzo[b]thiophene-2-carboxamide as a white solid (883 mg, yield: 76%). ESI-MS (M+H)$^+$: 412.2. $^1$H NMR (400 MHz, CDCl$_3$) δ: 7.65 (s, 1H), 7.63 (d, J=8.0 Hz, 1H), 7.29 (d, J=7.2 Hz, 1H), 7.16 (s, 1H), 5.88 (br, 1H), 4.61 (d, J=5.2 Hz, 2H), 2.77 (t, J=6.0 Hz, 2H), 2.56 (t, J=6.4 Hz, 2H), 2.35 (s, 3H), 1.86-1.76 (m, 4H), 1.34 (s, 12H).

Synthesis of N-(4-(6-acetamidopyrimidin-4-yl)-2-methylbenzyl)-4,5,6,7-tetrahydrobenzo[b]thiophene-2-carboxamide

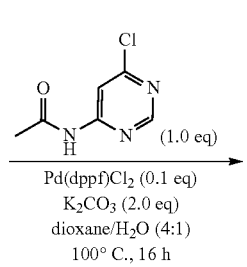

Synthesis of 4-bromo-2-(bromomethyl)benzonitrile

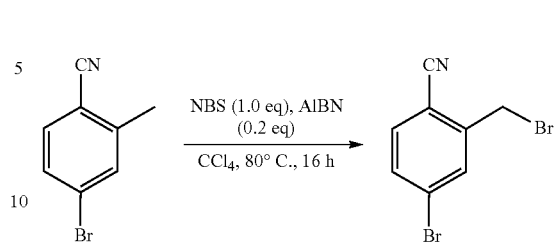

To a solution of 4-bromo-2-methylbenzonitrile (2 g, 10.2 mmol) in 15 mL CCl₄ were added NBS (1.8 g, 10.2 mmol) and AIBN (340 mg, 2.08 mmol). The mixture was stirred at 80° C. for 16 h. After diluted with water (30 mL), the mixture was extracted with DCM (50 mL×2). The combined organic layer was washed with H₂O (30 mL×2), dried (Na₂SO₄), filtered and concentrated. The crude product was used in the next step without further purification.

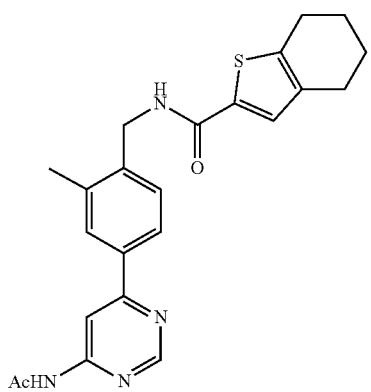

Synthesis of N-(4-(6-acetamidopyrimidin-4-yl)-2-methylbenzyl)-4,5,6,7-tetrahydrobenzo[b]thiophene-2-carboxamide was similar to that of tert-butyl 4-(2-chloropyrimidin-4-yl)-2-methylbenzylcarbamate. The crude product was purified by prep-HPLC (CH₃CN/H₂O with 0.05% NH₃·H₂O as mobile phase) to give N-(4-(6-acetamidopyrimidin-4-yl)-2-methylbenzyl)-4,5,6,7-tetrahydrobenzo[b]thiophene-2-carboxamide as a yellow solid (60 mg, yield: 41%). ESI-MS (M+H)⁺: 421.1. HPLC: (214 nm: 99%, 254 nm: 97%). ¹H NMR (400 MHz, CDCl₃) δ: 8.82 (s, 1H), 8.52 (s, 1H), 8.08 (br, 1H), 7.87 (s, 1H), 7.85 (d, J=7.6 Hz, 1H), 7.35 (d, J=7.6 Hz, 1H), 7.15 (s, 1H), 5.94 (br, 1H), 4.59 (d, J=5.6 Hz, 2H), 2.72 (t, J=5.2 Hz, 2H), 2.54 (t, J=6.0 Hz, 2H), 2.37 (s, 3H) 2.21 (s, 3H), 1.79-1.71 (m, 4H).

Synthesis of tert-butyl 5-bromo-2-cyanobenzyl(methyl)carbamate

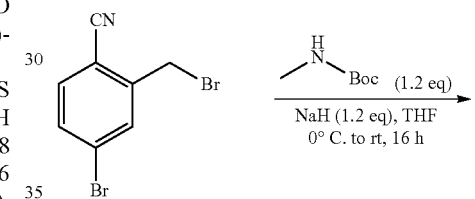

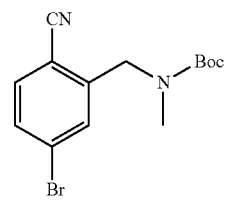

To a solution of tert-butyl methylcarbamate (3.5 g, 26.4 mmol) in dry DMF (15 mL) was added NaH (0.64 g, 26.4 mmol) in ice bath. The mixture was stirred at rt for 30 min, then a solution of 4-bromo-2-(bromomethyl)benzonitrile (6.0 g, 22 mmol) in DMF (15 mL) was added. The mixture was stirred at rt for another 16 h. After diluted with water (50 mL), the mixture was extracted with EtOAc (80 mL×2). The combined organic layer was washed with H₂O (60 mL×2), dried (Na₂SO₄), filtered and concentrated. The residue was purified by silica gel column chromatography (EA/PE=1:10) to give tert-butyl 5-bromo-2-cyanobenzyl(methyl)carbamate as yellow solid (900 mg, yield: 13%). ESI-MS (M+Na)⁺: 347.0. ¹H NMR (400 MHz, CDCl₃) δ: 7.54-7.51 (m, 3H). 4.60-4.58 (m, 2H), 2.95-2.89 (m, 3H), 1.50-1.43 (m, 9H).

Example 143: tert-butyl 5-(2-aminopyrimidin-4-yl)-2-((4,5,6,7-tetrahydrobenzo[b]thiophene-2-carboxamido)methyl)benzyl(methyl)carbamate (I-144)

I-144

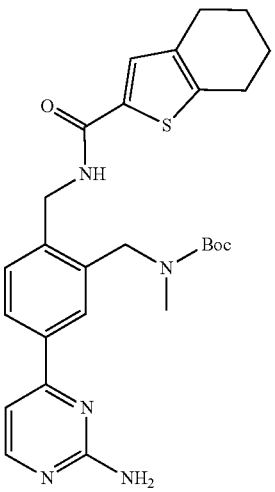

Synthesis of tert-butyl 5-(2-aminopyrimidin-4-yl)-2-cyanobenzyl(methyl)carbamate

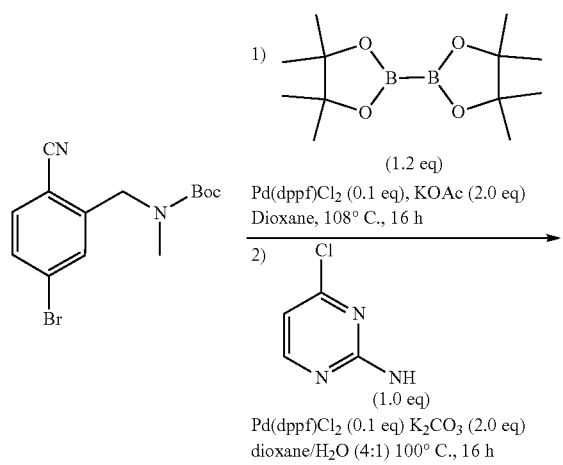

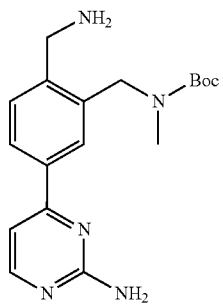

To a solution of tert-butyl 5-(2-aminopyrimidin-4-yl)-2-cyanobenzyl(methyl)carbamate (1.6 g, 4.7 mmol) in 30 mL MeOH were added Raney-Ni (160 mg) and NH$_3$.H$_2$O (3 mL). The mixture was stirred at rt for 16 h under hydrogen atmosphere. The catalyst was filtered off and the filtrate was concentrated to give tert-butyl 2-(aminomethyl)-5-(2-aminopyrimidin-4-yl)benzyl(methyl)carbamate as colorless oil (1.04 g, yield: 65%), which was used to next step without further purification. ESI-MS (M+H)$^+$: 344.1.

Synthesis of tert-butyl 5-(2-aminopyrimidin-4-yl)-2-((4,5,6,7-tetrahydrobenzo[b]thiophene-2-carboxamido)methyl)benzyl(methyl)carbamate

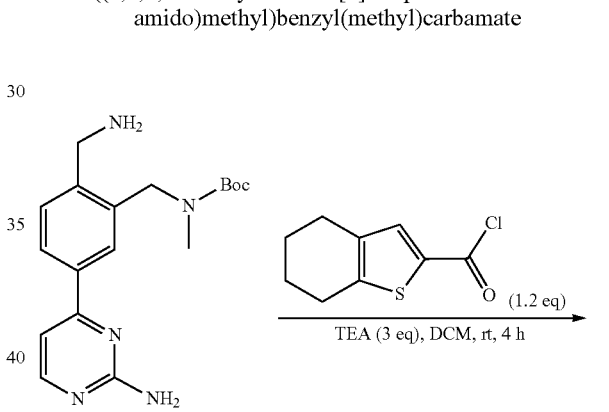

Synthesis of tert-butyl 5-(2-aminopyrimidin-4-yl)-2-cyanobenzyl(methyl)carbamate was similar to that of tert-butyl 4-(2-chloropyrimidin-4-yl)-2-methylbenzylcarbamate. The residue was purified by silica gel column chromatography (EtOAc/petroleum ether=1:5) to give tert-butyl 5-(2-aminopyrimidin-4-yl)-2-cyanobenzyl(methyl)carbamate as a yellow solid (1.6 g, yield: 64%). ESI-MS (M+H)$^+$: 340.2. $^1$H NMR (400 MHz, CDCl$_3$) δ: 8.33 (d, J=4.0 Hz, 1H), 7.98 (s, 1H), 7.94 (d, J=6.4 Hz, 1H), 7.70 (d, J=8.0 Hz, 1H), 6.99 (d, J=5.2 Hz, 1H), 4.64 (s, 2H), 2.91-2.89 (m, 3H), 1.17-1.15 (m, 9H).

Synthesis of tert-butyl 2-(aminomethyl)-5-(2-aminopyrimidin-4-yl)benzyl(methyl)carbamate

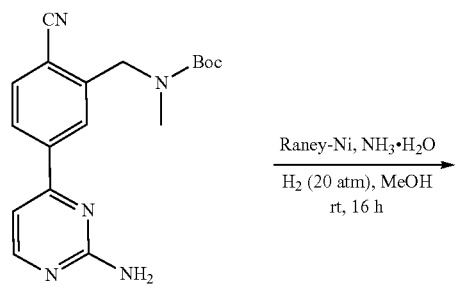

Synthesis of tert-butyl 5-(2-aminopyrimidin-4-yl)-2-((4,5,6,7-tetrahydrobenzo[b]thiophene-2-carboxamido)methyl)benzyl(methyl)carbamate was similar to that of Example I-7. The residue was purified by silica gel chromatography column (EtOAc/petroleum ether=1:4) to give tert-butyl 5-(2-aminopyrimidin-4-yl)-2-((4,5,6,7-tetrahydrobenzo[b]thiophene-2-carboxamido)methyl)benzyl(methyl)carbamate as a yellow solid (600 mg, yield: 51%). ESI-MS (M+H)$^+$: 508.2. $^1$H NMR (400 MHz, CD$_3$OD) δ: 8.28 (d, J=5.2 Hz, 1H), 7.97 (d, J=6.8 Hz, 1H), 7.90 (s, 1H), 7.48 (d, J=8.0 Hz, 1H), 7.39 (s, 1H), 7.11 (d, J=5.2 Hz, 1H), 4.65 (s, 2H), 4.60 (s, 2H), 2.90 (s, 3H), 2.76 (t, J=5.2 Hz, 2H), 2.58 (t, J=5.6 Hz, 2H), 1.87-1.82 (m, 4H), 1.47 (s, 9H).

Example 144: N-(4-(2-aminopyrimidin-4-yl)-2-((methylamino)methyl)benzyl)-4,5,6,7-tetrahydrobenzo[b]thiophene-2-carboxamide (I-145)

Example 145: N-(4-(2-aminopyrimidin-4-yl)-2-((N-methylacrylamido)methyl)benzyl)-4,5,6,7-tetrahydrobenzo[b]thiophene-2-carboxamide (I-146)

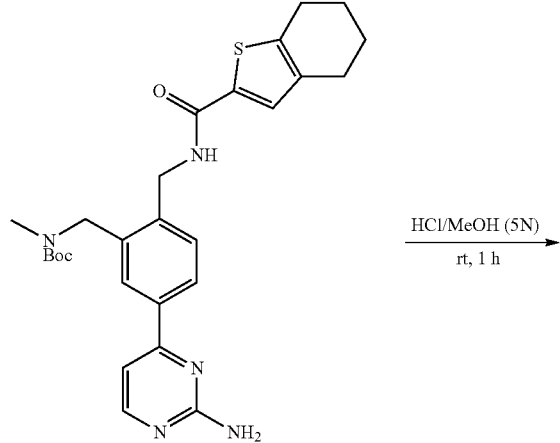

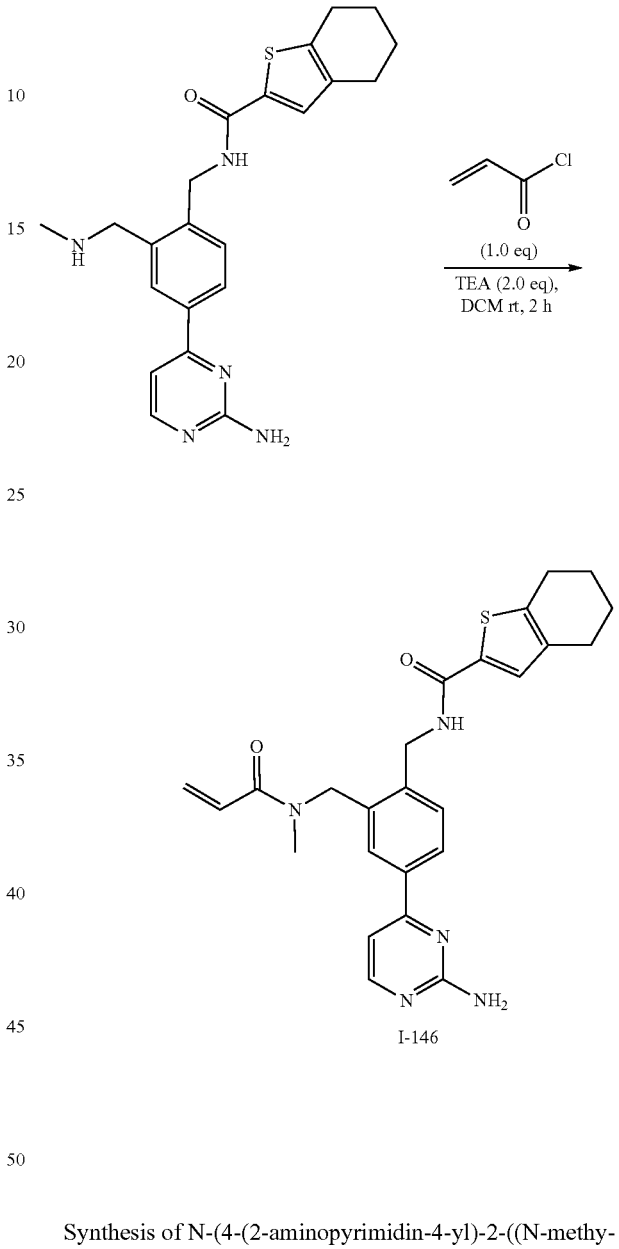

Synthesis of N-(4-(2-aminopyrimidin-4-yl)-2-((methylamino)methyl)benzyl)-4,5,6,7-tetrahydrobenzo[b]thiophene-2-carboxamide was similar to that of Example 139. The crude product was purified by prep-HPLC (CH$_3$CN/H$_2$O as mobile phase) to give N-(4-(2-aminopyrimidin-4-yl)-2-((methylamino)methyl)benzyl)-4,5,6,7-tetrahydrobenzo[b]thiophene-2-carboxamide as a white solid (21 mg, yield: 58%). ESI-MS (M+H)$^+$: 408.2. $^1$H NMR (400 MHz, DMSO-d$_6$) δ: 9.47-9.45 (m, 2H), 9.29 (s, 1H), 8.51 (d, J=5.2 Hz, 1H), 8.39 (s, 1H), 8.16 (d, J=8.0 Hz, 1H), 7.95 (br, 1H), 7.60 (s, 2H), 7.50-7.49 (m, 1H), 4.60 (d, J=5.2 Hz, 2H), 4.37 (s, 2H), 2.72-2.67 (m, 5H) 2.56-2.55 (m, 2H), 1.75-1.73 (m, 4H).

Synthesis of N-(4-(2-aminopyrimidin-4-yl)-2-((N-methylacrylamido)methyl)benzyl)-4,5,6,7-tetrahydrobenzo[b]thiophene-2-carboxamide was similar to that of Example 143. The crude product was purified by prep-HPLC (CH$_3$CN/H$_2$O with 0.05% NH$_3$.H$_2$O as mobile phase) to give N-(4-(2-aminopyrimidin-4-yl)-2-((N-methylacrylamido)methyl)benzyl)-4,5,6,7-tetrahydrobenzo[b]thiophene-2-carboxamide as a white solid (10 mg, yield: 28%). ESI-MS (M+H)$^+$: 462.2. $^1$H NMR (400 MHz, DMSO-d$_6$) δ: 8.91-8.89 (m, 1H), 8.30 (d, J=5.2 Hz, 1H), 7.93 (d, J=8.0 Hz, 1H), 7.79-7.63 (m, 1H), 7.53-7.52 (m, 1H), 7.44-7.38 (m, 1H), 7.05-6.97 (m, 1H), 6.91-6.70 (m, 2H), 6.22-6.19 (m, 1H), 5.78-5.63 (m, 1H), 4.87-4.76 (m, 2H), 4.47-4.46 (m, 2H), 3.02-2.97 (m, 3H), 2.73 (t, J=5.2 Hz, 2H), 2.58 (t, J=4.8 Hz, 2H), 1.78-1.72 (m, 4H).

Example 146: 2-(tert-butyl)-N-(2-methyl-4-(6-((5-methyl-5,6,7,8-tetrahydro-4H-pyrazolo[1,5-a][1,4]diazepin-2-yl)amino)pyrimidin-4-yl)benzyl)thiazole-5-carboxamide

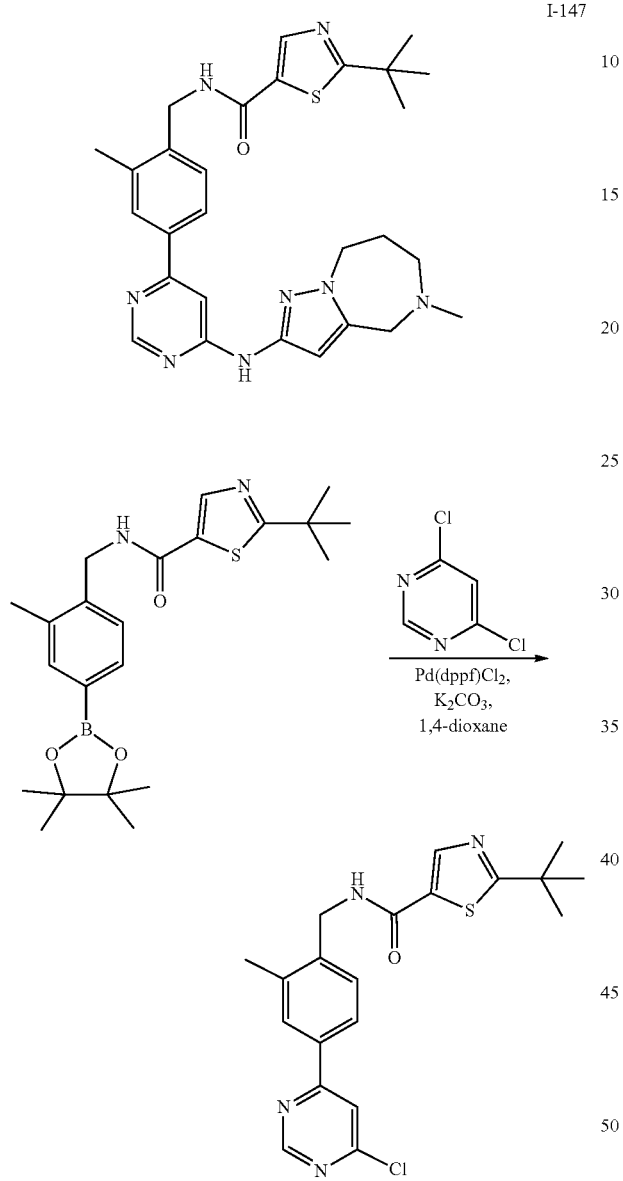

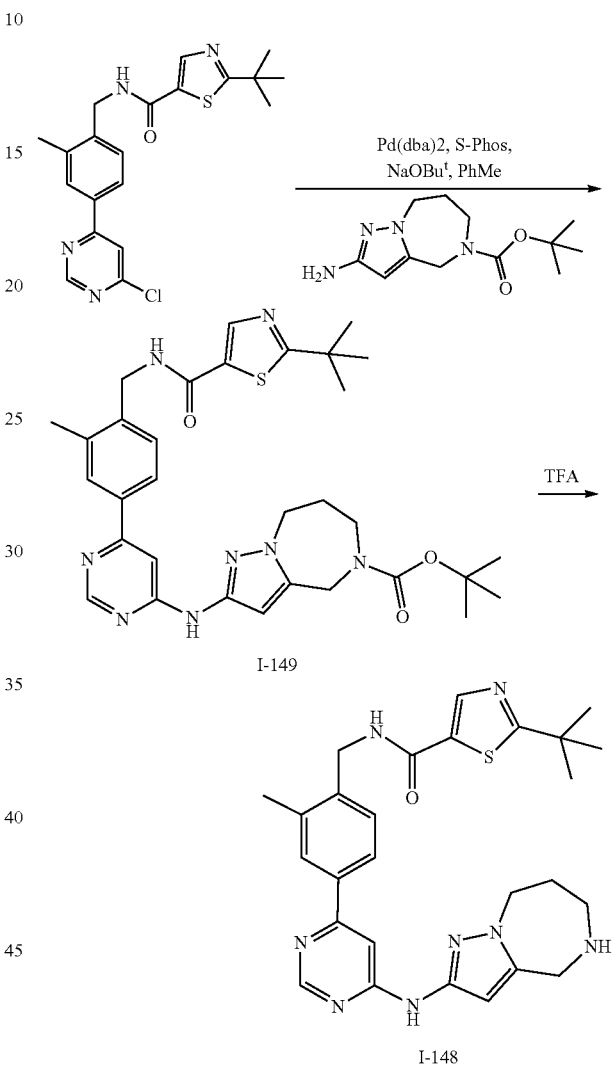

down, diluted with EtOAc, washed with water. The organic phase was dried, concentrated. The crude was purified on Si gel (EtOAc/heptane gradient from 10/90 to 100/0) to give the title compound as a light yellow powder (1.82 g). LCMS: RT 1.75 min.; MH+401.1; $^1$H NMR (400 MHz, DMSO-$d_6$) δ: 9.02-9.17 (m, 2H), 8.31 (d, J=12.80 Hz, 2H), 8.02-8.15 (m, 2H), 7.40 (d, J=8.03 Hz, 1H), 4.50 (d, J=5.52 Hz, 2H), 2.41 (s, 3H), 1.39 (s, 9H).

Synthesis of 2-(tert-butyl)-N-(4-(6-chloropyrimidin-4-yl)-2-methylbenzyl)thiazole-5-carboxamide A mixture of 2-(tert-butyl)-N-(2-methyl-4-(4,4,5,5-tetramethyl-1,3,2-dioxaborolan-2-yl)benzyl)thiazole-5-carboxamide (2.5 g, 6.0 mmol) and pyrimidine, 4,6-dichloro- (1.08 g, 7.24 mmol) in 1,4-dioxane (25 mL) was degassed for 5 min. water (2.0 mL, 110 mmol), [1,1'-bis(diphenylphosphino)ferrocene]dichloropalladium(II), complex with dichloromethane (1:1) (493 mg, 0.60 mmol) and potassium carbonate (1.67 g, 12.07 mmol) were then added, degassed for another 5 min, and the reaction was heated at 110° C. for 2 h. After the reaction, the mixture was cooled Synthesis of tert-butyl 2-((6-(4-((2-(tert-butyl)thiazole-5-carboxamido)methyl)-3-methylphenyl)pyrimidin-4-yl)amino)-7,8-dihydro-4H-pyrazolo[1,5-a][1,4]diazepine-5(6H)-carboxylate (I-149) and 2-(tert-butyl)-N-(2-methyl-4-(6-((5,6,7,8-tetrahydro-4H-pyrazolo[1,5-a][1,4]diazepin-2-yl)amino)pyrimidin-4-yl)benzyl)thiazole-5-carboxamide (I-148)

A mixture of 2-(tert-butyl)-N-(4-(6-chloropyrimidin-4-yl)-2-methylbenzyl)thiazole-5-carboxamide (200 mg, 0.50 mmol) and 2-amino-7,8-dihydro-4H,6H-1,5,8a-triaza-azulene-5-carboxylic acid tert-butyl ester (164 mg, 0.65 mmol) in toluene (6.0 mL, 56 mmol) was degassed for 5 min, 2-dicyclohexylphosphino-2',6'-dimethoxybiphenyl (41 mg, 0.1 mmol) and tris(dibenzylideneacetone)dipalladium(0)

(46 mg, 0.05 mmol) and sodium tert-butoxide (144 mg, 1.5 mmol) were then added, degassed for another 5 min, and the reaction was heated in microwave at 100° C. for 1 h. The reaction was then cooled down, diluted with EtOAc, washed with water. The organics was dried, concentrated. The crude was purified by ISCO (gradient DCM+1% to 10%2M NH₃/MeOH) to give tert-butyl 2-((6-(4-((2-(tert-butyl)thiazole-5-carboxamido)methyl)-3-methylphenyl)pyrimidin-4-yl)amino)-7,8-dihydro-4H-pyrazolo[1,5-a][1,4]diazepine-5(6H)-carboxylate (I-149) as a light yellow powder (LCMS: RT 1.37 min.; MH+617.3) which was then dissolved in methylene chloride (4.0 mL, 62 mmol), treated with trifluoroacetic acid (0.4 mL, 5 mmol). The reaction was stirred at RT for 1 h. Remove the solvent. The crude was purified by ISCO (reverse phase ACN/Water w/0.1% TFA gradient) to give 2-(tert-butyl)-N-(2-methyl-4-(6-((5,6,7,8-tetrahydro-4H-pyrazolo[1,5-a][1,4]diazepin-2-yl)amino)pyrimidin-4-yl)benzyl)thiazole-5-carboxamide (I-148) as a yellow powder (48 mg, TFA salt). LCMS: RT 0.97 min.; MH+517.3; ¹H NMR (400 MHz, DMSO-d₆) δ: 10.27 (br. s., 1H), 8.98-9.18 (m, 3H), 8.70 (s, 1H), 8.33 (s, 1H), 7.72-7.87 (m, 2H), 7.40 (d, J=8.03 Hz, 1H), 6.70 (br. s., 1H), 4.31-4.60 (m, 6H), 3.41 (br. s., 2H), 2.41 (s, 3H), 2.02 (br. s., 2H), 1.39 (s, 9H).

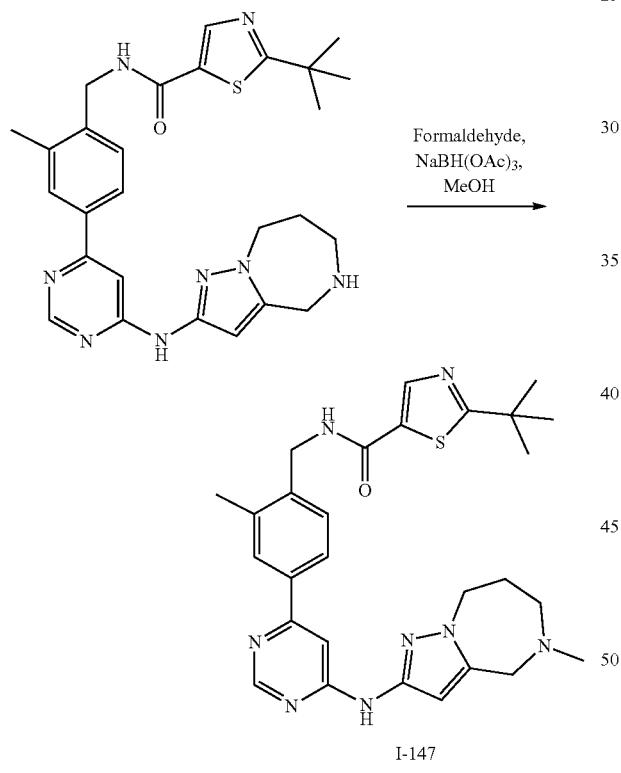

I-147

Synthesis of 2-(tert-butyl)-N-(2-methyl-4-(6-((5-methyl-5,6,7,8-tetrahydro-4H-pyrazolo[1,5-a][1,4]diazepin-2-yl)amino)pyrimidin-4-yl)benzyl)thiazole-5-carboxamide (I-147)

2-(tert-butyl)-N-(2-methyl-4-(6-((5,6,7,8-tetrahydro-4H-pyrazolo[1,5-a][1,4]diazepin-2-yl)amino)pyrimidin-4-yl)benzyl)thiazole-5-carboxamide (30.0 mg, 0.06 mmol) was dissolved in methanol (1.0 mL) and formaldehyde (0.5 mL, 20 mmol). Sodium triacetoxyborohydride (62 mg, 0.29 mmol) was then added. The mixture was heated in microwave at 100° C. for 10 min. LCMS showed the complete of the reaction. The crude was purified by HPLC to give the title compound as a light yellow powder (16 mg, TFA salt). LCMS: RT 0.96 min.; MH+531.3; ¹H NMR (400 MHz, DMSO-d₆) δ: 10.36 (br. s., 1H), 9.12 (t, J=5.65 Hz, 1H), 8.72 (s, 1H), 8.33 (s, 1H), 7.70-7.89 (m, 2H), 7.40 (d, J=8.03 Hz, 1H), 6.75 (br. s., 1H), 4.27-4.76 (m, 6H), 3.36-3.71 (m, 2H), 2.82 (s, 3H), 2.41 (s, 3H), 1.85-2.28 (m, 2H), 1.39 (s, 9H).

Example 147: 1-(tert-butyl)-N-(2-methyl-4-(6-((5-methyl-4,5,6,7-tetrahydropyrazolo[1,5-a]pyrazin-2-yl)amino)pyrimidin-4-yl)benzyl)-1H-pyrazole-4-carboxamide

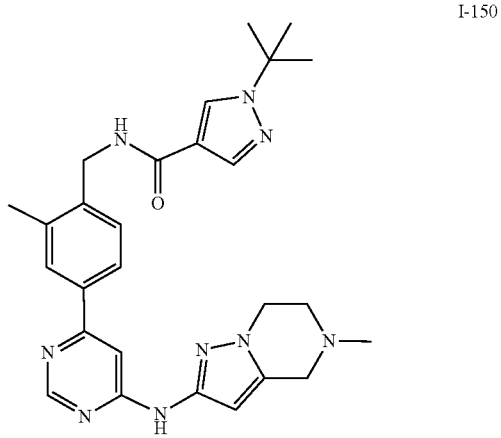

I-150

The synthesis of 1-(tert-butyl)-N-(2-methyl-4-(6-((5-methyl-4,5,6,7-tetrahydropyrazolo[1,5-a]pyrazin-2-yl)amino)pyrimidin-4-yl)benzyl)-1H-pyrazole-4-carboxamide (I-150) was similar to that of Example 62, except 1-tert-butyl-1H-pyrazole-4-carboxylic acid was substituted for 2-(tert-butyl)thiazole-5-carboxylic acid to give the title compound as a yellow solid powder (45 mg). ESI-MS (M+H)+: 500.3. ¹H NMR (400 MHz, METHANOL-d₄) δ: 8.80 (s, 1H), 8.68 (t, J=5.65 Hz, 1H), 8.29 (s, 1H), 7.98 (s, 1H), 7.67-7.81 (m, 2H), 7.53 (d, J=7.78 Hz, 1H), 6.61 (br. s., 1H), 4.61 (d, J=15.56 Hz, 4H), 4.47 (t, J=5.77 Hz, 2H), 3.87 (t, J=5.77 Hz, 2H), 3.12 (s, 3H), 2.52 (s, 3H), 1.63 (s, 9H).

Example 148: 3-(tert-butoxy)-N-(2-methyl-4-(2-((1-methyl-1H-pyrazol-4-yl)amino)pyrimidin-4-yl)benzyl)azetidine-1-carboxamide

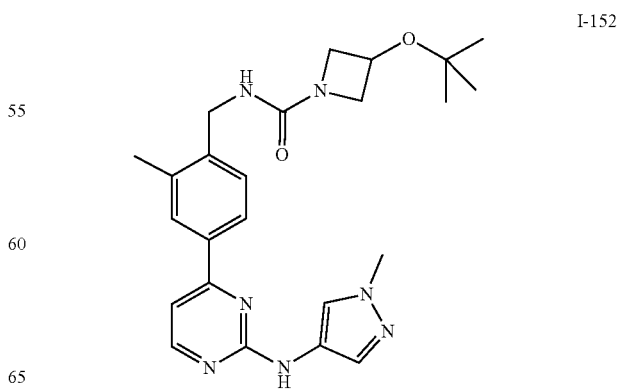

I-152

Synthesis of the 3-(tert-butoxy)-N-(2-methyl-4-(2-((1-methyl-1H-pyrazol-4-yl)amino)pyrimidin-4-yl)benzyl)azetidine-1-carboxamide (I-152) was the similar that of Example 19, except 3-(tert-butoxy)azetidine was substituted for 4-(trifluoromethyl)piperidine to give product as a solid (70 mg, yield: 20%). ESI-MS (M+H)+: 450.3. $^1$H NMR (400 MHz, DMSO-d$_6$) δ: 9.48 (s, 1H), 8.45 (d, J=5.02 Hz, 1H), 7.92 (s, 3H), 7.55 (br. s., 1H), 7.35 (d, J=8.28 Hz, 1H), 7.25 (d, J=5.02 Hz, 1H), 6.83 (t, J=5.65 Hz, 1H), 4.38-4.55 (m, 1H), 4.22 (d, J=5.27 Hz, 2H), 4.03 (t, J=7.65 Hz, 2H), 3.83 (s, 3H), 3.53-3.68 (m, 2H), 2.37 (s, 3H), 1.04-1.14 (m, 9H).

Example 149: 2-(tert-butyl)-N-(4-(6-((1-(2-hydroxyethyl)-1H-pyrazol-3-yl)amino)pyrimidin-4-yl)-2-methylbenzyl)thiazole-5-carboxamide

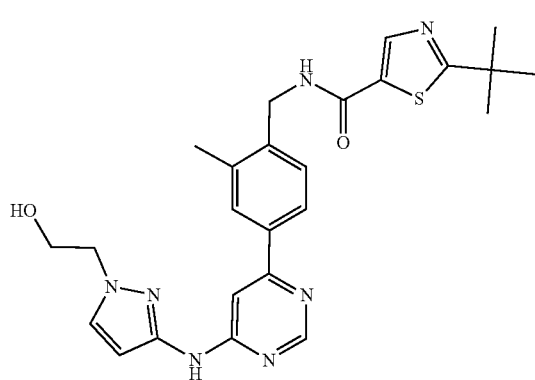

I-151

Synthesis of 2-(tert-butyl)-N-(4-(6-((1-(2-hydroxyethyl)-1H-pyrazol-3-yl)amino)pyrimidin-4-yl)-2-methylbenzyl)thiazole-5-carboxamide (I-151) was the similar to that of Example 62, starting from 2-(3-amino-1H-pyrazol-1-yl)ethanol. ESI-MS (M+H)+: 492.2. $^1$H NMR (400 MHz, DMSO-d$_6$) δ: 9.99 (s, 1H), 9.14 (m, 1H), 8.65 (s, 1H), 8.35 (s., 1H), 7.85 (m, 2H), 7.62 (d, J=2.4 Hz, 1H), 7.38 (d, J=8.0 Hz, 1H), 6.40 (brd, 1H), 4.92 (brd, 1H), 4.49 (d, J=5.2 Hz, 2H), 4.09 (t, J=7.65 Hz, 2H), 3.75 (m, 2H), 2.40 (s, 3H), 1.39 (s, 9H).

Example 150: 5-(tert-butyl)-N-(2-methyl-4-(2-((1-methyl-1H-pyrazol-4-yl)amino)pyrimidin-4-yl)benzyl)isoxazole-3-carboxamide

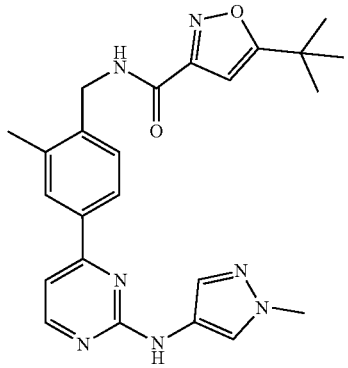

I-153

Synthesis of 5-(tert-butyl)-N-(2-methyl-4-(2-((1-methyl-1H-pyrazol-4-yl)amino)pyrimidin-4-yl)benzyl)isoxazole-3-carboxamide (I-153) was similar to that of Example 1, except 5-(tert-butyl)isoxazole-3-carboxylic acid was substituted for 2-(tert-butyl)thiazole-5-carboxylic acid. The crude product was purified by prep-HPLC to give product as a solid (39 mg, yield 50%). ESI-MS (M+H)+: 446. $^1$H NMR (400 MHz, CDCl$_3$) δ: 7.86-7.97 (m, 3H), 7.72-7.81 (m, 1H), 7.42-7.54 (m, 1H), 7.15-7.24 (m, 2H), 6.46 (s, 1H), 4.67-4.74 (m, 2H), 3.94 (s, 3H), 2.49 (s, 3H), 1.38 (s, 9H).

Example 151: 1-(tert-butyl)-N-(2-methyl-4-(2-((1-methyl-1H-pyrazol-4-yl)amino)pyrimidin-4-yl)benzyl)-1H-pyrazole-4-carboxamide

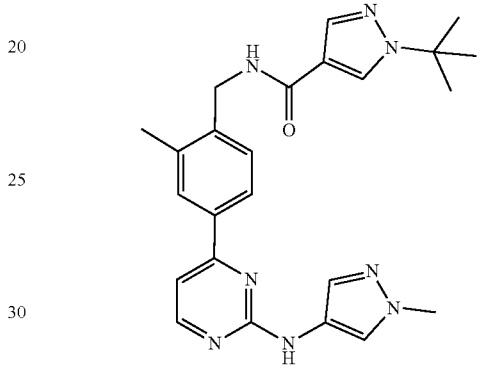

I-154

Synthesis of 1-(tert-butyl)-N-(2-methyl-4-(2-((1-methyl-1H-pyrazol-4-yl)amino)pyrimidin-4-yl)benzyl)-1H-pyrazole-4-carboxamide (I-154) was similar to that of Example 1, except 1-(tert-butyl)-1H-pyrazole-4-carboxylic acid was substituted for 2-(tert-butyl)thiazole-5-carboxylic acid. The crude product was purified by prep-HPLC to give product as a solid (30 mg, yield 23%). ESI-MS (M+H)+: 446. $^1$H NMR (400 MHz, METHANOL-d$_4$) δ: 7.97 (s, 1H), 7.94 (d, J=8.53 Hz, 1H), 7.86 (d, J=5.77 Hz, 2H), 7.59 (br. s., 1H), 7.34-7.41 (m, 2H), 4.51 (s, 2H), 3.84 (s, 3H), 2.56 (s, 3H), 2.38 (s, 3H), 1.48-1.52 (m, 9H).

Example 152: 1-Methyl-N-(2-methyl-4-(2-((1-methyl-1H-pyrazol-4-yl)amino)pyrimidin-4-yl)benzyl)-1H-pyrrole-3-carboxamide

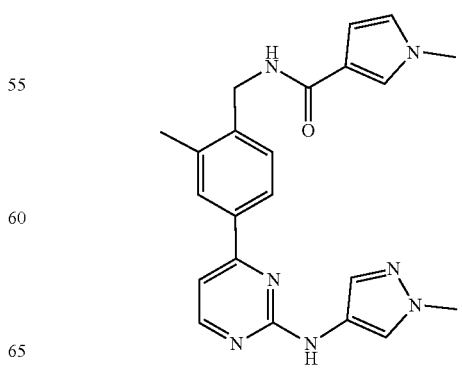

I-155

Synthesis of 1-Methyl-N-(2-methyl-4-(2-((1-methyl-1H-pyrazol-4-yl)amino)pyrimidin-4-yl)benzyl)-1H-pyrrole-3-carboxamide (I-155) was similar to that of Example 1, except 1-methyl-1H-pyrrole-3-carboxylic acid was substituted for 2-(tert-butyl)thiazole-5-carboxylic acid. The crude product was purified by prep-HPLC to give product as a solid (35 mg, yield 50%). ESI-MS (M+H)+: 402. $^1$H NMR (400 MHz, CD$_3$OD) δ: 8.21 (d, J=5.77 Hz, 1H), 7.79 (br. m, 4H), 7.67 (s, 1H), 7.40 (d, J=8.28 Hz, 1H), 7.14 (d, J=5.77 Hz, 1H), 4.55 (s, 2H), 4.06 (s, 3H), 3.83 (s, 3H), 2.39 (s, 3H).

Example 153: N-(2-Methyl-4-(2-((1-methyl-1H-pyrazol-4-yl)amino)pyrimidin-4-yl)benzyl)-5,6,7,8-tetrahydroimidazo[1,2-a]pyridine-2-carboxamide

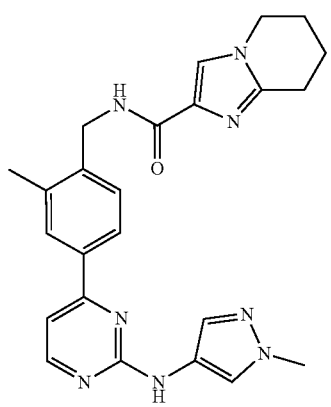

I-156

Synthesis of N-(2-Methyl-4-(2-((1-methyl-1H-pyrazol-4-yl)amino)pyrimidin-4-yl)benzyl)-5,6,7,8-tetrahydroimidazo[1,2-a]pyridine-2-carboxamide (I-156) was similar to that of Example 1, except 5,6,7,8-tetrahydroimidazo[1,2-a]pyridine-2-carboxylic acid was substituted for 2-(tert-butyl)thiazole-5-carboxylic acid. The crude product was purified by prep-HPLC to give product as a solid (20 mg, yield 27%). ESI-MS (M+H)+: 443. $^1$H NMR (400 MHz, METHANOL-d$_4$) δ: 8.21 (d, J=5.77 Hz, 1H), 7.79 (d, J=4.02 Hz, 3H), 7.67 (s, 2H), 7.40 (d, J=8.28 Hz, 1H), 7.14 (d, J=5.77 Hz, 1H), 4.55 (s, 2H), 4.05 (t, J=5.52 Hz, 2H), 3.83 (s, 3H), 3.28 (d, J=1.51 Hz, 2H), 2.84-2.96 (m, 3H), 2.56 (s, 2H), 2.39 (s, 3H), 1.90-2.06 (m, 4H).

Example 154: 1-Methyl-N-(2-methyl-4-(2-((1-methyl-1H-pyrazol-4-yl)amino)pyrimidin-4-yl)benzyl)-1H-pyrazole-4-carboxamide

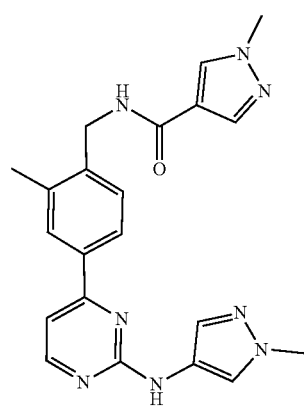

I-157

Synthesis of 1-Methyl-N-(2-methyl-4-(2-((1-methyl-1H-pyrazol-4-yl)amino)pyrimidin-4-yl)benzyl)-1H-pyrazole-4-carboxamide (I-157) was similar to that of Example 1, except 1-methyl-1H-pyrazole-4-carboxylic acid was substituted for 2-(tert-butyl)thiazole-5-carboxylic acid. The crude product was purified by prep-HPLC to give product as a solid (90 mg, yield 60%). ESI-MS (M+H)+: 403. $^1$H NMR (400 MHz, METHANOL-d$_4$) δ: 8.21 (d, J=6.27 Hz, 1H), 7.90 (s, 1H), 7.79-7.86 (m, 2H), 7.77 (s, 1H), 7.71 (br. s., 1H), 7.40 (d, J=8.28 Hz, 1H), 7.19 (d, J=6.02 Hz, 1H), 4.56 (s, 2H), 3.87 (br, s 6H), 2.41 (s, 3H).

Example 155: 1-Methyl-N-(2-methyl-4-(2-((1-methyl-1H-pyrazol-4-yl)amino)pyrimidin-4-yl)benzyl)-1H-pyrrole-2-carboxamide

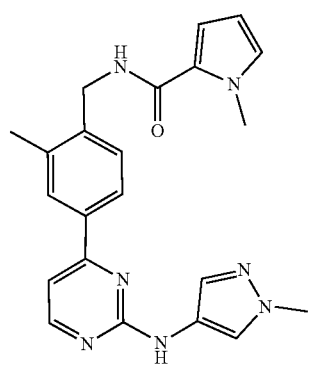

I-158

Synthesis of 1-Methyl-N-(2-methyl-4-(2-((1-methyl-1H-pyrazol-4-yl)amino)pyrimidin-4-yl)benzyl)-1H-pyrrole-2-carboxamide (I-158) was similar to that of Example 1, except 1-methyl-1H-pyrrole-2-carboxylic acid was substituted for 2-(tert-butyl)thiazole-5-carboxylic acid. The crude product was purified by prep-HPLC to give product as a solid (40 mg, yield 30%). ESI-MS (M+H)+: 402. $^1$H NMR (400 MHz, CDCl$_3$) δ: 8.13 (br. s., 1H), 8.01 (s, 1H), 7.90-7.95 (m, 4H), 7.76 (s, 1H), 7.50 (d, J=7.78 Hz, 1H), 7.23 (d, J=6.53 Hz, 1H), 6.77 (s, 1H), 6.63 (dd, J=1.38, 3.89 Hz, 1H), 6.24 (br. s., 1H), 6.12 (dd, J=2.76, 3.76 Hz, 1H), 4.65 (d, J=5.77 Hz, 2H), 3.97 (s, 3H), 3.95 (s, 3H).

Example 156: N-(2-Methyl-4-(2-((1-methyl-1H-pyrazol-4-yl)amino)pyrimidin-4-yl)benzyl)-4,5,6,7-tetrahydropyrazolo[1,5-a]pyridine-2-carboxamide

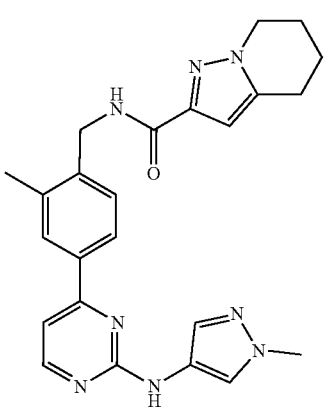

I-159

303

Synthesis of N-(2-Methyl-4-(2-((1-methyl-1H-pyrazol-4-yl)amino)pyrimidin-4-yl)benzyl)-4,5,6,7-tetrahydropyrazolo[1,5-a]pyridine-2-carboxamide (I-159) was similar to that of Example 1, except 4,5,6,7-tetrahydropyrazolo[1,5-a]pyridine-2-carboxylic acid was substituted for 2-(tert-butyl) thiazole-5-carboxylic acid. The crude product was purified by prep-HPLC to give product as a solid (50 mg, yield 50%). ESI-MS (M+H)⁺: 443. ¹H NMR (400 MHz, METHANOL-d₄) δ: 8.35 (d, J=5.77 Hz, 1H), 7.95-8.09 (m, 3H), 7.68 (s, 1H), 7.48 (d, J=8.03 Hz, 1H), 7.40 (d, J=5.77 Hz, 1H), 6.50 (s, 1H), 4.64 (s, 2H), 4.18 (t, J=6.02 Hz, 2H), 3.94 (s, 3H), 2.87 (t, J=6.27 Hz, 2H), 2.50 (s, 3H), 2.09 (d, J=5.52 Hz, 2H), 1.85-1.98 (m, 2H).

Example 157: 3-isopropoxy-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide

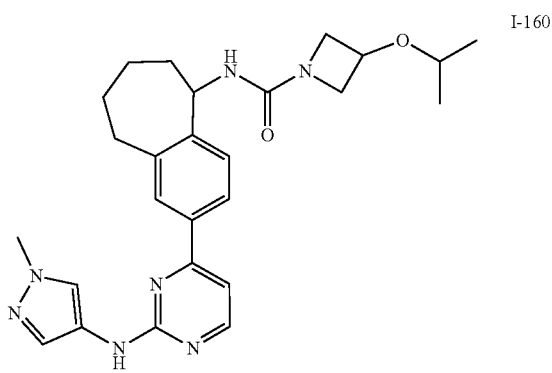 [SMILES: CC(C)OC1CN(C(=O)NC2CCCCc3cc(-c4ccnc(Nc5cnn(C)c5)n4)ccc32)C1]

I-160

1. Synthesis of N-(2-bromo-6,7,8,9-tetrahydro-5H-benzo[7]annulen-5-yl)-3-isopropoxyazetidine-1-carboxamide

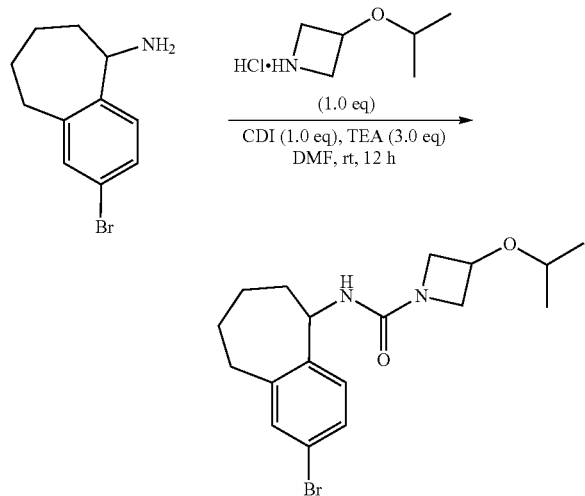

To a mixture of 2-bromo-6,7,8,9-tetrahydro-5H-benzo[7]annulen-5-amine (200 mg, 0.84 mmol) in DMF (5 mL), CDI (118 mg, 0.84 mmol) and TEA (340 mg, 3.40 mmol) was added. The mixture was stirred at room temperature for 1 h followed by addition of 3-isopropoxyazetidine hydrochloride (127 mg, 0.84 mmol). The resulting mixture was stirred at rt for another 12 h. After diluting with CH₂Cl₂ (150 mL), the mixture was washed with brine (50 mL×2). The organic phase was concentrated in vacuo and the residue was purified by prep-HPLC (Gradient: 5% B increase to 95% B, A: 0.5% NH₃ in water, B: CH₃CN) to give N-(2-bromo-6,7,8,9-tetrahydro-5H-benzo[7]annulen-5-yl)-3-isopropoxyazetidine-1-carboxamide (290 mg, yield: 74%) as a white solid. ESI-MS (M+1)⁺: 381.1. ¹H NMR (400 MHz, CDCl₃) δ: 7.27-7.23 (m, 2H), 7.08 (d, J=8.0 Hz, 1H), 4.98-4.97 (m, 1H), 4.41-4.32 (m, 2H), 4.16-4.11 (m, 2H), 3.89-3.84 (m, 2H), 3.64-3.58 (m, 1H), 2.87-2.70 (m, 2H), 1.89-1.74 (m, 5H), 1.54-1.49 (m, 1H), 1.16 (d, J=5.6 Hz, 6H).

2. Synthesis of 3-isopropoxy-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide

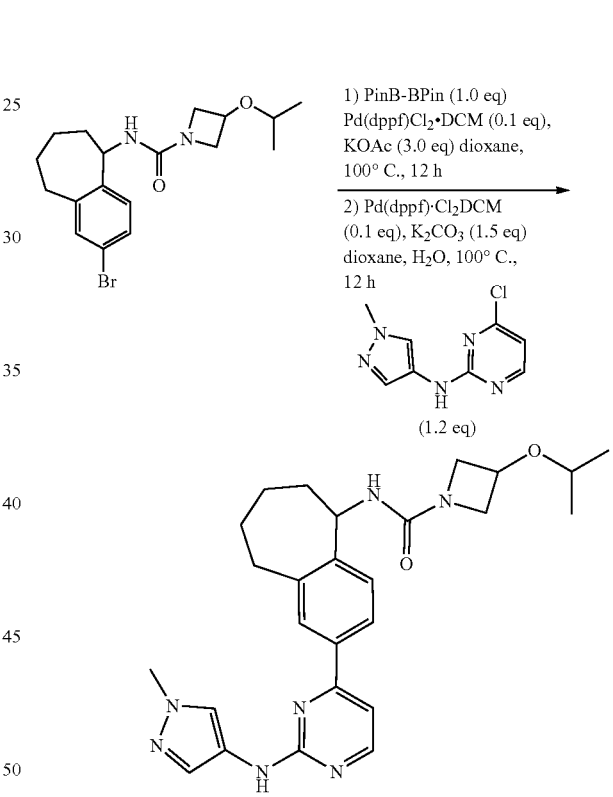

To a mixture of N-(2-bromo-6,7,8,9-tetrahydro-5H-benzo[7]annulen-5-yl)-3-isopropoxyazetidine-1-carboxamide (200 mg, 0.53 mmol) and bis(pinacolato)diboron (135 mg, 0.53 mmol) in dry 1,4-dioxane (10 mL), KOAc (97 mg, 1.0 mmol), Pd(dppf)Cl₂.DCM (37 mg, 0.05 mmol) was added. The mixture was stirred at 100° C. for 12 h under N₂. After cooling down, 4-chloro-N-(1-methyl-1H-pyrazol-4-yl)pyrimidin-2-amine (133 mg, 0.63 mmol), K₂CO₃ (110 mg, 0.8 mmol) and water (1 mL) was added. The resulting mixture was stirred at 100° C. for 12 h under N₂. After diluting with EtOAc (150 mL), the mixture was washed with water (50 mL×2). The organic phase was dried and concentrated in vacuo to afford a residue was purified by silica gel column (CH₂Cl₂:MeOH=50:1) to give 3-isopropoxy-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide (60 mg, yield: 24%) as a yellow solid. ESI-MS (M+H)+: 476.3. ¹H NMR (400 MHz, CDCl₃) δ: 8.41 (d, J=5.2 Hz, 1H), 7.89 (s, 1H), 7.81-7.78 (m, 2H), 7.54 (s, 1H), 7.35 (d, J=8.4 Hz, 1H), 7.05 (d, J=5.2 Hz, 1H), 6.90 (s, 1H), 5.10 (t, J=8.4 Hz, 1H), 4.47 (d, J=8.0 Hz, 1H), 4.40-4.34 (m, 1H), 4.18-4.17 (m, 2H), 3.93-3.87 (m, 5H), 3.65-3.59 (m, 1H), 3.01-2.86 (m, 2H), 1.90-1.79 (m, 5H), 1.60-1.50 (m, 1H), 1.17 (d, J=6.4 Hz, 6H).

Example 158: (R)-3-isopropoxy-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide and (S)-3-isopropoxy-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide

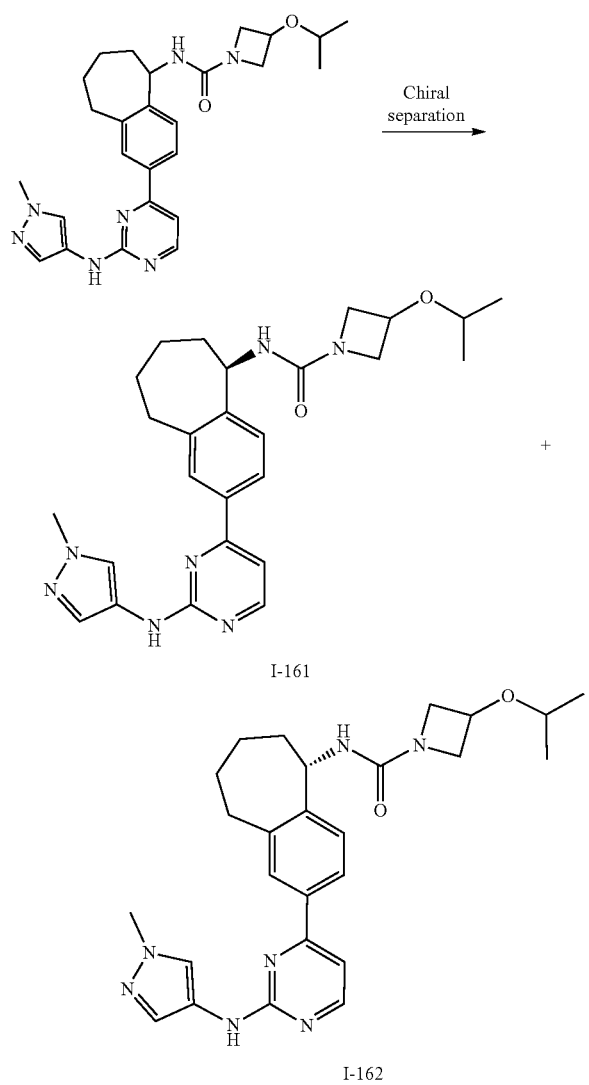

3-isopropoxy-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide (160 mg) was subjected to the following SFC separation (AS-H (2×25 cm), 20% methanol/CO2, 100 bar, 70 mL/min, 220 nm. inj vol.: 1 mL, 4 mg/mL methanol) yielded 53.5 mg of peak-1 (chemical purity 95%, ee>99%) and 69.4 mg of peak-2 (chemical purity 95%, ee>99%). Peak 1 was assigned as (S)-3-isopropoxy-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide: LCMS: Rt 1.20 min, m/z 476.30. ¹H NMR (300 MHz, CD₃OD) δ: 8.39 (d, J=5.29 Hz, 1H), 7.91-8.02 (m, 2H), 7.89 (s, 1H), 7.66 (s, 1H), 7.38 (d, J=7.93 Hz, 1H), 7.20 (d, J=5.29 Hz, 1H), 6.87 (d, J=7.93 Hz, 1H), 5.06 (t, J=8.88 Hz, 1H), 4.38-4.55 (m, 1H), 4.13-4.32 (m, 2H), 3.90 (s, 3H), 3.84 (d, J=8.69 Hz, 2H), 3.70 (td, J=6.09, 12.37 Hz, 1H), 3.39 (s, 3H), 2.80-3.19 (m, 2H), 1.26-2.19 (m, 6H), 1.18 (s, 6H).

Peak 2 was assigned as (R)-3-isopropoxy-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide: LCMS: Rt 1.20 min, m/z 476.20. ¹H NMR (300 MHz, CD₃OD) δ: 8.39 (d, J=5.29 Hz, 1H), 7.91-8.02 (m, 2H), 7.89 (s, 1H), 7.66 (s, 1H), 7.38 (d, J=7.93 Hz, 1H), 7.20 (d, J=5.29 Hz, 1H), 6.87 (d, J=7.93 Hz, 1H), 5.06 (t, J=8.88 Hz, 1H), 4.38-4.55 (m, 1H), 4.13-4.32 (m, 2H), 3.90 (s, 3H), 3.84 (d, J=8.69 Hz, 2H), 3.70 (td, J=6.09, 12.37 Hz, 1H), 3.39 (s, 3H), 2.80-3.19 (m, 2H), 1.26-2.19 (m, 6H), 1.18 (s, 6H).

Example 159: 3-(tert-butoxy)-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide

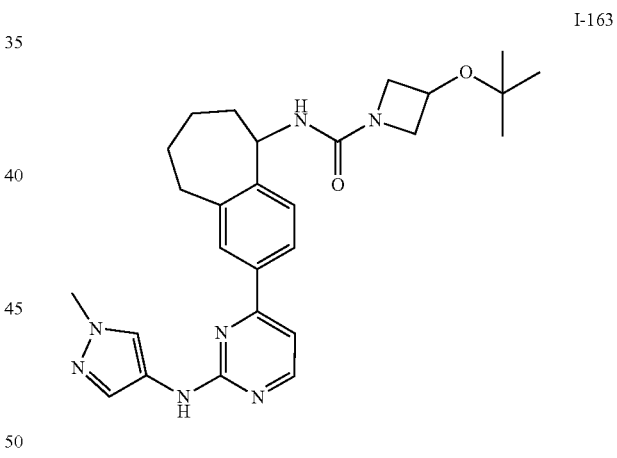

I-163

Synthesis of 3-(tert-butoxy)-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide was similar to that of Example 157, except starting from 3-tert-butoxyazetidine hydrochloride instead of 3-isopropoxyazetidine hydrochloride. The crude product was purified by silica gel column (CH₂Cl₂:MeOH=40:1) to give 3-(tert-butoxy)-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide (60 mg, yield: 35%) as a yellow solid. ESI-MS (M+H)+: 490.4. ¹H NMR (400 MHz, CDCl₃) δ: 8.41 (d, J=5.2 Hz, 1H), 7.89 (s, 1H), 7.81-7.78 (m, 2H), 7.54 (s, 1H), 7.36 (d, J=8.0 Hz, 1H), 7.05 (d, J=5.2 Hz, 1H), 7.02 (s, 1H), 5.09 (t, J=8.0 Hz, 1H), 4.53-4.48 (m, 2H), 4.18-4.16 (m, 2H), 3.91 (s, 3H), 3.90-3.86 (m, 2H), 3.00-2.86 (m, 2H), 1.90-1.73 (m, 5H), 1.58-1.51 (m, 1H), 1.19 (s, 9H).

Example 160: (R)-3-(tert-butoxy)-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide and (S)-3-(tert-butoxy)-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide

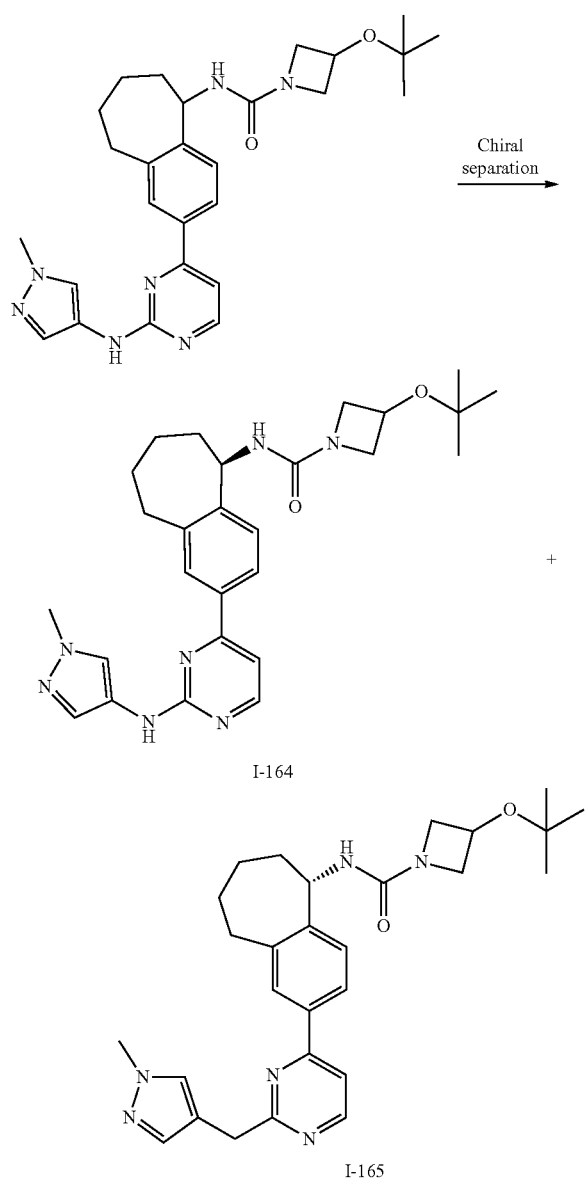

Chiral separation

I-164

I-165

3-(tert-butoxy)-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide (90 mg) was subjected to the following SFC separation: (IA (2×25 cm), 35% MeOH (0.1 DEA)/CO2, 100 bar, 70 mL/min, 220 nm. inj vol.: 1 mL, 9 mg/mL methanol) and yielded 42 mg of peak-1 (chemical purity 99%, ee>99%) and 42 mg of peak-2 (chemical purity 99%, ee>99%). Peak 1 was assigned as (R)-3-(tert-butoxy)-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide: LCMS: Rt 1.27 min, m/z 490.30. $^1$H NMR (400 MHz, CD$_3$OD-d4) δ: 8.40 (d, J=5.27 Hz, 1H), 7.94-8.05 (m, 2H), 7.90 (s, 1H), 7.67 (s, 1H), 7.39 (d, J=8.03 Hz, 1H), 7.22 (d, J=5.27 Hz, 1H), 4.95-5.20 (m, 1H), 4.54-4.71 (m, 1H), 4.14-4.33 (m, 2H), 3.91 (s, 3H), 3.82 (d, J=13.30 Hz, 2H), 2.79-3.12 (m, 2H), 1.27-2.16 (m, 6H), 1.24 (s, 9H).

Peak 2 was assigned as (S)-3-(tert-butoxy)-N-(2-(2-((1-methyl-1H-pyrazol-4-yl)amino)pyrimidin-4-yl)-6,7,8,9-tetrahydro-5H-benzo[7]annulen-5-yl)azetidine-1-carboxamide: LCMS: Rt 1.27 min, m/z 490.2. $^1$H NMR (400 MHz, CD$_3$OD) δ: 8.40 (d, J=5.27 Hz, 1H), 7.92-8.07 (m, 2H), 7.89 (s, 1H), 7.67 (s, 1H), 7.39 (d, J=8.03 Hz, 1H), 7.21 (d, J=5.27 Hz, 1H), 6.85 (d, J=8.03 Hz, 0H), 4.94-5.17 (m, 1H), 4.52-4.69 (m, 1H), 4.16-4.32 (m, 2H), 3.89 (br. s., 3H), 3.83 (dd, J=5.02, 13.80 Hz, 2H), 2.78-3.13 (m, 2H), 1.29-2.14 (m, 6H), 1.24 (s, 9H).

Example 161: N-(2-(2-((1-ethyl-1H-pyrazol-4-yl)amino)pyrimidin-4-yl)-6,7,8,9-tetrahydro-5H-benzo[7]annulen-5-yl)-3-isopropoxyazetidine-1-carboxamide

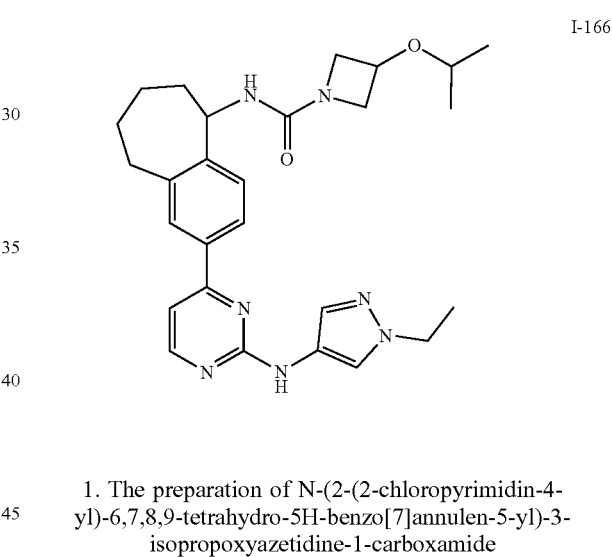

I-166

1. The preparation of N-(2-(2-chloropyrimidin-4-yl)-6,7,8,9-tetrahydro-5H-benzo[7]annulen-5-yl)-3-isopropoxyazetidine-1-carboxamide

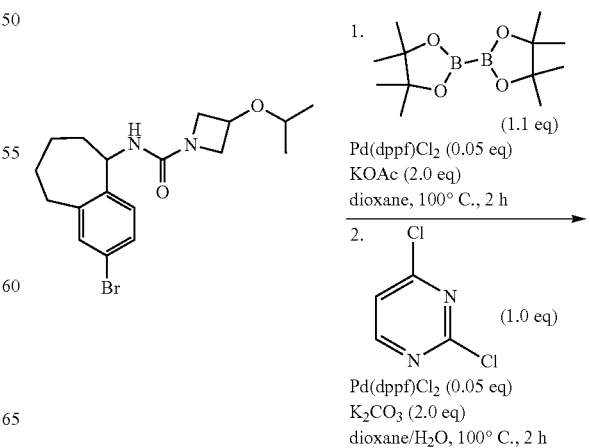

1.

(1.1 eq)
Pd(dppf)Cl$_2$ (0.05 eq)
KOAc (2.0 eq)
dioxane, 100° C., 2 h

2.

(1.0 eq)
Pd(dppf)Cl$_2$ (0.05 eq)
K$_2$CO$_3$ (2.0 eq)
dioxane/H$_2$O, 100° C., 2 h 309
-continued

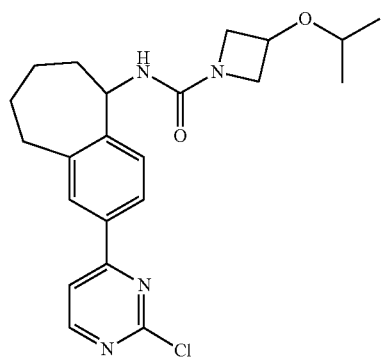

310
-continued

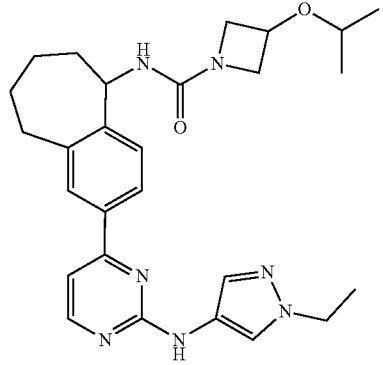

A mixture of N-(2-bromo-6,7,8,9-tetrahydro-5H-benzo[7]annulen-5-yl)-3-isopropoxyazetidine-1-carboxamide (1.6 g, 4.2 mmol), bis(pinacolato)diboron (1.2 g, 4.6 mmol), KOAc (848 mg, 8.4 mmol) and Pd(dppf)Cl$_2$·DCM (171 mg, 0.21 mmol) in 1,4-dioxane (20 mL) was stirred at 100° C. for 2 h under nitrogen. After the mixture was cooled to rt, 2,4-dichloropyrimidine (626 mg, 4.2 mmol), Pd(dppf)Cl$_2$·DCM (171 mg, 0.21 mmol), K$_2$CO$_3$ (1.16 g, 8.4 mmol) and H$_2$O (5 mL) were added and the resulting mixture was stirred at 100° C. for another 2 h. The mixture was diluted with EtOAc (200 mL), washed with water (80 mL×2), dried with Na$_2$SO$_4$ and concentrated in vacuo to afford a residue which was purified by prep-HPLC (CH$_3$CN/H$_2$O with 0.05% NH$_4$OH as mobile phase) to give N-(2-(2-chloropyrimidin-4-yl)-6,7,8,9-tetrahydro-5H-benzo[7]annulen-5-yl)-3-isopropoxyazetidine-1-carboxamide as a white solid (1.1 g, yield: 57%). ESI-MS (M+H)$^+$: 415.1. $^1$H NMR (400 MHz, CDCl$_3$) δ: 8.61 (d, J=5.6 Hz, 1H), 7.87 (s, 1H), 7.83 (d, J=8.0 Hz, 1H), 7.62 (d, J=5.2 Hz, 1H), 7.38 (d, J=8.0 Hz, 1H), 5.09 (t, J=8.4 Hz, 1H), 4.49-4.46 (m, 1H), 4.39-4.36 (m, 1H), 3.93-3.87 (m, 2H), 3.66-3.60 (m, 1H), 3.50-3.48 (m, 1H), 3.03-2.89 (m, 2H), 1.93-1.84 (m, 4H), 1.76-1.73 (m, 1H), 1.57-1.48 (m, 1H), 1.18 (d, J=6.4 Hz, 6H).

2. The preparation of N-(2-(2-((1-ethyl-1H-pyrazol-4-yl)amino)pyrimidin-4-yl)-6,7,8,9-tetrahydro-5H-benzo[7]annulen-5-yl)-3-isopropoxyazetidine-1-carboxamide

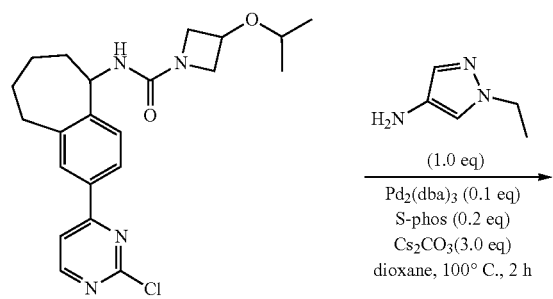

To a solution of N-(2-(2-chloropyrimidin-4-yl)-6,7,8,9-tetrahydro-5H-benzo[7]annulen-5-yl)-3-isopropoxyazetidine-1-carboxamide (130 mg, 0.32 mmol) in 1,4-dioxane (5 mL) were added 1-ethyl-1H-pyrazol-4-amine (36 mg, 0.32 mmol), Pd$_2$(dba)$_3$ (29 mg, 0.032 mmol), S-Phos (26 mg, 0.064 mmol) and Cs$_2$CO$_3$ (312 mg, 0.96 mmol). The mixture was stirred at 100° C. for 2 h. After diluted with water (50 mL), the mixture was extracted with EtOAc (60 mL×2). The combined organic layers were dried (Na$_2$SO$_4$), filtered and concentrated. The crude product was purified by prep-HPLC (CH$_3$CN/H$_2$O with 0.05% NH$_4$OH as mobile phase) to give N-(2-(2-((1-ethyl-1H-pyrazol-4-yl)amino)pyrimidin-4-yl)-6,7,8,9-tetrahydro-5H-benzo[7]annulen-5-yl)-3-isopropoxyazetidine-1-carboxamide as a yellow solid (129 mg, yield: 73%). ESI-MS (M+H)$^+$: 490.0. $^1$H NMR (400 MHz, CD$_3$OD) δ: 8.27 (d, J=4.8 Hz, 1H), 7.91 (s, 1H), 7.82 (d, J=8.0 Hz, 1H), 7.77 (s, 1H), 7.55 (s, 1H), 7.27 (d, J=8.0 Hz, 1H), 7.09 (d, J=4.8 Hz, 1H), 6.81 (d, J=8.0 Hz, 1H), 4.94 (t, J=8.4 Hz, 1H), 4.35-4.32 (m, 1H), 4.16-4.04 (m, 4H), 3.79-3.71 (m, 2H), 3.60-3.55 (m, 1H), 2.95-2.81 (m, 2H), 1.87-1.74 (m, 4H), 1.60-1.52 (m, 1H), 1.37 (t, J=7.2 Hz, 3H), 1.29-1.18 (m, 1H), 1.07 (d, J=6.0 Hz, 6H).

Example 162: 3-isopropoxy-N-(2-(2-((1-isopropyl-1H-pyrazol-4-yl)amino)pyrimidin-4-yl)-6,7,8,9-tetrahydro-5H-benzo[7]annulen-5-yl)azetidine-1-carboxamide

I-167

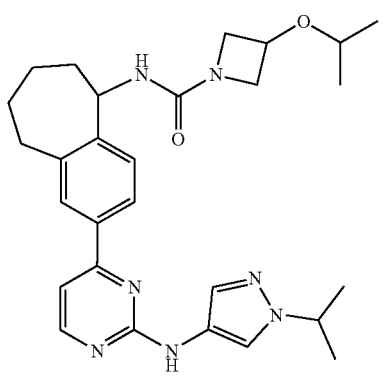

Synthesis of 3-isopropoxy-N-(2-(2-((1-isopropyl-1H-pyrazol-4-yl)amino)pyrimidin-4-yl)-6,7,8,9-tetrahydro-5H-benzo[7]annulen-5-yl)azetidine-1-carboxamide was similar to that of Example 161. The crude product was purified by prep-HPLC (CH$_3$CN/H$_2$O with 0.05% NH$_4$OH as mobile phase) to give 3-isopropoxy-N-(2-(2-((1-isopropyl-1H-pyrazol-4-yl)amino)pyrimidin-4-yl)-6,7,8,9-tetrahydro-5H-benzo[7]annulen-5-yl)azetidine-1-carboxamide as a yellow solid (128 mg, yield: 71%). ESI-MS (M+H)+: 504.3. 1H NMR (400 MHz, CD3OD) δ: 8.28 (d, J=5.2 Hz, 1H), 7.97 (s, 1H), 7.82-7.79 (m, 2H), 7.55 (s, 1H), 7.27 (d, J=8.4 Hz, 1H), 7.10-7.07 (m, 1H), 6.81 (d, J=8.0 Hz, 1H), 4.97-4.93 (m, 1H), 4.43-4.31 (m, 2H), 4.16-4.08 (m, 2H), 3.79-3.71 (m, 2H), 3.61-3.55 (m, 1H), 2.96-2.81 (m, 2H), 1.87-1.77 (m, 4H), 1.60-1.52 (m, 1H), 1.42 (d, J=6.8 Hz, 6H), 1.30-1.22 (m, 1H), 1.08 (d, J=6.0 Hz, 6H).

Example 163: N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropoxyazetidine-1-carboxamide

I-168

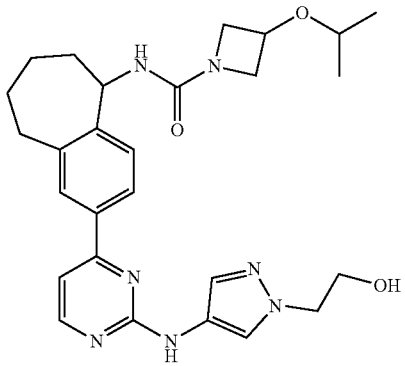

1. The preparation of N-(2-(2-((1-(2-((tert-butyldimethylsilyl)oxy)ethyl)-1H-pyrazol-4-yl)amino)pyrimidin-4-yl)-6,7,8,9-tetrahydro-5H-benzo[7]annulen-5-yl)-3-isopropoxyazetidine-1-carboxamide

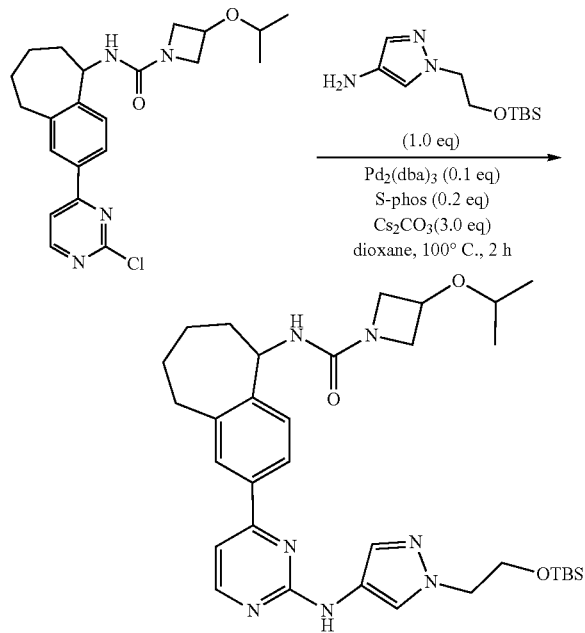

Synthesis of N-(2-(2-((1-(2-((tert-butyldimethylsilyl)oxy)ethyl)-1H-pyrazol-4-yl)amino)pyrimidin-4-yl)-6,7,8,9-tetrahydro-5H-benzo[7]annulen-5-yl)-3-isopropoxyazetidine-1-carboxamide was similar to that of Example 161. The residue was purified by silica gel column chromatography (EtOAc/MeOH=15:1) to give product as a yellow solid (150 mg, yield: 50%). ESI-MS (M+H)+: 620.0.

2. The preparation of N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropoxyazetidine-1-carboxamide

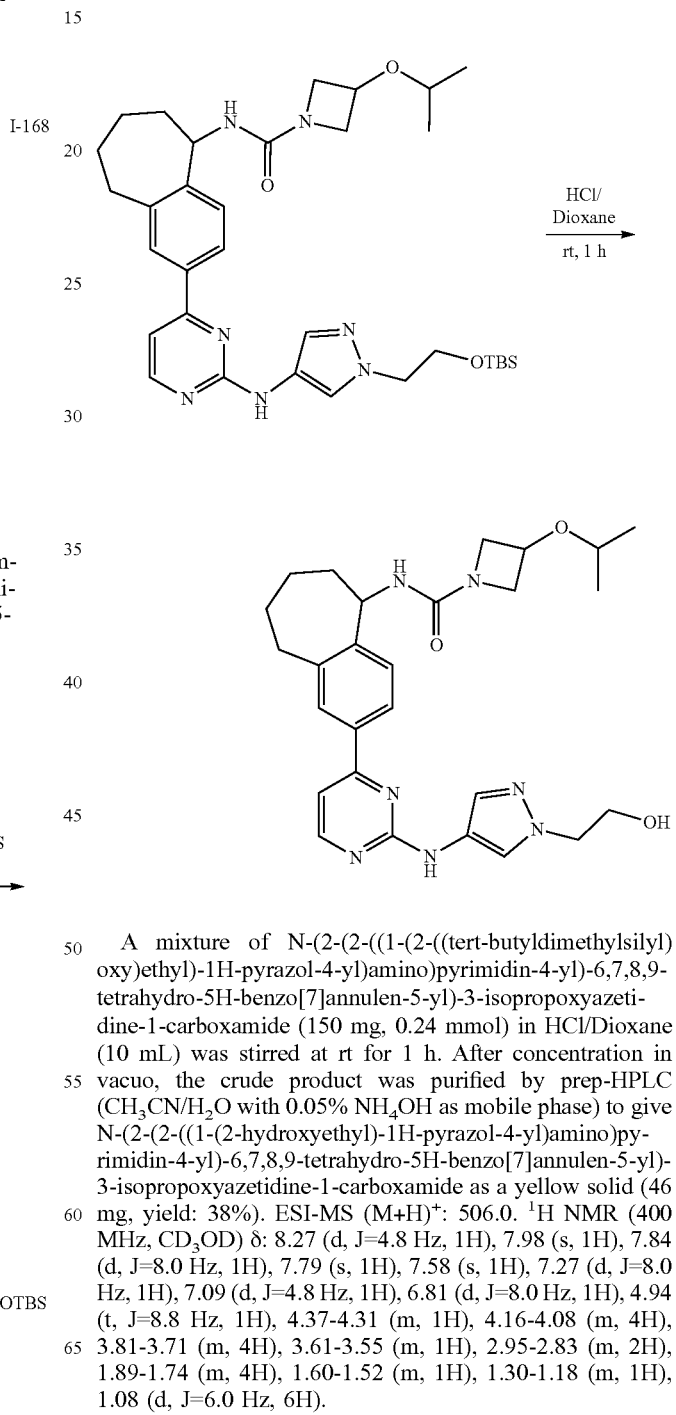

A mixture of N-(2-(2-((1-(2-((tert-butyldimethylsilyl)oxy)ethyl)-1H-pyrazol-4-yl)amino)pyrimidin-4-yl)-6,7,8,9-tetrahydro-5H-benzo[7]annulen-5-yl)-3-isopropoxyazetidine-1-carboxamide (150 mg, 0.24 mmol) in HCl/Dioxane (10 mL) was stirred at rt for 1 h. After concentration in vacuo, the crude product was purified by prep-HPLC (CH3CN/H2O with 0.05% NH4OH as mobile phase) to give N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropoxyazetidine-1-carboxamide as a yellow solid (46 mg, yield: 38%). ESI-MS (M+H)+: 506.0. 1H NMR (400 MHz, CD3OD) δ: 8.27 (d, J=4.8 Hz, 1H), 7.98 (s, 1H), 7.84 (d, J=8.0 Hz, 1H), 7.79 (s, 1H), 7.58 (s, 1H), 7.27 (d, J=8.0 Hz, 1H), 7.09 (d, J=4.8 Hz, 1H), 6.81 (d, J=8.0 Hz, 1H), 4.94 (t, J=8.8 Hz, 1H), 4.37-4.31 (m, 1H), 4.16-4.08 (m, 4H), 3.81-3.71 (m, 4H), 3.61-3.55 (m, 1H), 2.95-2.83 (m, 2H), 1.89-1.74 (m, 4H), 1.60-1.52 (m, 1H), 1.30-1.18 (m, 1H), 1.08 (d, J=6.0 Hz, 6H).

Example 164: (R)—N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropoxyazetidine-1-carboxamide and (S)—N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropoxyazetidine-1-carboxamide

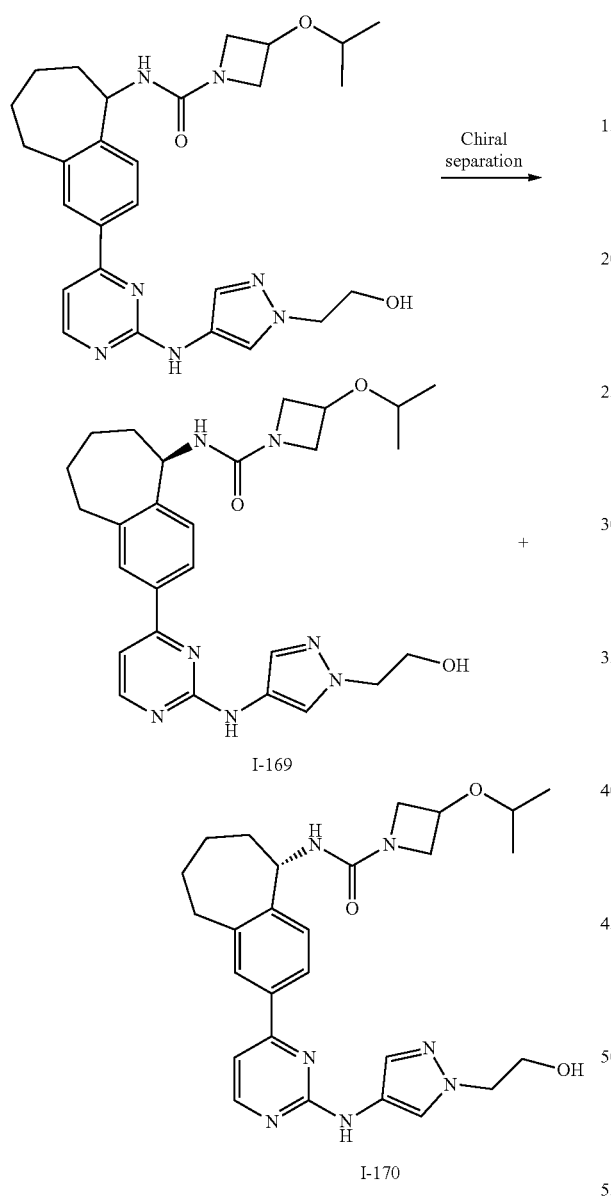

N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropoxyazetidine-1-carboxamide (40 mg) was subjected to the following SFC separation (IA (2×25 cm), 30% methanol (0.1 DEA)/CO2, 100 bar, 60 mL/min, 280 nm. inj vol.: 0.75 mL, 4 mg/mL methanol) yielded 16 mg of peak-1 (chemical purity 99%, ee>99%) and 14 mg of peak-2 (chemical purity 99%, ee>99%). Peak 1 was assigned as (S)—N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropoxyazetidine-1-carboxamide: LCMS: Rt 1.09 min, m/z 506.1. $^1$H NMR (400 MHz, CD$_3$OD) δ: 8.38 (d, J=5.27 Hz, 1H), 8.08 (s, 1H), 7.83-7.99 (m, 2H), 7.69 (s, 1H), 7.38 (d, J=8.09 Hz, 1H), 7.20 (d, J=5.33 Hz, 1H), 5.06 (d, J=10.04 Hz, 1H), 4.38-4.52 (m, 1H), 4.14-4.31 (m, 4H), 3.79-3.97 (m, 4H), 3.60-3.76 (m, 1H), 2.82-3.10 (m, 2H), 1.27-2.16 (m, 6H), 1.18 (s, 6H). Peak 2 was assigned as (R)—N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropoxyazetidine-1-carboxamide: LCMS: Rt 1.09 min, m/z 506.1. $^1$H NMR (400 MHz, CD$_3$OD) δ: 8.37 (br. s., 1H), 8.07 (s, 1H), 7.82-7.99 (m, 2H), 7.69 (s, 1H), 7.37 (d, J=8.03 Hz, 1H), 7.19 (br. s., 1H), 5.05 (d, J=10.23 Hz, 1H), 4.46 (br. s., 1H), 4.13-4.32 (m, 4H), 3.79-3.99 (m, 4H), 3.69 (dd, J=6.09, 8.53 Hz, 1H), 2.79-3.13 (m, 2H), 1.30-2.13 (m, 6H), 1.18 (d, J=6.09 Hz, 6H).

Example 165: 3-isopropoxy-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide

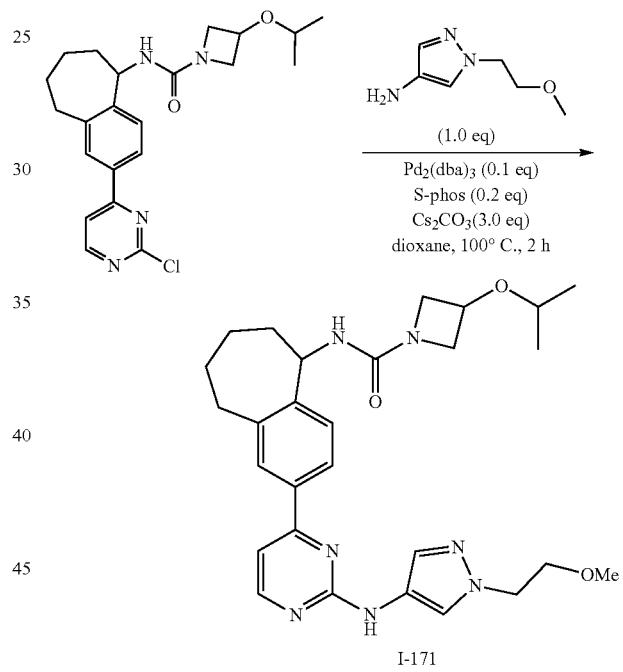

Synthesis of 3-isopropoxy-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide was similar to that of Example 161. The crude product was purified by prep-HPLC (CH$_3$CN/H$_2$O with 0.05% NH$_4$OH as mobile phase) to give 3-isopropoxy-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide as a yellow solid (47 mg, yield: 31%). ESI-MS (M+H)$^+$: 520.0. $^1$H NMR (400 MHz, CD$_3$OD) δ: 8.28 (d, J=5.2 Hz, 1H), 7.98 (s, 1H), 7.86 (d, J=8.0 Hz, 1H), 7.79 (s, 1H), 7.56 (s, 1H), 7.27 (d, J=8.4 Hz, 1H), 7.10 (d, J=5.2 Hz, 1H), 4.96-4.94 (m, 1H), 4.37-4.31 (m, 1H), 4.19-4.08 (m, 4H), 3.79-3.70 (m, 2H), 3.65 (t, J=5.2 Hz, 2H), 3.59-3.55 (m, 1H), 3.25 (s, 3H), 2.96-2.87 (m, 2H), 1.89-1.76 (m, 4H), 1.60-1.52 (m, 1H), 1.30-1.23 (m, 1H), 1.08 (d, J=6.0 Hz, 6H).

Example 166: 3-isopropoxy-N-(2-(2-((1-(tetrahydro-2H-pyran-4-yl)-1H-pyrazol-4-yl)amino)pyrimidin-4-yl)-6,7,8,9-tetrahydro-5H-benzo[7]annulen-5-yl)azetidine-1-carboxamide

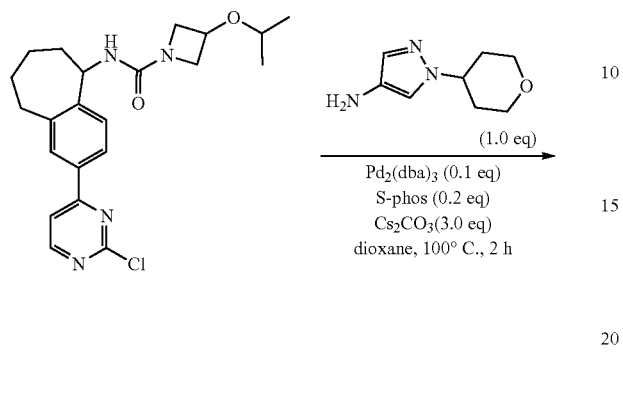

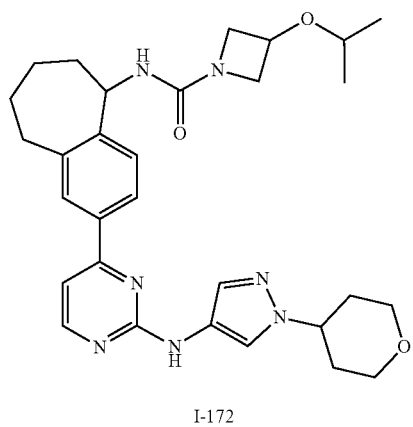

I-172

Synthesis of 3-isopropoxy-N-(2-(2-((1-(tetrahydro-2H-pyran-4-yl)-1H-pyrazol-4-yl)amino)pyrimidin-4-yl)-6,7,8,9-tetrahydro-5H-benzo[7]annulen-5-yl)azetidine-1-carboxamide was similar to that of Example 161. The crude product was purified by prep-HPLC (CH$_3$CN/H$_2$O with 0.05% NH$_4$OH as mobile phase) to give 3-isopropoxy-N-(2-(2-((1-(tetrahydro-2H-pyran-4-yl)-1H-pyrazol-4-yl)amino)pyrimidin-4-yl)-6,7,8,9-tetrahydro-5H-benzo[7]annulen-5-yl)azetidine-1-carboxamide as a yellow solid (75 mg, yield: 58%). ESI-MS (M+H)$^+$: 546.0. $^1$H NMR (400 MHz, CD$_3$OD) δ: 8.28 (d, J=5.6 Hz, 1H), 8.03 (s, 1H), 7.83-7.80 (m, 2H), 7.57 (s, 1H), 7.27 (d, J=8.4 Hz, 1H), 7.10 (d, J=5.2 Hz, 1H), 4.97-4.93 (m, 1H), 4.37-4.25 (m, 2H), 4.17-4.09 (m, 2H), 3.99-3.95 (m, 2H), 3.79-3.71 (m, 2H), 3.61-3.55 (m, 1H), 3.52-3.46 (m, 2H), 2.96-2.82 (m, 2H), 2.00-1.75 (m, 8H), 1.60-1.53 (m, 1H), 1.31-1.23 (m, 1H), 1.08 (d, J=6.8 Hz, 6H).

Example 167: 3-(tert-butoxy)-N-(2-(2-((1-ethyl-1H-pyrazol-4-yl)amino)pyrimidin-4-yl)-6,7,8,9-tetrahydro-5H-benzo[7]annulen-5-yl)azetidine-1-carboxamide

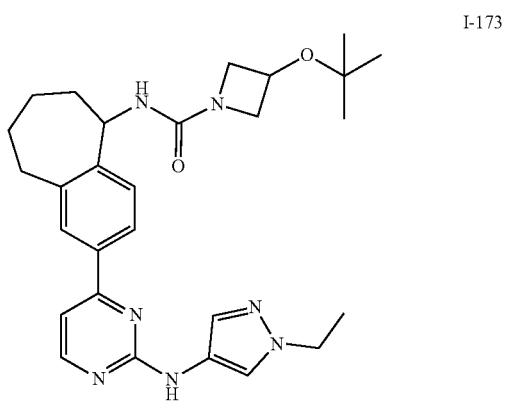 [SMILES: CCn1cc(Nc2nccc(-c3ccc4c(c3)CCCCC4NC(=O)N3CC(OC(C)(C)C)C3)n2)cn1]

I-173

Synthesis of 3-(tert-butoxy)-N-(2-(2-((1-ethyl-1H-pyrazol-4-yl)amino)pyrimidin-4-yl)-6,7,8,9-tetrahydro-5H-benzo[7]annulen-5-yl)azetidine-1-carboxamide was similar to that of Example 161. The crude product was purified by prep-HPLC (CH$_3$CN/H$_2$O with 0.05% NH$_4$OH as mobile phase) to give 3-(tert-butoxy)-N-(2-(2-((1-ethyl-1H-pyrazol-4-yl)amino)pyrimidin-4-yl)-6,7,8,9-tetrahydro-5H-benzo[7]annulen-5-yl)azetidine-1-carboxamide as a yellow solid (42 mg, yield: 40%). ESI-MS (M+H)$^+$: 504.0. $^1$H NMR (400 MHz, CD$_3$OD) δ: 8.27 (d, J=5.2 Hz, 1H), 7.91 (s, 1H), 7.82 (d, J=8.0 Hz, 1H), 7.78 (s, 1H), 7.55 (s, 1H), 7.27 (d, J=8.0 Hz, 1H), 7.08 (d, J=5.6 Hz, 1H), 6.78 (d, J=8.4 Hz, 1H), 4.94 (t, J=8.4 Hz, 1H), 4.52-4.46 (m, 1H), 4.15-4.04 (m, 4H), 3.76-3.68 (m, 2H), 2.94-2.80 (m, 2H), 1.88-1.76 (m, 4H), 1.58-1.55 (m, 1H), 1.37 (t, J=7.2 Hz, 3H), 1.27-1.18 (m, 1H), 1.11 (s, 9H).

Example 168: 3-(tert-butoxy)-N-(2-(2-((1-isopropyl-1H-pyrazol-4-yl)amino)pyrimidin-4-yl)-6,7,8,9-tetrahydro-5H-benzo[7]annulen-5-yl)azetidine-1-carboxamide

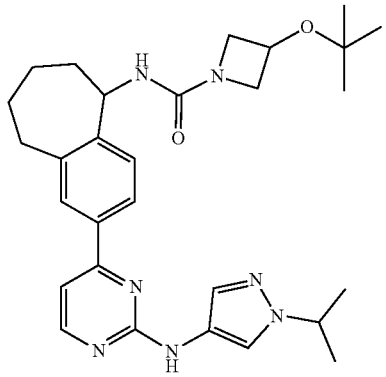

I-174

Synthesis of 3-(tert-butoxy)-N-(2-(2-((1-isopropyl-1H-pyrazol-4-yl)amino)pyrimidin-4-yl)-6,7,8,9-tetrahydro-5H-benzo[7]annulen-5-yl)azetidine-1-carboxamide was similar to that of Example 161. The crude product was purified by prep-HPLC (CH$_3$CN/H$_2$O with 0.05% NH$_4$OH as mobile phase) to give 3-(tert-butoxy)-N-(2-(2-((1-isopropyl-1H-pyrazol-4-yl)amino)pyrimidin-4-yl)-6,7,8,9-tetrahydro-5H-benzo[7]annulen-5-yl)azetidine-1-carboxamide as a yellow solid (11 mg, yield: 10%). ESI-MS (M+H)$^+$: 518.3. $^1$H NMR (400 MHz, CD$_3$OD) δ: 8.28 (d, J=5.2 Hz, 1H), 7.97 (s, 1H), 7.83-7.80 (m, 2H), 7.55 (s, 1H), 7.27 (d, J=7.6 Hz, 1H), 7.10 (d, J=5.6 Hz, 1H), 6.79 (d, J=8.0 Hz, 1H), 4.95-4.93 (m, 1H), 4.52-4.49 (m, 1H), 4.43-4.37 (m, 1H), 4.16-4.08 (m, 2H), 3.77-3.69 (m, 2H), 2.93-2.85 (m, 2H), 1.88-1.76 (m, 4H), 1.59-1.55 (m, 1H), 1.43 (d, J=6.8 Hz, 6H), 1.28-1.18 (m, 1H), 1.12 (s, 9H).

Example 169: 3-(tert-butoxy)-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide

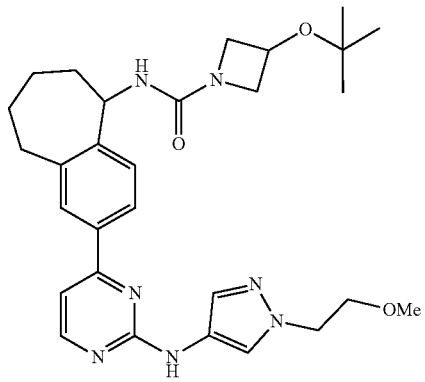

I-175

Synthesis of 3-(tert-butoxy)-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide was similar to that of Example 161. The crude product was purified by prep-HPLC (CH$_3$CN/H$_2$O with 0.05% NH$_4$OH as mobile phase) to give 3-(tert-butoxy)-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide as a yellow solid (41 mg, yield: 37%). ESI-MS (M+H)$^+$: 534.1. $^1$H NMR (400 MHz, CD$_3$OD) δ: 8.28 (d, J=5.2 Hz, 1H), 7.98 (s, 1H), 7.86 (d, J=9.2 Hz, 1H), 7.79 (s, 1H), 7.56 (s, 1H), 7.28 (d, J=8.4 Hz, 1H), 7.11 (d, J=5.2 Hz, 1H), 4.96-4.93 (m, 1H), 4.54-4.48 (m, 1H), 4.19 (t, J=5.2 Hz, 2H), 4.16-4.08 (m, 2H), 3.79-3.68 (m, 2H), 3.65 (t, J=5.2 Hz, 2H), 3.25 (s, 3H), 2.96-2.83 (m, 1H), 1.92-1.77 (m, 4H), 1.60-1.56 (m, 1H), 1.28-1.18 (m, 1H), 1.10 (s, 9H).

Example 170: (R)-3-(tert-butoxy)-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide and (S)-3-(tert-butoxy)-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide

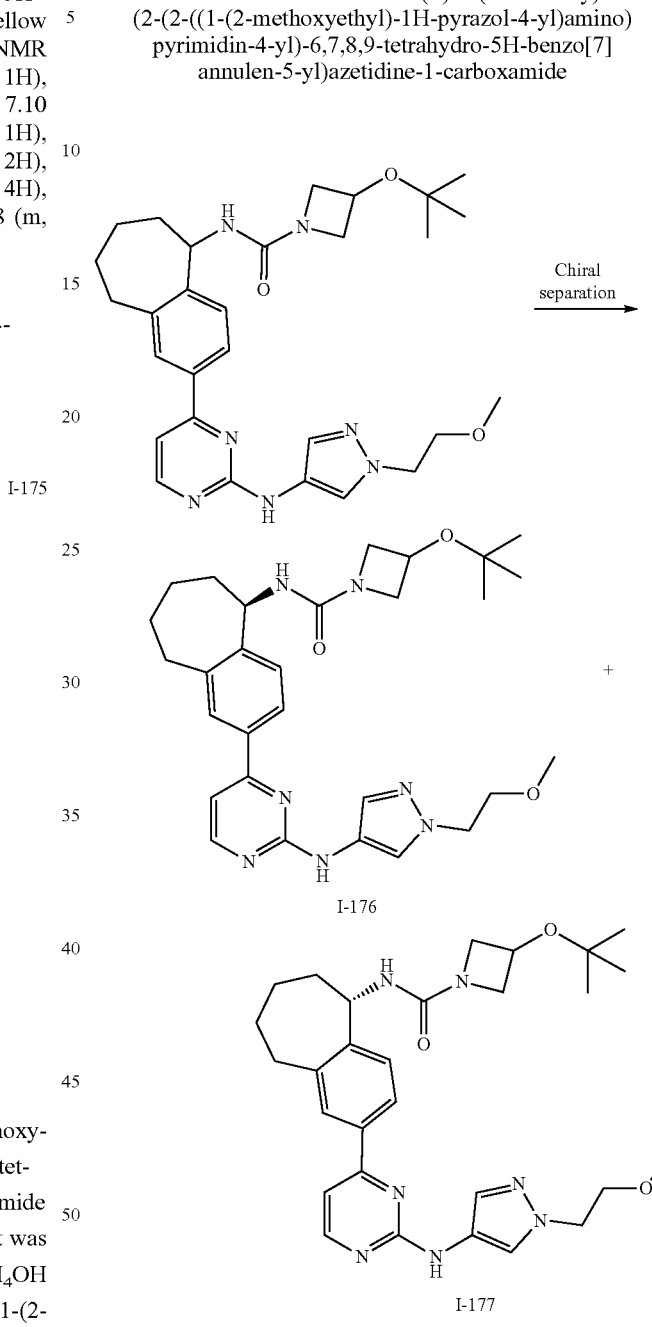

3-(tert-butoxy)-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide (100 mg) was subjected to the following SFC separation (AS-H (2×15 cm), 30% methanol (0.1 DEA)/CO2, 100 bar, 55 mL/min, 280 nm. inj vol.: 1.0 mL, 5 mg/mL methanol) yielded 34.4 mg of peak-1 (chemical purity 99%, ee>99%) and 28.8 mg of peak-2 (chemical purity 99%, ee>99%). Peak 1 was assigned as (S)-3-(tert-butoxy)-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide: LCMS: Rt 1.27 min, m/z 534.3. $^1$H NMR (400 MHz, CD$_3$OD) δ:0.37 (d, J=5.21 Hz, 1H), 8.07 (s, 1H), 7.93 (d, J=8.09 Hz, 1H), 7.88 (s, 1H), 7.67 (s, 1H), 7.37 (d, J=8.09 Hz, 1H), 7.18 (d, J=5.33 Hz, 1H), 5.05 (d, J=10.16 Hz, 1H), 4.58 (br. s., 1H), 4.10-4.32 (m, 4H), 3.80 (s, 2H), 3.76 (d, J=5.40 Hz, 2H), 3.32 (s, 3H), 2.80-3.10 (m, 2H), 1.26-2.09 (m, 6H), 1.22 (s, 9H). Peak 2 was assigned as (R)-3-(tert-butoxy)-N-(2-(2-((1-(2-methoxyethyl)-1H-pyrazol-4-yl)amino)pyrimidin-4-yl)-6,7,8,9-tetrahydro-5H-benzo[7]annulen-5-yl)azetidine-1-carboxamide: LCMS: Rt 1.27 min, m/z 534.2. $^1$H NMR (400 MHz, CD$_3$OD) δ: 8.38 (d, J=5.15 Hz, 1H), 8.08 (s, 1H), 7.95 (d, J=8.03 Hz, 1H), 7.89 (s, 1H), 7.68 (s, 1H), 7.38 (d, J=8.09 Hz, 1H), 7.20 (d, J=5.21 Hz, 1H), 5.05 (d, J=10.16 Hz, 1H), 4.59 (br. s., 2H), 4.08-4.35 (m, 4H), 3.79-3.92 (m, 2H), 3.69-3.76 (m, 2H), 3.36 (s, 3H), 2.78-3.12 (m, 2H), 1.26-2.09 (m, 6H), 1.23 (s, 9H).

Example 171: 3-(tert-butoxy)-N-(2-(2-((1-(2-hydroxyethyl)-1H-pyrazol-4-yl)amino)pyrimidin-4-yl)-6,7,8,9-tetrahydro-5H-benzo[7]annulen-5-yl)azetidine-1-carboxamide

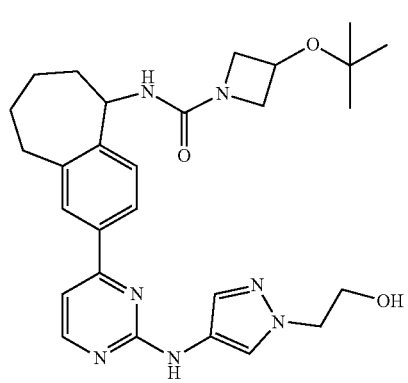

I-178

1. Synthesis of N-(2-bromo-6,7,8,9-tetrahydro-5H-benzo[7]annulen-5-yl)-3-(tert-butoxy)azetidine-1-carboxamide

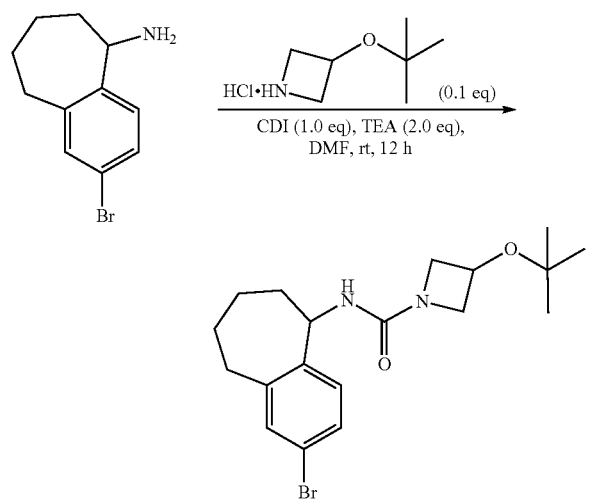

Synthesis of N-(2-bromo-6,7,8,9-tetrahydro-5H-benzo[7]annulen-5-yl)-3-(tert-butoxy)azetidine-1-carboxamide was similar to that of N-(2-bromo-6,7,8,9-tetrahydro-5H-benzo[7]annulen-5-yl)-3-isopropoxyazetidine-1-carboxamide. The residue was purified by silica gel column (petroleum ether/EtOAc=1:3) to give N-(2-bromo-6,7,8,9-tetrahydro-5H-benzo[7]annulen-5-yl)-3-(tert-butoxy)azetidine-1-carboxamide (2.9 g, yield: 50%) as a white solid. ESI-MS (M+1)$^+$: 395.1. $^1$H NMR (400 MHz, CDCl$_3$) δ: 7.27-7.23 (m, 2H), 7.09 (d, J=8.4 Hz, 1H), 4.96 (t, J=7.6 Hz, 1H), 4.51-4.45 (m, 1H), 4.38-4.36 (m, 1H), 4.15-4.10 (m, 2H), 3.88-3.82 (m, 2H), 2.87-2.70 (m, 2H), 1.88-1.74 (m, 5H), 1.56-1.44 (m, 1H), 1.18 (s, 9H).

2. The preparation of 3-(tert-butoxy)-N-(2-(2-chloropyrimidin-4-yl)-6,7,8,9-tetrahydro-5H-benzo[7]annulen-5-yl)azetidine-1-carboxamide

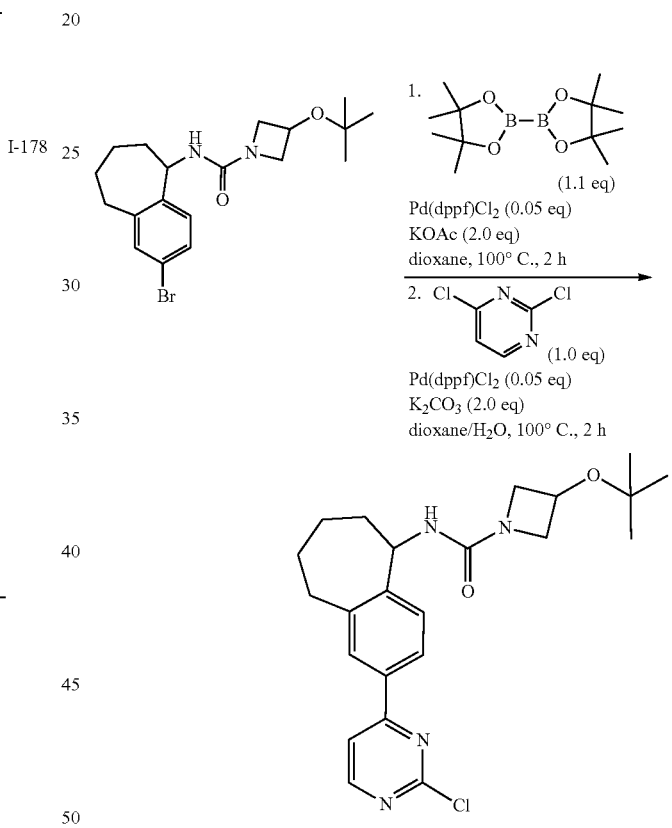

Synthesis of 3-(tert-butoxy)-N-(2-(2-chloropyrimidin-4-yl)-6,7,8,9-tetrahydro-5H-benzo[7]annulen-5-yl)azetidine-1-carboxamide was similar to that of N-(2-(2-chloropyrimidin-4-yl)-6,7,8,9-tetrahydro-5H-benzo[7]annulen-5-yl)-3-isopropoxyazetidine-1-carboxamide. The residue was purified by prep-HPLC (CH$_3$CN/H$_2$O with 0.05% NH$_4$OH as mobile phase) to give 3-(tert-butoxy)-N-(2-(2-chloropyrimidin-4-yl)-6,7,8,9-tetrahydro-5H-benzo[7]annulen-5-yl)azetidine-1-carboxamide as a yellow solid (720 mg, yield: 70%). ESI-MS (M+H)$^+$: 429.1. $^1$H NMR (400 MHz, CDCl$_3$) δ: 8.61 (d, J=5.2 Hz, 1H), 7.87 (s, 1H), 7.83 (d, J=8.0 Hz, 1H), 7.61 (d, J=5.2 Hz, 1H), 7.38 (d, J=8.0 Hz, 1H), 5.09 (t, J=8.0 Hz, 1H), 4.50-4.47 (m, 2H), 4.16-4.13 (m, 1H), 3.91-3.87 (m, 2H), 3.02-2.88 (m, 2H), 1.93-1.85 (m, 4H), 1.83-1.80 (m, 1H), 1.53-1.51 (m, 1H), 1.19 (s, 9H).

3. The preparation of 3-(tert-butoxy)-N-(2-(2-((1-(2-((tert-butyldimethylsilyl)oxy)ethyl)-1H-pyrazol-4-yl)amino)pyrimidin-4-yl)-6,7,8,9-tetrahydro-5H-benzo[7]annulen-5-yl)azetidine-1-carboxamide

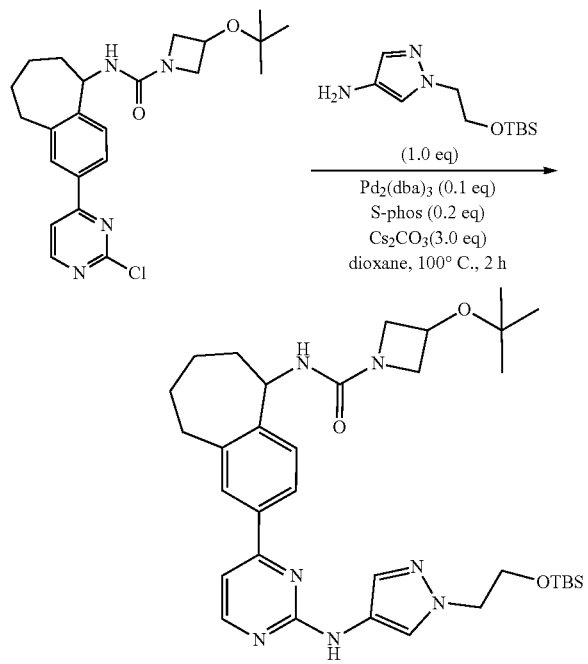

Synthesis of 3-(tert-butoxy)-N-(2-(2-((1-(2-((tert-butyldimethylsilyl)oxy)ethyl)-1H-pyrazol-4-yl)amino)pyrimidin-4-yl)-6,7,8,9-tetrahydro-5H-benzo[7]annulen-5-yl)azetidine-1-carboxamide was similar to that of Example 161. The residue was purified by silica gel column chromatography (EtOAc/MeOH=10:1) to give 3-(tert-butoxy)-N-(2-(2-((1-(2-((tert-butyldimethylsilyl)oxy)ethyl)-1H-pyrazol-4-yl)amino)pyrimidin-4-yl)-6,7,8,9-tetrahydro-5H-benzo[7]annulen-5-yl)azetidine-1-carboxamide as a yellow solid (160 mg, yield: 51%). ESI-MS (M+H)$^+$: 634.0.

4. The preparation of 3-(tert-butoxy)-N-(2-(2-((1-(2-hydroxyethyl)-1H-pyrazol-4-yl)amino)pyrimidin-4-yl)-6,7,8,9-tetrahydro-5H-benzo[7]annulen-5-yl)azetidine-1-carboxamide

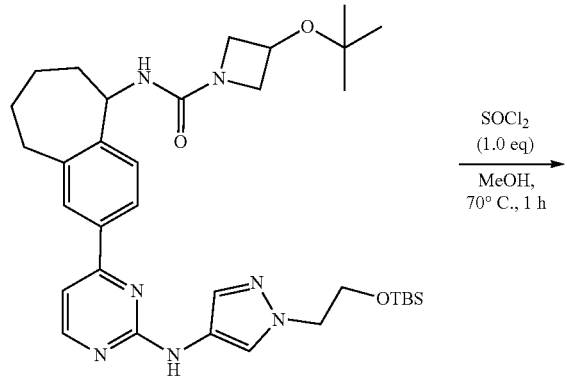

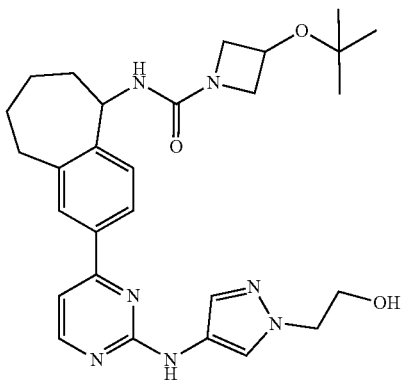

A mixture of 3-(tert-butoxy)-N-(2-(2-((1-(2-((tert-butyldimethylsilyl)oxy)ethyl)-1H-pyrazol-4-yl)amino)pyrimidin-4-yl)-6,7,8,9-tetrahydro-5H-benzo[7]annulen-5-yl)azetidine-1-carboxamide (140 mg, 0.22 mmol) and SOCl$_2$ (26 mg, 0.22 mmol) in MeOH (10 mL) was stirred at 70° C. for 1 h. After concentration, the crude product was purified by prep-HPLC (CH$_3$CN/H$_2$O with 0.05% NH$_4$OH as mobile phase) to give 3-(tert-butoxy)-N-(2-(2-((1-(2-hydroxyethyl)-1H-pyrazol-4-yl)amino)pyrimidin-4-yl)-6,7,8,9-tetrahydro-5H-benzo[7]annulen-5-yl)azetidine-1-carboxamide as a yellow solid (48 mg, yield: 37%). ESI-MS (M+H)$^+$: 520.0. $^1$H NMR (400 MHz, CD$_3$OD) δ: 8.27 (d, J=5.2 Hz, 1H), 7.97 (s, 1H), 7.84 (d, J=8.4 Hz, 1H), 7.79 (s, 1H), 7.58 (s, 1H), 7.27 (d, J=8.0 Hz, 1H), 7.09 (d, J=5.2 Hz, 1H), 4.96-4.94 (m, 1H), 4.53-4.47 (m, 1H), 4.16-4.08 (m, 4H), 3.80 (t, J=5.2 Hz, 2H), 3.77-3.68 (m, 2H), 2.95-2.83 (m, 2H), 1.89-1.74 (m, 4H), 1.60-1.52 (m, 1H), 1.27-1.18 (m, 1H), 1.12 (s, 9H).

Example 172: 3-(tert-butoxy)-N-(2-(2-((1-(tetrahydro-2H-pyran-4-yl)-1H-pyrazol-4-yl)amino)pyrimidin-4-yl)-6,7,8,9-tetrahydro-5H-benzo[7]annulen-5-yl)azetidine-1-carboxamide

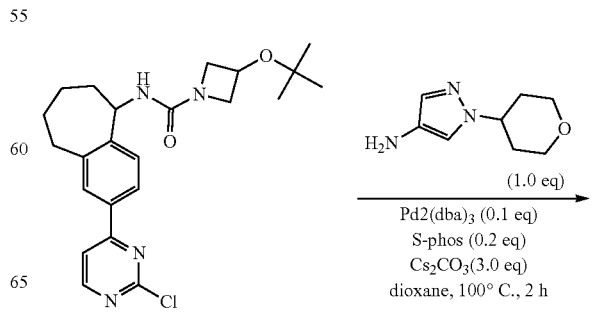

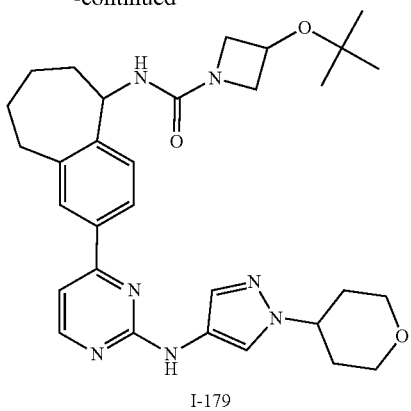

I-179

Synthesis of 3-(tert-butoxy)-N-(2-(2-((1-(tetrahydro-2H-pyran-4-yl)-1H-pyrazol-4-yl)amino)pyrimidin-4-yl)-6,7,8,9-tetrahydro-5H-benzo[7]annulen-5-yl)azetidine-1-carboxamide was similar to that of Example 161. The crude product was purified by prep-HPLC (CH₃CN/H₂O with 0.05% NH₄OH as mobile phase) to give 3-(tert-butoxy)-N-(2-(2-((1-(tetrahydro-2H-pyran-4-yl)-1H-pyrazol-4-yl)amino)pyrimidin-4-yl)-6,7,8,9-tetrahydro-5H-benzo[7]annulen-5-yl)azetidine-1-carboxamide as a yellow solid (57 mg, yield: 55%). ESI-MS (M+H)⁺: 560.0. ¹H NMR (400 MHz, CD₃OD) δ: 8.28 (d, J=4.8 Hz, 1H), 8.03 (s, 1H), 7.83-7.81 (m, 2H), 7.57 (s, 1H), 7.28 (d, J=7.6 Hz, 1H), 7.10-7.09 (m, 1H), 4.97-4.95 (m, 1H), 4.53-4.48 (m, 1H), 4.30-4.27 (m, 1H), 4.16-4.08 (m, 2H), 3.99-3.96 (m, 2H), 3.77-3.69 (m, 2H), 3.52-3.46 (m, 2H), 2.97-2.82 (m, 2H), 1.98-1.77 (m, 8H), 1.60-1.53 (m, 1H), 1.28-1.23 (m, 1H), 1.12 (s, 9H).

Example 173: 3-(tert-butoxy)-N-(2-(2-((1-(1-methylpiperidin-4-yl)-1H-pyrazol-4-yl)amino)pyrimidin-4-yl)-6,7,8,9-tetrahydro-5H-benzo[7]annulen-5-yl)azetidine-1-carboxamide

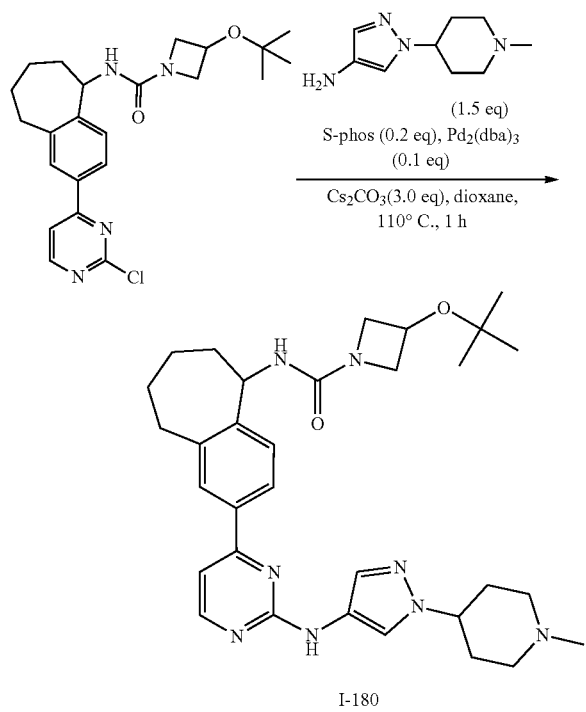

I-180

Synthesis of 3-(tert-butoxy)-N-(2-(2-((1-(1-methylpiperidin-4-yl)-1H-pyrazol-4-yl)amino)pyrimidin-4-yl)-6,7,8,9-tetrahydro-5H-benzo[7]annulen-5-yl)azetidine-1-carboxamide was similar to that of Example 161. The residue was purified by prep-TLC (DCM/MeOH=10/1) to give 3-(tert-butoxy)-N-(2-(2-((1-(1-methylpiperidin-4-yl)-1H-pyrazol-4-yl)amino)pyrimidin-4-yl)-6,7,8,9-tetrahydro-5H-benzo[7]annulen-5-yl)azetidine-1-carboxamide (33 mg, yield: 41%) as a yellow solid. ESI-MS (M+H)⁺: 573.3. ¹H NMR (400 MHz, CD₃OD) δ: 8.26 (d, J=5.2 Hz, 1H), 7.97 (s, 1H), 7.53 (d, J=7.6 Hz, 1H), 7.77 (s, 1H), 7.57 (s, 1H), 7.26 (d, J=8.0 Hz, 1H), 7.07 (d, J=5.2 Hz, 1H), 4.94 (d, J=10.0 Hz, 1H), 4.52-4.46 (m, 1H), 4.15-4.00 (m, 3H), 3.77-3.69 (m, 2H), 2.94-2.79 (m, 4H), 2.23 (s, 3H), 2.17-2.11 (m, 2H), 2.06-1.85 (m, 7H), 1.82-1.72 (m, 1H), 1.61-1.52 (m, 1H), 1.30-1.24 (m, 1H), 1.11 (s, 9H).

Example 174: N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropylpyrrolidine-1-carboxamide

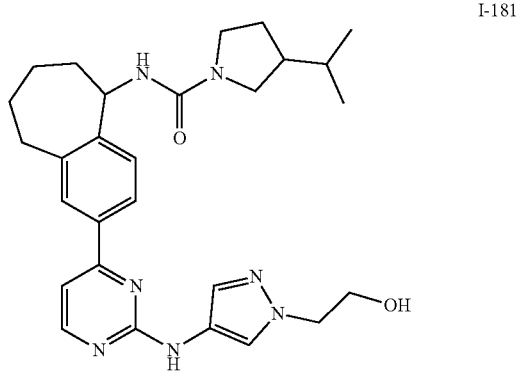 [SMILES: CC(C)C1CCN(C(=O)NC2CCCCc3cc(-c4ccnc(Nc5cnn(CCO)c5)n4)ccc32)C1]

I-181

1. The preparation of N-(2-bromo-6,7,8,9-tetrahydro-5H-benzo[7]annulen-5-yl)-3-isopropylpyrrolidine-1-carboxamide

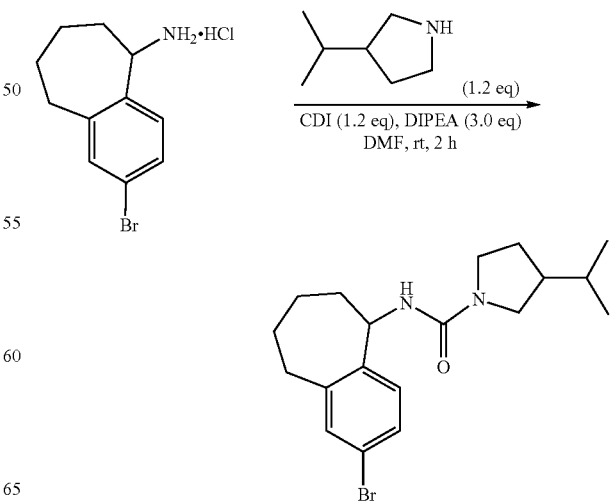

A mixture of 2-bromo-6,7,8,9-tetrahydro-5H-benzo[7]annulen-5-amine hydrochloride (1.5 g, 5.5 mmol), DIPEA (2.1 g, 16.5 mmol) and CDI (1.1 g, 6.6 mmol) in DMF (20 mL) was stirred at rt for 0.5 h before addition of 3-isopropylpyrrolidine (746 mg, 6.6 mmol). The mixture was stirred at rt for 2 h, water (60 mL) was added and the mixture was extracted with EtOAc (100 mL×2) The combine organics were concentrated in vacuo and purified by prep-HPLC (CH$_3$CN/H$_2$O with 0.05% NH$_4$OH as mobile phase) to give N-(2-bromo-6,7,8,9-tetrahydro-5H-benzo[7]annulen-5-yl)-3-isopropylpyrrolidine-1-carboxamide as a while solid (760 mg, yield: 35%). ESI-MS (M+H)$^+$: 379.1.

2. The preparation of N-(2-(2-chloropyrimidin-4-yl)-6,7,8,9-tetrahydro-5H-benzo[7]annulen-5-yl)-3-isopropylpyrrolidine-1-carboxamide

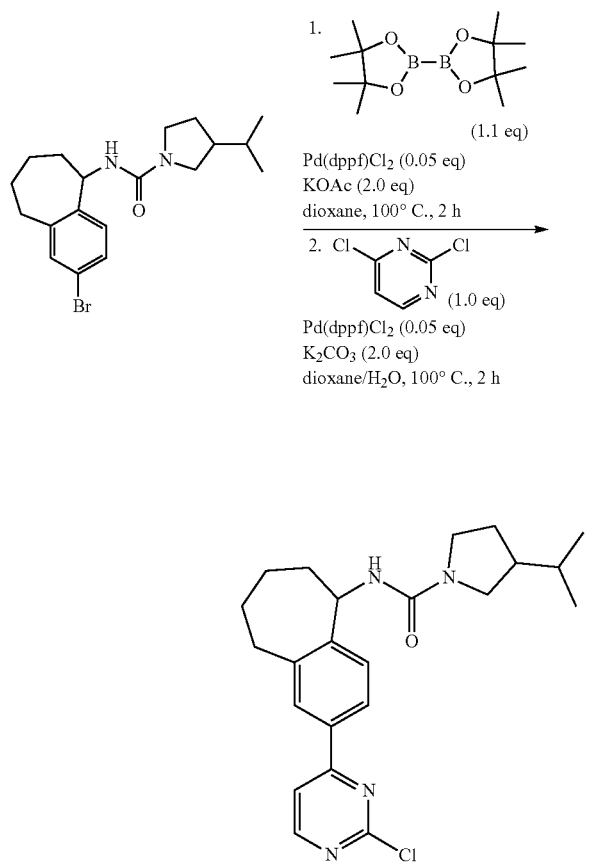

Synthesis of N-(2-(2-chloropyrimidin-4-yl)-6,7,8,9-tetrahydro-5H-benzo[7]annulen-5-yl)-3-isopropylpyrrolidine-1-carboxamide was similar to that of N-(2-(2-chloropyrimidin-4-yl)-6,7,8,9-tetrahydro-5H-benzo[7]annulen-5-yl)-3-isopropoxyazetidine-1-carboxamide. The crude product was purified by silica gel column chromatography (petroleum ether/EtOAc=1:4) to give N-(2-(2-chloropyrimidin-4-yl)-6,7,8,9-tetrahydro-5H-benzo[7]annulen-5-yl)-3-isopropylpyrrolidine-1-carboxamide as a yellow solid (480 mg, yield: 58%). ESI-MS (M+H)$^+$: 413.2. $^1$H NMR (400 MHz, CD$_3$OD) δ: 8.65 (d, J=5.2 Hz, 1H), 7.99-7.92 (m, 3H), 7.43-7.40 (m, 1H), 5.16-5.11 (m, 1H), 3.73-3.56 (m, 2H), 3.05-3.00 (m, 4H), 2.14-2.10 (m, 4H), 2.02-1.86 (m, 6H), 1.75-1.53 (m, 2H), 1.39-1.33 (m, 1H), 1.02-0.99 (m, 6H).

3. The preparation of N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropylpyrrolidine-1-carboxamide

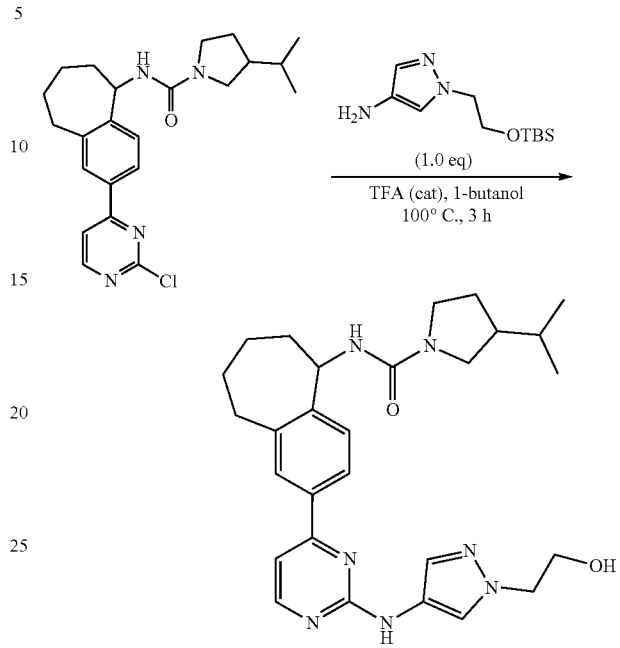

To a solution of N-(2-(2-chloropyrimidin-4-yl)-6,7,8,9-tetrahydro-5H-benzo[7]annulen-5-yl)-3-isopropylpyrrolidine-1-carboxamide (80 mg, 0.2 mmol) in 1-butanol (5 mL) were added 1-(2-((tert-butyldimethylsilyl)oxy)ethyl)-1H-pyrazol-4-amine (48 mg, 0.2 mmol) and TFA (cat). The mixture was stirred at 100° C. for 3 h. After concentration, the crude product was purified by prep-HPLC (CH$_3$CN/H$_2$O with 0.05% NH$_4$OH as mobile phase) to give N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropylpyrrolidine-1-carboxamide as a yellow solid (35 mg, yield: 29%). ESI-MS (M+H)$^+$: 504.0. $^1$H NMR (400 MHz, CD$_3$OD) δ: 8.27 (d, J=5.2 Hz, 1H), 7.97 (s, 1H), 7.84 (d, J=8.0 Hz, 1H), 7.79 (s, 1H), 7.58 (s, 1H), 7.29-7.26 (m, 1H), 7.09 (d, J=5.2 Hz, 1H), 6.44-6.39 (m, 1H), 5.04-5.01 (m, 1H), 4.11 (t, J=5.2 Hz, 2H), 3.80 (t, J=5.2 Hz, 2H), 3.63-3.46 (m, 2H), 3.28-3.21 (m, 1H), 2.94-2.87 (m, 3H), 2.04-1.99 (m, 1H), 1.91-1.85 (m, 6H), 1.62-1.44 (m, 2H), 1.29-1.27 (m, 1H), 0.91-0.89 (m, 6H).

Example 175: 3-(tert-butoxy)-N-(2-(2-((5,6-dihydro-4H-pyrrolo[1,2-b]pyrazol-3-yl)amino)pyrimidin-4-yl)-6,7,8,9-tetrahydro-5H-benzo[7]annulen-5-yl)azetidine-1-carboxamide

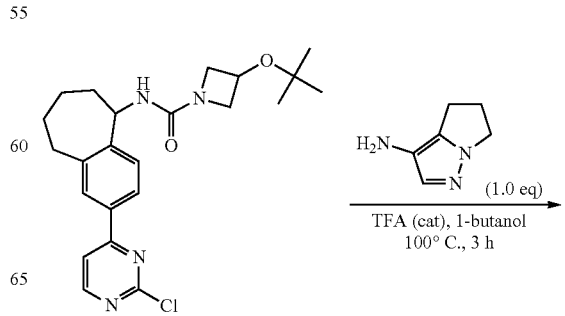

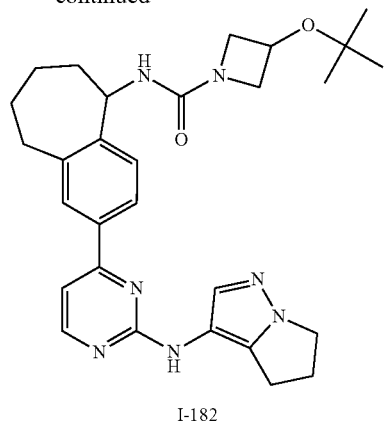

I-182

Synthesis of 3-(tert-butoxy)-N-(2-(2-((5,6-dihydro-4H-pyrrolo[1,2-b]pyrazol-3-yl)amino)pyrimidin-4-yl)-6,7,8,9-tetrahydro-5H-benzo[7]annulen-5-yl)azetidine-1-carboxamide was similar to that of Example 174. After concentration, the crude product was purified by prep-HPLC (CH₃CN/H₂O with 0.05% NH₄OH as mobile phase) to give 3-(tert-butoxy)-N-(2-(2-((5,6-dihydro-4H-pyrrolo[1,2-b]pyrazol-3-yl)amino)pyrimidin-4-yl)-6,7,8,9-tetrahydro-5H-benzo[7]annulen-5-yl)azetidine-1-carboxamide as a yellow solid (70 mg, yield: 29%). ESI-MS (M+H)⁺: 516.3. ¹H NMR (400 MHz, CD₃OD) δ: 8.22 (d, J=5.2 Hz, 1H), 7.79 (d, J=8.0 Hz, 1H), 7.75 (s, 1H), 7.57 (s, 1H), 7.25 (d, J=8.0 Hz, 1H), 7.09 (d, J=5.2 Hz, 1H), 4.94 (d, J=10.4 Hz, 1H), 4.51-4.48 (m, 1H), 4.16-4.09 (m, 2H), 4.05-4.01 (m, 2H), 3.76-3.68 (m, 2H), 2.90-2.82 (m, 4H), 2.54-2.50 (m, 2H), 1.87-1.76 (m, 4H), 1.57-1.54 (m, 1H), 1.27-1.23 (m, 1H), 1.11 (s, 9H).

Example 176: 3-Isopropyl-N-(2-(2-((1-(2-methoxyethyl)-1H-pyrazol-4-yl)amino)pyrimidin-4-yl)-6,7,8,9-tetrahydro-5H-benzo[7]annulen-5-yl)pyrrolidine-1-carboxamide

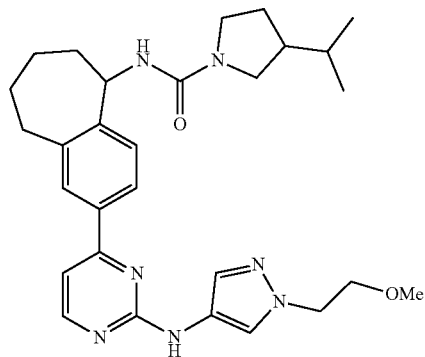

I-183

Synthesis of 3-isopropyl-N-(2-(2-((1-(2-methoxyethyl)-1H-pyrazol-4-yl)amino)pyrimidin-4-yl)-6,7,8,9-tetrahydro-5H-benzo[7]annulen-5-yl)pyrrolidine-1-carboxamide was similar to that of Example 161. The crude product was purified by prep-HPLC (CH₃CN/H₂O with 0.05% NH₄OH as mobile phase) to give 3-isopropyl-N-(2-(2-((1-(2-methoxyethyl)-1H-pyrazol-4-yl)amino)pyrimidin-4-yl)-6,7,8,9-tetrahydro-5H-benzo[7]annulen-5-yl)pyrrolidine-1-carboxamide as a yellow solid (17 mg, yield: 17%). ESI-MS (M+H)⁺: 518.1. ¹H NMR (400 MHz, CD₃OD) δ: 8.28 (d, J=5.2 Hz, 1H), 7.98 (s, 1H), 7.85 (d, J=8.0 Hz, 1H), 7.79 (s, 1H), 7.57 (s, 1H), 7.29-7.26 (m, 1H), 7.10 (d, J=5.2 Hz, 1H), 5.06-5.00 (m, 1H), 4.18 (t, J=5.2 Hz, 2H), 3.65 (t, J=5.2 Hz, 2H), 3.58-3.46 (m, 2H), 3.30-3.24 (m, 1H), 3.24 (s, 3H), 2.98-2.84 (m, 3H), 2.06-1.99 (m, 1H), 1.92-1.79 (m, 5H), 1.65-1.43 (m, 3H), 1.33-1.24 (m, 1H), 0.92-0.89 (m, 6H).

Example 177: 3-(tert-butyl)-N-(2-(2-((1-methyl-1H-pyrazol-4-yl)amino)pyrimidin-4-yl)-6,7,8,9-tetrahydro-5H-benzo[7]annulen-5-yl)pyrrolidine-1-carboxamide

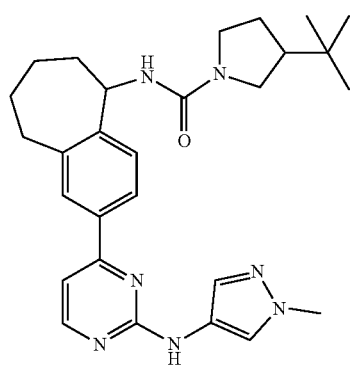

I-184

1. The preparation of N-(2-bromo-6,7,8,9-tetrahydro-5H-benzo[7]annulen-5-yl)-3-(tert-butyl)pyrrolidine-1-carboxamide

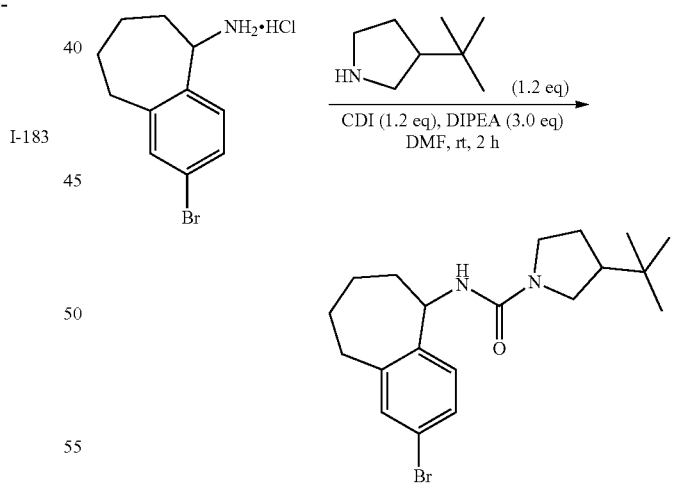

Synthesis of N-(2-bromo-6,7,8,9-tetrahydro-5H-benzo[7]annulen-5-yl)-3-(tert-butyl)pyrrolidine-1-carboxamide was similar to that of N-(2-bromo-6,7,8,9-tetrahydro-5H-benzo[7]annulen-5-yl)-3-isopropoxyazetidine-1-carboxamide. The residue was purified by prep-HPLC (MeCN/H₂O with 0.05% NH₄OH as mobile phase from 5% to 95%) to give N-(2-bromo-6,7,8,9-tetrahydro-5H-benzo[7]annulen-5-yl)-3-(tert-butyl)pyrrolidine-1-carboxamide (1.0 g, yield: 47%) as yellow solid. ESI-MS (M+H)⁺: 393.1.

2. The preparation of 3-(tert-butyl)-N-(2-(2-chloropyrimidin-4-yl)-6,7,8,9-tetrahydro-5H-benzo[7]annulen-5-yl)pyrrolidine-1-carboxamide

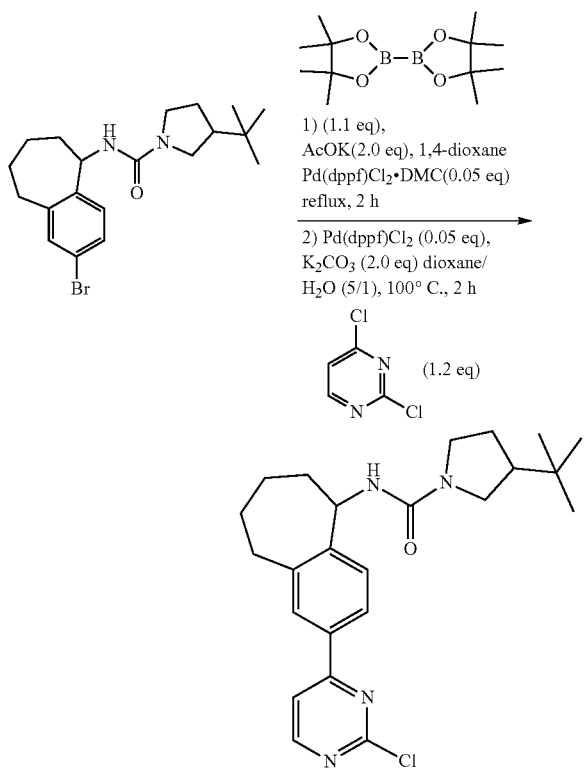

Synthesis of 3-(tert-butyl)-N-(2-(2-chloropyrimidin-4-yl)-6,7,8,9-tetrahydro-5H-benzo[7]annulen-5-yl)pyrrolidine-1-carboxamide was similar to that of N-(2-(2-chloropyrimidin-4-yl)-6,7,8,9-tetrahydro-5H-benzo[7]annulen-5-yl)-3-isopropoxyazetidine-1-carboxamide. The crude was purified by prep-HPLC (MeCN/H₂O with 0.05% NH₄OH as mobile phase from 5% to 95%) to give 3-(tert-butyl)-N-(2-(2-chloropyrimidin-4-yl)-6,7,8,9-tetrahydro-5H-benzo[7]annulen-5-yl)pyrrolidine-1-carboxamide (780 mg, yield: 72%) as yellow solid. ESI-MS (M+H)$^+$: 427.2.

3. The preparation of 3-(tert-butyl)-N-(2-(2-((1-methyl-1H-pyrazol-4-yl)amino)pyrimidin-4-yl)-6,7,8,9-tetrahydro-5H-benzo[7]annulen-5-yl)pyrrolidine-1-carboxamide

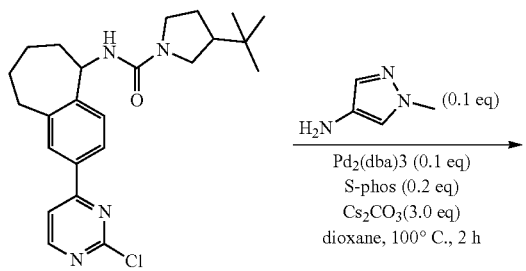

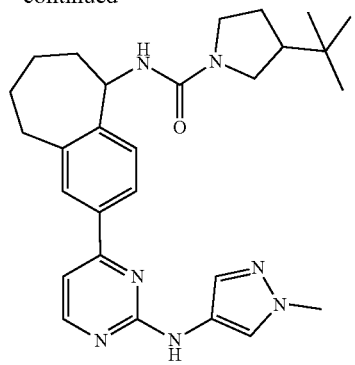

Synthesis of 3-(tert-butyl)-N-(2-(2-((1-methyl-1H-pyrazol-4-yl)amino)pyrimidin-4-yl)-6,7,8,9-tetrahydro-5H-benzo[7]annulen-5-yl)pyrrolidine-1-carboxamide was similar to that of Example 161. The residue was purified by prep-HPLC (MeCN/H₂O with 0.05% NH₄OH as mobile phase from 5% to 95%) to give 3-(tert-butyl)-N-(2-(2-((1-methyl-1H-pyrazol-4-yl)amino)pyrimidin-4-yl)-6,7,8,9-tetrahydro-5H-benzo[7]annulen-5-yl)pyrrolidine-1-carboxamide (48 mg, yield: 42%) as yellow solid. ESI-MS (M+H)$^+$: 488.3. $^1$H NMR (400 MHz, CD₃OD) δ: 8.36 (d, J=5.6 Hz, 1H), 7.95-7.86 (m, 3H), 7.65 (s, 1H), 7.39-7.36 (m, 1H), 7.17 (d, J=5.2 Hz, 1H), 5.15-5.10 (m, 1H), 3.87 (s, 3H), 3.68-3.48 (m, 2H), 3.36-3.35 (m, 1H), 3.20-2.90 (m, 3H), 2.15-1.85 (m, 6H), 1.75-1.67 (m, 2H), 1.38-1.33 (m, 1H), 0.98 (s, 9H).

Example 178: 3-(tert-butyl)-N-(2-(2-((1-(2-hydroxyethyl)-1H-pyrazol-4-yl)amino)pyrimidin-4-yl)-6,7,8,9-tetrahydro-5H-benzo[7]annulen-5-yl)pyrrolidine-1-carboxamide

I-185

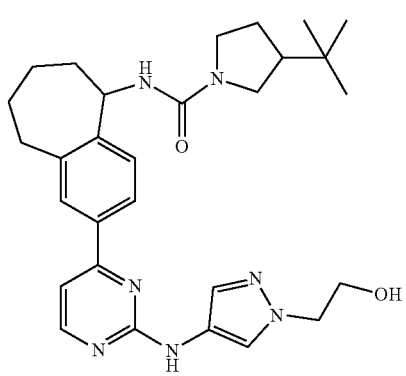

1. The preparation of 3-(tert-butyl)-N-(2-(2-((1-(2-((tert-butyldimethylsilyl)oxy)ethyl)-1H-pyrazol-4-yl)amino)pyrimidin-4-yl)-6,7,8,9-tetrahydro-5H-benzo[7]annulen-5-yl)pyrrolidine-1-carboxamide

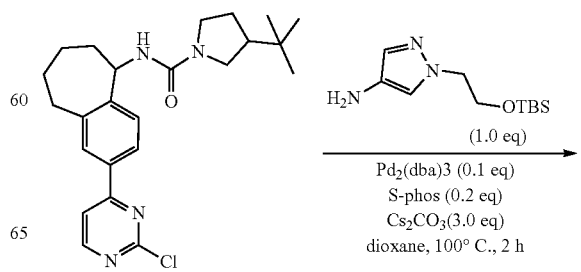

-continued

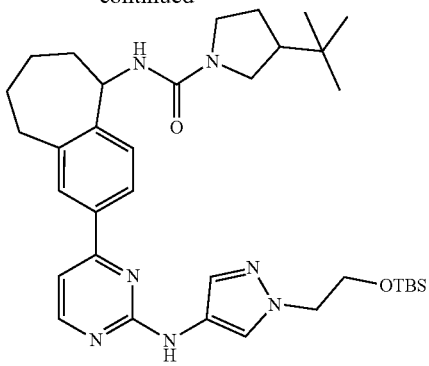

Synthesis of 3-(tert-butyl)-N-(2-(2-((1-(2-((tert-butyldimethylsilyl)oxy)ethyl)-1H-pyrazol-4-yl)amino)pyrimidin-4-yl)-6,7,8,9-tetrahydro-5H-benzo[7]annulen-5-yl)pyrrolidine-1-carboxamide was similar to that of Example 161. The residue was purified by prep-HPLC (MeCN/H$_2$O with 0.05% NH$_4$OH as mobile phase from 5% to 95%) to give 3-(tert-butyl)-N-(2-(2-((1-(2-((tert-butyldimethylsilyl)oxy)ethyl)-1H-pyrazol-4-yl)amino)pyrimidin-4-yl)-6,7,8,9-tetrahydro-5H-benzo[7]annulen-5-yl)pyrrolidine-1-carboxamide (144 mg, yield: 65%) as yellow solid. ESI-MS (M+H)$^+$: 632.4.

2. The preparation of 3-(tert-butyl)-N-(2-(2-((1-(2-hydroxyethyl)-1H-pyrazol-4-yl)amino)pyrimidin-4-yl)-6,7,8,9-tetrahydro-5H-benzo[7]annulen-5-yl)pyrrolidine-1-carboxamide

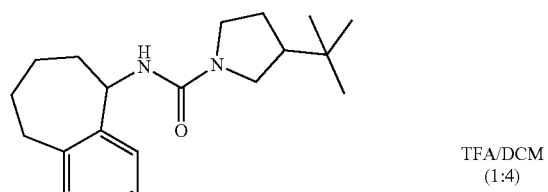

TFA/DCM
(1:4)
————→
rt, 1 h

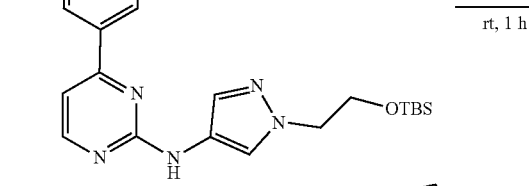

Synthesis of 3-(tert-butyl)-N-(2-(2-((1-(2-hydroxyethyl)-1H-pyrazol-4-yl)amino)pyrimidin-4-yl)-6,7,8,9-tetrahydro-5H-benzo[7]annulen-5-yl)pyrrolidine-1-carboxamide was similar to that of N-(2-(2-((1-(2-hydroxyethyl)-1H-pyrazol-4-yl)amino)pyrimidin-4-yl)-6,7,8,9-tetrahydro-5H-benzo[7]annulen-5-yl)-3-isopropoxyazetidine-1-carboxamide. The crude was purified through prep-HPLC (MeCN/H$_2$O with 0.05% NH$_4$OH as mobile phase from 5% to 95%) to give 3-(tert-butyl)-N-(2-(2-((1-(2-hydroxyethyl)-1H-pyrazol-4-yl)amino)pyrimidin-4-yl)-6,7,8,9-tetrahydro-5H-benzo[7]annulen-5-yl)pyrrolidine-1-carboxamide (90 mg, yield: 76%) as a yellow solid. ESI-MS (M+H)$^+$:518.3. $^1$H NMR (400 MHz, CD$_3$OD) δ: 8.25 (d, J=5.6 Hz, 1H), 7.96 (s, 1H), 7.83-7.77 (m, 2H), 7.59 (s, 1H), 7.28 (d, J=8.0 Hz, 1H), 7.06 (d, J=5.2 Hz, 1H), 5.04 (t, J=10.4 Hz, 1H), 4.11 (t, J=5.2 Hz, 2H), 3.80 (t, J=5.2 Hz, 2H), 3.58-3.38 (m, 2H), 3.22-3.20 (m, 1H), 3.10-2.81 (m, 3H), 2.02-1.77 (m, 6H), 1.65-1.60 (m, 2H), 1.28-1.25 (m, 1H), 0.88 (s, 9H).

Example 179: 3-(tert-butyl)-N-(2-(2-((1-(2-methoxyethyl)-1H-pyrazol-4-yl)amino)pyrimidin-4-yl)-6,7,8,9-tetrahydro-5H-benzo[7]annulen-5-yl) pyrrolidine-1-carboxamide

I-186

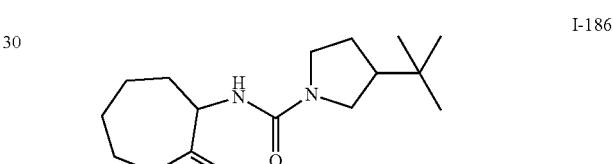
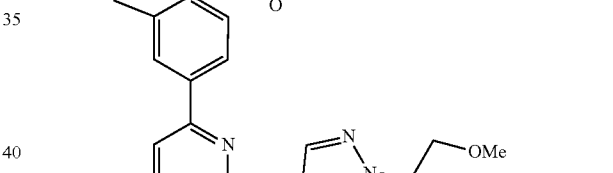
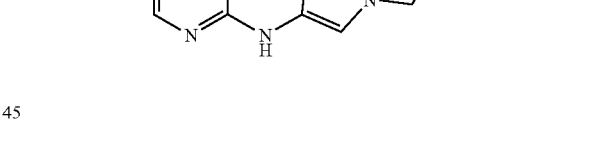

Synthesis of 3-(tert-butyl)-N-(2-(2-((1-(2-methoxyethyl)-1H-pyrazol-4-yl)amino)pyrimidin-4-yl)-6,7,8,9-tetrahydro-5H-benzo[7]annulen-5-yl)pyrrolidine-1-carboxamide was similar to that of Example 161 The residue was purified by prep-HPLC (MeCN/H$_2$O with 0.05% NH$_4$OH as mobile phase from 5% to 95%) to give 3-(tert-butyl)-N-(2-(2-((1-(2-methoxyethyl)-1H-pyrazol-4-yl)amino)pyrimidin-4-yl)-6,7,8,9-tetrahydro-5H-benzo[7]annulen-5-yl)pyrrolidine-1-carboxamide (70 mg, yield: 47%) as a yellow solid. ESI-MS (M+H)$^+$:532.3. $^1$H NMR (400 MHz, CD$_3$OD) δ: 8.28 (d, J=5.2 Hz, 1H), 7.99 (s, 1H), 7.85 (d, J=8.0 Hz, 1H), 7.79 (d, J=1.6 Hz, 1H), 7.58 (s, 1H), 7.32-7.28 (m, 1H), 7.09 (d, J=5.2 Hz, 1H), 5.09-5.02 (m, 1H), 4.19 (t, J=5.2 Hz, 2H), 3.66 (t, J=5.2 Hz, 2H), 3.59-3.40 (m, 2H), 3.25 (s, 3H), 3.12-2.84 (m, 3H), 2.06-1.80 (m, 6H), 1.67-1.59 (m, 2H), 1.30-1.20 (m, 1H), 0.90 (s, 9H).

Example 180: 3-isopropoxy-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)azetidine-1-carboxamide

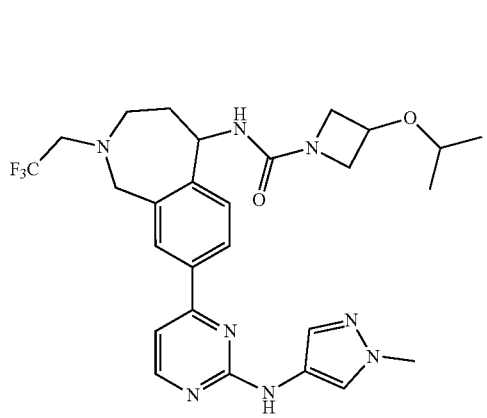

I-187

1. Preparation of 3-(3-Bromo-benzylamino)-propionic acid ethyl ester

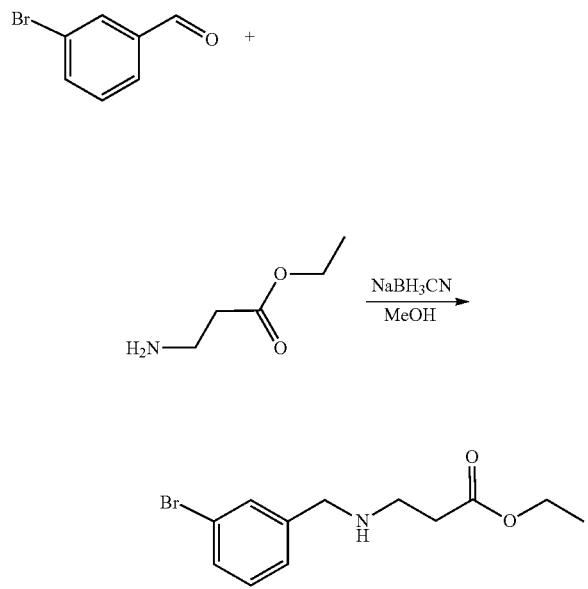

To a solution of ethyl 3-aminopropanoate (46.0 g, 0.3 mol) and 3-bromobenzaldehyde (55.5 g, 0.3 mol) in MeOH (1.2 L) were added Et$_3$N (60.7 g, 0.6 mol) and NaCNBH$_3$ (56.5 g, 0.9 mol) portion-wise. The resulting mixture was stirred at rt for 4 h. The reaction mixture was concentrated in vacuo and the residue was diluted with water (600 mL). The mixture was extracted with EtOAc (3×500 mL). The combined organic layer was washed with brine (100 mL), dried over anhydrous Na$_2$SO$_4$, filtered and concentrated in vacuo to give 3-(3-bromo-benzylamino)-propionic acid ethyl ester (46.5 g, yield: 54%) as a light yellow oil. $^1$H NMR (DMSO-d$_6$, 300 MHz): δ 7.52 (s, 1H), 7.40 (d, J=7.5 Hz, 1H), 7.31-7.25 (m, 2H), 4.04 (q, J=7.2 Hz, 2H), 3.67 (s, 2H), 2.69 (t, J=7.2 Hz, 2H), 2.42 (t, J=6.9 Hz, 2H), 1.17 (t, J=6.9 Hz, 3H).

2. Preparation of 3-[(3-Bromo-benzyl)-(toluene-4-sulfonyl)-amino]-propionic acid ethyl ester (3)

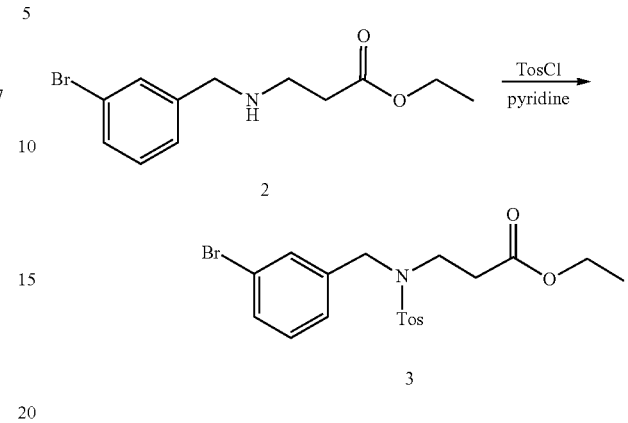

To a solution of 3-(3-bromo-benzylamino)-propionic acid ethyl ester (45.6 g, 0.16 mol) in pyridine (500 mL) was added TosCl (61.0 g, 0.32 mol) at rt. The reaction mixture was stirred at 120° C. for 16 h. The solvent was removed in vacuo to give the crude product. The crude product was purified by column chromatography on silica gel (petroleum ether:EtOAc=10:1 to 5:1) to afford 3-[(3-Bromo-benzyl)-(toluene-4-sulfonyl)-amino]-propionic acid ethyl ester (61 g, yield: 88%) as a light yellow oil. $^1$H NMR (DMSO-d$_6$, 300 MHz): δ 7.74 (d, J=8.4 Hz, 2H), 7.49-7.41 (m, 4H), 7.31 (d, J=5.1 Hz, 2H), 4.33 (s, 2H), 3.93 (q, J=7.2 Hz, 2H), 3.32 (t, J=7.2 Hz, 2H), 2.41 (s, 3H), 2.36 (t, J=6.9 Hz, 2H), 1.10 (t, J=6.9 Hz, 3H).

3. Preparation of 3-[(3-Bromo-benzyl)-(toluene-4-sulfonyl)-amino]-propionic acid

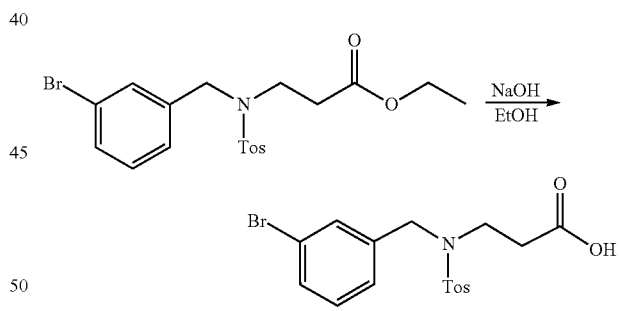

To a solution of 3-[(3-Bromo-benzyl)-(toluene-4-sulfonyl)-amino]-propionic acid ethyl ester (60.0 g, 0.14 mol) in a mixed solvent of EtOH (600 mL) and H$_2$O (60 mL) was added NaOH (11.2 g, 0.28 mol) portion-wise, the reaction solution was stirred at 60° C. for 4 h. The reaction solution was cooled to 0° C. and acidified to pH=5 with concentrated HCl. The solvent was concentrated in vacuo to give a residue which was extracted with EtOAc (3×150 mL). The organic layer was dried with Na$_2$SO$_4$, filtered and concentrated in vacuo to give 3-[(3-Bromo-benzyl)-(toluene-4-sulfonyl)-amino]-propionic acid (45.2 g, yield: 78.6%) as a white solid. $^1$H NMR (DMSO-d$_6$, 300 MHz): δ 12.28 (br, 1H), 7.74 (d, J=8.1 Hz, 2H), 7.49-7.41 (m, 4H), 7.32 (d, J=5.1 Hz, 2H), 4.33 (s, 2H), 3.29 (t, J=6.9 Hz, 2H), 2.41 (s, 3H), 2.27 (t, J=7.5 Hz, 2H).

4. Preparation of 3-[(3-Bromo-benzyl)-(toluene-4-sulfonyl)-amino]-propionyl chloride

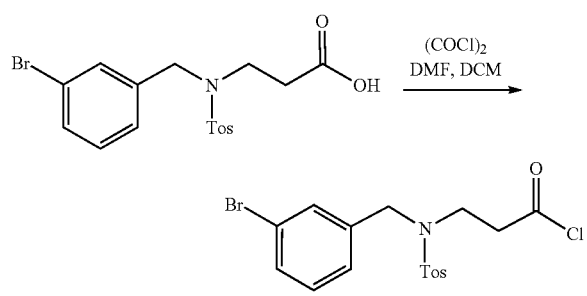

To a solution of 3-[(3-Bromo-benzyl)-(toluene-4-sulfonyl)-amino]-propionic acid (45.2 g, 0.11 mol) in DCM (1000 mL) were added dropwise DMF (1 mL) and oxalyl chloride (27.9 g, 0.22 mol) portion-wise. The reaction solution was stirred at 55° C. for 2 h. The mixture was concentrated in vacuo to give the crude 3-[(3-Bromo-benzyl)-(toluene-4-sulfonyl)-amino]-propionyl chloride (47.2 g, yield: 99%) as a black oil which was used in the next step without further purification.

5. Preparation of 8-Bromo-2-(toluene-4-sulfonyl)-1,2,3,4-tetrahydro-benzo[c]azepin-5-one

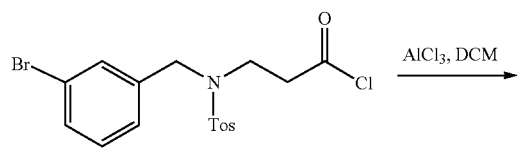

To a solution of 3-[(3-Bromo-benzyl)-(toluene-4-sulfonyl)-amino]-propionyl chloride (47.0 g, 0.11 mol) in anhydrous DCM (1200 mL) was added AlCl$_3$ (29.3 g, 0.22 mol) portion-wise at rt. The reaction mixture was stirred at 55° C. for 2 h. The reaction mixture was poured into ice water (1.2 L) and extracted with DCM (500 mL). The organic layer was concentrated in vacuo to give the crude product. The crude product was purified by column chromatography on silica gel (petroleum ether:EtOAc=5:1 to 2:1) to afford 8-bromo-2-(toluene-4-sulfonyl)-1,2,3,4-tetrahydro-benzo[c]azepin-5-one (35 g, yield: 81%) as a white solid. $^1$H NMR (DMSO-d$_6$, 300 MHz): δ 7.65 (d, J=8.4 Hz, 3H), 7.60-7.51 (m, 2H), 7.36 (d, J=8.1 Hz, 2H), 4.68 (s, 2H), 3.42 (t, J=9.2 Hz, 2H), 2.96 (t, J=6.3 Hz, 2H), 2.37 (s, 3H).

6. Preparation of [8-Bromo-2-(toluene-4-sulfonyl)-2,3,4,5-tetrahydro-1H-benzo[c]azepin-5-yl]-carbamic acid tert-butyl ester

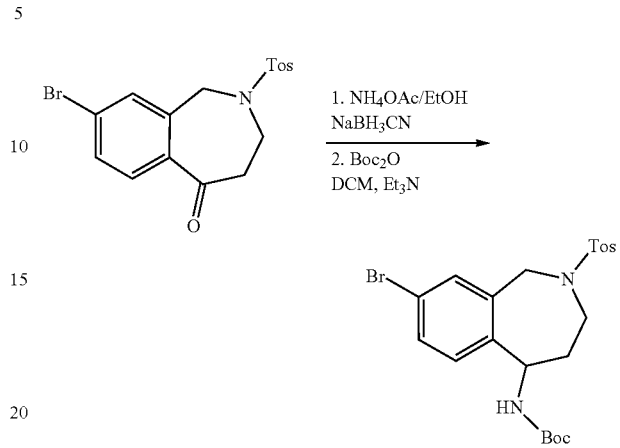

To a solution of 8-bromo-2-(toluene-4-sulfonyl)-1,2,3,4-tetrahydro-benzo[c]azepin-5-one (32.0 g, 0.08 mol) in EtOH (600 mL) were added NH$_4$OAc (18.5 g, 0.24 mol) and NaCNBH$_3$ (14.9 g, 0.24 mol) portion-wise at rt. Then the reaction mixture was stirred at 95° C. for 16 h. The mixture was poured into ice water (500 mL) and then EtOH was removed in vacuo. The residue was extracted with DCM (3×500 mL). The combined solvent was concentrated. The residue was redissolved in DCM (300 mL) and were added Et$_3$N (12.2 g, 0.12 mol) and (Boc)$_2$O (34.6 g, 0.12 mol) at rt. The mixture was stirred at rt for 4 h and then concentrated in vacuo to give the crude product. The crude product was purified by column chromatography on silica gel (peteroleum ether:EtOAc=8:1 to 2:1) to afford[8-bromo-2-(toluene-4-sulfonyl)-2,3,4,5-tetrahydro-1H-benzo[c]azepin-5-yl]-carbamic acid tert-butyl ester (16.7 g, yield: 42%) as a white solid. $^1$H NMR (DMSO_d$_6$, 300 MHz): δ 7.62-7.51 (m, 2H), 7.47 (d, J=9.9 Hz, 1H), 7.41-7.34 (m, 3H), 7.10 (d, J=8.4 Hz, 1H), 4.81-4.74 (m, 1H), 4.53 (d, J=15.0 Hz, 1H), 4.28 (d, J=15.3 Hz, 1H), 3.64-3.57 (m, 1H), 3.41-3.30 (m, 1H), 2.35 (s, 3H), 1.85-1.77 (m, 1H), 1.69-1.63 (m, 1H), 1.36 (s, 9H).

7. Preparation of 8-Bromo-2-(toluene-4-sulfonyl)-2,3,4,5-tetrahydro-1H-benzo[c]azepin-5-ylamine

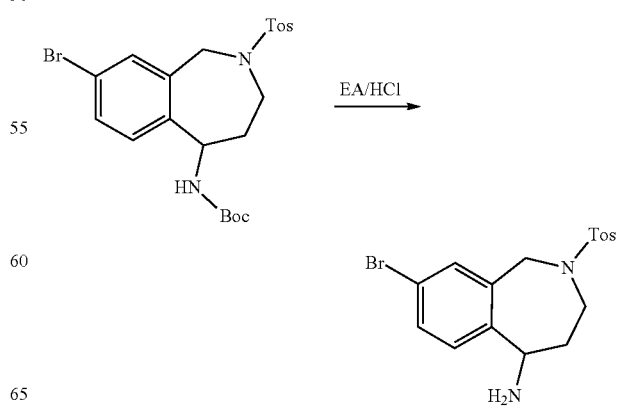

A solution of [8-bromo-2-(toluene-4-sulfonyl)-2,3,4,5-tetrahydro-1H-benzo[c]azepin-5-yl]-carbamic acid tert-butyl ester (14.8 g, 0.03 mol) in HCl/EtOAc (150 mL) was stirred at 25° C. for 4 h. The resulting solid was filtered and washed with MeOH and Et$_2$O to give the product 8-bromo-2-(toluene-4-sulfonyl)-2,3,4,5-tetrahydro-1H-benzo[c]azepin-5-ylamine (10.5 g, yield: 89%) as a white solid. $^1$H NMR (DMSO-d$_6$, 300 MHz): δ 8.79 (br, 3H), 7.64-7.58 (m, 3H), 7.53 (s, 1H), 7.36 (d, J=8.4 Hz, 2H), 7.15 (d, J=8.4 Hz, 1H), 4.71-4.61 (m, 2H), 4.31 (d, J=15.3 Hz, 1H), 3.82 (d, J=18.3 Hz, 1H), 2.38 (s, 3H), 2.14-2.07 (m, 1H), 1.77-1.71 (m, 1H). LC-MS: m/z 395.0/397.0 [M+H]$^+$.

8. Synthesis of 8-bromo-2,3,4,5-tetrahydro-1H-benzo[c]azepin-5-amine

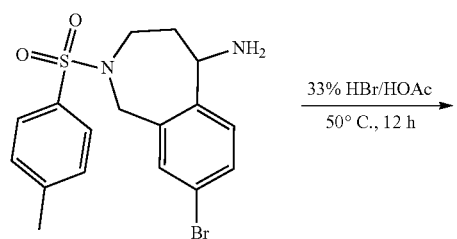

A solution of 8-bromo-2-(toluene-4-sulfonyl)-2,3,4,5-tetrahydro-1H-benzo[c]azepin-5-ylamine (2.00 g, 5.06 mmol) in HBr (33% solution in acetic acid, 20 mL) was heated at 50° C. for 12 h. After cooling to rt, the mixture was diluted EtOAc (50 mL). The white solid was collected by filtration and dried in vacuo to afford crude product 8-bromo-2,3,4,5-tetrahydro-1H-benzo[c]azepin-5-amine (1.66 g, yield: 82%), which was used directly in the next step. ESI-MS (M+H)$^+$241.1. $^1$H NMR (400 MHz, CD$_3$OD) δ: 7.72-7.55 (m, 2H), 7.18 (d, J=8.4 Hz, 1H), 4.99-4.98 (m, 1H), 4.51 (d, J=14.4 Hz, 1H), 4.39 (d, J=14.4 Hz, 1H), 3.62-3.49 (m, 2H), 2.38-2.24 (m, 1H), 2.16-2.00 (m, 1H).

9. Synthesis of tert-butyl 5-amino-8-bromo-4,5-dihydro-1H-benzo[c]azepine-2(3H)-carboxylate

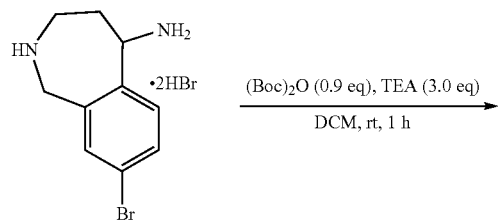

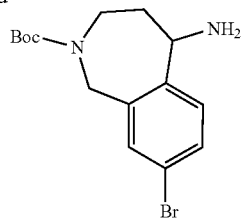

To a solution of 8-bromo-2,3,4,5-tetrahydro-1H-benzo[c]azepin-5-amine (640 mg, 1.60 mmol) and TEA (490 mg, 4.8 mmol) in DCM (20 mL) was added (Boc)$_2$O (314 mg, 1.44 mmol). The mixture was stirred at rt for 1 h. After diluting with DCM (100 mL), the mixture was washed with brine (20 mL×2). The organic phase was concentrated in vacuo and the residue was purified by prep-HPLC (CH$_3$CN/H$_2$O with 0.05% NH$_3$.H$_2$O as mobile phase) to give tert-butyl 5-amino-8-bromo-4,5-dihydro-1H-benzo[c]azepine-2(3H)-carboxylate as a colorless oil (364 mg, yield: 67%). ESI-MS (M+H)$^+$: 341.1.

10. Synthesis of tert-butyl 8-bromo-5-(3-isopropoxyazetidine-1-carboxamido)-4,5-dihydro-1H-benzo[c]azepine-2(3H)-carboxylate

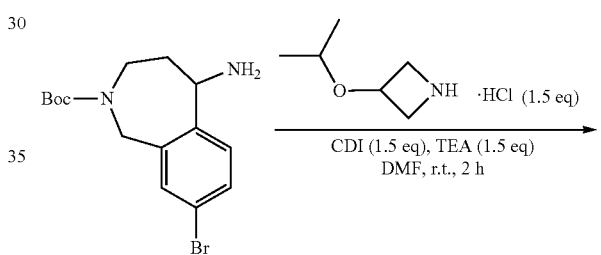

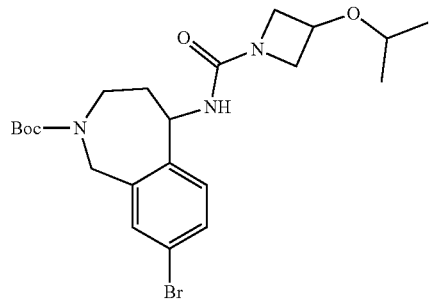

To a solution of tert-butyl 5-amino-8-bromo-4,5-dihydro-1H-benzo[c]azepine-2(3H)-carboxylate (300 mg, 0.90 mmol) in DMF (4 mL) was added TEA (138 mg, 1.35 mmol) and CDI (219 mg, 1.35 mmol). After stirring at rt for 1 h, 3-isopropoxyazetidine (204 mg, 1.35 mmol) was added to the solution. The resulting solution was stirred for another 1 h. The mixture was purified by prep-HPLC (CH$_3$CN/H$_2$O with 0.05% NH$_3$.H$_2$O as mobile phase) to give tert-butyl 8-bromo-5-(3-isopropoxyazetidine-1-carboxamido)-4,5-dihydro-1H-benzo[c]azepine-2-(3H)-carboxylate as white solid. (178 mg, yield: 42%). ESI-MS (M+H)+482.2.

11. Synthesis of Cert-butyl 5-(3-isopropoxyazetidine-1-carboxamido)-8-(2-((1-methyl-1H-pyrazol-4-yl)amino)pyrimidin-4-yl)-4,5-dihydro-1H-benzo[c]azepine-2(3H)-carboxylate

12. Synthesis of 3-isopropoxy-N-(8-(2-((1-methyl-1H-pyrazol-4-yl)amino)pyrimidin-4-yl)-2,3,4,5-tetrahydro-1H-benzo[c]azepin-5-yl)azetidine-1-carboxamide

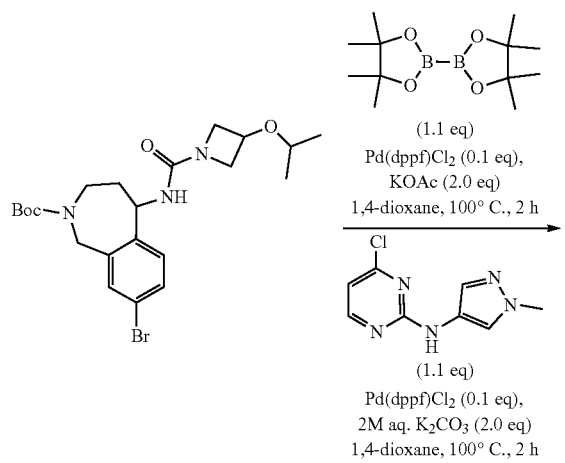

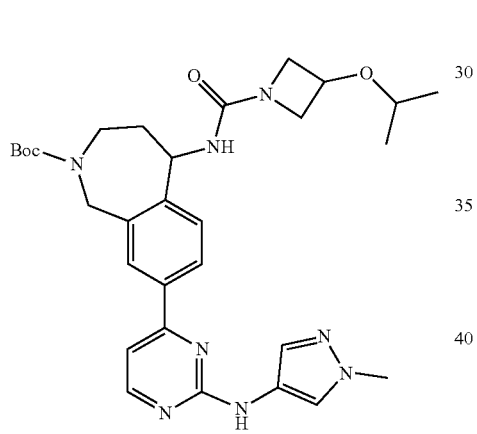

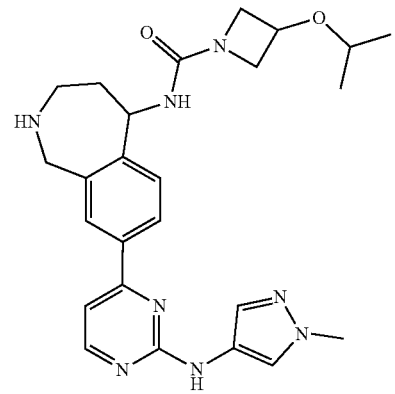

Synthesis of tert-butyl 5-(3-isopropoxyazetidine-1-carboxamido)-8-(2-((1-methyl-1H pyrazol-4-yl)amino)pyrimidin-4-yl)-4,5-dihydro-1H-benzo[c]azepine-2(3H)-carboxylate was similar to that of Example 157. The residue was purified by prep-HPLC (CH$_3$CN/H$_2$O with 0.05% NH$_3$.H$_2$O as mobile phase) to give tert-butyl 5-(3-isopropoxyazetidine-1-carboxamido)-8-(2-((1-methyl-1H pyrazol-4-yl)amino)pyrimidin-4-yl)-4,5-dihydro-1H-benzo[c]azepine-2(3H)-carboxylate (120 mg, yield: 60%) as white solid. ESI-MS (M+H)+577.3. $^1$H NMR (400 MHz, CD$_3$OD) δ: 8.43 (d, J=5.2 Hz, 1H), 8.11-7.98 (m, 3H), 7.67-7.64 (m, 1H), 7.49-7.45 (m, 1H), 7.25 (d, J=5.2 Hz, 1H), 5.27-5.24 (m, 1H), 4.78-4.74 (m, 1H), 4.50-4.45 (m, 2H), 4.29-4.22 (m, 2H), 3.96-3.85 (m, 6H), 3.74-3.68 (m, 1H), 3.38-3.33 (m, 1H), 2.00-1.91 (m, 2H), 1.44-1.31 (m, 9H), 1.20 (d, J=6.4 Hz, 6H).

tert-Butyl 5-(3-isopropoxyazetidine-1-carboxamido)-8-(2-((1-methyl-1H pyrazol-4-yl)amino)pyrimidin-4-yl)-4,5-dihydro-1H-benzo[c]azepine-2(3H)-carboxylate (120 mg, 0.21 mmol) was dissolved in TFA/DCM solution (1/1, 10 mL). The mixture was stirred at rt for 1 h. After concentration in vacuo, the residue was purified by prep-HPLC (CH$_3$CN/H$_2$O with 0.05% NH$_3$.H$_2$O as mobile phase) to give 3-isopropoxy-N-(8-(2-((1-methyl-1H-pyrazol-4-yl)amino)pyrimidin-4-yl)-2,3,4,5-tetrahydro-1H-benzo[c]azepin-5-yl)azetidine-1-carboxamide as brown solid (70 mg, yield: 71%). ESI-MS (M+H)+: 477.3. $^1$H NMR (400 MHz, CD$_3$OD) δ: 8.27 (d, J=5.2 Hz, 1H), 7.88 (dd, J=8.0, 1.4 Hz, 1H), 7.85 (s, 1H), 7.81 (s, 1H), 7.53 (s, 1H), 7.32 (d, J=8.0 Hz, 1H), 7.06 (d, J=5.6 Hz, 1H), 5.12 (d, J=9.2 Hz, 1H), 4.39-4.27 (m, 1H), 4.21-4.08 (m, 2H), 3.99-3.87 (m, 2H), 3.85-3.71 (m, 5H), 3.63-3.50 (m, 1H), 3.21-3.15 (m, 1H), 3.13-3.00 (m, 1H), 1.93-1.74 (m, 2H), 1.08 (d, J=6.0 Hz, 6H).

13. Synthesis of 3-isopropoxy-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)azetidine-1-carboxamide

Example 181: 3-isopropoxy-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)azetidine-1-carboxamide

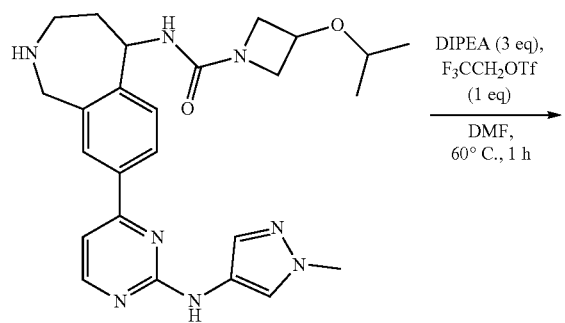
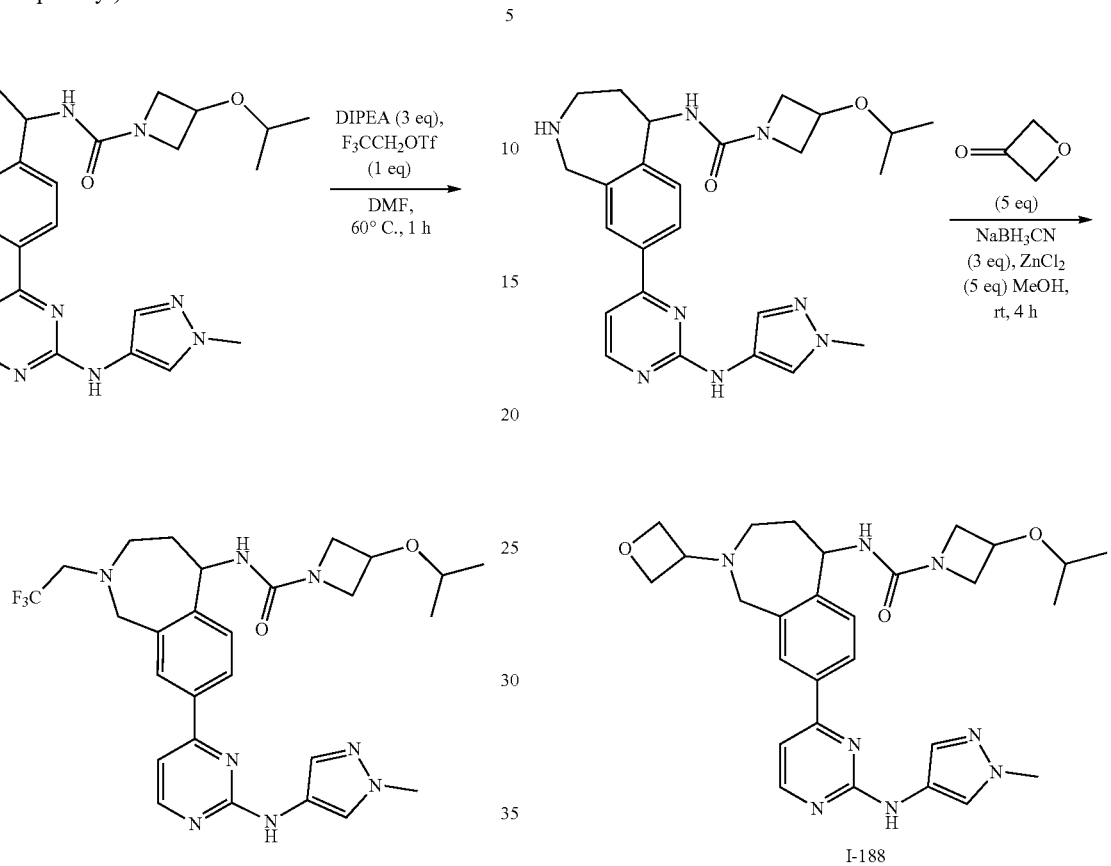

I-188

To a solution of 3-isopropoxy-N-(8-(2-((1-methyl-1H-pyrazol-4-yl)amino)pyrimidin-4-yl)-2,3,4,5-tetrahydro-1H-benzo[c]azepin-5-yl)azetidine-1-carboxamide (140 mg, 0.29 mmol) in DMF (6 mL) was added DIPEA (114 mg, 0.88 mmol) and 2,2,2-trifluoroethyl trifluoromethanesulfonate (69 mg, 0.29 mmol). The mixture was stirred at 60° C. for 1 h. After diluting with water (20 mL), the mixture was extracted with EtOAc (20 mL×3). The combined organic layers were washed with brine (20 mL×2), dried and concentrated in vacuo. The residue was purified by prep-HPLC (MeCN/Water with 0.05% NH$_4$OH) to give 3-isopropoxy-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)azetidine-1-carboxamide as a yellow solid (15 mg, yield: 9%). ESI-MS (M+H)$^+$: 559.3. $^1$H NMR (400 MHz, CD$_3$OD) δ: 8.30 (d, J=5.2 Hz, 1H), 7.92 (d, J=8.4 Hz, 1H), 7.88 (s, 1H), 7.82 (s, 1H), 7.50 (s, 1H), 7.33 (d, J=8.0 Hz, 1H), 7.10 (d, J=5.2 Hz, 1H), 5.09-5.07 (m, 1H), 4.37-4.32 (m, 1H), 4.20-4.08 (m, 3H), 3.96-3.93 (m, 1H), 3.78 (s, 3H), 3.76-3.71 (m, 2H), 3.59-3.56 (m, 1H), 3.28-3.25 (m, 1H), 3.17-3.15 (m, 1H), 2.98-2.90 (m, 2H), 1.96-1.87 (m, 1H), 1.72-1.69 (m, 1H), 1.07 (d, J=6.0 Hz, 6H).

To a mixture of 3-isopropoxy-N-(8-(2-((1-methyl-1H-pyrazol-4-yl)amino)pyrimidin-4-yl)-2,3,4,5-tetrahydro-1H-benzo[c]azepin-5-yl)azetidine-1-carboxamide (80 mg, 0.16 mmol) and oxetan-3-one (60 mg, 0.81 mmol) in MeOH (5 mL) was added zinc chloride (114 mg, 0.81 mmol) and NaBH$_3$CN (30 mg, 0.5 mmol). The mixture was stirred at rt for 4 h before addition of water (5 mL). After concentration, the residue was extracted with EtOAc (40 mL×2). The combined organic layers were washed with brine (120 mL×2), dried and concentrated in vacuo. The crude product was purified by prep-TLC (MeOH/EA=1/8) to give 3-isopropoxy-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)azetidine-1-carboxamide as a yellow solid (45 mg, yield: 45%). ESI-MS (M+H)$^+$: 533.2. $^1$H NMR (400 MHz, CD$_3$OD) δ: 8.35 (d, J=5.2 Hz, 1H), 7.97 (d, J=8.0 Hz, 1H), 7.92 (s, 1H), 7.86 (s, 1H), 7.56 (s, 1H), 7.36 (d, J=8.0 Hz, 1H), 7.16 (d, J=5.2 Hz, 1H), 5.13-5.10 (m, 1H), 4.69-4.66 (m, 1H), 4.61-4.54 (m, 3H), 4.42-4.37 (m, 1H), 4.21-4.13 (m, 2H), 3.83 (s, 3H), 3.82-3.76 (m, 3H), 3.73-3.68 (m, 2H), 3.64-3.61 (m, 1H), 2.97-2.94 (m, 1H), 2.80-2.74 (m, 1H), 1.98-1.93 (m, 1H), 1.89-1.83 (m, 1H), 1.12 (d, J=6.0 Hz, 6H).

Example 182: 3-(tert-butoxy)-N-(8-(2-((1-methyl-1H-pyrazol-4-yl)amino)pyrimidin-4-yl)-2,3,4,5-tetrahydrobenzo[b]oxepin-5-yl)azetidine-1-carboxamide

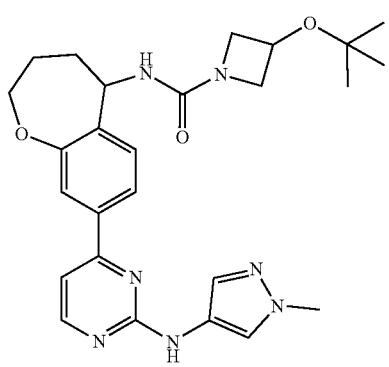

I-189

1. The preparation of methyl 4-(3-bromophenoxy)butanoate

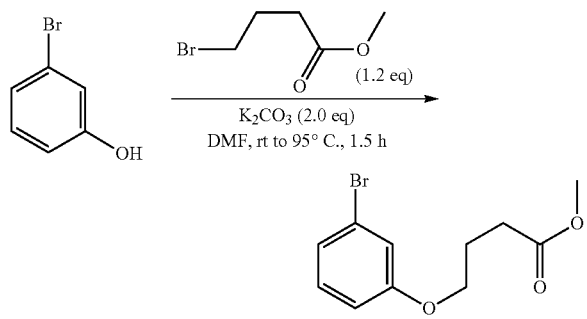

To a solution of 3-bromophenol (3.44 g, 20.0 mmol) and methyl 4-bromobutanoate (4.32 g, 24.0 mmol) in DMF (20 mL) was added K₂CO₃ (5.52 g, 40.0 mmol). The mixture was stirred at rt for 0.5 h and then heated with stirring at 90° C. for 1 h. After diluting with ethyl acetate (200 mL), the mixture was washed with water (50 mL×3), dried and concentrated in vacuo. The crude product was purified by silica gel column chromatography (petroleum ether: EtOAc/EA=10:1) to give methyl 4-(3-bromophenoxy)butanoate as a white liquid (5.2 g, yield: 96%). ESI-MS (M+H)⁺: 273.1.

2. The preparation of 4-(3-bromophenoxy)butanoic acid

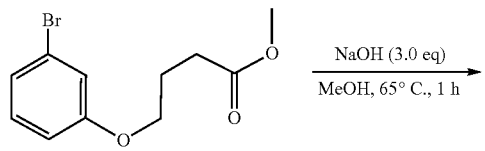

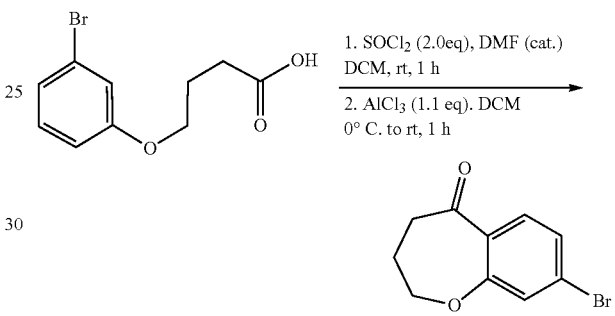

Synthesis of 4-(3-bromophenoxy)butanoic acid was similar to that of 3-[(3-bromo-benzyl)-(toluene-4-sulfonyl)-amino]-propionic acid. The crude product (4.8 g, yield: 98%) was used in next step without further purification. ESI-MS (M+H)⁺: 259.1. ¹H NMR (400 MHz, CDCl₃) δ: 7.24-7.20 (m, 1H), 7.10-7.08 (m, 2H), 6.93 (d, J=9.6 Hz, 1H), 3.97 (t, J=6.4 Hz, 2H), 2.35 (t, J=7.2 Hz, 2H), 1.92-1.88 (m, 2H).

3. The Preparation of 8-bromo-3,4-dihydrobenzo[b]oxepin-5(2H)-one

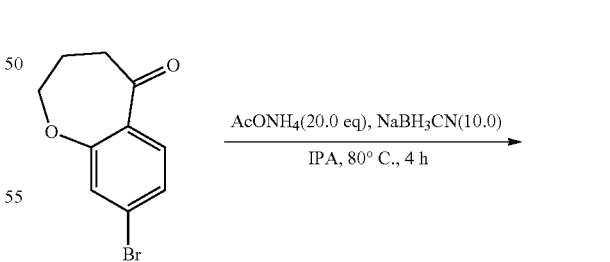

Synthesis of 8-bromo-3,4-dihydrobenzo[b]oxepin-5(2H)-one was similar to that of 8-bromo-2-(toluene-4-sulfonyl)-1,2,3,4-tetrahydro-benzo[c]azepin-5-one. The crude product was purified by silica gel column chromatography (petroleum ether:EtOAc=4:1) to give 8-bromo-3,4-dihydrobenzo[b]oxepin-5(2H)-one as a white solid (1.2 g, yield: 71%). ESI-MS (M+H)⁺: 241.1. ¹H NMR (400 MHz, CDCl₃) δ: 7.64 (d, J=8.8 Hz, 1H), 7.27-7.23 (m, 2H), 4.25 (t, J=6.8 Hz, 2H), 2.89 (t, J=7.2 Hz, 2H), 2.25-2.18 (m, 2H).

4. The preparation of 8-bromo-2,3,4,5-tetrahydrobenzo[b]oxepin-5-amine

Synthesis of 8-bromo-2,3,4,5-tetrahydrobenzo[b]oxepin-5-amine was similar to that of [8-Bromo-2-(toluene-4-sulfonyl)-2,3,4,5-tetrahydro-1H-benzo[c]azepin-5-yl]-carbamic acid tert-butyl ester. The crude product was purified by silica gel column chromatography to give the desired product as a white solid (900 mg, yield: 75%). ESI-MS (M+H)$^+$: 225.1.

5. The preparation of N-(8-bromo-2,3,4,5-tetrahydrobenzo[b]oxepin-5-yl)-3-(tert-butoxy)azetidine-1-carboxamide

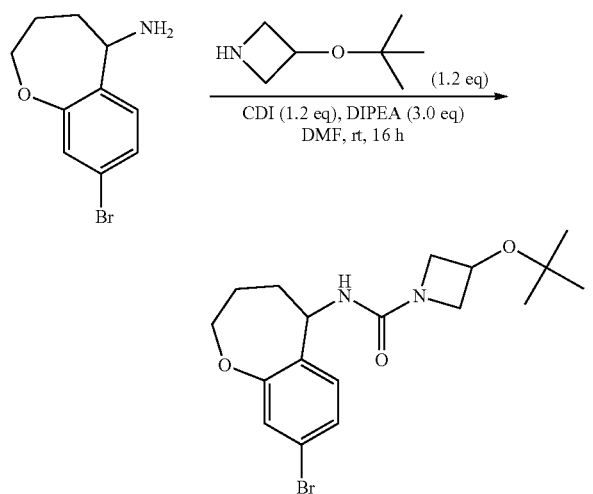

Synthesis of N-(8-bromo-2,3,4,5-tetrahydrobenzo[b]oxepin-5-yl)-3-(tert-butoxy)azetidine-1-carboxamide was similar to that of N-(2-bromo-6,7,8,9-tetrahydro-5H-benzo[7]annulen-5-yl)-3-isopropoxyazetidine-1-carboxamide. The crude product was purified by prep-HPLC (CH$_3$CN/H$_2$O with 0.05% NH$_4$OH as mobile phase) to give N-(8-bromo-2,3,4,5-tetrahydrobenzo[b]oxepin-5-yl)-3-(tert-butoxy)azetidine-1-carboxamide as a white solid (224 mg, yield: 50%). ESI-MS (M+H)$^+$: 397.0. $^1$H NMR (400 MHz, CDCl$_3$) δ: 7.15-7.12 (m, 3H), 5.06-5.03 (m, 1H), 4.77-4.74 (m, 1H), 4.44-4.41 (m, 1H), 4.34-4.31 (m, 1H), 4.09-4.04 (m, 2H), 3.81-3.69 (m, 3H), 2.22-2.11 (m, 2H), 1.84-1.61 (m, 2H), 1.16 (s, 9H).

6. The preparation of 3-(tert-butoxy)-N-(8-(2-((1-methyl-1H-pyrazol-4-yl)amino)pyrimidin-4-yl)-2,3,4,5-tetrahydrobenzo[b]oxepin-5-yl)azetidine-1-carboxamide

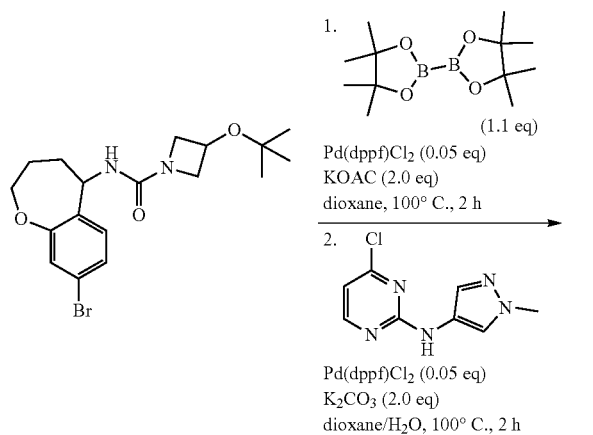

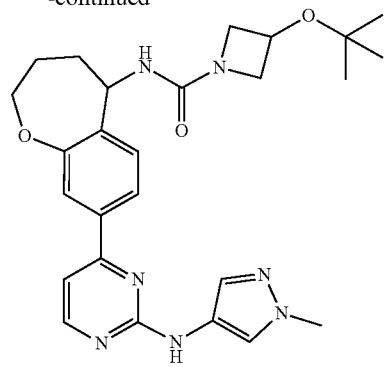

Synthesis of 3-(tert-butoxy)-N-(8-(2-((1-methyl-1H-pyrazol-4-yl)amino)pyrimidin-4-yl)-2,3,4,5-tetrahydrobenzo[b]oxepin-5-yl)azetidine-1-carboxamide was similar to that of Example 157. The residue was purified by prep-HPLC (CH$_3$CN/H$_2$O with 0.05% NH$_4$OH as mobile phase) to give 3-(tert-butoxy)-N-(8-(2-((1-methyl-1H-pyrazol-4-yl)amino)pyrimidin-4-yl)-2,3,4,5-tetrahydrobenzo[b]oxepin-5-yl)azetidine-1-carboxamide as a white solid (192 mg, yield: 69%). ESI-MS (M+H)$^+$: 492.0. $^1$H NMR (400 MHz, CD$_3$OD) δ: 8.29-8.28 (m, 1H), 7.85 (s, 1H), 7.73 (d, J=8.0 Hz, 1H), 7.63 (s, 1H), 7.53 (s, 1H), 7.28 (d, J=8.4 Hz, 1H), 7.07-7.05 (m, 1H), 5.00 (d, J=8.0 Hz, 1H), 4.51-4.46 (m, 1H), 4.18-4.06 (m, 3H), 3.78 (s, 3H), 3.74-3.68 (m, 3H), 2.00-1.87 (m, 3H), 1.81-1.72 (m, 1H), 1.10 (s, 9H).

Example 183: 3-(tert-butoxy)-N-(2-(2-hydroxyethyl)-4-(2-((1-methyl-1H-pyrazol-4-yl)amino)pyrimidin-4-yl)benzyl)azetidine-1-carboxamide

I-190

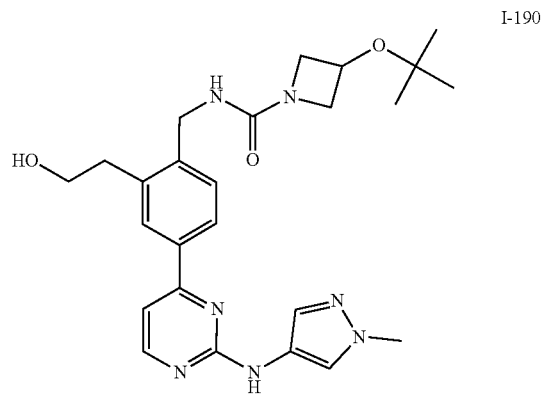

1. Synthesis of (E)-4-bromo-2-(2-(dimethylamino)vinyl)benzonitrile

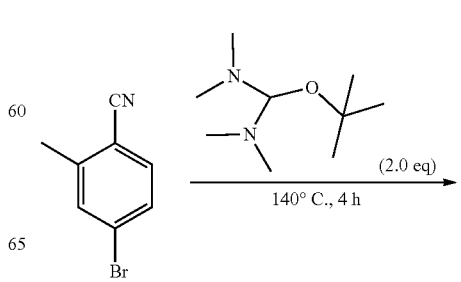

-continued

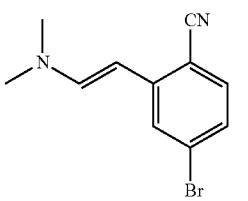

A solution of 4-bromo-2-methylbenzonitrile (3.92 g, 20.00 mmol) in 1-tert-butoxy-N,N,N',N'-tetramethylmethanediamine (8.2 mL, 40.00 mmol) was heated at 140° C. for 4 h. Then the reaction mixture was cooled down to rt and a yellow crystal precipitated. The solid was filtered off and washed with petroleum ether, then dried to give (E)-4-bromo-2-(2-(dimethylamino)vinyl)benzonitrile (4.16 g, yield: 83%) as a yellow solid. ESI-MS (M+H)$^+$: 251.0. $^1$H NMR (400 MHz, CD$_3$OD) δ: 7.69 (d, J=1.6 Hz, 1H), 7.33-7.28 (m, 2H), 7.05 (dd, J=8.4, 1.6 Hz, 1H), 5.22 (d, J=13.2 Hz, 1H), 2.94 (s, 6H).

2. Synthesis of 4-bromo-2-(2-oxoethyl)benzonitrile

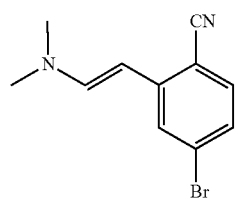

A mixture of (E)-4-bromo-2-(2-(dimethylamino)vinyl) benzonitrile (4.00 g, 0.10 mmol) in 4N acetic acid aqueous solution (30 mL) was stirred at rt for 4 h. Then the reaction mixture was filtered, and the cake was washed with water and dried to give compound 4-bromo-2-(2-oxoethyl)benzonitrile (3.30 g, yield: 92%) as a white solid. ESI-MS (M+H)$^+$: 223.9.

3. Synthesis of 2-(2-(aminomethyl)-5-bromophenyl)ethanol

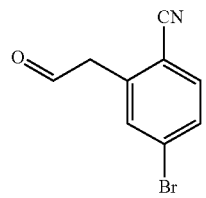

-continued

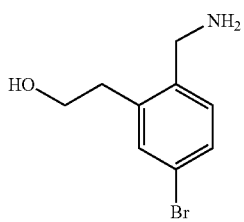

Synthesis of 2-(2-(aminomethyl)-5-bromophenyl)ethanol was similar to that of (4-bromo-2-methylphenyl)methanamine. Crude product 2-(2-(aminomethyl)-5-bromophenyl)ethanol (2.05 g, yield: 100%) was obtained as as a white solid. ESI-MS (M+H)$^+$: 230.0.

4. Synthesis of Cert-butyl 4-bromo-2-(2-((tert-butyldimethylsilyl)oxy)ethyl)benzylcarbamate

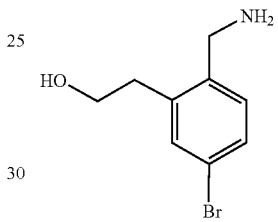

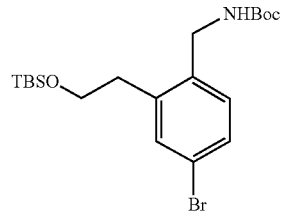

To a solution of 2-(2-(aminomethyl)-5-bromophenyl) ethanol (2.56 g, 11.2 mmmol) in DCM (30 mL) were added Boc$_2$O (3.66 g, 16.8 mmol, 1.5 equiv) and TEA (3.4 g, 33.6 mmol, 3 equiv). The mixture was stirred at rt for 1 h. The solvent was removed in vacuo. The crude was dissolved in EtOAc (60 mL), washed with water (30 mL×2), and brine (30 mL×2). The organic layer was dried and concentrated in vacuo. The residue was dissolved in THF (50 mL) and treated with TBSCl (2.38 g, 16 mmol, 1.5 equiv), DIPEA (4 g, 31.8 mmol, 2 equiv) and DMAP (129 mg, 1 mmol, 0.1 equiv). The mixture was stirred at rt for 16 h, diluted with EtOAc (100 mL), and washed with water (60 mL×2) and brine (60 mL×2). The organic layer was dried and concentrated in vacuo to give tert-butyl 4-bromo-2-(2-((tert-butyldimethylsilyl)oxy)ethyl)benzylcarbamate as a yellow oil (4.5 g, 85% purity, and total yield: 80%). ESI-MS (M+H)$^+$: 444.1. $^1$H NMR (400 MHz, CDCl$_3$) δ: 7.70 (s, 1H), 7.68 (d, J=7.6 Hz, 1H), 7.34 (d, J=7.6 Hz, 1H), 5.16 (br, 1H), 4.41 (d, J=5.2 Hz, 2H), 3.91 (t, J=6.4 Hz, 2H), 2.93 (t, J=6.4 Hz, 2H), 1.51 (s, 9H), 0.87 (s, 9H), 0.001 (s, 6H).

5. Synthesis of tert-butyl 2-(2-((tert-butyldimethyl-silyl)oxy)ethyl)-4-(2-((1-methyl-1H-pyrazol-4-yl)amino)pyrimidin-4-yl)benzylcarbamate

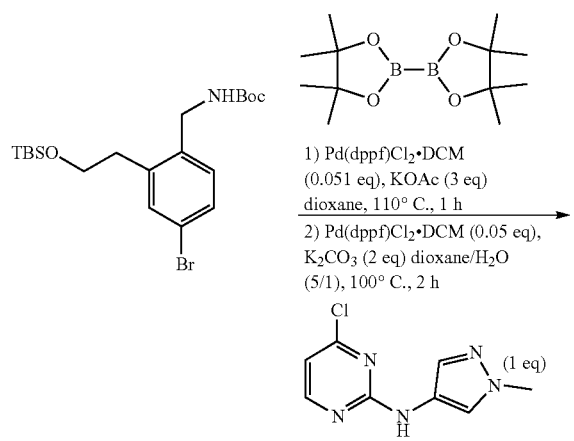

To a solution of tert-butyl 4-bromo-2-(2-((tert-butyldimethylsilyl)oxy)ethyl) benzylcarbamate (1 g, 2.26 mmmol) in dioxane (15 mL) was added 4,4,4',4',5,5,5',5'-octamethyl-2,2'-bi(1,3,2-dioxaborolane) (635 mg, 2.5 mmol, 1.1 equiv), Pd(dppf)Cl$_2$DCM (92 mg, 0.11 mmol, 0.05 equiv) and KOAc (664 mg, 6.78 mmol, 3 equiv). The mixture was heated to 110° C. for 1 h under an atmosphere of nitrogen. After cooling to rt, 4-chloro-N-(1-methyl-1H-pyrazol-4-yl)pyrimidin-2-amine (472 mg, 2.26 mmol, 1.0 equiv), Pd(dppf)Cl$_2$DCM (92 mg, 0.11 mmol, 0.05 equiv), K$_2$CO$_3$ (623 mg, 4.52 mmol, 2 equiv) and water (4 mL) were added. The mixture was heated to 100° C. for 2 h. The mixture was cooled to rt and filtered through a Celite pad. The filtrate was concentrated in vacuo and the residue was purified by silica gel column chromatography (EtOAc; petroleum ether=1/1) to give tert-butyl 2-(2-((tert-butyldimethylsilyl)oxy)ethyl)-4-(2-((1-methyl-1H-pyrazol-4-yl)amino)pyrimidin-4-yl) benzylcarbamate as a yellow solid (320 mg, total yield: 26%). ESI-MS (M+H)$^+$: 539.1.

6. Synthesis of 4-(4-(aminomethyl)-3-(2-((tert-butyldimethylsilyl)oxy)ethyl)phenyl)-N-(1-methyl-1H-pyrazol-4-yl)pyrimidin-2-amine

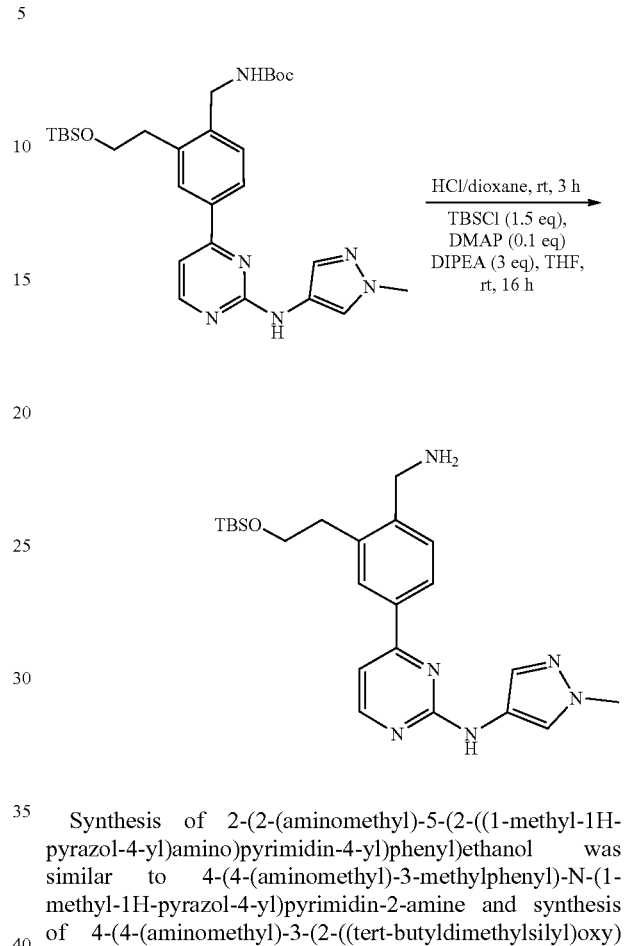

Synthesis of 2-(2-(aminomethyl)-5-(2-((1-methyl-1H-pyrazol-4-yl)amino)pyrimidin-4-yl)phenyl)ethanol was similar to 4-(4-(aminomethyl)-3-methylphenyl)-N-(1-methyl-1H-pyrazol-4-yl)pyrimidin-2-amine and synthesis of 4-(4-(aminomethyl)-3-(2-((tert-butyldimethylsilyl)oxy)ethyl)phenyl)-N-(1-methyl-1H-pyrazol-4-yl)pyrimidin-2-amine was similar to that of tert-butyl 4-bromo-2-(2-((tert-butyldimethylsilyl)oxy)ethyl)benzylcarbamate. The crude was purified by prep-(MeCN/Water with 0.05% NH$_4$OH as mobile phase) to give 4-(4-(aminomethyl)-3-(2-((tert-butyldimethylsilyl)oxy)ethyl)phenyl)-N-(1-methyl-1H-pyrazol-4-yl)pyrimidin-2-amine as a yellow solid (77 mg, total yield: 29%). ESI-MS (M+H)$^+$: 439.2.

7. Synthesis of 3-(tert-butoxy)-N-(2-(2-hydroxyethyl)-4-(2-((1-methyl-1H-pyrazol-4-yl)amino)pyrimidin-4-yl)benzyl)azetidine-1-carboxamide

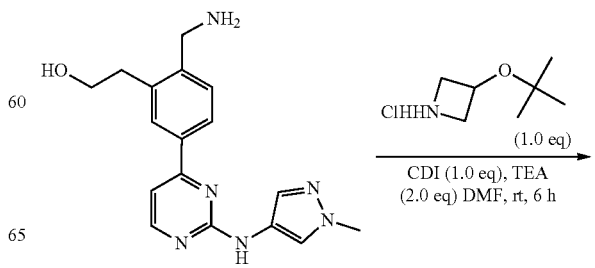

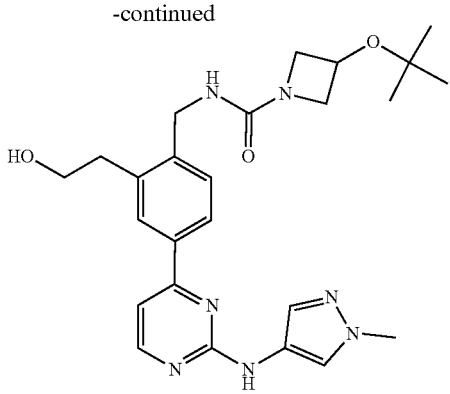

Synthesis of 3-(tert-butoxy)-N-(2-(2-hydroxyethyl)-4-(2-((1-methyl-1H-pyrazol-4-yl)amino)pyrimidin-4-yl)benzyl) azetidine-1-carboxamide was similar to that of Example 19. The reaction product was purified by prep-HPLC (CH$_3$CN/ H$_2$O with 0.05% NH$_4$OH as mobile phase) to give 3-(tert-butoxy)-N-(2-(2-hydroxyethyl)-4-(2-((1-methyl-1H-pyrazol-4-yl)amino)pyrimidin-4-yl)benzyl)azetidine-1-carboxamide as a yellow solid (75 mg, yield: 42%). ESI-MS (M+H)$^+$: 480.3. $^1$H NMR (400 MHz, CD$_3$OD) δ: 8.40 (d, J=5.2 Hz, 1H), 8.04 (d, J=1.2 Hz, 1H), 8.02 (s, 1H), 7.94 (dd, J=8.0 Hz, 1.2 Hz, 1H), 7.63 (s, 1H), 7.43 (d, J=8.0 Hz, 1H), 7.21 (d, J=5.2 Hz, 1H), 4.60-4.54 (m, 1H), 4.45 (s, 2H), 4.17-4.13 (m, 2H), 3.90 (s, 3H), 3.87 (t, J=6.8 Hz, 2H), 3.78-3.75 (m, 2H), 3.00 (t, J=6.4 Hz, 2H), 1.19 (s, 9H).

Example 184: 1-(tert-butyl)-N-(2-(2-hydroxyethyl)-4-(2-((1-methyl-1H-pyrazol-4-yl)amino)pyrimidin-4-yl)benzyl)-1H-pyrazole-4-carboxamide

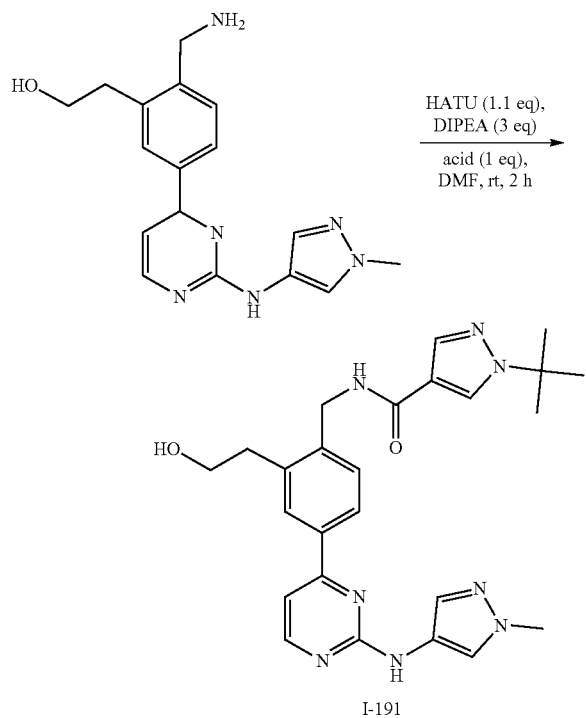

I-191

Synthesis of 1-(tert-butyl)-N-(2-(2-hydroxyethyl)-4-(2-((1-methyl-1H-pyrazol-4-yl)amino)pyrimidin-4-yl)benzyl)- 1H-pyrazole-4-carboxamide was similar to that of Example 1. The reaction product was purified through silica gel column chromatography (MeOH/EA=1/10) to give 1-(tert-butyl)-N-(2-(2-hydroxyethyl)-4-(2-((1-methyl-1H-pyrazol-4-yl)amino)pyrimidin-4-yl)benzyl)-1H-pyrazole-4-carboxamide as a yellow solid (40 mg, yield: 40%). ESI-MS (M+H)$^+$: 475.2. $^1$H NMR (400 MHz, CD$_3$OD) δ: 8.40 (d, J=5.2 Hz, 1H), 8.26 (s, 1H), 8.08 (s, 1H), 8.01 (s, 1H), 7.96-7.94 (m, 2H), 7.63 (s, 1H), 7.46 (d, J=8.0 Hz, 1H), 7.22 (d, J=5.2 Hz, 1H), 4.67 (s, 2H), 3.92-3.88 (m, 5H), 3.06 (t, J=6.8 Hz, 2H), 1.60 (s, 9H).

Example 185: 1-(tert-butyl)-5-(2-methyl-4-(2-((1-methyl-1H-pyrazol-4-yl)amino)pyrimidin-4-yl)benzyl)-6,7-dihydro-1H-pyrazolo[4,3-c]pyridin-4(5H)-one

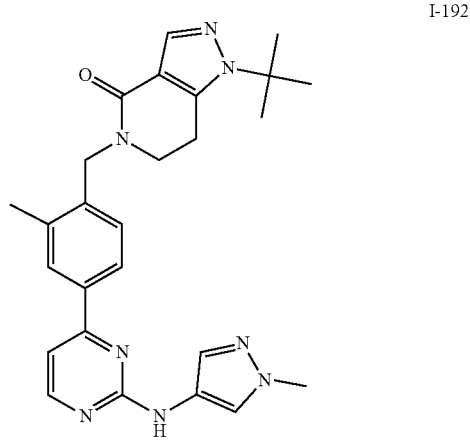 [SMILES: Cc1cc(-c2ccnc(Nc3cnn(C)c3)n2)ccc1CN1CCc2c(cnn2C(C)(C)C)C1=O]

I-192

1. Synthesis of methyl 5-(2-((tert-butoxycarbonyl)amino)ethyl)-1-(tert-butyl)-1H-pyrazole-4-carboxylate

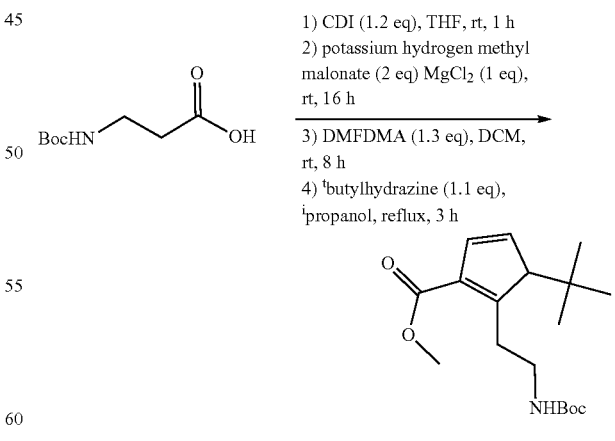

1) CDI (1.2 eq), THF, rt, 1 h
2) potassium hydrogen methyl malonate (2 eq) MgCl$_2$ (1 eq), rt, 16 h
3) DMFDMA (1.3 eq), DCM, rt, 8 h
4) $^t$butylhydrazine (1.1 eq), $^i$propanol, reflux, 3 h To a solution of CDI (972 mg, 6.0 mmol) in THF (18 mL) was added N-Boc-3-aminylpropanoic acid (945 mg, 5 mmol). The mixture was stirred at rt for 1 h. Then a well homogenized and powdered solid mixture of MgCl$_2$ (475 mg, 5 mmol) and potassium hydrogen methyl malonate (1.56 g, 10 mmol) were added. The mixture was stirred at rt for 16 h. The solvent was removed and the crude was dissolved in EtOAc (80 mL), washed with KHSO₄ (1M, 20 mL×2) and brine (20 mL). The organic layer was dried and concentrated in vacuo. The crude product was dissolved in DCM (16 mL) and DMF-DMA (773 mg, 6.5 mmol) was added. The mixture was stirred at rt for 6 h. The solvent was removed and the crude material was dissolved in isopropanol (10 mL) and treated with tertbutylhydrazine (682 mg, 5.5 mmol). The mixture was stirred at reflux for 3 h. After cooling to rt, the solvent was removed. The crude was dissolved in EtOAc (60 mL), washed with brine (20 mL×2). The organic layer was dried and concentrated in vacuo. The crude was purified by silica gel column chromatography (EtOAc/petroleum ether=1/4) to give methyl 5-(2-((tert-butoxycarbonyl) amino)ethyl)-1-(tert-butyl)-1H-pyrazole-4-carboxylate as yellow oil (250 mg, three steps yield: 15%). ESI-MS (M+H)⁺: 326.2.

2. Synthesis of 5-(4-bromo-2-methylbenzyl)-1-(tert-butyl)-6,7-dihydro-1H-pyrazolo[4,3-c]pyridin-4(5H)-one

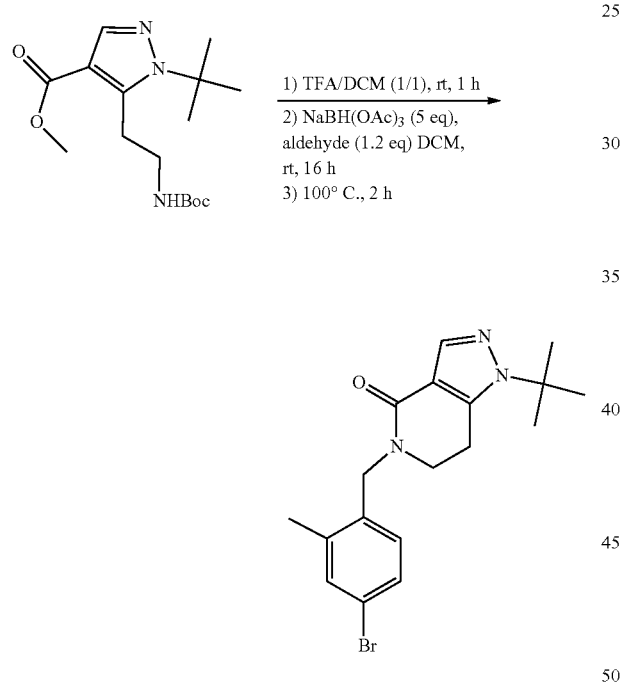

To a solution of methyl 5-(2-((tert-butoxycarbonyl) amino)ethyl)-1-(tert-butyl)-1H-pyrazole-4-carboxylate (500 mg, 1.54 mmol) in DCM (4 mL) was added TFA (4 mL). The mixture was stirred at rt for 1 h. The mixture was concentrated, the crude was dissolved in CH₂Cl₂ (10 mL) and 4-bromo-2-methylbenzaldehyde (370 mg, 1.87 mmol) was added. The mixture was stirred at rt for 10 min, then sodium triacetoxyborohydride (1.63 g, 7.7 mmol) was added. The mixture was stirred at rt for 16 h, diluted with DCM (60 mL), washed with brine and dried over Na₂SO₄, filtered and concentrated in vacuo to afford a crude residue which was was heated to 100° C. for 2 h. The residue was purified by prep-HPLC (CH₃CN/H₂O with 0.05% NH₄OH as mobile phase) to give 5-(4-bromo-2-methylbenzyl)-1-(tert-butyl)-6,7-dihydro-1H-pyrazolo[4,3-c]pyridin-4(5H)-one as a white solid (116 mg, yield: 20%). ESI-MS (M+H)⁺: 376.1.

3. Synthesis of 1-(tert-butyl)-5-(2-methyl-4-(2-((1-methyl-1H-pyrazol-4-yl)amino)pyrimidin-4-yl)benzyl)-6,7-dihydro-1H-pyrazolo[4,3-c]pyridin-4(5H)-one

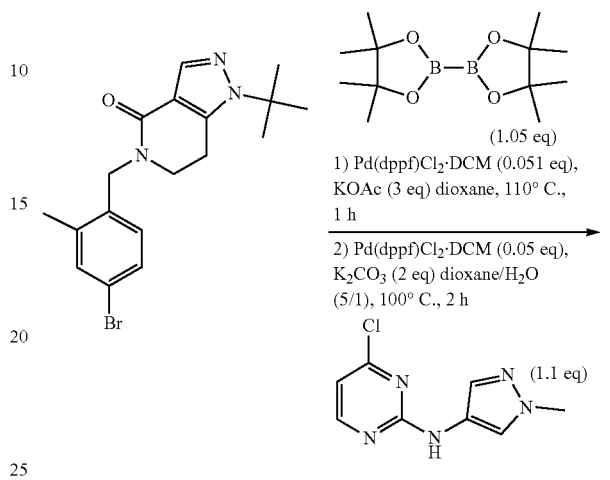

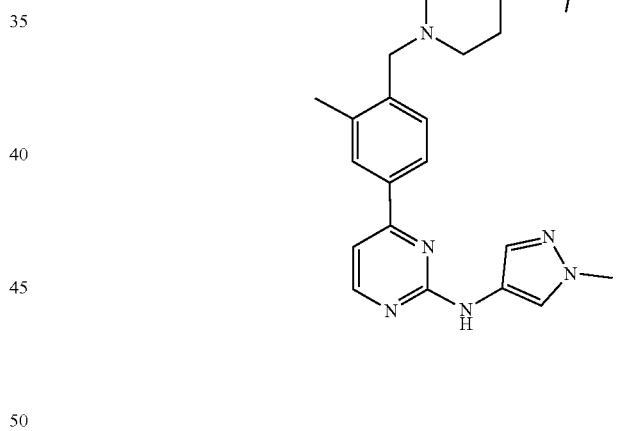

Synthesis of 1-(tert-butyl)-5-(2-methyl-4-(2-((1-methyl-1H-pyrazol-4-yl)amino)pyrimidin-4-yl)benzyl)-6,7-dihydro-1H-pyrazolo[4,3-c]pyridin-4(5H)-one was similar to that of Example 13. The reaction produce was purified through silica gel column chromatography (MeOH/DCM=1/15) to give 1-(tert-butyl)-5-(2-methyl-4-(2-((1-methyl-1H-pyrazol-4-yl)amino)pyrimidin-4-yl)benzyl)-6,7-dihydro-1H-pyrazolo[4,3-c]pyridin-4(5H)-one as a yellow solid (80 mg, yield: 55%). ESI-MS (M+H)⁺: 471.3. ¹H NMR (400 MHz, CD₃OD) δ: 8.41 (d, J=5.2 Hz, 1H), 7.99-7.95 (m, 3H), 7.80 (s, 1H), 7.64 (s, 1H), 7.36 (d, J=8.0 Hz, 1H), 7.21 (d, J=5.2 Hz, 1H), 4.80 (s, 2H), 3.89 (s, 3H), 3.60 (t, J=6.8 Hz, 2H), 3.25 (t, J=6.8 Hz, 2H), 2.44 (s, 3H), 1.64 (s, 9H).

Example 186: 1-(tert-butyl)-N-(4-(6-((5,6-dihydro-4H-pyrrolo[1,2-b]pyrazol-2-yl)amino)pyrimidin-4-yl)-2-methylbenzyl)-1H-pyrazole-4-carboxamide

I-193

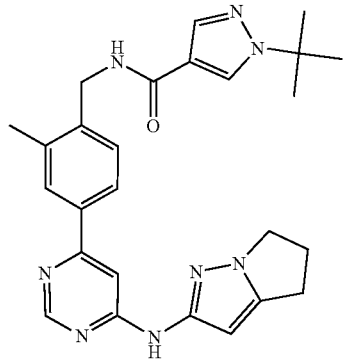

1. The preparation of (4-(6-chloropyrimidin-4-yl)-2-methylphenyl)methanamine

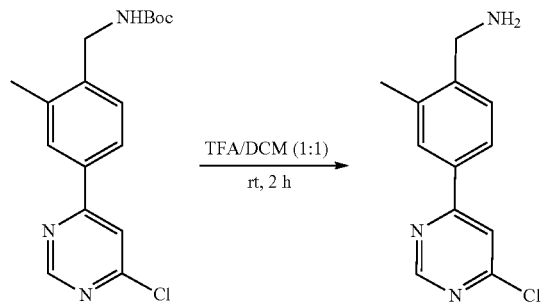 [SMILES: Cc1cc(-c2cc(Cl)ncn2)ccc1CNC(=O)OC(C)(C)C ; Cc1cc(-c2cc(Cl)ncn2)ccc1CN]

A mixture of tert-butyl 4-(6-chloropyrimidin-4-yl)-2-methylbenzylcarbamate (240 mg, 0.72 mmol) in TFA/DCM (8 mL, 1:1) was stirred at rt for 1 h. Then the solvent was removed in vacuo and the crude product (150 mg, yield: 89%) was used in the next step without further purification.

2. The preparation of 1-(tert-butyl)-N-(4-(6-chloropyrimidin-4-yl)-2-methylbenzyl)-1H-pyrazole-4-carboxamide

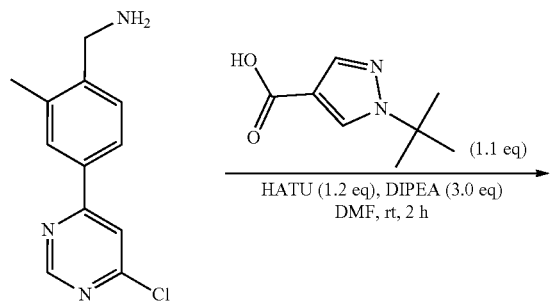

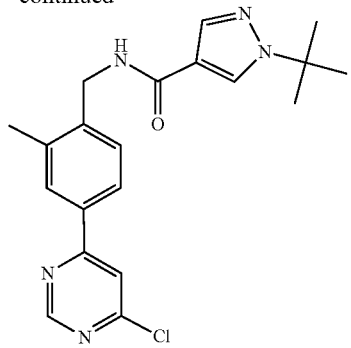

To a solution of (4-(6-chloropyrimidin-4-yl)-2-methylphenyl)methanamine (150 mg, 0.64 mmol) and acid (118 mg, 0.70 mmol) in DMF (5 mL) were added HATU (292 mg, 0.77 mmol) and DIPEA (247 mg, 1.92 mmol). The mixture was stirred at rt for 2 h. After diluting with water (60 mL), the mixture was extracted with EtOAc (80 mL×2). The combined organic layers were dried and concentrated in vacuo to afford a crude product which was purified by silica gel column chromatography (petroleum ether:EtOAc=1:2) to give 1-(tert-butyl)-N-(4-(6-chloropyrimidin-4-yl)-2-methylbenzyl)-1H-pyrazole-4-carboxamide as a white solid (230 mg, yield: 93%). ESI-MS (M+H)$^+$: 384.1.

3. The Preparation of 5,6-dihydro-4H-pyrrolo[1,2-c][1,2,3]oxadiazol-7-ium-3-olate

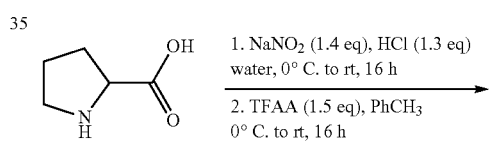

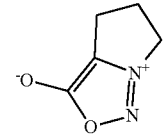

To a solution of pyrrolidine-2-carboxylic acid (17.2 g, 150 mmol) and sodium nitrite (14.5 g, 210 mmol) in water (100 mL) was slowly added HCl (7.6 g, 200 mmol) at 0° C. The mixture was stirred at rt for 16 h, diluted with water (100 mL), and extracted with diethyl ether (100 mL×2). The combined organic phase was dried and concentrated in vacuo to afford a residue which was taken up in PhCH$_3$ (50 mL). The solution was treated with trifluoroacetic anhydride (47.3 g, 230 mmol) and stirred at rt for 16 h. The mixture was concentrated and the crude product was purified by silica gel column chromatography (DCM/MeOH=10:1) to give 5,6-dihydro-4H-pyrrolo[1,2-c][1,2,3]oxadiazol-7-ium-3-olate as a brown liquid (17.0 g, yield: 90%). ESI-MS (M+H)$^+$: 127.1.

4. The preparation of methyl 5,6-dihydro-4H-pyrrolo[1,2-c]pyrazole-2-carboxylate and methyl 5,6-dihydro-4H-pyrrolo[1,2-b]pyrazole-3-carboxylate

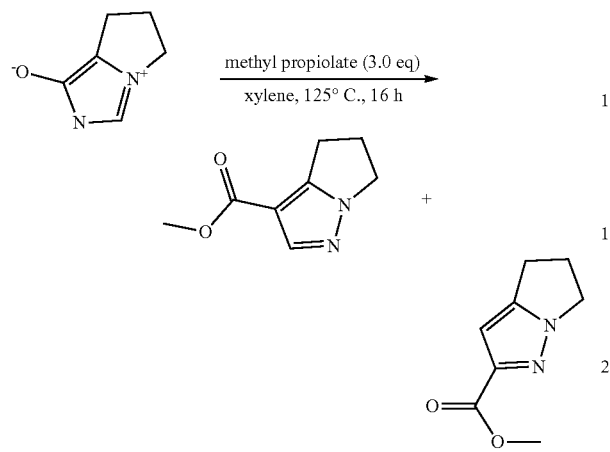

To a solution of 5,6-dihydro-4H-pyrrolo[1,2-c][1,2,3]oxadiazol-7-ium-3-olate (9.4 g, 75 mmol) in xylene (150 mL) was added methyl propiolate (18.9 g, 225 mmol). The mixture was stirred at 125° C. for 16 h. After concentration, the crude product was purified by silica gel column chromatography (petroleum ether:EtOAc=5:1) to give a mixture of methyl 5,6-dihydro-4H-pyrrolo[1,2-b]pyrazole-2-carboxylate and methyl 5,6-dihydro-4H-pyrrolo[1,2-b]pyrazole-3-carboxylate as a yellow liquid (7.9 g, yield: 35%). ESI-MS (M+H)$^+$: 167.1.

5. The preparation of 5,6-dihydro-4H-pyrrolo[1,2-h]pyrazole-2-carboxylic acid and 5,6-dihydro-4H-pyrrolo[1,2-h]pyrazole-3-carboxylic acid

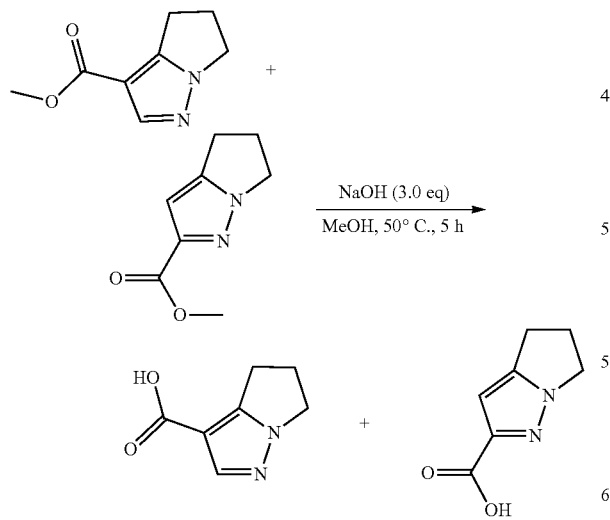

To a solution of methyl 5,6-dihydro-4H-pyrrolo[1,2-b]pyrazole-2-carboxylate and methyl 5,6-dihydro-4H-pyrrolo[1,2-b]pyrazole-3-carboxylate (3.5 g, 21.0 mmol) in MeOH (50 mL) was added NaOH (2.5 g, 63.0 mmol) and stirred at 50° C. for 5 h. Water (50 mL) was added, the mixture was adjusted to pH=6 with concentrated HCl, extracted with EtOAc (100 mL×2), dried and concentrated in vacuo to afford the crude product (2.2 g, yield: 69%) which was used in the next step without further purification. $^1$H NMR (400 MHz, CDCl$_3$) δ: 7.90 (s, 1H), 3.09 (t, J=7.2 Hz, 2H), 2.47 (t, J=7.2 Hz, 2H), 2.22-2.15 (m, 2H).

6. The preparation of ethyl (5,6-dihydro-4H-pyrrolo[1,2-b]pyrazol-3-yl)carbamate and ethyl (5,6-dihydro-4H-pyrrolo[1,2-b]pyrazol-2-yl)carbamate

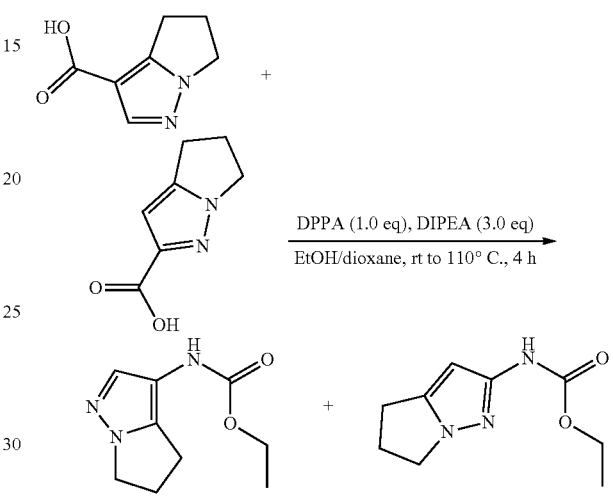

To a solution of the above mixture (1.0 g, 6.6 mmol) in dioxane (20 mL) was added DIPEA (2.5 g, 19.8 mmol) and DPPA (1.8 g, 6.6 mmol) and stirred at rt for 2 h. EtOH (10 mL) was added and the mixture was heated to 110° C. for 2 h. The solvent was removed in vacuo, the crude product was purified by silica gel column chromatography (petroleum ether:EtOAc=1:3) to give a white solid. The solid was suspended in MeOH (15 mL), filtered, and the filtrate was concentrated in vacuo to give (5,6-dihydro-4H-pyrrolo[1,2-b]pyrazol-3-yl)carbamate (300 mg, yield: 23%) as a white solid. The white precipitate is ethyl (5,6-dihydro-4H-pyrrolo[1,2-b]pyrazol-2-yl)carbamate (120 mg, yield: 9%). ESI-MS (M+H)$^+$: 196.1.

7. The Preparation of 5,6-dihydro-4H-pyrrolo[1,2-b]pyrazol-3-amine

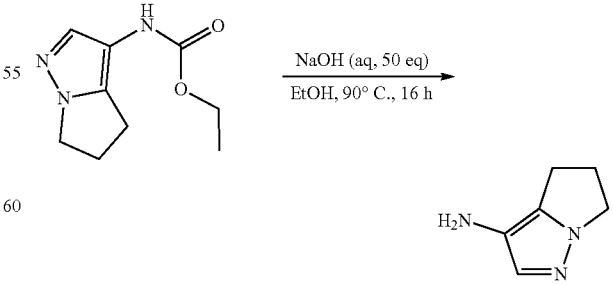

To a solution of ethyl (5,6-dihydro-4H-pyrrolo[1,2-b]pyrazol-3-yl)carbamate (130 mg, 0.67 mmol) in EtOH (20 mL) was added NaOH (1.3 g, 33.3 mmol). The mixture was stirred at 90° C. for 16 h. After concentration, the mixture was dissolved in water (50 mL) and extracted with DCM (50 mL×2). The combined organic layers were dried, concentrated in vacuo to afford the crude product (31 mg, yield: 33%) which was used in the next step without further purification. ¹H NMR (400 MHz, CDCl₃) δ: 7.18 (s, 1H), 4.06 (t, J=7.2 Hz, 2H), 2.80 (t, J=7.2 Hz, 2H), 2.60-2.53 (m, 2H).

8. The Preparation of 5,6-dihydro-4H-pyrrolo[1,2-b]pyrazol-2-amine

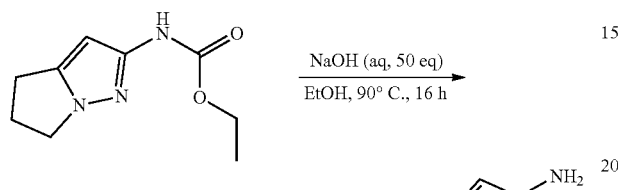

Synthesis of 5,6-dihydro-4H-pyrrolo[1,2-b]pyrazol-2-amine was similar to that of 5,6-dihydro-4H-pyrrolo[1,2-b]pyrazol-3-amine. The crude product (85 mg, yield: 90%) was used in the next step without further purification.

9. The Preparation of 1-(tert-butyl)-N-(4-(6-((5,6-dihydro-4H-pyrrolo[1,2-b]pyrazol-2-yl)amino)pyrimidin-4-yl)-2-methylbenzyl)-1H-pyrazole-4-carboxamide

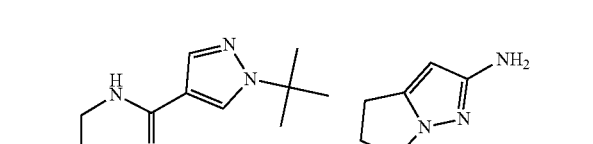

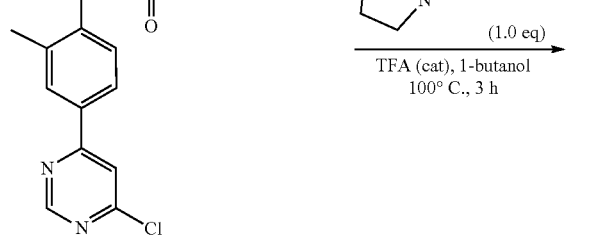

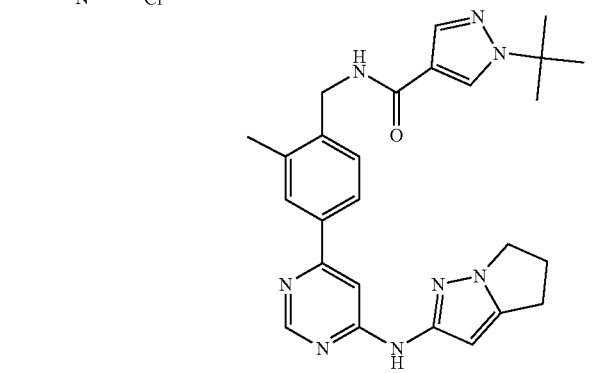

Synthesis of 1-(tert-butyl)-N-(4-(6-((5,6-dihydro-4H-pyrrolo[1,2-b]pyrazol-2-yl)amino)pyrimidin-4-yl)-2-methylbenzyl)-1H-pyrazole-4-carboxamide was similar to that of Example 171. The crude product was purified by prep-HPLC (CH₃CN/H₂O with 0.05% NH₄OH as mobile phase) to give 1-(tert-butyl)-N-(4-(6-((5,6-dihydro-4H-pyrrolo[1,2-b]pyrazol-2-yl)amino)pyrimidin-4-yl)-2-methylbenzyl)-1H-pyrazole-4-carboxamide as a white solid (30 mg, yield: 41%). ESI-MS (M+H)⁺: 471.2. ¹H NMR (400 MHz, CD₃OD) δ: 8.47 (s, 1H), 8.17 (s, 1H), 7.87 (s, 1H), 7.69 (s, 1H), 7.65 (d, J=8.0 Hz, 1H), 7.38 (s, 1H), 7.31 (d, J=8.0 Hz, 1H), 6.04 (s, 1H), 4.48 (s, 2H), 3.99 (t, J=7.2 Hz, 2H), 2.83 (t, J=7.2 Hz, 2H), 2.50-2.46 (m, 2H), 2.35 (s, 3H), 1.50 (s, 9H).

Example 187: 3-(tert-butyl)-N-(4-(2-((5,6-dihydro-4H-pyrrolo[1,2-b]pyrazol-3-yl)amino)pyrimidin-4-yl)-2-methylbenzyl)pyrrolidine-1-carboxamide

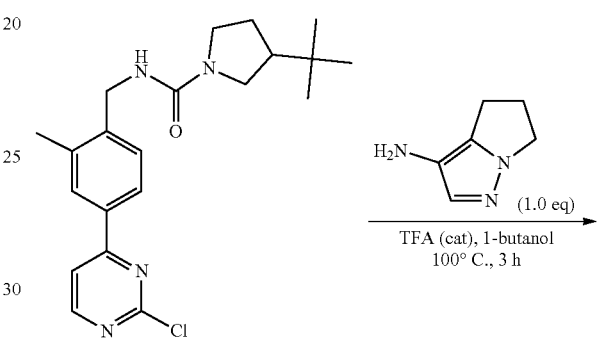

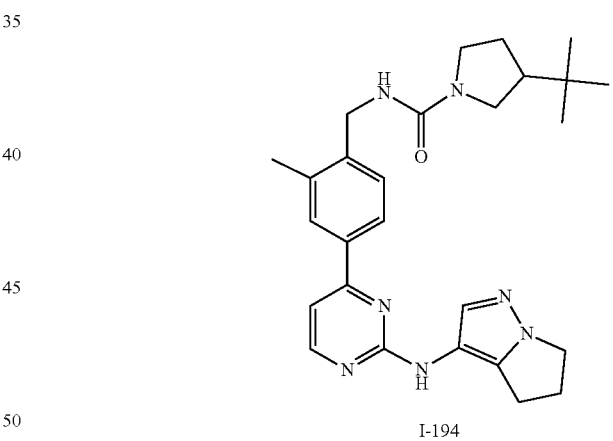

I-194

Synthesis of 3-(tert-butyl)-N-(4-(2-((5,6-dihydro-4H-pyrrolo[1,2-b]pyrazol-3-yl)amino)pyrimidin-4-yl)-2-methylbenzyl)pyrrolidine-1-carboxamide was similar to that of Example 174. The crude product was purified by prep-HPLC (CH₃CN/H₂O with 0.05% NH₄OH as mobile phase) to give 3-(tert-butyl)-N-(4-(2-((5,6-dihydro-4H-pyrrolo[1,2-b]pyrazol-3-yl)amino)pyrimidin-4-yl)-2-methylbenzyl)pyrrolidine-1-carboxamide as a yellow solid (27 mg, yield: 31%). ESI-MS (M+H)⁺: 474.1. ¹H NMR (400 MHz, CD₃OD) δ: 8.22 (d, J=5.2 Hz, 1H), 7.79-7.78 (m, 2H), 7.57 (s, 1H), 7.28 (d, J=7.6 Hz, 1H), 7.08 (d, J=5.2 Hz, 1H), 4.36-4.26 (m, 2H), 4.03 (t, J=7.2 Hz, 2H), 3.67 (t, J=8.8 Hz, 1H), 3.47 (t, J=8.8 Hz, 1H), 3.18-3.15 (m, 1H), 2.83 (t, J=7.2 Hz, 2H), 2.56-2.49 (m, 2H), 2.31 (s, 3H), 2.04-2.00 (m, 1H), 1.84-1.79 (m, 1H), 1.64-1.59 (m, 1H), 0.80 (s, 9H).

Example 188: cis-4-(4-((4-(4-((1-(tert-butyl)-1H-pyrazole-4-carboxamido)methyl)-3-methylphenyl)pyrimidin-2-yl)amino)-1H-pyrazol-1-yl)cyclohexanecarboxylic acid

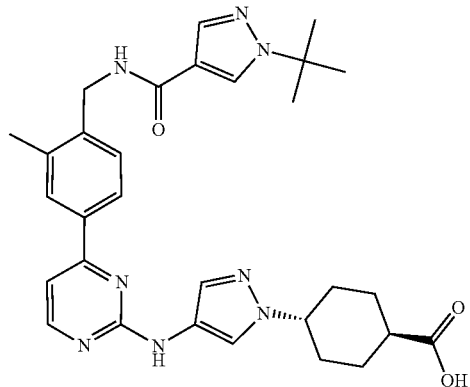

I-195

1. Synthesis of methyl 4-(4-((4-(4-((1-(tert-butyl)-1H-pyrazole-4-carboxamido)methyl)-3-methylphenyl)pyrimidin-2-yl)amino)-1H-pyrazol-1-yl)cyclohexanecarboxylate Synthesis of methyl 4-(4-((4-(4-((1-(tert-butyl)-1H-pyrazole-4-carboxamido)methyl)-3-methylphenyl)pyrimidin-2-yl)amino)-1H-pyrazol-1-yl)cyclohexanecarboxylate was similar to that of Example 1. Methyl 4-(4-((4-(4-((1-(tert-butyl)-1H-pyrazole-4-carboxamido)methyl)-3-methylphenyl)pyrimidin-2-yl)amino)-1H-pyrazol-1-yl)cyclohexanecarboxylate (160 mg, yield: 73%) was obtained as a yellow solid. ESI-MS (M+H)$^+$: 571.3. $^1$H NMR (400 MHz, CDCl$_3$) δ: 8.42 (d, J=5.2 Hz, 1H), 8.05 (s, 1H), 7.99 (s, 1H), 7.89-7.78 (m, 3H), 7.53 (s, 1H), 7.41 (d, J=8.0 Hz, 1H), 7.14 (s, 1H), 7.06 (d, J=5.2 Hz, 1H), 6.08 (t, J=5.2 Hz, 1H), 4.65 (d, J=5.6 Hz, 2H), 4.18-4.16 (m, 1H), 3.70 (s, 3H), 2.68-2.67 (m, 1H), 2.44 (s, 3H), 2.26-2.22 (m, 2H), 2.09-2.06 (m, 2H), 1.84-1.67 (m, 4H), 1.60 (s, 9H).

2. Synthesis of trans-4-(44(4-(44(1-(tert-butyl)-1H-pyrazole-4-carboxamido)methyl)-3-methylphenyl)pyrimidin-2-yl)amino)-1H-pyrazol-1-yl)cyclohexanecarboxylic acid

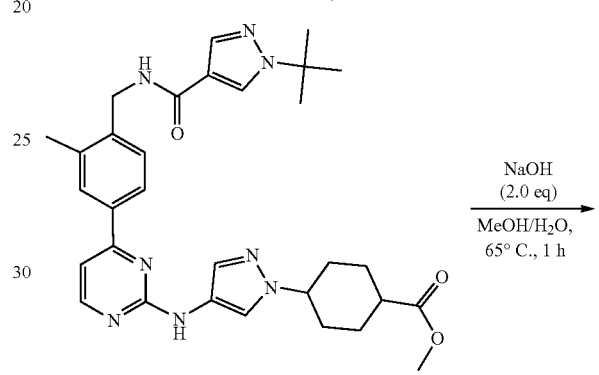

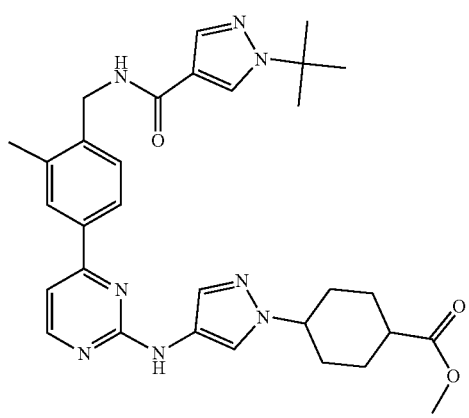

-continued

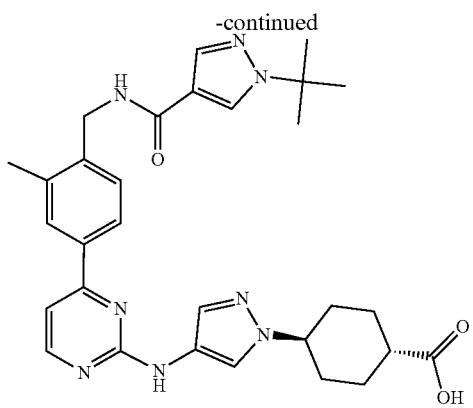

trans-A

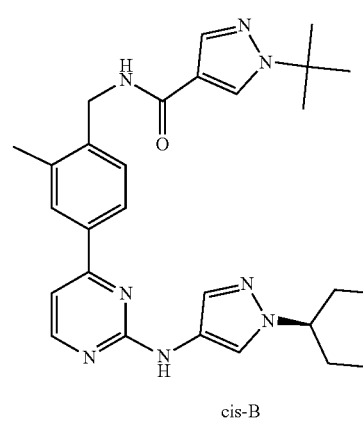

cis-B

To a mixture of methyl 4-(4-((4-(4-((1-(tert-butyl)-1H-pyrazole-4-carboxamido)methyl)-3-methylphenyl)pyrimidin-2-yl)amino)-1H-pyrazol-1-yl)cyclohexanecarboxylate (160 mg, 0.28 mmol) in MeOH (5 mL) and H$_2$O (3 mL), NaOH (22 mg, 0.56 mmol) was added. The mixture was stirred at 65° C. for 1 h. After removal of MeOH, the mixture was diluted with water (5 mL) and acidified to pH=5 with HCl (1 N), the precipitate was collected by filtration and purified by prep-HPLC (Gradient: 5% B increase to 95% B, A: 0.5% TFA in water, B: CH$_3$CN) to give trans-4-(4-((4-(4-((1-(tert-butyl)-1H-pyrazole-4-carboxamido)methyl)-3-methylphenyl)pyrimidin-2-yl)amino)-1H-pyrazol-1-yl)cyclohexanecarboxylic acid (30 mg, yield: 19%) as a yellow solid and cis-4-(4-((4-(4-((1-(tert-butyl)-1H-pyrazole-4-carboxamido)methyl)-3-methylphenyl)pyrimidin-2-yl)amino)-1H-pyrazol-1-yl)cyclohexanecarboxylic acid (77 mg, yield: 49%) as a yellow solid. ESI-MS (M+H)$^+$:557.3. trans-A $^1$H NMR (400 MHz, CD$_3$OD) δ: 8.36-8.34 (m, 1H), 8.21 (s, 1H), 7.98 (s, 1H), 7.93 (d, J=8.0 Hz, 1H), 7.79 (s, 1H), 7.57-7.56 (m, 2H), 7.48 (d, J=8.0 Hz, 1H), 7.31 (d, J=5.2 Hz, 1H), 4.62 (s, 2H), 4.19-4.13 (m, 1H), 2.49 (s, 3H), 2.43-2.35 (m, 1H), 2.30-2.20 (m, 4H), 1.91-1.78 (m, 2H), 1.72-1.66 (m, 2H), 1.62 (s, 9H). cis-B $^1$H NMR (400 MHz, CD$_3$OD) δ: 8.36-8.34 (m, 1H), 8.21 (s, 1H), 8.09 (s, 1H), 8.00-7.99 (m, 1H), 7.95-7.93 (m, 2H), 7.69 (s, 1H), 7.54-7.50 (m, 1H), 7.26 (d, J=6.0 Hz, 1H), 4.62 (s, 2H), 4.24-4.18 (m, 1H), 2.72-2.71 (m, 1H), 2.50 (s, 3H), 2.31-2.27 (m, 2H), 2.10-2.02 (m, 4H), 1.81-1.73 (m, 2H), 1.63 (s, 9H).

Example 189: 5-(tert-butyl)-N-(2-methyl-4-(2-((1-(1-methylpiperidin-4-yl)-1H-pyrazol-4-yl)amino)pyrimidin-4-yl)benzyl)isoxazole-3-carboxamide

I-196

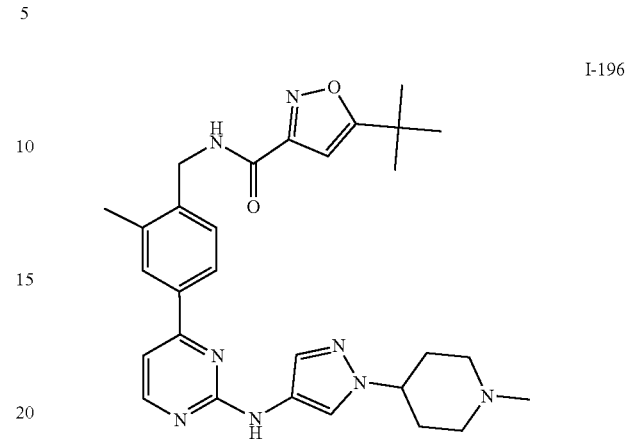

1. Synthesis of tert-butyl 4-(4-((4-methoxypyrimidin-2-yl)amino)-1H-pyrazol-1-yl)piperidine-1-carboxylate

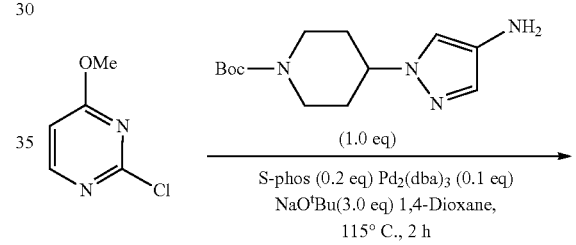

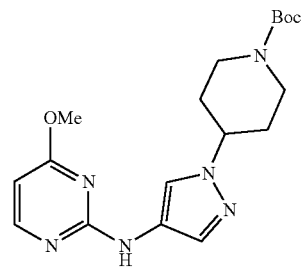

A mixture of 2-chloro-4-methoxypyrimidine (970 mg, 6.7 mmol), tert-butyl 4-(4-amino-1H-pyrazol-1-yl)piperidine-1-carboxylate (1.8 g, 6.77 mmol), S-phos (548 mg, 1.35 mmol), Pd$_2$(dba)$_3$ (577 mg, 0.63 mmol) and NaO$^t$Bu (1.9 g, 20.2 mmol) in 1,4-dioxane (18 mL) was stirred at 115° C. for 2 h under nitrogen. After dilution with EtOAc (200 mL), the mixture was washed with water and brine. The organic phase was concentrated and the residue was purified by silica gel column (petroleum ether: EtOAc, 4:1 to 2:1) to give the compound tert-butyl 4-(4-((4-methoxypyrimidin-2-yl)amino)-1H-pyrazol-1-yl)piperidine-1-carboxylate (1.15 g, yield: 48%) as a gray solid. ESI-MS (M+H)$^+$: 375.2.

2. Synthesis of 4-methoxy-N-(1-(piperidin-4-yl)-1H-pyrazol-4-yl)pyrimidin-2-amine

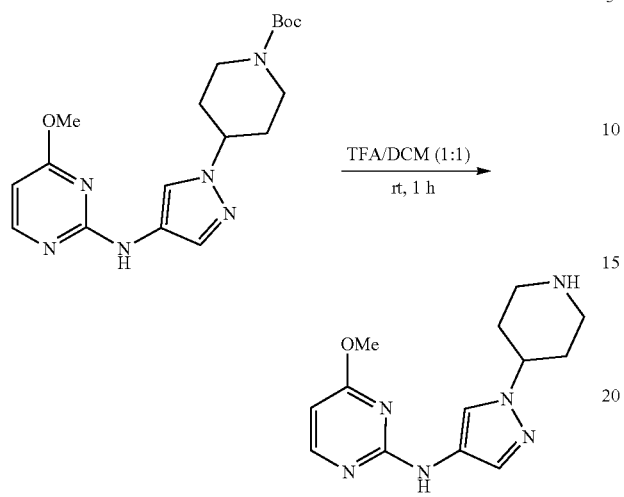

Compound tert-butyl 4-(4-((4-methoxypyrimidin-2-yl)amino)-1H-pyrazol-1-yl)piperidine-1-carboxylate (1.14 g, 3.0 mmol) was dissolved in TFA/DCM (10 mL, 1:1). The solution was stirred at rt for 1 h and concentrated in vacuo to afford a residue, which was diluted with saturated aqueous Na$_2$CO$_3$ solution (50 mL) and extracted with EtOAc (60 mL×3). The combined organic layers were dried over MgSO$_4$ and concentrated in vacuo to give crude 4-methoxy-N-(1-(piperidin-4-yl)-1H-pyrazol-4-yl)pyrimidin-2-amine (0.9 g, yield: 100%) as a light yellow solid, which was used to next step without further purification. ESI-MS (M+H)$^+$: 275.1.

3. Synthesis of 4-methoxy-N-(1-(1-methylpiperidin-4-yl)-1H-pyrazol-4-yl)pyrimidin-2-amine

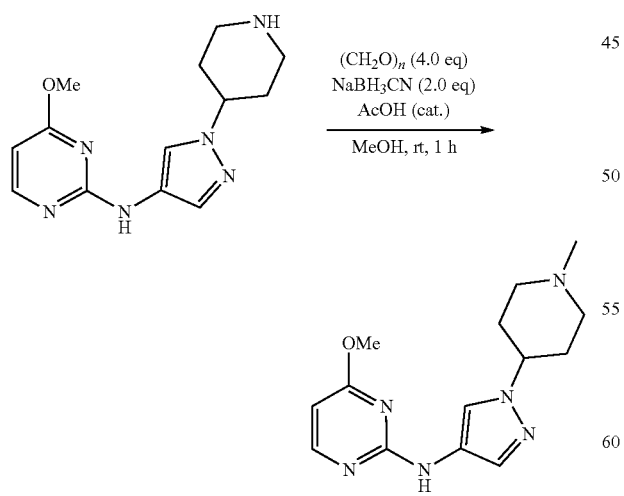

A mixture of 4-methoxy-N-(1-(piperidin-4-yl)-1H-pyrazol-4-yl)pyrimidin-2-amine (0.9 g, 3.28 mmol), paraformaldehyde (594 mg, 19.8 mmol), NaBH$_3$CN (623 mg, 9.9 mmol) and AcOH (0.1 mL) in MeOH (35 mL) was stirred at rt for 16 h. After concentration, the residue was diluted with DCM (150 mL) and washed with brine (50 mL×2). The organic phase was concentrated in vacuo to afford a residue which was purified by silica gel column (DCM/MeOH, 20:1 with 0.5% NH$_3$H$_2$O) to give 4-methoxy-N-(1-(1-methylpiperidin-4-yl)-1H-pyrazol-4-yl)pyrimidin-2-amine (895 mg, yield: 94%) as a light yellow solid. ESI-MS (M+H)$^+$: 545.2. $^1$H NMR (400 MHz, CDCl$_3$) δ: 8.07 (d, J=5.6 Hz, 1H), 7.85 (s, 1H), 7.52 (s, 1H), 6.10 (d, J=5.6 Hz, 1H), 4.22-4.07 (m, 1H), 3.92 (s, 3H), 3.09-3.05 (m, 1H), 2.41 (s, 3H), 2.36-2.31 (m, 2H), 2.24-2.16 (m, 2H), 2.15-2.03 (m, 3H).

4. Synthesis of 2-((1-(1-methylpiperidin-4-yl)-1H-pyrazol-4-yl)amino)pyrimidin-4-ol

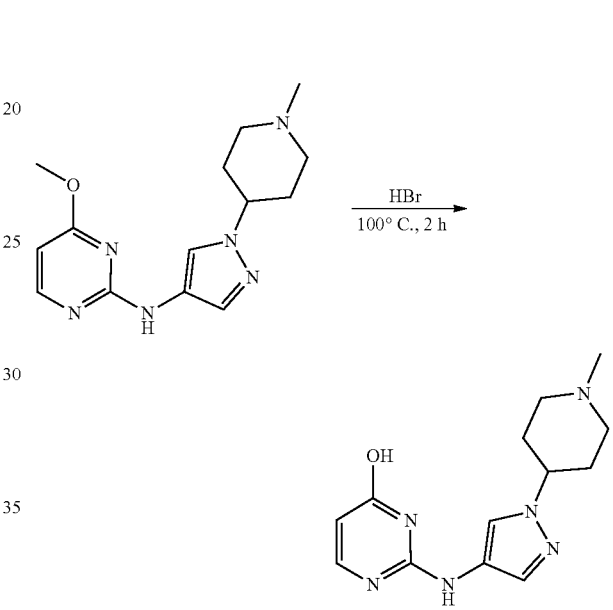

4-Methoxy-N-(1-(1-methylpiperidin-4-yl)-1H-pyrazol-4-yl)pyrimidin-2-amine (890 mg, 3.1 mmol) was dissolved in 40% HBr (aq. 12 mL). The solution was stirred at 100° C. for 2 h. The resulting mixture was concentrated in vacuo to give product 2-((1-(1-methylpiperidin-4-yl)-1H-pyrazol-4-yl)amino)pyrimidin-4-ol (crude 900 mg, yield: 100%) as a white solid which was used in the next step without further purification. ESI-MS (M+H)$^+$: 275.1.

5. Synthesis of 4-chloro-N-(1-(1-methylpiperidin-4-yl)-1H-pyrazol-4-yl)pyrimidin-2-amine

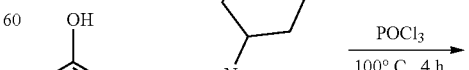

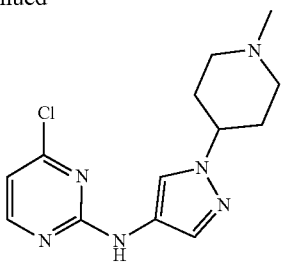

2-((1-(1-Methylpiperidin-4-yl)-1H-pyrazol-4-yl)amino)pyrimidin-4-ol (0.9 g, 3.1 mmol) was suspended in POCl$_3$ (10 mL). The mixture was stirred at 100° C. for 4 h. After removal of excess POCl$_3$, the residue was poured over ice cold water (10 mL). The pH value was adjusted to 7.0-8.0 with saturated NaHCO$_3$(aq.). The resulting solution was extracted with EtOAc (50 mL×4). The combined organic layers were dried over MgSO$_4$ and concentrated in vacuo to give a crude residue which was purified by silica gel chromatography (EA/MeOH, 20:1 with 0.5% NH$_4$OH) to give 4-chloro-N-(1-(1-methylpiperidin-4-yl)-1H-pyrazol-4-yl)pyrimidin-2-amine (560 mg, yield: 77%) as a light yellow solid. ESI-MS (M+H)$^+$: 293.2. $^1$H NMR (400 MHz, CD$_3$OD) δ: 8.28 (d, J=5.2 Hz, 1H), 8.01 (s, 1H), 7.59 (s, 1H), 6.75 (d, J=5.2 Hz, 1H), 4.20-4.12 (m, 1H), 3.02-2.99 (m, 2H), 2.34 (s, 3H), 2.29-2.22 (m, 2H), 2.16-2.01 (m, 4H).

6. Synthesis of tert-butyl 2-methyl-4-(2-((1-(1-methylpiperidin-4-yl)-1H-pyrazol-4-yl)amino)pyrimidin-4-yl)benzylcarbamate

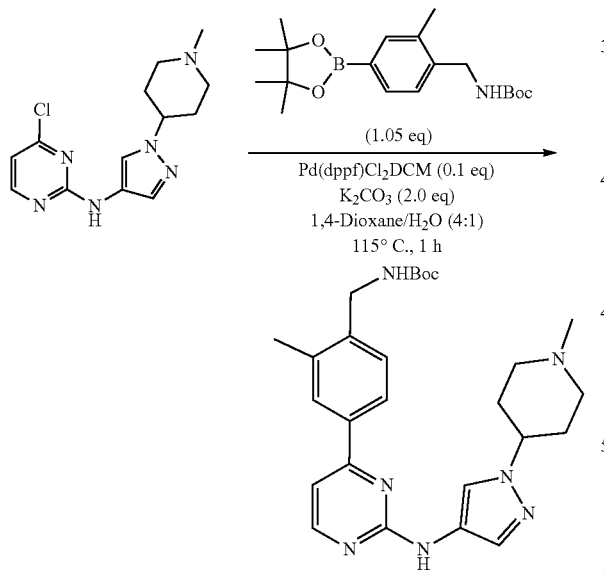

A mixture of 4-chloro-N-(1-(1-methylpiperidin-4-yl)-1H-pyrazol-4-yl)pyrimidin-2-amine (518 mg, 1.77 mmol), tert-butyl 2-methyl-4-(4,4,5,5-tetramethyl-1,3,2-dioxaborolan-2-yl)benzylcarbamate (640 mg, 1.84 mmol), Pd(dppf)Cl$_2$.DCM (120 mg, 0.15 mmol) and K$_2$CO$_3$ (488 mg, 3.5 mmol) in 1,4-dioxane/H$_2$O (20 mL, 4:1) was stirred at 115° C. for 2 h under nitrogen. After dilution with EtOAc (150 mL), the mixture was washed with water and dried over Na$_2$SO$_4$. The organic phase was concentrated in vacuo and the residue was purified by silica gel column chromatography (DCM/MeOH, 80:1 to 50:1) to give the compound tert-butyl 2-methyl-4-(2-((1-(1-methylpiperidin-4-yl)-1H-pyrazol-4-yl)amino)pyrimidin-4-yl)benzylcarbamate (720 mg, yield: 85%) as a light yellow solid. ESI-MS (M+H)$^+$: 478.3. $^1$H NMR (400 MHz, CDCl$_3$) δ: 8.41 (d, J=5.2 Hz, 1H), 7.94 (s, 1H), 7.86 (s, 1H), 7.83 (d, J=8.0 Hz, 1H), 7.57 (s, 1H), 7.46-7.28 (m, 2H), 7.06 (d, J=5.2 Hz, 1H), 4.91 (br, 1H), 4.37 (d, J=5.4 Hz, 2H), 4.14-4.09 (m, 1H), 2.99-2.97 (m, 2H), 2.40 (s, 3H), 2.34 (s, 3H), 2.23-2.02 (m, 6H), 1.48 (s, 9H).

7. Synthesis of 4-(4-(aminomethyl)-3-methylphenyl)-N-(1-(1-methylpiperidin-4-yl)-1H-pyrazol-4-yl)pyrimidin-2-amine

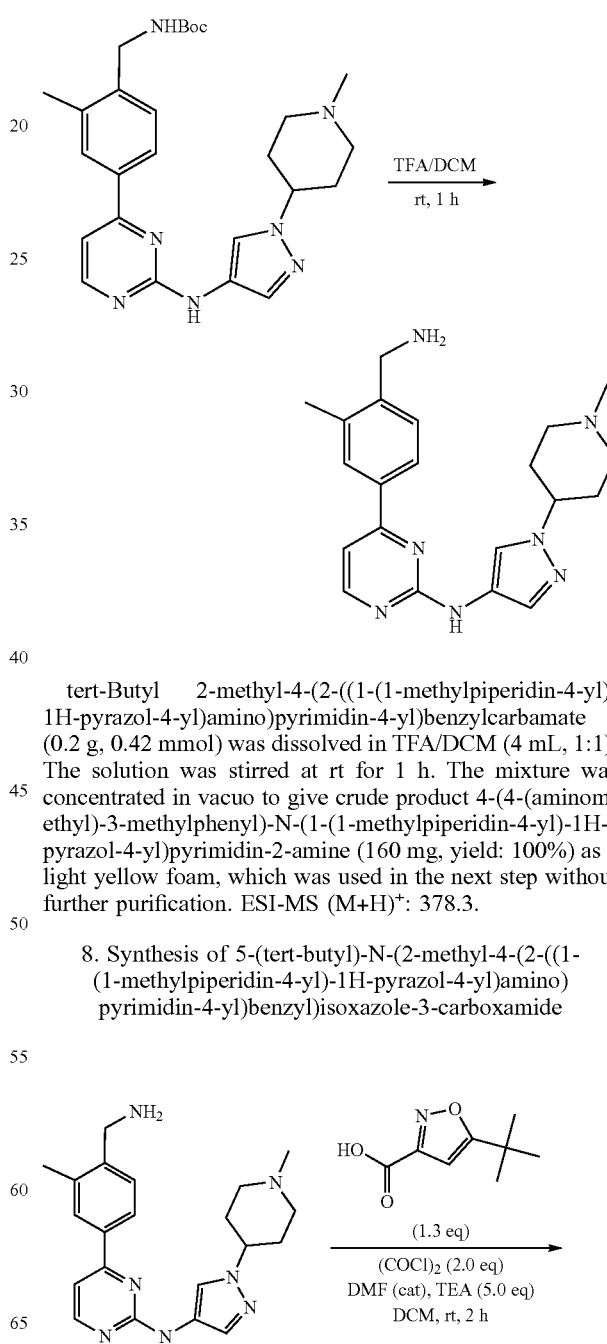

tert-Butyl 2-methyl-4-(2-((1-(1-methylpiperidin-4-yl)-1H-pyrazol-4-yl)amino)pyrimidin-4-yl)benzylcarbamate (0.2 g, 0.42 mmol) was dissolved in TFA/DCM (4 mL, 1:1). The solution was stirred at rt for 1 h. The mixture was concentrated in vacuo to give crude product 4-(4-(aminomethyl)-3-methylphenyl)-N-(1-(1-methylpiperidin-4-yl)-1H-pyrazol-4-yl)pyrimidin-2-amine (160 mg, yield: 100%) as a light yellow foam, which was used in the next step without further purification. ESI-MS (M+H)$^+$: 378.3.

8. Synthesis of 5-(tert-butyl)-N-(2-methyl-4-(2-((1-(1-methylpiperidin-4-yl)-1H-pyrazol-4-yl)amino)pyrimidin-4-yl)benzyl)isoxazole-3-carboxamide -continued

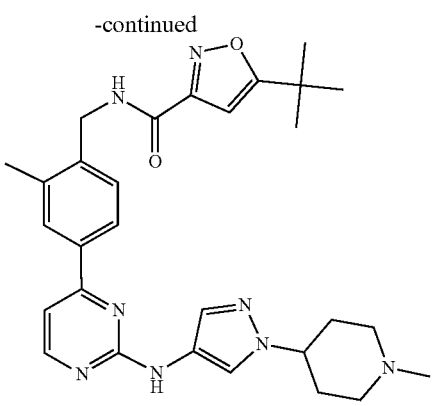

Synthesis of 5-(tert-butyl)-N-(2-methyl-4-(2-((1-(1-methylpiperidin-4-yl)-1H-pyrazol-4-yl)amino)pyrimidin-4-yl)benzyl)isoxazole-3-carboxamide was similar to that of Example 71. The residue was purified by prep-HPLC (MeCN/H$_2$O with 0.05% TFA as mobile phase) to afford 5-(tert-butyl)-N-(2-methyl-4-(2-((1-(1-methylpiperidin-4-yl)-1H-pyrazol-4-yl)amino)pyrimidin-4-yl)benzyl)isoxazole-3-carboxamide (23 mg, yield: 24%) as a light yellow solid. ESI-MS (M+H)$^+$: 529.2. $^1$H NMR (400 MHz, CD$_3$OD) δ: 8.27 (d, J=5.2 Hz, 1H), 7.99 (s, 1H), 7.85 (s, 1H), 7.81 (dd, J=8.0, 1.6 Hz, 1H), 7.55 (s, 1H), 7.31 (d, J=8.0 Hz, 1H), 7.08 (d, J=5.2 Hz, 1H), 6.39 (s, 1H), 4.52 (s, 2H), 4.11-4.00 (m, 1H), 2.93-2.90 (m, 2H), 2.35 (s, 3H), 2.25 (s, 3H), 2.22-2.15 (m, 2H), 2.07-2.04 (m, 2H), 2.02-1.92 (m, 2H), 1.28 (s, 9H).

Example 190: 1-(tert-butyl)-N-(2-methyl-4-(2-((1-(1-methylpiperidin-4-yl)-1H-pyrazol-4-yl)amino)pyrimidin-4-yl)benzyl)-1H-pyrazole-4-carboxamide

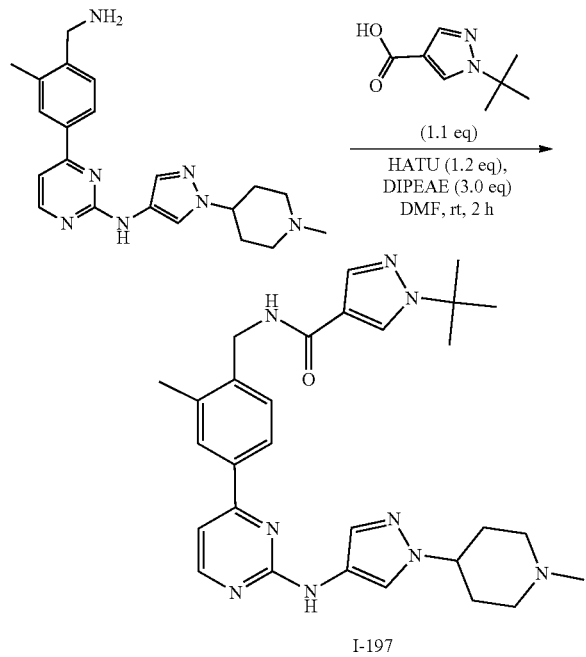

I-197

A mixture of 1-tert-butyl-1H-pyrazole-4-carboxylic acid (252 mg, 0.15 mmol), 4-(4-(aminomethyl)-3-methylphenyl)-N-(1-(1-methylpiperidin-4-yl)-1H-pyrazol-4-yl)pyrimidin-2-amine (58 mg, 0.15 mmol), HATU (69 mg, 0.18 mmol) and DIPEA (60 mg, 0.45 mmol) in DMF (5 mL) was stirred at rt for 2 h. The reaction mixture was diluted with water (20 ml) and the mixture was extracted with EtOAc (60 mL×2). The combined organic layers were washed with H$_2$O (40 mL×2), dried (Na$_2$SO$_4$), filtered and concentrated in vacuo to afford a residue which was purified by prep-HPLC (CH$_3$CN/H$_2$O with 0.05% NH$_3$.H$_2$O as mobile phase) to give 1-(tert-butyl)-N-(2-methyl-4-(2-((1-(1-methylpiperidin-4-yl)-1H-pyrazol-4-yl)amino)pyrimidin-4-yl)benzyl)-1H-pyrazole-4-carboxamide as a yellow solid (82 mg, yield: 75%). ESI-MS (M+H)$^+$: 528.3. $^1$H NMR (400 MHz, CD$_3$OD) δ: 8.26 (d, J=5.6 Hz, 1H), 8.17 (s, 1H), 7.97 (s, 1H), 7.87 (s, 1H), 7.84 (s, 1H), 7.80 (d, J=8.0 Hz, 1H), 7.55 (s, 1H), 7.30 (d, J=8.0 Hz, 1H), 7.07 (d, J=5.2 Hz, 1H), 4.48 (s, 2H), 4.05-3.99 (m, 1H), 2.90-2.88 (m, 2H), 2.34 (s, 3H), 2.22 (s, 3H), 2.14-2.12 (m, 2H), 2.05-1.90 (m, 4H), 1.49 (s, 9H).

Example 191: 3-(tert-butoxy)-N-(4-(2-((1-methyl-1H-pyrazol-4-yl)amino)pyrimidin-4-yl)-2-(trifluoromethyl)benzyl)azetidine-1-carboxamide

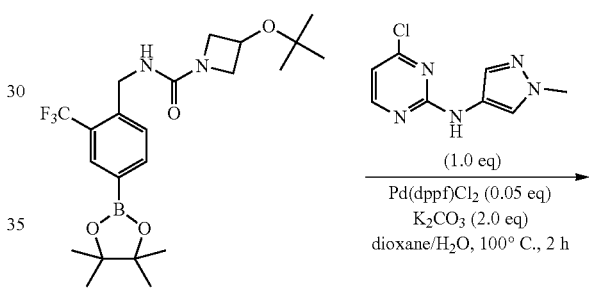

I-198

Synthesis of 3-(tert-butoxy)-N-(4-(2-((1-methyl-1H-pyrazol-4-yl)amino)pyrimidin-4-yl)-2-(trifluoromethyl)benzyl)azetidine-1-carboxamide was similar to that of Example 157. The crude product was purified by prep-HPLC (CH$_3$CN/H$_2$O with 0.05% NH$_4$OH as mobile phase) to give 3-(tert-butoxy)-N-(4-(2-((1-methyl-1H-pyrazol-4-yl)amino)pyrimidin-4-yl)-2-(trifluoromethyl)benzyl)azetidine-1-carboxamide as a yellow solid (34 mg, yield: 26%). ESI-MS (M+H)$^+$: 504.2. $^1$H NMR (400 MHz, CD$_3$OD) δ: 8.41 (s, 1H), 8.37 (d, J=5.6 Hz, 1H), 8.23 (d, J=4.4 Hz, 1H), 7.88 (s, 1H), 7.59 (d, J=8.4 Hz, 1H), 7.52 (br, 1H), 7.18 (d, J=5.2 Hz, 1H), 4.54-4.49 (m, 1H), 4.49 (s, 2H), 4.11-4.08 (m, 2H), 3.79 (s, 3H), 3.73-3.69 (m, 2H), 1.10 (s, 9H).

Example 192: 3-(tert-butoxy)-N-(4-(2-((1-isopropyl-1H-pyrazol-4-yl)amino)pyrimidin-4-yl)-2-(trifluoromethyl)benzyl)azetidine-1-carboxamide

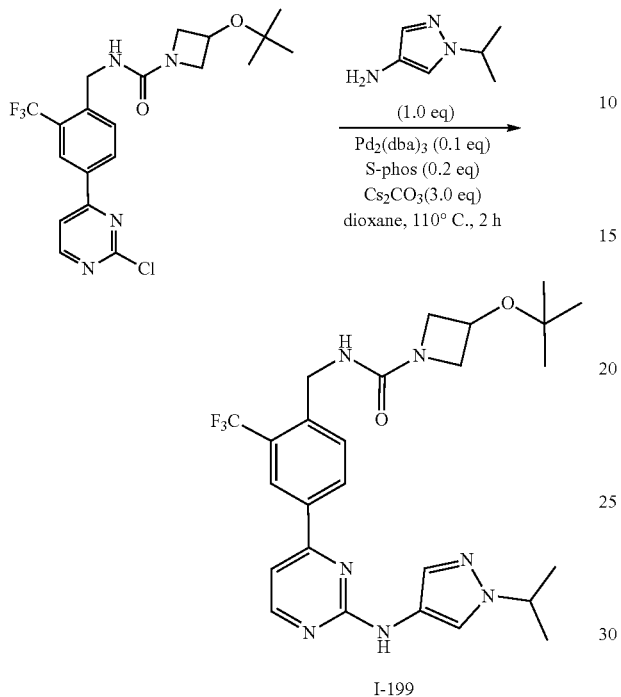

I-199

Synthesis of 3-(tert-butoxy)-N-(4-(2-((1-isopropyl-1H-pyrazol-4-yl)amino)pyrimidin-4-yl)-2-(trifluoromethyl)benzyl)azetidine-1-carboxamide was similar to that of Example 161. The crude product was purified by prep-HPLC (CH$_3$CN/H$_2$O with 0.05% NH$_4$OH as mobile phase) to give 3-(tert-butoxy)-N-(4-(2-((1-isopropyl-1H-pyrazol-4-yl)amino)pyrimidin-4-yl)-2-(trifluoromethyl)benzyl)azetidine-1-carboxamide as a yellow solid (67 mg, yield: 37%). ESI-MS (M+H)$^+$: 532.3. $^1$H NMR (400 MHz, CD$_3$OD) δ: 8.42 (s, 1H), 8.37 (d, J=4.8 Hz, 1H), 8.21 (d, J=8.0 Hz, 1H), 7.95 (s, 1H), 7.60 (d, J=8.4 Hz, 1H), 7.53 (s, 1H), 7.17 (d, J=4.8 Hz, 1H), 4.53-4.47 (m, 1H), 4.49 (s, 2H), 4.44-4.37 (m, 1H), 4.11-4.08 (m, 2H), 3.73-3.69 (m, 2H), 1.42 (d, J=6.4 Hz, 6H), 1.10 (s, 9H).

Example 193: 3-(tert-butoxy)-N-(4-(2-((1-(1-methylpiperidin-4-yl)-1H-pyrazol-4-yl)amino)pyrimidin-4-yl)-2-(trifluoromethyl)benzyl)azetidine-1-carboxamide

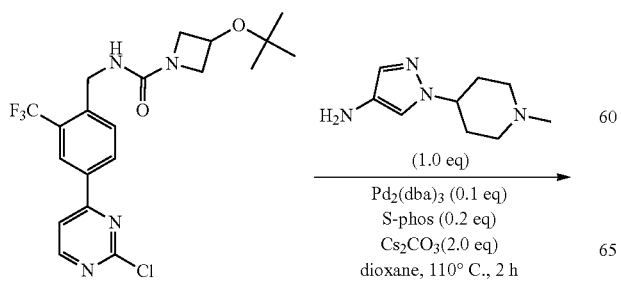

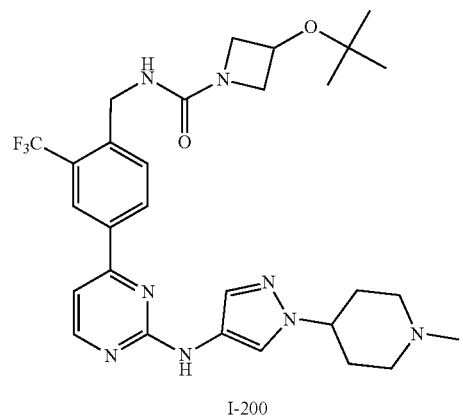

I-200

Synthesis of 3-(tert-butoxy)-N-(4-(2-((1-(1-methylpiperidin-4-yl)-1H-pyrazol-4-yl)amino)pyrimidin-4-yl)-2-(trifluoromethyl)benzyl)azetidine-1-carboxamide was similar to that of Example 161. The crude product was purified by prep-HPLC (CH$_3$CN/H$_2$O with 0.05% NH$_4$OH as mobile phase) to give 3-(tert-butoxy)-N-(4-(2-((1-(1-methylpiperidin-4-yl)-1H-pyrazol-4-yl)amino)pyrimidin-4-yl)-2-(trifluoromethyl)benzyl)azetidine-1-carboxamide as a yellow solid (65 mg, yield: 33%). ESI-MS (M+H)$^+$: 587.3. $^1$H NMR (400 MHz, CD$_3$OD) δ: 8.39 (s, 1H), 8.36 (d, J=5.2 Hz, 1H), 8.21 (d, J=8.0 Hz, 1H), 7.96 (s, 1H), 7.59 (d, J=8.0 Hz, 1H), 7.55 (s, 1H), 7.17 (d, J=5.2 Hz, 1H), 4.53-4.47 (m, 1H), 4.49 (s, 2H), 4.11-4.05 (m, 3H), 3.73-3.69 (m, 2H), 2.94-2.91 (m, 2H), 2.24 (s, 3H), 2.19-2.13 (m, 2H), 2.04-1.96 (m, 4H), 1.10 (s, 9H).

Example 194: 1-(tert-butyl)-N-(4-(2-((1-(1-methylazetidin-3-yl)-1H-pyrazol-4-yl)amino)pyrimidin-4-yl)-2-(trifluoromethyl)benzyl)-1H-pyrazole-4-carboxamide

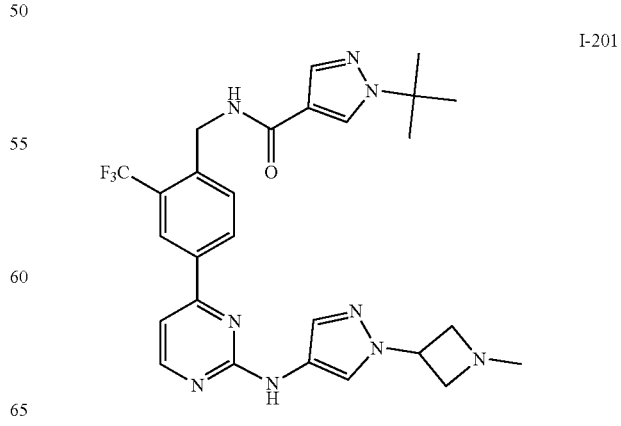

I-201

1. The preparation of 1-(tert-butyl)-N-(4-(2-chloropyrimidin-4-yl)-2-(trifluoromethyl)benzyl)-1H-pyrazole-4-carboxamide

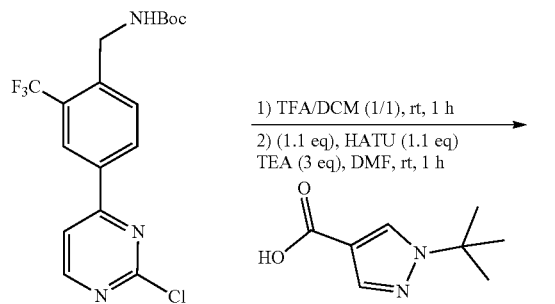

Synthesis of 1-(tert-butyl)-N-(4-(2-chloropyrimidin-4-yl)-2-(trifluoromethyl)benzyl)-1H-pyrazole-4-carboxamide was similar to that of Example 1. The crude was purified by silica gel chromatography (petroleum ether:EtOAc=1:1) to give 1-(tert-butyl)-N-(4-(2-chloropyrimidin-4-yl)-2-(trifluoromethyl)benzyl)-1H-pyrazole-4-carboxamide as a white solid (215 mg, yield: 78%). ESI-MS (M+H)$^+$: 438.1.

2. The preparation of 1-(tert-butyl)-N-(4-(2-((1-(1-methylazetidin-3-yl)-1H-pyrazol-4-yl)amino)pyrimidin-4-yl)-2-(trifluoromethyl)benzyl)-1H-pyrazole-4-carboxamide

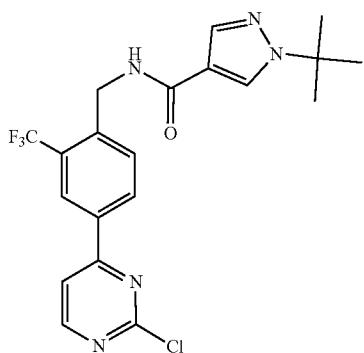

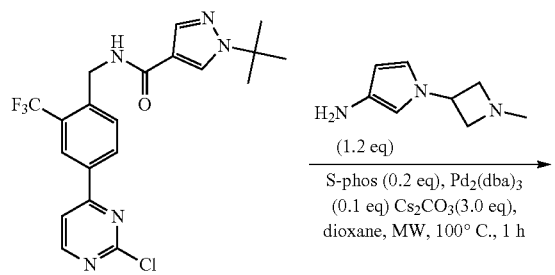

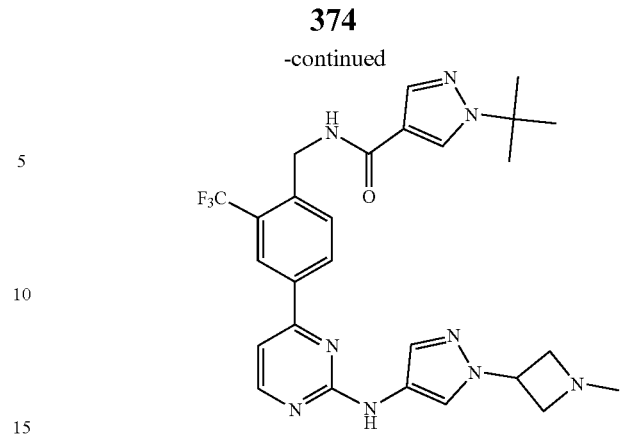

Synthesis of 1-(tert-butyl)-N-(4-(2-((1-(1-methylazetidin-3-yl)-1H-pyrazol-4-yl)amino)pyrimidin-4-yl)-2-(trifluoromethyl)benzyl)-1H-pyrazole-4-carboxamide was similar to that of Example 161. The crude was purified prep-HPLC (MeOH/H$_2$O with 0.05% NH$_3$.H$_2$O as mobile phase) to give 1-(tert-butyl)-N-(4-(2-((1-(1-methylazetidin-3-yl)-1H-pyrazol-4-yl)amino)pyrimidin-4-yl)-2-(trifluoromethyl)benzyl)-1H-pyrazol-4-yl)amino)pyrimidin-4-yl)-2-(trifluoromethyl)benzyl)-1H-pyrazole-4-carboxamide as a yellow solid (50 mg, yield: 35%). ESI-MS (M+H)$^+$: 554.1. $^1$H NMR (400 MHz, CDCl$_3$) δ: 8.47 (d, J=4.8 Hz, 1H), 8.40 (s, 1H), 8.13 (d, J=8.4 Hz, 1H), 8.09 (s, 1H), 8.05 (s, 1H), 7.78 (s, 1H), 7.75 (d, J=8.0 Hz, 1H), 7.58 (s, 1H), 7.23 (s, 1H), 7.09 (d, J=4.8 Hz, 1H), 6.30 (t, J=6.0 Hz, 1H), 4.92-4.89 (m, 1H), 4.84 (d, J=6.0 Hz, 2H), 3.86-3.82 (m, 2H), 3.54-3.50 (m, 2H), 2.45 (s, 3H), 1.60 (s, 9H).

Example 195: 1-(tert-butyl)-N-(4-(2-((1-methyl-1H-pyrazol-4-yl)amino)pyrimidin-4-yl)-2-(trifluoromethyl)benzyl)-1H-pyrazole-4-carboxamide

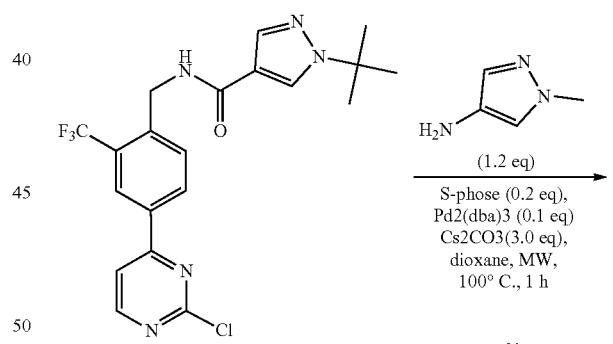

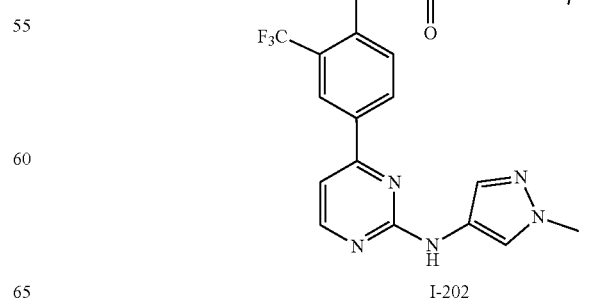

I-202

Synthesis of 1-(tert-butyl)-N-(4-(2-((1-methyl-1H-pyrazol-4-yl)amino)pyrimidin-4-yl)-2-(trifluoromethyl)benzyl)-1H-pyrazole-4-carboxamide was similar to that of Example 161. The crude was purified by prep-HPLC (CH₃CN/H₂O with 0.05% NH₃H₂O as mobile phase) to give -(tert-butyl)-N-(4-(2-((1-methyl-1H-pyrazol-4-yl)amino)pyrimidin-4-yl)-2-(trifluoromethyl)benzyl)-1H-pyrazole-4-carboxamide as a yellow solid (85 mg, yield: 69%). ESI-MS (M+H)⁺: 499.2. ¹H NMR (400 MHz, CDCl₃) δ: 8.48 (d, J=4.8 Hz, 1H), 8.41 (s, 1H), 8.14 (d, J=7.2 Hz, 1H), 8.03 (s, 1H), 7.91 (s, 1H), 7.78-7.76 (m, 2H), 7.52 (s, 1H), 7.09 (d, J=5.2 Hz, 1H), 6.96 (s, 1H), 6.18 (t, J=5.6 Hz, 1H), 4.85 (d, J=6.0 Hz, 2H), 3.92 (s, 3H), 1.60 (s, 9H).

Example 196: 3-(tert-butoxy)-N-(4-(2-((1-ethyl-1H-pyrazol-4-yl)amino)pyrimidin-4-yl)-2-(trifluoromethyl)benzyl)azetidine-1-carboxamide

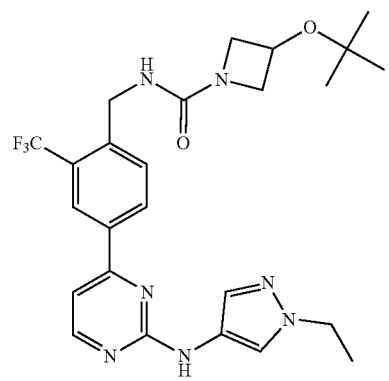

I-203

1. Synthesis of N-(4-bromo-2-(trifluoromethyl)benzyl)-3-(tert-butoxy)azetidine-1-carboxamide

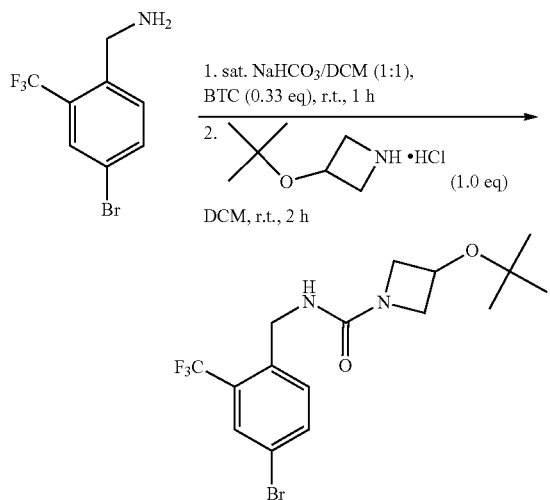

Synthesis of N-(4-bromo-2-(trifluoromethyl)benzyl)-3-(tert-butoxy)azetidine-1-carboxamide was similar to that of 3-(tert-butyl)-N-(4-(2-chloropyrimidin-4-yl)-2-(trifluoromethyl)benzyl)pyrrolidine-1-carboxamide in Example 200 except the 3-(tert-butyl)pyrrolidine was substituted with 3-(tert-butoxy)azetidine hydrochloride. The crude product was purified by prep-HPLC (CH₃CN/H₂O with 0.05% NH₄OH as mobile phase) to give N-(4-bromo-2-(trifluoromethyl)benzyl)-3-(tert-butoxy)azetidine-1-carboxamide as a white solid (1.1 g, yield: 54%). ESI-MS (M+H)⁺: 409.1. ¹H NMR (400 MHz, CD₃OD) δ: 7.80 (s, 1H), 7.77 (d, J=8.4 Hz, 1H), 7.47 (d, J=8.4 Hz, 1H), 4.61-4.57 (m, 1H), 4.47 (s, 2H), 3.81-3.77 (m, 2H), 3.32-3.31 (m, 2H), 1.19 (s, 9H).

2. Synthesis of 3-(tert-butoxy)-N-(4-(2-chloropyrimidin-4-yl)-2-(trifluoromethyl)benzyl) azetidine-1-carboxamide

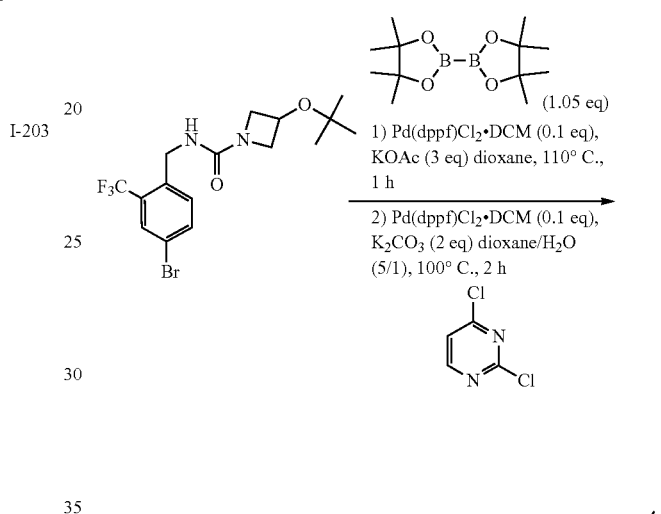

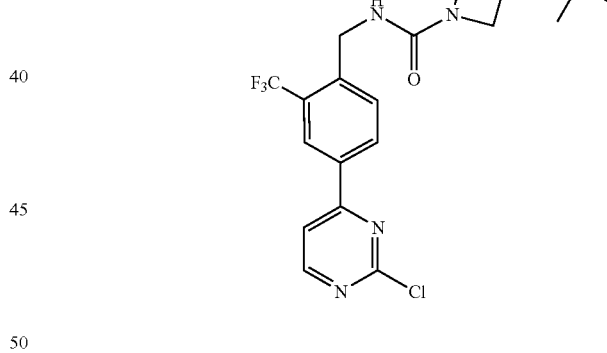

Synthesis of 3-(tert-butoxy)-N-(4-(2-chloropyrimidin-4-yl)-2-(trifluoromethyl)benzyl) azetidine-1-carboxamide was similar to that of 3-(tert-butyl)-N-(4-(2-chloropyrimidin-4-yl)-2-(trifluoromethyl)benzyl)pyrrolidine-1-carboxamide.

The residue was purified by silica gel chromatography column (EtOAc: petroleum ether=1:1) to give 3-(tert-butoxy)-N-(4-(2-chloropyrimidin-4-yl)-2-(trifluoromethyl)benzyl)azetidine-1-carboxamide as a yellow solid (830 mg, yield: 86%). ESI-MS (M+H)⁺: 442.2. ¹H NMR (400 MHz, CDCl₃) δ: 8.70 (d, J=5.6 Hz, 1H), 8.38 (s, 1H), 8.20 (d, J=8.0 Hz, 1H), 7.80 (d, J=7.6 Hz, 1H), 7.68 (d, J=5.6 Hz, 1H), 4.64 (d, J=6.4 Hz, 2H), 4.54-4.46 (m, 2H), 4.11-4.08 (m, 2H), 3.85-3.83 (m, 2H), 1.17 (s, 9H).

3. Synthesis of 3-(tert-butoxy)-N-(4-(2-((1-ethyl-1H-pyrazol-4-yl)amino)pyrimidin-4-yl)-2-(trifluoromethyl)benzyl)azetidine-1-carboxamide

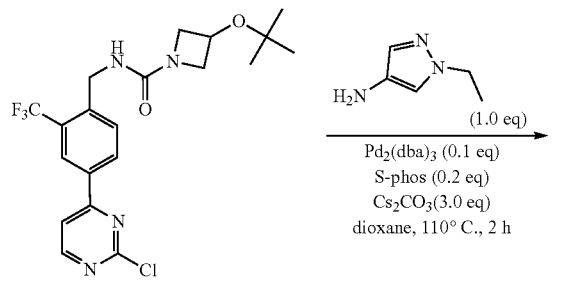

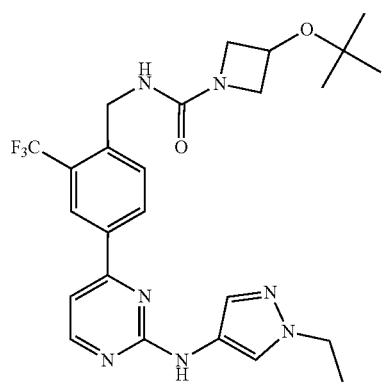

Synthesis of 3-(tert-butoxy)-N-(4-(2-((1-ethyl-1H-pyrazol-4-yl)amino)pyrimidin-4-yl)-2-(trifluoromethyl)benzyl)azetidine-1-carboxamide was similar to that of Example 161. The crude product was purified by prep-HPLC (CH$_3$CN/H$_2$O with 0.05% NH$_4$OH as mobile phase) to give 3-(tert-butoxy)-N-(4-(2-((1-ethyl-1H-pyrazol-4-yl)amino)pyrimidin-4-yl)-2-(trifluoromethyl)benzyl)azetidine-1-carboxamide as a yellow solid (73 mg, yield: 41%). ESI-MS (M+H)$^+$: 518.3. $^1$H NMR (400 MHz, CD$_3$OD) δ: 8.41 (s, 1H), 8.36 (d, J=4.8 Hz, 1H), 8.22 (d, J=1.6 Hz, 1H), 7.92 (s, 1H), 7.59 (d, J=8.4 Hz, 1H), 7.53 (s, 1H), 7.17 (d, J=5.2 Hz, 1H), 4.52-4.49 (m, 1H), 4.51 (s, 2H), 4.11-4.04 (m, 4H), 3.73-3.69 (m, 2H), 1.38 (t, J=7.2 Hz, 3H), 1.10 (s, 9H).

Example 197: 3-(tert-butoxy)-N-(4-(2-((1-(2-methoxyethyl)-1H-pyrazol-4-yl)amino)pyrimidin-4-yl)-2-(trifluoromethyl)benzyl)azetidine-1-carboxamide

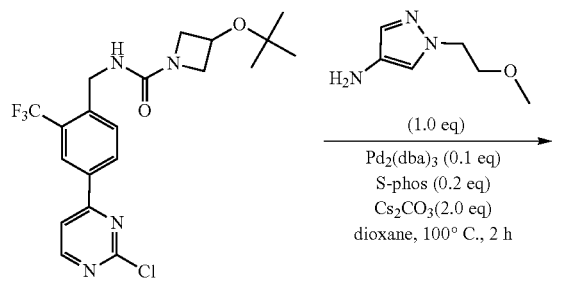

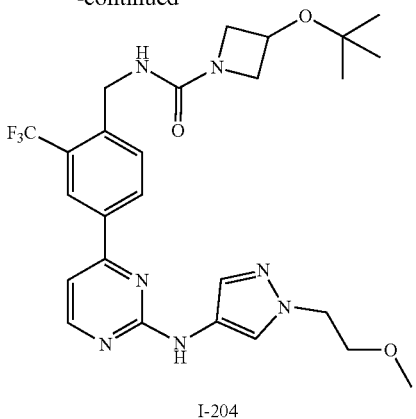

I-204

Synthesis of 3-(tert-butoxy)-N-(4-(2-((1-(2-methoxyethyl)-1H-pyrazol-4-yl)amino)pyrimidin-4-yl)-2-(trifluoromethyl)benzyl)azetidine-1-carboxamide was similar to that of Example 161. The crude product was purified by prep-HPLC (CH$_3$CN/H$_2$O with 0.05% NH$_4$OH as mobile phase) to give 3-(tert-butoxy)-N-(4-(2-((1-(2-methoxyethyl)-1H-pyrazol-4-yl)amino)pyrimidin-4-yl)-2-(trifluoromethyl)benzyl)azetidine-1-carboxamide as a yellow solid (75 mg, yield: 40%). ESI-MS (M+H)$^+$: 548.2. $^1$H NMR (400 MHz, CD$_3$OD) δ: 8.37 (s, 1H), 8.36 (d, J=5.2 Hz, 1H), 8.22 (d, J=8.4 Hz, 1H), 7.94 (s, 1H), 7.59 (d, J=8.4 Hz, 1H), 7.55 (s, 1H), 7.16 (d, J=5.2 Hz, 1H), 4.53-4.47 (m, 1H), 4.49 (s, 2H), 4.18 (t, J=5.2 Hz, 2H), 4.11-4.07 (m, 2H), 3.73-3.69 (m, 2H), 3.64 (t, J=5.2 Hz, 2H), 3.23 (s, 3H), 1.10 (s, 9H).

Example 198: 3-(tert-butoxy)-N-(4-(2-((1-(2-hydroxyethyl)-1H-pyrazol-4-yl)amino)pyrimidin-4-yl)-2-(trifluoromethyl)benzyl)azetidine-1-carboxamide

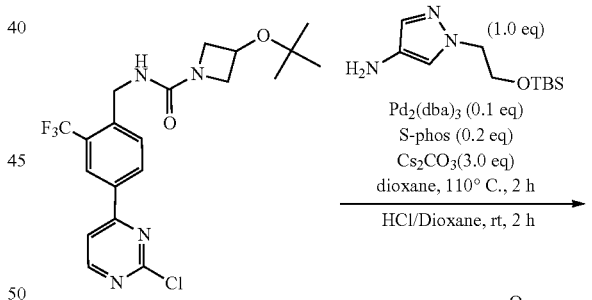

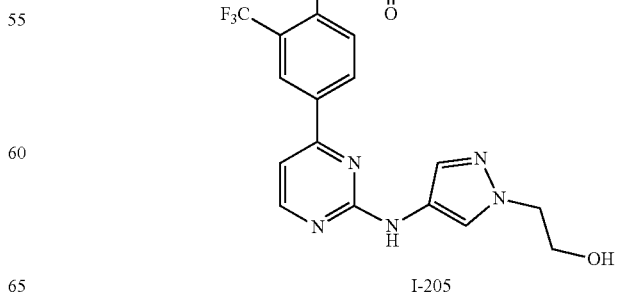

I-205

Synthesis of 3-(tert-butoxy)-N-(4-(2-((1-(2-hydroxyethyl)-1H-pyrazol-4-yl)amino)pyrimidin-4-yl)-2-(trifluoromethyl)benzyl)azetidine-1-carboxamide was similar to that of 3-(tert-butoxy)-N-(4-(2-((1-(2-hydroxyethyl)-1H-pyrazol-4-yl)amino)pyrimidin-4-yl)-2-methylbenzyl)azetidine-1-carboxamide. After concentration in vacuo, the crude product was purified by prep-HPLC (CH$_3$CN/H$_2$O with 0.05% NH$_4$OH as mobile phase) to give 3-(tert-butoxy)-N-(4-(2-((1-(2-hydroxyethyl)-1H-pyrazol-4-yl)amino)pyrimidin-4-yl)-2-(trifluoromethyl)benzyl)azetidine-1-carboxamide as a yellow solid (64 mg, yield: 58%). ESI-MS (M+H)$^+$: 534.2. $^1$H NMR (400 MHz, CD$_3$OD) δ: 8.39 (s, 1H), 8.36 (d, J=5.2 Hz, 1H), 8.24 (d, J=8.0 Hz, 1H), 7.96 (s, 1H), 7.59-7.57 (m, 2H), 7.18 (d, J=4.8 Hz, 1H), 4.54-4.47 (m, 1H), 4.50 (s, 2H), 4.12-4.07 (m, 4H), 3.80 (t, J=5.2 Hz, 2H), 3.73-3.70 (m, 2H), 1.10 (s, 9H).

Example 199: 3-(tert-butoxy)-N-(4-(2-((1-(1-methylazetidin-3-yl)-1H-pyrazol-4-yl)amino)pyrimidin-4-yl)-2-(trifluoromethyl)benzyl)azetidine-1-carboxamide

I-206

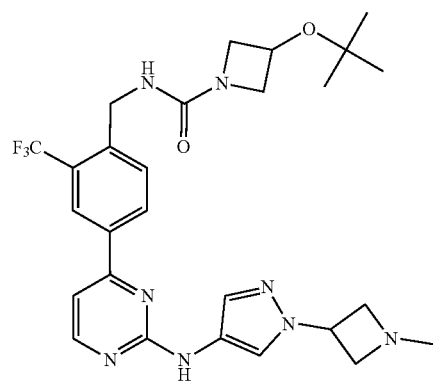

1. Synthesis of tert-butyl 3-(4-((4-(4-((3-(tert-butoxy)azetidine-1-carboxamido)methyl)-3-(trifluoromethyl)phenyl)pyrimidin-2-yl)amino)-1H-pyrazol-1-yl)azetidine-1-carboxylate

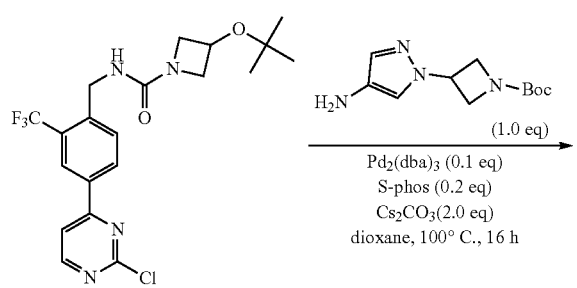

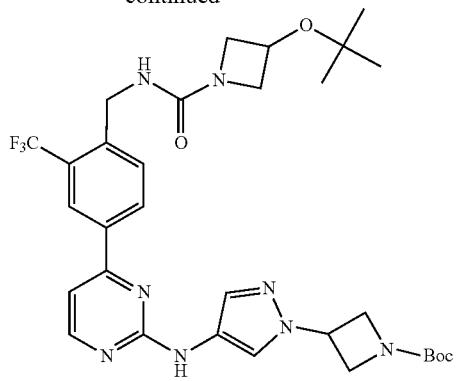

Synthesis of tert-butyl 3-(4-((4-(4-((3-(tert-butoxy)azetidine-1-carboxamido)methyl)-3-(trifluoromethyl)phenyl)pyrimidin-2-yl)amino)-1H-pyrazol-1-yl)azetidine-1-carboxylate was similar to that of Example 161. The residue was purified by silica gel chromatography column (EtOAc:petroleum ether=10:1) to give tert-butyl 3-(4-((4-(4-((3-(tert-butoxy)azetidine-1-carboxamido)methyl)-3-(trifluoromethyl)phenyl)pyrimidin-2-yl)amino)-1H-pyrazol-1-yl)azetidine-1-carboxylate as a yellow solid (230 mg, yield: 46%). ESI-MS (M+H)$^+$: 645.2.

2. Synthesis of 3-(tert-butoxy)-N-(4-(2-((1-(1-methylazetidin-3-yl)-1H-pyrazol-4-yl)amino)pyrimidin-4-yl)-2-(trifluoromethyl)benzyl)azetidine-1-carboxamide

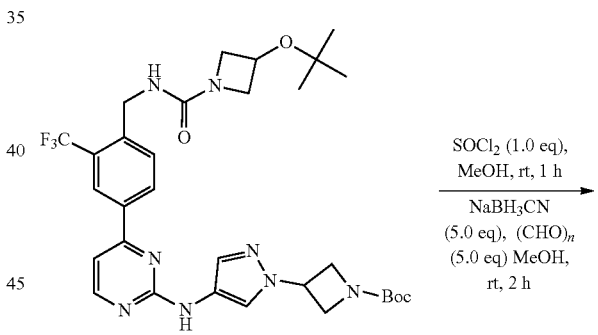

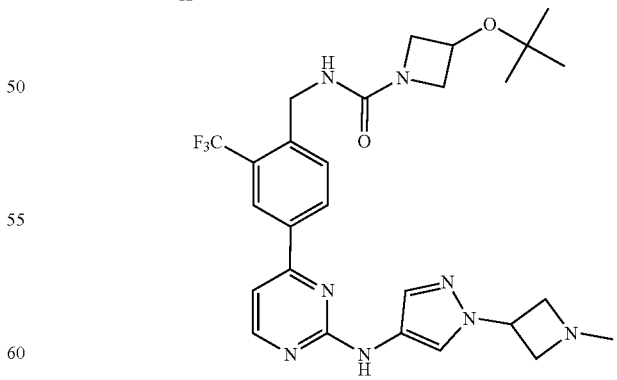

The synthesis of 3-(tert-butoxy)-N-(4-(2-((1-(1-methylazetidin-3-yl)-1H-pyrazol-4-yl)amino)pyrimidin-4-yl)-2-(trifluoromethyl)benzyl)azetidine-1-carboxamide. A mixture of tert-butyl 3-(4-((4-(4-((3-(tert-butoxy)azetidine-1-carboxamido)methyl)-3-(trifluoromethyl)phenyl)

pyrimidin-2-yl)amino)-1H-pyrazol-1-yl)azetidine-1-carboxylate (230 mg, 0.36 mmol) and SOCl$_2$ (43 mg, 0.36 mmol) in MeOH (10 mL) was stirred at rt for 1 h. After concentration, the crude material (80 mg, 0.16 mmol) was dissolved in MeOH (5 mL), treated with NaBH$_3$CN (41 mg, 0.64 mmol) and (CHO). (24 mg, 0.64 mmol). The mixture was stirred at rt for 2 h. After concentration in vacuo, the crude product was purified by silica gel chromatography (EtOAc/MeOH=10:1) to give 3-(tert-butoxy)-N-(4-(2-((1-(1-methylazetidin-3-yl)-1H-pyrazol-4-yl)amino)pyrimidin-4-yl)-2-(trifluoromethyl)benzyl)azetidine-1-carboxamide as a yellow solid (11 mg, yield: 11%). ESI-MS (M+H)$^+$: 559.2. $^1$H NMR (400 MHz, CD$_3$OD) δ: 8.40 (s, 1H), 8.38 (d, J=5.2 Hz, 1H), 8.23 (d, J=8.0 Hz, 1H), 8.06 (s, 1H), 7.63 (s, 1H), 7.60 (d, J=8.0 Hz, 1H), 7.19 (d, J=5.2 Hz, 1H), 4.95-4.91 (m, 1H), 4.52-4.48 (m, 1H), 4.49 (s, 2H), 4.11-4.08 (m, 2H), 3.89-3.85 (m, 2H), 3.73-3.69 (m, 2H), 3.65-3.60 (m, 2H), 2.46 (s, 3H), 1.10 (s, 9H).

Example 200: 3-(tert-butyl)-N-(4-(2-(0-((S)-1-methylpyrrolidin-3-yl)-1H-pyrazol-4-yl)amino)pyrimidin-4-yl)-2-(trifluoromethyl)benzyl)pyrrolidine-1-carboxamide

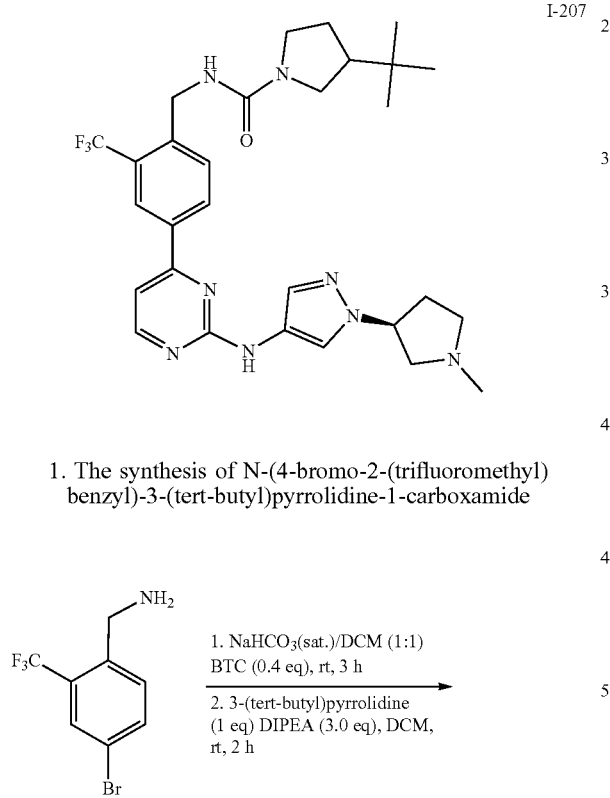

I-207

1. The synthesis of N-(4-bromo-2-(trifluoromethyl)benzyl)-3-(tert-butyl)pyrrolidine-1-carboxamide To a solution of 4-bromo-2-(trifluoromethyl)phenyl)methanamine (1.46 g, 5.8 mmol) in saturated aqueous NaHCO$_3$/DCM (30 mL, 1:1) was added BTC (690 mg, 2.3 mmol) at 0° C. The mixture was stirred at rt for 1 h. After diluting with DCM (120 mL), the mixture was washed with brine (50 mL). The organic phase was dried (Na$_2$SO$_4$), filtered and the solvent was reduced to about 20 mL. Then DIPEA (2.24 g, 17.4 mmol) and 3-(tert-butyl)pyrrolidine (737 mg, 5.8 mmol) was added and the mixture was stirred at rt for 2 h, diluted with CH$_2$Cl$_2$ (100 mL) and washed with brine (50 mL). The organic phase was concentrated in vacuo and the residue was purified by prep-HPLC (MeCN/water with 0.05% NH$_4$OH as mobile phase) to give N-(4-bromo-2-(trifluoromethyl)benzyl)-3-(tert-butyl)pyrrolidine-1-carboxamide (1.5 g, yield: 64%) as yellow solid. ESI-MS (M+H)$^+$: 407.1. $^1$H NMR (400 MHz, CD$_3$OD): δ: 7.72-7.67 (m, 2H), 7.40 (d, J=8.4 Hz, 1H), 4.45-4.42 (m, 2H), 3.50-3.48 (m, 1H), 3.41-3.38 (m, 1H), 3.20-3.18 (m, 1H), 3.04-2.99 (m, 1H), 2.03-2.02 (m, 1H), 1.88-1.82 (m, 1H), 1.66-1.61 (m, 1H), 0.88 (s, 9H).

2. The synthesis of 3-(tert-butyl)-N-(4-(2-chloropyrimidin-4-yl)-2-(trifluoromethyl)benzyl) pyrrolidine-1-carboxamide

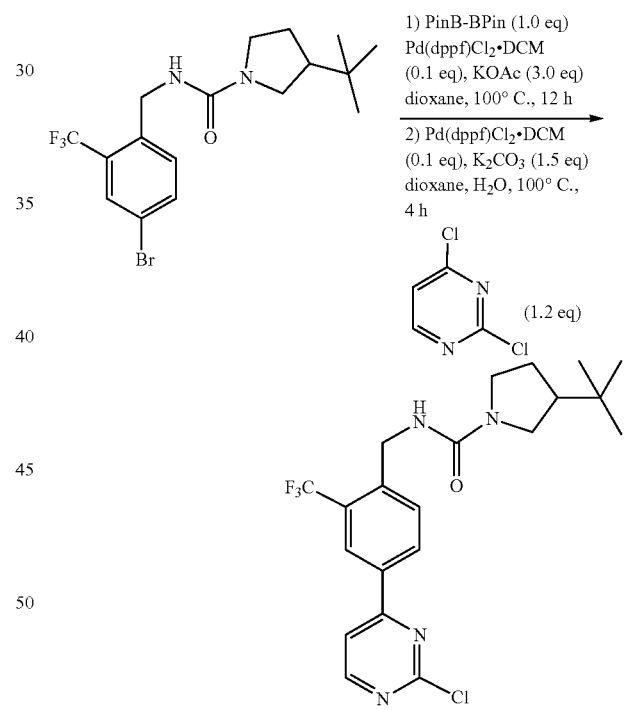

To a mixture of N-(4-bromo-2-(trifluoromethyl)benzyl)-3-(tert-butyl)pyrrolidine-1-carboxamide (1.5 g, 3.7 mmol) and PinB-BPin (940 mg, 3.7 mmol) in 1,4-dioxane (20 mL), KOAc (718 mg, 7.4 mmol), Pd(dppf)Cl$_2$.CH$_2$Cl$_2$ (300 mg, 0.37 mmol) was added. The mixture was stirred at 100° C. for 12 h under N$_2$. After cooling to rt, 2,4-dichloropyrimidine (658 mg, 4.44 mmol), K$_2$CO$_3$ (766 mg, 5.55 mmol) and H$_2$O (5 mL) were added. The resulting mixture was stirred at 100° C. for 4 h under N$_2$. After diluting with EtOAc (200 mL), the mixture was washed with water (50 mL×2). The organic phase was dried and concentrated in vacuo to afford a residue which was purified by prep-HPLC (MeCN/water with 0.05% NH₄OH as mobile phase) to give 3-(tert-butyl)-N-(4-(2-chloropyrimidin-4-yl)-2-(trifluoromethyl)benzyl)pyrrolidine-1-carboxamide (750 mg, yield: 50%) as yellow solid. ESI-MS (M+H)⁺: 441.2. ¹H NMR (400 MHz, CD₃OD): δ: 8.76-8.74 (m, 1H), 8.50 (d, J=1.2 Hz, 1H), 8.41-8.38 (m, 1H), 8.06-8.03 (m, 1H), 7.75 (d, J=8.0 Hz, 1H), 4.66 (s, 2H), 3.63-3.59 (m, 1H), 3.53-3.49 (m, 1H), 3.36-3.34 (m, 1H), 3.15-3.11 (m, 1H), 2.18-2.15 (m, 1H), 1.98-1.93 (m, 1H), 1.77-1.72 (m, 1H), 0.98 (s, 9H).

3. Synthesis of (3S)-tert-butyl 3-(4-((4-(4-((3-(tert-butyl)pyrrolidine-1-carboxamido)methyl)-3-(trifluoromethyl)phenyl)pyrimidin-2-yl)amino)-1H-pyrazol-1-yl)pyrrolidine-1-carboxylate

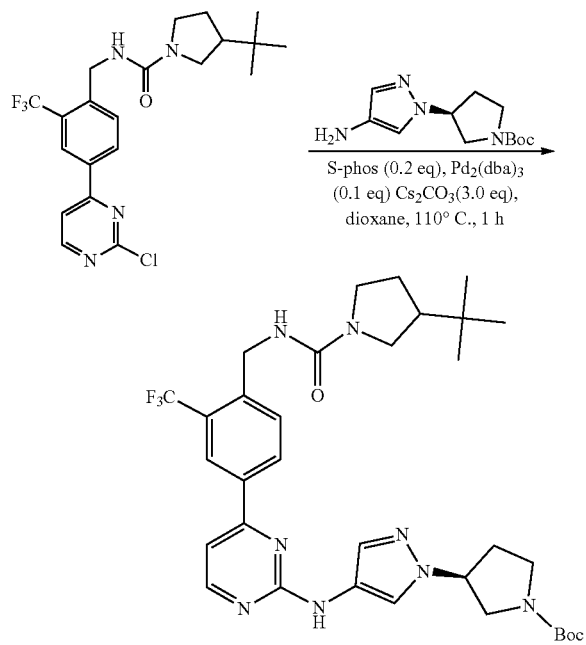

Synthesis of (3 S)-tert-butyl 3-(44(4-(44(3-(tert-butyl)pyrrolidine-1-carboxamido)methyl)-3-(trifluoromethyl)phenyl)pyrimidin-2-yl)amino)-1H-pyrazol-1-yl)pyrrolidine-1-carboxylate was similar to that of Example 161. The residue was purified by prep-TLC (PE:EA=1/3) to give (3 S)-tert-butyl 3-(44(4-(44(3-(tert-butyl)pyrrolidine-1-carboxamido)methyl)-3-(trifluoromethyl)phenyl)pyrimidin-2-yl)amino)-1H-pyrazol-1-yl)pyrrolidine-1-carboxylate (280 mg, yield: 63%) as a yellow solid. ESI-MS (M+H)⁺: 657.3.

4. Synthesis of 3-(tert-butyl)-N-(4-(2-((1-((S)-pyrrolidin-3-yl)-1H-pyrazol-4-yl)amino)pyrimidin-4-yl)-2-(trifluoromethyl)benzyl)pyrrolidine-1-carboxamide

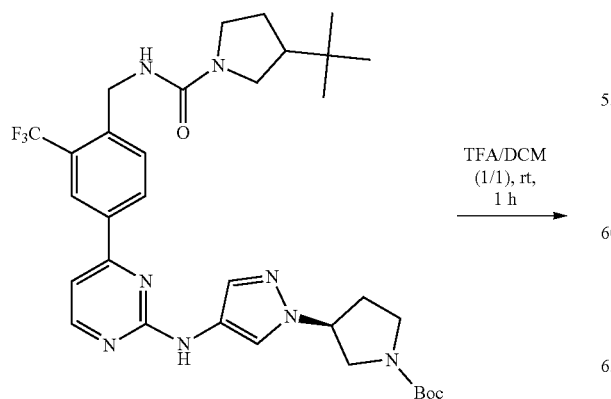

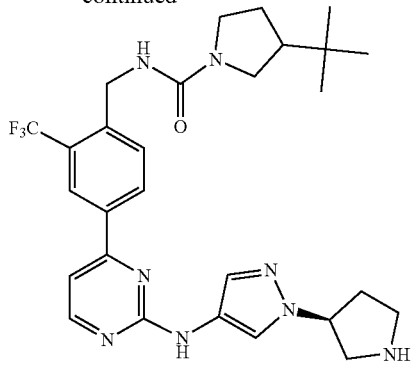

Synthesis of 3-(tert-butyl)-N-(4-(2-((1-((S)-pyrrolidin-3-yl)-1H-pyrazol-4-yl)amino)pyrimidin-4-yl)-2-(trifluoromethyl)benzyl)pyrrolidine-1-carboxamide was similar to that of Example 121. The crude product was purified by prep-HPLC (MeCN/water with 0.05% NH₄OHas mobile phase) to give 3-(tert-butyl)-N-(4-(2-((1-((S)-pyrrolidin-3-yl)-1H-pyrazol-4-yl)amino)pyrimidin-4-yl)-2-(trifluoromethyl)benzyl)pyrrolidine-1-carboxamide (144 mg, yield: 68%) as yellow solid. ESI-MS (M+H)⁺:557.3. ¹H NMR (400 MHz, CD₃OD) δ: 8.36 (s, 1H), 8.32 (d, J=5.2 Hz, 1H), 8.15 (d, J=8.4 Hz, 1H), 7.94 (s, 1H), 7.58-7.56 (m, 2H), 7.11 (d, J=4.8 Hz, 1H), 4.87-4.82 (m, 1H), 4.56-4.52 (m, 2H), 3.51-3.49 (m, 2H), 3.40-3.38 (m, 1H), 3.31-3.17 (m, 3H), 3.07-2.99 (m, 2H), 2.34-2.25 (m, 1H), 2.18-2.10 (m, 1H), 2.05-1.97 (m, 1H), 1.85-1.79 (m, 1H), 1.67-1.56 (m, 1H), 0.85 (s, 9H).

5. Synthesis of 3-(tert-butyl)-N-(4-(2-((1-((S)-1-methylpyrrolidin-3-yl)-1H-pyrazol-4-yl)amino)pyrimidin-4-yl)-2-(trifluoromethyl)benzyl)pyrrolidine-1-carboxamide

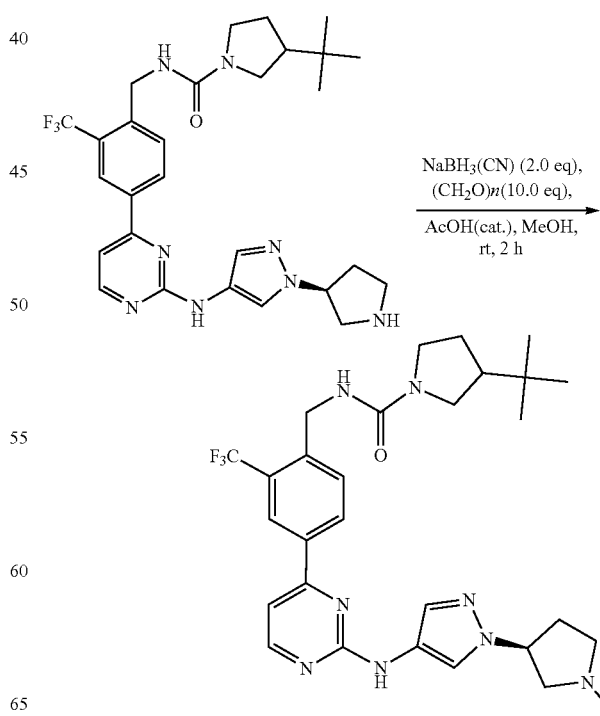

To a solution of 3-(tert-butyl)-N-(4-(2-((1-((S)-1-methylpyrrolidin-3-yl)-1H-pyrazol-4-yl)amino)pyrimidin-4-yl)-2-(trifluoromethyl)benzyl)pyrrolidine-1-carboxamide (86 mg, 0.155 mmol) in MeOH (10 mL) was added NaBH$_3$CN (20 mg, 0.74 mmol), (CH$_2$O)$_n$ (47 mg, 1.55 mmol) and AcOH (cat.) in MeOH (10 mL). The mixture was stirred at rt for 16 h. After filtration through a Celite pad, the filtrate was concentrated in vacuo to afford a residue which was purified by prep-HPLC (MeCN/water with 0.05% NH$_4$HCO$_3$ as mobile phase) to give 3-(tert-butyl)-N-(4-(2-((1-((S)-1-methylpyrrolidin-3-yl)-1H-pyrazol-4-yl)amino)pyrimidin-4-yl)-2-(trifluoromethyl) benzyl)pyrrolidine-1-carboxamide as a yellow solid (53 mg, yield: 40%). ESI-MS (M+H)$^+$: 571.3. $^1$H NMR (400 MHz, CDCl$_3$) δ: 8.46 (d, J=5.2 Hz, 1H), 8.36 (s, 1H), 8.14 (d, J=8.0 Hz, 1H), 8.06 (s, 1H), 7.78 (d, J=8.0 Hz, 1H), 7.55 (s, 1H), 7.06 (d, J=5.2 Hz, 1H), 4.91-4.87 (m, 1H), 4.78-4.76 (m, 1H), 4.67-4.65 (m, 2H), 3.54-3.45 (m, 2H), 3.30-3.24 (m, 1H), 3.07-2.86 (m, 4H), 2.65-2.59 (m, 1H), 2.53-2.45 (m, 1H), 2.42 (s, 3H), 2.29-2.21 (m, 1H), 2.10-2.09 (m, 1H), 1.91-1.85 (m, 1H), 1.73-1.65 (m, 1H), 0.92 (s, 9H).

Example 201: 3-(tert-butyl)-N-(4-(2-((1-((R)-1-methylpyrrolidin-3-yl)-1H-pyrazol-4-yl)amino)pyrimidin-4-yl)-2-(trifluoromethyl)benzyl)pyrrolidine-1-carboxamide

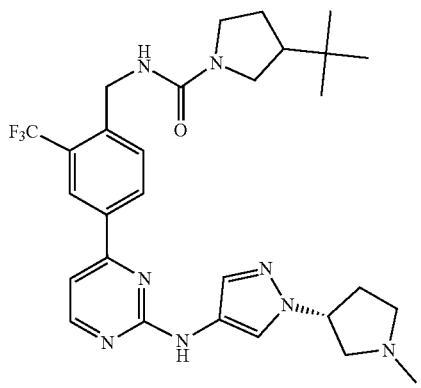

I-208

Synthesis of 3-(tert-butyl)-N-(4-(2-((1-((R)-1-methylpyrrolidin-3-yl)-1H-pyrazol-4-yl)amino)pyrimidin-4-yl)-2-(trifluoromethyl)benzyl)pyrrolidine-1-carboxamide was similar to that of Example 200. The residue was purified by column chromatography (silica, DCM/MeOH=10:1) to give 3-(tert-butyl)-N-(4-(2-((1-((R)-1-methylpyrrolidin-3-yl)-1H-pyrazol-4-yl)amino)pyrimidin-4-yl)-2-(trifluoromethyl)benzyl)pyrrolidine-1-carboxamide (36 mg, yield: 35%) as a slight yellow solid. ESI-MS (M+H)$^+$: 571.3. $^1$H NMR (400 MHz, CD$_3$OD) δ: 8.36-8.33 (m, 2H), 8.19 (d, J=8.4 Hz, 1H), 8.03 (s, 1H), 7.60-7.55 (m, 2H), 7.14 (d, J=5.2 Hz, 1H), 4.89-4.85 (m, 1H), 4.57-4.50 (m, 2H), 3.52-3.47 (m, 1H), 3.42-3.37 (m, 1H), 3.21-3.15 (m, 1H), 3.07-2.93 (m, 4H), 2.74-2.68 (m, 1H), 2.43 (s, 3H), 2.41-2.39 (m, 1H), 2.16-2.10 (m, 1H), 2.02-2.01 (m, 1H), 1.87-1.80 (m, 1H), 1.65-1.60 (m, 1H), 0.86 (s, 9H).

Example 202: 3-(tert-butyl)-N-(4-(2-((1-(2-hydroxyethyl)-1H-pyrazol-4-yl)amino)pyrimidin-4-yl)-2-(trifluoromethyl)benzyl)pyrrolidine-1-carboxamide

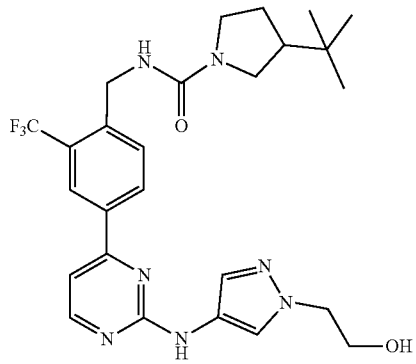

I-209

Synthesis of 3-(tert-butyl)-N-(4-(2-((1-(2-hydroxyethyl)-1H-pyrazol-4-yl)amino)pyrimidin-4-yl)-2-(trifluoromethyl)benzyl)pyrrolidine-1-carboxamide was similar to Example 198. The crude material was purified by prep-HPLC (MeCN/water with 0.05% NH$_4$OH as mobile phase) to give N-(4-(2-((1-(2-((tert-butyldimethylsilyl)oxy)ethyl)-1H-pyrazol-4-yl)amino)pyrimidin-4-yl)-2-methylbenzyl)-3-isopropoxyazetidine-1-carboxamide (68 mg, yield: 59%) as a yellow solid. ESI-MS (M+H)$^+$: 532.3. $^1$H NMR (400 MHz, CD$_3$OD) δ: 8.45 (s, 1H), 8.40 (d, J=5.2 Hz, 1H), 8.26 (d, J=7.6 Hz, 1H), 8.03 (s, 1H), 7.68-7.66 (m, 2H), 7.21 (d, J=5.6 Hz, 1H), 4.64-4.63 (m, 2H), 4.21 (t, J=5.2 Hz, 2H), 3.91 (t, J=5.6 Hz, 2H), 3.62-3.57 (m, 1H), 3.52-3.48 (m, 1H), 3.30-3.28 (m, 1H), 3.15-3.10 (m, 1H), 2.13-2.11 (m, 1H), 1.93-1.91 (m, 1H), 1.73-1.70 (m, 1H), 0.96 (s, 9H).

Example 203: 3-(tert-butyl)-N-(2-cyano-4-(2-((1-methyl-1H-pyrazol-4-yl)amino)pyrimidin-4-yl)benzyl)pyrrolidine-1-carboxamide

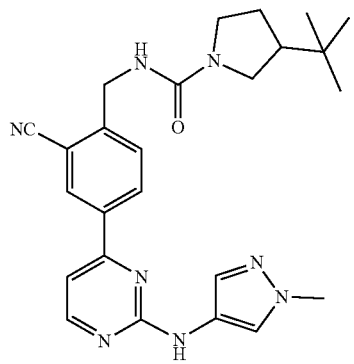

I-210

1. The Preparation of tert-butyl 2-chloro-4-(2-chloropyrimidin-4-yl)benzylcarbamate

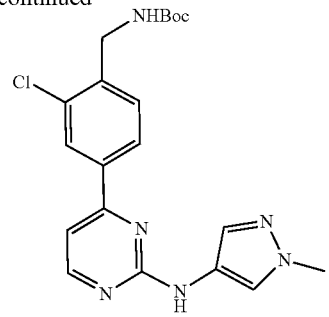

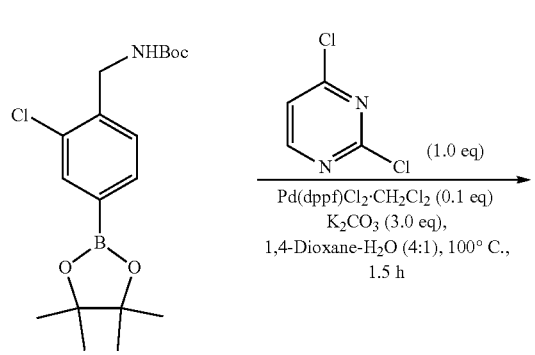

Synthesis of tert-butyl 2-chloro-4-(2-chloropyrimidin-4-yl)benzylcarbamate was similar to that of tert-butyl 4-(2-chloropyrimidin-4-yl)-2-methylbenzylcarbamate. The crude was purified by silica gel column (petroleum ether: EtOAc=5:1-3:1) to give tert-butyl 2-chloro-4-(2-chloropyrimidin-4-yl)benzylcarbamate as a white solid (1.3 g, yield: 78%). ESI-MS (M+H)+: 354.1. $^1$H NMR (400 MHz, CD$_3$OD) δ: 8.73 (d, J=5.2 Hz, 1H), 8.24 (J=1.6 Hz, 1H), 8.12 (dd, J=8.0, 1.6 Hz, 1H), 7.98 (d, J=5.6 Hz, 1H), 7.55 (d, J=8.4 Hz, 1H), 4.42 (s, 2H), 1.26 (s, 9H).

2. The preparation of tert-butyl 2-chloro-4-(2-((1-methyl-1H-pyrazol-4-yl)amino)pyrimidin-4-yl)benzylcarbamate

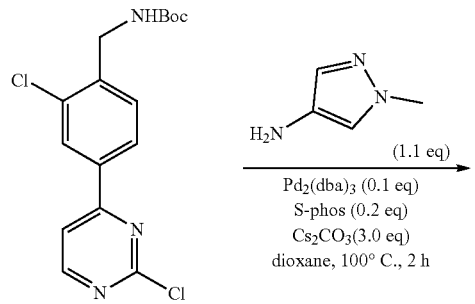

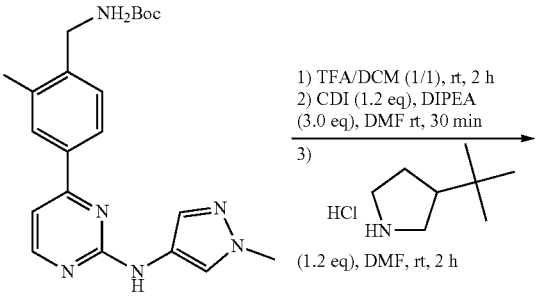

Synthesis of tert-butyl 2-chloro-4-(2-((1-methyl-1H-pyrazol-4-yl)amino)pyrimidin-4-yl)benzylcarbamate was similar to that of tert-butyl 2-methyl-4-(2-((1-methyl-1H-pyrazol-4-yl)amino)pyrimidin-4-yl)benzylcarbamate. The residue was purified by column chromatography (silica, petroleum ether/EtOAc=1:4) to give tert-butyl 2-chloro-4-(2-((1-methyl-1H-pyrazol-4-yl)amino)pyrimidin-4-yl)benzylcarbamate as a yellow solid (143 mg, yield: 41%). ESI-MS (M+H)+: 415.2.

3. Synthesis of 3-(tert-butyl)-N-(2-chloro-4-(2-((1-methyl-1H-pyrazol-4-yl)amino)pyrimidin-4-yl)benzyl)pyrrolidine-1-carboxamide

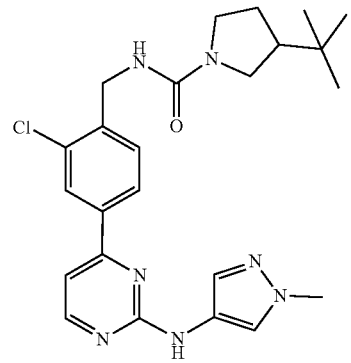

To a solution of 4-(4-(aminomethyl)-3-chlorophenyl)-N-(1-methyl-1H-pyrazol-4-yl)pyrimidin-2-amine (200 mg, 0.64 mmol) in DMF (5 mL) was added DIPEA (248 mg, 1.92 mmol) and CDI (125 mg, 0.77 mmol). After stirring at rt for 30 min, 3-(tert-butyl)pyrrolidine (126 mg, 0.77 mmol) was added to the solution. The resulting solution was stirred for another 2 h, and then purified by prep-HPLC (CH$_3$CN/H$_2$O with 0.05% NH$_4$OH as mobile phase) to give 3-(tert-butyl)-N-(2-chloro-4-(2-((1-methyl-1H-pyrazol-4-yl)amino)pyrimidin-4-yl)benzyl)pyrrolidine-1-carboxamide as a yellow solid (120 mg, yield: 53%). ESI-MS (M+H)+:

468.2. ¹H NMR (400 MHz, CDCl₃) δ: 8.44 (d, J=5.2 Hz, 1H), 8.06 (d, J=1.2 Hz, 1H), 7.88-7.86 (m, 2H), 7.60 (d, J=8.4 Hz, 1H), 7.54 (s, 1H), 7.04 (d, J=5.2 Hz, 1H), 6.94 (s, 1H), 4.78-4.76 (m, 1H), 4.57-4.55 (m, 2H), 3.93 (s, 3H), 3.59-3.40 (m, 2H), 3.28-3.25 (m, 1H), 3.04 (t, 10.0 Hz, 1H), 2.15-2.01 (m, 1H), 1.87-1.85 (m, 1H), 1.67-1.63 (m, 1H), 0.92 (s, 9H).

4. Synthesis of 3-(tert-butyl)-N-(2-cyano-4-(2-((1-methyl-1H-pyrazol-4-yl)amino)pyrimidin-4-yl)benzyl)pyrrolidine-1-carboxamide

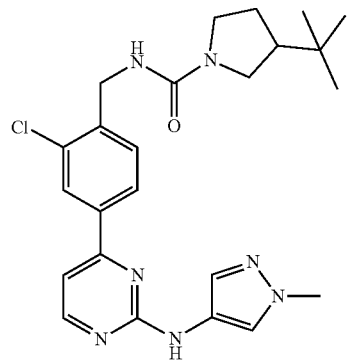

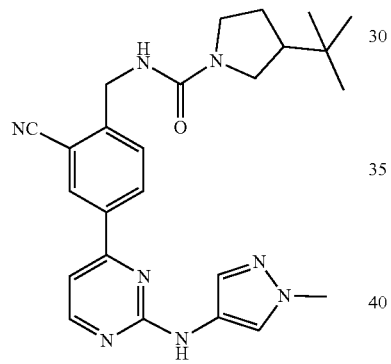

An oven-dried pressure tube, which was equipped with a magnetic stir bar, was charged with Pd(OAc)₂ (6 mg, 0.026 mmol), X-phos (25 mg, 0.052), K₄[Fe(CN)₆].3H₂O (27 mg, 0.065 mmol), K₂CO₃ (36 mg, 0.26 mmol). The tube was evacuated and backfilled with N₂ for 3 times and then 3-(tert-butyl)-N-(2-chloro-4-(2-((1-methyl-1H-pyrazol-4-yl)amino)pyrimidin-4-yl)benzyl)pyrrolidine-1-carboxamide (120 mg, 0.26 mmol) and 1,4-dioxane/water (4:1, 2.0 mL) were added. The pressure tube was sealed and the mixture was stirred at 100° C. for 10 h and then cooled to rt. The mixture was filtered and the filtrate was concentrated in vacuo to give a residue that was purified by prep-HPLC (CH₃CN/H₂O with 0.05% NH₄OH as mobile phase) to give 3-(tert-butyl)-N-(2-cyano-4-(2-((1-methyl-1H-pyrazol-4-yl)amino)pyrimidin-4-yl)benzyl)pyrrolidine-1-carboxamide as a yellow solid (54 mg, yield: 46%). ESI-MS (M+H)⁺: 459.3. ¹H NMR (400 MHz, CDCl₃) δ: 8.47 (d, J=5.2 Hz, 1H), 8.29 (s, 1H), 8.16 (d, J=8.0 Hz, 1H), 7.86 (s, 1H), 7.74 (d, J=8.4 Hz, 1H), 7.53 (s, 1H), 7.21 (s, 1H), 7.03 (d, J=5.2 Hz, 1H), 5.06 (t, J=5.6 Hz, 1H), 4.70-4.54 (m, 2H), 3.93 (s, 3H), 3.64-3.39 (m, 2H), 3.35-3.20 (m, 1H), 3.05 (t, J=10.0 Hz, 1H), 2.13-1.98 (m, 1H), 1.94-1.83 (m, 1H), 1.73-1.58 (m, 1H), 0.92 (s, 9H).

Example 204: 1-(tert-butyl)-N-(2-cyano-4-(2-((1-methyl-1H-pyrazol-4-yl)amino)pyrimidin-4-yl)benzyl)-1H-pyrazole-4-carboxamide

I-211

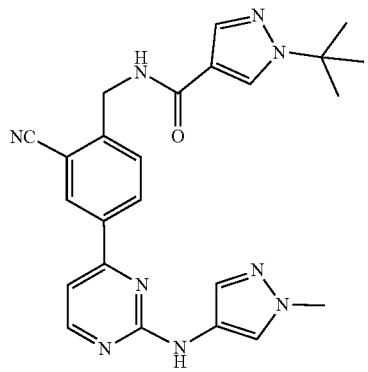

1. The preparation of 1-(tert-butyl)-N-(2-chloro-4-(2-((1-methyl-1H-pyrazol-4-yl)amino)pyrimidin-4-yl)benzyl)-1H-pyrazole-4-carboxamide

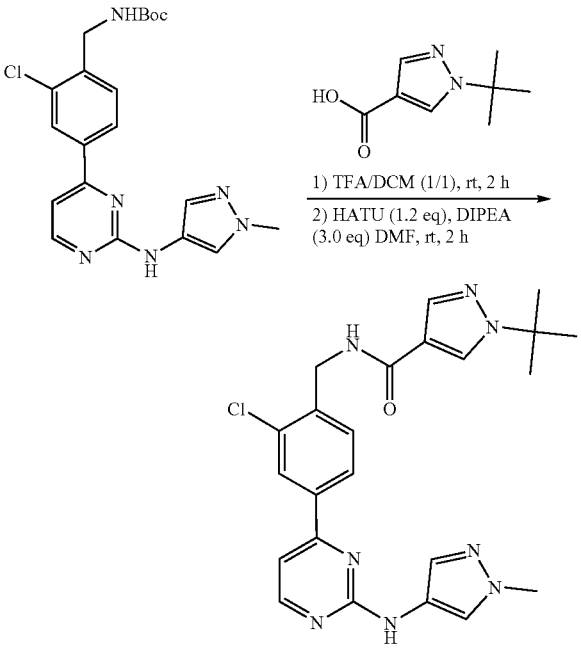

Synthesis of 1-(tert-butyl)-N-(2-chloro-4-(2-((1-methyl-1H-pyrazol-4-yl)amino)pyrimidin-4-yl)benzyl)-1H-pyrazole-4-carboxamide was similar to that of Example 1. The residue was purified by prep-HPLC (CH₃CN/H₂O with 0.05% NH₃.H₂O as mobile phase) to give 1-(tert-butyl)-N-(2-chloro-4-(2-((1-methyl-1H-pyrazol-4-yl)amino)pyrimidin-4-yl)benzyl)-1H-pyrazole-4-carboxamide as a yellow solid (58 mg, yield: 62%). ESI-MS (M+H)⁺: 465.2. ¹H NMR (400 MHz, CD₃OD) δ: 8.61 (t, J=5.6 Hz, 1H), 8.31-8.29 (m, 1H), 8.18 (s, 1H), 8.07 (s, 1H), 7.91-7.88 (m, 2H), 7.83 (s, 1H), 7.51 (s, 1H), 7.41 (d, J=8.0 Hz, 1H), 7.08-7.06 (m, 1H), 4.56 (s, 2H), 3.77 (s, 3H), 1.49 (s, 9H).

2. The preparation of 1-(tert-butyl)-N-(2-cyano-4-(2-((1-methyl-1H-pyrazol-4-yl)amino)pyrimidin-4-yl)benzyl)-1H-pyrazole-4-carboxamide

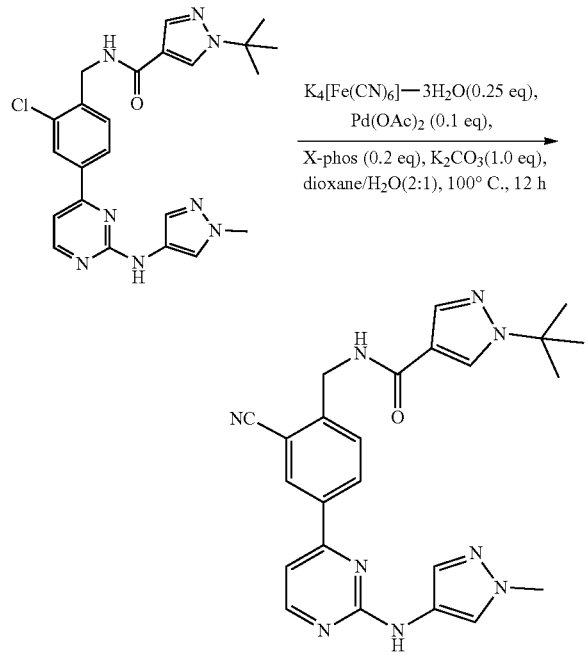

Synthesis of 1-(tert-butyl)-N-(2-cyano-4-(2-((1-methyl-1H-pyrazol-4-yl)amino)pyrimidin-4-yl)benzyl)-1H-pyrazole-4-carboxamide was similar to that of Example 203. The crude product was purified by prep-TLC (petroleum ether: EtOAc=1/3) to give 1-(tert-butyl)-N-(2-cyano-4-(2-((1-methyl-1H-pyrazol-4-yl)amino)pyrimidin-4-yl)benzyl)-1H-pyrazole-4-carboxamide as a yellow solid (6 mg, yield: 4%). ESI-MS (M+H)$^+$: 456.2. $^1$H NMR (400 MHz, CDCl$_3$) δ: 8.47 (d, J=4.8 Hz, 1H), 8.31 (d, J=1.2 Hz, 1H), 8.18 (dd, J=6.8, 1.2 Hz, 1H), 8.05 (s, 1H), 7.85-7.84 (m, 1H), 7.72 (d, J=8.4 Hz, 1H), 7.52 (s, 1H), 7.27 (s, 1H), 7.03 (d, J=5.6 Hz, 1H), 6.59 (br, 1H), 4.82 (d, J=6.4 Hz, 2H), 3.92 (s, 3H), 1.60 (s, 9H).

Example 205: 3-isopropoxy-N-(2-methyl-4-(2-((1-(2-methyl-1-(methylamino)-1-oxopropan-2-yl)-1H-pyrazol-4-yl)amino)pyrimidin-4-yl)benzyl)azetidine-1-carboxamide

I-212

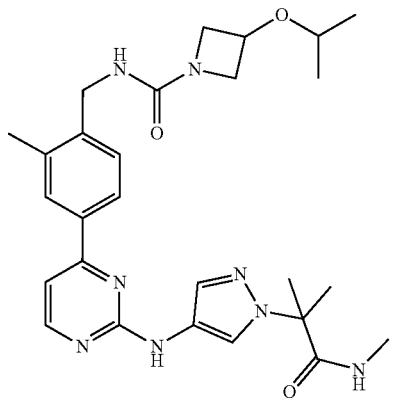

1. Synthesis of N-(4-(6-chloropyrimidin-4-yl)-2-methylbenzyl)-3-isopropoxyazetidine-1-carboxamide

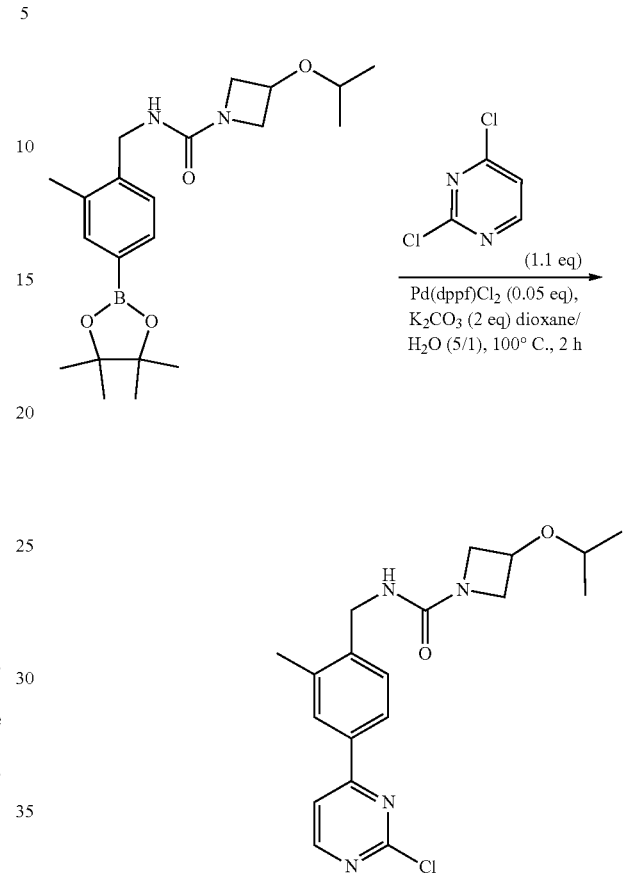

Synthesis of N-(4-(2-chloropyrimidin-4-yl)-2-methylbenzyl)-3-isopropoxyazetidine-1-carboxamide was similar to that of N-(4-(6-chloropyrimidin-4-yl)-2-methylbenzyl)-3-isopropoxyazetidine-1-carboxamide. The crude was purified through silica gel column chromatography (MeOH/DCM=1/30) to give N-(4-(6-chloropyrimidin-4-yl)-2-methylbenzyl)-3-isopropoxyazetidine-1-carboxamide (130 mg, yield: 77%) as yellow oil. ESI-MS (M+H)$^+$: 375.0.

2. Synthesis of 3-isopropoxy-N-(2-methyl-4-(2-((1-(2-methyl-1-(methylamino)-1-oxopropan-2-yl)-1H-pyrazol-4-yl)amino)pyrimidin-4-yl)benzyl)azetidine-1-carboxamide

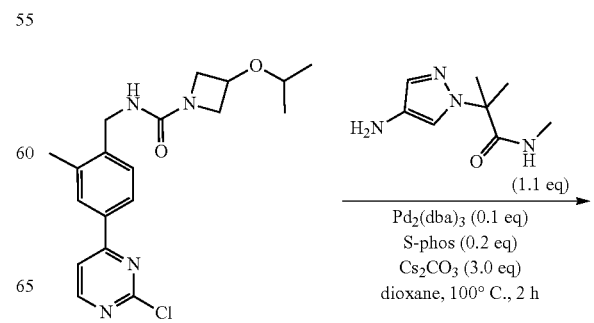

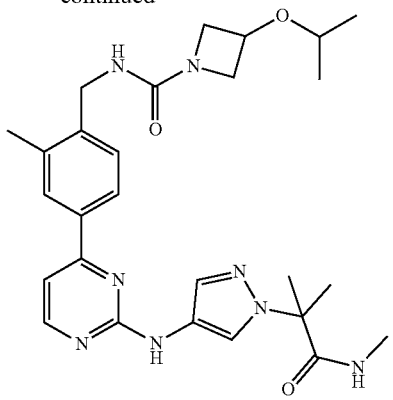

Synthesis of 3-isopropoxy-N-(2-methyl-4-(2-((1-(2-methyl-1-(methylamino)-1-oxopropan-2-yl)-1H-pyrazol-4-yl)amino)pyrimidin-4-yl)benzyl)azetidine-1-carboxamide was similar to that of tert-butyl 2-methyl-4-(2-((1-methyl-1H-pyrazol-4-yl)amino)pyrimidin-4-yl)benzylcarbamate. The crude product was purified by prep-HPLC (CH$_3$CN/H$_2$O with 0.05% NH$_4$OH as mobile phase) to give 3-isopropoxy-N-(2-methyl-4-(2-((1-(2-methyl-1-(methylamino)-1-oxopropan-2-yl)-1H-pyrazol-4-yl)amino)pyrimidin-4-yl)benzyl)azetidine-1-carboxamide as a yellow solid (112 mg, yield: 54%). ESI-MS (M+H)$^+$: 521.3. $^1$H NMR (400 MHz, CD$_3$OD) δ: 8.40 (d, J=5.2 Hz, 1H), 8.26 (s, 1H), 7.96 (s, 1H), 7.94 (d, J=8.0 Hz, 1H), 7.75 (s, 1H), 7.40 (d, J=8.0 Hz, 1H), 7.23 (d, J=5.2 Hz, 1H), 4.46-4.40 (m, 1H), 4.39 (s, 2H), 4.19-4.16 (m, 2H), 3.82-3.79 (m, 2H), 3.69-3.64 (m, 1H), 2.71 (s, 3H), 2.43 (s, 3H), 1.83 (s, 6H), 1.17 (d, J=5.6 Hz, 6H).

Example 206: 3-isopropoxy-N-(4-(2-((1-(2-methoxyethyl)-1H-pyrazol-4-yl)amino)pyrimidin-4-yl)-2-methylbenzyl)azetidine-1-carboxamide

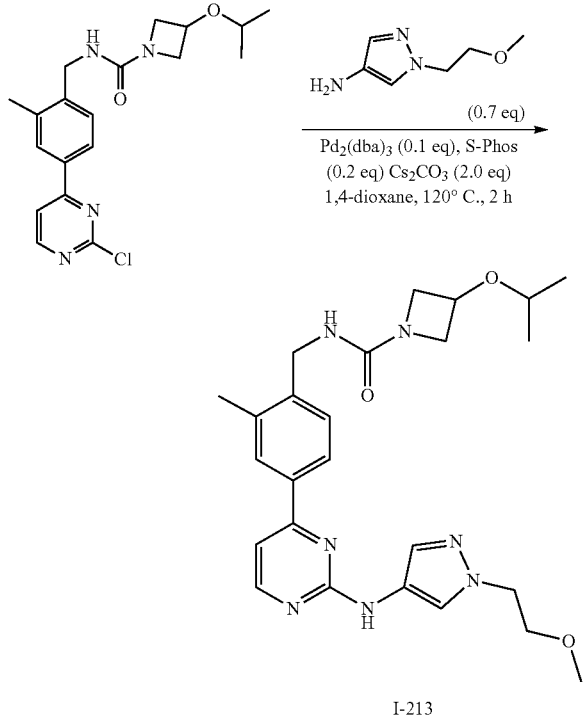

I-213

Synthesis of 3-isopropoxy-N-(4-(2-((1-(2-methoxyethyl)-1H-pyrazol-4-yl)amino)pyrimidin-4-yl)-2-methylbenzyl)azetidine-1-carboxamide was similar to that of tert-butyl 2-methyl-4-(2-((1-methyl-1H-pyrazol-4-yl)amino)pyrimidin-4-yl)benzylcarbamate. The residue was purified by silica gel column chromatography (EtOAc: petroleum ether=2:1) to give 3-isopropoxy-N-(4-(2-((1-(2-methoxyethyl)-1H-pyrazol-4-yl)amino)pyrimidin-4-yl)-2-methylbenzyl)azetidine-1-carboxamide as a yellow solid (85 mg, yield: 25%). ESI-MS (M+H)$^+$: 480.2. $^1$H NMR (400 MHz, CD$_3$OD) δ: 8.28 (d, J=5.2 Hz, 1H), 7.98 (s, 1H), 7.85-7.83 (m, 2H), 7.56 (s, 1H), 7.27 (d, J=8.4 Hz, 1H), 7.09 (d, J=5.2 Hz, 1H), 4.33-4.30 (m, 1H), 4.28 (s, 2H), 4.19 (t, J=5.2 Hz, 2H), 4.09-4.05 (m, 2H), 3.72-3.68 (m, 2H), 3.65 (t, J=5.2 Hz, 2H), 3.59-3.53 (m, 1H), 3.25 (s, 3H), 2.33 (s, 3H), 1.05 (d, J=6.4 Hz, 6H).

Example 207: 3-(tert-butoxy)-N-(4-(2-((1-(2-hydroxyethyl)-1H-pyrazol-4-yl)amino)pyrimidin-4-yl)-2-methylbenzyl)azetidine-1-carboxamide

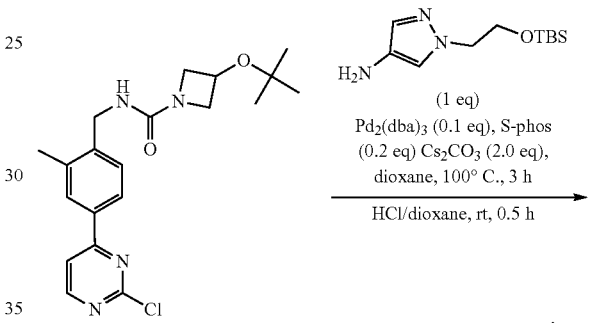

I-214

Synthesis of 3-(tert-butoxy)-N-(4-(2-((1-(2-hydroxyethyl)-1H-pyrazol-4-yl)amino)pyrimidin-4-yl)-2-methylbenzyl)azetidine-1-carboxamide was similar to that of N-(4-(2-((1-(2-((tert-butyldimethylsilyl)oxy)ethyl)-1H-pyrazol-4-yl)amino)pyrimidin-4-yl)-2-methylbenzyl)-3-isopropoxyazetidine-1-carboxamide except the 3-isopropoxyazetidine was substituted for the 3-(tert-butoxy)azetidine. The crude was purified by prep-HPLC (MeCN/H$_2$O with 0.05% NH$_4$OH as mobile phase) to give 3-(tert-butoxy)-N-(4-(2-((1-(2-hydroxyethyl)-1H-pyrazol-4-yl)amino)pyrimidin-4-yl)-2-methylbenzyl)azetidine-1-carboxamide as a yellow solid (80 mg, yield: 54%). ESI-MS (M+H)$^+$: 480.3. $^1$H NMR (400 MHz, CD$_3$OD) δ: 8.38 (d, J=5.2 Hz, 1H), 8.10 (s, 1H), 7.95-7.93 (m, 2H), 7.68 (s, 1H), 7.39 (d, J=8.8 Hz, 1H), 7.20 (d, J=5.2 Hz, 1H), 4.61-4.55 (m, 1H), 4.38 (s, 2H), 4.23 (t, J=5.2 Hz, 2H), 4.19-4.15 (m, 2H), 3.91 (t, J=5.2 Hz, 2H), 3.80-3.77 (m, 2H), 2.43 (s, 3H), 1.20 (s, 9H).

Example 208: 3-(tert-butoxy)-N-(2-methyl-4-(2-((1-(1-methylazetidin-3-yl)-1H-pyrazol-4-yl)amino)pyrimidin-4-yl)benzyl)azetidine-1-carboxamide

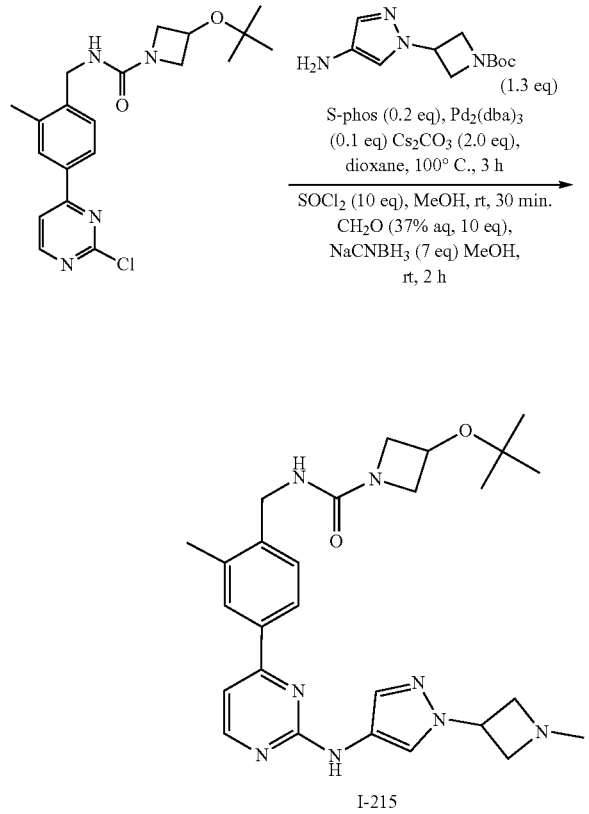

Synthesis of 3-(tert-butoxy)-N-(2-methyl-4-(2-((1-(1-methylazetidin-3-yl)-1H-pyrazol-4-yl)amino)pyrimidin-4-yl)benzyl)azetidine-1-carboxamide was similar to that of 3-(tert-butoxy)-N-(4-(2-((1-(1-methylazetidin-3-yl)-1H-pyrazol-4-yl)amino)pyrimidin-4-yl)-2-(trifluoromethyl)benzyl)azetidine-1-carboxamide. The crude product was purified by silica gel column chromatography (MeOH/DCM=1/8) to give 3-(tert-butoxy)-N-(2-methyl-4-(2-((1-(1-methylazetidin-3-yl)-1H-pyrazol-4-yl)amino)pyrimidin-4-yl)benzyl)azetidine-1-carboxamide as a yellow solid (95 mg, yield: 40%). ESI-MS (M+H)⁺: 505.3. ¹H NMR (400 MHz, CD₃OD) δ: 8.28 (d, J=5.2 Hz, 1H), 8.08 (s, 1H), 7.83-7.82 (m, 2H), 7.63 (s, 1H), 7.27 (d, J=8.4 Hz, 1H), 7.09 (d, J=5.2 Hz, 1H), 4.93-4.85 (m, 1H), 4.50-4.44 (m, 1H), 4.27 (s, 2H), 4.07-4.03 (m, 2H), 3.81-3.77 (m, 2H), 3.69-3.66 (m, 2H), 3.54-3.50 (m, 2H), 2.40 (s, 3H), 2.31 (s, 3H), 1.09 (s, 9H).

Example 209: 3-(tert-butoxy)-N-(4-(2-((1-ethyl-1H-pyrazol-4-yl)amino)pyrimidin-4-yl)-2-methylbenzyl)azetidine-1-carboxamide

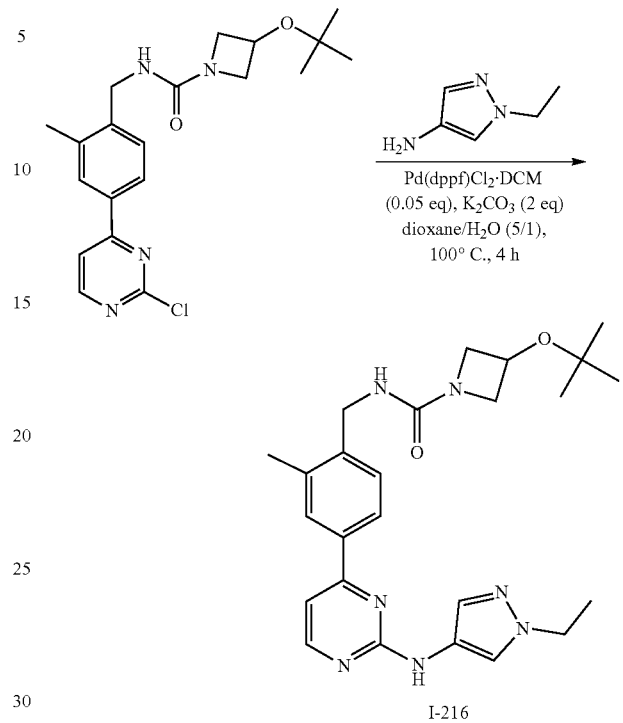

Synthesis of 3-(tert-butoxy)-N-(4-(2-((1-ethyl-1H-pyrazol-4-yl)amino)pyrimidin-4-yl)-2-methylbenzyl)azetidine-1-carboxamide was similar to that of 3-(tert-butyl)-N-(4-(2-((1-ethyl-1H-pyrazol-4-yl)amino)pyrimidin-4-yl)-2-(trifluoromethyl)benzyl)pyrrolidine-1-carboxamide. The crude product was purified by silica gel column chromatography (EtOAc: petroleum ether=4/1) to give 3-(tert-butoxy)-N-(4-(2-((1-ethyl-1H-pyrazol-4-yl)amino)pyrimidin-4-yl)-2-methylbenzyl)azetidine-1-carboxamideas as a yellow solid (100 mg, yield: 57%). ESI-MS (M+H)⁺: 464.2. ¹H NMR (400 MHz, CD₃OD) δ: 8.39 (d, J=5.2 Hz, 1H), 8.03 (s, 1H), 7.94-7.92 (m, 2H), 7.66 (s, 1H), 7.38 (d, J=8.0 Hz, 1H), 7.20 (d, J=5.2 Hz, 1H), 4.61-4.55 (m, 1H), 4.38 (s, 2H), 4.21-4.15 (m, 4H), 3.80-3.77 (m, 2H), 2.43 (s, 3H), 1.49 (t, J=7.2 Hz, 3H), 1.20 (s, 9H).

Example 210: N-(4-(2-((1-(2-hydroxyethyl)-1H-pyrazol-4-yl)amino)pyrimidin-4-yl)-2-methylbenzyl)-3-isopropoxyazetidine-1-carboxamide

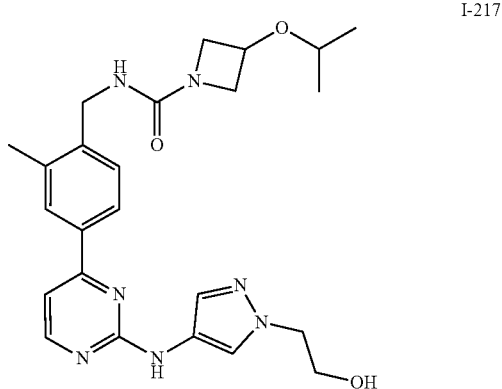 [SMILES: Cc1cc(-c2ccnc(Nc3cnn(CCO)c3)n2)ccc1CNC(=O)N1CC(OC(C)C)C1]

1. Synthesis of N-(4-(2-((1-(2-((tert-butyldimethylsilyl)oxy)ethyl)-1H-pyrazol-4-yl)amino)pyrimidin-4-yl)-2-methylbenzyl)-3-isopropoxyazetidine-1-carboxamide

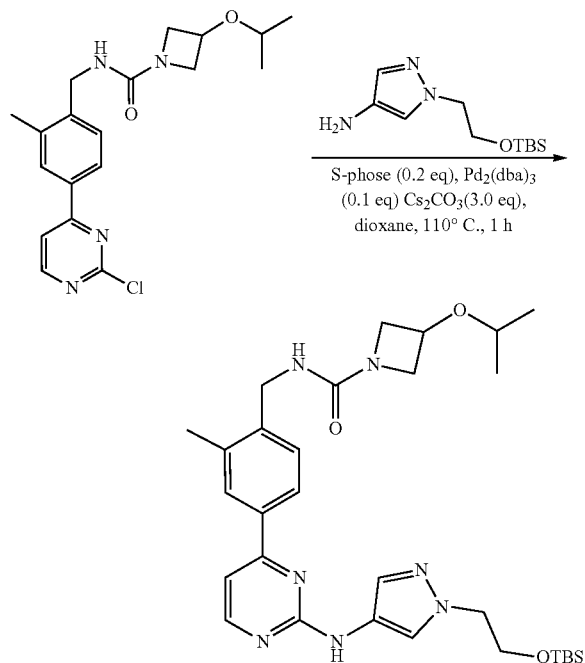

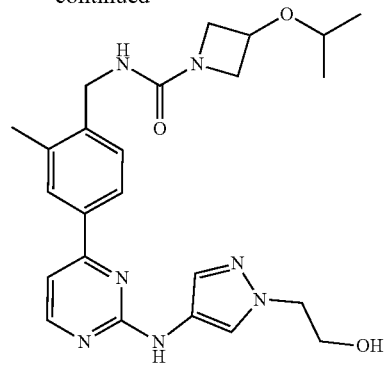

Synthesis of N-(4-(2-((1-(2-((tert-butyldimethylsilyl)oxy)ethyl)-1H-pyrazol-4-yl)amino)pyrimidin-4-yl)-2-methylbenzyl)-3-isopropoxyazetidine-1-carboxamide was similar to that of tert-butyl 2-methyl-4-(2-((1-methyl-1H-pyrazol-4-yl)amino)pyrimidin-4-yl)benzylcarbamate. The crude product was purified by silica gel column chromatography (EA/PE=3/1) to give N-(4-(2-((1-(2-((tert-butyldimethylsilyl)oxy)ethyl)-1H-pyrazol-4-yl)amino)pyrimidin-4-yl)-2-methylbenzyl)-3-isopropoxyazetidine-1-carboxamide as a yellow solid (70 mg, yield: 53%). ESI-MS (M+H)⁺: 580.4.

2. Synthesis of N-(4-(2-((1-(2-hydroxyethyl)-1H-pyrazol-4-yl)amino)pyrimidin-4-yl)-2-methylbenzyl)-3-isopropoxyazetidine-1-carboxamide

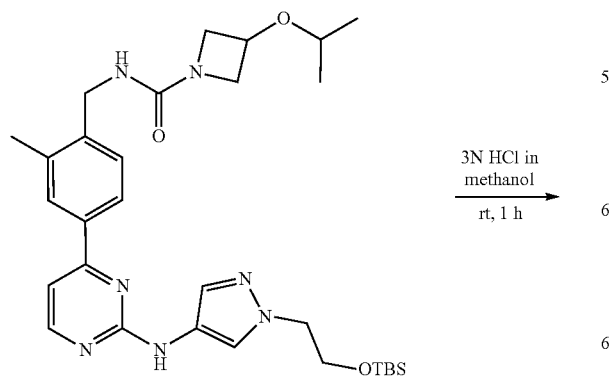

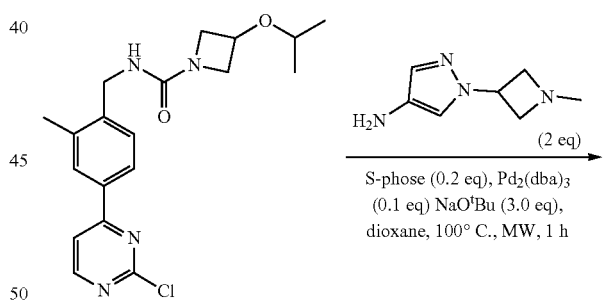

A mixture of N-(4-(2-((1-(2-((tert-butyldimethylsilyl)oxy)ethyl)-1H-pyrazol-4-yl)amino)pyrimidin-4-yl)-2-methylbenzyl)-3-isopropoxyazetidine-1-carboxamide (70 mg, 0.12 m mol) in 3 N HCl in methanol (4 mL) was stirred at rt for 1 h. The solvent was removed in vacuo and the residue was purified by prep-HPLC (MeCN/H₂O with 0.05% NH₃H₂O as mobile phase) to give N-(4-(2-((1-(2-hydroxyethyl)-1H-pyrazol-4-yl)amino)pyrimidin-4-yl)-2-methylbenzyl)-3-isopropoxyazetidine-1-carboxamide as a yellow solid (32 mg, yield: 57%). ESI-MS (M+H)⁺: 466.2. $^1$H NMR (400 MHz, CDCl₃) δ: 8.36 (d, J=4.8 Hz, 1H), 7.90 (s, 1H), 7.78 (s, 1H), 7.77 (s, 1H), 7.54 (s, 1H), 7.51 (s, 1H), 7.33 (d, J=8.0 Hz, 1H), 7.02 (d, J=5.6 Hz, 1H), 4.54 (t, J=5.6 Hz, 1H), 4.40 (d, J=5.2 Hz, 2H), 4.37-4.31 (m, 1H), 4.21 (t, J=4.8 Hz, 2H), 4.14-4.12 (m, 2H), 3.98 (t, J=5.2 Hz, 2H), 3.88-3.85 (m, 2H), 3.63-3.57 (m, 1H), 2.37 (s, 3H), 1.50 (d, J=5.6 Hz, 6H).

Example 211: 3-isopropoxy-N-(2-methyl-4-(2-((1-(1-methylazetidin-3-yl)-1H-pyrazol-4-yl)amino)pyrimidin-4-yl)benzyl)azetidine-1-carboxamide

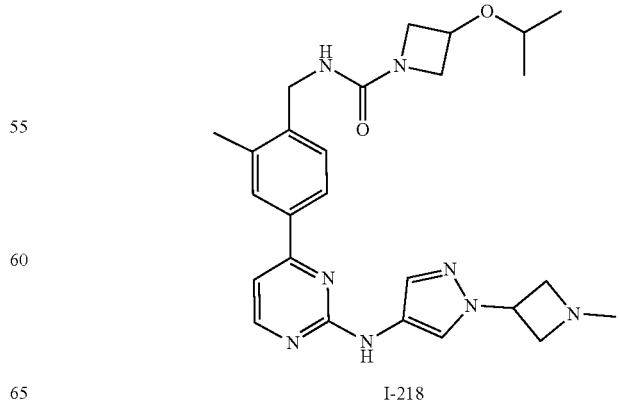

I-218

Synthesis of 3-isopropoxy-N-(2-methyl-4-(2-((1-(1-methylazetidin-3-yl)-1H-pyrazol-4-yl)amino)pyrimidin-4-yl)benzyl)azetidine-1-carboxamide was similar to that of tert-butyl 2-methyl-4-(2-((1-methyl-1H-pyrazol-4-yl)amino)pyrimidin-4-yl)benzylcarbamate. The residue was purified by silica gel column chromatography (EtOAc/petroleum ether=2:1) to give 3-isopropoxy-N-(2-methyl-4-(2-((1-(1-methylazetidin-3-yl)-1H-pyrazol-4-yl)amino)pyrimidin-4-yl)benzyl)azetidine-1-carboxamide as yellow solid (48 mg, yield: 30%). ESI-MS (M+H)$^+$: 491.2. $^1$H NMR (400 MHz, CD$_3$OD) δ: 8.29 (d, J=5.6 Hz, 1H), 8.09 (s, 1H), 7.84-7.83 (m, 2H), 7.63 (s, 1H), 7.28 (d, J=8.8 Hz, 1H), 7.10 (d, J=5.2 Hz, 1H), 4.93-4.85 (m, 1H), 4.35-4.30 (m, 1H), 4.28 (s, 2H), 4.09-4.05 (m, 2H), 3.79-3.68 (m, 4H), 3.59-3.48 (m, 3H), 2.38 (s, 3H), 2.32 (s, 3H), 1.05 (d, J=6.4 Hz, 6H).

Example 212: 3-isopropoxy-N-(2-methyl-4-(2-((1-(1-methylpiperidin-4-yl)-1H-pyrazol-4-yl)amino)pyrimidin-4-yl)benzyl)azetidine-1-carboxamide

I-219

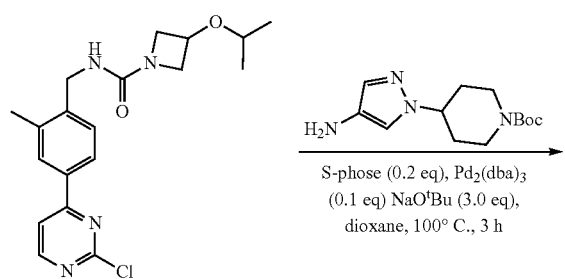

1. Synthesis of tert-butyl 4-(4-((4-(4-((3-isopropoxyazetidine-1-carboxamido)methyl)-3-methylphenyl)pyrimidin-2-yl)amino)-1H-pyrazol-1-yl)piperidine-1-carboxylate

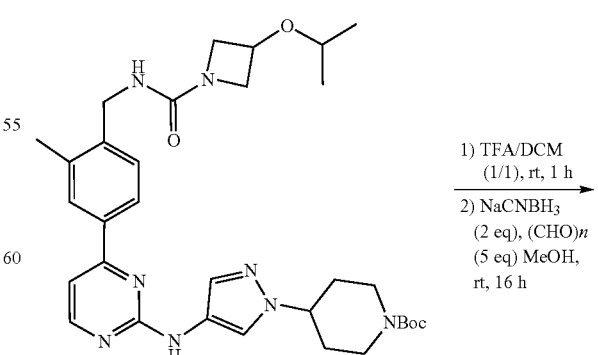

-continued

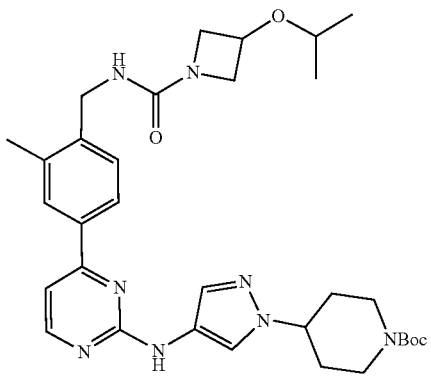

Synthesis of tert-butyl 4-(4-((4-(4-((3-isopropoxyazetidine-1-carboxamido)methyl)-3-methylphenyl)pyrimidin-2-yl)amino)-1H-pyrazol-1-yl)piperidine-1-carboxylate was similar to that of 3-isopropoxy-N-(2-methyl-4-(2-((1-(1-methylazetidin-3-yl)-1H-pyrazol-4-yl)amino)pyrimidin-4-yl)benzyl)azetidine-1-carboxamide. The crude product was purified through silica gel column chromatography (MeOH/CH$_2$Cl$_2$=1/20) to give tert-butyl 4-(4-((4-(4-((3-isopropoxyazetidine-1-carboxamido)methyl)-3-methylphenyl)pyrimidin-2-yl)amino)-1H-pyrazol-1-yl)piperidine-1-carboxylate as a yellow oil (105 mg, yield: 32%). ESI-MS (M+H)$^+$: 605.3. $^1$H NMR (400 MHz, CDCl$_3$) δ: 8.42 (d, J=5.2 Hz, 1H), 7.99 (s, 1H), 7.86 (s, 1H), 7.82 (d, J=8.0 Hz, 1H), 7.59 (s, 1H), 7.38 (d, J=8.0 Hz, 1H), 7.07 (d, J=5.2 Hz, 1H), 6.89 (s, 1H), 4.45 (d, J=5.6 Hz, 2H), 4.38-4.33 (m, 1H), 4.30-4.22 (m, 3H), 4.16-4.11 (m, 2H), 3.88-3.85 (m, 2H), 3.64-3.58 (m, 1H), 2.94-2.86 (m, 2H), 2.42 (s, 3H), 2.18-2.16 (m, 2H), 2.00-1.91 (m, 2H), 1.48 (s, 9H), 1.16 (d, J=6.4 Hz, 6H).

2. Synthesis of 3-isopropoxy-N-(2-methyl-4-(2-((1-(1-methylpiperidin-4-yl)-1H-pyrazol-4-yl)amino)pyrimidin-4-yl)benzyl)azetidine-1-carboxamide -continued

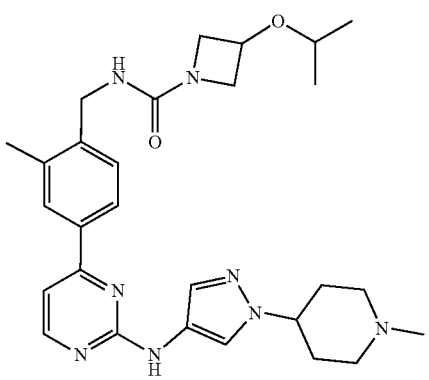

Synthesis of 3-isopropoxy-N-(2-methyl-4-(2-((1-(1-methylpiperidin-4-yl)-1H-pyrazol-4-yl)amino)pyrimidin-4-yl)benzyl)azetidine-1-carboxamide was similar to that of 3-(tert-butoxy)-N-(4-(2-((1-(1-methylazetidin-3-yl)-1H-pyrazol-4-yl)amino)pyrimidin-4-yl)-2-(trifluoromethyl)benzyl)azetidine-1-carboxamide in Example 199. The crude product was purified through prep-TLC (silica gel, MeOH/CH$_2$Cl$_2$=1/9) to give 3-isopropoxy-N-(2-methyl-4-(2-((1-(1-methylpiperidin-4-yl)-1H-pyrazol-4-yl)amino)pyrimidin-4-yl)benzyl)azetidine-1-carboxamide as a white solid (30 mg, yield: 33%). ESI-MS (M+H)$^+$: 519.2. $^1$H NMR (400 MHz, CD$_3$OD) δ: 8.32 (d, J=5.2 Hz, 1H), 8.04 (s, 1H), 7.87 (s, 1H), 7.86 (d, J=8.0 Hz, 1H), 7.62 (s, 1H), 7.32 (d, J=7.6 Hz, 1H), 7.14 (d, J=5.6 Hz, 1H), 4.38-4.34 (m, 1H), 4.31 (s, 2H), 4.26-4.21 (m, 1H), 4.12-4.08 (m, 2H), 3.75-3.71 (m, 2H), 3.62-3.56 (m, 1H), 3.21-3.18 (m, 2H), 2.63-2.58 (m, 2H), 2.51 (s, 3H), 2.36 (s, 3H), 2.20-2.06 (m, 4H), 1.09 (d, J=6.4 Hz, 6H).

Example 213: trans-N-(4-(2-((1-((3-fluoropiperidin-4-yl)-1H-pyrazol-4-yl)amino)pyrimidin-4-yl)-2-methylbenzyl)-3-isopropoxyazetidine-1-carboxamide

I-220

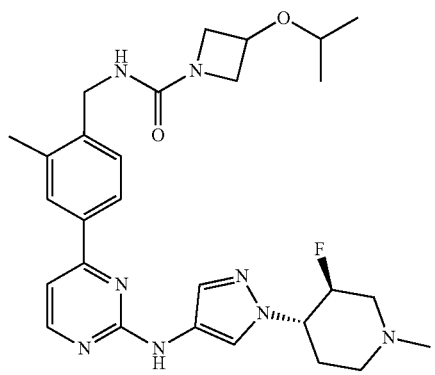

1. Synthesis of tert-butyl 3-fluoro-4-hydroxypiperidine-1-carboxylate

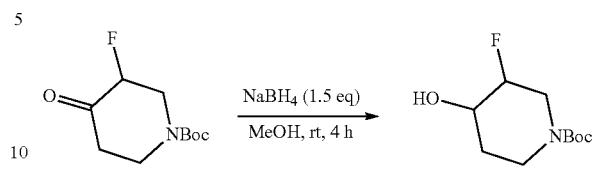

To the solution of tert-butyl 3-fluoro-4-oxopiperidine-1-carboxylate (2.0 g, 9.2 mmol, 1.0 equiv) in MeOH (15 mL), NaBH$_4$ (525 mg, 13.8 mmol, 1.5 equiv) was slowly added at 0° C. The reaction mixture was stirred at rt for 4 h. After diluting with water (80 mL), the mixture was extracted with ethyl acetate (100 mL×2). The combined organic layers were washed with brine, dried, concentrated and purified by silica gel column chromatography (petroleum ether: EtOAc=5:1) to give tert-butyl 3-fluoro-4-hydroxypiperidine-1-carboxylate (1.8 g, yield: 90%) as a yellow solid. ESI-MS (M+H-56)$^+$: 164.1.

2. Synthesis of tert-butyl 3-fluoro-4-(4-nitro-1H-pyrazol-1-yl)piperidine-1-carboxylate

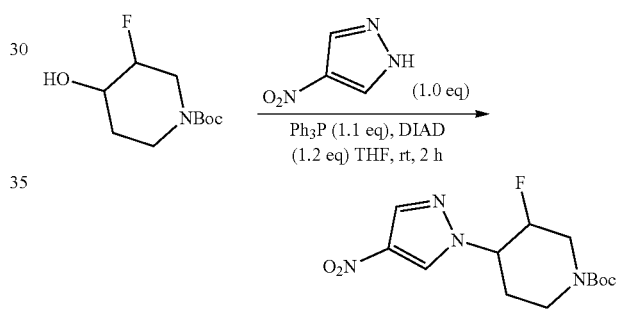

To a solution of 4-nitro-1H-pyrazole (1.13 g, 10 mmol), tert-butyl 3-fluoro-4-hydroxypiperidine-1-carboxylate (2.19 g, 10 mmol) and PPh$_3$ (2.88 g, 11 mmol) in THF (25 mL) was added DIAD (2.22 g, 11 mmol) under nitrogen. The mixture was stirred at rt for 2 h. The mixture was diluted with EtOAc (150 mL) and washed with water (50 mL×2). The organic phase was concentrated in vacuo and the residue was purified by column chromatography (silica gel, petroleum ether:EtOAc=3:1) to give the title product tert-butyl 3-fluoro-4-(4-nitro-1H-pyrazol-1-yl)piperidine-1-carboxylate (1.3 g, yield: 91%) as a yellow solid. ESI-MS (M+H)$^+$: 315.1. $^1$H NMR (400 MHz, CDCl$_3$) δ: 8.70 (s, 1H), 8.19 (s, 1H), 4.91-4.88 (m, 2H), 4.72-4.61 (m, 1H), 4.48-4.47 (m, 2H), 4.11-4.10 (m, 1H), 2.10-2.09 (m, 2H), 1.49 (s, 9H).

3. Synthesis of tert-butyl 3-fluoro-4-(4-nitro-1H-pyrazol-1-yl)piperidine-1-carboxylate

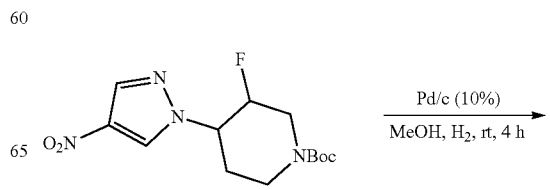

-continued

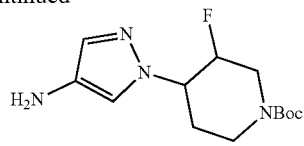

Synthesis of tert-butyl 3-fluoro-4-(4-nitro-1H-pyrazol-1-yl)piperidine-1-carboxylate was similar to that of (R)-tert-butyl 3-(4-amino-1H-pyrazol-1-yl)pyrrolidine-1-carboxylate in Example 121. After the catalyst was removed, the solvent was removed and the crude product (410 mg, yield: 91%) was used to next step without further purification. ESI-MS (M+H)⁺: 285.2.

4. Synthesis of N-(4-(2-chloropyrimidin-4-yl)-2-methylbenzyl)-3-isopropoxyazetidine-1-carboxamide

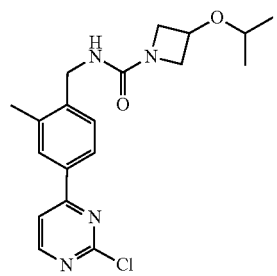 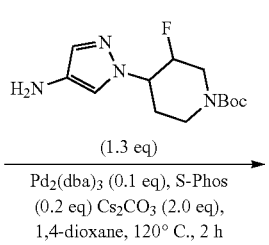

Synthesis of N-(4-(2-chloropyrimidin-4-yl)-2-methylbenzyl)-3-isopropoxyazetidine-1-carboxamide was similar to that of Example 205. The crude was purified through prep-HPLC (NH$_3$H$_2$O (0.05%)/MeCN as a mobile phase) to give trans-tert-butyl 3-fluoro-4-(4-((4-(4-((3-isopropoxyazetidine-1-carboxamido)methyl)-3-methylphenyl)pyrimidin-2-yl)amino)-1H-pyrazol-1-yl)piperidine-1-carboxylate (88 mg, yield: 26%) as a yellow solid. ESI-MS (M+H)⁺:623.3.

5. Synthesis of trans-tert-butyl 3-fluoro-4-(4-((4-(4-((3-isopropoxyazetidine-1-carboxamido)methyl)-3-methylphenyl)pyrimidin-2-yl)amino)-1H-pyrazol-1-yl)piperidine-1-carboxylate

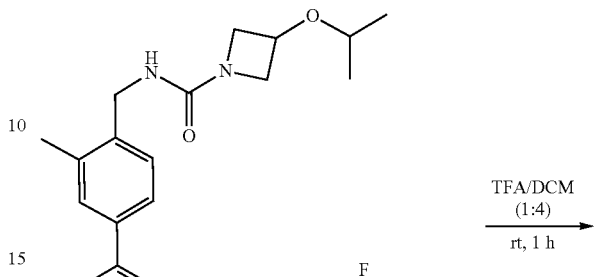

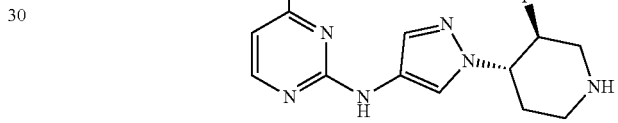

Synthesis of trans-tert-butyl 3-fluoro-4-(4-((4-(4-((3-isopropoxyazetidine-1-carboxamido)methyl)-3-methylphenyl)pyrimidin-2-yl)amino)-1H-pyrazol-1-yl)piperidine-1-carboxylate was similar to that of trans-N-(4-(2-((1-(3-fluoropiperidin-4-yl)-1H-pyrazol-4-yl)amino)pyrimidin-4-yl)-2-methylbenzyl)-3-isopropoxyazetidine-1-carboxamide. The crude product was purified by prep-HPLC (CH$_3$CN/H$_2$O with 0.05% NH$_4$OH as mobile phase) to give trans-N-(4-(2-((1-(3-fluoropiperidin-4-yl)-1H-pyrazol-4-yl)amino)pyrimidin-4-yl)-2-methylbenzyl)-3-isopropoxyazetidine-1-carboxamide (72 mg, yield: 97%) as a yellow solid. ESI-MS (M+H)⁺:523.3.

6. Synthesis of trans-N-(4-(2-((1-((-3-fluoropiperidin-4-yl)-1H-pyrazol-4-yl)amino)pyrimidin-4-yl)-2-methylbenzyl)-3-isopropoxyazetidine-1-carboxamide

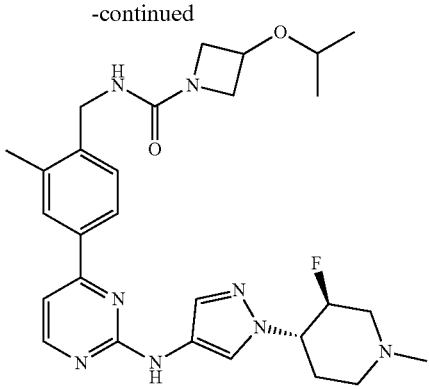

Synthesis of trans-N-(4-(2-((1-((-3-fluoropiperidin-4-yl)-1H-pyrazol-4-yl)amino)pyrimidin-4-yl)-2-methylbenzyl)-3-isopropoxyazetidine-1-carboxamide was similar to that of Example 199. The crude product was purified by prep-HPLC (CH₃CN/H₂O with 0.05% NH₄OH as mobile phase) to give trans-N-(4-(2-((1-(-3-fluoro-1-methylpiperidin-4-yl)-1H-pyrazol-4-yl)amino)pyrimidin-4-yl)-2-methylbenzyl)-3-isopropoxyazetidine-1-carboxamide (28 mg, yield: 38%) as yellow solid. ESI-MS (M+H)⁺:537.3. ¹H NMR (400 MHz, CD₃OD) δ: 8.28 (d, J=5.2 Hz, 1H), 8.00 (s, 1H), 7.81-7.79 (m, 2H), 7.60 (s, 1H), 7.26 (d, J=7.6 Hz, 1H), 7.06 (d, J=5.2 Hz, 1H), 4.71-4.65 (m, 1H), 4.31-4.26 (m, 3H), 4.13-4.03 (m, 3H), 3.71-3.67 (m, 2H), 3.56-3.50 (m, 1H), 3.18-3.14 (m, 1H), 2.82-2.80 (m, 1H), 2.29 (s, 3H), 2.27 (s, 3H), 2.15-2.00 (m, 4H), 1.04 (d, J=6.4 Hz, 6H).

Example 214: 3-isopropoxy-N-(2-methyl-4-(2-((1-(tetrahydro-2H-pyran-4-yl)-1H-pyrazol-4-yl)amino)pyrimidin-4-yl)benzyl)azetidine-1-carboxamide

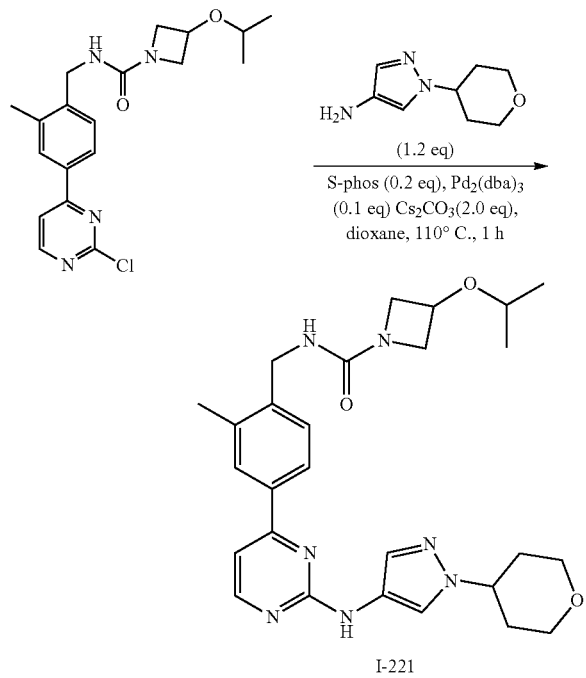

Synthesis of 3-isopropoxy-N-(2-methyl-4-(2-((1-(tetrahydro-2H-pyran-4-yl)-1H-pyrazol-4-yl)amino)pyrimidin-4-yl)benzyl)azetidine-1-carboxamide was similar to that of 3-isopropoxy-N-(4-(2-((1-(2-methoxyethyl)-1H-pyrazol-4-yl)amino)pyrimidin-4-yl)-2-methylbenzyl)azetidine-1-carboxamide. The residue was purified by prep-HPLC (MeCN/water with 0.05% NH₄OH as mobile phase) to give 3-isopropoxy-N-(2-methyl-4-(2-((1-(tetrahydro-2H-pyran-4-yl)-1H-pyrazol-4-yl)amino)pyrimidin-4-yl)benzyl)azetidine-1-carboxamide (63 mg, yield: 39%) as a yellow solid. ESI-MS (M+H)⁺: 506.2. ¹H NMR (400 MHz, CDCl₃) δ: 8.42 (d, J=5.2 Hz, 1H), 7.97 (s, 1H), 7.85 (s, 1H), 7.81 (d, J=8.0 Hz, 1H), 7.65 (s, 1H), 7.55 (s, 1H), 7.36 (d, J=8.0 Hz, 1H), 7.06 (d, J=5.2 Hz, 1H), 4.50-4.47 (m, 1H), 4.43 (d, J=5.2 Hz, 2H), 4.38-4.29 (m, 2H), 4.16-4.10 (m, 4H), 3.89-3.85 (m, 2H), 3.64-3.52 (m, 3H), 2.39 (s, 3H), 2.15-2.04 (m, 4H), 1.15 (d, J=6.4 Hz, 6H).

Example 215: N-(4-(2-((1H-pyrazol-4-yl)amino)pyrimidin-4-yl)-2-methylbenzyl)-3-isopropoxyazetidine-1-carboxamide

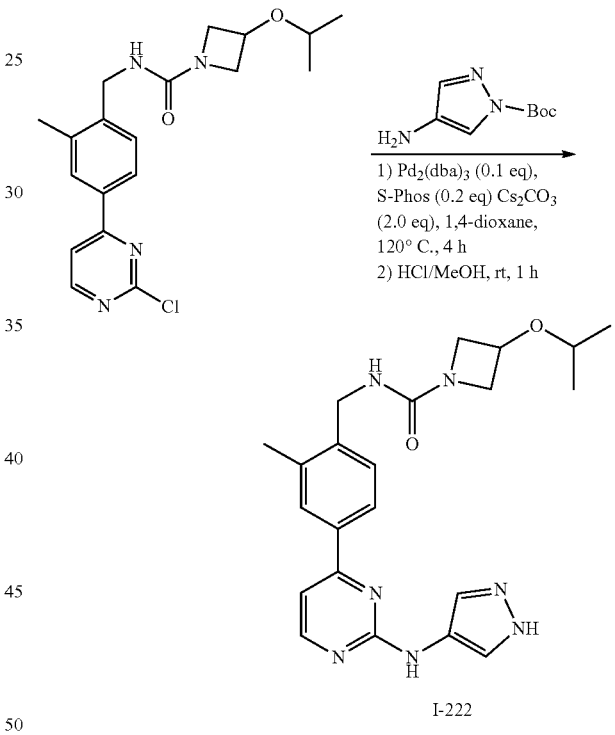

To a solution of N-(4-(2-chloropyrimidin-4-yl)-2-methylbenzyl)-3-isopropoxyazetidine-1-carboxamide (220 mg, 0.60 mmol) and tert-butyl 4-amino-1H-pyrazole-1-carboxylate (132 mg, 0.72 m mol) in dry 1,4-dioxane (8 mL) was added Pd₂(dba)₃ (55 mg, 0.06 mmol), S-phos (49 mg, 0.12 mmol) and Cs₂CO₃ (390 mg, 1.2 mmol). The mixture was stirred at 120° C. for 4 h under N₂. After cooling to rt, the mixture was diluted with EtOAc (150 mL) and washed with water (60 mL×2). The organic phase was dried over Na₂SO₄, filtered and concentrated in vacuo. The residue was dissolved in 3 N HCl in MeOH (10 mL) and the resulting mixture was stirred at rt for 1 h. After concentration in vacuo, the residue was purified by prep-HPLC (CH₃CN/H₂O with 0.05% NH₄OH as mobile phase) to give N-(4-(2-((1H-pyrazol-4-yl)amino)pyrimidin-4-yl)-2-methylbenzyl)-3-isopropoxyazetidine-1-carboxamide as a white solid (88 mg, yield: 35%). ESI-MS (M+H)⁺: 544.2. ¹H NMR (400 MHz, CD₃OD) δ: 8.38 (d, J=4.8 Hz, 1H), 8.05 (s, 1H), 7.91-7.90 (m, 2H), 7.75 (s, 1H), 7.37 (d, J=8.4 Hz, 1H), 7.16 (d, J=5.2 Hz, 1H), 4.42-4.36 (m, 3H), 4.18-4.14 (m, 2H), 3.81-3.78 (m, 2H), 3.67-3.61 (m, 1H), 2.41 (s, 3H), 1.14 (d, J=6.0 Hz, 6H).

Example 216: 3-(tert-butoxy)-N-(4-(2-((1,5-dimethyl-1H-pyrazol-4-yl)amino)pyrimidin-4-yl)-2-methylbenzyl)azetidine-1-carboxamide

I-223

1. Synthesis of N-(1,5-dimethyl-1H-pyrazol-4-yl)-4-methoxypyrimidin-2-amine

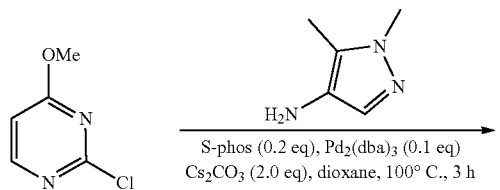

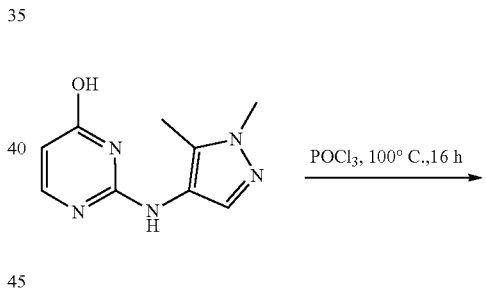

To a solution of 2-chloro-4-methoxypyrimidine (1.44 g, 10 mmol) in 1,4-dioxane (25 mL) were added 1,5-dimethyl-1H-pyrazol-4-amine (1.21 g, 11 mmol), Pd₂(dba)₃ (915 mg, 1.0 mmol), S-Phos (822 mg, 2.0 mmol) and Cs₂CO₃ (6.5 g, 20 mmol). The mixture was stirred at 100° C. for 3 h. After cooling to rt, the mixture was filtered through a Celite pad. The filtrate was concentrated in vacuo and the crude was purified by silica gel column chromatography (petroleum ether: EtOAc=2/1) to give N-(1,5-dimethyl-1H-pyrazol-4-yl)-4-methoxypyrimidin-2-amine as a yellow solid (1.75 g, yield: 80%). ESI-MS (M+H)⁺: 220.1.

2. Synthesis of 2-((1,5-dimethyl-1H-pyrazol-4-yl)amino)pyrimidin-4-ol

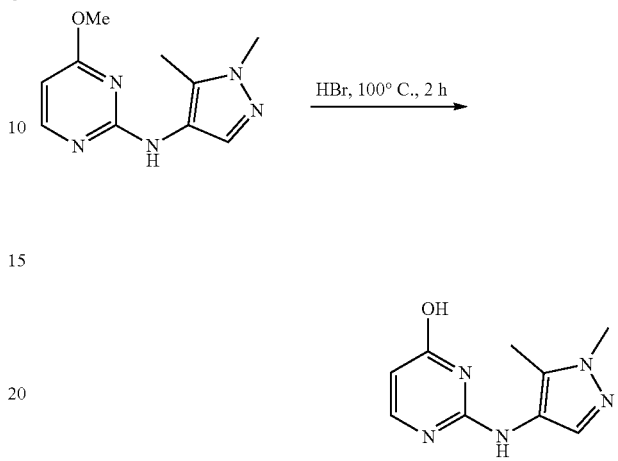

A solution of N-(1,5-dimethyl-1H-pyrazol-4-yl)-4-methoxypyrimidin-2-amine (1.0 g, 4.57 mmol) in HBr (15 mL) was stirred at 100° C. for 2 h. The mixture was concentrated and the crude product (930 mg) was used to next step without further purification. ESI-MS (M+H)⁺: 206.1

3. Synthesis of 4-chloro-N-(1,5-dimethyl-1H-pyrazol-4-yl)pyrimidin-2-amine

A solution of 2-((1,5-dimethyl-1H-pyrazol-4-yl)amino)pyrimidin-4-ol (930 mg, 4.51 mmol) in POCl₃ (20 mL) was stirred at 100° C. for 16 h. After cooling to rt, the mixture was poured onto ice-water and adjusted to pH=8 with Na₂CO₃ (sat). The mixture was extracted with ethyl acetate (200 mL×2). The combined organic layers were washed with brine, dried, concentrated in vacuo to afford a residue which was purified by silica gel column chromatography (petroleum ether:EtOAc=1:1) to give 4-chloro-N-(1,5-dimethyl-1H-pyrazol-4-yl)pyrimidin-2-amine (680 mg, yield: 67%) as a yellow solid. ESI-MS (M+H)⁺: 224.1.

4. Synthesis of 3-(tert-butoxy)-N-(4-(2-((1,5-dimethyl-1H-pyrazol-4-yl)amino)pyrimidin-4-yl)-2-methylbenzyl)azetidine-1-carboxamide

Example 217: 3-(tert-butyl)-N-(2-methyl-4-(2-((1-methyl-1H-pyrazol-4-yl)amino)pyrimidin-4-yl)benzyl)pyrrolidine-1-carboxamide

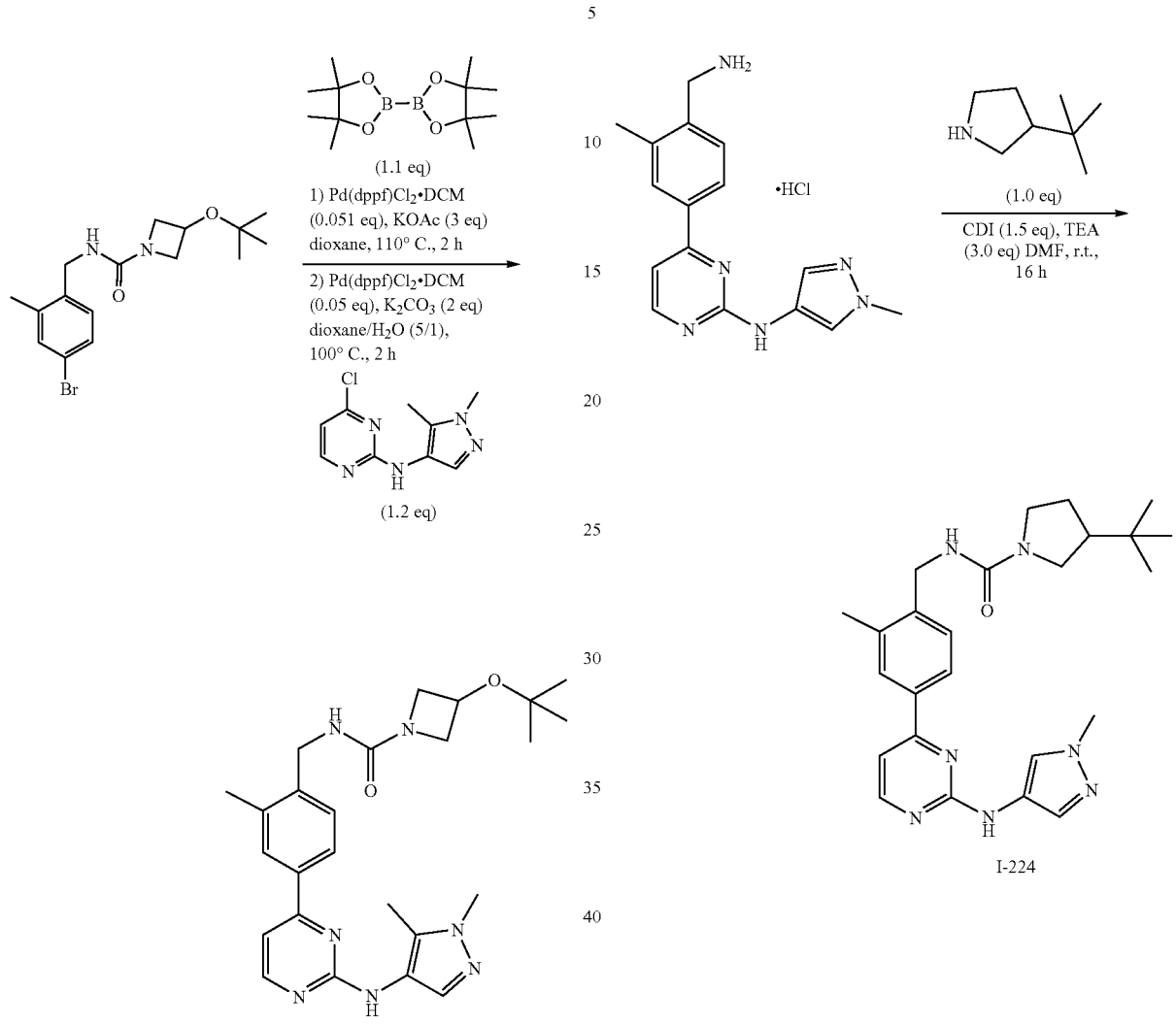

I-224

A mixture of N-(4-bromo-2-methylbenzyl)-3-(tert-butoxy)azetidine-1-carboxamide (193 mg, 0.5 mmol), bis(pinacolato)diboron (134 mg, 0.55 mmol), KOAc (98 mg, 1.0 mmol) and Pd(dppf)Cl$_2$.DCM (41 mg, 0.05 mmol) in 5 mL dry 1,4-dioxane was stirred at 100° C. for 2 h under nitrogen. After cooling to rt, 4-chloro-N-(1,5-dimethyl-1H-pyrazol-4-yl)pyrimidin-2-amine (134 mg, 0.6 mmol), K$_2$CO$_3$ (138 mg, 1.0 mmol) and H$_2$O (2 mL) were added. The resulting mixture was stirred at 100° C. for another 2 h. The mixture was dilute with EtOAc (200 mL), washed with water (80 mL×2), dried with Na$_2$SO$_4$ and concentrated. The residue was purified by prep-HPLC (MeCN/H$_2$O with 0.05% NH$_4$OH as mobile phase from 5% to 95%) to give 3-(tert-butoxy)-N-(4-(2-((1,5-dimethyl-1H-pyrazol-4-yl)amino)pyrimidin-4-yl)-2-methylbenzyl)azetidine-1-carboxamide (43 mg, yield: 22%) as yellow solid. ESI-MS (M+H)$^+$:464.3. $^1$H NMR (400 MHz, CD$_3$OD): 8.26 (d, J=5.2 Hz, 1H), 7.88-7.86 (m, 2H), 7.60 (s, 1H), 7.34 (d, J=8.0 Hz, 1H), 7.16 (d, J=5.6 Hz, 1H), 4.55-4.53 (m, 1H), 4.35 (s, 2H), 4.16-4.12 (m, 2H), 3.79 (s, 3H), 3.78-3.75 (m, 2H), 2.38 (s, 3H), 2.21 (s, 3H), 1.18 (s, 9H).

A solution of 4-(4-(aminomethyl)-3-methylphenyl)-N-(1-methyl-1H-pyrazol-4-yl)pyrimidin-2-amine hydrochloride (165 mg, 0.50 mmol), CDI (123 mg, 0.75 mmol) and TEA (151 mg, 1.5 mmol) in DMF (4 mL) was stirred at rt for 1 h, then 3-(tert-butyl)pyrrolidine (65 mg, 0.50 mmol) was added. The resulting solution was stirred for another 16 h. After diluting with water (15 mL), the mixture was extracted with CH$_2$Cl$_2$ (40 mL×3). The combined organic phases were washed with brine, dried (Na$_2$SO$_4$) and concentrated in vacuo. The residue was purified by prep-HPLC (MeCN/water with 0.05% ammonia as mobile phase) to give 3-(tert-butyl)-N-(2-methyl-4-(2-((1-methyl-1H-pyrazol-4-yl)amino)pyrimidin-4-yl)benzyl)pyrrolidine-1-carboxamide (89 mg, yield: 41%) as a yellow solid. ESI-MS (M+H)$^+$: 448.1. $^1$H NMR (400 MHz, CD$_3$OD) δ: 8.38 (d, J=5.2 Hz, 1H), 7.97 (s, 1H), 7.94-7.92 (m, 2H), 7.65 (s, 1H), 7.39 (d, J=8.4 Hz, 1H), 7.19 (d, J=5.2 Hz, 1H), 4.42 (ABq, J=23.2, 16.0 Hz, 2H), 3.89 (s, 3H), 3.61-3.56 (m, 1H), 3.50-3.46 (m, 1H), 3.28-3.26 (m, 1H), 3.12-3.10 (m, 1H), 2.44 (s, 3H), 2.12-2.08 (m, 1H), 1.97-1.90 (m, 1H), 1.78-1.67 (m, 1H), 0.97 (s, 9H).

Example 218: 1-(tert-butyl)-N-(2-methyl-4-(6-((5-(4-methylpiperazin-1-yl)pyridin-2-yl)amino)pyrimidin-4-yl)benzyl)-1H-pyrazole-4-carboxamide

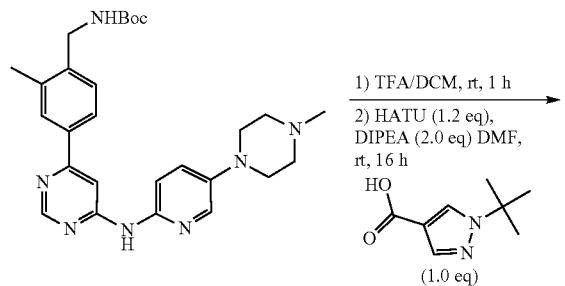

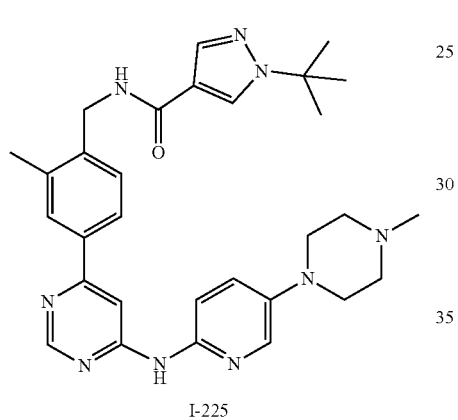

Example 219: 1-(tert-butyl)-N-(2-methyl-4-(6-((5-(4-methylpiperazin-1-yl)pyridin-2-yl)amino)pyrimidin-4-yl)benzyl)-1H-pyrazole-3-carboxamide

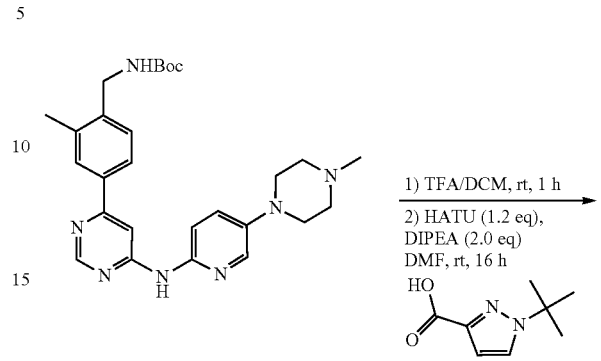

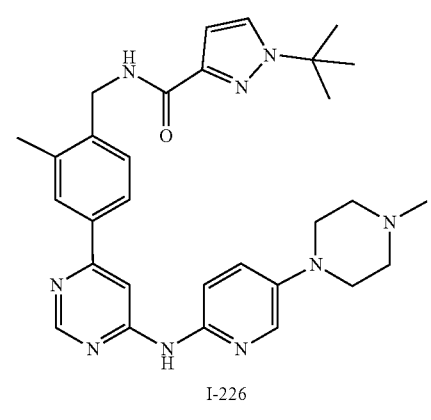

Synthesis of 1-(tert-butyl)-N-(2-methyl-4-(6-((5-(4-methylpiperazin-1-yl)pyridin-2-yl)amino)pyrimidin-4-yl)benzyl)-1H-pyrazole-4-carboxamide was similar to that of 2-(tert-butyl)-N-(2-methyl-4-(6-((5-(4-methylpiperazin-1-yl)pyridin-2-yl)amino)pyrimidin-4-yl)benzyl)thiazole-5-carboxamide. The residue was purified by prep-HPLC (CH$_3$CN/H$_2$O with 0.05% TFA as mobile phase) to give 1-(tert-butyl)-N-(2-methyl-4-(6-((5-(4-methylpiperazin-1-yl)pyridin-2-yl)amino)pyrimidin-4-yl)benzyl)-1H-pyrazole-4-carboxamide as a white solid (10 mg, yield: 30%). ESI-MS (M+H)$^+$: 540.2. $^1$H NMR (400 MHz, DMSO-d$_6$) δ ppm 1.54 (d, J=2.51 Hz, 11H) 2.42 (s, 2H) 2.86-2.89 (m, 2H) 2.95-3.04 (m, 1H) 3.15-3.25 (m, 1H) 3.52-3.57 (m, 1H) 3.80-3.88 (m, 1H) 4.45-4.49 (m, 1H) 7.39-7.42 (m, 1H) 7.55-7.59 (m, 1H) 7.77-7.81 (m, 1H) 7.81-7.83 (m, 1H) 7.83-7.86 (m, 1H) 7.93 (d, J=0.50 Hz, 1H) 8.04-8.09 (m, 1H) 8.12-8.16 (m, 1H) 8.25 (s, 1H) 8.33 (d, J=0.75 Hz, 1H) 8.48-8.53 (m, 1H) 8.76-8.80 (m, 1H).

Synthesis 1-(tert-butyl)-N-(2-methyl-4-(6-((5-(4-methylpiperazin-1-yl)pyridin-2-yl)amino)pyrimidin-4-yl)benzyl)-1H-pyrazole-3-carboxamide was similar to that of 2-(tert-butyl)-N-(2-methyl-4-(6-((5-(4-methylpiperazin-1-yl)pyridin-2-yl)amino)pyrimidin-4-yl)benzyl)thiazole-5-carboxamide. The residue was purified by prep-HPLC (CH$_3$CN/H$_2$O with 0.05% TFA as mobile phase) to give 1-(tert-butyl)-N-(2-methyl-4-(6-((5-(4-methylpiperazin-1-yl)pyridin-2-yl)amino)pyrimidin-4-yl)benzyl)-1H-pyrazole-3-carboxamide as a white solid (56 mg, yield: 56%). ESI-MS (M+H)$^+$: 540.2 $^1$H NMR (400 MHz, DMSO-d$_6$) δ: ppm 1.54 (d, J=2.51 Hz, 11H) 2.42 (s, 2H) 2.86-2.89 (m, 2H) 2.95-3.04 (m, 1H) 3.15-3.25 (m, 1H) 3.52-3.57 (m, 1H) 3.80-3.88 (m, 1H) 4.45-4.49 (m, 1H) 7.39-7.42 (m, 1H) 7.55-7.59 (m, 1H) 7.77-7.79 (m, 1H) 7.83-7.86 (m, 1H) 7.93 (d, J=0.50 Hz, 1H) 8.04-8.09 (m, 1H) 8.12-8.16 (m, 1H) 8.25 (s, 1H) 8.33 (d, J=0.75 Hz, 1H) 8.48-8.53 (m, 1H) 8.76-8.80 (m, 1H).

Example 220: (R)-3-isopropoxy-N-(2-(2-((1-(2-methoxyethyl)-1H-pyrazol-4-yl)amino)-pyrimidin-4-yl)-6,7,8,9-tetrahydro-5H-benzo[7]annulen-5-yl)azetidine-1-carboxamide and (S)-3-isopropoxy-N-(2-(2-((1-(2-methoxyethyl)-1H-pyrazol-4-yl)amino)-pyrimidin-4-yl)-6,7,8,9-tetrahydro-5H-benzo[7]annulen-5-yl)azetidine-1-carboxamide

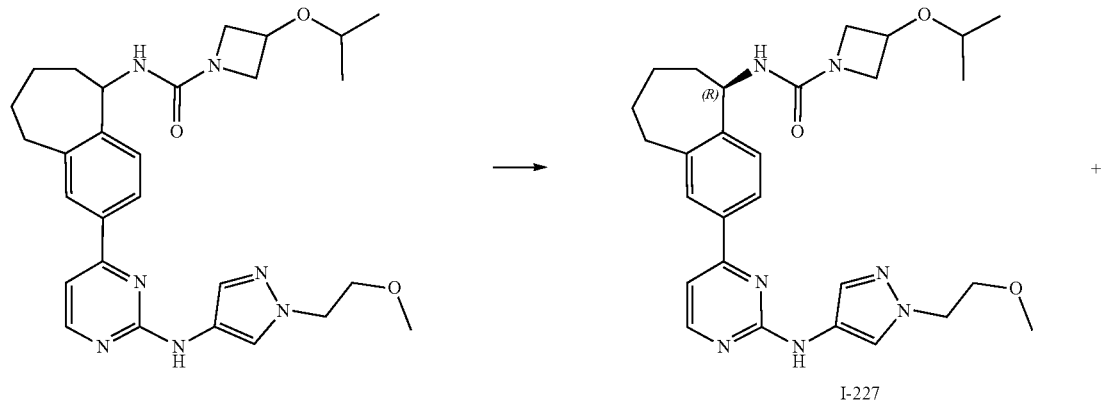

+

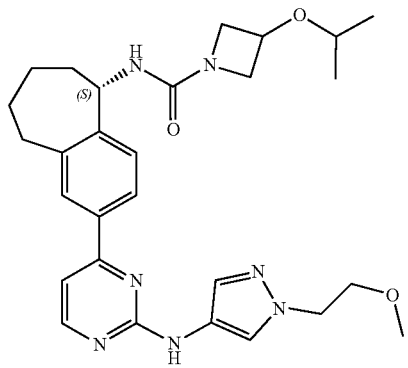

3-isopropoxy-azetidine-1-carboxylic acid (2-{2-[1-(2-methoxy-ethyl)-1H-pyrazol-4-ylamino]-pyrimidin-4-yl}-6,7,8,9-tetrahydro-5H-benzocyclohepten-5-yl)-amide (20 mg, 0.04 mmol) was separated by chiral column. The following SFC method was used: OZ—H (2×25 cm) 40% methanol (0.1% DEA)/CO$_2$, 100 bar; 50 mL/min, 220 nm.; inj vol.: 1 mL, 2 mg/mL methanol. Two isomers were obtained: 9 mg of (R)-3-isopropoxy-N-(2-(2-((1-(2-methoxyethyl)-1H-pyrazol-4-yl)amino)-pyrimidin-4-yl)-6,7,8,9-tetrahydro-5H-benzo[7]annulen-5-yl)azetidine-1-carboxamide (chemical purity>99%, ee>99%). LCMS: RT 1.21 min.; MH+520.2; $^1$H NMR (400 MHz, CD$_3$OD) δ: 8.38 (d, J=3.51 Hz, 1H), 8.08 (s, 1H), 7.83-7.99 (m, 2H), 7.58-7.76 (m, 1H), 7.37 (d, J=8.03 Hz, 1H), 7.19 (d, J=5.27 Hz, 1H), 6.86 (d, J=8.03 Hz, 1H), 4.98-5.10 (m, 1H), 4.39-4.51 (m, 1H), 4.15-4.35 (m, 4H), 3.75 (t, J=5.15 Hz, 5H), 3.35 (s, 3H), 2.89-3.10 (m, 2H), 1.80-2.09 (m, 3H), 1.57-1.75 (m, 1H), 1.31-1.49 (m, 2H), 1.11-1.23 (m, 6H); and 8 mg of (S)-3-isopropoxy-N-(2-(2-((1-(2-methoxyethyl)-1H-pyrazol-4-yl)amino)-pyrimidin-4-yl)-6,7,8,9-tetrahydro-5H-benzo[7]annulen-5-yl)azetidine-1-carboxamide (chemical purity>99%, ee>99%). LCMS: RT 1.21 min.; MH+520.2; $^1$H NMR (400 MHz, CD$_3$OD) δ: 8.38 (d, J=4.52 Hz, 1H), 8.08 (s, 1H), 7.84-7.99 (m, 2H), 7.58-7.76 (m, 1H), 7.37 (d, J=8.03 Hz, 1H), 7.19 (d, J=5.27 Hz, 1H), 6.86 (d, J=8.03 Hz, 1H), 5.04 (d, J=10.04 Hz, 1H), 4.39-4.51 (m, 1H), 4.14-4.34 (m, 4H), 3.60-3.94 (m, 5H), 3.35 (s, 3H), 2.90-3.09 (m, 2H), 1.84-2.06 (m, 3H), 1.59-1.75 (m, 1H), 1.31-1.50 (m, 2H), 1.13-1.23 (m, 6H).

Example 221: (R)-3-(tert-butoxy)-N-(2-(2-((1-(2-hydroxyethyl)-1H-pyrazol-4-yl)amino)-pyrimidin-4-yl)-6,7,8,9-tetrahydro-5H-benzo[7]annulen-5-yl)azetidine-1-carboxamide and (S)-3-(tert-butoxy)-N-(2-(2-((1-(2-hydroxyethyl)-1H-pyrazol-4-yl)amino)-pyrimidin-4-yl)-6,7,8,9-tetrahydro-5H-benzo[7]annulen-5-yl)azetidine-1-carboxamide

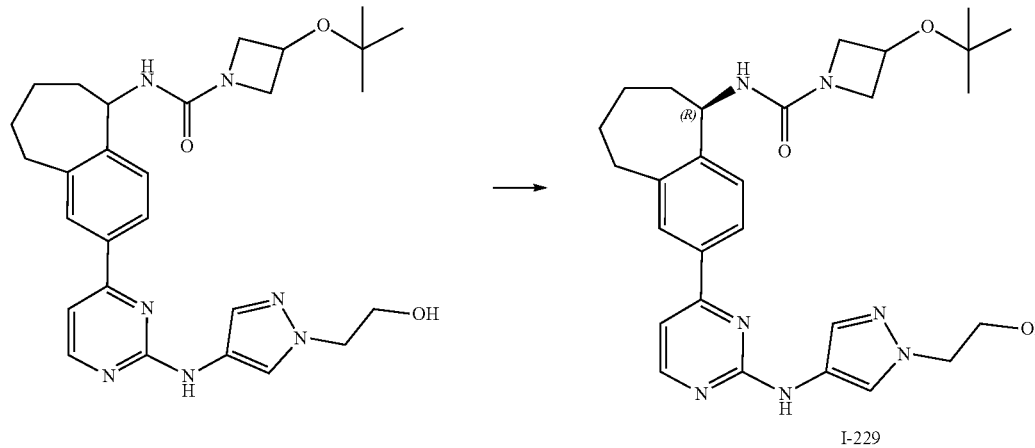

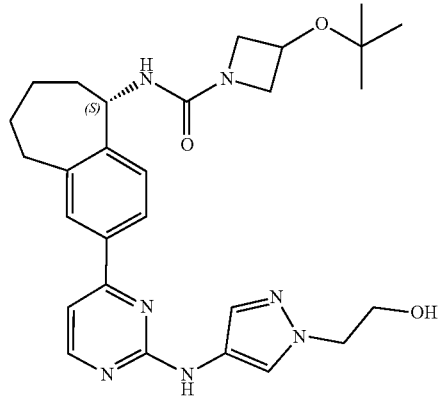

3-tert-Butoxy-azetidine-1-carboxylic acid (2-{2-[1-(2-hydroxy-ethyl)-1H-pyrazol-4-ylamino]-pyrimidin-4-yl}-6,7,8,9-tetrahydro-5H-benzocyclohepten-5-yl)-amide (40 mg, 0.08 mmol) was separated by chiral column. The following SFC method was used: IA (2×15 cm), 35% methanol (0.1% DEA)/CO₂, 100 bar; 60 mL/min, 220 nm.; inj vol.: 1 mL, 4 mg/mL methanol. Two isomers were obtained: 11 mg of (R)-3-(tert-butoxy)-N-(2-(2-((1-(2-hydroxyethyl)-1H-pyrazol-4-yl)amino)-pyrimidin-4-yl)-6,7,8,9-tetrahydro-5H-benzo[7]annulen-5-yl)azetidine-1-carboxamide (chemical purity>99%, ee>99%). LCMS: RT 1.16 min.; MH+520.2; $^1$H NMR (400 MHz, CD$_3$OD) δ: 8.37 (d, J=4.52 Hz, 1H), 8.07 (s, 1H), 7.84-7.99 (m, 2H), 7.59-7.75 (m, 1H), 7.37 (d, J=8.03 Hz, 1H), 7.19 (d, J=5.02 Hz, 1H), 5.04 (d, J=10.04 Hz, 1H), 4.53-4.67 (m, 1H), 4.13-4.29 (m, 4H), 3.73-3.98 (m, 4H), 2.87-3.09 (m, 2H), 1.79-2.06 (m, 4H), 1.55-1.75 (m, 1H), 1.31-1.47 (m, 2H), 1.22 (s, 9H); and 9 mg of (S)-3-(tert-butoxy)-N-(2-(2-((1-(2-hydroxyethyl)-1H-pyrazol-4-yl)amino)-pyrimidin-4-yl)-6,7,8,9-tetrahydro-5H-benzo[7]annulen-5-yl)azetidine-1-carboxamide (chemical purity>99%, ee>99%). LCMS: RT 1.16 min.; MH+520.2; $^1$H NMR (400 MHz, CD$_3$OD) δ: 8.37 (d, J=4.52 Hz, 1H), 8.07 (s, 1H), 7.84-7.99 (m, 2H), 7.60-7.76 (m, 1H), 7.37 (d, J=8.03 Hz, 1H), 7.19 (d, J=5.27 Hz, 1H), 5.04 (d, J=10.29 Hz, 1H), 4.55-4.66 (m, 1H), 4.12-4.32 (m, 4H), 3.74-3.98 (m, 4H), 2.89-3.09 (m, 2H), 1.78-2.06 (m, 4H), 1.55-1.75 (m, 1H), 1.30-1.49 (m, 2H), 1.22 (s, 9H).

Scheme 12
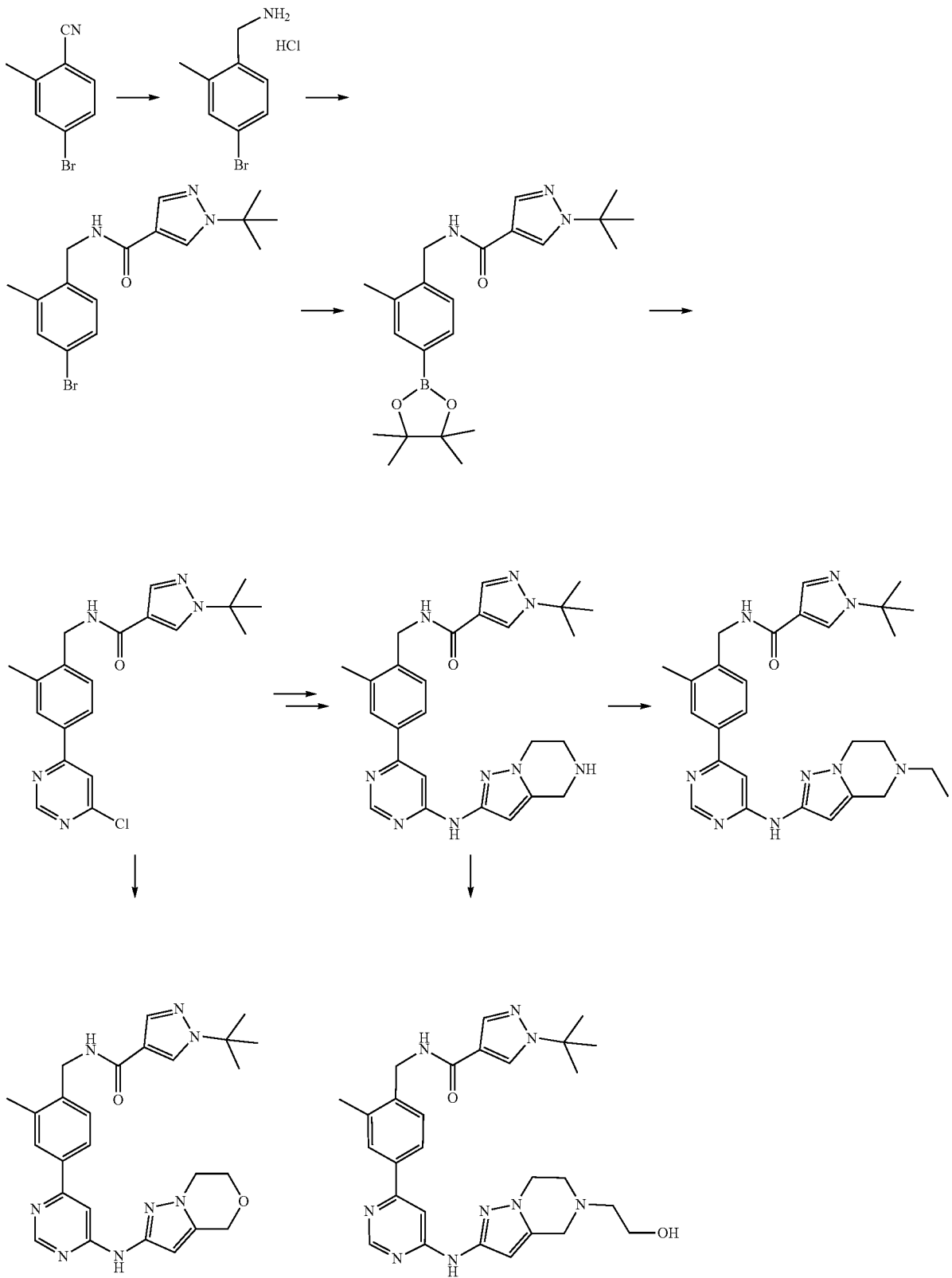

Example 222: 1-(tert-butyl)-N-(2-methyl-4-(6-((4,5,6,7-tetrahydropyrazolo[1,5-a]pyrazin-2-yl)amino)-pyrimidin-4-yl)benzyl)-1H-pyrazole-4-carboxamide

I-231

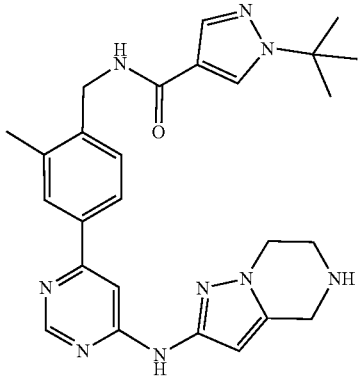

1. Synthesis of (4-bromo-2-methylphenyl)methanamine hydrochloride

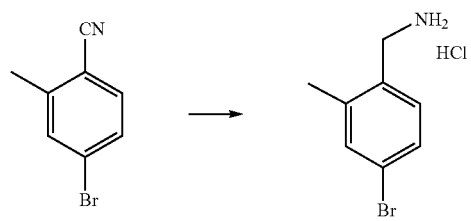

To a solution of 4-bromo-2-methylbenzonitrile (3.0 g, 15 mmol) in anhydrous THF (20 mL) under nitrogen at 0° C. was added 1.0 M solution of borane in THF (46 mL). The reaction mixture was stirred at 0° C. for 1 h, and heated at 80° C. overnight. The reaction mixture was cooled to 0° C. and slowly quenched with MeOH, concentrated in vacuo. The crude product was treated with EtOAc (20 mL) and 4 M of HCl in 1,4-dioxane (8.0 mL, 32 mmol) for 5 min. The solid was filtered, rinsed with diethyl ether, dried to give the title compound as a white powder (3.24 g, yield: 100%). LCMS: RT 0.75 min.; MH+200.0. $^1$H NMR (300 MHz, DMSO-d$_6$) δ: 8.28 (br. s., 2H), 7.42-7.54 (m, 2H), 7.34 (d, J=7.93 Hz, 1H), 3.99 (d, J=4.15 Hz, 2H), 2.35 (s, 3H).

2. Synthesis of N-(4-bromo-2-methylbenzyl)-1-(tert-butyl)-1H-pyrazole-4-carboxamide

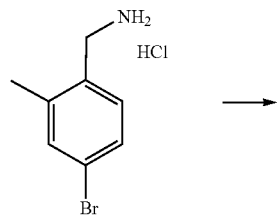

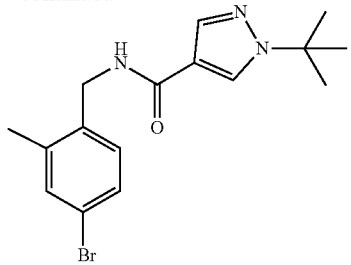

To a solution of 1-tert-Butyl-1H-pyrazole-4-carboxylic acid (1.4 g, 8.4 mmol) in DMF (20 mL) was added HATU (3.5 g, 9.2 mmol) and DIEA (4.4 mL, 25 mmol). The mixture was stirred at rt for 5 min, followed by the addition of (4-bromo-2-methylphenyl)methanamine hydrochloride (2.0 g, 8.4 mmol). The reation was stirred at rt overnight, diluted with EtOAc, washed with water, and the organic phase was then dried (Na$_2$SO$_4$) and concentrated in vacuo to afford the crude product, which was purified by silica gel chromatography (EtOAc/heptane gradient) to give the title compound as a white powder (2.21 g, yield: 92%). LCMS: RT 1.59 min.; MH+350.0; $^1$H NMR (400 MHz, DMSO-d$_6$) δ: 8.41 (t, J=5.65 Hz, 1H), 8.29 (s, 1H), 7.89 (s, 1H), 7.28-7.44 (m, 2H), 7.16 (d, J=8.03 Hz, 1H), 4.34 (d, J=5.52 Hz, 2H), 2.30 (s, 3H), 1.52 (s, 9H).

3. Synthesis of 1-(tert-butyl)-N-(2-methyl-4-(4,4,5,5-tetramethyl-1,3,2-dioxaborolan-2-yl)-benzyl)-1H-pyrazole-4-carboxamide

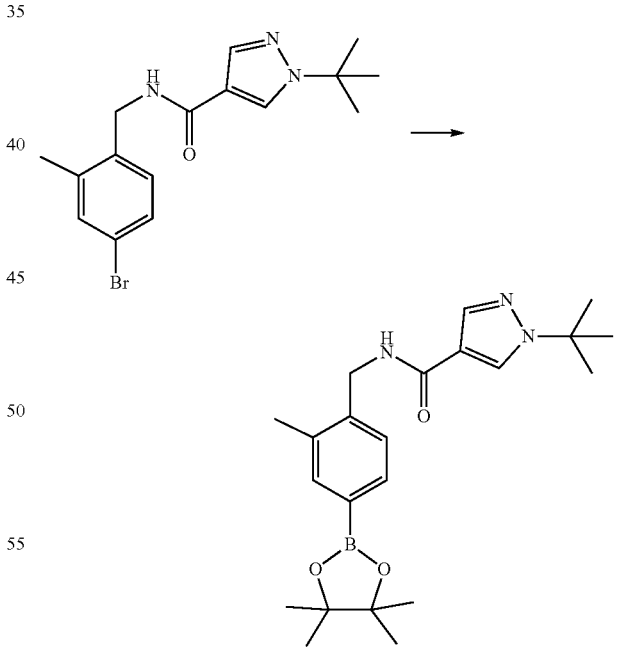

To a degassed solution of N-(4-bromo-2-methylbenzyl)-1-(tert-butyl)-1H-pyrazole-4-carboxamide (2.0 g, 5.7 mmol) and KOAc (1.68 g, 17.1 mmol) in 1,4-dioxane (50 mL) was added Pd(dppf)Cl$_2$.CH$_2$Cl$_2$ (1:1) (0.23 g, 0.28 mmol) and bis(pinacolato)diboron (1.6 g, 6.3 mmol). The solution was heated to reflux for 2 h, cooled to rt, diluted with EtOAc and filtered. The filtrate was concentrated in vacuo, and purified by silica gel chromatography (EtOAc/Heptane gradient) to give the title compound as an off white powder (2.1 g, yield: 95%). LCMS: RT 1.71 min.; MH+398.3; ¹H NMR (400 MHz, DMSO-d₆) δ: 8.41 (t, J=5.65 Hz, 1H), 8.30 (s, 1H), 7.90 (s, 1H), 7.42-7.50 (m, 2H), 7.23 (d, J=7.53 Hz, 1H), 4.40 (d, J=5.77 Hz, 2H), 2.30 (s, 3H), 1.45-1.59 (m, 9H), 1.28 (s, 12H).

4. Synthesis of 1-(tert-butyl)-N-(4-(6-chloropyrimidin-4-yl)-2-methylbenzyl)-1H-pyrazole-4-carboxamide

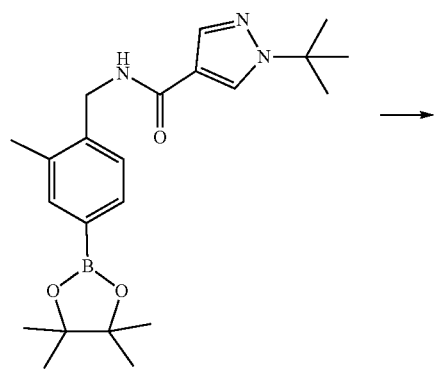

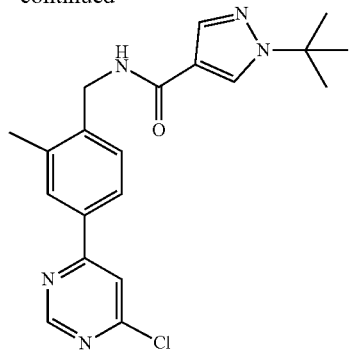

A mixture of 1-(tert-butyl)-N-(2-methyl-4-(4,4,5,5-tetramethyl-1,3,2-dioxaborolan-2-yl)benzyl)-1H-pyrazole-4-carboxamide (1.33 g, 3.35 mmol) and 4,6-dichloropyrimidine (0.60 g, 4.0 mmol) in 1,4-dioxane (20.0 mL) was degassed with nitrogen, follow by the addition of. [Pd(dppf)Cl₂.CH₂Cl₂ (273 mg, 0.33 mmol) and a solution of K₂CO₃ (0.92 g, 6.7 mmol) in water (1.0 mL). The reaction was heated at 110° C. for 2 h, cooled down to rt, diluted with EtOAc and washed with water. The organic layer was dried (Na₂SO₄), concentrated in vacuo, and purified by silica gel chromatography (EtOAc/heptane) to give the title compound as a white powder (0.74 g, yield: 55%). LCMS: RT 1.52 min.; MH+384.0; ¹H NMR (400 MHz, DMSO-d₆) δ: 9.07 (d, J=0.50 Hz, 1H), 8.50 (t, J=5.65 Hz, 1H), 8.31 (d, J=13.05 Hz, 2H), 8.00-8.15 (m, 2H), 7.92 (s, 1H), 7.39 (d, J=8.03 Hz, 1H), 4.46 (d, J=5.77 Hz, 2H), 2.41 (s, 3H), 1.53 (s, 9H).

5. Synthesis of 1-(tert-butyl)-N-(2-methyl-4-(6-((4,5,6,7-tetrahydropyrazolo[1,5-a]pyrazin-2-yl)amino)-pyrimidin-4-yl)benzyl)-1H-pyrazole-4-carboxamide

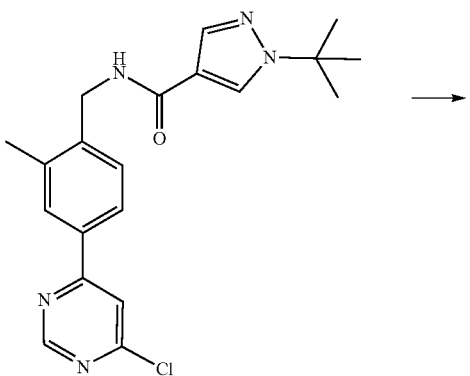

423

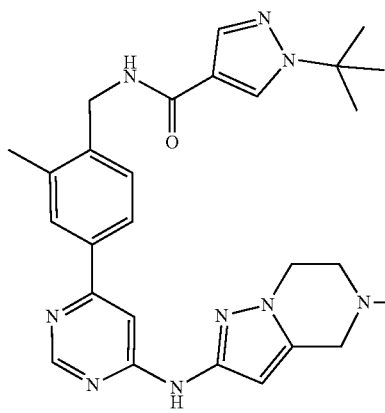

424

-continued

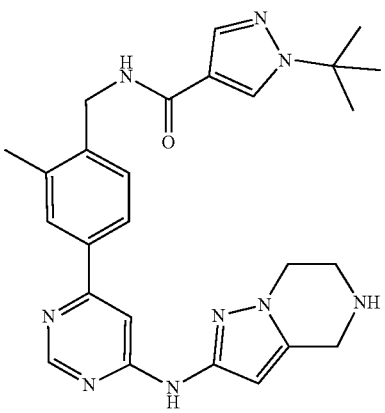

A mixture of 1-(tert-butyl)-N-(4-(6-chloropyrimidin-4-yl)-2-methylbenzyl)-1H-pyrazole-4-carboxamide (350.0 mg, 0.912 mmol) and 2-amino-6,7-dihydro-4H-pyrazolo[1,5-a]pyrazine-5-carboxylic acid tert-butyl ester (282.4 mg, 1.18 mmol) in PhCH₃ (10.0 mL) was degassed. To the solution was added 2-dicyclohexylphosphino-2',6'-dimethoxybiphenyl (75 mg, 0.18 mmol) and Pd₂(dba)₃ (83 mg, 0.09 mmol) and sodium tert-butoxide (263 mg, 2.7 mmol). The mixture was degassed, and then heated in a microwave to 100° C. for 1 h. The reaction was cooled to rt, diluted with EtOAc, washed with water, and the organic phase was separated, dried (Na₂SO₄), concentrated in vacuo, and purified by reverse phase chromatography (C₁₈-gradient 10 to 90% ACN/water with 0.1% TFA). The product was extracted with EtOAc to give an oil (LCMS: RT 1.29 min.; MH+586.3) which was then dissolved in 1,4-dioxane (2.0 mL, 26 mmol) and treated with 4 M solution of HCl in 1,4-dioxane (2.0 mL, 8.0 mmol). The reaction was stirred overnight and concentrated in vacuo to afford a residue which was then precipitated from dietheyl ether to afford a solid, which was used without further purification (320 mg, yield: 67% as HCl salt). LCMS: RT 0.85 min.; MH+486.3; ¹H NMR (400 MHz, DMSO-d₆) δ: 10.00 (br. s., 2H), 8.85 (s, 1H), 8.60 (t, J=5.65 Hz, 1H), 8.36 (s, 1H), 7.93 (s, 1H), 7.68-7.84 (m, 2H), 7.44 (d, J=8.03 Hz, 1H), 4.36-4.53 (m, 4H), 4.30 (t, J=5.52 Hz, 2H), 3.66 (br. s., 2H), 2.42 (s, 3H), 1.53 (s, 9H).

Example 223: 1-(tert-butyl)-N-(4-(6-((5-ethyl-4,5,6,7-tetrahydropyrazolo[1,5-a]pyrazin-2-yl)amino)pyrimidin-4-yl)-2-methylbenzyl)-1H-pyrazole-4-carboxamide

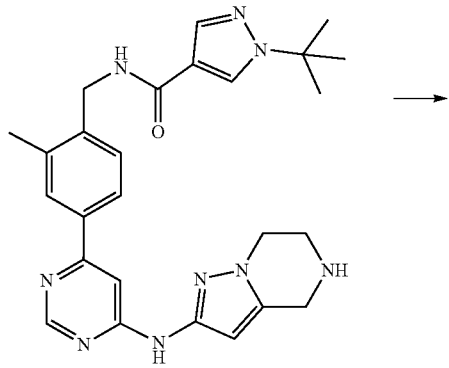

-continued

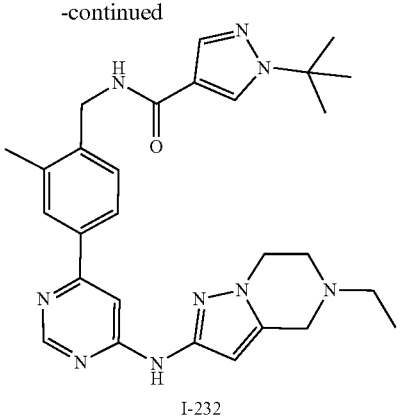

I-232

To a solution of 1-(tert-butyl)-N-(2-methyl-4-(6-((4,5,6,7-tetrahydropyrazolo[1,5-c]pyrazin-2-yl)amino)pyrimidin-4-yl)benzyl)-1H-pyrazole-4-carboxamide 1-(tert-butyl)-N-(2-methyl-4-(6-((4,5,6,7-tetrahydropyrazolo[1,5-a]pyrazin-2-yl)amino)pyrimidin-4-yl)benzyl)-1H-pyrazole-4-carboxamide (100 mg, 0.20 mmol), triethylamine (0.03 mL, 0.20 mmol), and 5.0 M of acetaldehyde in water (2 mL, 9 mmol) was added sodium triacetoxyborohydride (87 mg, 0.41 mmol) and heated heated in a microwave at 90° C. for 20 min. The reaction mixture was then diluted with EtOAc, washed with brine, dried and concentrated in vacuo to afford a residue which was purified by silica gel chromatography (DCM+10% to 100% 2M NH₃/MeOH) to give the title compound as a white powder (86 mg, yield: 84%). LCMS: RT 0.82 min.; MH+514.2; ¹H NMR (400 MHz, CD₃OD) δ: 8.59 (d, J=0.75 Hz, 1H), 8.27 (s, 1H), 7.96 (s, 1H), 7.69-7.83 (m, 2H), 7.52 (br. s., 1H), 7.40 (d, J=8.03 Hz, 1H), 6.25 (br. s., 1H), 4.59 (s, 2H), 4.12 (t, J=5.52 Hz, 2H), 3.72 (s, 2H), 3.01 (t, J=5.65 Hz, 2H), 2.67 (q, J=7.19 Hz, 2H), 2.45 (s, 3H), 1.60 (s, 9H), 1.20 (t, J=7.28 Hz, 3H).

Example 224: 1-(tert-butyl)-N-(4-(64(5-(2-hydroxy-ethyl)-4,5,6,7-tetrahydropyrazolo[1,5-a]pyrazin-2-yl)amino)pyrimidin-4-yl)-2-methylbenzyl)-1H-pyrazole-4-carboxamide

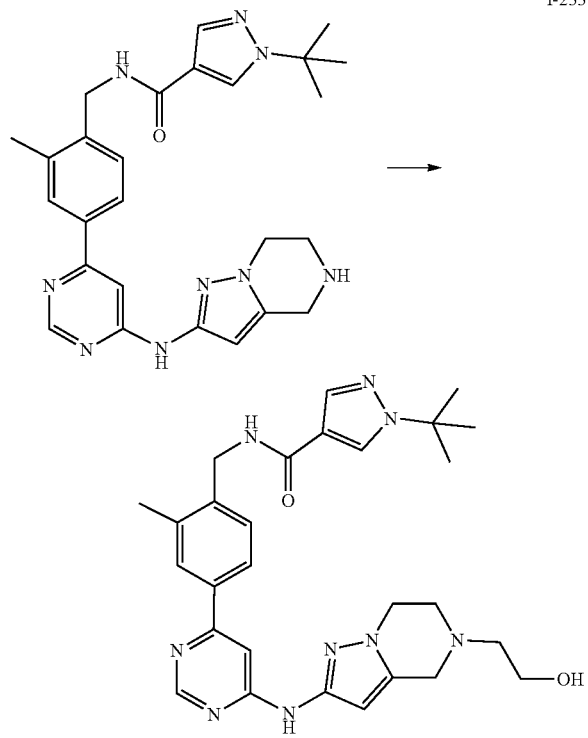

I-233

To a solution of 1-(tert-butyl)-N-(2-methyl-4-(6-((4,5,6,7-tetrahydropyrazolo[1,5-a]pyrazin-2-yl)amino)pyrimidin-4-yl)benzyl)-1H-pyrazole-4-carboxamide (240 mg, 0.49 mmol) and Et$_3$N (69 uL, 0.49 mmol) in 1,2-dichloroethane (4.0 mL), was added AcOH (28 uL, 0.49 mmol), [1,4]dioxane-2,5-diol (89 mg, 0.74 mmol) and sodium triacetoxyborohydride (200 mg, 0.99 mmol). The reaction mixture was stirred at rt for 1 h, extracted with EtOAc, and washed with aqueous NaHCO$_3$ and brine. The organic layer was separated, dried (MgSO$_4$), filtered and concentrated in vacuo to afford a residue which was purified by reverse phase chromatography (CH$_3$CN/H$_2$O with 0.05% TFA as mobile phase) to give the title compound as a white powder (178 mg, yield: 51% as TFA salt). LCMS: RT 0.85 min.; MH+530.3; $^1$H NMR (400 MHz, DMSO-d$_6$) δ: 10.41 (br. s., 1H), 8.73 (d, J=1.00 Hz, 1H), 8.51 (t, J=5.77 Hz, 1H), 8.32 (d, J=0.75 Hz, 1H), 7.92 (d, J=0.50 Hz, 1H), 7.71-7.87 (m, 1H), 7.63 (br. s., 1H), 7.39 (d, J=8.03 Hz, 1H), 6.52 (br. s., 1H), 4.17-4.76 (m, 6H), 3.65-3.97 (m, 4H), 3.38 (br. s., 2H), 2.41 (s, 3H), 1.53 (s, 9H).

Example 225: 1-(tert-butyl)-N-(2-methyl-4-(6-((5,6,7,8-tetrahydro-4H-pyrazolo[1,5-a][1,4]diazepin-2-yl)amino)pyrimidin-4-yl)benzyl)-1H-pyrazole-4-carboxamide

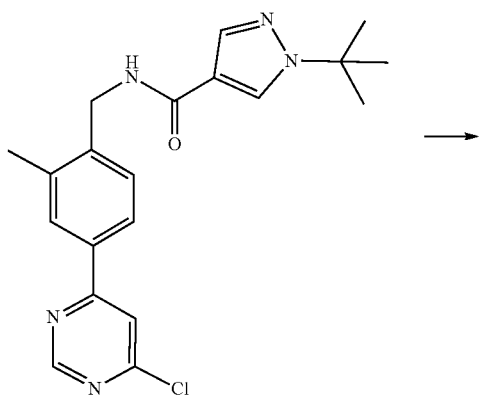

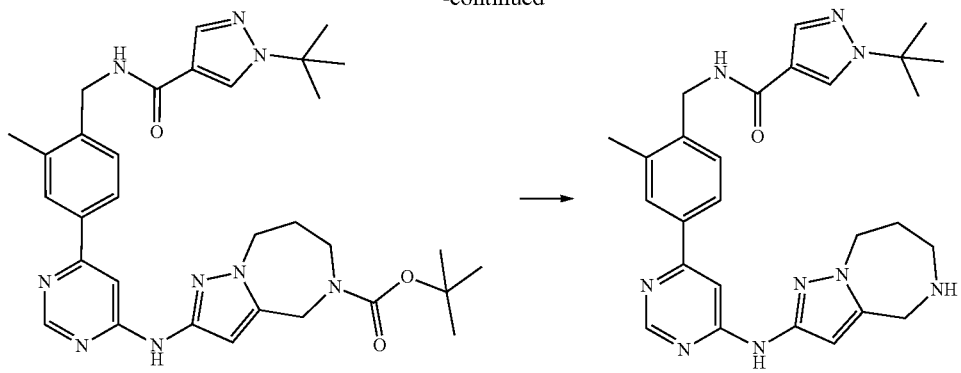

A solution of 1-(tert-butyl)-N-(4-(6-chloropyrimidin-4-yl)-2-methylbenzyl)-1H-pyrazole-4-carboxamide (350 mg, 0.91 mmol) and tert-butyl 2-amino-7,8-dihydro-4H-pyrazolo[1,5-a][1,4]diazepine-5(6H)-carboxylate (406 mg, 1.2 mmol) in PhCH₃ (10 mL, 94 mmol) was degassed for 5 min, followed by the addition of 2-dicyclohexylphosphino-2',6'-dimethoxybiphenyl (75 mg, 0.18 mmol) and tris(dibenzylideneacetone)dipalladium(0) (83 mg, 0.09 mmol) and sodium tert-butoxide (263 mg, 2.7 mmol), and degassed for another 5 min. The mixture was heated in a microwave at 100° C. for 1 h, cooled to rt and diluted with EtOAc. The organic phase was washed with water, separated, dried (Na₂SO₄), and concentrated in vacuo to afford a residue. The crude material was purified by prep HPLC (C₁₈-gradient 10 to 90% ACN/water with 0.1% TFA), followed by extraction with EtOAc and concentrating in vacuo to give a light yellow oil (LCMS: RT 1.27 min.; MH+600.3). The Boc protected intermediate was dissolved in 1,4-dioxane (2.0 mL) and treated with a 4 M solution of HCl in 1,4-dioxane (2.0 mL, 8.0 mmol). The reaction was stirred at rt overnight, concentrated in vacuo to afford a residue which was then precipitated from dithyl ether, filtered and washed with ether (3×5 mL) to give the title compound as a light yellow solid (289 mg, yield: 59% as HCl salt). LCMS: RT 0.88 min.; MH+500.3; ¹H NMR (400 MHz, DMSO-d₆) δ: 9.35 (br. s., 2H), 8.74 (s, 1H), 8.51 (t, J=5.65 Hz, 1H), 8.28 (s, 1H), 7.86 (s, 1H), 7.62-7.80 (m, 2H), 7.30-7.41 (m, 1H), 4.26-4.49 (m, 6H), 3.32 (br. s., 2H), 2.36 (s, 3H), 1.97 (br. s., 2H), 1.47 (s, 9H).

Example 226: 1-(tert-butyl)-N-(4-(6-((5-(2-hydroxyethyl)-5,6,7,8-tetrahydro-4H-pyrazolo[1,5-a][1,4]diazepin-2-yl)amino)pyrimidin-4-yl)-2-methylbenzyl)-1H-pyrazole-4-carboxamide

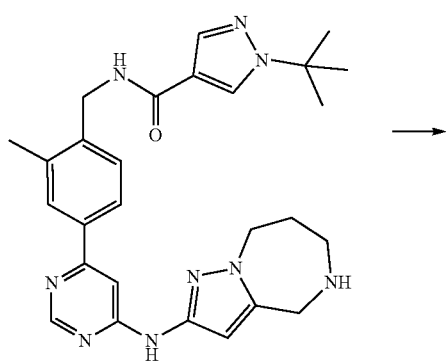

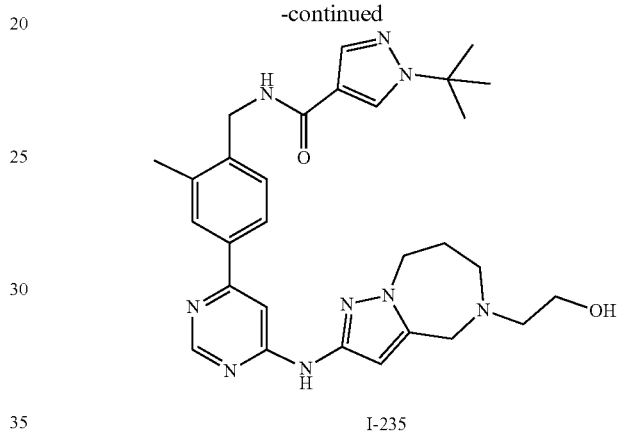

I-235

To a solution of 1-(tert-butyl)-N-(2-methyl-4-(6-((5,6,7,8-tetrahydro-4H-pyrazolo[1,5-a][1,4]diazepin-2-yl)amino)pyrimidin-4-yl)benzyl)-1H-pyrazole-4-carboxamide (100 mg, 0.20 mmol) and Et₃N (28 uL, 0.20 mmol) in 1,2-dichloroethane (2 mL), was added AcOH (11 uL, 0.20 mmol), [1,4]dioxane-2,5-diol (36 mg, 0.30 mmol) and then sodium triacetoxyborohydride (84.8 mg, 0.40 mmol). The reaction mixture was stirred at rt for 1 h, diluted with EtOAc, and washed with saturated aqueous NaHCO₃ and brine. The organic phase was dried (MgSO₄), filtered, and concentrated in vacuo to afford the crude product which was purified by prep HPLC (CH₃CN/H₂O with 0.05% TFA as mobile phase) to give the title compound as a white powder (48 mg, yield: 37% as TFA salt). LCMS: RT 0.87 min.; MH+544.2; ¹H NMR (400 MHz, DMSO-d₆) δ: 10.38 (br. s., 1H), 10.10 (br. s., 1H), 8.66-8.79 (m, 1H), 8.51 (t, J=5.65 Hz, 1H), 8.32 (s, 1H), 7.92 (s, 1H), 7.72-7.86 (m, 2H), 7.58 (br. s., 1H), 7.39 (d, J=8.03 Hz, 1H), 6.77 (br. s., 1H), 4.26-4.83 (m, 6H), 3.40-3.86 (m, 4H), 2.98-3.22 (m, 2H), 2.41 (s, 3H), 1.97-2.24 (m, 2H), 1.42-1.65 (m, 9H).

429

Example 227: 1-(tert-butyl)-N-(2-methyl-4-(6-((5-methyl-5,6,7,8-tetrahydro-4H-pyrazolo[1,5-a][1,4]diazepin-2-yl)amino)pyrimidin-4-yl)benzyl)-1H-pyrazole-4-carboxamide

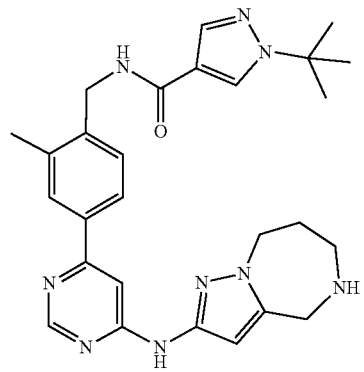

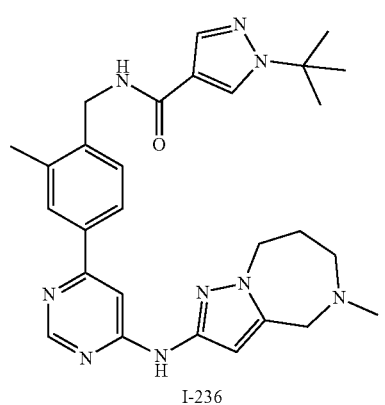

I-236

430

Example 228: 1-(tert-butyl)-N-(4-(6-((6,7-dihydro-4H-pyrazolo[5,1-c][1,4]oxazin-2-yl)amino)pyrimidin-4-yl)-2-methylbenzyl)-1H-pyrazole-4-carboxamide

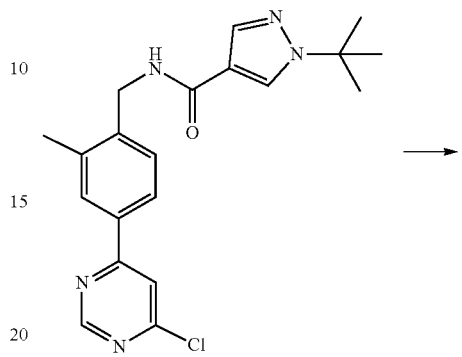

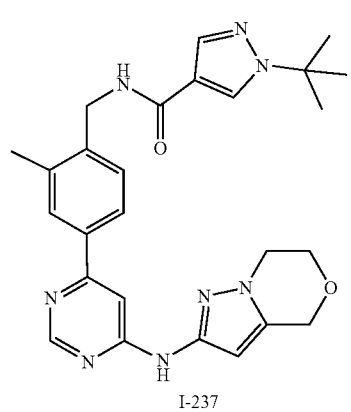

I-237

To a mixture of 1-(tert-butyl)-N-(2-methyl-4-(6-((5-methyl-5,6,7,8-tetrahydro-4H-pyrazolo[1,5-a][1,4]diazepin-2-yl)amino)pyrimidin-4-yl)benzyl)-1H-pyrazole-4-carboxamide hydrochloride (150 mg, 0.28 mmol) and Et$_3$N (39 uL, 0.28 mmol) in 1,2-dichloroethane (4.0 mL) was added formaldehyde (0.75 mL, 27 mmol) and AcOH (16 uL, 0.28 mmol). The mixture was stirred at rt for 10 min, followed by the addition of sodium triacetoxyborohydride (119 mg, 0.56 mmol). The mixture was stirred at rt for 1 h, and concentrated in vacuo to afford the crude material which was purified by prep HPLC (CH$_3$CN/H$_2$O with 0.05% TFA as mobile phase) to give desired product as a light yellow powder (98 mg, yield: 57% as TFA salt). LCMS: RT 0.80 min.; MH+514.2; $^1$H NMR (400 MHz, DMSO-d$_6$) δ: 10.40 (br. s., 1H), 10.27 (br. s., 1H), 8.73 (s, 1H), 8.51 (t, J=5.65 Hz, 1H), 8.32 (s, 1H), 7.92 (s, 1H), 7.72-7.85 (m, 2H), 7.39 (d, J=8.03 Hz, 1H), 6.75 (br. s., 1H), 4.29-4.76 (m, 6H), 3.39-3.72 (m, 2H), 2.82 (s, 3H), 2.41 (s, 3H), 2.16 (br. s., 1H), 1.99 (br. s., 1H), 1.53 (s, 9H).

To a solution of 1-(tert-butyl)-N-(4-(6-chloropyrimidin-4-yl)-2-methylbenzyl)-1H-pyrazole-4-carboxamide e (85 mg, 0.22 mmol) and 6,7-dihydro-4H-pyrazolo[5,1-c][1,4]oxazin-2-amine (62 mg, 0.44 mmol) in 2-butanol (5.0 mL) was added a solution of 4 M HCl in 1,4-dioxane (0.10 mL, 0.40 mmol) and heated at 50° C. overnight. The reaction was cooled to rt, diluted with EtOAc, and washed with water. The organic layer was separated, dried (Na$_2$SO$_4$), and concentrated in vacuo to afford a residue which was purified by prep HPLC (CH$_3$CN/H$_2$O with 0.05% TFA as mobile phase) to give the title compound as light yellow powder (36 mg, yield: 28% as TFA salt). RT 1.04 min.; MH+487.2; $^1$H NMR (400 MHz, DMSO-d$_6$) δ: 10.59 (br. s., 1H), 8.76 (s, 1H), 8.50 (t, J=5.65 Hz, 1H), 8.32 (d, J=0.75 Hz, 1H), 7.92 (d, J=0.50 Hz, 1H), 7.58-7.81 (m, 3H), 7.40 (d, J=8.03 Hz, 1H), 6.29 (br. s., 1H), 4.68-4.86 (m, 2H), 4.46 (d, J=5.52 Hz, 2H), 3.97-4.12 (m, 4H), 2.41 (s, 3H), 1.42-1.62 (m, 9H).

Example 229: 3-Ethyl-N-(2-methyl-4-(2-((1-methyl-1H-pyrazol-4-yl)amino)pyrimidin-4-yl)benzyl)azetidine-1-carboxamide

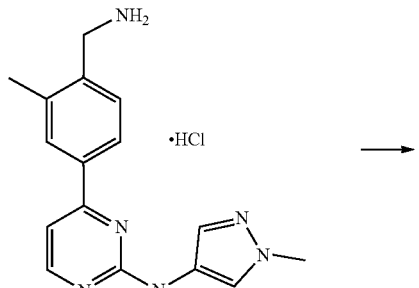

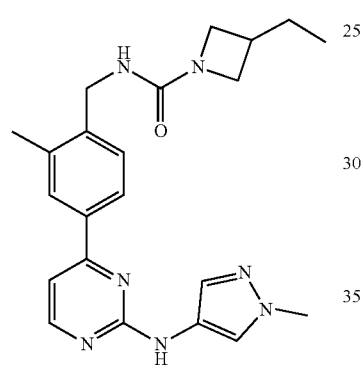

I-238

To a solution of N,N-carbonyldiimidazole (49 mg, 0.30 mmol) in DMF (4.0 mL) was added 4-(4-(aminomethyl)-3-methylphenyl)-N-(1-methyl-1H-pyrazol-4-yl)pyrimidin-2-amine hydrochloride (100 mg, 0.30 mmol) and Et$_3$N (0.13 mL, 0.91 mmol). The mixture was stirred at 35° C. for 2 h, followed by the addition of 3-ethylazetidine hydrochloride (55 mg, 0.45 mmol), and then stirred at rt overnight. The mixture was diluted with EtOAc and washed with brine. The organic phase was separated, dried and concentrated in vacuo to afford the crude which was purified by prep HPLC (CH$_3$CN/H$_2$O with 0.05% TFA as mobile phase) to give the title compound as a yellow powder (114 mg, yield: 76% as TFA salt). LCMS: RT 1.12 min.; MH+406.2; $^1$H NMR (400 MHz, DMSO-d$_6$) δ: 9.54 (s, 1H), 8.45 (d, J=5.27 Hz, 1H), 7.93 (d, J=2.01 Hz, 3H), 7.56 (br. s., 1H), 7.36 (d, J=8.03 Hz, 1H), 7.27 (d, J=5.27 Hz, 1H), 6.75 (br. s., 1H), 4.23 (d, J=4.02 Hz, 2H), 3.91 (t, J=7.91 Hz, 2H), 3.83 (s, 3H), 3.45 (dd, J=5.65, 7.91 Hz, 2H), 2.28-2.46 (m, 4H), 1.54 (quin, J=7.34 Hz, 2H), 0.83 (t, J=7.28 Hz, 3H).

Example 230: 3-(tert-butoxy)-N-(2-methyl-4-(6-((5-methyl-6-oxo-4,5,6,7-tetrahydropyrazolo-[1,5-a]pyrazin-2-yl)amino)pyrimidin-4-yl)benzyl)azetidine-1-carboxamide

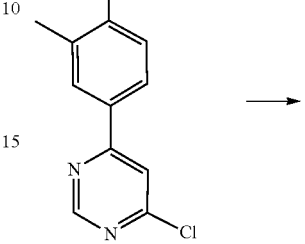

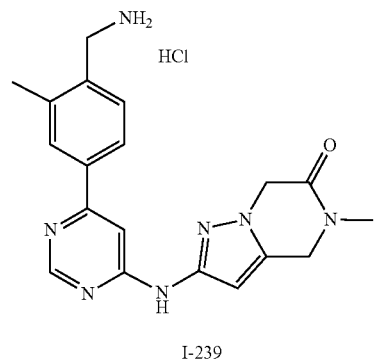

I-239

1. Synthesis of 2-((6-(4-(aminomethyl)-3-methylphenyl)pyrimidin-4-yl)amino)-5-methyl-4,5-dihydro-pyrazolo[1,5-a]pyrazin-6(7H)-one hydrochloride To a solution of tert-butyl 4-(6-chloropyrimidin-4-yl)-2-methylbenzylcarbamate (200 mg, 0.60 mmol) and 2-amino-5-methyl-4,5-dihydro-pyrazolo[1,5-a]pyrazin-6-one (149 mg, 0.9 mmol) in 2-butanol (6.0 mL) was added a solution of 4 M HCl in 1,4-dioxane (0.4 mL, 1.5 mmol) and water (1.0 mL). The mixture was heated at 50° C. for 12 h, cooled to rt and concentrated in vacuo to afford a residue which was dissolved in EtOAc and washed with aqueous NaHCO$_3$ and water. The organic phase was separated, dried (Na$_2$SO$_4$) and concentrated in vacuo. The crude material was diluted with diethyl ether and treated with a 4 M solution of HCl in 1,4-dioxane (2.0 mL, 8.0 mmol). The reaction was stirred at rt for 4 h to afford a solid which was filtered and washed with diethyl ether to give the title compound as a light yellow powder (145 mg, 60% yield: as HCl salt), which was used in the next step without further purifications. LCMS: RT 0.33 min.; MH+364.1.

2. Synthesis of 3-(tert-butoxy)-N-(2-methyl-4-(6-((5-methyl-6-oxo-4,5,6,7-tetrahydropyrazolo-[1,5-a]pyrazin-2-yl)amino)pyrimidin-4-yl)benzyl)azetidine-1-carboxamide

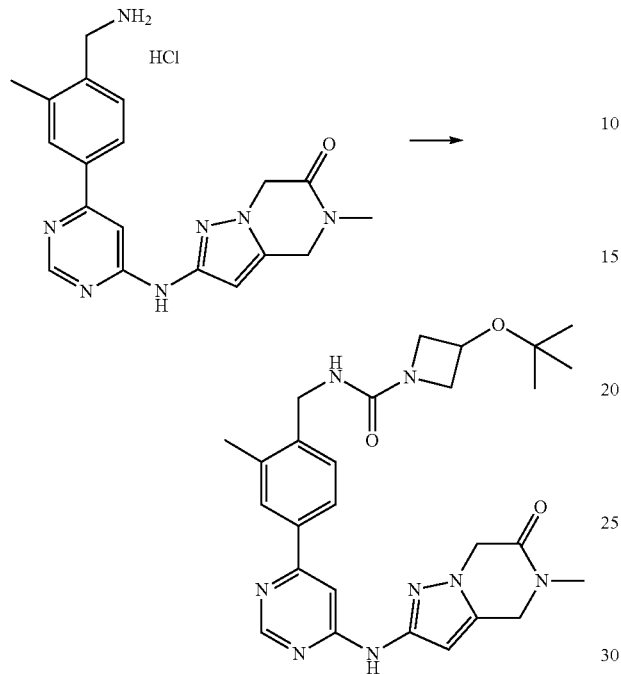

To a solution of CDI (14 mg, 0.08 mmol) in DMF (2.0 mL1) was added 2-[6-(4-aminomethyl-3-methyl-phenyl)-pyrimidin-4-ylamino]-5-methyl-6,7-dihydro-5H-pyrazolo[1,5-a]pyrazin-4-one (30 mg, 0.08 mmoll) and triethylamine (0.03 mL, 0.24 mmol). The mixture was stirred at 35° C. for 1 h, followed by the addition of 3-(tert-butoxy)azetidine hydrochloride (20 mg, 0.12 mmol). The reaction mixture was stirred at rt for 12 h, diluted with MeOH, and filtered. The filtrate was concentrated in vacuo to afford the crude produce which was purified by prep HPLC (CH₃CN/H₂O with 0.05% TFA as mobile phase) to give the title compound as an off white powder (12 mg, 25% yield:). LCMS: RT 1.00 min.; MH+519.2; ¹H NMR (400 MHz, CD₃OD) δ: 8.84 (s, 1H), 7.60-8.01 (m, 3H), 7.51 (d, J=7.78 Hz, 1H), 7.10 (br. s., 1H), 4.52-4.65 (m, 1H), 4.40 (s, 4H), 4.10-4.26 (m, 2H), 3.84-3.94 (m, 2H), 3.72-3.83 (m, 2H), 3.15 (s, 3H), 2.46 (s, 3H), 1.20 (s, 9H).

Example 231: 1-(tert-butyl)-N-(2-chloro-4-(6-((5-methyl-4,5,6,7-tetrahydropyrazolo[1,5-a]-pyrazin-2-yl)amino)pyrimidin-4-yl)benzyl)-1H-pyrazole-4-carboxamide

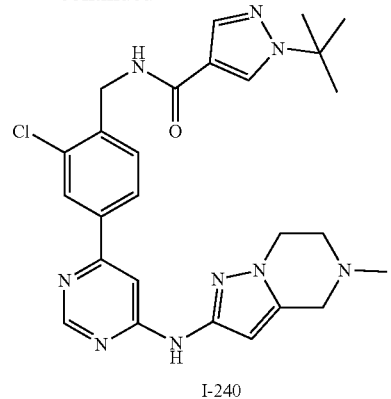

A mixture of 1-tert-butyl-1H-pyrazole-4-carboxylic acid (45 mg, 0.27 mmol) HATU (113 mg, 0.30 mmol), and DIEA (0.10 mL, 0.54 mmol) in DMF (4.0 mL) was stirred at rt for 5 min, followed by the addition of [6-(4-aminomethyl-3-chloro-phenyl)-pyrimidin-4-yl]-((5-methyl-4,5,6,7-tetrahydro-pyrazolo[1,5-a]pyrazin-2-yl)-amine (100 mg, 0.27 mmol), and the mixture was stirred at rt overnight. The reaction mixture was then diluted with EtOAc and washed with water. The organic phase was separated, dried (Na₂SO₄) and concentrated in vacuo. The crude was purified by silica gel chromatography (EtOAc/heptane gradient) to give the title compound as a white powder (32 mg, yield: 22%). LCMS: RT 0.87 min.; MH+520.2; ¹H NMR (400 MHz, DMSO-d₆/CD₃OD) δ: 9.97 (s, 1H), 8.56-8.74 (m, 2H), 8.31 (s, 1H), 8.05 (d, J=1.51 Hz, 1H), 7.84-7.97 (m, 2H), 7.61 (br. s., 1H), 7.48 (d, J=8.03 Hz, 1H), 6.23 (br. s., 1H), 4.47-4.59 (m, 2H), 3.99 (t, J=5.27 Hz, 2H), 3.65-3.72 (m, 2H), 2.82 (t, J=5.52 Hz, 2H), 2.36 (s, 3H), 1.52 (s, 9H).

Example 232: 1-(tert-butyl)-N-(4-(64(5-methyl-4,5,6,7-tetrahydropyrazolo[1,5-a]pyrazin-2-yl)amino)pyrimidin-4-yl)-2-(trifluoromethyl)benzyl)-1H-pyrazole-4-carboxamide

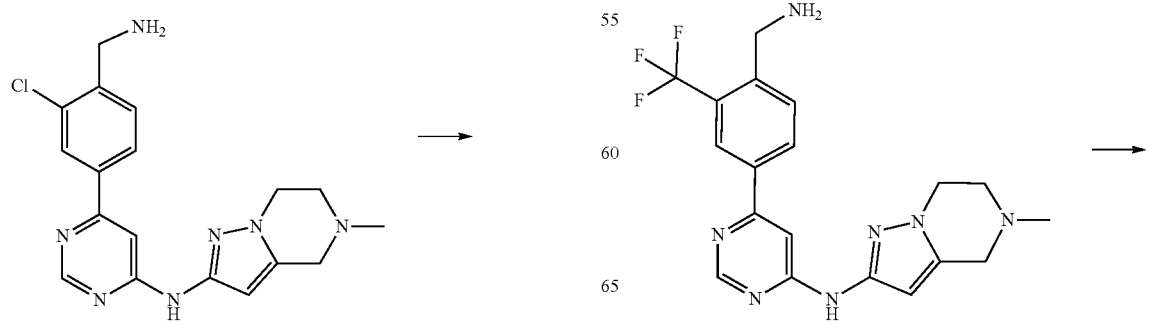

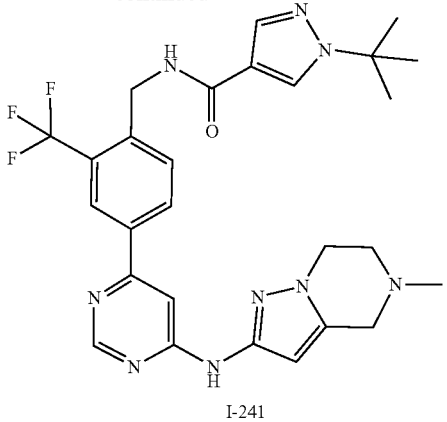

I-241

A mixture of 1-tert-butyl-1H-pyrazole-4-carboxylic acid (63 mg, 0.37 mmol), HATU (156 mg, 0.41 mmol) and DIEA (0.13 mL, 0.74 mmol) in DMF (6.0 mL) was stirred at rt for 5 min, followed by the addition of [6-(4-aminomethyl-3-trifluoromethyl-phenyl)-pyrimidin-4-yl]-(5-methyl-4,5,6,7-tetrahydro-pyrazolo[1,5-a]pyrazin-2-yl)-amine (150 mg, 0.37 mmol). The solution was stirred at rt overnight, diluted with EtOAc, washed with water, and the organic phase was separated, dried ($Na_2SO_4$) and concentrated in vacuo to afford the crude material which was purified by silica gel chromatography (EtOAc/heptane gradient) to give the title compound as a white powder (106 mg, 52% yield:). LCMS: RT 0.96 min.; MH+554.2; $^1$H NMR (400 MHz, $CD_3OD$) δ: 8.61-8.70 (m, 1H), 8.36 (s, 1H), 8.29 (s, 1H), 8.18 (d, J=8.28 Hz, 1H), 7.99 (s, 1H), 7.58-7.74 (m, 2H), 6.25 (br. s., 1H), 4.80 (s, 2H), 4.12 (t, J=5.65 Hz, 2H), 3.68 (s, 2H), 2.98 (t, J=5.65 Hz, 2H), 2.51 (s, 3H), 1.62 (s, 9H).

Example 233: 1-(tert-butyl)-N-(4-(6-((5,5-dioxido-6,7-dihydro-4H-pyrazolo[5,1-c][1,4]thiazin-2-yl)amino)pyrimidin-4-yl)-2-methylbenzyl)-1H-pyrazole-4-carboxamide

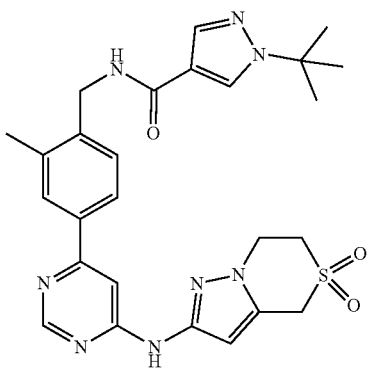

I-242

1. Synthesis of (3-nitropyrazol-5-yl)methanol

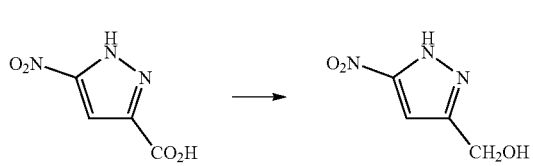 [SMILES: O=C(O)c1cc([N+](=O)[O-])[nH]n1 ; O=[N+]([O-])c1cc(CO)n[nH]1]

To a solution of 3-nitropyrazol-5-carboxylic acid (17 g, 110 mmol) in THF (200 mL) was slowly added a solution of borane-THF complex (1.0M in THF, 200 mL) at 0° C. under an atmosphere of nitrogen. The mixture was then stirred at rt for 20 hrs, cooled to 0° C., and water (40 mL) and 4N HCl (40 mL) was slowly added and the mixture was stirred at reflux for 1 h. The mixture was cooled, was concentrated in vacuo, and extracted with ethyl acetate (4×100 mL). The organic phase washed with aqueous $NaHCO_3$ and brine, separated, dried ($MgSO_4$), filtered, and concentrated in vacuo to afford (3-nitropyrazol-5-yl)methanol (10 g, yield: 64%).

2. Synthesis of (1-(2-bromoethyl)-3-nitro-1H-pyrazol-5-yl)methanol

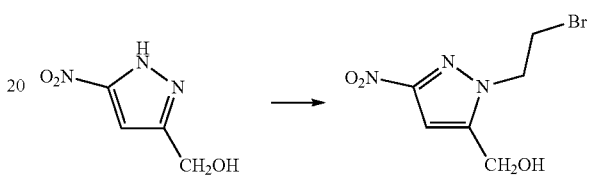

A mixture of (3-nitropyrazol-5-yl) MeOH (10 g, 0.07 mol) and cesium carbonate (35 g, 0.11 mol) in DMF (100 ml) was heated at 100° C. for 5 min and cooled to rt, followed by the addition of dibromoethane (13 g, 0.07 mol). The mixture was stirred at rt for 6 h, poured into ice water, to which aqueous citric acid was added to adjust the pH=7. The product was extracted with EtOAc, washed with water and brine, and the organic layer was separated, dried ($MgSO_4$), filtered and concentrated in vacuo. The crude was purified by column chromatography to afford (1-(2-bromoethyl)-3-nitro-1H-pyrazol-5-yl)methanol (6 g, yield: 34%).

3. Synthesis of S-(2-(5-(hydroxymethyl)-3-nitro-1H-pyrazol-1-yl)ethyl) ethanethioate

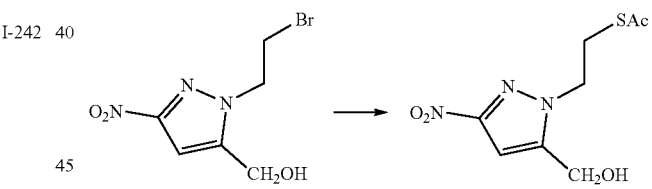

To a solution of (1-bromoethyl-3-nitropyrazol-5-yl)methanol (5.5 g, 22 mmol) in DMF (50 ml) was added potassium thioacetate (5.0 g, 44 mmol). The resulting mixture was stirred at 60° C. for 4 hr. The solvent was reduced to afford a residue which was diluted with DCM and water. The organic layer was separated, washed with brine, dried ($MgSO_4$), filtered and concentrated in vacuo. The crude was purified by column ($DCM/CH_3OH$=98/2 as eluent) to afford S-(2-(5-(hydroxymethyl)-3-nitro-1H-pyrazol-1-yl)ethyl) ethanethioate (4 g, yield: 74%).

4. Synthesis of S-(2-(5-(hydroxymethyl)-3-nitro-1H-pyrazol-1-yl)ethyl) ethanethioate

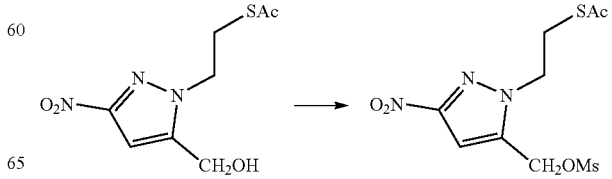

A solution of S-(2-(5-(hydroxymethyl)-3-nitro-1H-pyrazol-1-yl)ethyl) ethanethioate (4.0 g, 16.4 mmol) in CH$_2$Cl$_2$ (50 mL) was cooled to 0° C. Et$_3$N (2.5 g, 25 mmol) was added, follow by methanesulfonic chloride (2.2 g, 19.2 mmol). The mixture was stirred at 0° C. for 3 hours and washed with aqueous NaHCO$_3$. The organic layer was separated, dried over MgSO$_4$, filtered and concentrated. The crude was purified by column (DCM/CH$_3$OH=99/1 as eluent) to give S-(2-(5-(((methylsulfonyl)oxy)methyl)-3-nitro-1H-pyrazol-1-yl)ethyl) ethanethioate (4.2 g, yield: 79%).

5. Synthesis of 2-nitro-6,7-dihydro-4H-pyrazolo[5,1-c][1,4]thiazine

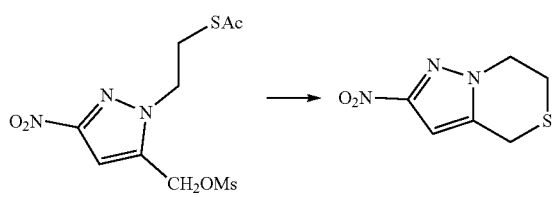

To a solution of S-(2-(5-(((methylsulfonyl)oxy)methyl)-3-nitro-1H-pyrazol-1-yl)ethyl) ethanethioate (4.2 g, 13 mmol) in CH$_3$OH (60 mL) was added LiOH (0.62 g, 26 mmol). The mixture was stirred at rt for 6 hr. The solvent was reduced and the residue was diluted with CH$_2$Cl$_2$ and water. The organic layer was separated, washed with brine, then dried (MgSO$_4$), filtered and concentrated in vacuo to afford the crude which was purified by column (CH$_2$Cl$_2$ as eluent) to give 2-nitro-6,7-dihydro-4H-pyrazolo[5,1-c][1,4]thiazine (2.0 g, yield: 83%).

6. Synthesis of 2-nitro-6,7-dihydro-4H-pyrazolo[5,1-c][1,4]thiazine 5,5-dioxide

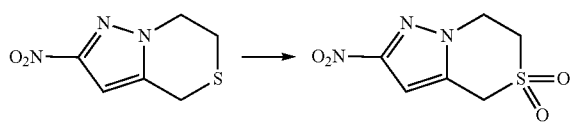 [SMILES: O=[N+]([O-])c1cc2n(n1)CCSC2 ; O=[N+]([O-])c1cc2n(n1)CCS(=O)(=O)C2]

To a solution of 2-nitro-6,7-dihydro-4H-pyrazolo[5,1-c][1,4]thiazine (1.3 g, 7 mmol) in CH$_3$OH (150 mL) was added a solution of oxone (12 g) in water (150 mL). The reaction was stirred at rt for 8 hr. The solvent was reduced and the resulting aqueous mixture was extracted with CH$_2$Cl$_2$. The organic layer was separated, dried (MgSO$_4$), filtered and concentrated in vacuo to afford the crude 2-nitro-6,7-dihydro-4H-pyrazolo[5,1-c][1,4]thiazine 5,5-dioxide (1.5 g) which was used in the next step without further purifications.

7. Synthesis of 2-amino-6,7-dihydro-4H-pyrazolo[5,1-c][1,4]thiazine

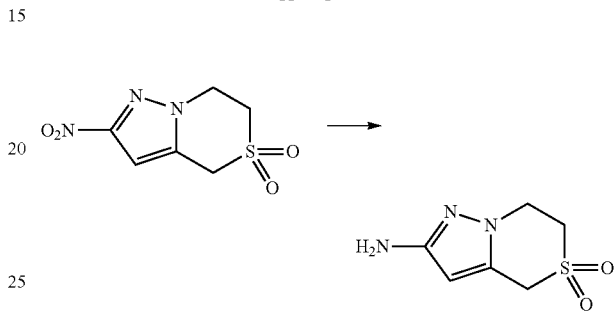

A 500 ml hydrogenation flask was charged with 2-nitro-6,7-dihydro-4H-pyrazolo[5,1-c][1,4]thiazine 5,5-dioxide (1.2 g, 5.5 mmol), CH$_3$OH (200 ml) and 10% palladium on carbon (50% wet, 400 mg). The flask was placed under an atmosphere of hydrogen to pressure 35 psi and stirred at rt for 1 h. The mixture was filtrated through a pad of celite and washed with MeOH. The filtrate was concentrated in vacuo to afford 2-amino-6,7-dihydro-4H-pyrazolo[5,1-c][1,4]thiazine 5,5-dioxide (700 mg, yield: 68%). MH+188.0; $^1$H NMR (400 MHz, DMSO-d$_6$) δ: 5.44 (s, 1H), 4.53 (s, 2H), 4.24 (t, J=6.02 Hz, 2H), 3.70 (t, J=5.90 Hz, 2H).

8. Synthesis of 1-(tert-butyl)-N-(4-(6-((5,5-dioxido-6,7-dihydro-4H-pyrazolo[5,1-c][1,4]thiazin-2-yl)amino)pyrimidin-4-yl)-2-methylbenzyl)-1H-pyrazole-4-carboxamide

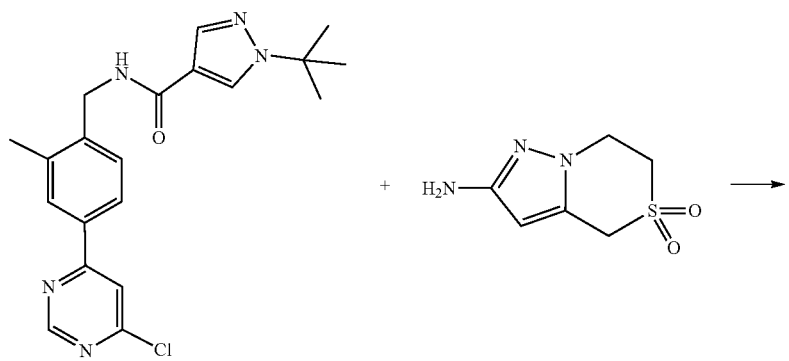

-continued

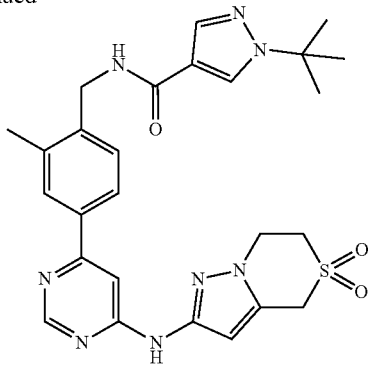

A mixture of 1-(tert-butyl)-N-(4-(6-chloropyrimidin-4-yl)-2-methylbenzyl)-1H-pyrazole-4-carboxamide (100 mg, 0.26 mmol), 2-amino-6,7-dihydro-4H-pyrazolo[5,1-c][1,4]thiazine 5,5-dioxide (98 mg, 0.52 mmol) and 4 M solution of HCl in 1,4-dioxane (0.07 mL, 0.26 mmol) in 2-butanol (2.0 mL) and water (2.0 mL) was heated at 50° C. for 12 h. The reaction was then cooled to rt, diluted with EtOAc and washed with water. The organic layer was separated, dried (Na$_2$SO$_4$), and concentrated in vacuo to afford the crude which was purified by silica gel chromatography (DCM+1% to 10% 2M NH$_3$/MeOH) to give the title compound as yellow powder (88 mg, yield: 62%). LCMS: RT 0.99 min.; MH+535.2; $^1$H NMR (400 MHz, DMSO-d$_6$) δ: 10.11 (s, 1H), 8.67 (d, J=0.50 Hz, 1H), 8.46 (t, J=5.65 Hz, 1H), 8.32 (s, 1H), 7.92 (s, 1H), 7.73-7.88 (m, 2H), 7.62 (br. s., 1H), 7.37 (d, J=8.03 Hz, 1H), 6.45 (br. s., 1H), 4.72 (s, 2H), 4.37-4.58 (m, 4H), 3.82 (t, J=5.65 Hz, 2H), 2.40 (s, 3H), 1.53 (s, 9H).

Example 234: (S)-3-(tert-butyl)-N-(2-methyl-4-(6-((5-methyl-4,5,6,7-tetrahydropyrazolo[1,5-a]pyrazin-2-yl)amino)pyrimidin-4-yl)benzyl)pyrrolidine-1-carboxamide and (R)-3-(tert-butyl)-N-(2-methyl-4-(6-((5-methyl-4,5,6,7-tetrahydropyrazolo[1,5-a]pyrazin-2-yl)amino)pyrimidin-4-yl)benzyl)pyrrolidine-1-carboxamide

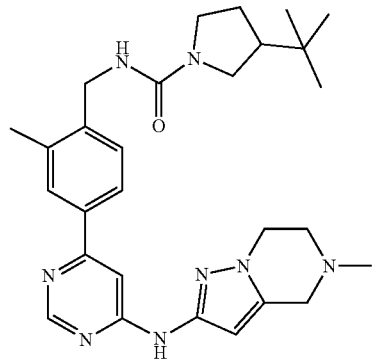 → 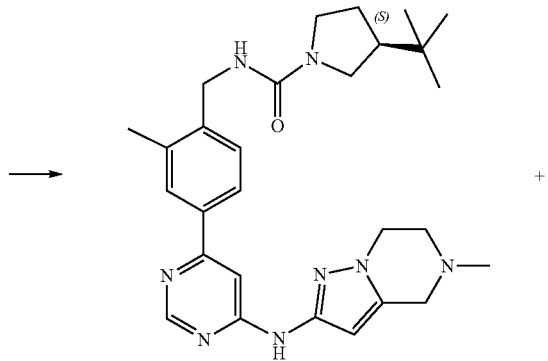

I-244

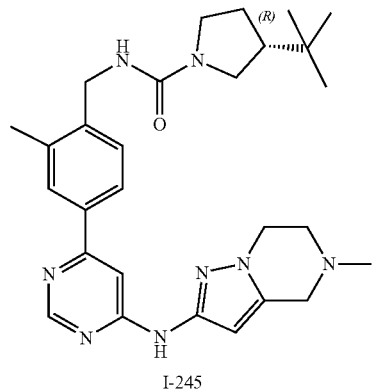

I-245

3-(tert-butyl)-N-(2-methyl-4-(6-((5-methyl-4,5,6,7-tetrahydropyrazolo[1,5-c]pyrazin-2-yl)amino)-pyrimidin-4-yl)benzyl)pyrrolidine-1-carboxamide) (6.7 g, 9.2 mmol) was separated by chiral column. The following SFC method was used: AS-H (2×25 cm) 30% ACN:ethanol/CO$_2$, 100 bar; 60 mL/min, 220 nm.; inj vol.: 2 mL, 20 mg/mL DCM:CH$_3$OH (1% DEA). Two isomers were obtained: 2.7 g of (S)-3-(tert-butyl)-N-(2-methyl-4-(6-((5-methyl-4,5,6,7-tetrahydropyrazolo[1,5-a]pyrazin-2-yl)amino)pyrimidin-4-yl)benzyl)pyrrolidine-1-carboxamide (chemical purity>99%, ee>99%). LCMS: RT 1.04 min.; MH+503.2; $^1$H NMR (400 MHz, CD$_3$OD) δ: 8.85 (br. s., 1H), 8.36 (s, 1H), 7.63-7.75 (m, 2H), 7.54 (d, J=8.03 Hz, 1H), 7.24 (s, 1H), 6.96 (s, 1H), 6.15-6.37 (m, 1H), 4.36-4.77 (m, 6H), 3.95 (br. s., 2H), 3.53-3.63 (m, 1H), 3.43-3.52 (m, 1H), 3.06-3.19 (m, 4H), 2.41-2.53 (m, 3H), 2.06-2.20 (m, 1H), 1.88-2.00 (m, 1H), 1.63-1.80 (m, 2H), 0.77-1.08 (m, 9H); and 2.3 g of (R)-3-(tert-butyl)-N-(2-methyl-4-(6-((5-methyl-4,5,6,7-tetrahydro-pyrazolo[1,5-a]pyrazin-2-yl)amino)pyrimidin-4-yl)benzyl)pyrrolidine-1-carboxamide (chemical purity>99%, ee>99%). LCMS: RT 1.03 min.; MH+503.2; $^1$H NMR (400 MHz, METHANOL-d$_4$) δ: 8.85 (br. s., 1H), 8.36 (s, 1H), 7.62-7.77 (m, 2H), 7.54 (d, J=7.78 Hz, 1H), 7.25 (br. s., 1H), 6.98 (br. s., 1H), 6.26 (s, 1H), 4.44 (d, J=5.77 Hz, 5H), 3.83-4.05 (m, 2H), 3.53-3.64 (m, 1H), 3.43-3.53 (m, 1H), 3.16 (s, 4H), 2.48 (s, 3H), 2.23-2.40 (m, 1H), 2.06-2.19 (m, 1H), 1.88-2.01 (m, 1H), 1.63-1.80 (m, 2H), 0.76-1.09 (m, 9H). The chiral center was confirmed by VCD study.

Example 235: 1-(tert-butyl)-N-(4-(2-((1-ethyl-1H-pyrazol-4-yl)amino)pyrimidin-4-yl)-2-methylbenzyl)-1H-pyrazole-4-carboxamide

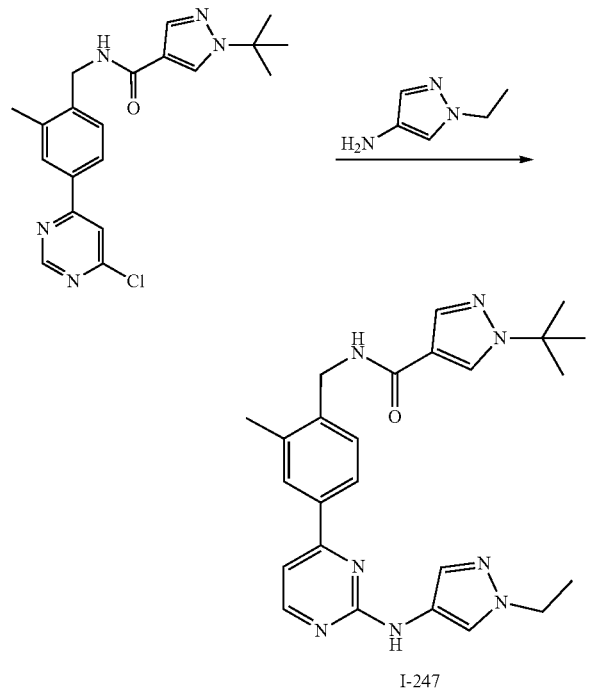

I-247

A mixture of 1-tert-Butyl-1H-pyrazole-4-carboxylic acid 4-(6-chloro-pyrimidin-4-yl)-2-methyl-benzylamide (215 mg, 0.560 mmol) and 1-Ethyl-1H-pyrazol-4-ylamine (80.9 mg, 0.73 mmol) in PhCH$_3$ (6.7 mL, 63 mmol) was degassed for 5 min, 2-Dicyclohexylphosphino-2',6'-dimethoxybiphenyl (45.98 mg, 0.112 mmol) and tris(dibenzylideneacetone)dipalladium(0) (51.3 mg, 0.056 mmol) and sodium tert-butoxide (161.5 mg, 1.68 mmol) were then added, degassed for another 5 min, and the reaction was heated in a microwave at 100° C. overnight. The reaction was then cooled to rt, diluted with EtOAc, and washed with water. The organic layer was separated, dried (Na$_2$SO$_4$), and concentrated in vacuo to afford the crude which was purified by prep HPLC (CH$_3$CN/H$_2$O with 0.05% TFA as mobile phase) to give the desired product as yellow powder. $^1$H NMR (400 MHz, CD$_3$OD) δ: ppm 8.21-8.34 (m, 2H) 7.97 (m, J=6.80 Hz, 4H) 7.69 (s, 1H) 7.42 (t, J=7.80 Hz, 2H) 4.58 (s, 2H) 4.19 (dd, J=8.03, 7.28 Hz, 2H) 3.35 (s, 2H) 2.43 (s, 3H) 1.60 (s, 9H) 1.48 (t, J=7.28 Hz, 3H).

Example 236: 3-(tert-butoxy)-N-(7-(2-((1-methyl-1H-pyrazol-4-yl)amino)pyrimidin-4-yl)-2,3,4,5-tetrahydro-1H-benzo[d]azepin-1-yl)azetidine-1-carboxamide

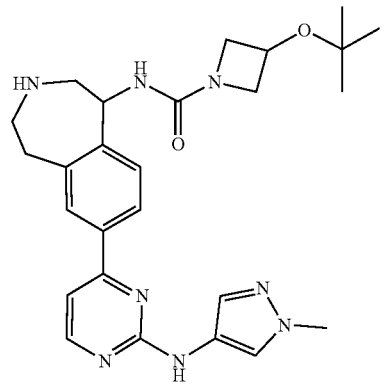

1. Synthesis of N-(3-bromophenethyl)-4-methylbenzenesulfonamide

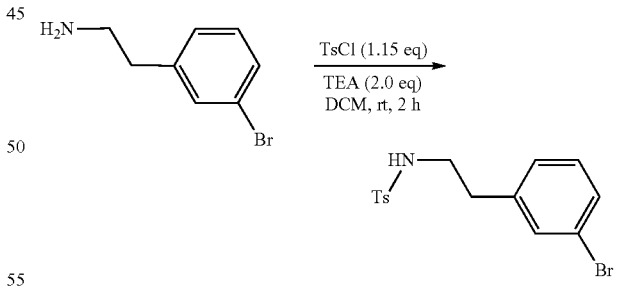

To a mixture of 2-(3-bromophenyl)ethanamine (2 g, 10 mmol) in CH$_2$Cl$_2$ (10 mL), TEA (2.02 g, 20 mmol) and TsCl (2.18 g, 11.5 mmol) were added at 0° C. The mixture was stirred at rt for 2 h, diluted with NaOH (1N, 100 mL) and extracted with CH$_2$Cl$_2$ (100 mL). The organic layer was washed with water (100 mL), brine (100 mL), dried (Na$_2$SO$_4$) and concentrated in vacuo to give N-(3-bromophenethyl)-4-methylbenzenesulfonamide (3.5 g, yield: 100%) as a yellow oil. ESI-MS (M+H)$^+$: 354.0. $^1$H NMR (400 MHz, CDCl$_3$) δ: 7.69 (d, J=8.0 Hz, 2H), 7.34 (d, J=8.4 Hz, 1H), 7.30 (d, J=8.0 Hz, 2H), 7.17 (t, J=1.6 Hz, 1H), 7.13

(t, J=8.0 Hz, 1H), 7.03-7.02 (m, 1H), 4.52 (t, J=6.0 Hz, 1H), 3.22-3.17 (m, 2H), 2.73 (t, J=6.8 Hz, 2H), 2.45 (s, 3H).

2. Synthesis of ethyl 2-(N-(3-bromophenethyl)-4-methylphenylsulfonamido)acetate

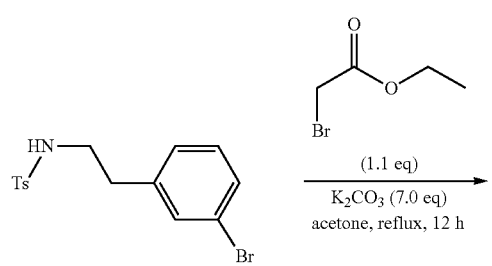

To a mixture of N-(3-bromophenethyl)-4-methylbenzenesulfonamide (7.2 g, 20 mmol) in (CH₃)₂C₀ (80 mL), K₂CO₃ (19.3 g, 140 mmol) and ethyl 2-bromoacetate (3.67 g, 22 mmol) were added. The mixture was stirred at 60° C. for 12 h, cooled to rt and the salt was filtered out. The resulting filtrate was concentrated in vacuo to give ethyl 2-(N-(3-bromophenethyl)-4-methylphenylsulfonamido)acetate (8.78 g, yield: 100%) as a yellow oil. ESI-MS (M+H)⁺: 440.0. ¹H NMR (400 MHz, CDCl₃) δ: 7.70 (d, J=8.4 Hz, 2H), 7.34 (d, J=8.4 Hz, 1H), 7.28 (d, J=8.0 Hz, 2H), 7.14 (t, J=7.6 Hz, 1H), 7.10-7.08 (m, 2H), 4.08 (q, J=7.6 Hz, 2H), 3.98 (s, 2H), 3.44 (t, J=7.6 Hz, 2H), 2.85 (t, J=7.2 Hz, 2H), 2.42 (s, 3H), 1.19 (t, J=7.2 Hz, 3H).

3. Synthesis of 2-(N-(3-bromophenethyl)-4-methylphenylsulfonamido)acetic Acid

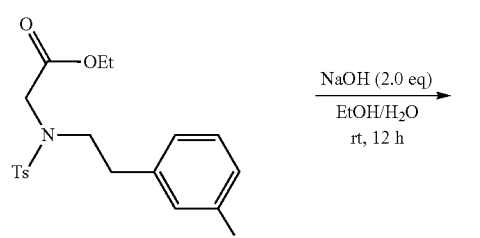

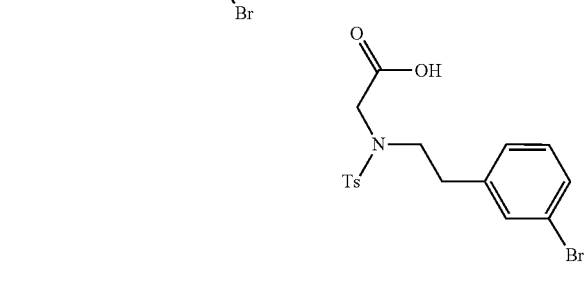

To a solution of ethyl 2-(N-(3-bromophenethyl)-4-methylphenylsulfonamido)acetate (8.78 mg, 20 mmol) in EtOH (40 mL) and H₂O (40 mL) was added NaOH (1.6 g, 40 mmol). The reaction mixture was stirred at rt for 12 h. Then the solvent was reduced and the residue was adjusted to pH=3 with HCl (1 N). The mixture was extracted with EtOAc (100 mL×3). The organic layers were dried over (Na₂SO₄) and concentrated in vacuo to give 2-(N-(3-bromophenethyl)-4-methylphenylsulfonamido)acetic acid as a yellow solid (8.2 g, yield: 100%). ESI-MS (M+H)⁺: 412.0. ¹H NMR (400 MHz, CDCl₃) δ: 7.69 (d, J=8.0 Hz, 2H), 7.34 (d, J=7.6 Hz, 1H), 7.29 (d, J=8.4 Hz, 2H), 7.22 (s, 1H), 7.14 (t, J=8.0 Hz, 1H), 7.08-7.06 (m, 1H), 4.00 (s, 2H), 3.45 (t, J=7.6 Hz, 2H), 2.83 (t, J=7.6 Hz, 2H), 2.42 (s, 3H).

4. Synthesis of 7-bromo-3-tosyl-2,3,4,5-tetrahydro-1H-benzo[d]azepin-1-one

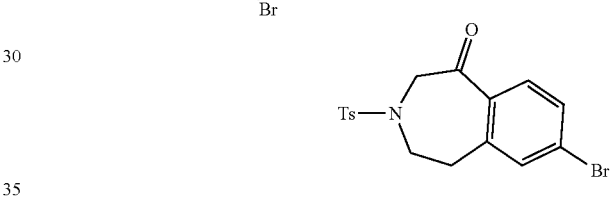

To a solution of 2-(N-(3-bromophenethyl)-4-methylphenylsulfonamido)acetic acid (8.2 g, 20 mmol) in CH₂Cl₂ (100 mL) was added SOCl₂ (11.9 g, 100 mmol) and DMF (cat.). The reaction mixture was stirred at 40° C. for 1 h. Then the solvent was removed under reduced pressure and dried in vacuo for 2 h. The residue was dissolved in CH₂Cl₂ (100 mL) and cooled in an ice bath. AlCl₃ (10.56 g, 80 mmol) was added and the mixture was stirred at 0° C.-rt for 12 h. The mixture was poured into conc. HCl (20 mL) and extracted with EtOAc (100 mL×2). The organic layers were washed with water (100 mL), brine (100 mL), dried (Na₂SO₄), and concentrated in vacuo to afford a residue which was purified by silica gel column (petroleum ether:EtOAc=4:1) to give 7-bromo-3-tosyl-2,3,4,5-tetrahydro-1H-benzo[d]azepin-1-one as a yellow solid (1.88 g, yield: 24%). ESI-MS (M+H)⁺: 394.1. ¹H NMR (400 MHz, CDCl₃) δ: 7.42 (d, J=8.4 Hz, 2H), 7.38 (dd, J=8.4, 1.6 Hz, 1H), 7.31-7.29 (m, 2H), 7.14 (d, J=8.0 Hz, 2H), 4.21 (s, 2H), 3.68 (t, J=6.8 Hz, 2H), 2.93 (t, J=7.2 Hz, 2H), 2.39 (s, 3H).

5. Synthesis of 7-bromo-3-tosyl-2,3,4,5-tetrahydro-1H-benzo[d]azepin-1-amine

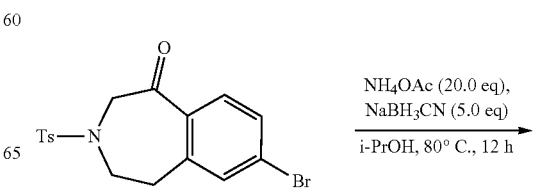

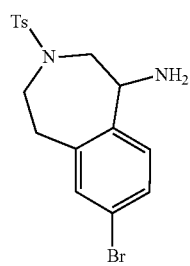

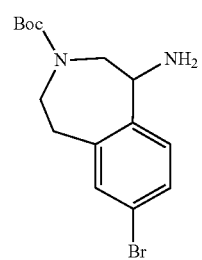

Synthesis of 7-bromo-3-tosyl-2,3,4,5-tetrahydro-1H-benzo[d]azepin-1-amine was similar to that of Example 180. The residue was purified by silica gel column (CH$_2$Cl$_2$:MeOH=20:1) to give 7-bromo-3-tosyl-2,3,4,5-tetrahydro-1H-benzo[d]azepin-1-amine as a yellow solid (154 mg, yield: 64%). ESI-MS (M+H)$^+$: 395.1. $^1$H NMR (400 MHz, CDCl$_3$) δ: 7.66 (d, J=8.4 Hz, 2H), 7.37 (d, J=8.4 Hz, 2H), 7.31 (dd, J=8.4, 1.6 Hz, 1H), 7.27 (d, J=1.6 Hz, 1H), 7.18 (d, J=8.4 Hz, 1H), 4.12-4.40 (m, 1H), 3.42-3.36 (m, 2H), 3.19-3.12 (m, 2H), 2.96-2.89 (m, 2H), 2.41 (s, 3H).

6. Synthesis of 7-bromo-3-tosyl-2,3,4,5-tetrahydro-1H-benzo[d]azepin-1-amine

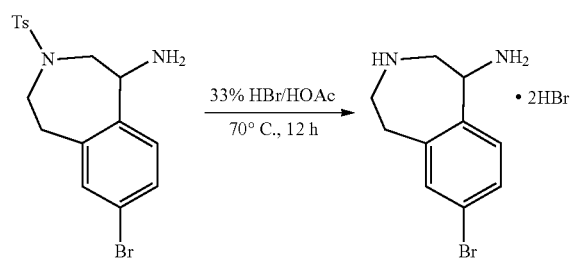 [SMILES: Cc1ccc(S(=O)(=O)N2CCc3cc(Br)ccc3C(N)C2)cc1 ; NC1CNCCc2cc(Br)ccc21]

A mixture of 7-bromo-3-tosyl-2,3,4,5-tetrahydro-1H-benzo[d]azepin-1-amine (1.2 g, 3.04 mmol) in HBr/HOAc (33%, 20 mL) was stirred at 70° C. for 12 h. After cooling down, the mixture was diluted with EtOAc (60 mL) and the resulting precipitate was filtered and dried under vacuum to give 7-bromo-3-tosyl-2,3,4,5-tetrahydro-1H-benzo[d]azepin-1-amine (870 mg, yield: 71%) as a white solid. ESI-MS (M+H)$^+$: 241.1. $^1$H NMR (400 MHz, CDCl$_3$) δ: 7.65-7.63 (m, 2H), 7.25 (d, J=8.8 Hz, 1H), 5.17-5.14 (m, 1H), 3.84-3.80 (m, 1H), 3.69-3.65 (m, 1H), 3.44-3.40 (m, 2H), 3.27-3.14 (m, 2H).

7. Synthesis of tert-butyl 1-amino-7-bromo-4,5-dihydro-1H-benzo[d]azepine-3(2H)-carboxylate

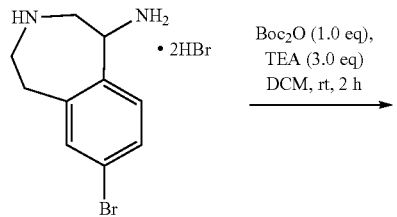

To a mixture of 7-bromo-3-tosyl-2,3,4,5-tetrahydro-1H-benzo[d]azepin-1-amine (680 mg, 1.7 mmol) and TEA (515 mg, 5.1 mmol) in CH$_2$Cl$_2$ (10 mL), Boc$_2$O (333 mg, 1.0 mmol) was added. The mixture was stirred at rt for 2 h. After diluting with CH$_2$Cl$_2$ (100 mL), the organic layer was washed with water (30 mL) and brine (30 mL), dried (Na$_2$SO$_4$), filtered and concentrated in vacuo to give tert-butyl 1-amino-7-bromo-4,5-dihydro-1H-benzo[d]azepine-3(2H)-carboxylate (450 mg, yield: 77%) as a yellow oil. ESI-MS (M+H)$^+$: 341.0. $^1$H NMR (400 MHz, CDCl$_3$) δ: 7.31 (d, J=8.0 Hz, 1H), 7.26 (s, 1H), 7.19-7.11 (m, 1H), 4.17-4.10 (m, 1H), 3.83-3.66 (m, 2H), 3.48-3.45 (m, 1H), 3.37-3.14 (m, 2H), 2.78-2.73 (m, 1H), 1.47 (s, 9H).

8. Synthesis of tert-butyl 7-bromo-1-(3-(tert-butoxy)azetidine-1-carboxamido)-4,5-dihydro-1H-benzo[d]azepine-3(2H)-carboxylate

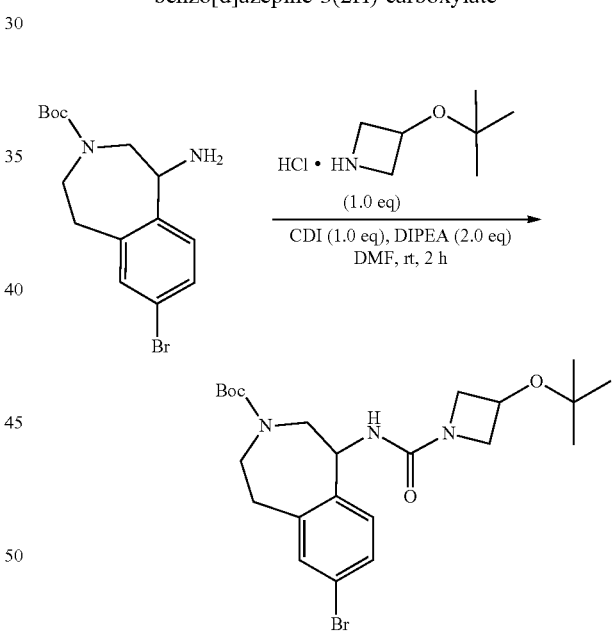

To a mixture of tert-butyl 1-amino-7-bromo-4,5-dihydro-1H-benzo[d]azepine-3(2H)-carboxylate (300 mg, 0.88 mmol) in DMF (4 mL), CDI (142 mg, 0.88 mmol) and DIPEA (227 mg, 1.76 mmol) was added. The mixture was stirred at rt for 1 h before 3-(tert-butoxy)azetidine HCl (145 mg, 0.88 mmol) was added and the solution was stirred at rt for another 4 h. The mixture was purified by prep-HPLC (MeCN/water with 0.05% NH$_4$HCO$_3$ mobile phase) to give tert-butyl 7-bromo-1-(3-(tert-butoxy)azetidine-1-carboxamido)-4,5-dihydro-1H-benzo[d]azepine-3(2H)-carboxylate (300 mg, yield: 69%) as a white solid. ESI-MS (M+H)$^+$: 496.2. $^1$H NMR (400 MHz, CD$_3$OD) δ: 7.37-7.34 (m, 2H), 7.19 (d, J=8.0 Hz, 1H), 5.04 (t, J=6.4 Hz, 1H), 4.60-4.51 (m, 1H), 4.18-4.12 (m, 2H), 3.78-3.75 (m, 2H), 3.67-3.55 (m, 4H), 3.17-2.91 (m, 2H), 1.42-1.36 (m, 9H), 1.19 (s, 9H).

9. Synthesis of Cert-butyl 1-(3-(tert-butoxy)azetidine-1-carboxamido)-7-(2-((1-methyl-1H-pyrazol-4-yl)amino)pyrimidin-4-yl)-4,5-dihydro-1H-benzo[d]azepine-3(2H)-carboxylate

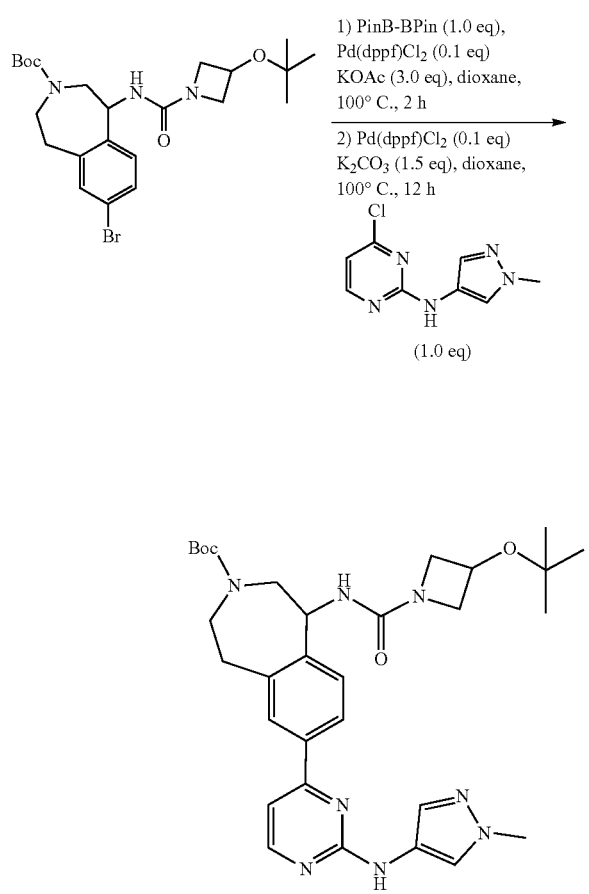

Synthesis of tert-butyl 1-(3-(tert-butoxy)azetidine-1-carboxamido)-7-(2-((1-methyl-1H-pyrazol-4-yl)amino)pyrimidin-4-yl)-4,5-dihydro-1H-benzo[d]azepine-3(2H)-carboxylate was similar to that of Example 157. The mixture was concentrated and purified by silica gel column (CH$_2$Cl$_2$:MeOH=40:1) to give tert-butyl 1-(3-(tert-butoxy)azetidine-1-carboxamido)-7-(2-((1-methyl-1H-pyrazol-4-yl)amino)pyrimidin-4-yl)-4,5-dihydro-1H-benzo[d]azepine-3(2H)-carboxylate (200 mg, yield: 56%) as a yellow solid. ESI-MS (M+H)$^+$: 591.3. $^1$H NMR (400 MHz, CD$_3$OD) δ: 8.40 (d, J=5.2 Hz, 1H), 7.99-7.97 (m, 2H), 7.94 (s, 1H), 7.64 (s, 1H), 7.43 (d, J=8.0 Hz, 1H), 7.21 (d, J=5.2 Hz, 1H), 5.16 (t, J=5.6 Hz, 1H), 4.61-4.54 (m, 1H), 4.21-4.15 (m, 2H), 3.89 (s, 3H), 3.81-3.62 (m, 6H), 3.28-3.03 (m, 2H), 1.43-1.34 (m, 9H), 1.20 (s, 9H).

10. Synthesis of 3-(tert-butoxy)-N-(7-(2-((1-methyl-1H-pyrazol-4-yl)amino)pyrimidin-4-yl)-2,3,4,5-tetrahydro-1H-benzo[d]azepin-1-yl)azetidine-1-carboxamide

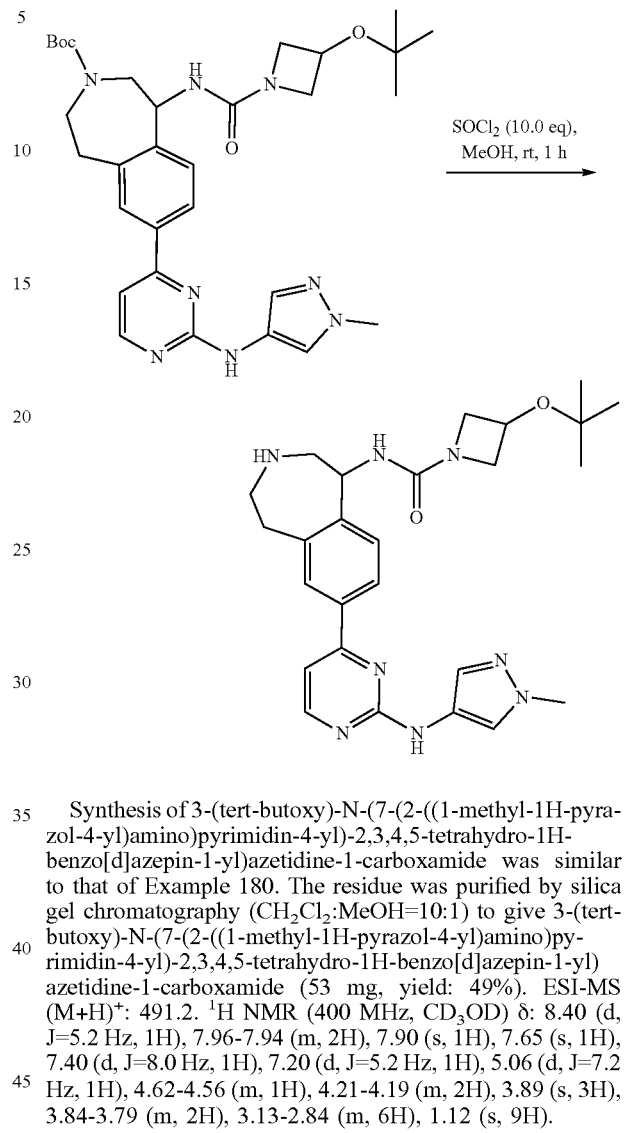

Synthesis of 3-(tert-butoxy)-N-(7-(2-((1-methyl-1H-pyrazol-4-yl)amino)pyrimidin-4-yl)-2,3,4,5-tetrahydro-1H-benzo[d]azepin-1-yl)azetidine-1-carboxamide was similar to that of Example 180. The residue was purified by silica gel chromatography (CH$_2$Cl$_2$:MeOH=10:1) to give 3-(tert-butoxy)-N-(7-(2-((1-methyl-1H-pyrazol-4-yl)amino)pyrimidin-4-yl)-2,3,4,5-tetrahydro-1H-benzo[d]azepin-1-yl)azetidine-1-carboxamide (53 mg, yield: 49%). ESI-MS (M+H)$^+$: 491.2. $^1$H NMR (400 MHz, CD$_3$OD) δ: 8.40 (d, J=5.2 Hz, 1H), 7.96-7.94 (m, 2H), 7.90 (s, 1H), 7.65 (s, 1H), 7.40 (d, J=8.0 Hz, 1H), 7.20 (d, J=5.2 Hz, 1H), 5.06 (d, J=7.2 Hz, 1H), 4.62-4.56 (m, 1H), 4.21-4.19 (m, 2H), 3.89 (s, 3H), 3.84-3.79 (m, 2H), 3.13-2.84 (m, 6H), 1.12 (s, 9H).

Example 237: 4-isobutyl-1-(2-methyl-4-(2-((1-methyl-1H-pyrazol-4-yl)amino)pyrimidin-4-yl)benzyl)piperazin-2-one

I-249

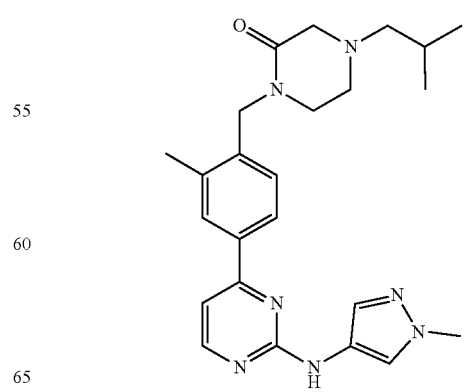

1. The preparation of tert-butyl 4-(4-bromo-2-methylbenzyl)-3-oxopiperazine-1-carboxylate

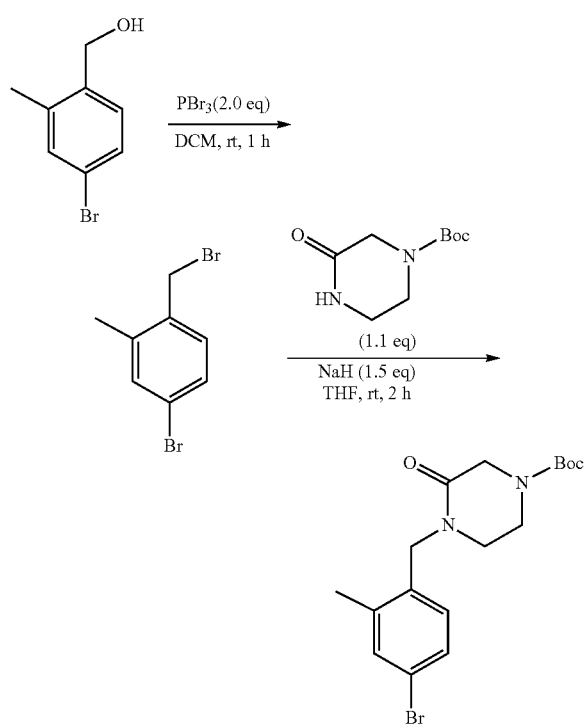

2. The preparation of 1-(4-bromo-2-methylbenzyl)-4-isobutylpiperazin-2-one

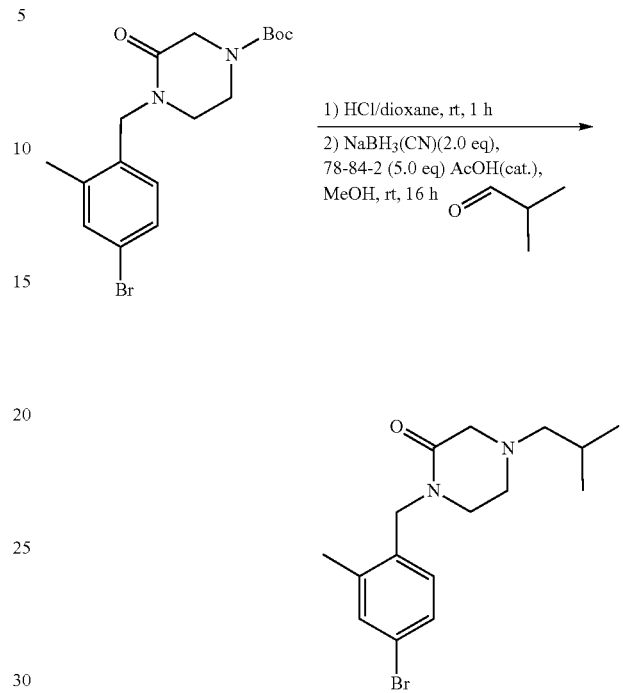

To a solution of (4-bromo-2-methylphenyl)methanol (1.3 g, 6.7 mmol) in CH$_2$Cl$_2$ (50 mL) was added PBr$_3$ (0.95 mL, 10 mmol) at 0° C. The mixture was stirred at rt for 1 h, quenched with ice-water (50 mL) and the pH value was adjusted to 7.0 with 50% aqueous NaOH solution. The mixture was extracted with EtOAc (100 mL×2) and the combined organic layers were washed with water (50 mL), dried (Na$_2$SO$_4$) and concentrated in vacuo to give 4-bromo-1-(bromomethyl)-2-methylbenzene (1.56 g, yield: 89%) as a white solid which was used in next step without further purification.

To a solution of tert-butyl 3-oxopiperazine-1-carboxylate (1.2 g, 6.0 mmol) in THF (200 mL) was added NaH (320 mg, 8.1 mmol) with ice-bath cooling. After stirring at 0° C. for 1 h, a solution of 4-bromo-1-(bromomethyl)-2-methylbenzene (1.42 g, 5.4 mmol) in THF (5 mL) was added dropwise over a period of 10 min, the ice-bath was removed and the mixture was stirred at rt for 2 h. The mixture was diluted with ice-water (50 mL) and extracted with EtOAc (100 mL×2) and the combined organic phases were washed with brine (50 mL), dried (Na$_2$SO$_4$) and concentrated in vacuo to afford a residue which was purified by silica gel column (petroleum ether/EtOAc=5:1) to give tert-butyl 4-(4-bromo-2-methylbenzyl)-3-oxopiperazine-1-carboxylate (1.6 g, yield: 77%) as white solid. ESI-MS (M+H-56)$^+$: 327.0. $^1$H NMR (400 MHz, CDCl$_3$) δ: 7.34 (s, 1H), 7.30 (d, J=8.4 Hz, 1H), 6.99 (d, J=8.4 Hz, 1H), 4.61 (s, 2H), 4.16 (s, 2H), 3.60 (t, J=5.2 Hz, 2H), 3.24 (t, J=5.2 Hz, 2H), 2.27 (s, 3H), 1.47 (s, 9H).

Synthesis of 1-(4-bromo-2-methylbenzyl)-4-isobutylpiperazin-2-one was similar to that of Example 199. The organic phase was concentrated and the crude was purified by prep-HPLC (CH$_3$CN/H$_2$O with 0.05% NH$_4$OH as mobile phase) to give 1-(4-bromo-2-methylbenzyl)-4-isobutylpiperazin-2-one as a yellow oil (120 mg, yield: 79%). ESI-MS (M+H)$^+$: 339.1. $^1$H NMR (400 MHz, CDCl$_3$) δ: 7.31 (d, J=2.0 Hz, 1H), 7.29 (dd, J=8.0, 2.0 Hz, 1H), 6.99 (d, J=8.0 Hz, 1H), 4.57 (s, 2H), 3.18 (s, 2H), 3.14 (t, J=5.2 Hz, 2H), 2.60 (t, J=5.6 Hz, 2H), 2.27 (s, 3H), 2.14 (d, J=7.2 Hz, 2H), 1.80-1.73 (m, 1H), 0.90 (d, J=6.8 Hz, 6H).

3. The preparation of 4-isobutyl-1-(2-methyl-4-(2-((1-methyl-1H-pyrazol-4-yl)amino)pyrimidin-4-yl)benzyl)piperazin-2-one

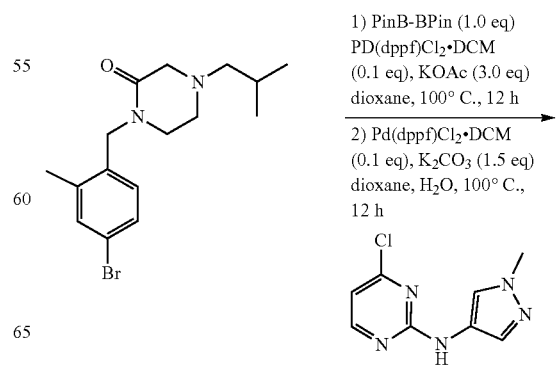

-continued

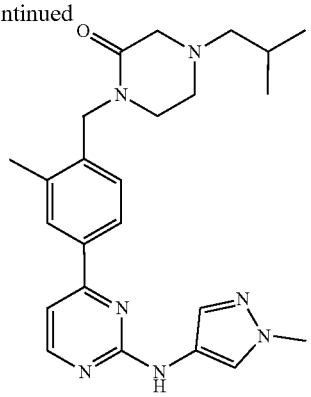

Synthesis of 4-isobutyl-1-(2-methyl-4-(2-((1-methyl-1H-pyrazol-4-yl)amino)pyrimidin-4-yl)benzyl)piperazin-2-one was similar to that of Example 157. The crude was purified by silica gel column (petroleum ether/EtOAc=1:1=1:4) to give 4-isobutyl-1-(2-methyl-4-(2-((1-methyl-1H-pyrazol-4-yl)amino)pyrimidin-4-yl)benzyl)piperazin-2-one as a yellow solid (180 mg, yield: 69%). ESI-MS (M+H)+: 434.2. 1H NMR (400 MHz, CDCl3) δ: 8.43 (d, J=4.8 Hz, 1H), 7.88 (s, 1H), 7.85-7.83 (m, 2H), 7.55 (s, 1H), 7.24 (d, J=8.0 Hz, 1H), 7.09 (br, 1H), 7.07 (d, J=5.6 Hz, 1H), 4.69 (s, 2H), 3.92 (s, 3H), 3.22 (s, 2H), 3.20 (t, J=5.6 Hz, 2H), 2.62 (t, J=5.6 Hz, 2H), 2.39 (s, 3H), 2.16 (d, J=7.6 Hz, 2H), 1.81-1.74 (m, 1H), 0.91 (d, J=6.8 Hz, 6H).

Example 238

The following compounds I-250 through I-360 can be synthesized according to the procedures described in Examples 1-237.

| Chemical name | Compound# | H-NMR | MH+ |
|---|---|---|---|
| 1-tert-butyl-N-[[4-[2-[[1-(2-hydroxyethyl)pyrazol-4-yl]amino]pyrimidin-4-yl]-2-methyl-phenyl]methyl]pyrazole-4-carboxamide | I-250 | 1H NMR (400 MHz, METHANOL-d4) δ ppm 8.68 (s, 1 H) 8.19 (s, 1 H) 7.97 (s, 1 H) 7.71 (s, 1 H) 7.63 (br. s., 1 H) 7.48 (s, 1 H) 7.03 (s, 1 H) 4.59 (s, 2 H) 4.26 (s, 1 H) 3.91-3.98 (m, 1 H) 2.48 (s, 1 H) 1.62 (s, 4H). | 475.1 |
| 3-tert-butoxy-N-[[2-methyl-4-[6-[[5-(4-methylpiperazin-1-yl)-2-pyridyl]amino]pyrimidin-4-yl]phenyl]methyl]azetidine-1-carboxamide | I-251 | 1H NMR (400 MHz, METHANOL-d4) δ ppm 8.85 (br. s., 1 H) 8.72 (br. s., 1 H) 7.98 (br. s., 2 H) 7.91 (br. s., 1 H) 7.76-7.88 (m, 3 H) 7.81 (br. s., 1 H) 7.42 (br. s., 1 H) 4.51 (br. s., 1 H) 4.41 (br. s., 2 H) 4.16 (d, J = 7.03 Hz, 2 H) 3.87 (br. s., 2 H) 2.99 (d, J = 2.01 Hz, 3 H) 2.91 (dd, J = 15.44, 1.88 Hz, 4H) 2.42 (br. s., 3 H) 1.20 (d, J = 2.26 Hz, 9 H). | |
| 1-tert-butyl-N-[[2-methyl-4-[2-[(1-methylpyrazol-4-yl)amino]pyrimidin-4-yl]phenyl]methyl]pyrazole-3-carboxamide | I-252 | 1H NMR (400 MHz, METHANOL-d4) δ ppm 8.34 (d, J = 6.02 Hz, 1H), 8.00-8.12 (m, 2H), 7.98 (s, 1H), 7.83 (s, 1H), 7.68 (s, 1H), 7.48 (d, J = 8.03 Hz, 1H), 7.41 (br. s., 1H), 6.76 (d, J = 2.51 Hz, 1H), 4.67 (s, 2H), 3.94 (s, 3H), 2.51 (s, 3H), 1.65 (s, 9H). | 445.2 |
| (3R)-3-tert-butyl-N-[[2-methyl-4-[2-[(1-methylpyrazol-4-yl)amino]pyrimidin-4-yl]phenyl]methyl]pyrrolidine-1-carboxamide | I-253 | 1H NMR (400 MHz, METHANOL-d4) δ ppm 8.40 (d, J = 5.27 Hz, 1H), 7.98 (s, 1H), 7.94 (br. s., 2H), 7.66 (s, 1H), 7.42 (d, J = 8.53 Hz, 1H), 7.21 (d, J = 5.27 Hz, 1H), 4.59 (br. s., 1H), 4.32-4.52 (m, 2H), 3.91 (s, 3H), 3.59 (t, J = 8.91 Hz, 1H), 3.44-3.53 (m, 1H), 3.04-3.19 (m, 1H), 2.45 (s, 3H), 1.59-2.26 (m, 2H), 0.98 (s, 9H). | 448.2 |
| (3S)-3-tert-butyl-N-[[2-methyl-4-[2-[(1-methylpyrazol-4-yl)amino]pyrimidin-4-yl]phenyl]methyl]pyrrolidine-1-carboxamide | I-254 | 1H NMR (400 MHz, METHANOL-d4) δ ppm 8.40 (d, J = 5.27 Hz, 1H), 7.98 (s, 1H), 7.94 (br. s., 2H), 7.66 (s, 1H), 7.42 (d, J = 8.53 Hz, 1H), 7.21 (d, J = 5.27 Hz, 1H), 4.59 (br. s., 1H), 4.33-4.52 (m, 2H), 3.91 (s, 3H), 3.59 (t, J = 8.91 Hz, 1H), 3.43-3.53 (m, 1H), 3.03-3.19 (m, 1H), 2.45 (s, 3H), 1.63-2.25 (m, 2H), 0.98 (s, 9H). | 448.2 |
| (3S)-3-isopropyl-N-[[2-methyl-4-[2-[(1-methylpyrazol-4-yl)amino]pyrimidin-4-yl]phenyl]methyl]pyrrolidine-1-carboxamide | I-255 | 1H NMR (400 MHz, METHANOL-d4) δ ppm 8.40 (d, J = 5.27 Hz, 1H), 7.99 (s, 1H), 7.94 (br. s., 2H), 7.66 (s, 1H), 7.42 (d, J = 8.53 Hz, 1H), 7.21 (d, J = 5.27 Hz, 1H), 6.52-6.72 (m, 1H), 4.31-4.52 (m, 2H), 3.91 (s, 3H), 3.45-3.73 (m, 2H), 3.38 (br. s., 1H), 2.99 (t, J = 9.79 Hz, 1H), 2.45 (s, 3H), 1.38-2.23 (m, 4H), 1.01 (d, J = 8.03 Hz, 6H). | 434.2 |

-continued

| Chemical name | Compound# | H-NMR | MH+ |
| --- | --- | --- | --- |
| 3-tert-butoxy-N-[[2-methyl-4-[6-[(5-methyl-6,7-dihydro-4H-pyrazolo[1,5-a]pyrazin-2-yl)amino]pyrimidin-4-yl]phenyl]methyl]azetidine-1-carboxamide | I-256 | 1H NMR (300 MHz, METHANOL-d4) δ ppm 8.81 (s, 1H), 7.63-7.88 (m, 3H), 7.51 (d, J = 7.93 Hz, 1H), 6.61 (br. s., 1H), 4.60 (s, 3H), 4.47 (t, J = 5.85 Hz, 2H), 4.40 (s, 2H), 4.11-4.24 (m, 2H), 3.88 (br. s., 2H), 3.79 (dd, J = 4.91, 9.06 Hz, 2H), 3.12 (s, 3H), 2.46 (s, 3H), 1.21 (s, 9H). | 506.3 |
| 1-tert-butyl-N-[2-[2-[(1-methylpyrazol-4-yl)amino]pyrimidin-4-yl]-6,7,8,9-tetrahydro-5H-benzo[7]annulen-5-yl]pyrazole-4-carboxamide | I-257 | 1H NMR (400 MHz, METHANOL-d4) δ ppm 8.66 (d, J = 7.78 Hz, 1H), 8.27-8.47 (m, 2H), 8.08 (d, 1H), 7.98 (d, J = 12.55 Hz, 3H), 7.68 (s, 1H), 7.31-7.46 (m, 2H), 5.38 (d, J = 10.54 Hz, 1H), 3.93 (s, 3H), 2.91-3.23 (m, 2H), 1.76-2.21 (m, 5H), 1.65 (s, 9H), 1.26-1.55 (m, 1H) | 485.1 |
| 1-tert-butyl-N-[[4-[2-[(1-isopropylpyrazol-4-yl)amino]pyrimidin-4-yl]-2-methyl-phenyl]methyl]pyrazole-4-carboxamide | I-258 | 1H NMR (400 MHz, DMSO-d6) δ ppm 9.49 (s, 1H), 8.41-8.54 (m, 2H), 8.32 (s, 1H), 7.86-8.09 (m, 4H), 7.56 (s, 1H), 7.39 (d, J = 8.03 Hz, 1H), 7.25 (d, J = 5.27 Hz, 1H), 4.39-4.54 (m, 3H), 2.41 (s, 3H), 1.53 (s, 9H), 1.42 (d, J = 6.53 Hz, 6H). | 473.2 |
| 3-isopropoxy-N-[[4-[2-[(1-isopropylpyrazol-4-yl)amino]pyrimidin-4-yl]-2-methyl-phenyl]methyl]azetidine-1-carboxamide | I-259 | 1H NMR (400 MHz, DMSO-d6) δ ppm 9.48 (s, 1H), 8.45 (d, J = 5.27 Hz, 1H), 7.83-8.06 (m, 3H), 7.56 (s, 1H), 7.35 (d, J = 8.03 Hz, 1H), 7.25 (d, J = 5.27 Hz, 1H), 6.85 (t, J = 5.52 Hz, 1H), 4.47 (quin, J = 6.65 Hz, 1H), 4.28-4.37 (m, 1H), 4.23 (d, J = 5.52 Hz, 2H), 3.96-4.12 (m, 2H), 3.50-3.68 (m, 3H), 2.37 (s, 3H), 1.43 (d, J = 6.78 Hz, 6H), 1.08 (d, J = 6.02 Hz, 6H). | 464.2 |
| 1-tert-butyl-N-[[4-[2-[(1-cyclopropylpyrazol-4-yl)amino]pyrimidin-4-yl]-2-methyl-phenyl]methyl]pyrazole-4-carboxamide | I-260 | 1H NMR (400 MHz, DMSO-d6) δ ppm 9.50 (s, 1H), 8.41-8.52 (m, 2H), 8.33 (s, 1H), 7.86-8.06 (m, 4H), 7.53 (br. s., 1H), 7.39 (d, J = 8.03 Hz, 1H), 7.26 (d, J = 5.02 Hz, 1H), 4.47 (d, J = 5.52 Hz, 2H), 3.65-3.76 (m, 1H), 2.42 (s, 3H), 1.53 (s, 9H), 0.88-1.08 (m, 4H). | 471 |
| N-[[4-[2-[(1-ethylpyrazol-4-yl)amino]pyrimidin-4-yl]-2-methyl-phenyl]methyl]-3-(1,1,1,3,3,3-d6)isopropoxy-azetidine-1-carboxamide | I-262 | 1H NMR (400 MHz, DMSO-d6) δ ppm 9.48 (s, 1H), 8.45 (d, J = 5.02 Hz, 1H), 7.85-8.02 (m, 3H), 7.56 (br. s., 1H), 7.35 (d, J = 8.28 Hz, 1H), 7.25 (d, J = 5.27 Hz, 1H), 6.84 (t, J = 5.65 Hz, 1H), 4.27-4.37 (m, 1H), 4.23 (d, J = 5.52 Hz, 2H), 4.00-4.17 (m, 4H), 3.62 (dd, J = 4.64, 8.91 Hz, 2H), 3.55 (s, 1H), 2.36 (s, 3H), 1.38 (t, J = 7.15 Hz, 3H). | 456.2 |
| N-[[2-methyl-4-[2-[(1-methylpyrazol-4-yl)amino]pyrimidin-4-yl]phenyl]methyl]-3-propyl-azetidine-1-carboxamide | I-263 | 1H NMR (400 MHz, DMSO-d6) δ ppm 9.50 (s, 1H), 8.45 (d, J = 5.27 Hz, 1H), 7.92 (d, J = 2.26 Hz, 3H), 7.55 (br. s., 1H), 7.35 (d, J = 8.28 Hz, 1H), 7.25 (d, J = 5.02 Hz, 1H), 6.74 (t, J = 5.52 Hz, 1H), 4.22 (d, J = 5.27 Hz, 2H), 3.91 (t, J = 7.91 Hz, 2H), 3.83 (s, 3H), 3.45 (dd, J = 5.77, 7.78 Hz, 2H), 2.36 (s, 3H), 1.52 (q, J = 7.53 Hz, 2H), 1.24 (sxt, J = 7.43 Hz, 2H), 0.88 (t, J = 7.28 Hz, 3H). | 420.1 |
| 5-tert-butyl-N-[[2-methyl-4-[2-[(1-methylpyrazol-4-yl)amino]pyrimidin-4-yl]phenyl]methyl]-1,2,4-oxadiazole-3-carboxamide | I-264 | 1H NMR (400 MHz, METHANOL-d4) δ ppm 9.37 (br. s., 1H), 8.33 (d, J = 5.77 Hz, 1H), 7.91-8.10 (m, 3H), 7.67 (s, 1H), 7.48 (d, J = 8.03 Hz, 1H), 7.40 (d, J = 6.02 Hz, 1H), 4.63-4.71 (m, 2H), 3.92 (s, 3H), 2.50 (s, 3H), 1.49 (s, 9H). | 447.2 |
| 5-tert-butyl-N-[[2-methyl-4-[6-[(5-methyl-6,7-dihydro-4H-pyrazolo[1,5-a]pyrazin-2-yl)amino]pyrimidin-4-yl]phenyl]methyl]isoxazole-3-carboxamide | I-265 | 1H NMR (400 MHz, METHANOL-d4) δ ppm 9.16 (t, J = 5.65 Hz, 1H), 8.78 (s, 1H), 7.62-7.83 (m, 2H), 7.52 (d, J = 8.03 Hz, 1H), 6.43-6.67 (m, 2H), 4.52-4.74 (m, 4H), 4.44 (t, J = 5.77 Hz, 2H), 3.76-3.92 (m, 2H), 3.09 (s, 3H), 2.51 (s, 3H), 1.39 (s, 9H). | 501.3 |
| 2-tert-butyl-N-[[2-methyl-4-[6-(5,6,7,8-tetrahydro-1,6-naphthyridin-2-ylamino)pyrimidin-4-yl]phenyl]methyl]thiazole-5- | I-266 | 1H NMR (400 MHz, METHANOL-d4) δ ppm 9.11 (t, J = 5.65 Hz, 1H), 8.88 (s, 1H), 8.42 (br. s., 1H), 8.24 (s, 1H), 7.76-7.86 (m, 2H), 7.73 (d, J = 8.53 Hz, 1H), 7.47-7.63 (m, 2H), 4.64 (s, 2H), | 514.2 |

| Chemical name | Compound# | H-NMR | MH+ |
|---|---|---|---|
| carboxamide | | 4.41 (s, 2H), 3.65 (t, J = 6.40 Hz, 2H), 3.23-3.28 (m, 2H), 2.52 (s, 3H), 1.47 (s, 9H). | |
| 2-tert-butyl-N-[[2-methyl-4-[6-(5,6,7,8-tetrahydro-2,7-naphthyridin-3-ylamino)pyrimidin-4-yl]phenyl]methyl]thiazole-5-carboxamide | I-267 | 1H NMR (400 MHz, METHANOL-d4) δ ppm 9.09 (s, 1H), 8.89 (s, 1H), 8.35 (s, 1H), 8.24 (s, 1H), 8.13 (br. s., 1H), 7.75-7.85 (m, 2H), 7.61 (s, 1H), 7.53 (d, J = 8.03 Hz, 1H), 4.64 (s, 2H), 4.44 (s, 2H), 3.57 (t, J = 6.40 Hz, 2H), 3.22 (t, J = 6.40 Hz, 2H), 2.51 (s, 3H), 1.46 (s, 9H). | 514.3 |
| 2-tert-butyl-N-[[4-[6-[[7-(2-hydroxyethyl)-6,8-dihydro-5H-2,7-naphthyridin-3-yl]amino]pyrimidin-4-yl]-2-methyl-phenyl]methyl]thiazole-5-carboxamide | I-268 | 1H NMR (400 MHz, METHANOL-d4) δ ppm 9.08 (s, 1H), 8.87 (s, 1H), 8.33 (s, 1H), 8.24 (s, 1H), 8.12 (s, 1H), 7.76-7.87 (m, 2H), 7.68 (s, 1H), 7.52 (d, J = 8.03 Hz, 1H), 4.50-4.70 (m, 3H), 3.94-4.04 (m, 2H), 3.42-3.51 (m, 2H), 2.66 (s, 6H), 2.51 (s, 3H), 1.46 (s, 9H). | 558.3 |
| 2-tert-butyl-N-[[2-methyl-4-[6-[(7-methyl-6,8-dihydro-5H-2,7-naphthyridin-3-yl)amino]pyrimidin-4-yl]phenyl]methyl]thiazole-5-carboxamide | I-269 | 1H NMR (400 MHz, METHANOL-d4) δ ppm 9.08 (br. s., 1H), 8.86 (d, J = 1.00 Hz, 1H), 8.31 (s, 1H), 8.24 (s, 1H), 8.10 (s, 1H), 7.77-7.86 (m, 2H), 7.70 (s, 1H), 7.51 (d, J = 8.03 Hz, 1H), 4.63 (s, 2H), 4.51 (br. s., 2H), 3.52-3.78 (m, 4H), 3.10 (s, 3H), 2.50 (s, 3H), 1.46 (s, 9H). | 528.3 |
| 2-tert-butyl-N-[[2-methyl-4-[6-(4,5,6,7-tetrahydropyrazolo[1,5-a]pyrazin-2-ylamino)pyrimidin-4-yl]phenyl]methyl]thiazole-5-carboxamide | I-270 | 1H NMR (400 MHz, METHANOL-d4) δ ppm 9.11 (t, J = 5.77 Hz, 1H), 8.80 (d, J = 1.00 Hz, 1H), 8.23 (s, 1H), 7.63-7.79 (m, 3H), 7.54 (d, J = 8.03 Hz, 1H), 6.61 (br. s., 1H), 4.61-4.67 (m, 2H), 4.56 (s, 2H), 4.42 (t, J = 5.90 Hz, 2H), 3.78-3.88 (m, 2H), 2.51 (s, 3H), 1.46 (s, 9H). | 503.4 |
| 2-tert-butyl-N-[[4-[6-[[5-(2-hydroxyethyl)-6,7-dihydro-4H-pyrazolo[1,5-a]pyrazin-2-yl]amino]pyrimidin-4-yl]-2-methyl-phenyl]methyl]thiazole-5-carboxamide | I-271 | 1H NMR (400 MHz, METHANOL-d4) δ ppm 8.82 (s, 1H), 8.24 (s, 1H), 7.67-7.83 (m, 3H), 7.52-7.57 (m, 1H), 6.56-6.68 (m, 1H), 4.64 (s, 4H), 4.42-4.55 (m, 2H), 3.89-4.06 (m, 4H), 3.44-3.56 (m, 2H), 2.51 (s, 3H), 1.46 (s, 9H). | 547.4 |
| 3-isopropoxy-N-[[2-methyl-4-[6-(4,5,6,7-tetrahydropyrazolo[1,5-a]pyrazin-2-ylamino)pyrimidin-4-yl]phenyl]methyl]azetidine-1-carboxamide | I-272 | 1H NMR (400 MHz, DMSO-d6) δ ppm 9.55 (br. s., 2H), 8.73 (s, 1H), 7.70-7.83 (m, 2H), 7.36 (d, J = 8.28 Hz, 1H), 6.87 (t, J = 5.65 Hz, 1H), 4.43 (br. s., 2H), 4.18-4.36 (m, 5H), 3.98-4.10 (m, 2H), 3.49-3.75 (m, 5H), 2.36 (s, 3H), 1.08 (d, J = 6.02 Hz, 6H). | 477.2 |
| 3-isopropoxy-N-[[2-methyl-4-[6-(5,6,7,8-tetrahydro-4H-pyrazolo[1,5-a][1,4]diazepin-2-ylamino)pyrimidin-4-yl]phenyl]methyl]azetidine-1-carboxamide | I-273 | 1H NMR (400 MHz, DMSO-d6) δ ppm 10.13 (br. s., 1H), 8.99 (br. s., 1H), 8.67 (s, 1H), 7.71-7.83 (m, 2H), 7.34 (d, J = 7.78 Hz, 1H), 6.85 (t, J = 5.77 Hz, 1H), 4.28-4.50 (m, 5H), 4.22 (d, J = 5.52 Hz, 2H), 3.98-4.09 (m, 2H), 3.52-3.68 (m, 3H), 3.41 (br. s., 2H), 2.36 (s, 3H), 2.02 (br. s., 2H), 1.08 (d, J = 6.02 Hz, 6H). | 491.2 |
| N-[[4-[6-[[5-(2-hydroxyethyl)-4,6,7,8-tetrahydropyrazolo[1,5-a][1,4]diazepin-2-yl]amino]pyrimidin-4-yl]-2-methyl-phenyl]methyl]-3-isopropoxy-azetidine-1-carboxamide | I-274 | 1H NMR (400 MHz, DMSO-d6) δ ppm 10.38 (br. s., 1H), 8.72 (s, 1H), 7.67-7.85 (m, 2H), 7.36 (d, J = 8.28 Hz, 1H), 6.69-6.97 (m, 2H), 4.50-4.79 (m, 2H), 4.27-4.47 (m, 3H), 4.22 (d, J = 5.52 Hz, 2H), 3.99-4.09 (m, 2H), 3.75 (br. s., 2H), 3.52-3.68 (m, 5H), 3.03-3.22 (m, 2H), 2.36 (s, 3H), 1.99-2.25 (m, 2H), 1.08 (d, J = 6.27 Hz, 6H). | 535.2 |
| 3-tert-butyl-N-[[2-methyl-4-[6-[(5-methyl-6,7-dihydro-4H-pyrazolo[1,5-a]pyrazin-2-yl)amino]pyrimidin-4-yl]phenyl]methyl]pyrrolidine-1-carboxamide | I-275 | 1H NMR (400 MHz, DMSO-d6) δ ppm 10.45 (br. s., 1H), 8.74 (s, 1H), 7.50-7.86 (m, 3H), 7.39 (d, J = 7.78 Hz, 1H), 6.42-6.70 (m, 2H), 4.14-4.42 (m, 4H), 3.80 (br. s., 2H), 3.29-3.54 (m, 2H), 3.16 (dt, J = 6.53, 10.29 Hz, 2H), 2.88-3.05 (m, 4H), 2.54 (s, 1H), 2.37 (s, 3H), 1.93-2.08 (m, 1H), 1.71-1.90 (m, 1H), 1.48-1.67 (m, 1H), 0.87-0.92 (m, 9H). | 503.3 |

-continued

| Chemical name | Compound# | H-NMR | MH+ |
|---|---|---|---|
| 2-tert-butyl-N-[[4-[6-(6,7-dihydro-4H-pyrazolo[5,1-c][1,4]oxazin-2-ylamino)pyrimidin-4-yl]-2-methyl-phenyl]methyl]thiazole-5-carboxamide | I-276 | 1H NMR (400 MHz, DMSO-d6) δ ppm 10.74 (br. s., 1H), 9.13 (t, J = 5.77 Hz, 1H), 8.79 (s, 1H), 8.33 (s, 1H), 7.53-7.84 (m, 3H), 7.43 (d, J = 8.03 Hz, 1H), 6.31 (br. s., 1H), 4.79 (s, 2H), 4.50 (d, J = 5.77 Hz, 2H), 4.07 (s, 4H), 2.42 (s, 3H), 1.39 (s, 9H). | 504.2 |
| N-[[4-[6-(6,7-dihydro-4H-pyrazolo[5,1-c][1,4]oxazin-2-ylamino)pyrimidin-4-yl]-2-methyl-phenyl]methyl]-3-isopropoxy-azetidine-1-carboxamide | I-277 | 1H NMR (400 MHz, DMSO-d6) δ ppm 10.80 (br. s., 1H), 8.80 (s, 1H), 7.66-7.80 (m, 2H), 7.39 (d, J = 8.53 Hz, 1H), 6.88 (t, J = 5.65 Hz, 1H), 6.31 (br. s., 1H), 4.79 (s, 2H), 4.28-4.37 (m, 1H), 4.23 (d, J = 5.52 Hz, 2H), 3.99-4.13 (m, 6H), 3.52-3.69 (m, 3H), 2.37 (s, 3H), 1.08 (d, J = 6.02 Hz, 6H). | 478.2 |
| 2-tert-butyl-N-[[2-methyl-4-[6-[(5-methyl-4-oxo-6,7-dihydropyrazolo[1,5-a]pyrazine-2-yl]amino]pyrimidin-4-yl]phenyl]methyl]thiazole-5-carboxamide | I-278 | 1H NMR (400 MHz, METHANOL-d4) δ ppm 9.10 (t, J = 5.40 Hz, 1H), 8.83 (s, 1H), 8.23 (s, 1H), 7.66-7.81 (m, 3H), 7.54 (d, J = 8.03 Hz, 1H), 7.02-7.17 (m, 1H), 4.64 (s, 2H), 4.41 (t, J = 6.27 Hz, 2H), 3.88 (t, J = 6.27 Hz, 2H), 3.15 (s, 3H), 2.51 (s, 3H), 1.46 (s, 9H). | 531.2 |
| 2-tert-butyl-N-[[4-[6-[(5,6-dimethyl-6,7-dihydro-4H-pyrazolo[1,5-a]pyrazin-2-yl)amino]pyrimidin-4-yl]-2-methyl-phenyl]methyl]thiazole-5-carboxamide | I-279 | 1H NMR (400 MHz, METHANOL-d4) δ ppm 9.11 (t, J = 5.65 Hz, 1H), 8.81 (s, 1H), 8.23 (s, 1H), 7.66-7.82 (m, 2H), 7.54 (d, J = 8.03 Hz, 1H), 6.62 (br. s., 1H), 4.70-4.80 (m, 1H), 4.52-4.69 (m, 4H), 4.03-4.30 (m, 2H), 3.05 (s, 3H), 2.51 (s, 3H), 1.56 (d, J = 6.53 Hz, 3H), 1.46 (s, 9H). | 531.1 |
| 1-tert-butyl-N-[[4-[6-[(5,6-dimethyl-6,7-dihydro-4H-pyrazolo[1,5-a]pyrazin-2-yl)amino]pyrimidin-4-yl]-2-methyl-phenyl]methyl]pyrazole-4-carboxamide | I-280 | 1H NMR (400 MHz, METHANOL-d4) δ ppm 8.80 (s, 1H), 8.27 (s, 1H), 7.96 (s, 1H), 7.63-7.82 (m, 3H), 7.52 (d, J = 8.03 Hz, 1H), 6.61 (br. s., 1H), 4.69-4.79 (m, 1H), 4.51-4.64 (m, 4H), 4.03-4.26 (m, 2H), 3.04 (s, 3H), 2.51 (s, 3H), 1.61 (s, 9H), 1.56 (d, J = 6.53 Hz, 3H). | 514.2 |
| 3-tert-butyl-N-[[2-methyl-4-[6-[(5-methyl-6-oxo-4,7-dihydropyrazolo[1,5-a]pyrazine-2-yl)amino]pyrimidin-4-yl]phenyl]methyl]pyrrolidine-1-carboxamide | I-281 | 1H NMR (400 MHz, METHANOL-d4) δ ppm 8.69 (s, 1H), 7.53-7.75 (m, 3H), 7.43 (d, J = 7.78 Hz, 1H), 4.71 (s, 2H), 4.60 (s, 2H), 4.25-4.42 (m, 2H), 3.44-3.52 (m, 1H), 3.34-3.42 (m, 1H), 3.04-3.06 (m, 3H), 2.37 (s, 3H), 1.94-2.10 (m, 1H), 1.77-1.91 (m, 1H), 1.53-1.71 (m, 1H), 0.81-0.93 (m, 9H). | 517.2 |
| 1-tert-butyl-N-[[4-[6-[(4,5-dimethyl-6,7-dihydro-4H-pyrazolo[1,5-a]pyrazin-2-yl)amino]pyrimidin-4-yl]-2-methyl-phenyl]methyl]pyrazole-4-carboxamide | I-282 | 1H NMR (400 MHz, METHANOL-d4) δ ppm 8.81 (s, 1H), 8.27 (s, 1H), 7.96 (s, 1H), 7.57-7.84 (m, 3H), 7.52 (d, J = 8.03 Hz, 1H), 6.67 (br. s., 1H), 4.75 (q, J = 6.53 Hz, 1H), 4.61 (s, 2H), 4.36-4.58 (m, 2H), 4.01 (td, J = 4.08, 12.93 Hz, 1H), 3.82-3.94 (m, 1H), 3.09 (s, 3H), 2.51 (s, 3H), 1.79 (d, J = 6.78 Hz, 3H), 1.61 (s, 9H). | 514.2 |
| 2-tert-butyl-N-[[4-[6-[(4,5-dimethyl-6,7-dihydro-4H-pyrazolo[1,5-a]pyrazin-2-yl)amino]pyrimidin-4-yl]-2-methyl-phenyl]methyl]thiazole-5-carboxamide | I-283 | 1H NMR (400 MHz, METHANOL-d4) δ ppm 8.79-8.90 (m, 1H), 8.24 (s, 1H), 7.61-7.95 (m, 3H), 7.50-7.59 (m, 1H), 6.55-6.78 (m, 1H), 4.71-4.83 (m, 1H), 4.63 (s, 2H), 4.38-4.58 (m, 2H), 3.97-4.09 (m, 1H), 3.80-3.97 (m, 1H), 3.10 (s, 3H), 2.51 (s, 3H), 1.80 (d, J = 6.78 Hz, 3H), 1.46 (s, 9H). | 531.2 |
| 3-tert-butyl-N-[[4-[6-[(4,5-dimethyl-6,7-dihydro-4H-pyrazolo[1,5-a]pyrazin-2-yl)amino]pyrimidin-4-yl]-2-methyl-phenyl]methyl]pyrrolidine-1-carboxamide | I-284 | 1H NMR (400 MHz, METHANOL-d4) δ ppm 8.84 (s, 1H), 7.62-8.45 (m, 3H), 7.53 (d, J = 7.78 Hz, 1H), 6.70 (br. s., 1H), 4.79 (q, J = 6.53 Hz, 1H), 4.43 (d, J = 5.77 Hz, 4H), 3.98-4.10 (m, 1H), 3.80-3.98 (m, 1H), 3.42-3.65 (m, 2H), 3.11 (s, 4H), 2.34-2.53 (m, 3H), 2.04-2.22 (m, 1H), 1.94 (td, J = 6.18, 11.98 Hz, 1H), 1.60-1.86 (m, 5H), 0.94 (br. s., 9H). | 517.3 |
| 2-tert-butyl-N-[[4-[6-[[5-(2-hydroxyethyl)-4,6,7,8-tetrahydropyrazolo[1,5-a][1,4]diazepin-2- | I-285 | 1H NMR (400 MHz, DMSO-d6) δ ppm 10.35 (br. s., 1H), 9.12 (t, J = 5.65 Hz, 1H), 8.67-8.77 (m, 1H), 8.33 (s, 1H), 7.70-7.87 (m, 2H), 7.40 (d, J = 8.03 | 561.4 |

| Chemical name | Compound# | H-NMR | MH+ |
|---|---|---|---|
| yl]amino]pyrimidin-4-yl]-2-methyl-phenyl]methyl]thiazole-5-carboxamide | | Hz, 1H), 4.32-4.79 (m, 6H), 3.49-3.84 (m, 3H), 3.01-3.20 (m, 2H), 2.41 (s, 3H), 2.08 (br. s., 2H), 1.39 (s, 9H). | |
| 2-tert-butyl-N-[[2-methyl-4-[6-[(5-methyl-6-oxo-4,7-dihydropyrazolo[1,5-a]pyrazin-2-yl)amino]pyrimidin-4-yl]phenyl]methyl]thiazole-5-carboxamide | I-286 | 1H NMR (400 MHz, DMSO-d6) δ ppm 11.14 (br. s., 1H), 9.19 (t, J = 5.40 Hz, 1H), 8.85 (s, 1H), 8.36 (s, 1H), 7.69-7.85 (m, 2H), 7.45 (d, J = 8.03 Hz, 1H), 6.46 (br. s., 1H), 4.75 (s, 2H), 4.64 (s, 2H), 4.51 (d, J = 5.52 Hz, 2H), 3.01 (s, 3H), 2.43 (s, 3H), 1.39 (s, 9H). | 531.1 |
| 3-tert-butoxy-N-[[4-[6-(6,7-dihydro-4H-pyrazolo[5,1-c][1,4]oxazin-2-ylamino)pyrimidin-4-yl]-2-methyl-phenyl]methyl]azetidine-1-carboxamide | I-287 | 1H NMR (400 MHz, DMSO-d6) δ ppm 10.70 (br. s., 1H), 8.78 (s, 1H), 7.48-8.01 (m, 3H), 7.38 (d, J = 8.53 Hz, 1H), 6.86 (t, J = 5.77 Hz, 1H), 6.30 (br. s., 1H), 4.79 (s, 2H), 4.43-4.53 (m, 1H), 4.23 (d, J = 5.52 Hz, 2H), 3.98-4.13 (m, 6H), 3.60 (dd, J = 4.89, 8.66 Hz, 2H), 2.37 (s, 3H), 1.12 (s, 9H). | 492.2 |
| 3-tert-butyl-N-[[4-[6-(6,7-dihydro-4H-pyrazolo[5,1-c][1,4]oxazin-2-ylamino)pyrimidin-4-yl]-2-methyl-phenyl]methyl]pyrrolidine-1-carboxamide | I-288 | 1H NMR (400 MHz, METHANOL-d4) δ ppm 8.78 (s, 1H), 7.62-8.27 (m, 3H), 7.53 (d, J = 8.03 Hz, 1H), 6.30 (br. s., 1H), 4.84 (s, 2H), 4.34-4.53 (m, 2H), 4.15 (s, 4H), 3.42-3.64 (m, 2H), 3.11 (t, J = 10.16 Hz, 1H), 2.47 (s, 3H), 2.04-2.22 (m, 1H), 1.94 (td, J = 6.18, 11.98 Hz, 1H), 1.58-1.82 (m, 1H), 0.97 (s, 9H). | 490.1 |
| 2-tert-butyl-5-[[2-methyl-4-[2-[[1-(1-methyl-4-piperidyl)pyrazol-4-yl]amino]pyrimidin-4-yl]phenyl]methyl]-4H-pyrrolo[3,4-d]thiazol-6-one | I-289 | $^1$H NMR (400 MHz, CD$_3$OD) δ ppm: 8.25 (d, J = 5.2 Hz, 1H), 7.98 (s, 1H), 7.88 (s, 1H), 7.82 (d, J = 8.0 Hz, 1H), 7.55 (s, 1H), 7.21 (d, J = 7.6 Hz, 1H), 7.08 (d, J = 5.2 Hz, 1H), 4.75 (s, 2H), 4.24 (s, 2H), 4.09-4.01 (m, 1H), 2.92-2.89 (m, 2H), 2.32 (s, 3H), 2.24 (s, 3H), 2.20-2.15 (m, 2H), 2.06-1.95 (m, 4H), 1.37 (s, 9H). | 557.2 |
| 3-isopropoxy-N-[[4-[2-[(1-methylpyrazol-4-yl)amino]pyrimidin-4-yl]-2-(trifluoromethyl)phenyl]methyl]azetidine-1-carboxamide | I-290 | $^1$H NMR (400 MHz, CDCl$_3$) δ: 8.48 (d, J = 5.2 Hz, 1H), 8.38 (s, 1H), 8.14 (d, J = 8.0 Hz, 1H), 7.93 (s, 1H), 7.76 (d, J = 8.0 Hz, 1H), 7.53 (s, 1H), 7.10 (d, J = 5.2 Hz, 1H), 6.96 (s, 1H), 4.63 (d, J = 5.6 Hz, 2H), 4.54-4.52 (m, 1H), 4.37-4.34 (m, 1H), 4.14-4.12 (m, 2H), 3.93 (s, 3H), 3.88-3.37 (m, 2H), 3.62-3.59 (m, 1H), 1.15 (d, J = 6.0 Hz, 6H). | 490.2 |
| 1-tert-butyl-N-[[2-chloro-4-[2-[(1-methylpyrazol-4-yl)amino]pyrimidin-4-yl]phenyl]methyl]pyrazole-4-carboxamide | I-291 | $^1$H NMR (400 MHz, CD$_3$OD) δ: 8.61 (t, J = 5.6 Hz, 1H), 8.31-8.29 (m, 1H), 8.18 (s, 1H), 8.07 (s, 1H), 7.91-7.88 (m, 2H), 7.83 (s, 1H), 7.51 (s, 1H), 7.41 (d, J = 8.0 Hz, 1H), 7.08-7.06 (m, 1H), 4.56 (s, 2H), 3.77 (s, 3H), 1.49 (s, 9H). | 465.2 |
| 4-[4-[[4-[[(1-tert-butylpyrazole-4-carbonyl)amino]methyl]-3-methyl-phenyl]pyrimidin-2-yl]amino]pyrazol-1-yl]cyclohexanecarboxylic acid | I-292 | $^1$H NMR (400 MHz, CD$_3$OD) δ: 8.36-8.34 (m, 1H), 8.21 (s, 1H), 8.09 (s, 1H), 8.00-7.99 (m, 1H), 7.95-7.93 (m, 2H), 7.69 (s, 1H), 7.54-7.50 (m, 1H), 7.26 (d, J = 6.0 Hz, 1H), 4.62 (s, 2H), 4.24-4.18 (m, 1H), 2.72-2.71 (m, 1H), 2.50 (s, 3H), 2.31-2.27 (m, 2H), 2.10-2.02 (m, 4H), 1.81-1.73 (m, 2H), 1.63 (s, 9H). | 557.3 |
| 3-tert-butyl-N-[[4-[2-[(1-isopropylpyrazol-4-yl)amino]pyrimidin-4-yl]-2-(trifluoromethyl)phenyl]methyl]pyrrolidine-1-carboxamide | I-293 | $^1$H NMR (400 MHz, CD$_3$OD) δ: 8.49 (s, 1H), 8.42 (d, J = 5.2 Hz, 1H), 8.24 (d, J = 8.4 Hz, 1H), 8.03 (s, 1H), 7.68 (d, J = 8.0 Hz, 1H), 7.62 (s, 1H), 7.23-7.21 (d, J = 5.2 Hz, 1H), 4.65-4.64 (m, 2H), 4.52-4.45 (m, 1H), 3.62-3.47 (m, 2H), 3.29-3.27 (m, 1H), 3.13-3.10 (m, 1H), 2.11-2.10 (m, 1H), 1.95-1.89 (m, 1H), 1.74-1.69 (m, 1H), 1.50 (d, J = 6.4 Hz, 6H), 0.95 (s, 9H). | 530.3 |

| Chemical name | Compound# | H-NMR | MH+ |
|---|---|---|---|
| 3-tert-butoxy-N-[[4-2-[(1-cyclopropylpyrazol-4-yl)amino]pyrimidin-4-yl]-2-(trifluoromethyl)phenyl]methyl]azetidine-1-carboxamide | I-294 | $^1$H NMR (400 MHz, CD$_3$OD) δ: 8.53 (s, 1H), 8.48 (d, J = 5.2 Hz, 1H), 8.31 (d, J = 8.0 Hz, 1H), 8.06 (s, 1H), 7.69 (d, J = 8.4 Hz, 1H), 7.61 (s, 1H), 7.28 (d, J = 5.2 Hz, 1H), 4.64-4.60 (m, 3H), 4.22-4.18 (m, 2H), 3.84-3.80 (m, 2H), 3.66-3.60 (m, 1H), 1.21 (s, 9H), 1.10-1.05 (m, 4H). | 530.2 |
| 3-tert-butyl-N-[[4-[2-[[1-(2-methoxyethyl)pyrazol-4-yl]amino]pyrimidin-4-yl]-2-(trifluoromethyl)phenyl]methyl]pyrrolidine-1-carboxamide | I-295 | $^1$H NMR (400 MHz, CD$_3$OD) δ: 8.44 (s, 1H), 8.44 (d, J = 5.2 Hz, 1H), 8.25 (d, J = 8.0 Hz, 1H), 8.02 (s, 1H), 7.68-7.64 (m, 2H), 7.20 (d, J = 5.2 Hz, 1H), 4.65-4.63 (m, 2H), 4.26 (t, J = 5.2 Hz, 2H), 3.74 (t, J = 5.6 Hz, 2H), 3.68-3.57 (m, 2H), 3.35 (s, 3H), 3.27-3.20 (m, 1H), 3.14-3.10 (m, 1H), 2.13-2.10 (m, 1H), 1.93-1.91 (m, 1H), 1.73-1.68 (m, 1H), 0.95 (s, 9H). | 546.2 |
| 3-tert-butyl-N-[[4-[2-[(1-cyclopropylpyrazol-4-yl)amino]pyrimidin-4-yl]-2-(trifluoromethyl)phenyl]methyl]pyrrolidine-1-carboxamide | I-296 | $^1$H NMR (400 MHz, CD$_3$OD) δ: 8.39 (s, 1H), 8.33 (d, J = 4.8 Hz, 1H), 8.15 (d, J = 8.0 Hz, 1H), 7.94 (s, 1H), 7.59 (d, J = 8.4 Hz, 1H), 7.50 (s, 1H), 7.13 (d, J = 5.2 Hz, 1H), 4.56-4.55 (m, 2H), 3.55-3.49 (m, 2H), 3.43-3.39 (m, 1H), 3.06-3.01 (m, 1H), 2.04-2.03 (m, 1H), 1.85-1.81 (m, 1H), 1.66-1.61 (m, 1H), 1.02-0.92 (m, 5H), 0.87 (s, 9H). | 528.3 |
| 3-tert-butyl-N-[[4-[2-[(1-ethylpyrazol-4-yl)amino]pyrimidin-4-yl]-2-(trifluoromethyl)phenyl]methyl]pyrrolidine-1-carboxamide | I-297 | $^1$H NMR (400 MHz, CD$_3$OD) δ: 8.42 (s, 1H), 8.37 (d, J = 5.2 Hz, 1H), 8.21 (d, J = 8.0 Hz, 1H), 7.93 (s, 1H), 7.60 (d, J = 8.4 Hz, 1H), 7.53 (s, 1H), 7.18 (d, J = 5.2 Hz, 1H), 4.63-4.47 (m, 2H), 4.08 (q, J = 7.4 Hz, 2H), 3.54-3.44 (m, 1H), 3.44-3.34 (m, 1H), 3.27-3.22 (m, 1H), 3.04-3.02 (m, 1H), 2.12-1.98 (m, 1H), 1.91-1.77 (m, 1H), 1.71-1.58 (m, 1H), 1.38 (t, J = 7.4 Hz, 3H), 0.88 (s, 9H). | 516.3 |
| 3-tert-butyl-N-[[4-[2-[[1-(1-methyl-4-piperidyl)pyrazol-4-yl]amino]pyrimidin-4-yl]-2-(trifluoromethyl)phenyl]methyl]pyrrolidine-1-carboxamide | I-298 | $^1$H NMR (400 MHz, CD$_3$OD) δ: 8.39 (s, 1H), 8.35 (d, J = 5.2 Hz, 1H), 8.18 (d, J = 8.4 Hz, 1H), 7.96 (s, 1H), 7.62-7.57 (m, 2H), 7.14 (d, J = 5.2 Hz, 1H), 4.57-4.52 (m, 2H), 4.07-4.01 (m, 1H), 3.54-3.51 (m, 1H), 3.43-3.40 (m, 1H), 3.22-3.10 (m, 1H), 3.05-3.02 (m, 1H), 2.92-2.89 (m, 2H), 2.25 (s, 3H), 2.18-1.82 (m, 8H), 1.67-1.62 (m, 1H), 0.88 (s, 9H). | 585.3 |
| 3-isopropoxy-N-[[4-[2-[(1-isopropylpyrazol-4-yl)amino]pyrimidin-4-yl]-2-(trifluoromethyl)phenyl]methyl]azetidine-1-carboxamide | I-299 | $^1$H NMR (400 MHz, CD$_3$OD) δ: 8.42 (s, 1H), 8.37 (d, J = 5.2 Hz, 1H), 8.21 (d, J = 8.4 Hz, 1H), 7.95 (s, 1H), 7.59 (d, J = 8.4 Hz, 1H), 7.53 (s, 1H), 7.18 (d, J = 5.2 Hz, 1H), 4.50 (s, 2H), 4.46-4.30 (m, 2H), 4.18-4.02 (m, 2H), 3.79-3.67 (m, 2H), 3.65-3.49 (m, 1H), 1.42 (d, J = 6.8 Hz, 6H), 1.07 (d, J = 6.2 Hz, 6H). | 518.2 |
| 3-methoxy-N-[[2-methyl-4-[2-[(1-methylpyrazol-4-yl)amino]pyrimidin-4-yl]phenyl]methyl]azetidine-1-carboxamideacid | I-300 | 1H NMR (400 MHz, METHANOL-d4) δ: 8.33 (d, J = 6.02 Hz, 1H), 8.00 (d, J = 17.88 Hz, 3H), 7.69 (s, 1H), 7.35-7.52 (m, 2H), 4.41 (s, 2H), 4.26 (s, 1H), 4.09-4.19 (m, 2H), 3.91-3.99 (m, 3H), 3.83 (dd, J = 3.89, 9.73 Hz, 2H), 2.45 (s, 3H) | 408 |
| N-[[4-[2-[[1-(2-hydroxyethyl)pyrazol-4-yl]amino]pyrimidin-4-yl]-2-(trifluoromethyl)phenyl]methyl]-3-isopropoxy-azetidine-1-carboxamide | I-301 | $^1$H NMR (400 MHz, CD$_3$OD) δ: 8.43 (s, 1H), 8.40 (d, J = 5.2 Hz, 1H), 8.25 (d, J = 8.0 Hz, 1H), 8.02 (s, 1H), 7.65-7.63 (m, 2H), 7.19 (d, J = 5.2 Hz, 1H), 4.58 (s, 2H), 4.46-4.38 (m, 1H), 4.25-4.13 (m, 4H), 3.91 (t, J = 5.4 Hz, 2H), 3.88-3.81 (m, 2H), 3.70-3.60 (m, 1H), 1.16 (d, J = 6.4 Hz, 6H). | 520.2 |
| 3-tert-butoxy-N-[[2-methyl-4-[2-[[1-(1-methyl-4-piperidyl)pyrazol-4-yl]amino]pyrimidin-4-yl]phenyl]methyl]azetidine-1-carboxamide | I-302 | $^1$H NMR (400 MHz, CD$_3$OD) δ: 8.39 (d, J = 5.2 Hz, 1H), 8.10 (s, 1H), 7.95 (s, 1H), 7.93 (d, J = 8.0 Hz, 1H), 7.68 (s, 1H), 7.39 (d, J = 8.0 Hz, 1H), 7.20 (d, J = 5.2 Hz, 1H), 4.61-4.56 (m, 1H), 4.39 (s, 2H), 4.21-4.13 (m, 3H), 3.80-3.77 (m, 2H), 3.04-3.01 (m, 2H), 2.43 | 533.3 |

-continued

| Chemical name | Compound# | H-NMR | MH+ |
|---|---|---|---|
| | | (s, 3H), 2.35 (s, 3H), 2.30-2.24 (m, 2H), 2.19-2.04 (m, 4H), 1.20 (s, 9H). | |
| 3-tert-butyl-N-[[4-[2-[[1-(2-methoxyethyl)pyrazol-4-yl]amino]pyrimidin-4-yl]-2-methyl-phenyl]methyl]pyrrolidine-1-carboxamide | I-303 | $^1$H NMR (400 MHz, CD$_3$OD) δ: 8.28 (d, J = 4.8 Hz, 1H), 7.99 (s, 1H), 7.83 (d, J = 6.8 Hz, 1H), 7.58 (s, 1H), 7.30 (d, J = 8.4 Hz, 1H), 7.08 (d, J = 5.2 Hz, 1H), 6.56 (s, 1H), 4.38-4.28 (m, 2H), 4.19 (t, J = 4.8 Hz, 2H), 3.66 (t, J = 5.2 Hz, 2H), 3.51-3.46 (m, 1H), 3.40-3.36 (m, 1H), 3.25 (s, 3H), 3.20-3.18 (m, 1H), 3.02-2.99 (m, 1H), 2.34 (s, 3H), 2.01-2.00 (m, 1H), 1.84-1.81 (m, 1H), 1.64-1.59 (m, 1H), 0.87 (s, 9H). | 492.3 |
| 3-tert-butoxy-N-[[4-[2-[[1-(2-methoxyethyl)pyrazol-4-yl]amino]pyrimidin-4-yl]-2-methyl-phenyl]methyl]azetidine-1-carboxamide | I-304 | $^1$H NMR (400 MHz, CD$_3$OD) δ: 8.39 (d, J = 5.2 Hz, 1H), 8.09 (s, 1H), 7.96-7.95 (m, 2H), 7.67 (s, 1H), 7.39 (d, J = 8.4 Hz, 1H), 7.22 (d, J = 4.8 Hz, 1H), 4.61-4.56 (m, 1H), 4.39 (s, 2H), 4.30 (t, J = 5.2 Hz, 2H), 4.19-4.15 (m, 2H), 3.80-3.75 (m, 4H), 3.35 (s, 3H), 2.44 (s, 3H), 1.20 (s, 9H). | 494.3 |
| 3-tert-butyl-N-[[4-[2-[(1-ethylpyrazol-4-yl)amino]pyrimidin-4-yl]-2-methyl-phenyl]methyl]pyrrolidine-1-carboxamide | I-305 | $^1$H NMR (400 MHz, CD$_3$OD) δ: 8.28 (d, J = 5.6 Hz, 1H), 7.92 (s, 1H), 7.82 (d, J = 7.2 Hz, 1H), 7.56 (s, 1H), 7.30 (d, J = 8.4 Hz, 1H), 7.09 (d, J = 5.2 Hz, 1H), 4.37-4.28 (m, 2H), 4.06 (q, J = 7.2 Hz, 2H), 3.49-3.47 (m, 1H), 3.39-3.37 (m, 1H), 3.19-3.16 (m, 1H), 3.04-2.98 (m, 1H), 2.33 (s, 3H), 2.04-1.99 (m, 1H), 1.86-1.80 (m, 1H), 1.64-1.59 (m, 1H), 1.39 (t, J = 7.2 Hz, 3H), 0.87 (s, 9H). | 462.3 |
| 3-tert-butoxy-N-[[4-[2-[(1-isopropylpyrazol-4-yl)amino]pyrimidin-4-yl]-2-methyl-phenyl]methyl]azetidine-1-carboxamide | I-306 | $^1$H NMR (400 MHz, CD$_3$OD) δ: 8.42 (s, 1H), 8.37 (d, J = 4.8 Hz, 1H), 8.21 (d, J = 8.0 Hz, 1H), 7.95 (s, 1H), 7.60 (d, J = 8.4 Hz, 1H), 7.53 (s, 1H), 7.17 (d, J = 4.8 Hz, 1H), 4.53-4.47 (m, 1H), 4.49 (s, 2H), 4.44-4.37 (m, 1H), 4.11-4.08 (m, 2H), 3.73-3.69 (m, 2H), 1.42 (d, J = 6.4 Hz, 3H), 1.10 (s, 9H). | 532.3 |
| 3-(2-fluoroethoxy)-N-[[2-methyl-4-[2-[(1-methylpyrazol-4-yl)amino]pyrimidin-4-yl]phenyl]methyl]azetidine-1-carboxamide | I-307 | $^1$H NMR (400 MHz, CD$_3$OD) δ: 8.28-8.26 (m, 1H), 7.86 (s, 1H), 7.82-7.81 (m, 2H), 7.53 (s, 1H), 7.28 (d, J = 8.0 Hz, 1H), 7.08-7.06 (m, 1H), 4.49 (t, J = 4.0 Hz, 1H), 4.37 (t, J = 4.0 Hz, 1H), 4.32-4.26 (m, 1H), 4.27 (s, 2H), 4.08-4.05 (m, 2H), 3.78 (s, 3H), 3.76-3.74 (m, 2H), 3.62 (t, J = 4.0 Hz, 1H), 3.54 (t, J = 4.0 Hz, 1H), 2.31 (s, 3H). | 440.2 |
| 3-tert-butyl-N-[[4-[2-[(1-cyclopropylpyrazol-4-yl)amino]pyrimidin-4-yl]-2-methyl-phenyl]methyl]pyrrolidine-1-carboxamide | I-308 | $^1$H NMR (400 MHz, CD$_3$OD) δ: 8.33 (d, J = 5.2 Hz, 1H), 8.03 (s, 1H), 7.89-7.85 (m, 2H), 7.61 (s, 1H), 7.37 (d, J = 8.0 Hz, 1H), 7.13 (d, J = 5.6 Hz, 1H), 4.45-4.35 (m, 2H), 3.63-3.54 (m, 2H), 3.48-3.43 (m, 1H), 3.28-3.23 (m, 1H), 3.08 (t, J = 10.0 Hz, 1H), 2.40 (s, 3H), 2.07-2.05 (m, 1H), 1.92-1.85 (m, 1H), 1.71-1.65 (m, 1H), 1.10-1.02 (m, 4H), 0.93 (s, 9H). | 474.3 |
| 1-tert-butyl-5-[[2-methyl-4-[6-[(5-methyl-6,7-dihydro-4H-pyrazolo[1,5-a]pyrazin-2-yl)amino]pyrimidin-4-yl]phenyl]methyl]-6,7-dihydropyrazolo[4,3-c]pyridin-4-one | I-309 | $^1$H NMR (400 MHz, CD$_3$OD) δ: 8.56 (d, J = 1.2 Hz, 1H), 7.77-7.72 (m, 3H), 7.51 (s, 1H), 7.31 (d, J = 7.6 Hz, 1H), 6.23 (s, 1H), 4.75 (s, 2H), 4.10 (t, J = 5.2 Hz, 2H), 3.69 (s, 2H), 3.55 (t, J = 7.2 Hz, 2H), 3.21 (t, J = 6.8 Hz, 2H), 2.99 (t, J = 5.6 Hz, 2H), 2.50 (s, 3H), 2.38 (s, 3H), 1.60 (s, 9H). | 526.3 |
| 1-[[4-[2-[[1-(2-hydroxyethyl)pyrazol-4-yl]amino]pyrimidin-4-yl]-2-(trifluoromethyl)phenyl]methyl]-4-isobutyl-piperazin-2-one | I-310 | $^1$H NMR (400 MHz, CD$_3$OD) δ: 8.59 (s, 1H), 8.48 (d, J = 5.6 Hz, 1H), 8.40 (d, J = 8.4 Hz, 1H), 8.05 (s, 1H), 7.71-7.64 (m, 2H), 7.36 (d, J = 5.2 Hz, 1H), 4.97 (s, 2H), 4.23 (t, J = 5.6 Hz, 2H), 4.10 (s, 2H), 3.91 (t, J = 5.6 Hz, 2H), 3.68 (brs, 4H), 3.16 (d, J = 7.6 Hz, 2H), 2.26-2.19 (m, 1H), 1.09 (d, J = 6.8 Hz, 6H). | 518.2 |
| 3-tert-butyl-N-[[4-[2-[[1-(1-methylazetidin-3-yl)pyrazol- | I-311 | $^1$H NMR (400 MHz, CD$_3$OD) δ: 8.36-8.33 (m, 2H), 8.18 (d, J = 8.4 Hz, 1H), | 557.3 |

-continued

| Chemical name | Compound# | H-NMR | MH+ |
|---|---|---|---|
| 4-yl]amino]pyrimidin-4-yl]-2-(trifluoromethyl)phenyl]methyl]pyrrolidine-1-carboxamide | | 8.02 (s, 1H), 7.64 (s, 1H), 7.58 (d, J = 8.8 Hz, 1H), 7.14 (d, J = 4.8 Hz, 1H), 5.00-4.95 (m, 1H), 4.58-4.49 (m, 2H), 4.07-4.03 (m, 2H), 3.84-3.80 (m, 2H), 3.51-3.47 (m, 1H), 3.41-3.37 (m, 1H), 3.24-3.22 (m, 1H), 3.03-3.00 (m, 1H), 2.58 (s, 3H), 2.05-2.00 (m, 1H), 1.84-1.80 (m, 1H), 1.64-1.59 (m, 1H), 0.86 (s, 9H). | |
| N-[[4-[2-[[1-[1,1-dimethyl-2-oxo-2-(2,2,2-trifluoroethylamino)ethyl]pyrazol-4-yl]amino]pyrimidin-4-yl]-2-methyl-phenyl]methyl]-3-isopropoxy-azetidine-1-carboxamide | I-312 | $^1$H NMR (400 MHz, CD$_3$OD) δ: 8.28 (d, J = 4.8 Hz, 1H), 8.17 (br, 1H), 7.85 (s, 1H), 7.82 (d, J = 8.0 Hz, 1H), 7.64 (s, 1H), 7.28 (d, J = 8.0 Hz, 1H), 7.10-7.09 (m, 1H), 4.32-4.29 (m, 1H), 4.29 (s, 2H), 4.08-4.05 (m, 2H), 3.77 (q, J = 9.2 Hz, 2H), 3.71-3.68 (m, 2H), 3.58-3.52 (m, 1H), 2.31 (s, 3H), 1.74 (s, 6H), 1.06 (d, J = 6.0 Hz, 6H). | 589.3 |
| 3-isopropoxy-N-[[4-[2-[[1-[(3S)-tetrahydrofuran-3-yl]pyrazol-4-yl]amino]pyrimidin-4-yl]-2-(trifluoromethyl)phenyl]methyl]azetidine-1-carboxamide | I-313 | $^1$H NMR (400 MHz, CD$_3$OD): 8.37 (d, J = 5.2 Hz, 1H), 8.23-8.21 (m, 2H), 8.01 (s, 1H), 7.61-7.56 (m, 2H), 7.17 (d, J = 5.2 Hz, 1H), 4.95-4.90 (m, 1H), 4.52 (s, 2H), 4.38-4.34 (m, 1H), 4.15-4.02 (m, 3H), 3.98-3.93 (m, 2H), 3.87-3.75 (m, 3H), 3.62-3.56 (m, 1H), 2.45-2.38 (m, 1H), 2.27-2.20 (m, 1H), 1.09 (d, J = 6.4 Hz, 1H). | 546.2 |
| 3-isopropoxy-N-[[4-[2-[[1-[(3R)-tetrahydrofuran-3-yl]pyrazol-4-yl]amino]pyrimidin-4-yl]-2-(trifluoromethyl)phenyl]methyl]azetidine-1-carboxamide | I-314 | $^1$H NMR (400 MHz, CDCl$_3$) δ: 8.48 (d, J = 5.2 Hz, 1H), 8.36 (s, 1H), 8.14 (d, J = 8.0 Hz, 1H), 8.04 (s, 1H), 7.75 (d, J = 8.4 Hz, 1H), 7.57 (s, 1H), 7.13 (s, 1H), 7.10 (d, J = 5.2 Hz, 1H), 5.00-4.95 (m, 1H), 4.62 (d, J = 6.4 Hz, 2H), 4.55 (t, J = 6.0 Hz, 1H), 4.38-4.32 (m, 1H), 4.19-4.07 (m, 5H), 3.99-3.93 (m, 1H), 3.87-3.85 (m, 2H), 3.63-3.57 (m, 1H), 2.53-2.36 (m, 2H), 1.15 (d, J = 6.4 Hz, 6H). | 546.2 |
| 2-tert-butyl-N-[[4-[2-(5,6-dihydro-4H-pyrrolo[1,2-b]pyrazol-3-ylamino)pyrimidin-4-yl]-2-methyl-phenyl]methyl]thiazole-5-carboxamide | I-315 | $^1$H NMR (400 MHz, CD$_3$OD) δ: 8.23-8.20 (m, 1H), 8.12 (s, 1H), 7.82 (s, 1H), 7.78 (d, J = 6.8 Hz, 1H), 7.56 (s, 1H), 7.29 (d, J = 8.0 Hz, 1H), 7.08-7.05 (m, 1H), 4.49 (s, 2H), 4.01-3.90 (m, 2H), 2.82-2.79 (m, 2H), 2.51-2.48 (m, 2H), 2.33 (s, 3H), 1.35 (s, 9H). | 488 |
| 3-tert-butyl-N-[[4-[2-[[1-[(3S)-pyrrolidin-3-yl]pyrazol-4-yl]amino]pyrimidin-4-yl]-2-(trifluoromethyl)phenyl]methyl]pyrrolidine-1-carboxamide | I-316 | $^1$H NMR (400 MHz, CD$_3$OD) δ: 8.36 (s, 1H), 8.32 (d, J = 5.2 Hz, 1H), 8.15 (d, J = 8.4 Hz, 1H), 7.94 (s, 1H), 7.58-7.56 (m, 2H), 7.11 (d, J = 4.8 Hz, 1H), 4.87-4.82 (m, 1H), 4.56-4.52 (m, 2H), 3.51-3.49 (m, 2H), 3.40-3.38 (m, 1H), 3.31-3.17 (m, 3H), 3.07-2.99 (m, 2H), 2.34-2.25 (m, 1H), 2.18-2.10 (m, 1H), 2.05-1.97 (m, 1H), 1.85-1.79 (m, 1H), 1.67-1.56 (m, 1H), 0.85 (s, 9H). | 557.3 |
| 3-isopropyl-N-[[4-[2-[[1-(2-methoxyethyl)pyrazol-4-yl]amino]pyrimidin-4-yl]-2-(trifluoromethyl)phenyl]methyl]pyrrolidine-1-carboxamide | I-317 | $^1$H NMR (400 MHz, CDCl$_3$) δ: 8.46 (d, J = 5.2 Hz, 1H), 8.36 (s, 1H), 8.15 (d, J = 8.0 Hz, 1H), 7.98 (s, 1H), 7.80 (d, J = 8.0 Hz, 1H), 7.60 (s, 1H), 7.09 (d, J = 5.2 Hz, 1H), 7.01 (s, 1H), 4.69-4.64 (m, 3H), 4.30 (t, J = 5.2 Hz, 2H), 3.78 (t, J = 5.2 Hz, 2H), 3.58-3.50 (m, 2H), 3.36 (s, 3H), 2.94-2.89 (m, 1H), 2.92 (t, J = 9.6 Hz, 1H), 2.08-2.02 (m, 1H), 1.90-1.82 (m, 1H), 2.15-1.45 (m, 2H), 0.93-0.90 (m, 6H). | 523.3 |
| 3-tert-butyl-N-[[4-[2-[[1-[(3R)-pyrrolidin-3-yl]pyrazol-4-yl]amino]pyrimidin-4-yl]-2-(trifluoromethyl)phenyl]methyl]pyrrolidine-1-carboxamide | I-318 | $^1$H NMR (400 MHz, CD$_3$OD) δ: 8.39 (s, 1H), 8.35 (d, J = 5.2 Hz, 1H), 8.19 (d, J = 8.4 Hz, 1H), 7.97 (s, 1H), 7.60-7.57 (m, 2H), 7.16 (d, J = 5.6 Hz, 1H), 4.86-4.82 (m, 1H), 4.56-4.52 (m, 2H), 3.52-3.48 (m, 1H), 3.42-3.38 (m, 1H), 3.27-3.24 (m, 3H), 3.18-3.17 (m, 1H), 3.05-2.96 (m, 2H), 2.31-2.26 (m, 1H), 2.17-2.02 (m, 2H), 1.85-1.81 (m, 1H), 1.66-1.61 (m, 1H), 0.87 (s, 9H). | 557.3 |
| 3-tert-butoxy-N-[[2-(2-methoxyethyl)-4-[2-[(1- | I-319 | $^1$H NMR (400 MHz, CD$_3$OD) δ: 8.40 (d, J = 5.2 Hz, 1H), 8.02 (d, J = 1.6 Hz, | 494.3. |

| Chemical name | Compound# | H-NMR | MH+ |
|---|---|---|---|
| methylpyrazol-4-yl)amino]pyrimidin-4-yl]phenyl]methyl]azetidine-1-carboxamide | | 1H), 8.00 (s, 1H), 7.95 (dd, J = 8.0, 1.6 Hz, 1H), 7.64 (s, 1H), 7.42 (d, J = 8.0 Hz, 1H), 7.21 (d, J = 5.2 Hz, 1H), 4.59-4.56 (m, 1H), 4.44 (s, 2H), 4.17-4.13 (m, 2H), 3.90 (s, 3H), 3.79-3.76 (m, 2H), 3.70 (t, J = 6.8 Hz, 2H), 3.36 (s, 3H), 3.04 (t, J = 6.8 Hz, 2H), 1.19 (s, 9H). | |
| 3-tert-butyl-N-[[2-(2-methoxyethyl)-4-[2-[(1-methylpyrazol-4-yl)amino]pyrimidin-4-yl]phenyl]methyl]pyrrolidine-1-carboxamide | I-320 | $^1$H NMR (400 MHz, CD$_3$OD) δ: 8.40 (d, J = 5.2 Hz, 1H), 8.02 (s, 1H), 8.00 (s, 1H), 7.95 (d, J = 8.4 Hz, 1H), 7.64 (s, 1H), 7.44 (d, J = 8.0 Hz, 1H), 7.21 (d, J = 5.2 Hz, 1H), 4.49 (s, 2H), 3.90 (s, 3H), 3.71 (t, J = 6.8 Hz, 2H), 3.59-3.54 (m, 1H), 3.48-3.44 (m, 1H), 3.36 (s, 3H), 3.29-3.25 (m, 1H), 3.12-3.07 (m, 1H), 3.06 (t, J = 6.8 Hz, 2H), 2.16-2.07 (m, 1H), 1.95-1.89 (m, 1H), 1.77-1.69 (m, 1H), 0.96 (s, 9H). | 492.3 |
| 3-tert-butyl-N-[[4-[2-[(1,5-dimethylpyrazol-4-yl)amino]pyrimidin-4-yl]-2-(2-hydroxyethyl)phenyl]methyl]pyrrolidine-1-carboxamide | I-321 | $^1$H NMR (400 MHz, CD$_3$OD) δ: 8.27 (d, J = 5.2 Hz, 1H), 7.96 (s, 1H), 7.89 (d, J = 8.0 Hz, 1H), 7.59 (s, 1H), 7.41 (d, J = 8.0 Hz, 1H), 7.17 (d, J = 5.6 Hz, 1H), 4.51-.4.43 (m, 2H), 3.85-3.82 (m, 2H), 3.79 (s, 3H), 3.56-3.51 (m, 1H), 3.45-3.41 (m, 1H), 3.28-3.21 (m, 1H), 3.08-2.97 (m, 3H), 2.21 (s, 3H), 2.06-2.04 (m, 1H), 1.89-1.86 (m, 1H), 1.69-1.64 (m, 1H), 0.93 (s, 9H). | 492.3 |
| 3-tert-butoxy-N-[[4-[2-(5,6-dihydro-4H-pyrrolo[1,2-b]pyrazol-3-ylamino)pyrimidin-4-yl]-2-methyl-phenyl]methyl]azetidine-1-carboxamide | I-322 | $^1$H NMR (400 MHz, CD$_3$OD) δ: 8.22 (d, J = 5.2 Hz, 1H), 7.79-7.77 (m, 2H), 7.57 (s, 1H), 7.27 (d, J = 7.6 Hz, 1H), 7.08 (d, J = 5.6 Hz, 1H), 4.49-4.46 (m, 1H), 4.26 (s, 2H), 4.08-4.01 (m, 4H), 3.69-3.65 (m, 2H), 2.83 (t, J = 7.2 Hz, 2H), 2.56-2.49 (m, 2H), 2.30 (s, 3H), 1.00 (s, 9H). | 476.2 |
| 3-tert-butoxy-N-[[4-[2-(5,6-dihydro-4H-pyrrolo[1,2-b]pyrazol-3-ylamino)pyrimidin-4-yl]-2-(2-methoxyethyl)phenyl]methyl]azetidine-1-carboxamide | I-323 | $^1$H NMR (400 MHz, CD$_3$OD) δ: 8.24 (d, J = 5.2 Hz, 1H), 7.87 (s, 1H), 7.81 (d, J = 8.0 Hz, 1H), 7.57 (s, 1H), 7.30 (d, J = 7.6 Hz, 1H), 7.09 (d, J = 5.2 Hz, 1H), 4.48-4.45 (m, 1H), 4.33 (s, 2H), 4.06-4.01 (m, 4H), 3.68-3.65 (m, 2H), 3.57 (t, J = 6.8 Hz, 2H), 3.25 (s, 3H), 2.92 (t, J = 6.8 Hz, 2H), 2.84 (t, J = 7.2 Hz, 2H), 2.55-2.51 (m, 2H), 1.09 (s, 9H). | 520 |
| 3-tert-butyl-N-[[4-[2-(5,6-dihydro-4H-pyrrolo[1,2-b]pyrazol-3-ylamino)pyrimidin-4-yl]-2-(2-hydroxyethyl)phenyl]methyl]pyrrolidine-1-carboxamide | I-324 | $^1$H NMR (400 MHz, CD$_3$OD) δ: 8.23 (d, J = 5.2 Hz, 1H), 7.87 (d, J = 8.0 Hz, 1H), 7.81 (d, J = 8.0 Hz, 1H), 7.56 (s, 1H), 7.33 (d, J = 8.4 Hz, 1H), 7.09 (d, J = 5.6 Hz, 1H), 4.23-4.33 (m, 2H), 4.03 (t, J = 7.2 Hz, 2H), 3.73 (t, J = 7.2 Hz, 2H), 3.45 (t, J = 9.2 Hz, 1H), 3.35 (t, J = 9.2 Hz, 1H), 3.18-3.13 (m, 1H), 2.92 (t, J = 10.4 Hz, 1H), 2.89 (t, J = 6.8 Hz, 2H), 2.83 (t, J = 7.2 Hz, 2H), 2.56-2.49 (m, 2H), 2.01-1.98 (m, 1H), 1.84-1.78 (m, 1H), 1.63-1.57 (m, 1H), 0.85 (s, 9H). | 504.2 |
| (3S)-3-tert-butyl-N-[[4-[2-(5,6-dihydro-4H-pyrrolo[1,2-b]pyrazol-3-ylamino)pyrimidin-4-yl]-2-(2-methoxyethyl)phenyl]methyl]pyrrolidine-1-carboxamide | I-325 | $^1$H NMR (400 MHz, CD$_3$OD) δ: 8.20 (d, J = 5.2 Hz, 1H), 7.85 (d, J = 1.6 Hz, 1H), 7.77 (dd, J = 8.0, 1.6 Hz, 1H), 7.57 (s, 1H), 7.30 (d, J = 8.0 Hz, 1H), 7.05 (d, J = 5.2 Hz, 1H), 4.37-4.35 (m, 2H), 4.00 (t, J = 7.2 Hz, 2H), 3.55 (t, J = 6.8 Hz, 2H), 3.46-3.31 (m, 2H), 3.23 (s, 3H), 3.18-3.12 (m, 1H), 2.99-2.89 (m, 3H), 2.82-2.79 (m, 2H), 2.53-2.45 (m, 2H), 1.97-1.95 (m, 1H), 1.80-1.75 (m, 1H), 1.60-1.55 (m, 1H), 0.83 (s, 9H). | 518.3 |
| 3-isopropoxy-N-[6-[2-[[1-(1-methyl-4-piperidyl)pyrazol-4-yl]amino]pyrimidin-4-yl]tetralin-1-yl]azetidine-1-carboxamide | I-326 | 1H NMR (400 MHz, CD3OD) δ: 8.39 (d, J = 5.2 Hz, 1H), 8.10 (s, 1H), 7.94-7.86 (m, 2H), 7.67 (s, 1H), 7.41 (d, J = 8.0 Hz, 1H), 7.19 (d, J = 5.2 Hz, 1H), 4.99-4.94 (m, 1H), 4.45-4.34 (m, 1H), 4.20-4.11 (m, 3H), 3.82-3.75 (m, 2H), 3.71-3.63 (m, 1H), 3.03-3.00 (m, 2H), | 545.4 |

-continued

| Chemical name | Compound# | H-NMR | MH+ |
|---|---|---|---|
| | | 2.95-2.83 (m, 2H), 2.35 (s, 3H), 2.30-2.24 (m, 2H), 2.19-2.14 (m, 2H), 2.13-1.98 (m, 4H), 1.88-1.76 (m, 2H), 1.16 (d, J = 6.4 Hz, 6H). | |
| 3-tert-butyl-N-[6-[2-[[1-(2-hydroxyethyl)pyrazol-4-yl]amino]pyrimidin-4-yl]tetralin-1-yl]pyrrolidine-1-carboxamide | I-327 | 1H NMR (400 MHz, CD3OD) δ: 8.33 (d, J = 5.2 Hz, 1H), 8.07 (s, 1H), 7.89-7.83 (m, 2H), 7.66 (s, 1H), 7.41 (d, J = 8.4 Hz, 1H), 7.13 (d, J = 5.6 Hz, 1H), 5.04-5.02 (m, 1H), 4.20 (t, J = 5.2 Hz, 2H), 3.90 (t, J = 5.6 Hz, 2H), 3.56-3.44 (m, 2H), 3.29-3.24 (m, 1H), 3.11-3.04 (m, 1H), 2.89-2.86 (m, 2H), 2.09-1.98 (m, 3H), 1.92-1.65 (m, 4H), 0.93 (s, 9H). | 504.3 |
| 3-tert-butyl-N-[2-[2-[(1-ethylpyrazol-4-yl)amino]pyrimidin-4-yl]-6,7,8,9-tetrahydro-5H-benzo[7]annulen-5-yl]pyrrolidine-1-carboxamide | I-328 | 1H NMR (400 MHz, CD3OD) δ: 8.25 (d, J = 5.2 Hz, 1H), 7.89 (s, 1H), 7.81-7.76 (m, 2H), 7.55 (s, 1H), 7.29-7.25 (m, 1H), 7.06 (d, J = 5.6Hz, 1H), 6.49-6.43 (m, 1H), 5.06-4.99 (m, 1H), 4.05 (q, J = 7.2 Hz, 2H), 3.57-3.37 (m, 2H), 3.25-3.23 (m, 1H), 3.09-2.79 (m, 3H), 2.02-1.76 (m, 6H), 1.64-1.56 (m, 2H), 1.36 (t, J = 7.2 Hz, 3H), 1.27-1.17 (m, 1H), 0.86 (s, 9H). | 502.3 |
| N-[2-formyl-8-[2-[(1-methylpyrazol-4-yl)amino]pyrimidin-4-yl]-1,3,4,5-tetrahydro-2-benzazepin-5-yl]-3-isopropoxy-azetidine-1-carboxamide | I-329 | 1H NMR (400 MHz, CD3OD) δ: 8.42-8.40 (m, 1H), 8.21-8.15 (m, 1H), 8.08-7.98 (m, 3H), 7.64-7.59 (m, 1H), 7.48-7.43 (m, 1H), 7.23 (d, J = 5.6 Hz, 1H), 5.30-5.24 (m, 1H), 5.06-5.02 (m, 1H), 4.49-4.32 (m, 2H), 4.29-4.20 (m, 2H), 3.93-3.83 (m, 6H), 3.78-3.66 (m, 2H), 2.13-2.05 (m, 1H), 1.97-1.88 (m, 1H), 1.19-1.17 (m, 6H). | 505.3 |
| 3-tert-butyl-N-[2-[2-[(1-tetrahydropyran-4-ylpyrazol-4-yl)amino]pyrimidin-4-yl]-6,7,8,9-tetrahydro-5H-benzo[7]annulen-5-yl]pyrrolidine-1-carboxamide | I-330 | 1H NMR (400 MHz, CD3OD) δ: 8.27 (d, J = 5.2 Hz, 1H), 8.02 (s, 1H), 7.81-7.79 (m, 2H), 7.58 (s, 1H), 7.31-7.27 (m, 1H), 7.07 (d, J = 5.2 Hz, 1H), 5.07-5.02 (m, 1H), 4.27-4.21 (m, 1H), 3.97-3.94 (m, 2H), 3.59-3.40 (m, 4H), 3.28-3.26 (m, 1H), 3.11-2.80 (m, 3H), 2.07-1.78 (m, 10H), 1.66-1.58 (m, 2H), 1.28-1.24 (m, 1H), 0.88 (s, 9H). | 558.3 |
| 3-ethoxy-N-[2-[2-[(1-methylpyrazol-4-yl)amino]pyrimidin-4-yl]-6,7,8,9-tetrahydro-5H-benzo[7]annulen-5-yl]azetidine-1-carboxamide | I-331 | 1H NMR (400 MHz, CDCl3) δ: 8.39 (d, J = 5.2 Hz, 1H), 7.87 (s, 1H), 7.81-7.77 (m, 2H), 7.55 (s, 1H), 7.36-7.30 (m, 2H), 7.05 (d, J = 5.2 Hz, 1H), 5.09 (t, J = 8.0 Hz, 1H), 4.53 (d, J = 8.4 Hz, 1H), 4.34-4.28 (m, 1H), 4.19-4.13 (m, 2H), 3.94-3.88 (m, 5H), 3.46 (q, J = 7.2 Hz, 2H), 3.01-2.85 (m, 2H), 1.91-1.74 (m, 5H), 1.58-1.51 (m, 1H), 1.23 (t, J = 7.2 Hz, 3H). | 462.2 |
| 3-tert-butoxy-N-[2-[6-(6,7-dihydro-4H-pyrazolo[5,1-c][1,4]oxazin-2-ylamino)pyrimidin-4-yl]-6,7,8,9-tetrahydro-5H-benzo[7]annulen-5-yl]azetidine-1-carboxamide | I-332 | 1H NMR (400 MHz, CDCl3) δ: 8.76 (d, J = 0.8 Hz, 1H), 7.80 (d, J = 1.6 Hz, 1H), 7.71 (dd, J = 8.0, 1.6 Hz, 1H), 7.48 (s, 1H), 7.40 (s, 1H), 7.33 (d, J = 8.0 Hz, 1H), 6.10 (s, 1H), 5.08 (t, J = 8.0 Hz, 1H), 4.84 (s, 2H), 4.53-4.42 (m, 2H), 4.20-4.05 (m, 6H), 3.94-3.80 (m, 2H), 3.04-2.81 (m, 2H), 2.03-1.72 (m, 5H), 1.61-1.49 (m, 1H), 1.19 (s, 9H). | 532.3 |
| 3-isopropoxy-N-[2-[2-[[1-[(3R)-tetrahydrofuran-3-yl]pyrazol-4-yl]amino]pyrimidin-4-yl]-6,7,8,9-tetrahydro-5H-benzo[7]annulen-5-yl]azetidine-1-carboxamide | I-333 | 1H NMR (400 MHz, CD3OD) δ: 8.28 (d, J = 5.2 Hz, 1H), 8.08 (br, 1H), 7.84-7.81 (m, 1H), 7.79 (s, 1H), 7.53 (d, J = 2.0 Hz, 1H), 7.26 (d, J = 8.0 Hz, 1H), 7.11 (d, J = 4.8 Hz, 1H), 4.97-4.89 (m, 2H), 4.37-4.32 (m, 1H), 4.17-3.91 (m, 5H), 3.86-3.71 (m, 3H), 3.61-3.55 (m, 1H), 2.96-2.89 (m, 2H), 2.46-2.37 (m, 1H), 2.23-2.17 (m, 1H), 1.89-1.78 (m, 4H), 1.61-1.56 (m, 1H), 1.28-1.23 (m, 1H), 1.08 (d, J = 6.0 Hz, 6H) | 532 |
| 3-tert-butoxy-N-[2-[2-[[1-[(3S)-tetrahydrofuran-3-yl]pyrazol-4-yl]amino]pyrimidin-4-yl]-6,7,8,9-tetrahydro-5H- | I-334 | 1H NMR (400 MHz, CD3OD) δ: 8.27 (d, J = 5.2 Hz, 1H), 8.07 (s, 1H), 7.84-7.80 (m, 1H), 7.78 (s, 1H), 7.53 (d, J = 2.4 Hz, 1H), 7.27 (d, J = 8.0 Hz, 1H), 7.09 (d, J = 5.6 Hz, 1H), 4.95-4.89 (m, | 546.3 |

-continued

| Chemical name | Compound# | H-NMR | MH+ |
|---|---|---|---|
| benzo[7]annulen-5-yl]azetidine-1-carboxamide | | 2H), 4.53-4.47 (m, 1H), 4.16-3.90 (m, 5H), 3.85-3.69 (m, 3H), 2.95-2.84 (m, 2H), 2.45-2.36 (m, 1H), 2.22-2.16 (m, 1H), 1.89-1.86 (m, 3H), 1.82-1.76 (m, 1H), 1.62-1.52 (m, 1H), 1.30-1.26 (m, 1H), 1.10 (s, 9H). | |
| 3-isopropoxy-N-[8-[2-[(1-methylpyrazol-4-yl)amino]pyrimidin-4-yl]-2,3,4,5-tetrahydro-1-benzoxepin-5-yl]azetidine-1-carboxamide | I-335 | 1H NMR (400 MHz, CDCl3) δ: 8.43 (d, J = 5.2 Hz, 1H), 7.88 (s, 1H), 7.72-7.64 (m, 2H), 7.53 (s, 1H), 7.39 (d, J = 7.8 Hz, 1H), 7.19 (s, 1H), 7.03 (d, J = 5.2 Hz, 1H), 5.21-5.09 (m, 1H), 4.89 (d, J = 9.2 Hz, 1H), 4.46-4.26 (m, 2H), 4.15-4.04 (m, 2H), 3.92 (s, 3H), 3.87-3.70 (m, 3H), 3.64-3.51 (m, 1H), 2.32-2.13 (m, 2H), 1.88-1.69 (m, 2H), 1.14 (d, J = 5.6 Hz, 6H). | 478 |
| N-[2-[2-[[1-(2-hydroxy-2-methyl-propyl)pyrazol-4-yl]amino]pyrimidin-4-yl]-6,7,8,9-tetrahydro-5H-benzo[7]annulen-5-yl]-3-isopropoxy-azetidine-1-carboxamide | I-336 | 1H NMR (400 MHz, CDCl3) δ: 8.40 (d, J = 5.2 Hz, 1H), 7.95 (s, 1H), 7.80 (d, J = 8.0 Hz, 1H), 7.76 (s, 1H), 7.60 (s, 1H), 7.35 (d, J = 8.0 Hz, 1H), 7.05 (d, J = 5.2 Hz, 1H), 5.09 (t, J = 8.4 Hz, 1H), 4.54 (d, J = 7.6 Hz, 1H), 4.48-4.30 (m, 1H), 4.23-4.10 (m, 2H), 4.05 (s, 2H), 3.99-3.83 (m, 3H), 3.68-3.55 (m, 1H), 3.03-2.80 (m, 2H), 1.88-1.69 (m, 5H), 1.64-1.43 (m, 1H), 1.21 (s, 6H), 1.17 (d, J = 5.2 Hz, 6H) | 534.3 |
| 3-tert-butoxy-N-[2-[2-[[1-(2-hydroxy-2-methyl-propyl)pyrazol-4-yl]amino]pyrimidin-4-yl]-6,7,8,9-tetrahydro-5H-benzo[7]annulen-5-yl]azetidine-1-carboxamide | I-337 | 1H NMR (400 MHz, CDCl3) δ: 8.39 (d, J = 5.2 Hz, 1H), 7.94 (s, 1H), 7.79 (d, J = 8.0 Hz, 1H), 7.75 (s, 1H), 7.59 (s, 1H), 7.53 (s, 1H), 7.34 (d, J = 8.0 Hz, 1H), 7.05 (d, J = 5.2 Hz, 1H), 5.09 (t, J = 8.4 Hz, 1H), 4.57 (d, J = 7.8 Hz, 1H), 4.54-4.43 (m, 1H), 4.23-4.09 (m, 2H), 4.05 (s, 2H), 3.95-3.81 (m, 2H), 3.02-2.81 (m, 2H), 1.94-1.68 (m, 5H), 1.61-1.43 (m, 1H), 1.20 (s, 6H), 1.19 (s, 9H). | 548.3 |
| 3-isopropoxy-N-[2-[2-[[1-[(3S)-tetrahydrofuran-3-yl]pyrazol-4-yl]amino]pyrimidin-4-yl]-6,7,8,9-tetrahydro-5H-benzo[7]annulen-5-yl]azetidine-1-carboxamide | I-338 | 1H NMR (400 MHz, CD3OD) δ: 8.27 (d, J = 4.8 Hz, 1H), 8.06 (s, 1H), 7.83-7.78 (m, 2H), 7.53 (s, 1H), 7.26 (d, J = 8.0 Hz, 1H), 7.09 (d, J = 5.2 Hz, 1H), 4.95-4.89 (m, 2H), 4.37-4.31 (m, 1H), 4.16-4.02 (m, 5H), 3.90-3.71 (m, 3H), 4.61-3.55 (m, 1H), 2.94-2.88 (m, 2H), 2.45-2.36 (m, 1H), 2.19-2.17 (m, 1H), 1.89-1.76 (m, 4H), 1.60-1.52 (m, 1H), 1.31-1.18 (m, 1H), 1.07 (d, J = 6.0 Hz, 6H) | 532.3 |
| 3-methoxy-N-[2-[2-[(1-methylpyrazol-4-yl)amino]pyrimidin-4-yl]-6,7,8,9-tetrahydro-5H-benzo[7]annulen-5-yl]azetidine-1-carboxamide | I-339 | 1H NMR (400 MHz, CD3OD) δ: 8.27 (d, J = 5.2 Hz, 1H), 7.85 (s, 1H), 7.82 (dd, J = 6.4, 1.6 Hz, 1H), 7.77 (d, J = 1.2 Hz, 1H), 7.55 (s, 1H), 7.26 (d, J = 8.0 Hz, 1H), 7.08 (d, J = 5.2 Hz, 1H), 4.94 (d, J = 10.4 Hz, 1H), 4.18-4.06 (m, 3H), 3.80-3.73 (m, 5H), 3.23 (s, 3H), 2.95-2.81 (m, 2H), 1.89-1.73 (m, 4H), 1.62-1.53 (m, 1H), 1.31-1.19 (m, 1H). | 448 |
| 3-isopropyl-N-[2-[2-[(1-methylpyrazol-4-yl)amino]pyrimidin-4-yl]-6,7,8,9-tetrahydro-5H-benzo[7]annulen-5-yl]pyrrolidine-1-carboxamide | I-340 | 1H NMR (400 MHz, CD3OD) δ: 8.28 (d, J = 5.2 Hz, 1H), 7.86 (s, 1H), 7.83 (d, J = 8.0 Hz, 1H), 7.77 (s, 1H), 7.55 (s, 1H), 7.29-7.26 (m, 1H), 7.09 (d, J = 5.2 Hz, 1H), 6.46-6.40 (m, 1H), 5.06-4.99 (m, 1H), 3.78 (s, 3H), 3.63-3.46 (m, 2H), 3.28-3.24 (m, 1H), 2.98-2.82 (m, 3H), 2.05-1.99 (m, 1H), 1.91-1.76 (m, 5H), 1.65-1.43 (m, 3H), 1.32-1.24 (m, 1H), 0.91-0.89 (m, 6H) | 474.3 |
| N-[2-[2-[(1-ethylpyrazol-4-yl)amino]pyrimidin-4-yl]-6,7,8,9-tetrahydro-5H-benzo[7]annulen-5-yl]-3-isopropyl-pyrrolidine-1-carboxamide | I-341 | 1H NMR (400 MHz, CD3OD) δ: 8.28 (d, J = 5.2 Hz, 1H), 7.91 (s, 1H), 7.83 (d, J = 8.4 Hz, 1H), 7.79 (s, 1H), 7.56 (s, 1H), 7.29-7.26 (m, 1H), 7.09 (d, J = 5.2 Hz, 1H), 5.02 (t, J = 8.8 Hz, 1H), 4.08 (q, J = 7.2 Hz, 2H), 3.63-3.46 (m, 2H), 3.26-3.24 (m, 1H), 2.98-2.82 (m, 3H), 2.04-1.99 (m, 1H), 1.91-1.78 (m, | 488.1 |

| Chemical name | Compound# | H-NMR | MH+ |
|---|---|---|---|
| | | 5H), 1.63-1.43 (m, 3H), 1.38 (t, J = 7.2 Hz, 3H), 1.29-1.27 (m, 1H), 0.92-0.89 (m, 6H). | |
| 3-isopropyl-N-[2-[2-[(1-tetrahydropyran-4-ylpyrazol-4-yl)amino]pyrimidin-4-yl]-6,7,8,9-tetrahydro-5H-benzo[7]annulen-5-yl]pyrrolidine-1-carboxamide | I-342 | 1H NMR (400 MHz, CD3OD) δ: 8.29 (d, J = 5.2 Hz, 1H), 8.04 (s, 1H), 7.92-7.71 (m, 2H), 7.59 (s, 1H), 7.34-7.22 (m, 1H), 7.10 (d, J = 5.2 Hz, 1H), 6.55-6.33 (m, 1H), 5.12-4.98 (m, 1H), 4.35-4.19 (m, 1H), 3.99-3.97 (m, 2H), 3.69-3.41 (m, 4H), 3.34-3.24 (m, 1H), 3.10-2.77 (m, 3H), 2.11-1.73 (m, 10H), 1.72-1.36 (m, 3H), 1.35-1.22 (m, 1H), 0.98-0.80 (m, 6H) | 544.3 |
| 3-tert-butoxy-N-[2-[2-[[1-(4-piperidyl)pyrazol-4-yl]amino]pyrimidin-4-yl]-6,7,8,9-tetrahydro-5H-benzo[7]annulen-5-yl]azetidine-1-carboxamide | I-343 | 1H NMR (400 MHz, CD3OD) δ: 8.40 (d, J = 5.2 Hz, 1H), 8.10 (s, 1H), 7.92 (d, J = 8.0 Hz, 1H), 7.89 (d, J = 8.0 Hz, 1H), 7.73 (s, 1H), 7.38 (d, J = 8.0 Hz, 1H), 7.21 (d, J = 6.4 Hz, 1H), 5.05 (d, J = 10.4 Hz, 1H), 4.64-4.59 (m, 1H), 4.53-4.45 (m, 1H), 4.27-4.19 (m, 2H), 3.88-3.70 (m, 2H), 3.53-3.50 (m, 2H), 3.21-3.13 (m, 2H), 3.07-2.92 (m, 2H), 2.34-2.14 (m, 4H), 2.01-1.86 (m, 4H), 1.72-1.64 (m, 1H), 1.43-1.37 (m, 1H), 1.23 (s, 9H). | 559.4 |
| 3-isopropyl-N-[2-[2-[[1-[(3R)-tetrahydrofuran-3-yl]pyrazol-4-yl]amino]pyrimidin-4-yl]-6,7,8,9-tetrahydro-5H-benzo[7]annulen-5-yl]pyrrolidine-1-carboxamide | I-344 | 1H NMR (400 MHz, CD3OD) δ: 8.28 (d, J = 5.6 Hz, 1H), 8.07 (s, 1H), 7.83 (d, J = 8.4 Hz, 1H), 7.79 (s, 1H), 7.54 (s, 1H), 7.29-7.26 (m, 1H), 7.10 (d, J = 5.2 Hz, 1H), 6.46-6.40 (m, 1H), 5.04-5.02 (m, 1H), 4.94-4.90 (m, 1H), 4.04-3.93 (m, 3H), 3.82-3.80 (m, 1H), 3.61-3.49 (m, 2H), 3.28-3.26 (m, 1H), 2.95-2.90 (m, 3H), 2.41-2.39 (m, 3H), 2.04-2.01 (m, 1H), 1.93-1.92 (m, 1H), 1.91-1.82 (m, 5H), 1.63-1.50 (m, 3H), 1.30-1.28 (m, 1H), 0.92-0.89 (m, 6H). | 530 |
| 3-isopropyl-N-[2-[2-[[1-[(3S)-tetrahydrofuran-3-yl]pyrazol-4-yl]amino]pyrimidin-4-yl]-6,7,8,9-tetrahydro-5H-benzo[7]annulen-5-yl]pyrrolidine-1-carboxamide | I-345 | 1H NMR (400 MHz, CD3OD) δ: 8.28 (d, J = 5.2 Hz, 1H), 8.08 (s, 1H), 7.86-7.74 (m, 2H), 7.56 (s, 1H), 7.30 (dd, J = 8.0, 1.6 Hz, 1H), 7.10 (d, J = 5.2 Hz, 1H), 6.51-6.37 (m, 1H), 5.06-5.04 (m, 1H), 4.93-4.91 (m, 1H), 4.10-3.87 (m, 3H), 3.86-3.77 (m, 1H), 3.65-3.43 (m, 2H), 3.35-3.25 (m, 1H), 3.01-2.85 (m, 3H), 2.47-2.35 (m, 1H), 2.26-2.16 (m, 1H), 2.10-1.97 (m, 1H), 1.96-1.74 (m, 4H), 1.69-1.18 (m, 5H), 0.91 (d, J = 5.6 Hz, 6H). | 530.3 |
| N-[2-(2-hydroxyethyl)-8-[2-[(1-methylpyrazol-4-yl)amino]pyrimidin-4-yl]-1,3,4,5-tetrahydro-2-benzazepin-5-yl]-3-isopropoxy-azetidine-1-carboxamide | I-346 | $^1$H NMR (500 MHz, CD$_3$OD) δ: 8.29 (d, J = 3.6 Hz, 1H), 7.91-7.87 (m, 3H), 7.53 (s, 1H), 7.31 (d, J = 6.4 Hz, 1H), 7.11 (d, J = 4.0 Hz, 1H), 5.08 (d, J = 8.0 Hz, 1H), 4.36-4.33 (m, 1H), 4.16-4.09 (m, 2H), 4.03-3.99 (m, 1H), 3.94-3.91 (m, 1H), 3.79 (s, 3H), 3.79-3.73 (m, 2H), 3.61-3.57 (m, 3H), 3.15-3.12 (m, 1H), 3.06-3.04 (m, 1H), 2.54-2.46 (m, 2H), 1.99-1.96 (m, 1H), 1.76-1.73 (m, 1H), 1.08 (d, J = 4.8 Hz, 1H). | 521 |
| 3-tert-butoxy-N-[2-[2-[(1,5-dimethylpyrazol-4-yl)amino]pyrimidin-4-yl]-6,7,8,9-tetrahydro-5H-benzo[7]annulen-5-yl]azetidine-1-carboxamide | I-347 | 1H NMR (400 MHz, CDCl3) δ: 8.36 (d, J = 5.2 Hz, 1H), 7.79-7.78 (m, 2H), 7.70 (s, 1H), 7.32 (d, J = 8.4 Hz, 1H), 7.04 (d, J = 5.2 Hz, 1H), 6.41 (s, 1H), 5.08 (t, J = 8.0 Hz, 1H), 4.54-4.41 (m, 2H), 4.20-4.10 (m, 2H), 3.94-3.84 (m, 2H), 3.81 (s, 3H), 3.02-2.83 (m, 2H), 2.23 (s, 3H), 1.98-1.69 (m, 6H), 1.20 (s, 9H). | 504.3 |
| N-[2-[2-[[1-(3-fluoro-1-methyl-4-piperidyl)pyrazol-4-yl]amino]pyrimidin-4-yl]-6,7,8,9-tetrahydro-5H-benzo[7]annulen-5-yl]-3-isopropoxy-azetidine-1-carboxamide | I-348 | $^1$H NMR (400 MHz, CD$_3$OD) δ: 8.39 (d, J = 6.4 Hz, 1H), 8.13 (s, 1H), 7.94-7.90 (m, 2H), 7.72 (s, 1H), 7.38 (d, J = 10.8 Hz, 1H), 7.21 (d, J = 6.8 Hz, 1H), 5.06-5.03 (m, 1H), 4.99-4.95 (m, 1H), 4.46-4.43 (m, 1H), 4.28-4.18 (m, 3H), 3.89-3.87 (m, 2H), 3.70-3.66 (m, 1H), | 577.5 |

| Chemical name | Compound# | H-NMR | MH+ |
|---|---|---|---|
| | | 3.08-2.95 (m, 3H), 2.39 (s, 3H), 2.29-1.65 (m, 9H), 1.39-1.35 (m, 2H), 1.19 (d, J = 7.6 Hz, 6H). | |
| 4-isobutyl-1-[[2-methyl-4-[2-[[1-(1-methylazetidin-3-yl)pyrazol-4-yl]amino]pyrimidin-4-yl]phenyl]methyl]piperazin-2-oneacid | I-349 | $^1$H NMR (400 MHz, CD$_3$OD) δ: 8.31 (s, 1H), 8.00 (s, 1H), 7.95-7.87 (m, 2H), 7.80 (s, 1H), 7.29 (d, J = 8.0 Hz, 1H), 7.25 (d, J = 5.6 Hz, 1H), 5.30 (d, J = 6.8 Hz, 1H), 4.81-4.73 (m, 1H), 4.69 (s, 2H), 4.66-4.54 (m, 1H), 4.51-4.28 (m, 2H), 4.00 (s, 2H), 3.63-3.43 (m, 4H), 3.10-2.99 (m, 4H), 2.94 (s, 1H), 2.33 (s, 3H), 2.17-2.03 (m, 1H), 0.96 (d, J = 6.4 Hz, 6H). | 488.3 |
| 4-(2,2-dimethylpropyl)-1-[[4-[2-[[1-(2-hydroxyethyl)pyrazol-4-yl]amino]pyrimidin-4-yl]-2-(trifluoromethyl)phenyl]methyl]piperazin-2-oneacid | I-350 | $^1$H NMR (400 MHz, CD$_3$OD) δ: 8.58 (s, 1H), 8.49 (d, J = 5.6 Hz, 1H), 8.40 (d, J = 8.4 Hz, 1H), 8.05 (s, 1H), 7.70-7.63 (m, 2H), 7.34 (d, J = 5.6 Hz, 1H), 4.96 (s, 2H), 4.23 (t, J = 5.2 Hz, 2H), 4.10 (s, 2H), 3.91 (t, J = 5.6 Hz, 2H) 3.64 (brs, 4H), 3.13 (s, 2H), 1.14 (s, 9H). | 532.3 |
| 3-isopropoxy-N-[[4-[2-[[1-(2-methoxyethyl)pyrazol-4-yl]amino]pyrimidin-4-yl]-2-(trifluoromethyl)phenyl]methyl]azetidine-1-carboxamide | I-351 | $^1$H NMR (400 MHz, CD$_3$OD) δ: 8.44-8.31 (m, 2H), 8.22 (d, J = 8.0 Hz, 1H), 7.95 (s, 1H), 7.62-7.50 (m, 2H), 7.16 (d, J = 5.2 Hz, 1H), 4.50 (s, 2H), 4.38-4.29 (m, 1H), 4.18 (t, J = 5.2 Hz, 2H), 4.13-4.03 (m, 2H), 3.76-3.70 (m, 2H), 3.65 (t, J = 5.2 Hz, 2H), 3.61-3.51 (m, 1H), 3.24 (s, 3H), 1.07 (d, J = 6.0 Hz, 6H). | 534.2 |
| 3-isopropoxy-N-[7-[2-[(1-methylpyrazol-4-yl)amino]pyrimidin-4-yl]-2,3,4,5-tetrahydro-1H-3-benzazepin-1-yl]azetidine-1-carboxamide | I-352 | 1H NMR (400 MHz, CD3OD) δ: 8.29 (d, J = 5.2 Hz, 1H), 7.86-7.85 (m, 2H), 7.80 (s, 1H), 7.55 (s, 1H), 7.30 (d, J = 8.0 Hz, 1H), 7.10 (d, J = 5.2 Hz, 1H), 4.98 (d, J = 6.4 Hz, 1H), 4.35-4.31 (m, 1H), 4.14-4.08 (m, 2H), 3.79 (s, 3H), 3.76-3.72 (m, 2H), 3.60-3.54 (m, 1H), 3.02-2.79 (m, 6H), 1.06 (d, J = 6.4 Hz, 6H). | 477 |
| N-[[2-chloro-4-[2-[[1-(1-methylazetidin-3-yl)pyrazol-4-yl]amino]pyrimidin-4-yl]phenyl]methyl]-3-isopropoxy-azetidine-1-carboxamide | I-353 | $^1$H NMR (400 MHz, CD$_3$OD) δ: 8.34 (d, J = 5.2 Hz, 1H), 8.06 (s, 1H), 8.01 (s, 1H), 7.93 (d, J = 8.4 Hz, 1H), 7.74 (s, 1H), 7.39 (d, J = 8.0 Hz, 1H), 7.13 (d, J = 5.2 Hz, 1H), 5.24-5.19 (m, 1H), 4.53-4.48 (m, 2H), 4.38-4.30 (m, 5H), 4.11-4.07 (m, 2H), 3.74-3.70 (m, 2H), 3.59-3.53 (m, 1H), 2.94 (s, 3H), 1.06 (d, J = 6.0 Hz, 6H). | 511.2 |
| 5-tert-butyl-N-[[2-chloro-4-[2-[[1-(1-methylazetidin-3-yl)pyrazol-4-yl]amino]pyrimidin-4-yl]phenyl]methyl]isoxazole-3-carboxamide | I-354 | $^1$H NMR (400 MHz, CD$_3$OD) δ: 8.34 (d, J = 4.8 Hz, 1H), 8.13 (d, J = 2.0 Hz, 1H), 8.09 (s, 1H), 7.95 (dd, J = 8.0, 2.0 Hz, 1H), 7.59 (s, 1H), 7.44 (d, J = 8.4 Hz, 1H), 7.13 (d, J = 5.2 Hz, 1H), 6.39 (s, 1H), 4.90-4.78 (m, 1H), 4.62 (s, 2H), 3.78-3.74 (m, 2H), 3.52-3.47 (m, 2H), 2.36 (s, 3H), 1.29 (s, 9H). | 521.3 |
| 5-tert-butyl-N-[[4-[2-[[1-(1-methylazetidin-3-yl)pyrazol-4-yl]amino]pyrimidin-4-yl]-2-(trifluoromethyl)phenyl]methyl]isoxazole-3-carboxamide | I-355 | $^1$H NMR (400 MHz, CD$_3$OD) δ: 8.44 (s, 1H), 8.38 (d, J = 5.2 Hz, 1H), 8.24 (d, J = 7.6 Hz, 1H), 8.06 (s, 1H), 7.64 (s, 1H), 7.61 (d, J = 8.4 Hz, 1H), 7.19 (d, J = 5.2 Hz, 1H), 6.41 (s, 1H), 5.00-4.93 (m, 1H), 4.74 (s, 2H), 3.99-3.94 (m, 2H), 3.74-3.72 (m, 2H), 2.52 (s, 3H), 1.30 (s, 9H). | 555.3 |
| 1-tert-butyl-N-[[2-chloro-4-[2-[[1-(1-methylazetidin-3-yl)pyrazol-4-yl]amino]pyrimidin-4-yl]phenyl]methyl]pyrazole-4-carboxamide | I-356 | $^1$H NMR (400 MHz, CD$_3$OD) δ: 8.46 (d, J = 5.2 Hz, 1H), 8.29 (s, 1H), 8.24 (s, 1H), 8.20 (br, 1H), 8.06 (d, J = 8.0 Hz, 1H), 7.99 (s, 1H), 7.71 (s, 1H), 7.54 (d, J = 8.0 Hz, 1H), 7.25 (d, J = 4.0 Hz, 1H), 5.01-4.90 (m, 1H), 4.69 (s, 2H), 3.88 (t, J = 8.0 Hz, 2H), 3.61 (t, J = 8.0 Hz, 2H), 2.48 (s, 3H), 1.63 (s, 9H). | 520.3 |
| 2-tert-butyl-N-[[2-methyl-4-[6-[[1-[(3R)-tetrahydrofuran-3-yl]pyrazol-3-yl]amino]pyrimidin-4-yl]phenyl]methyl]thiazole-5-carboxamide | I-357 | $^1$H NMR (400 MHz, CDCl$_3$) δ: 8.77 (s, 1H), 8.04 (s, 1H), 7.91 (s, 1H), 7.82 (d, J = 8.0 Hz, 1H), 7.67 (s, 1H), 7.43 (d, J = 2.4 Hz, 1H), 7.39 (d, J = 8.4 Hz, 1H), 7.24 (s, 1H), 6.26 (s, 1H), 6.08 (t, J = 5.2 Hz, 1H), 4.92-4.88 (m, 1H), 4.67 (d, J = 6.4 Hz, 2H), 4.20-4.07 (m, 3H), | 518.2 |

-continued

| Chemical name | Compound# | H-NMR | MH+ |
|---|---|---|---|
| 2-tert-butyl-N-[[2-methyl-4-[6-[[1-(1-methyl-4-piperidyl)pyrazol-3-yl]amino]pyrimidin-4-yl]phenyl]methyl]thiazole-5-carboxamide | I-358 | 4.01-3.95 (m, 1H), 2.49-2.36 (m, 5H), 1.45 (s, 9H). $^1$H NMR (400 MHz, CD$_3$OD) δ: 8.48 (s, 1H), 8.13 (s, 1H), 7.69 (s, 1H), 7.65 (d, J = 8.0 Hz, 1H), 7.53-7.50 (m, 1H), 7.49 (d, J = 2.4 Hz, 1H), 7.31 (d, J = 8.0 Hz, 1H), 6.26 (s, 1H), 4.50 (s, 2H), 4.05-3.97 (m, 1H), 2.89 (d, J = 11.6 Hz, 2H), 2.35 (s, 3H), 2.22 (s, 3H), 2.17-2.09 (m, 2H), 2.04-1.99 (m, 4H), 1.35 (s, 9H). | 545.2 |
| 3-tert-butoxy-N-[6-[2-[(1-methylpyrazol-4-yl)amino]pyrimidin-4-yl]tetralin-1-yl]azetidine-1-carboxamide | I-359 | $^1$H NMR (400 MHz, CD$_3$OD) δ: 8.36 (d, J = 5.2 Hz, 1H), 7.95 (s, 1H), 7.89 (d, J = 8.2 Hz, 1H), 7.83 (s, 1H), 7.63 (s, 1H), 7.39 (d, J = 8.2 Hz, 1H), 7.15 (d, J = 5.2 Hz, 1H), 4.97-4.96 (m, 1H), 4.60-4.52 (m, 1H), 4.19-4.10 (m, 2H), 3.88 (s, 3H), 3.81-3.71 (m, 2H), 2.87-2.85 (m, 2H), 2.11-1.95 (m, 2H), 1.90-1.72 (m, 2H), 1.19 (s, 9H). | 476.2 |
| N-[[4-[2-[(1-ethylpyrazol-4-yl)amino]pyrimidin-4-yl]-2-methyl-phenyl]methyl]-3-isopropoxy-azetidine-1-carboxamideacid | I-360 | 1H NMR (400 MHz, METHANOL-d4) δ: 8.15-8.40 (m, 1 H) 7.92-8.11 (m, 3 H) 7.63-7.80 (m, 1 H) 7.53 (d, J = 6.53 Hz, 1 H) 7.45 (d, J = 8.53 Hz, 1 H) 4.35-4.48 (m, 3 H) 4.12-4.29 (m, 4 H) 3.81 (dd, J = 9.04, 4.52 Hz, 2 H) 3.57-3.72 (m, 1 H) 2.43 (s, 3 H) 2.03 (s, 2 H) 1.51 (t, J = 7.28 Hz, 3 H) 1.16 (d, J = 6.02 Hz, 6H) | 450.3 |

Example 239: Protocol for Human B Cell Stimulation

Human B cells are purified from 150 ml of blood. Briefly, the blood is diluted 1/2 with PBS and centrifuged through a Ficoll density gradient. The B cells are isolated from the mononuclear cells by negative selection using the B cell isolation kit II from Milenyi (Auburn, Calif.). 50,000 B cells per well are then stimulated with 10 ug/ml of goat F(ab')$_2$ anti-human IgM antibodies (Jackson ImmunoResearch Laboratories, West Grove, Pa.) in a 96-well plate. Compounds are diluted in DMSO and added to the cells. Final concentration of DMSO is 0.5%. Proliferation is measured after 3 days using Promega CellTiter-Glo (Madison, Wis.).

Example 240: In Vitro BTK Kinase Assay: BTK-POLYGAT-LS ASSAY

The purpose of the BTK in vitro assay is to determine compound potency against BTK through the measurement of IC$_{50}$. Compound inhibition is measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction was done in a black 96 well plate (costar 3694). For a typical assay, a 24 µL aliquot of a ATP/peptide master mix (final concentration; ATP 10 µM, polyGAT 100 nM) in kinase buffer (10 mM Tris-HCl pH 7.5, 10 mM MgCl$_2$, 200 µM Na$_3$PO$_4$, 5 mM DTT, 0.01% Triton X-100, and 0.2 mg/ml casein) is added to each well. Next, 1 µL of a 4-fold, 40× compound titration in 100% DMSO solvent is added, followed by adding 15 uL of BTK enzyme mix in 1× kinase buffer (with a final concentration of 0.25 nM). The assay is incubated for 30 minutes before being stopped with 28 µL of a 50 mM EDTA solution. Aliquots (5 µL) of the kinase reaction are transferred to a low volume white 384 well plate (Corning 3674), and 5 µL of a 2× detection buffer (Invitrogen PV3574, with 4 nM Tb-PY20 antibody, Invitrogen PV3552) is added. The plate is covered and incubated for 45 minutes at room temperature. Time resolved fluorescence (TRF) on Molecular Devices M5 (332 nm excitation; 488 nm emission; 518 nm fluorescein emission) is measured. IC$_{50}$ values are calculated using a four parameter fit with 100% enzyme activity determined from the DMSO control and 0% activity from the EDTA control.

Table 1 shows the activity of selected compounds of this invention in the in vitro Btk kinase assay, wherein each compound number corresponds to the compound numbering set forth in Examples 1-238 herein, supra. Compounds have an activity designated as "A" provided an IC$_{50}$<10 nM; compounds having an activity designated as "B" provided an IC$_{50}$ of 10-99 nM; compounds having an activity designated as "C" provided an IC$_{50}$ of 100-999 nM; compounds having an activity designated as "D" provided an IC$_{50}$ of 1,000-10,000 nM; and compounds having an activity designated as "E" provided an IC$_{50}$ of >10,000 nM. In some instances where a compound tested has activity "E", other structurally similar compounds beyond the measurable limits of the assay are not included in Table 1.

TABLE 1

Inhibitory Data for Exemplary Compounds

| Compound tested | IC50(10 uMATP) |
|---|---|
| I-1 | A |
| I-2 | A |
| I-3 | A |
| I-4 | A |
| I-5 | A |
| I-6 | A |
| I-7 | A |
| I-8 | A |
| I-9 | A |
| I-10 | A |
| I-11 | B |

TABLE 1-continued

Inhibitory Data for Exemplary Compounds

| Compound tested | IC50(10 uMATP) |
|---|---|
| I-12 | A |
| I-13 | A |
| I-14 | B |
| I-15 | A |
| I-16 | E |
| I-17 | C |
| I-18 | C |
| I-19 | A |
| I-20 | A |
| I-21 | A |
| I-22 | B |
| I-23 | C |
| I-24 | B |
| I-25 | D |
| I-26 | D |
| I-27 | E |
| I-28 | E |
| I-29 | D |
| I-30 | D |
| I-31 | C |
| I-32 | C |
| I-33 | C |
| I-34 | B |
| I-35 | D |
| I-36 | A |
| I-37 | A |
| I-38 | A |
| I-39 | A |
| I-40 | A |
| I-41 | A |
| I-42 | A |
| I-43 | A |
| I-44 | A |
| I-45 | A |
| I-46 | A |
| I-47 | A |
| I-48 | A |
| I-49 | A |
| I-50 | A |
| I-51 | A |
| I-52 | A |
| I-53 | C |
| I-54 | A |
| I-55 | A |
| I-56 | A |
| I-57 | A |
| I-58 | B |
| I-59 | B |
| I-60 | B |
| I-61 | B |
| I-62 | A |
| I-63 | A |
| I-64 | A |
| I-65 | A |
| I-66 | A |
| I-67 | A |
| I-68 | B |
| I-69 | A |
| I-70 | A |
| I-71 | B |
| I-72 | D |
| I-73 | D |
| I-74 | D |
| I-75 | D |
| I-76 | E |
| I-77 | D |
| I-78 | E |
| I-79 | D |
| I-80 | D |
| I-81 | D |
| I-82 | C |
| I-83 | C |
| I-84 | D |
| I-85 | B |
| I-86 | B |
| I-87 | C |
| I-88 | C |
| I-89 | A |
| I-90 | B |
| I-91 | A |
| I-92 | B |
| I-93 | B |
| I-94 | C |
| I-95 | A |
| I-96 | B |
| I-97 | A |
| I-98 | B |
| I-99 | A |
| I-100 | B |
| I-101 | B |
| I-102 | B |
| I-103 | B |
| I-104 | C |
| I-105 | B |
| I-106 | A |
| I-107 | D |
| I-108 | A |
| I-109 | B |
| I-110 | B |
| I-111 | A |
| I-112 | A |
| I-113 | C |
| I-114 | C |
| I-115 | A |
| I-116 | A |
| I-117 | B |
| I-118 | A |
| I-119 | C |
| I-120 | A |
| I-121 | A |
| I-122 | A |
| I-123 | A |
| I-124 | A |
| I-125 | A |
| I-126 | A |
| I-127 | A |
| I-128 | A |
| I-129 | A |
| I-130 | A |
| I-131 | A |
| I-132 | A |
| I-133 | A |
| I-134 | A |
| I-135 | A |
| I-136 | B |
| I-137 | A |
| I-138 | D |
| I-139 | B |
| I-140 | B |
| I-141 | C |
| I-142 | A |
| I-143 | A |
| I-144 | B |
| I-145 | C |
| I-146 | C |
| I-147 | A |
| I-148 | A |
| I-149 | A |
| I-150 | A |
| I-151 | A |
| I-152 | A |
| I-153 | A |
| I-154 | A |
| I-155 | B |
| I-156 | C |
| I-157 | B |
| I-158 | C |
| I-159 | A |
| I-160 | A |
| I-161 | A |
| I-163 | A |
| I-164 | A |

TABLE 1-continued

Inhibitory Data for Exemplary Compounds

| Compound tested | IC50(10 uMATP) |
|---|---|
| I-166 | A |
| I-167 | A |
| I-168 | A |
| I-169 | A |
| I-171 | A |
| I-172 | A |
| I-173 | A |
| I-174 | A |
| I-175 | A |
| I-176 | A |
| I-178 | A |
| I-179 | A |
| I-180 | A |
| I-181 | A |
| I-182 | A |
| I-183 | A |
| I-184 | A |
| I-185 | A |
| I-186 | A |
| I-187 | A |
| I-188 | A |
| I-189 | A |
| I-190 | A |
| I-191 | A |
| I-192 | A |
| I-193 | A |
| I-194 | A |
| I-195 | A |
| I-196 | A |
| I-197 | A |
| I-198 | A |
| I-199 | A |
| I-200 | A |
| I-201 | A |
| I-202 | A |
| I-203 | A |
| I-204 | A |
| I-205 | A |
| I-206 | A |
| I-207 | A |
| I-208 | A |
| I-209 | A |
| I-210 | A |
| I-211 | A |
| I-212 | A |
| I-213 | A |
| I-214 | A |
| I-215 | A |
| I-216 | A |
| I-217 | A |
| I-218 | A |
| I-219 | A |
| I-220 | A |
| I-221 | A |
| I-222 | A |
| I-223 | A |
| I-224 | A |
| I-225 | A |
| I-226 | A |
| I-227 | A |
| I-229 | A |
| I-231 | A |
| I-232 | A |
| I-233 | A |
| I-234 | A |
| I-235 | A |
| I-236 | A |
| I-237 | A |
| I-238 | A |
| I-239 | A |
| I-240 | A |
| I-241 | A |
| I-242 | A |
| I-243 | A |
| I-244 | A |
| I-245 | A |
| I-246 | A |
| I-247 | A |
| I-248 | A |
| I-249 | A |
| I-250 | A |
| I-251 | A |
| I-252 | A |
| I-253 | A |
| I-254 | A |
| I-255 | A |
| I-256 | A |
| I-257 |   |
| I-258 | A |
| I-259 | A |
| I-260 | A |
| I-261 | A |
| I-262 |   |
| I-263 | A |
| I-264 | A |
| I-265 | A |
| I-266 | A |
| I-267 | A |
| I-268 | A |
| I-269 | A |
| I-270 | A |
| I-271 | A |
| I-272 | A |
| I-273 | A |
| I-274 | A |
| I-275 | A |
| I-276 | A |
| I-277 | A |
| I-278 | A |
| I-279 | A |
| I-280 | A |
| I-281 | A |
| I-282 | A |
| I-283 | A |
| I-284 | A |
| I-285 | A |
| I-286 | A |
| I-287 | A |
| I-288 | A |
| I-289 | A |
| I-290 | A |
| I-291 | A |
| I-292 | A |
| I-293 | A |
| I-294 | A |
| I-295 | A |
| I-296 | A |
| I-297 | A |
| I-298 | A |
| I-299 | A |
| I-300 | B |
| I-301 | A |
| I-302 | A |
| I-303 | A |
| I-304 | A |
| I-305 | A |
| I-306 | A |
| I-307 | A |
| I-308 | A |
| I-309 | A |
| I-310 | A |
| I-311 | A |
| I-312 | A |
| I-313 | A |
| I-314 | A |
| I-315 | A |
| I-316 | A |
| I-317 | A |
| I-318 | A |
| I-319 | A |
| I-320 | A |
| I-321 | A |

TABLE 1-continued

Inhibitory Data for Exemplary Compounds

| Compound tested | IC50(10 uMATP) |
|---|---|
| I-322 | A |
| I-323 | A |
| I-324 | A |
| I-325 | A |
| I-326 | A |
| I-327 | A |
| I-328 | A |
| I-329 | A |
| I-330 | A |
| I-331 | A |
| I-332 | A |
| I-333 | A |
| I-334 | A |
| I-335 | A |
| I-336 | A |
| I-337 | A |
| I-338 | A |
| I-339 | B |
| I-340 | A |
| I-341 | A |
| I-342 | A |
| I-343 | A |
| I-344 | A |
| I-345 | A |
| I-346 | A |
| I-347 | A |
| I-348 | A |
| I-349 | A |
| I-350 | A |
| I-351 | A |
| I-352 | B |
| I-353 | A |

Whole blood is collected from DBA/1 mice in 16×100 sodium heparin tubes (Becton Dickinson, Cat No. 367874). Blood from multiple DBA/1 mice is pooled. 96 uL of whole blood per well is aliquotted into a 96-round bottom plate changing tips each time. 4 uL diluted test compound is added to each sample, mixed, and incubated for 30 min at 37° C.

For serial dilutions of test compound, 1000× plate is produced with serial dilutions of test compound in 100% DMSO. Ten dilutions, done 1:3, starting at 10 mM are created by: adding 15 uL of test compound at 10 mM in 100% DMSO to well A1; adding 10 uL 100% DMSO to wells A2-A12; diluting 5 uL from well A1 to well A2 and mixing; continuing 1:3 serial dilutions, changing tips between transfers, to well A10. Wells A11 and A12 contain 100% DMSO without test compound.

For dilution 1, a 1:40 plate is created. Using a 12-well multi-channel pipette, each concentration of test compound or DMSO is diluted 1:40 by adding 2 uL from each well of 1000× stock plate to 78 uL water and mixing.

For dilution 2, test compound or DMSO are added to whole blood by diluting 1:25. Using a 12-well multi-channel pipette, 4 uL from 1:40 plate (B) is added to 96 uL whole blood and mixed.

The final concentration of test compounds are shown below. The concentration of DMSO is 0.1% final in each well.

|   | 1 | 2 | 3 | 4 | 5 | 6 | 7 | 8 | 9 | 10 | (+PPi) 11 | (−PPi) 12 |
|---|---|---|---|---|---|---|---|---|---|---|---|---|
| A | 10000 nM | 3333 nM | 1111 nM | 370 nM | 123 nM | 41 nM | 14 nM | 5 nM | 2 nM | 0.5 nM | 0 nM | 0 nM |
| B | 10000 nM | 3333 nM | 1111 nM | 370 nM | 123 nM | 41 nM | 14 nM | 5 nM | 2 nM | 0.5 nM | 0 nM | 0 nM |
| C | 10000 nM | 3333 nM | 1111 nM | 370 nM | 123 nM | 41 nM | 14 nM | 5 nM | 2 nM | 0.5 nM | 0 nM | 0 nM |

TABLE 1-continued

Inhibitory Data for Exemplary Compounds

| Compound tested | IC50(10 uMATP) |
|---|---|
| I-354 | A |
| I-355 | A |
| I-356 | A |
| I-357 | A |
| I-358 | A |
| I-359 | A |
| I-360 | A |

Example 241: —In Vitro Inhibition of BTK Activity in Mouse Whole Blood

Anti-rabbit MSD plates (Meso Scale Discovery, Rockville, Md.) are coated with 35 uL/well of rabbit anti-BTK C82B8 (Cell Signaling Technology, Danvers, Mass.) diluted 1:50 in PBS. Plates are incubated for 2 hours±1 hour at room temp, shaking (setting 3-5) or ON at 4° C. Plates are blocked with MSD Blocker A (Meso Scale Discovery, Rockville, Md.) using 3% MSD Blocker A in TBST. Coated plates are first washed 3× with 250 uL/well TBST followed by addition of 200 uL/well 3% Blocker A/TBST. Plates are blocked for >2 hour at RT, shaking or ON at 4° C.

Lysing buffer used to lyse whole blood is prepared as follows. A 10× Lysis buffer is prepared using 1500 mM NaCl; 200 mM Tris, pH 7.5; 10 mM EDTA; 10 mM EGTA; and 10% Triton-X-100. The 10× Lysis buffer is diluted to 1× in dH$_2$O, and complete lysing buffer (+/−phosphatase inhibitors) is prepared as follows:

|   | +PPi (mL) | −PPi (mL) |
|---|---|---|
| 1X Lysis buffer | 10 | 10 |
| 500 mM PMSF in DMSO | 0.02 | 0.02 |
| Phosphatase Inhibitor 3 | 0.1 |  |
| Phosphatase Inhibitor 2 | 0.1 |  |
| Protease Inhibitor (cOmplete) (1 tablet for 10 mL) | 1 tablet | 1 tablet |
| PhosStop (1 tablet for 10 mL) | 1 tablet |  |
| Sodium Orthovanadate (Na$_3$VO$_4$) (50 uM final) | 0.1 |  |
| Sodium Fluoride (NaF) (10 mM final) | 0.005 |  |
| 1% Deoxycholate (0.25% final) | 2.5 | 2.5 |

100 uL of complete lysing buffer (+/−phosphatase inhibitors) is added to each well, and mixed well by pipetting up and down a few times. Wells 1-10 and 12 received 1× Lysis buffer containing phosphatase inhibitors (+PPi) and well 11 receive 1× Lysis buffer without phosphatase inhibitors (−PPi). Samples are incubated for 1 hour on ice or at 4° C. Samples are mixed again at half time point for complete lysing.

Blocking buffer is washed off blocked MSD plates with 250 uL TBST per well 3 times. 100-150 uL of whole blood lysates is added to each well of the coated and blocked MSD plates followed by incubation overnight in a cold room with shaking.

The plates are then washed 4 times with 250 µL TBST per well. Biotinylated phospho-tyrosine mouse mAb (pY100, Cell Signaling Technology, Danvers, Mass.) was diluted 1:125 in 1% Blocker A. Mouse anti-BTK mAb (Fitzgerald Industries International, Acton, Mass.) is diluted 1:900 in 1% Blocker A. 35 µL of diluted pY100 or diluted anti-BTK mAb is added to each well and incubated for 2 hours at room temperature, shaking.

Plates are then washed 3 times with 250 uL TBST/well. 35 uL of 1:500 Streptavidin-Sulfo-Tag labeled antibody in 3% Blocker A is added to each well. For anti-BTK, 35 uL of 1:500 anti-mouse-Tag labeled antibody in 3% Blocker A is added to each well. Plates are incubated for 1 hour at RT, shaking.

To develop and read the plates, 1× Read Buffer in $dH_2O$ is prepared from 4× stock. Plates are washed 3 times with 250 uL TBST/well. 150 uL of 1×MSD Read Buffer is added to each well. Plates are read in a SECTOR Imager 6000 (Meso Scale Discovery, Rockville, Md.).

| Materials | | |
|---|---|---|
| ITEM | VENDOR | CATALOG NO. |
| Anti-rabbit MSD plates | MSD | L45RA-1 |
| Rabbit anti-BTK (C82B8) | Cell Signaling | 3533S |
| PBS | Media Prep | |
| MSD Blocker A | MSD | R93BA-4 |
| TBST (1xTBS/0.1% Tween20) | Media Prep | |
| 10X Lysing Buffer | Media Prep | |
| PMSF in DMSO (500 mM) | Media Prep | |
| Phosphatase Cocktail Inhibitor 3 | Sigma Aldrich | P0044-5ML |
| Phosphatase Cocktail Inhibitor 2 | Sigma Aldrich | P5726-1ML |
| cOmplete Mini | Roche | 11 836 153 001 |
| PhosStop Inhibitor | Roche | 04 906 837 001 |
| Sodium Orthovanadate 100 mM | Media Prep | |
| Sodium Fluoride 1M | Media Prep | |
| 1% Deoxycholate | Media Prep | |
| pTyr 100 ms mAb biotinylated | Cell Signaling | 9417S |
| Streptavidin Sulfo-Tag | MSD | R32AD-1 |
| MSD Read Buffer 4X | MSD | R92TC-1 |
| Costar 96-round bottom | Costar/Fisher | 3799 |
| Mouse anti-BTK (7F12H4) | Fitzgerald | 10R-1929 |
| Anti-mouse Sulfo-Tag | MSD | R32AC-5 |

Example 242—PK/PD Correlation in DBA1 Mice

Mice are dosed orally (PO) with test compound in CMC-Tween and killed by $CO_2$ asphyxiation at various times after dosing. Heparinized whole blood is immediately collected by cardiac puncture and split into two samples. One sample is used to quantify the amount of test compound present and the other is lysed in MSD lysis buffer in the presence of phosphatase inhibitors. Heparinized whole blood from cardiac punctures of vehicle (CMC-Tween) dosed mice are lysed either in the presence (high control) or absence (low control) of phosphatase inhibitors. Lysed whole blood samples are analyzed for phospho-BTK as described above. The percent inhibition of phospho-BTK in each whole blood sample from dosed mice is calculated as follows: (1−((pBTK(x+PPi)−pBTK(vehicle−PPi))/(pBTK(vehicle+PPi))))*100, where pBTK(x+PPi) is the ECL signal for whole blood from each test compound-treated mouse, pBTK (vehicle−PPi) is the average ECL signal of whole blood from vehicle-treated mice lysed in the absence of phosphatase inhibitors (low control) and pBTK(vehicle+PPi) is the average ECL signal of whole blood from vehicle-treated mice lysed in the presence of phosphatase inhibitors (high control).

Example 243: In Vitro PD Assay in Human Whole Blood

Human heparinized venous blood was purchased from Bioreclamation, Inc. or SeraCare Life Sciences and shipped overnight. Whole blood was aliquoted into 96-well plate and "spiked" with serial dilutions of test compound in DMSO or with DMSO without drug. The final concentration of DMSO in all wells was 0.1%. The plate was incubated at 37° C. for 30 min. Lysis buffer containing protease and phosphatase inhibitors was added to the drug-containing samples and one of the DMSO-only samples (+PPi, high control), while lysis buffer containing protease inhibitors was added to the other DMSO-only samples (−PPi, low control). All of the lysed whole blood samples were subjected to the total BTK capture and phosphotyrosine detection method described in Example 241. ECL values were graphed in Prism and a best-fit curve with restrictions on the maximum and minimum defined by the +PPi high and −PPi low controls was used to estimate the test compound concentration that results in 50% inhibition of ECL signal by interpolation.

Table 2 shows the activity of selected compounds of this invention in the pBTK assay, wherein each compound number corresponds to the compound numbering set forth in Examples 1-238 herein, supra. Compounds have an activity designated as "A" provided an $IC_{50}$<500 nM; compounds having an activity designated as "B" provided an $IC_{50}$ of 500-1499 nM; compounds having an activity designated as "C" provided an $IC_{50}$ of 1500-10000 nM. In some instances where a compound tested has activity "C", other structurally similar compounds beyond the measurable limits of the assay are not included in Table 2.

TABLE 2

| pBTK Inhibitory Data for Exemplary Compounds | |
|---|---|
| Compound Tested | pBTK IC50 |
| I-1 | A |
| I-2 | B |
| I-3 | C |
| I-4 | C |
| I-5 | B |
| I-6 | B |
| I-7 | B |
| I-9 | B |
| I-10 | A |
| I-12 | A |
| I-13 | C |
| I-15 | A |
| I-19 | B |
| I-20 | B |
| I-21 | A |
| I-23 | C |
| I-24 | C |
| I-36 | A |
| I-37 | A |
| I-38 | B |
| I-39 | A |
| I-40 | A |
| I-41 | A |
| I-42 | A |
| I-43 | A |
| I-44 | A |
| I-45 | A |

TABLE 2-continued pBTK Inhibitory Data for Exemplary Compounds

| Compound Tested | pBTK IC50 |
|---|---|
| I-46 | A |
| I-47 | B |
| I-48 | A |
| I-49 | A |
| I-50 | A |
| I-51 | B |
| I-52 | A |
| I-54 | B |
| I-55 | C |
| I-56 | B |
| I-62 | C |
| I-63 | A |
| I-64 | C |
| I-65 | B |
| I-66 | B |
| I-67 | B |
| I-69 | A |
| I-70 | A |
| I-89 | B |
| I-91 | C |
| I-95 | B |
| I-99 | C |
| I-108 | C |
| I-111 | C |
| I-115 | B |
| I-116 | B |
| I-118 | A |
| I-120 | B |
| I-121 | A |
| I-122 | A |
| I-123 | A |
| I-124 | A |
| I-125 | A |
| I-126 | A |
| I-127 | B |
| I-128 | A |
| I-129 | B |
| I-130 | A |
| I-131 | B |
| I-132 | C |
| I-135 | C |
| I-142 | C |
| I-160 | A |
| I-161 | A |
| I-163 | A |
| I-164 | A |
| I-166 | A |
| I-167 | A |
| I-168 | A |
| I-169 | A |
| I-171 | A |
| I-172 | A |
| I-173 | A |
| I-174 | A |
| I-175 | A |
| I-176 | A |
| I-178 | A |
| I-179 | A |
| I-180 | A |
| I-181 | A |
| I-182 | A |
| I-183 | A |
| I-184 | A |
| I-185 | A |
| I-186 | A |
| I-187 | A |
| I-188 | B |
| I-189 | A |
| I-190 | A |
| I-191 | A |
| I-192 | A |
| I-193 | A |
| I-194 | A |
| I-195 | A |
| I-196 | A |
| I-197 | A |
| I-198 | A |
| I-199 | A |
| I-200 | A |
| I-201 | A |
| I-202 | A |
| I-203 | A |
| I-204 | A |
| I-205 | A |
| I-206 | A |
| I-207 | A |
| I-208 | A |
| I-209 | A |
| I-210 | A |
| I-211 | A |
| I-212 | A |
| I-213 | A |
| I-214 | A |
| I-215 | A |
| I-216 | A |
| I-217 | A |
| I-218 | A |
| I-219 | A |
| I-220 | A |
| I-221 | A |
| I-222 | B |
| I-223 | B |
| I-224 | A |
| I-225 | A |
| I-226 | A |
| I-227 | A |
| I-229 | A |
| I-231 | A |
| I-232 | A |
| I-233 | A |
| I-234 | A |
| I-235 | A |
| I-236 | A |
| I-237 | A |
| I-238 | A |
| I-239 | A |
| I-240 | A |
| I-241 | A |
| I-242 | A |
| I-243 | A |
| I-244 | A |
| I-245 | A |
| I-246 | A |
| I-247 | A |
| I-248 | A |
| I-249 | A |
| I-250 | A |
| I-251 | A |
| I-252 | A |
| I-253 | A |
| I-254 | A |
| I-255 | A |
| I-256 | A |
| I-257 | A |
| I-258 | A |
| I-259 | A |
| I-260 | A |
| I-261 | A |
| I-262 | A |
| I-263 | A |
| I-264 | A |
| I-265 | A |
| I-266 | A |
| I-267 | A |
| I-268 | A |
| I-269 | A |
| I-270 | A |
| I-271 | A |
| I-272 | A |
| I-273 | A |
| I-274 | A |
| I-275 | A |

TABLE 2-continued pBTK Inhibitory Data for Exemplary Compounds

| Compound Tested | pBTK IC50 |
|---|---|
| I-276 | A |
| I-277 | A |
| I-278 | A |
| I-279 | A |
| I-280 | A |
| I-281 | A |
| I-282 | A |
| I-283 | A |
| I-284 | A |
| I-285 | A |
| I-286 | A |
| I-287 | A |
| I-288 | A |
| I-289 | A |
| I-290 | A |
| I-291 | A |
| I-292 | A |
| I-293 | A |
| I-294 | A |
| I-295 | A |
| I-296 | A |
| I-297 | A |
| I-298 | A |
| I-299 | A |
| I-300 | A |
| I-301 | A |
| I-302 | A |
| I-303 | A |
| I-304 | A |
| I-305 | A |
| I-306 | A |
| I-307 | A |
| I-308 | A |
| I-309 | A |
| I-310 | A |
| I-311 | A |
| I-312 | A |
| I-313 | A |
| I-314 | A |
| I-315 | A |
| I-316 | A |
| I-317 | A |
| I-318 | A |
| I-319 | A |
| I-320 | A |
| I-321 | A |
| I-322 | A |
| I-323 | A |
| I-324 | A |
| I-325 | A |
| I-326 | A |
| I-327 | A |
| I-328 | A |
| I-329 | A |
| I-330 | A |
| I-331 | A |
| I-332 | A |
| I-333 | A |
| I-334 | A |
| I-335 | A |
| I-336 | A |
| I-337 | A |
| I-338 | A |
| I-339 | A |
| I-340 | A |
| I-341 | A |
| I-342 | A |
| I-343 | A |
| I-344 | A |
| I-345 | A |
| I-346 | A |
| I-347 | A |
| I-348 | A |
| I-349 | A |
| I-350 | A |
| I-351 | A |

TABLE 2-continued pBTK Inhibitory Data for Exemplary Compounds

| Compound Tested | pBTK IC50 |
|---|---|
| I-352 | A |
| I-353 | A |
| I-354 | A |
| I-355 | A |
| I-356 | A |
| I-357 | A |
| I-358 | A |
| I-359 | A |
| I-360 | A |

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of decreasing the enzymatic activity of Bruton's tyrosine kinase comprising contacting Bruton's tyrosine kinase with an effective amount of a compound of Formula I':

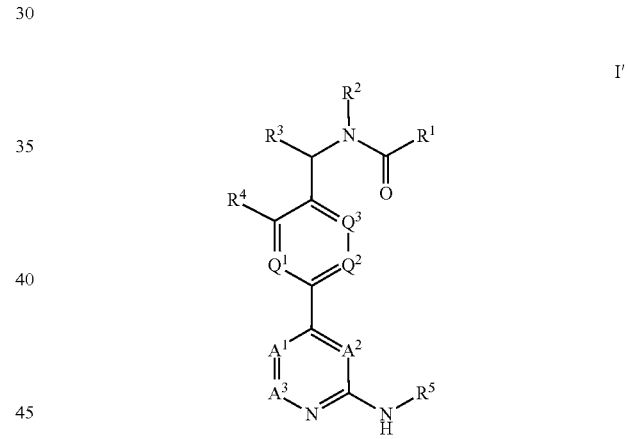

or a pharmaceutically acceptable salt, wherein:
one of $A^1$ and $A^2$ is C—$R^6$, and the other of $A^1$ and $A^2$ is selected from C—$R^6$ or N;
$A^3$ is selected from C—H or N, and is C—H when $A^1$ or $A^2$ is N;
$Q^1$ is selected from C—$R^7$ and N;
$Q^2$ is selected from C—$R^7$ and N;
$Q^3$ is selected from C—$R^7$ and N;
wherein at most one of $Q^1$, $Q^2$, and $Q^3$ is N;
$R^1$ is selected from —N(R)$_2$, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, wherein said phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl are optionally substituted with one or more $R^{10}$;

$R^2$ is H or $C_{1-6}$ aliphatic;

or $R^1$ and $R^2$, together with their intervening atoms, form a ring selected from 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, or 7- to 10-membered bicyclic heteroaryl having 1-4 heteroatoms selected from oxygen, nitrogen, wherein said ring is optionally substituted with one or more $R^{20}$;

$R^3$ is selected from H, halogen, —C(O)N(R)$_2$, —C(O)OR, —C(O)R, and $C_{1-6}$ aliphatic, wherein the $C_{1-6}$ aliphatic group is optionally substituted with hydroxyl;

each $R^4$ is independently selected from halogen, —NO$_2$, —CN, —OR, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, or $C_{1-6}$ aliphatic, wherein said $C_{1-6}$ aliphatic is optionally substituted with one or more $R^{40}$;

or $R^3$ and $R^4$ together with their intervening atoms form fused Ring A selected from fused 5- to 7-membered monocyclic carbocycle, fused 5- to 7-membered monocyclic heterocycle having 1-2 heteroatoms selected from oxygen, nitrogen, or sulfur, wherein said fused Ring A is optionally substituted with one or more $R^{40}$;

$R^5$ is selected from H, —C(O)R, —C(O)OR, —S(O)R, —S(O)$_2$R, —C(O)N(R)$_2$, or $C_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, wherein said $C_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, are optionally substituted with one or more $R^{50}$;

each of $R^6$ and $R^7$ is independently selected from H, halogen, —NO$_2$, —CN, —OR, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, or $C_{1-6}$ aliphatic;

each R is independently hydrogen or $C_{1-6}$ aliphatic, phenyl, 3- to 8-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said $C_{1-6}$ aliphatic, phenyl, 3- to 7-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, are optionally substituted with one or more $R^{50}$; or two R groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said ring is optionally substituted with one or more $R^{50}$;

each $R^{10}$ is independently selected from halogen, —OR$^{10a}$, $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, wherein said $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, are optionally substituted with one or more $R^{15}$;

each $R^{15}$ is independently selected from halogen and —OR$^{15a}$;

$R^{10a}$ is $C_{1-6}$alkyl optionally substituted with halogen;

$R^{15a}$ is $C_{1-6}$alkyl;

each $R^{20}$ is independently selected from halogen, $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, wherein said $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, are optionally substituted with one or more $R^{15}$;

each $R^{40}$ is independently selected from halogen, $C_{1-6}$alkyl, 4- to 6-membered monocyclic heterocyclyl having 1-2 heteroatoms selected from oxygen, nitrogen, or sulfur, —C(O)H, —N(R$^{40a}$)$_2$, —N(R$^{40a}$)C(O)(R$^{40b}$), —N(R$^{40a}$)C(O)$_2$(R$^{40a}$), —OR$^{40a}$, —SR$^{40a}$, and —C(O)₂R⁴⁰ᵃ, wherein said C₁₋₆alkyl group is optionally substituted with halogen or —OR⁴⁰ᵃ;

each R⁴⁰ᵃ is independently selected from H and C₁₋₆alkyl; or two R⁴⁰ᵃ groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur;

each R⁴⁰ᵇ is independently selected from C₂₋₆alkenyl and 5- or 6-membered heterocyclyl having 1-2 heteroatoms selected from oxygen, nitrogen, or sulfur, wherein said 5- or 6-membered heterocyclyl having 1-2 heteroatoms selected from oxygen, nitrogen, or sulfur, is optionally substituted with one or more R⁴⁵;

R⁴⁵ is C₁₋₆alkyl;

each R⁵⁰ is independently selected from C₁₋₆aliphatic, —OR⁵⁰ᵃ, —N(R⁵⁰ᵃ)₂, —C(O)N(R⁵⁰ᵃ)₂, —C(O)₂R⁵⁰ᵃ, oxo, 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclyalkyl having 1-4 heteroatoms selected from oxygen, nitrogen, or sulfur, wherein said C₁₋₆alkyl, 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclyalkyl having 1-4 heteroatoms selected from oxygen, nitrogen, or sulfur, are optionally substituted with one or more R⁵⁵;

R⁵⁰ᵃ is selected from H and C₁₋₆alkyl;

each R⁵⁵ is independently selected from 5- to 6-membered heterocyclyl having 1-2 heteroatoms selected from nitrogen, oxygen, or sulfur, C₁₋₆alkyl, —OR⁵⁵ᵃ, —C(O)N(R⁵⁵ᵃ)₂, halogen, —N(R⁵⁵ᵃ)₂, —C(O)₂R⁵⁵ᵃ, —S(O)₂R⁵⁵ᵇ, and —S(O)₂(NR⁵⁵ᵃ)₂;

R⁵⁵ᵃ is selected from H and C₁₋₆alkyl, wherein said C₁₋₆alkyl is optionally substituted with halogen; and R⁵⁵ᵇ is C₁₋₆alkyl or a composition thereof.

2. A method of treating a disorder responsive to inhibition of Bruton's tyrosine kinase comprising administering to a subject an effective amount of a compound of Formula I':

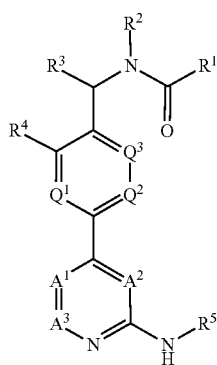

or a pharmaceutically acceptable salt, wherein:

one of A¹ and A² is C—R⁶, and the other of A¹ and A² is selected from C—R⁶ or N;

A³ is selected from C—H or N, and is C—H when A¹ or A² is N;

Q¹ is selected from C—R⁷ and N;

Q² is selected from C—R⁷ and N;

Q³ is selected from C—R⁷ and N;

wherein at most one of Q¹, Q², and Q³ is N;

R¹ is selected from —N(R)₂, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, wherein said phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl are optionally substituted with one or more R¹⁰;

R² is H or C₁₋₆ aliphatic;

or R¹ and R², together with their intervening atoms, form a ring selected from 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, or 7- to 10-membered bicyclic heteroaryl having 1-4 heteroatoms selected from oxygen, nitrogen, wherein said ring is optionally substituted with one or more R²⁰;

R³ is selected from H, halogen, —C(O)N(R)₂, —C(O)OR, —C(O)R, and C₁₋₆ aliphatic, wherein the C₁₋₆ aliphatic group is optionally substituted with hydroxyl;

each R⁴ is independently selected from halogen, —NO₂, —CN, —OR, —SR, —N(R)₂, —C(O)R, —C(O)OR, —S(O)R, —S(O)₂R, —C(O)N(R)₂, —SO₂N(R)₂, —OC(O)R, —N(R)C(O)R, —N(R)C(O)OR, —N(R)SO₂R, —OC(O)N(R)₂, or C₁₋₆ aliphatic, wherein said C₁₋₆ aliphatic is optionally substituted with one or more R⁴⁰;

or R³ and R⁴ together with their intervening atoms form fused Ring A selected from fused 5- to 7-membered monocyclic carbocycle, fused 5- to 7-membered monocyclic heterocycle having 1-2 heteroatoms selected from oxygen, nitrogen, or sulfur, wherein said fused Ring A is optionally substituted with one or more R⁴⁰;

R⁵ is selected from H, —C(O)R, —C(O)OR, —S(O)R, —S(O)₂R, —C(O)N(R)₂, or C₁₋₆ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, wherein said $C_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, are optionally substituted with one or more $R^{50}$;

each of $R^6$ and $R^7$ is independently selected from H, halogen, $-NO_2$, $-CN$, $-OR$, $-SR$, $-N(R)_2$, $-C(O)R$, $-C(O)OR$, $-S(O)R$, $-S(O)_2R$, $-C(O)N(R)_2$, $-SO_2N(R)_2$, $-OC(O)R$, $-N(R)C(O)R$, $-N(R)C(O)OR$, $-N(R)SO_2R$, $-OC(O)N(R)_2$, or $C_{1-6}$ aliphatic;

each R is independently hydrogen or $C_{1-6}$aliphatic, phenyl, 3- to 8-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said $C_{1-6}$ aliphatic, phenyl, 3- to 7-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, are optionally substituted with one or more $R^{50}$; or two R groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said ring is optionally substituted with one or more $R^{50}$;

each $R^{10}$ is independently selected from halogen, $-OR^{10a}$, $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, wherein said $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, are optionally substituted with one or more $R^{15}$;

each $R^{15}$ is independently selected from halogen and $-OR^{15a}$;

$R^{10a}$ is $C_{1-6}$alkyl optionally substituted with halogen;

$R^{15a}$ is $C_{1-6}$alkyl;

each $R^{20}$ is independently selected from halogen, $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, wherein said $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, are optionally substituted with one or more $R^{15}$;

each $R^{40}$ is independently selected from halogen, $C_{1-6}$ alkyl, 4- to 6-membered monocyclic heterocyclyl having 1-2 heteroatoms selected from oxygen, nitrogen, or sulfur, $-C(O)H$, $-N(R_{40a})_2$, $-N(R^{40a})C(O)(R^{40b})$, $-N(R^{40a})C(O)_2(R^{40a})$, $-OR^{40a}$, $-SR^{40a}$, and $-C(O)_2R^{40a}$, wherein said $C_{1-6}$ alkyl group is optionally substituted with halogen or $-OR^{40a}$;

each $R^{40a}$ is independently selected from H and $C_{1-6}$alkyl; or two $R^{40a}$ groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur;

each $R^{40b}$ is independently selected from $C_{2-6}$ alkenyl and 5- or 6-membered heterocyclyl having 1-2 heteroatoms selected from oxygen, nitrogen, or sulfur, wherein said 5- or 6-membered heterocyclyl having 1-2 heteroatoms selected from oxygen, nitrogen, or sulfur, is optionally substituted with one or more $R^{45}$;

$R^{45}$ is $C_{1-6}$ alkyl;

each $R^{50}$ is independently selected from $C_{1-6}$aliphatic, $-OR^{50a}$, $-N(R^{50a})_2$, $-C(O)N(R^{50a})_2$, $-C(O)_2R^{50a}$, oxo, 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclyalkyl having 1-4 heteroatoms selected from oxygen, nitrogen, or sulfur, wherein said $C_{1-6}$ alkyl, 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclyalkyl having 1-4 heteroatoms selected from oxygen, nitrogen, or sulfur, are optionally substituted with one or more $R^{55}$;

$R^{50a}$ is selected from H and $C_{1-6}$alkyl;

each $R^{55}$ is independently selected from 5- to 6-membered heterocyclyl having 1-2 heteroatoms selected from nitrogen, oxygen, or sulfur, $C_{1-6}$ alkyl, $-OR^{55a}$, $-C(O)N(R^{55a})_2$, halogen, $-N(R^{55a})_2$, $-C(O)_2R^{55a}$, $-S(O)_2R^{55b}$, and $-S(O)_2(NR^{55a})_2$;

$R^{55a}$ is selected from H and $C_{1-6}$alkyl, wherein said $C_{1-6}$ alkyl is optionally substituted with halogen; and $R^{55b}$ is $C_{1-6}$ alkyl or a composition thereof.

3. A method of treating a disorder selected from the group consisting of autoimmune disorders, inflammatory disorders, and cancers comprising administering to a subject an effective amount of a compound of Formula I':

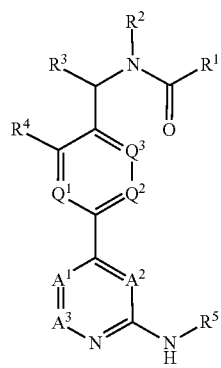

or a pharmaceutically acceptable salt, wherein:
one of $A^1$ and $A^2$ is C—$R^6$, and the other of $A^1$ and $A^2$ is selected from C—$R^6$ or N;
$A^3$ is selected from C—H or N, and is C—H when $A^1$ or $A^2$ is N;
$Q^1$ is selected from C—$R^7$ and N;
$Q^2$ is selected from C—$R^7$ and N;
$Q^3$ is selected from C—$R^7$ and N;
wherein at most one of $Q^1$, $Q^2$, and $Q^3$ is N;
$R^1$ is selected from —N(R)$_2$, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, wherein said phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl are optionally substituted with one or more $R^{10}$;
$R^2$ is H or $C_{1-6}$ aliphatic;
or $R^1$ and $R^2$, together with their intervening atoms, form a ring selected from 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or 7- to 10-membered bicyclic heteroaryl having 1-4 heteroatoms selected from oxygen, nitrogen, wherein said ring is optionally substituted with one or more $R^{20}$;
$R^3$ is selected from H, halogen, —C(O)N(R)$_2$, —C(O)OR, —C(O)R, and $C_{1-6}$ aliphatic, wherein the $C_{1-6}$ aliphatic group is optionally substituted with hydroxyl;
each $R^4$ is independently selected from halogen, —NO$_2$, —CN, —OR, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, or $C_{1-6}$ aliphatic, wherein said $C_{1-6}$ aliphatic is optionally substituted with one or more $R^{40}$;
or $R^3$ and $R^4$ together with their intervening atoms form fused Ring A selected from fused 5- to 7-membered monocyclic carbocycle, fused 5- to 7-membered monocyclic heterocycle having 1-2 heteroatoms selected from oxygen, nitrogen, or sulfur, wherein said fused Ring A is optionally substituted with one or more $R^{40}$;
$R^5$ is selected from H, —C(O)R, —C(O)OR, —S(O)R, —S(O)$_2$R, —C(O)N(R)$_2$, or $C_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, wherein said $C_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl, are optionally substituted with one or more $R^{50}$;
each of $R^6$ and $R^7$ is independently selected from H, halogen, —NO$_2$, —CN, —OR, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, or $C_{1-6}$ aliphatic;
each R is independently hydrogen or $C_{1-6}$ aliphatic, phenyl, 3- to 8-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said $C_{1-6}$ aliphatic, phenyl, 3- to 7-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, are optionally substituted with one or more $R^{50}$; or
two R groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said ring is optionally substituted with one or more $R^{50}$;

each $R^{10}$ is independently selected from halogen, —$OR^{10}a$, $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, wherein said $C_{1-6}$ aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, are optionally substituted with one or more $R^{15}$;

each $R^{15}$ is independently selected from halogen and —$OR^{15a}$;

$R^{10a}$ is $C_{1-6}$alkyl optionally substituted with halogen;

$R^{15a}$ is $C_{1-6}$alkyl;

each $R^{20}$ is independently selected from halogen, $C_{1-6}$ aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, wherein said $C_{1-6}$ aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, are optionally substituted with one or more $R^{15}$;

each $R^{40}$ is independently selected from halogen, $C_{1-6}$ alkyl, 4- to 6-membered monocyclic heterocyclyl having 1-2 heteroatoms selected from oxygen, nitrogen, or sulfur, —C(O)H, —N($R^{40a}$)$_2$, —N($R^{40a}$)C(O)($R^{40b}$), —N($R^{40a}$)C(O)$_2$($R^{40a}$), —$OR^{40a}$, —$SR^{40a}$, and —C(O)$_2R^{40a}$, wherein said $C_{1-6}$ alkyl group is optionally substituted with halogen or —$OR^{40a}$;

each $R^{40a}$ is independently selected from H and $C_{1-6}$alkyl; or two $R^{40a}$ groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur;

each $R^{40b}$ is independently selected from $C_{2-6}$ alkenyl and 5- or 6-membered heterocyclyl having 1-2 heteroatoms selected from oxygen, nitrogen, or sulfur, wherein said 5- or 6-membered heterocyclyl having 1-2 heteroatoms selected from oxygen, nitrogen, or sulfur, is optionally substituted with one or more $R^{45}$;

$R^{45}$ is $C_{1-6}$ alkyl;

each $R^{50}$ is independently selected from $C_{1-6}$ aliphatic, —$OR^{50a}$, —N($R^{50a}$)$_2$, —C(O)N($R^{50a}$)$_2$, —C(O)$_2R^{50a}$, oxo, 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclylalkyl having 1-4 heteroatoms selected from oxygen, nitrogen, or sulfur, wherein said $C_{1-6}$ alkyl, 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclyalkyl having 1-4 heteroatoms selected from oxygen, nitrogen, or sulfur, are optionally substituted with one or more $R^{55}$;

$R^{50a}$ is selected from H and $C_{1-6}$alkyl;

each $R^{55}$ is independently selected from 5- to 6-membered heterocyclyl having 1-2 heteroatoms selected from nitrogen, oxygen, or sulfur, $C_{1-6}$ alkyl, —$OR^{55a}$, —C(O)N($R^{55a}$)$_2$, halogen, —N($R^{55a}$)$_2$, —C(O)$_2R^{55a}$, —S(O)$_2R^{55b}$, and —S(O)$_2$(NR$^{55a}$)$_2$;

$R^{55a}$ is selected from H and $C_{1-6}$alkyl, wherein said $C_{1-6}$ alkyl is optionally substituted with halogen; and $R^{55b}$ is $C_{1-6}$ alkyl or a composition thereof.

4. The method of claim 3, wherein the disorder is rheumatoid arthritis.

5. The method of claim 3, wherein the disorder is systemic lupus erythematosus.

6. The method of claim 3, wherein the disorder is atopic dermatitis.

7. The method of claim 3, wherein the disorder is leukemia or lymphoma.

8. The method of claim 3, wherein $R^1$ is selected from 5- to 6-membered heteroaryl having 1-4 heteroatoms selected from oxygen, nitrogen, and sulfur, phenyl, and 3- to 7-membered saturated or partially unsaturated monocyclic heterocyclyl having 1-2 heteroatoms selected from oxygen, nitrogen, and sulfur, wherein $R^1$ is optionally substituted with one or more $R^{10}$.

9. The method of claim 3, wherein $R^3$ is hydrogen.

10. The method of claim 3, $R^4$ is halogen or $C_{1-6}$ aliphatic optionally substituted with one or more $R^{40}$, wherein $R^{40}$ is halogen.

11. The method of claim 3, wherein $R^3$ and $R^4$, together with their intervening atoms, form fused Ring A selected from fused 5- to 7-membered monocyclic carbocycle, and fused 5- to 7-membered heterocyclyl having 1-2 heteroatoms selected from oxygen, nitrogen, and sulfur.

12. The method of claim 3, wherein $R^5$ is selected from hydrogen, —C(O)R, and 5- to 6-membered heteroaryl having 1-4 heteroatoms selected from oxygen, nitrogen, and sulfur, wherein the 5- to 6-membered heteroaryl having 1-4 heteroatoms selected from oxygen, nitrogen, and sulfur is optionally substituted with one or more $R^{50}$.

13. The method of claim 12, wherein $R^5$ is selected from pyrazolyl, imidazolyl, isoxazolyl, triazolyl, tetrazolyl, thiadiazolyl, and pyridyl, wherein $R^5$ is optionally substituted with one or more $R^{50}$.

14. The method of claim 13, wherein $R^5$ is

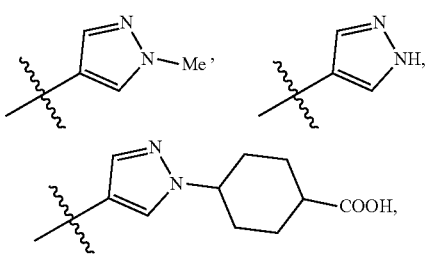

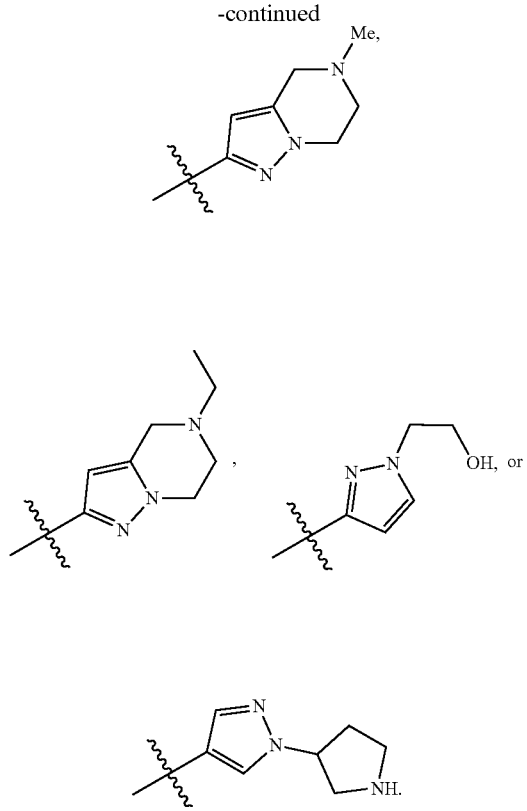
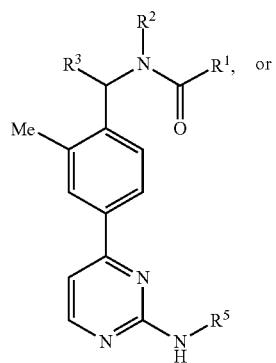
VI-a
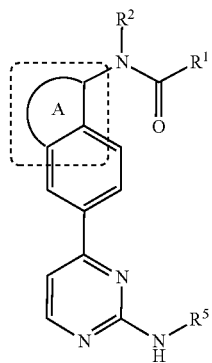
VI-c
or a pharmaceutically acceptable salt thereof.
15. The method of claim 3, wherein each $R^6$ is independently selected from hydrogen, halogen, and $C_{1-6}$ aliphatic.
16. The method of claim 3, wherein the compound is of formula VI-a or VI-c:
17. The method of claim 3, wherein the disorder is multiple sclerosis.
* * * * *